(12) United States Patent
Sugawara et al.

(10) Patent No.: US 8,119,626 B2
(45) Date of Patent: Feb. 21, 2012

(54) OXIME DERIVATIVE AND PREPARATIONS THEREOF

(75) Inventors: Kazutoshi Sugawara, Osaka (JP); Tetsuji Matsudaira, Osaka (JP); Hiroshi Sugama, Osaka (JP); Masao Nawano, Osaka (JP); Rikiya Ohashi, Osaka (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 65 days.

(21) Appl. No.: 12/274,674

(22) Filed: Nov. 20, 2008

(65) Prior Publication Data

US 2009/0291936 A1 Nov. 26, 2009

Related U.S. Application Data

(62) Division of application No. 11/660,905, filed as application No. PCT/JP2006/314117 on Jul. 10, 2006, now Pat. No. 7,514,439.

(30) Foreign Application Priority Data

Jul. 11, 2005 (JP) .................................. 2005-202014
Apr. 18, 2006 (JP) .................................. 2006-114243

(51) Int. Cl.
*A61K 31/427* (2006.01)
*A61K 31/496* (2006.01)
*A61K 31/497* (2006.01)
*C07D 417/12* (2006.01)
*C07D 413/14* (2006.01)
*C07D 405/12* (2006.01)

(52) U.S. Cl. ................ 514/210.2; 514/370; 514/254.02; 514/255.05; 544/369; 544/408; 548/194

(58) Field of Classification Search ............. 514/254.02, 514/370, 471; 544/369; 548/194, 202; 549/472
See application file for complete search history.

(56) References Cited

U.S. PATENT DOCUMENTS

| | | | |
|---|---|---|---|
| 3,903,113 A | 9/1975 | Bradshaw et al. | |
| 4,355,172 A | 10/1982 | Koppel et al. | |
| 4,415,743 A | 11/1983 | Martin | |
| 4,736,026 A | 4/1988 | Imaizumi et al. | |
| 4,851,422 A | 7/1989 | Natsugari et al. | |
| 6,130,251 A * | 10/2000 | Seitz et al. .................... | 514/620 |
| 6,369,232 B1 | 4/2002 | Sidduri | |
| 7,514,439 B2 * | 4/2009 | Sugawara et al. ........ | 514/254.02 |
| 2003/0225283 A1 | 12/2003 | Corbett et al. | |
| 2004/0181067 A1 | 9/2004 | Fyfe et al. | |
| 2008/0146625 A1 | 6/2008 | Berthel et al. | |

FOREIGN PATENT DOCUMENTS

| | | |
|---|---|---|
| CH | 622 824 A5 | 4/1981 |
| DE | 2 255 167 A1 | 11/1973 |
| DE | 27 47 573 A1 | 5/1978 |
| DE | 28 08 317 A1 | 9/1978 |
| EP | 0 069 872 A2 | 1/1983 |
| EP | 0 137 442 A2 | 4/1985 |
| EP | 0 254 426 A2 | 1/1988 |
| EP | 0 386 940 A1 | 9/1990 |
| EP | 0 490 263 A1 | 6/1992 |
| EP | 1 229 025 A1 | 8/2002 |
| ES | 2 099 014 A1 | 5/1997 |
| FR | 2 204 403 A2 | 5/1974 |
| FR | 2 287 231 A1 | 5/1976 |
| FR | 2 564 840 A1 | 11/1985 |
| GB | 1 399 089 A | 6/1975 |
| GB | 1 445 979 | 8/1976 |
| GB | 1 601 752 | 11/1981 |
| IE | 37782 | 10/1977 |
| WO | WO-95/31448 A1 | 11/1995 |
| WO | WO-96/23763 A1 | 8/1996 |
| WO | WO-97/30049 A1 | 8/1997 |
| WO | WO-00/26202 A1 | 5/2000 |
| WO | WO-01/12189 A1 | 2/2001 |
| WO | WO-01/12590 A1 | 2/2001 |
| WO | WO-01/55144 A1 | 8/2001 |
| WO | WO-02/059078 A1 | 8/2002 |
| WO | WO-03/080606 A1 | 10/2003 |
| WO | WO-2004/058724 A1 | 7/2004 |
| WO | WO-2004/072066 A1 | 8/2004 |
| WO | WO-2004/111044 A1 | 12/2004 |
| WO | WO-2005/023761 A2 | 3/2005 |
| WO | WO-2005/068415 A1 | 7/2005 |

OTHER PUBLICATIONS

Padwal et al. Diabetes Care, vol. 28 (3), p. 736-744, (2005).*

(Continued)

*Primary Examiner* — Yong Chu
(74) *Attorney, Agent, or Firm* — Birch, Stewart, Kolasch & Birch, LLP

(57) ABSTRACT

The problem of the present invention is to provide a useful compound as a glucokinase activating agent, which is the oxime derivative of the formula [I]:

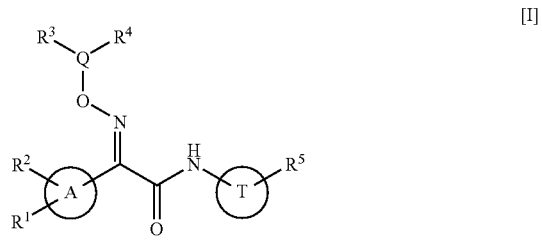

wherein Ring A is aryl or heteroaryl;
Q is cycloalkyl, heterocycle, alkyl or alkenyl;
Ring T is heteroaryl or heterocycle;
$R^1$ and $R^2$ are independently hydrogen atom, halogen atom, cycloalkylsulfonyl or the like;
$R^3$ and $R^4$ are independently hydrogen atom, hydroxy, oxo, halogen atom or the like;
$R^5$ is hydrogen atom, halogen atom, cyano, nitro, tetrazolyl or the like;
or a pharmaceutically acceptable salt thereof.

27 Claims, No Drawings

OTHER PUBLICATIONS

Garuti et al., Synthesis and Antimicrobial Activity of Some N-Monosubstituted 2-2 Aminothiazol-4-YL-Z-2-Methoxyimino-acetamid Es, Die Pharmazie, vol. 43, No. 8, pp. 535-536 (1988) XP001247983.

Kanai et al., Bull. Chem. Soc. Jpn., vol. 66, No. 8, pp. 2335-2338 (1993).

STN-preliminary research report—07282008 (listed in PTO-892 attached to PTO Communication dated Aug. 5, 2008 in 11/660,905).

* cited by examiner

OXIME DERIVATIVE AND PREPARATIONS THEREOF

This application is a Divisional of application Ser. No. 11/660,905 filed on Feb. 23, 2007 now U.S. Pat. No. 7,514,439, and for which priority is claimed under 35 U.S.C. §120. Application Ser. No. 11/660,905 is a National Stage Entry of PCT International Application No. PCT/JP2006/314117, filed on Jul. 10, 2006, which designates the United States, and for which priority is claimed under 35 U.S.C. §120. This application also claims priority under 35 U.S.C. §119(a) on Patent Application No. 2005-202014 filed in Japan on Jul. 11, 2005 and Patent Application No. 2006-114243 filed in Japan on Apr. 18, 2006. The entire contents of each of the above documents are hereby incorporated by reference.

TECHNICAL FIELD

The present invention relates to a novel oxime derivative having an excellent glucokinase activation effect, which is useful as a medicine.

BACKGROUND ART

Glucokinase (GK) is one of four hexokinases found in mammalian animals. The hexokinases catalyze a conversion of glucose into glucose-6-phosphate which is the first step of glucose metabolism. GK is localized mainly in hepatic parenchymal cells and pancreatic β cells, and plays an important role in whole body glucose homeostasis as a rate-controlling enzyme for glucose metabolism in these cells. The hepatic and pancreatic forms of the enzyme are different in N-terminal 15 amino-acid sequence depending on the difference of each splicing, but are functionally indistinguishable.

Three hexokinases except GK are saturated in enzymatic activity at a glucose concentration below 1 mM, but Km of GK is 8 mM, which is within a physiological range of blood-glucose levels. Therefore, GK-mediated intracellular glucose metabolism is activated as the concentration of blood-glucose increases from normal level (5 mM) to postprandial level (10 to 15 mM).

A hypothesis that GK functions as a glucose sensor of pancreatic β cells and hepatocyte has been proposed (nonpatent document 1).

Thereafter, it has been clarified that GK actually plays a definitely important role in whole body glucose homeostasis according to the results of GK genetically-modified animal studies. GK KO mice die soon after birth (nonpatent document 2), while both normal and diabetic mice overexpressing GK showed lower glucose level than wild type animals (nonpatent document 3).

In maturity-onset diabetes of the young type II (MODY-2), which is one of the genetically determined diabetes, loss of function mutations in the GK has been found and it is thought that the low GK activity in MODY-2 results in hyperglycemia (nonpatent document 4). On the other hand, families having a GK mutation with increased enzymatic activity have been found and these people show hypoglycemia (nonpatent document 5). Accordingly, GK is believed to be a glucose sensor and to play an important role in maintenance of glucose homeostasis in human as well. It is expected that a GK activating compound has an insulinotropic action in β cells, an enhancing effect of glucose uptake in liver and inhibitory effect of hepatic output since such a compound activates a GK sensor system, and hence, it is believed that such a compound is useful for treating, for example, Type 2 diabetes.

Recently, it has been shown that a pancreatic β cell type glucokinase is distributed locally in feeding center (Ventromedial hypothalamus, VMH) in rat brain. About 20% of nerve cells in VMH are referred to as glucose responsive neurons and it has been thought from the past that they play important roles in controlling of body weights. An intracerebral administration of glucose in rat decreases food intake, but on the contrary, rat becomes overeating by an intracerebral administration of a glucose analog glucosamine, which cause the suppression of glucose metabolism. In electrophysiological experiments, glucose responsive neurons in VMH are stimulated when glucose increases from 5 to 20 mM, and the activity is blocked by glucosamine or the like (nonpatent document: Diabetes. 1999 September; 48(9): 1763-72). It is thought that a glucose sensor mechanism of VEIM is similar to that of pancreatic β cells. Therefore, a GK activating substance has a possibility of ameliorating obesity which is one of the major problems in Type 2 diabetes as well as correcting hyperglycemia.

Accordingly, a compound having a GK activation effect is useful as a treating and/or preventing agent of diabetes, or chronic complication of diabetes such as retinopathy, nephropathy, neuropathy, ischemic heart disease or arteriosclerosis, or even obesity.

A compound having a GK activation effect includes, for example, pyridinecarboxylic acid derivatives (patent document 1), 2-pyridine-carboxamide derivatives (patent document 2), heteroarylcarbamoyl-benzene derivatives (patent document 3), heteroaryl derivatives (patent document 4), substituted arylcyclopropylacetamide derivatives (patent document 5), 5-substituted pyrazine or pyridine derivatives (patent document 6), substituted (thiazol-2-yl)amide or sulfonamide derivatives (patent document 7), substituted phenylacetamide derivatives (patent document 8) or amide derivatives (patent document 9).

A method for preparing a 5-substituted 2-aminothiazole, which is an intermediate for the oxime derivative of the present invention, has been described in patent documents 10 and 11, wherein 5-fluoro-2-aminothiazole hydrochloride is prepared by treating 5-bromo-2-trifluoroacetyl aminothiazole derived from 5-bromo-2-aminothiazole hydrochloride with n-butyllithium, followed by treating the resultant with N-fluorobenzenesulfonylimide (patent document 10, Preparation 61; patent document 11, Preparation 21). It is also described in patent document 12 that 5-formyl-2-aminothiazole hydrobromide is prepared by a reaction of bromomalonaldehyde with thiourea. However, the methods disclosed in patent document 10 and patent document 11 give the product in low yield and are not advantageous as an industrial method. Additionally, the method disclosed in patent document 12 gives 2-aminothiazole as a by-product which is difficult to remove, and hence it is difficult to obtain the desired compound in a high purity. Besides, said method can not be applied to preparations of wide range of 5-substituted 2-fluoro aminothiazoles other than 5-formyl-2-aminothiazole.

Compounds having an oxime structure therein have been described in patent documents 13 to 16 and nonpatent documents 6 to 8.

[patent document 1] WO05/044801
[patent document 2] WO04/081001
[patent document 3] WO04/076420
[patent document 4] WO04/063194
[patent document 5] WO04/063179
[patent document 6] WO04/052869
[patent document 7] WO04/050645
[patent document 8] WO03/095438

[patent document 9] WO03/055482
[patent document 10] WO04/072031
[patent document 11] WO04/072066
[patent document 12] U.S. Pat. No. 4,225,719
[patent document 13] WO05/023761
[patent document 14] WO01/012189
[patent document 15] WO00/026202
[patent document 16] WO96/023763
[nonpatent document 1] American Journal Physiology, volume 247 (3Pt2) 1984, p 527-536
[nonpatent document 2] Cell, volume 83, 1995, p 69-78
[nonpatent document 3] Proceedings of the National Academy of Sciences of the U.S.A., volume 93, 1996, p 7225-7230
[nonpatent document 4] Nature Genetics, volume 356, 1992, p 721-722
[nonpatent document 5] New England Journal of Medicine, volume 338, 1998, p 226-230
[nonpatent document 6] Bulletin des Societes Chimiques Belges (1994), 103(5-6), 213-18
[nonpatent document 7] Bulletin of the Chemical Society of Japan (1993), 66(8), 2335-8
[nonpatent document 8] Pharmazie (1988), 43(8), 535-6

DISCLOSURE OF INVENTION

The present invention provides a novel glucokinase activator, which is for the prophylaxis and/or treatment of diseases involving glucokinase, such as diabetes, complication associated with diabetes, or obesity.

The present invention also provides a novel compound having an excellent glucokinase activation effect which is useful as an active ingredient of a medicine.

According to extensive studies for problems to be solved by the present inventions, it has been found that an oxime derivative of the following formula has an excellent glucokinase activation effect, and the present invention has been completed.

The present invention includes the following embodiments.

(1) An oxime derivative of the general formula [I]:

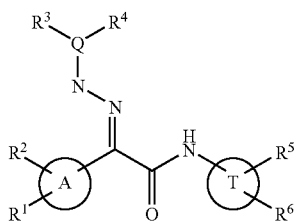

wherein Ring A is aryl or heteroaryl;
Q is cycloalkyl, heterocycle, alkyl or alkenyl;
Ring T is heteroaryl or heterocycle;
$R^1$ is hydrogen atom, halogen atom, cycloalkylsulfonyl, alkylsulfonyl, alkylsulfinyl, alkylthio, or substituted or unsubstituted tetrazolyl;
$R^2$ is hydrogen atom, halogen atom, cycloalkylsulfonyl, substituted or unsubstituted alkylsulfonyl, substituted or unsubstituted alkylthio, nitro, substituted or unsubstituted amino, substituted or unsubstituted aminosulfonyl, substituted or unsubstituted heterocyclyl-thio, substituted or unsubstituted heterocyclyl-sulfinyl, substituted or unsubstituted heterocyclyl-sulfonyl, substituted or unsubstituted heteroarylsulfonyl, alkenyloxy, substituted or unsubstituted alkoxy, substituted or unsubstituted alkylsulfinyl, substituted or unsubstituted heteroaryl, or substituted or unsubstituted heteroarylthio;
$R^3$ and $R^4$ are independently hydrogen atom, alkoxy, substituted or unsubstituted heterocycle, substituted or unsubstituted heteroaryl, alkoxyalkoxy, substituted or unsubstituted cycloalkyl, cyano, substituted or unsubstituted aryl, substituted or unsubstituted carbamoyl, hydroxy, alkanoyl, alkylthio, alkoxycarbonyl, substituted or unsubstituted aryloxy, halogen atom, oxo, or substituted or unsubstituted arylcarbonyloxy;
$R^5$ is hydrogen atom, formyl, halogen atom, oxo, substituted or unsubstituted alkoxy, substituted or unsubstituted aminosulfonyl, substituted or unsubstituted alkylthio, cyano, substituted or unsubstituted heterocyclyl-sulfonyl, nitro, substituted or unsubstituted cycloalkyl, alkoxycarbonyl, alkenyl, alkylsulfonyl, substituted or unsubstituted carbamoyl, substituted or unsubstituted heteroarylthio, substituted or unsubstituted amino, carboxyl, substituted or unsubstituted heteroaryl, substituted or unsubstituted alkynyl, substituted or unsubstituted heterocyclyl-carbonyl, substituted or unsubstituted heterocyclyl-oxy, substituted or unsubstituted heterocycle, substituted or unsubstituted heterocyclyl-thio, substituted or unsubstituted cycloalkyloxy, alkanoyl, or substituted or unsubstituted alkyl;
$R^6$ is hydrogen atom, substituted or unsubstituted alkyl, halogen atom, or carboxyl;
or a pharmaceutically acceptable salt thereof.

(2) The oxime derivative of (1) wherein Ring A is aryl or heteroaryl, provided that Ring A is not thiazolyl or thiadiazolyl, or a pharmaceutically acceptable salt thereof.

(3) The oxime derivative of (1) wherein Ring A is aryl, or a pharmaceutically acceptable salt thereof.

(4) The oxime derivative of (1) wherein Ring A is phenyl or pyridyl, or a pharmaceutically acceptable salt thereof.

(5) The oxime derivative of any one of (1) to (4) wherein Q is cycloalkyl, heterocycle or alkyl, or a pharmaceutically acceptable salt thereof.

(6) The oxime derivative of any one of (1) to (4) wherein Q is cycloalkyl or heterocycle, or a pharmaceutically acceptable salt thereof.

(7) The oxime derivative of any one of (1) to (4) wherein Q is heterocycle, or a pharmaceutically acceptable salt thereof.

(8) The oxime derivative of any one of (1) to (4) wherein Q is tetrahydrofuryl group, or a pharmaceutically acceptable salt thereof.

(9) The oxime derivative of any one of (1) to (8) wherein Ring T is heteroaryl or heterocycle of

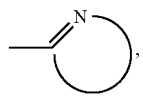, or a pharmaceutically acceptable salt thereof.

(10) The oxime derivative of any one of (1) to (8) wherein Ring T is heteroaryl of

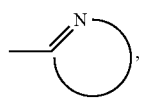, or a pharmaceutically acceptable salt thereof

(11) The oxime derivative of any one of (1) to (8) wherein Ring T is thiazolyl, thiazolopyridinyl, pyridyl, pyrazinyl, benzothiazolyl, quinolyl, thiadiazolyl, pyrazolyl, thiazolopyrazinyl, thiazolopyrimidinyl, cyclohexanothiazolyl or dihydrothiazolopyridinyl, or a pharmaceutically acceptable salt thereof.

(12) The oxime derivative of any one of (1) to (8) wherein Ring T is thiazolyl, thiazolopyridinyl, pyridyl, pyrazinyl, benzothiazolyl, thiadiazolyl, thiazolopyrazinyl, thiazolopyrimidinyl, cyclohexanothiazolyl or dihydrothiazolopyridinyl, or a pharmaceutically acceptable salt thereof.

(13) The oxime derivative of any one of (1) to (8) wherein Ring T is thiazolyl, thiazolopyridinyl, pyrazinyl, thiadiazolyl, thiazolopyrazinyl or thiazolopyrimidinyl, or a pharmaceutically acceptable salt thereof.

(14) The oxime derivative of any one of (1) to (8) wherein Ring T is thiazolyl or thiazolopyridinyl, or a pharmaceutically acceptable salt thereof.

(15) The oxime derivative of any one of (1) to (14) wherein $R^1$ is hydrogen atom or halogen atom, or a pharmaceutically acceptable salt thereof.

(16) The oxime derivative of any one of (1) to (14) wherein $R^1$ is hydrogen atom, or a pharmaceutically acceptable salt thereof.

(17) The oxime derivative of any one of (1) to (16) wherein $R^2$ is cycloalkylsulfonyl, substituted or unsubstituted alkylsulfonyl, substituted or unsubstituted alkylthio, nitro, substituted or unsubstituted amino, substituted or unsubstituted aminosulfonyl, substituted or unsubstituted heterocyclyl-thio, substituted or unsubstituted heterocyclyl-sulfonyl, substituted or unsubstituted alkylsulfinyl, substituted or unsubstituted heteroarylsulfonyl, substituted or unsubstituted heteroarylthio, or substituted or unsubstituted heteroaryl, or a pharmaceutically acceptable salt thereof.

(18) The oxime derivative of any one of (1) to (16) wherein $R^2$ is cycloalkylsulfonyl, substituted or unsubstituted alkylsulfonyl, substituted or unsubstituted aminosulfonyl, or substituted or unsubstituted heterocyclyl-sulfonyl, or a pharmaceutically acceptable salt thereof.

(19) The oxime derivative of any one of (1) to (16) wherein $R^2$ is cycloalkylsulfonyl, substituted or unsubstituted alkylsulfonyl, or substituted or unsubstituted aminosulfonyl, or a pharmaceutically acceptable salt thereof.

(20) The oxime derivative of any one of (1) to (16) wherein $R^2$ is cycloalkylsulfonyl, substituted or unsubstituted aminosulfonyl, substituted or unsubstituted heterocyclyl-sulfonyl, or substituted or unsubstituted heteroarylsulfonyl, or a pharmaceutically acceptable salt thereof.

(21) The oxime derivative of any one of (1) to (16) wherein $R^2$ is cycloalkylsulfonyl, or a pharmaceutically acceptable salt thereof.

(22) The oxime derivative of any one of (1) to (20) wherein the substituent of the "substituted aminosulfonyl" in $R^2$ is substituted or unsubstituted alkyl, cycloalkyl, substituted or unsubstituted heterocycle, or alkoxy, or a pharmaceutically acceptable salt thereof.

(23) The oxime derivative of any one of (1) to (19) wherein the substituent of the "substituted alkylsulfonyl" in $R^2$ is alkoxy, or a pharmaceutically acceptable salt thereof.

(24) The oxime derivative of any one of (1) to (23) wherein $R^3$ and $R^4$ are independently hydrogen atom, alkoxy, substituted or unsubstituted heterocycle, substituted or unsubstituted heteroaryl, substituted or unsubstituted cycloalkyl, substituted or unsubstituted aryl, substituted or unsubstituted carbamoyl, hydroxy, alkanoyl, alkylthio, substituted or unsubstituted aryloxy, halogen atom, oxo, or substituted or unsubstituted arylcarbonyloxy, or a pharmaceutically acceptable salt thereof.

(25) The oxime derivative of any one of (1) to (23) wherein $R^3$ and $R^4$ are independently hydrogen atom, alkoxy, substituted or unsubstituted heteroaryl, substituted or unsubstituted cycloalkyl, or hydroxy, or a pharmaceutically acceptable salt thereof.

(26) The oxime derivative of any one of (1) to (4) and (9) to (23) wherein the group of $-Q(R^3)(R^4)$ is cycloalkyl substituted with one or two groups selected from alkoxy and hydroxy, heterocycle, or alkyl substituted with 1 to 2 groups selected from hydroxy and substituted or unsubstituted heteroaryl, or a pharmaceutically acceptable salt thereof.

(27) The oxime derivative of any one of (1) to (26) wherein when Q is cycloalkyl, alkyl or alkenyl, then $R^3$ and $R^4$ are not any combination of two groups independently selected from hydrogen, alkoxy, cyano, substituted or unsubstituted aryl, hydroxy, alkylthio, alkoxycarbonyl, or halogen atom, or a pharmaceutically acceptable salt thereof.

(28) The oxime derivative of any one of (1) to (4) and (9) to (23) wherein Q is heterocycle and both of $R^3$ and $R^4$ are hydrogen atom, or a pharmaceutically acceptable salt thereof.

(29) The oxime derivative of any one of (1) to (28) wherein $R^5$ is hydrogen atom, formyl, halogen atom, oxo, substituted or unsubstituted alkoxy, substituted or unsubstituted aminosulfonyl, substituted or unsubstituted alkylthio, cyano, substituted or unsubstituted heterocyclyl-sulfonyl, nitro, substituted or unsubstituted cycloalkyl, alkoxycarbonyl, alkenyl, alkanoyl, substituted or unsubstituted carbamoyl, substituted or unsubstituted heteroarylthio, substituted or unsubstituted amino, substituted or unsubstituted heteroaryl, substituted or unsubstituted alkynyl, substituted or unsubstituted heterocyclyl-oxy, or substituted or unsubstituted alkyl, or a pharmaceutically acceptable salt thereof.

(30) The oxime derivative of any one of (1) to (28) wherein $R^5$ is hydrogen atom, halogen atom, substituted or unsubstituted alkoxy, substituted or unsubstituted alkylthio, cyano, substituted or unsubstituted cycloalkyl, alkanoyl, substituted or unsubstituted carbamoyl, substituted or unsubstituted amino, substituted or unsubstituted heterocyclyl-oxy, or substituted or unsubstituted alkyl, or a pharmaceutically acceptable salt thereof.

(31) The oxime derivative of any one of (1) to (28) wherein $R^5$ is halogen atom, substituted or unsubstituted alkoxy, substituted or unsubstituted alkylthio, substituted or unsubstituted amino, substituted or unsubstituted heterocyclyl-oxy, or substituted or unsubstituted alkyl, or a pharmaceutically acceptable salt thereof.

(32) The oxime derivative of any one of (1) to (28) wherein $R^5$ is substituted or unsubstituted alkoxy, substituted or unsubstituted amino, substituted or unsubstituted heterocyclyl-oxy, or substituted or unsubstituted alkyl, or a pharmaceutically acceptable salt thereof.

(33) The oxime derivative of any one of (1) to (32) wherein the substituent of the "substituted alkyl" in $R^5$ is substituted or unsubstituted heterocycle, substituted or unsubstituted amino, substituted or unsubstituted alkoxy, substituted or unsubstituted carbamoyl, hydroxy, trialkylsilyloxy, alkylthio, alkylsulfonyl, substituted or unsubstituted heterocyclyl-oxy, heteroaryl, substituted or unsubstituted hydroxyimino, halogen atom, carboxyl, alkoxycarbonyl, or alkanoyloxy, or a pharmaceutically acceptable salt thereof.

(34) The oxime derivative of any one of (1) to (33) wherein $R^6$ is hydrogen atom, or substituted or unsubstituted alkyl, or a pharmaceutically acceptable salt thereof.

(35) The oxime derivative of any one of (1) to (33) wherein $R^6$ is hydrogen atom, or a pharmaceutically acceptable salt thereof.

(36) A pharmaceutical composition comprising a compound of any one of (1) to (35) or a pharmaceutically acceptable salt thereof as an active ingredient.

(37) A method for preventing or treating diabetes, or complication associated with diabetes including retinopathy, nephropathy, neuropathy, ischemic heart disease or arteriosclerosis, or obesity, which comprises administering an effective dose of a compound of any one of (1) to (35) or a pharmaceutically acceptable salt thereof.

(38) Use of a compound of any one of (1) to (35) or a pharmaceutically acceptable salt thereof in the manufacture of a medicament for treating or preventing diabetes, or complication associated with diabetes including retinopathy, nephropathy, neuropathy, ischemic heart disease or arteriosclerosis, or obesity.

The substituents on the group of each symbol in the compound [I] mean as defined below.

In $R^1$-$R^6$ of the compound [I], substituents in "substituted amino", "substituted aminosulfonyl", "substituted aminoalkyl", "substituted aminoalkanoyl", "substituted carbamoyl", "substituted carbamoylalkyl", "substituted alkyl", "substituted alkylthio", "substituted alkylsulfinyl", "substituted alkylsulfonyl", "substituted alkoxy", "substituted alkanoyl", "substituted alkynyl", "substituted cycloalkyl", "substituted cycloalkyloxy", "substituted cycloalkylcarbonyl", "substituted cycloalkylsulfonyl", "substituted aryl", "substituted aryloxy", "substituted arylcarbonyl", "substituted arylcarbonyloxy", "substituted arylsulfonyl", "substituted arylalkylcarbonyl", "substituted heteroaryl", "substituted heteroarylthio", "substituted heteroarylsulfonyl", "substituted heteroarylalkyl", "substituted heterocycle", "substituted heterocyclyl-oxy", "substituted heterocyclyl-carbonyl", "substituted heterocyclyl-thio", "substituted heterocyclyl-sulfinyl", "substituted heterocyclyl-sulfonyl", "substituted hydroxyimino", and "substituted phenyl", "substituted pyridyl", "substituted thiazolopyridinyl", "substituted pyrazinyl", "substituted pyrazolyl", "substituted imidazolyl", "substituted thiazolyl", "substituted benzothiazolyl", "substituted quinolyl", "substituted thiadiazolyl", "substituted pyrazolyl", "substituted thiazolopyrazinyl", "substituted thiazolopyrimidinyl", "substituted cyclohexanothiazolyl", "substituted dihydrothiazolopyridinyl", "substituted triazolyl", "substituted pyrimidinyl", "substituted pyrrolidinyl", "substituted tetrahydrofuryl", "substituted thiacyclohexyl", "substituted cyclopentyrl", "substituted piperazinyl", "substituted piperazinylsulfonyl", "substituted homopiperazinyl", "substituted piperidinyl", "substituted morpholinyl", "substituted thiomorpholinyl", "substituted perhydrodiazepinyl", and "substituted tetrazolyl" include those specifically indicated in EXAMPLES. Such substituents include (1) alkyl being optionally substituted with hydroxy, alkoxy, amino, mono- or di-alkylamino, carbamoyl, tetrahydrofuryl or pyridyl, (2) cycloalkyl, (3) hydroxy, (4) alkoxy, (5) cyano, (6) halogen atom, (7) mono- or di-alkylamino, (8) amino being optionally substituted with alkanoyl, alkoxyalkanoyl or alkoxycarbonyl, (9) pyridyl, (10) carboxyl, (11) formyl, (12) alkanoyl being optionally substituted with mono- or di-alkylamino, hydroxy, alkoxy or alkanoyloxy, (13) cycloalkylcarbonyl, (14) alkoxycarbonyl, (15) oxo, (16) alkylsulfonyl, or the like. The $R^1$-$R^6$ groups may have the same or different 1 to 3 substituents selected from the above groups.

Additionally, each substituent is explained depending on each symbol (A, Q, T, $R^1$-$R^6$) of the compound [I]. The groups of those symbols may have the same or different 1 to 3 substitutents selected from the groups as defined below.

A preferable substituent of substituted tetrazolyl in $R^1$ includes alkyl.

A preferable substituent of substituted alkylsulfonyl in $R^2$ includes alkoxycarbonyl, alkoxy, cycloalkyl (preferably, cyclopropyl), hydroxy, substituted or unsubstituted amino (substituent(s): 1 or 2 groups selected from alkyl, alkanoyl), substituted or unsubstituted heteroaryl (preferably, imidazolyl, triazolyl) (substituent(s): alkyl), alkylsulfonyl, cyano, substituted or unsubstituted heterocycle (preferably, tetrahydrofuryl, tetrahydropyranyl, dihydro-3H-isoindolyl) (substituent(s): oxo, dioxo). More preferable one among them is alkoxy, cycloalkyl (preferably, cyclopropyl), hydroxy, particularly preferable one is alkoxy.

A preferable substituent of substituted alkylthio in $R^2$ includes alkoxy, cycloalkyl, alkoxycarbonyl, hydroxy, cyano, alkylthio, substituted or unsubstituted heterocycle (preferably, tetrahydrofuryl, tetrahydropyranyl, dihydro-3H-isoindolyl) (substituent(s): oxo, dioxo), heteroaryl (preferably, pyridyl). More preferable one among them is alkoxy, cycloalkyl, alkoxycarbonyl, hydroxy, cyano; alkylthio, heteroaryl (preferably, pyridyl).

A preferable substituent of substituted amino in $R^2$ includes heteroarylcarbonyl (preferably, pyridylcarbonyl), heteroarylalkanoyl (thienylalkanoyl), cycloalkylcarbonyl, cycloalkylsulfonyl, alkoxycarbonylcarbonyl, heteroarylsulfonyl, alkylsulfonyl. More preferable one among them is alkoxycarbonylcarbonyl, alkylsulfonyl.

A preferable substituent of the substituted alkyl which is the substituent of substituted aminosulfonyl in $R^2$ includes amino being optionally substituted with mono- or di-alkyl; carbamoyl being optionally substituted with mono- or di-alkyl; hydroxy; alkoxy; heteroaryl being optionally substituted with alkyl; cycloalkyl; alkoxycarbonyl; hydroxyalkoxy; heterocycle being optionally substituted with alkyl; halogen; alkylthio. More preferabale one among them is amino being optionally substituted with mono- or di-alkyl; carbamoyl being optionally substituted with mono- or di-alkyl; hydroxy; alkoxy; cycloalkyl; alkoxycarbonyl; heterocycle being optionally substituted with alkyl; halogen atom; particularly hydroxy, alkoxy.

A preferable substituent of the substituted heterocycle which is a substituent of substituted aminosulfonyl in $R^2$ includes alkyl.

A preferable substituent of substituted heterocyclyl-thio in $R^2$ includes hydroxy; alkyl; oxo; alkanoyl; hydroxyalkyl; carbamoyl being optionally substituted with mono- or di-alkyl; heteroaryl; aminosulfonyl being optionally substituted with mono or di-alkyl; amino being optionally substituted with mono- or di-alkyl; alkylsulfonyl; alkoxy; alkoxyalkyl. More preferable one among them is hydroxy; alkyl; carbamoyl being optionally substituted with mono- or di-alkyl; oxo; alkoxy; alkoxyalkyl; particularly alkyl.

A preferable substituent of substituted heterocyclyl-sulfinyl in $R^2$ includes hydroxy; alkyl; oxo; alkanoyl; hydroxyalkyl; carbamoyl being optionally substituted with mono- or di-alkyl; heteroaryl; aminosulfonyl being optionally substituted with mono- or di-alkyl; amino being optionally substituted with mono- or di-alkyl; alkylsulfonyl; alkoxy; alkoxyalkyl. More preferable one among them is hydroxy; alkyl; carbamoyl being optionally substituted with mono- or di-alkyl; oxo; alkoxy; alkoxyalkyl; particularly alkyl.

A preferable substituent of substituted heterocyclyl-sulfonyl in $R^2$ includes hydroxy; alkyl; oxo; alkanoyl; hydroxyalkyl; carbamoyl being optionally substituted with mono- or di-alkyl; heteroaryl; aminosulfonyl being optionally substituted with mono- or di-alkyl; amino being optionally substituted with mono- or di-alkyl; alkylsulfonyl; alkoxy; alkoxyalkyl. More preferable one among them is hydroxy; alkyl; carbamoyl being optionally substituted with mono- or di-alkyl; oxo; alkoxy; alkoxyalkyl.

A preferable substituent of substituted heteroarylsulfonyl in $R^2$ includes alkyl.

A preferable substituent of substituted alkoxy in $R^2$ includes cycloalkyl.

A preferable substituent of substituted alkylsulfinyl in $R^2$ includes alkoxycarbonyl, alkoxy, alkoxyalkyl, cycloalkyl (preferably, cyclopropyl), hydroxy, substituted or unsubstituted amino (substituent(s): 1 or 2 groups selected from alkyl, alkanoyl), substituted or unsubstituted heteroaryl (preferably, imidazolyl, triazolyl) (substituent(s): alkyl), alkylsulfonyl, cyano, substituted or unsubstituted heterocycle (preferably, tetrahydrofuryl, tetrahydropyranyl, dihydro-3H-isoindolyl) (substituent(s): oxo, dioxo). More preferable one among them is alkoxy, cycloalkyl (preferably, cyclopropyl), hydroxy, particularly hydroxy.

A preferable substituent of substituted heteroaryl in $R^2$ includes alkyl.

A preferable substituent of substituted heterocycle in $R^3$ and $R^4$ includes alkoxycarbonyl, oxo, alkyl, alkanoyl.

A preferable substituent of substituted heteroaryl in $R^3$ and $R^4$ includes alkyl; amino being optionally substituted with mono- or di-alkyl. More preferable one among them is alkyl.

A preferable substituent of substituted cycloalkyl in $R^3$ and $R^4$ includes benzoyloxy, oxo, hydroxy, alkanoyl. More preferable one among them is oxo, hydroxy.

A preferable substiutent of substituted aryl in $R^3$ and $R^4$ includes alkyl, cyano, halogen atom, alkoxy.

A preferable substituent of substituted carbamoyl in $R^3$ and $R^4$ includes alkyl.

A preferable substituent of substituted aryloxy in $R^3$ and $R^4$ includes alkyl, cyano, halogen atom, alkoxy.

A preferable substituent of substituted arylcarbonyloxy in $R^3$ and $R^4$ includes alkyl, cyano, halogen atom, alkoxy.

A preferable substituent of substituted alkoxy in $R^5$ includes substituted or unsubstituted amino (substituent(s): 1 or 2 groups selected from alkyl, alkoxycarbonyl); alkoxycarbonyl; carbamoyl being optionally substituted with mono- or di-alkyl; carboxyl; hydroxy; substituted or unsubstituted heterocycle (substituent(s): oxo); trialkylsilyloxy; alkoxy. More preferable one is amino being optionally substituted with mono- or di-alkyl; carbamoyl being optionally substituted with mono- or di-alkyl; hydroxy; particularly amino being optionally substituted with mono- or di-alkyl; hydroxy.

A preferable substituent of substituted aminosulfonyl in $R^5$ includes alkyl. Therefore, said substituent is mono-alkyl or di-alkyl, preferably di-alkyl.

A preferable substituent of substituted alkylthio in $R^5$ includes amino being optionally substituted with mono- or di-alkyl; alkoxycarbonylamino; halogen atom; hydroxy; carboxyl; carbamoyl being optionally substituted with mono- or di-alkyl; alkoxycarbonyl. More preferable one among them is amino being optionally substituted with mono- or di-alkyl; alkoxycarbonylamino; hydroxy; carbamoyl being optionally substituted with mono- or di-alkyl; particularly dialkylcarbamoyl.

A preferable substituent of substituted heterocyclyl-sulfonyl in $R^5$ includes alkyl.

A preferable substituent of substituted cycloalkyl in $R^5$ includes amino being optionally substituted with mono- or di-alkyl.

A preferable substituent of substituted cycloalkyloxy in $R^5$ includes amino being optionally substituted with mono- or di-alkyl.

A preferable substituent of substituted carbamoyl in $R^5$ includes substituted or unsubstituted alkyl (substituent(s): 1 or 2 groups selected from hydroxy; cycloalkyl; heterocycle; amino being optionally substituted with mono- or di-alkyl; heteroaryl), cycloalkyl, heteroaryl. More preferable one among them is substituted or unsubstituted alkyl (substituent(s): 1 or 2 groups selected from hydroxy, heterocycle, dialkylamino, heteroaryl), cycloalkyl.

A preferable substituent of substituted heteroarylthio in $R^5$ includes alkyl.

A preferable substituent of substituted amino in $R^5$ includes alkyl, substituted or unsubstituted aminoalkyl (substituent(s): 1 or 2 groups selected from alkyl, alkanoyl), alkanoyl, hydroxyalkyl, alkoxycarbonyl. More preferable one among them is alkyl, and hence, mono-alkyl or di-alkyl, particularly di-alkyl.

A preferable substituent of substituted heteroaryl in $R^5$ includes alkyl.

A preferable substituent of substituted alkynyl in $R^5$ includes hydroxy, amino being optionally substituted with mono- or di-alkyl. More preferable one among them is hydroxy, dialkylamino.

A preferable substituent of substituted heterocyclyl-carbonyl in $R^5$ includes hydroxy, alkyl, oxo, hydroxyalkyl, alkanoyl. More preferable one among them is hydroxy, alkyl, hydroxyalkyl.

A preferable substituent of substituted heterocyclyl-oxy in $R^5$ includes hydroxy, alkyl, oxo, hydroxyalkyl, alkanoyl. More preferable one among them is alkyl, oxo.

A preferable substituent of substituted heterocycle in $R^5$ includes hydroxy, alkyl, oxo, hydroxyalkyl, alkanoyl. More preferable one among them is oxo.

A preferable substituent of substituted heterocyclyl-thio in $R^5$ includes hydroxy, alkyl, oxo, hydroxyalkyl, alkanoyl. More preferable one is alkyl, alkanoyl.

A preferable substituent of substituted alkyl in $R^5$ includes substituted or unsubstituted heterocycle, substituted or unsubstituted amino, substituted or unsubstituted alkoxy, substituted or unsubstituted carbamoyl, hydroxy, trialkylsilyloxy, substituted or unsubstituted alkylthio, substituted or unsubstituted heterocyclyl-oxy, heteroaryl, substituted or unsubstituted hydroxyimino, halogen atom, more preferably substituted or unsubstituted heterocycle, substituted or unsubstituted amino, substituted or unsubstituted alkoxy, hydroxy, substituted or unsubstituted alkylthio, substituted or unsubstituted heterocyclyl-oxy, substituted or unsubstituted hydroxyimino, halogen atom, further preferably substituted or unsubstituted heterocycle, substituted or unsubstituted alkoxy, substituted or unsubstituted heterocyclyl-oxy, particularly substituted or unsubstituted heterocycle, substituted or unsubstituted alkoxy, further particularly substituted or unsubstituted heterocycle.

A preferable substituent of substituted heterocycle which is the substituent of substituted alkyl in $R^5$ includes alkyl; oxo; alkoxyalkanoyl; alkanoyl; alkoxy; alkanoylamino; cycloalkyl-carbonylamino; tri(halogeno)alkanoylamino; formylamino; alkoxycarbonylamino; hydroxy; cycloalkyl-carbonyl; tri(halogeno)alkyl; alkoxycarbonyl; formyl; amino being optionally substituted with mono- or di-alkyl; aminosulfonyl being optionally substituted with mono- or di-alkyl; alkylsulfonyl; heteroaryl; alkoxycarbonylalkyl; alkanoyloxyalkanoyl; alkoxycarbonylcarbonyl; aminoalkanoyl being optionally substituted with mono- or di-alkyl; substituted or unsubstituted carbamoyl (substituent(s): 1 or 2 groups selected from alkyl, alkoxy); hydroxyalkanoyl; di(halogeno)alkanoyl; substituted or unsubstituted heterocyclyl-carbonyl (substituent(s): oxo); substituted or unsubstituted hydroxyimino (substituent(s): alkoxycarbonyl); carboxyl; hydroxyalkoxy; alkoxyalkoxy; halogen atom; alkanoyloxy. More preferable one among them is alkyl; oxo; alkoxyalkanoyl; alkanoyl; alkoxy; alkanoylamino; cycloalkylcarbonylamino; tri(halogeno)alkanoylamino; formylamino; alkoxycarbonylamino; cycloalkylcarbonyl; tri(halogeno)alkyl; alkoxycarbonyl; formyl; amino being optionally substituted with mono- or di-alkyl; aminosulfonyl being optionally substituted with mono- or di-alkyl; alkylsulfonyl; heteroaryl; alkoxycarbonylalkyl; alkanoyloxyalkanoyl; alkoxycarbonylcarbonyl; aminoalkanoyl being optionally substituted with mono- or di-alkyl; carbamoyl being optionally substituted with mono- or di-alkyl; hydroxyalkanoyl; di(halogeno)alkanoyl; substituted or unsubstituted heterocyclyl-carbonyl (substituent(s): oxo); substituted or unsubstituted hydroxyimino (substituent(s): alkoxycarbonyl); more preferably alkyl; oxo; alkoxyalkanoyl; alkanoyl; formyl; amino being optionally substituted with mono- or di-alkyl; alkylsulfonyl; alkanoyloxyalkanoyl; aminoalkanoyl being optionally substituted with mono- or di-alkyl; hydroxyalkanoyl; more preferably alkyl, alkanoyl, formyl, hydroxyalkanoyl, particularly alkyl, alkanoyl.

A preferable substituent of the substituted amino which is the substituent of substituted alkyl in $R^5$ includes alkyl; carbamoylalkyl being optionally substituted with mono- or di-alkyl; substituted or unsubstituted aminoalkyl (substituent(s): 1 or 2 groups selected from alkyl, alkanoyl); alkoxyalkyl; hydroxyalkyl; alkoxyalkanoyl; heteroaryl; heteroarylalkyl. More preferable one among them is alkyl; carbamoylalkyl being optionally substituted with mono- or di-alkyl; aminoalkyl being optionally substituted with mono- or di-alkyl; alkoxyalkyl; heteroaryl; particularly alkyl.

A preferable substituent of the substituted alkoxy which is the substituent of substituted alkyl in $R^5$ includes hydroxy, alkoxy.

A preferable substituent of the substituted carbamoyl which is the substituent of substituted alkyl in $R^5$ includes alkyl, alkoxy.

A preferable substituent of the substituted heterocyclyloxy which is the substituent of substituted alkyl in $R^5$ includes alkanoyl, alkyl, formyl, cycloalkylcarbonyl, alkoxyalkanoyl, alkylsulfonyl. More preferable one among them is alkanoyl, alkyl, particularly alkanoyl.

A preferable substituent of the substituted hydroxyimino which is the substituent of substituted alkyl in $R^5$ includes alkoxycarbonyl.

Among the compounds [I] of the present invention, an example of prefererable compounds are those in which $R^5$ is substituted or unsubstituted alkyl.

Among the compounds [I], other preferable compounds are those of formula [1-A] as shown below, and the present invention includes also the following embodiments:
(1) An oxime derivative of the general formula [I-A]:

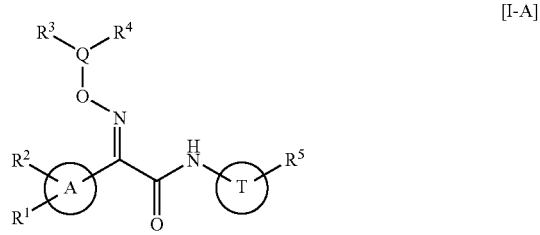

wherein Ring A is aryl or heteroaryl;
Q is cycloalkyl, heterocycle, alkyl or alkenyl;
Ring T is heteroaryl or heterocycle;
$R^1$ and $R^2$ are independently hydrogen atom, halogen atom, cycloalkylsulfonyl, alkylsulfonyl, alkylsulfinyl, alkylthio, or substituted or unsubstituted tetrazolyl;

$R^3$ and $R^4$ are independently hydrogen atom, hydroxy, oxo, halogen atom, cyano, alkylthio, alkoxy, alkanoyl, alkoxyalkoxy, alkoxycarbonyl, substituted or unsubstituted carbamoyl, substituted or unsubstituted aryl, substituted or unsubstituted heteroaryl, substituted or unsubstituted heterocycle, substituted or unsubstituted cycloalkyl, or substituted or unsubstituted aryloxy;

$R^5$ is hydrogen atom, halogen atom, cyano, nitro, tetrazolyl, oxo, cycloalkyl, alkenyl, alkylthio, alkylsulfonyl, alkoxy, formyl, alkanoyl, alkoxycarbonyl, substituted or unsubstituted carbamoyl, substituted or unsubstituted aminosulfonyl, substituted or unsubstituted heterocyclyl-carbonyl, substituted or unsubstituted heterocyclylsulfonyl, or substituted or unsubstituted alkyl;

or a pharmaceutically acceptable salt thereof.
(2) The oxime derivative of (1) wherein Ring A is phenyl or pyridyl, or a pharmaceutically acceptable salt thereof.
(3) The oxime derivative of (1) wherein Ring A is phenyl, or a pharmaceutically acceptable salt thereof.
(4) The oxime derivative of any one of (1) to (3) wherein Q is cycloalkyl, tetrahydrofuryl, alkyl or alkenyl, or a pharmaceutically acceptable salt thereof.
(5) The oxime derivative of any one of (1) to (3) wherein Q is tetrahydrofuryl, or a pharmaceutically acceptable salt thereof.
(6) The oxime derivative of any one of (1) to (3) wherein Q is (3R)-3-tetrahydrofuryl, or a pharmaceutically acceptable salt thereof.
(7) The oxime derivative of any one of (1) to (6) wherein Ring T is thiazolyl, pyrazinyl, thiadiazolyl, thiazolopyridinyl, benzothiazolyl, cyclohexanothiazolyl or dihydrothiazolopyridinyl, or a pharmaceutically acceptable salt thereof.
(8) The oxime derivative of any one of (1) to (6) wherein Ring T is thiazolyl, or a pharmaceutically acceptable salt thereof.
(9) The oxime derivative of any one of (1) to (6) wherein Ring T is 2-thiazolyl, or a pharmaceutically acceptable salt thereof.
(10) The oxime derivative of any one of (1) to (9) wherein one of $R^1$ and $R^2$ is hydrogen atom and the other is cycloalkylsulfonyl, alkylsulfonyl, alkylsulfinyl, alkylthio, or substituted or unsubstituted tetrazolyl, or a pharmaceutically acceptable salt thereof.
(11) The oxime derivative of any one of (1) to (9) wherein one of $R^1$ and $R^2$ is hydrogen atom and the other is cycloalkylsulfonyl, or a pharmaceutically acceptable salt thereof.
(12) The oxime derivative of (11) wherein Ring A is phenyl and the cycloalkylsulfonyl is substituted to the 4-position of the phenyl, or a pharmaceutically acceptable salt thereof.
(13) The oxime derivative of any one of (1) to (12) wherein $R^3$ and $R^4$ are independently hydrogen atom, hydroxy, alkoxy, substituted or unsubstituted aryl, substituted or unsubstituted heteroaryl, substituted or unsubstituted heterocycle, or substituted or unsubstituted cycloalkyl, or a pharmaceutically acceptable salt thereof.
(14) The oxime derivative of any one of (1) to (12) wherein $R^3$ and $R^4$ are independently hydrogen atom, hydroxy, alkoxy, substituted or unsubstituted phenyl, substituted or unsubstituted pyrazolyl, substituted or unsubstituted imidazolyl, substituted or unsubstituted thiazolyl, substituted or unsubstituted triazolyl, substituted or unsubstituted pyridyl, substituted or unsubstituted pyrimidinyl, substituted or unsubstituted pyrrolidinyl, substituted or unsubstituted thiacyclohexyl, or substituted or unsubstituted cyclopentyl, or a pharmaceutically acceptable salt thereof.

(15) The oxime derivative of any one of (1) to (12) wherein both of $R^3$ and $R^4$ are hydrogen atom, or a pharmaceutically acceptable salt thereof.
(16) The oxime derivative of any one of (1) to (15) wherein $R^5$ is hydrogen atom, halogen atom, cyano, oxo, alkenyl, alkylthio, formyl, alkanoyl, substituted or unsubstituted carbamoyl, substituted or unsubstituted aminosulfonyl, substituted or unsubstituted heterocyclyl-sulfonyl, or substituted or unsubstituted alkyl, or a pharmaceutically acceptable salt thereof.
(17) The oxime derivative of any one of (1) to (16) wherein a substituent of the substituted alkyl in $R^5$ is 1 to 3 substituents selected from substituted or unsubstituted amino, substituted or unsubstituted hydroxyimino, hydroxy, alkoxy, halogen atom, carboxyl, alkoxycarbonyl, substituted or unsubstituted carbamoyl, alkanoyloxy, and substituted or unsubstituted heterocycle, or a pharmaceutically acceptable salt thereof.
(18) The oxime derivative of any one of (1) to (15) wherein $R^5$ is hydrogen atom, halogen atom, cyano, oxo, alkenyl, alkylthio, formyl, alkanoyl, substituted or unsubstituted carbamoyl, substituted or unsubstituted aminosulfonyl, substituted or unsubstituted piperazinylsulfonyl, or alkyl, or alkyl substituted with 1 to 3 groups selected from substituted or unsubstituted amino, substituted or unsubstituted hydroxyimino, hydroxy, alkoxy, halogen atom, alkoxycarbonyl, substituted or unsubstituted piperazinyl, substituted or unsubstituted homopiperazinyl, substituted or unsubstituted piperidinyl, substituted or unsubstituted morpholinyl and substituted or unsubstituted thiomorpholinyl, or a pharmaceutically acceptable salt thereof.
(19) The oxime derivative of any one of (1) to (15) wherein $R^5$ is fluorine atom, or alkyl substituted with 1 to 3 groups selected from substituted or unsubstituted piperazinyl, substituted or unsubstituted morpholinyl and substituted or unsubstituted thiomorpholinyl, or a pharmaceutically acceptable salt thereof.
(20) The oxime derivative of any one of (1) to (15) wherein $R^5$ is fluorine atom, or alkyl substituted with piperazinyl being optionally substituted with 1 to 3 substituents selected from alkyl, oxo, alkanoyl and alkoxyalkanoyl, or a pharmaceutically acceptable salt thereof.
(21) The oxime derivative of any one of (1) to (15) wherein $R^5$ is fluorine atom, or piperazinylmethyl being optionally substituted with alkyl or oxo on the carbon or being optionally substituted with alkyl, alkanoyl or alkoxyalkanoyl on the nitrogen, or a pharmaceutically acceptable salt thereof.
(22) A medicine comprising as an active ingredient the oxime derivative of any one of (1) to (21) or a pharmaceutically acceptable salt thereof.
(23) A glucokinase activating agent comprising as an active ingredient the oxime derivative of any one of (1) to (21) or a pharaceutically acceptable salt thereof as an active ingredient.

The substituents on the group of each symbol of the compound [I-A] means as defined below.

A substituent on the substituted alkyl in $R^5$ includes substituted or unsubstituted amino, substituted or unsubstituted hydroxyimino, hydroxy, alkoxy, halogen atom, carboxyl, alkoxycarbonyl, substituted or unsubstituted carbamoyl, alkanoyloxy, substituted or unsubstituted heterocycle, preferably substituted or unsubstituted amino, substituted or unsubstituted hydroxyimino, hydroxy, alkoxy, halogen atom, alkoxycarbonyl, substituted or unsubstituted piperazinyl, substituted or unsubstituted homopiperazinyl, substituted or unsubstituted piperidinyl, substituted or unsubstituted morpholinyl, substituted or unsubstituted thiomorpholinyl, or the like. The alkyl is substituted with the same or different 1 to 3 substituents selected from the above groups.

In the compound [I-A], substituents in "substituted aryl", "substituted aryloxy", "substituted heteroaryl", "substituted heterocycle", "substituted heterocyclyl-carbonyl", "substituted heterocyclyl-sulfonyl", "substituted cycloalkyl", "substituted phenyl", "substituted pyrazolyl", "substituted imidazolyl", "substituted thiazolyl", "substituted triazolyl", "substituted pyridyl", "substituted pyrimidinyl", "substituted pyrrolidinyl", "substituted thiacyclohexyl", "substituted cyclopentyl", "substituted piperazinyl", "substituted piperazinylsulfonyl", "substituted homopiperazinyl", "substituted piperidinyl", "substituted morpholinyl", "substituted thiomorpholinyl", "substituted tetrazolyl", "substituted carbamoyl", "substituted aminosulfonyl", "substituted amino" or "substituted hydroxyimino" are the same or different 1 to 3 substituents selected from those groups which include (1) alkyl being optionally substituted with hydroxy, alkoxy, amino, mono- or di-alkylamino, carbamoyl, tetrahydrofuryl or pyridyl, (2) cycloalkyl, (3) hydroxy, (4) alkoxy, (5) cyano, (6) halogen, (7) mono- or di-alkylamino, (8) amino being optionally substituted with alkanoyl, alkoxyalkanoyl or alkoxycarbonyl, (9) pyridyl, (10) carboxyl, (11) formyl, (12) alkanoyl being optionally substituted with mono or di-alkylamino, hydroxy, alkoxy or alkanoyloxy, (13) cycloalkylcarbonyl, (14) alkoxycarbonyl, (15) oxo, (16) alkylsulfonyl, or the like.

In the compound [I-A], a preferable substituent in substituted tetrazolyl on $R^1$ and $R^2$ includes alkyl or the like.

A preferable substituent in substituted carbamoyl in $R^3$ and $R^4$ includes alkyl or the like, and it may be the same or different 1 to 2 groups.

A preferable substituent in substituted aryl, substituted aryloxy and substituted phenyl on $R^3$ and $R^4$ includes cyano, halogen atom, alkoxy, alkyl, mono- or di-alkylamino or the like, particularly cyano or halogen atom. The substituent may be the same or different 1 to 3 groups selected from these groups.

A preferable substituent in substituted heteroaryl, substituted pyrazolyl, substituted imidazolyl, substituted thiazolyl, substituted triazolyl, substituted pyridyl and substituted pyrimidinyl on $R^3$ and $R^4$ includes alkyl, mono- or di-alkylamino or the like, particularly alkyl. The substituent may be the same or different 1 to 2 groups selected from these groups.

A preferable substituent in substituted heterocycle, substituted pyrrolidinyl and substituted thiacyclohexyl on $R^3$ and $R^4$ includes oxo, alkoxycarbonyl, alkyl, alkanoyl or the like, particularly oxo or alkyl. The substituent may be the same or different 1 to 2 groups selected from these groups.

A preferable substituent in substituted cycloalkyl and substituted cyclopentyl in $R^3$ and $R^4$ includes oxo, hydroxy or the like, particularly hydroxy.

A preferable substituent in substituted carbamoyl in $R^5$ includes alkoxy, alkyl, cycloalkyl, hydroxyalkyl, dialkylaminoalkyl, cycloalkyl, tetrahydrofurylalkyl, pyridylalkyl, alkoxy, pyridyl or the like, particularly hydroxyalkyl, dialkylaminoalkyl, pyridylalkyl, pyridyl or the like. The substituent may be the same or different 1 to 2 groups selected from these groups.

A preferable substituent in substituted aminosulfonyl in $R^5$ includes alkyl or the like, and the substituent may be the same or different 1 to 2 groups selected from these groups.

A preferable substituent in substituted heterocycle, substituted heterocyclyl-carbonyl, substituted heterocyclyl-sulfonyl, substituted piperazinyl, substituted piperazinylsulfonyl, substituted homopiperazinyl, substituted piperidinyl, substituted morpholinyl and substituted thiomorpholinyl in $R^5$ includes alkoxycarbonylamino, hydroxy, hydroxyalkyl, alkanoylamino, alkoxyalkanoylamino, oxo, alkyl, formyl, alkanoyl, hydroxyalkanoyl, cycloalkylcarbonyl, carboxyl, alkoxycarbonyl, alkoxyalkanoyl, alkanoyloxyalkanoyl, mono or di-alkylaminoalkanoyl, alkylsulfonyl or the like, particularly oxo, alkyl, formyl, alkanoyl, hydroxyalkanoyl, cycloalkylcarbonyl, alkoxycarbonyl, alkoxyalkanoyl, alkanoyloxyalkanoyl or alkylsulfonyl. The substituent may be the same or different 1 to 3 groups selected from these groups.

A preferable substituent in substituted amino in $R^5$ includes alkyl, alkoxyalkyl, pyridyl, pyridylalkyl, dialkylaminoalkyl, carbamoylalkyl or the like. The substituent may be the same or different 1 to 2 groups selected from these groups.

A preferable substituent in substituted hydroxyimino in $R^5$ includes alkoxycarbonyl or the like.

In the compound [I-A], the aryl in Ring A includes preferably phenyl.

The heteroaryl in Ring A includes preferably thienyl or pyridyl, particularly pyridyl.

The heterocycle in Q includes, for example, 5 to 6-membered monocyclic heterocycle, specifically tetrahydrofuryl, pyrrolidinyl, tetrahydropyranyl, thiacyclohexyl, piperidinyl or the like, particularly tetrahydrofuryl.

The heteroaryl in Ring T includes, for example, 5 to 9-membered monocyclic or bicyclic aromatic ring, specifically thiazolyl, thiadiazolyl, pyridyl, pyrazinyl, benzothiazolyl, thiazolopyridinyl or the like. The heterocycle in Ring T includes, for example, 9-membered bicyclic aromatic ring, specifically cyclohexanothiazolyl, dihydrothiazolopyridinyl or the like.

The aryl in $R^3$ and $R^4$ includes preferably phenyl.

The heteroaryl in $R^3$ and $R^4$ includes, for example, 5 to 6-membered monocyclic aromatic ring, specifically pyrazolyl, imidazolyl, isoxazolyl, thiazolyl, triazolyl, pyridyl, pyrimidinyl or the like.

The heterocycle in $R^3$ and $R^4$ includes, for example, 5 to 6 membered monocyclic heterocycle, specifically pyrrolidinyl, tetrahydrofuryl, dioxolanyl, piperidinyl, thiacyclohexyl or the like.

The cycloalkyl in $R^3$ and $R^4$ includes preferably 3 to 6-membered cycloalkyl, specifically cyclopropyl or cyclopentyl.

The heterocycle in $R^5$ includes, for example, 4 to 6-membered monocyclic heterocycle, specifically azetidinyl, pyrrolidinyl, piperidinyl, piperazinyl, morpholinyl, thiomorpholinyl or the like.

Among the compound [I-A], a preferable compound includes a compound wherein Ring A is phenyl, Q is 3-tetrahydrofuryl, Ring T is 2-thiazolyl, one of $R^1$ and $R^2$ is hydrogen atom, the other is cyclopropylsulfonyl, both of $R^3$ and $R^4$ are hydrogen atom, $R^5$ is piperazinyl substituted alkyl being optionally substituted with 1 to 3 substituents selected from alkyl, oxo, alkanoyl and alkoxyalkanoyl.

Other preferable compound among the compounds [I] of the present invention includes a compound described in any of all EXAMPLES.

The following terms used herein mean as defined below.

A "halogen atom" includes fluorine atom, chlorine atom, bromine atom or iodine atom, preferably fluorine atom or chlorine atom.

An "alkyl", which includes "alkyl" moiety in a group bound with other groups such as "alkylthio" or "hydroxyalkyl" (the same for other groups defined hereinafter), includes, for example, straight- or branched-chain alkyl of $C_{1-6}$, preferably $C_{1-4}$, specifically methyl, ethyl, propyl, isopropyl, isobutyl, tert-butyl, pentyl, hexyl or the like.

An "alkenyl" includes, for example, straight- or branched-chain alkenyl of $C_{2-6}$, preferably $C_{2-4}$, specifically vinyl, propenyl, isopropenyl, butenyl, pentenyl, hexenyl or the like.

An "alkynyl" includes, for example, straight- or branched-chain alkynyl of $C_{2-6}$, preferably $C_{2-4}$, specifically acetylenyl, propynyl, butynyl, pentynyl, hexynyl or the like.

An "alkoxy" includes, for example, stragiht- or branched-chain alkoxy of $C_{1-6}$, preferably $C_{1-4}$, specifically methoxy, ethoxy, propoxy, isopropoxy, butoxy, tert-butoxy, pentyloxy, hexyloxy or the like.

An "alkanoyl" includes, for example, straight- or branched-chain alkanoyl of $C_{2-7}$, preferably $C_{2-5}$, specifically acetyl, propionyl, butyryl, pentanoyl or the like.

A "cycloalkyl" includes, for example, cycloalkyl of $C_{3-8}$, preferably $C_{3-6}$, specifically cyclopropyl, cyclobutyl, cyclopentyl, cyclohexyl or cycloheptyl.

An "aryl" includes 6 to 14-membered, preferably 6 to 10-membered monocyclic, bicyclic or tricyclic aromatic hydrocarbon, specifically phenyl, naphthyl, phenanthryl, anthryl or the like, preferably phenyl in particular.

A "heteroaryl" includes 4 to 10-membered, preferably 5 to 9-membered, monocyclic or bicyclic aromatic hydrocarbon wherein 1 to 3 carbon atoms are substituted with heteroatoms independently selected from oxygen atom, sulfur atom and nitrogen atom, specifically thienyl, thiazolyl, pyrazolyl, imidazolyl, isoxazolyl, triazolyl, thiadiazolyl, pyridyl, pyrimidinyl, pyrazinyl, quinolyl, benzothiazolyl, thiazolopyridinyl, thiazolopyrazinyl, thiazolopyrimidinyl or the like.

A "heterocycle" includes 4 to 10-membered, preferably 4 to 9-membered, monocyclic or bicyclic non-aromatic hydrocarbon wherein 1 to 3 carbon atoms are substituted with heteroatoms independently selected from oxygen atom, sulfur atom and nitrogen atom, specifically oxetanyl, azetidinyl, pyrrolidinyl, tetrahydrofuryl, dioxolanyl, piperidinyl, piperazinyl, homopiperazinyl, tetrahydropyranyl, thiacyclohexyl, morpholinyl, thiomorpholinyl, cyclohexanothiazolyl, dihydrothiazolopyridinyl, tetrahydrothiazolopyridinyl or the like.

Alternatively, illustrative embodiments of "halogen atom", "alkyl", "alkenyl", "alkynyl", "alkoxy", "alkanoyl", "cycloalkyl", "aryl", "heteroaryl", "heterocycle" include those specifically indicated in EXAMPLES.

Additionally, each term is explained depending on each symbol (A, Q, T, $R^1$-$R^6$) of the compound [I].

A preferable "aryl" in Ring A includes phenyl.

A preferable "heteroaryl" in Ring A includes thienyl, pyridyl, particularly pyridyl.

A preferable "cycloalkyl" in Q includes, for example, 5 to 6-membered monocyclic cycloalkyl, specifically cyclopentyl, cyclohexyl or the like, particularly cyclopentyl.

A preferable "heterocycle" in Q includes, for example, 4 to 6-membered monocyclic heterocycle optionally having 1 to 3 heteroatoms independently selected from oxygen atom, sulfur atom and nitrogen atom, specifically oxetanyl, tetrahydrofuryl, pyrrolidinyl, piperidinyl, tetrahydropyranyl, tetrahydrothiopyranyl or the like, particularly tetrahydrofuryl.

A heteroaryl in Ring T includes, for example, 5 to 9-membered monocyclic, bicyclic heteroaryl optionally having 1 to 3 heteroatoms independently selected from oxygen atom, sulfur atom and nitrogen atom, specifically thiazolyl, pyrazolyl, thiadiazolyl, pyridyl, pyrazinyl, benzothiazolyl, thiazolopyridinyl, thiazolopyrazinyl, thiazolopyrimidinyl, quinolyl or the like. A preferable one among them is thiazolyl, thiadiazolyl, pyridyl, pyrazinyl, benzothiazolyl, thiazolopyridinyl, thiazolopyrazinyl, thiazolopyrimidinyl, more preferably thiazolyl, thiadiazolyl, pyrazinyl, thiazolopyridinyl, thiazolopyrazinyl, particularly thiazolyl, thiazolopyridinyl, further particularly thiazolyl.

A "heterocycle" in Ring T includes, for example, 5 to 9-membered monocyclic, bicyclic heterocycle optionally having 1 to 3 heteroatoms independently selected from oxygen atom, sulfur atom and nitrogen atom, preferably 9-membered bicyclic heterocycle, specifically cyclohexanothiazolyl, dihydrothiazolopyridinyl or the like.

A "cycloalkyl" of cycloalkylsulfonyl in $R^2$ includes, for example, 3 to 4-membered cycloalkyl, specifically cyclopropyl, cyclobutyl or the like, preferably cyclopropyl in particular.

A "heterocycle" which is the substituent of the substituted or unsubstituted alkyl which is the substituent of substituted or unsubstituted aminosulfonyl in $R^2$ includes, for example, 5 to 9-membered monocyclic, bicyclic heterocycle optionally having 1 to 3 heteroatoms independently selected from oxygen atom, sulfur atom and nitrogen atom, preferably 5-membered monocyclic heterocycle. Particularly, tetrahydrofuryl is preferable.

A "heterocycle" of substituted or unsubstituted heterocyclylsulfonyl in $R^2$ includes, for example, 5 to 9-membered monocyclic, bicyclic heterocycle optionally having 1 to 3 heteroatoms independently selected from oxygen atom, sulfur atom and nitrogen atom, preferably 5 to 7-membered monocyclic heterocycle, specifically azetidinyl, pyrrolidinyl, tetrahydrofuryl, piperidinyl, piperazinyl, morpholinyl, thiomorpholinyl, oxazepidinyl, perhydrodiazepinyl.

A "heteroaryl" of substituted or unsubstituted heteroaryl in $R^3$ and $R^4$ includes, for example, 5 to 9-membered monocyclic, bicyclic heteroaryl optionally having 1 to 3 heteroatoms independently selected from oxygen atom, sulfur atom and nitrogen atom, preferably 5 to 6-membered monocyclic heteroaryl optionally having 1 to 3 nitrogen atoms, specifically pyrazolyl, imidazolyl, thiazolyl, triazolyl, pyridyl, pyrimidinyl or the like, particularly pyrimidinyl.

A "cycloalkyl" of substituted or unsubstituted cycloalkyl in $R^3$ and $R^4$ includes preferably 3 to 6-membered monocyclic cycloalkyl, specifically cyclopropyl, cyclopentyl.

A "heterocycle" of substituted or unsubstituted heterocycle which is the substituent of substituted or unsubstituted alkyl in $R^5$ includes, for example, 5 to 9-membered monocyclic, bicyclic heterocycle optionally having 1 to 3 heteroatoms independently selected from oxygen atom, sulfur atom and nitrogen atom, preferably 4 to 6-membered monocyclic heterocycle optionally having 1 to 3 nitrogen atoms, specifically azetidinyl, pyrrolidinyl, piperidinyl, piperazinyl, morpholinyl, thiomorpholinyl, perhydrodiazepinyl, octahydropyrrolo[1,2-a]piperazinyl or the like. More preferable one among them is piperazinyl, morpholinyl, particularly piperazinyl.

A "heterocycle" of the substituted or unsubstituted heterocyclyloxy which is the substituent of substituted alkyl in $R^5$ includes, for example, 5 to 9-membered monocyclic, bicyclic heterocycle optionally having 1 to 3 heteroatoms independently selected from oxygen atom, sulfur atom and nitrogen atom, preferably 4 to 6-membered monocyclic heterocycle optionally having 1 to 3 nitrogen atoms, specifically azetidinyl, pyrrolidinyl, piperidinyl, piperazinyl, morpholinyl, thiomorpholinyl, perhydrodiazepinyl, octahydropyrrolo[1,2-a]piperazinyl or the like. More preferable one among them is piperidinyl.

The compound [I] of the present invention includes a mixture of stereoisomers, or each stereoisomer with pure or substantively pure forms. For example, the compound [I] can exist in enantiomer or diastereomer or a mixture thereof when the compound of the present invention has one or more asymmetric centers in any of carbon atoms. The compound of the present invention includes its isomers or a mixture thereof.

Also, in case that the compound [I] of the present invention contains double bonds, geometric isomers (cis isomer, trans isomer) may exist and in case that the compound [I] of the present invention contains unsaturated bonds such as carbonyl, tautomers may exist, but the compound of the present invention includes all these isomers or a mixture thereof.

A pharmaceutically acceptable salt of the compound [I] includes, for example, an inorganic acid salt such as hydrochloride, sulfate, phosphate or hydrobromide, or an organic acid salt such as acetate, fumarate, oxalate, citrate, methanesulfonate, benzenesulfonate, tosylate or maleate. Also, in case of having a substituent such as carboxyl, said salt includes a salt with a base such as, for example, alkali metal salt such as sodium salt or potassium salt, or alkali earth metal salt such as calcium salt.

The pharmaceutically acceptable salt of the compound [I] of the present invention includes also an intramolecular salt, and the compounds [I] and their salts may be in the form of a solvate thereof such as a hydrate.

The compound [I] of the present invention or a pharmaceutically acceptable salt thereof can be formulated to a pharmaceutical composition comprising a therapeutically effective amount of the compound and a pharmaceutically acceptable carrier. The pharmaceutically acceptable carrier can include diluents, binding agents (syrup, gum acacia, gelatin, sorbit, tragacanth or polyvinylpyrrolidone), excipients (lactose, sucrose, cornstarch, potassium phosphate, sorbit or glycine), lubricants (magnesium stearate, talc, polyethylene glycol or silica), disintegrants (Irish potato starch) and wetting agents (sodium lauryl sulfate), or the like.

The compound [I] of the present invention or a pharmaceutically acceptable salt thereof can be administered orally or parenterally and used in an appropriate pharmaceutical formulation. The appropriate pharmaceutical formulation for oral administration includes, for example, solid formulations such as tablet, granule, capsule or powder, or in the form of a solution, a suspension or an emulsion. The appropriate pharmaceutical formulation for parenteral administration includes a suppository, an injectable solution or an intravenous fluid preparation using distilled water for injection, saline or glucose aqueous solution, or an inhaler, or the like.

The compound [I] of the present invention or a pharmaceutically acceptable salt thereof, or a pharmaceutical formulation thereof can be combined with other one or more medicines selected from antidiabetic and antihyperglycemic agents. In this case, the concept of the term "combine" includes administering with these other medicines simultaneously or separately with optional interval as well as administering as one pharmaceutical formulation formulated together with these other medicines. These other medicines include sulfonylurea (for example, glyburide, glimepiride, glipiride, glipizide, chlorpropamide, gliclazide, glisoxepide, acetohexamide, glibonuride, tolbutamide, tolazamide, carbutamide, gliquidone, glihexamid, phenbutamide, tolcyclamide or the like), biguanide (for example, metformin, phenformin, buformin or the like), glucagon antagonist (for example, peptidic or nonpeptidic glucagon antagonist), glucosidase inhibitor (for example, acarbose, miglitol or the like), insulin sensitizer (for example, troglitazone, rosiglitazone, pioglitazone or the like), antiobesity agent (for example, sibutramine, orlistat or the like) or the like.

The dose of the compound [I] of the present invention or a pharmaceutically acceptable salt thereof depends on methods of administration, ages, body weights or conditions of patients, but usually about 0.01 to about 100 mg/kg per day, preferably about 0.1 to about 10 mg/kg.

The compound [I] of the present invention can be prepared according to the following methods.

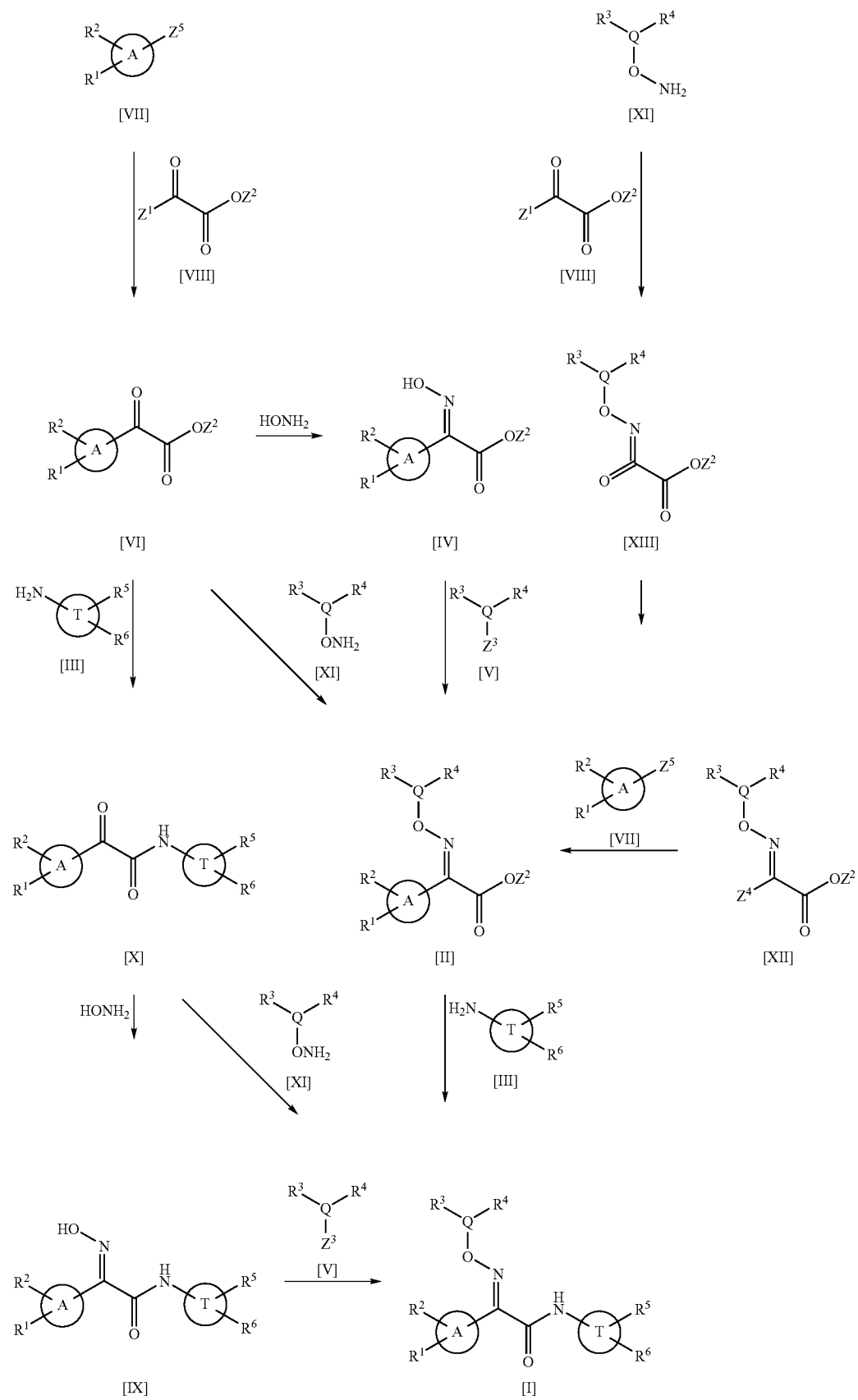

(In the above scheme, $Z^1$ is halogen atom, hydroxy or alkoxy, $Z^2$ is hydrogen atom or alkyl, $Z^3$ is hydroxy, halogen atom or arylsulfonyloxy, alkylsulfonyloxy, $Z^4$ is halogen atom, dialkoxyboryl, dihydroxyboryl or trialkylstannyl, lithio, $Z^5$ is hydrogen atom, halogen atom, dialkoxyboryl, dihydroxyboryl or trialkylstannyl, lithio, and the other symbols have the same meanings as mentioned above.)

(1) The reaction of preparing the compound [VI] ($Z^2$ is alkyl) from the compound [VIII] ($Z^5$ is hydrogen atom) and the compound [VIII] ($Z^1$ is halogen atom, $Z^2$ is alkyl) can be carried out under so-called Friedel-Crafts reaction condition. For example, the reaction can be carried out in an appropriate solvent (chloroform, methylene chloride, nitromethane or the like) in the presence of an appropriate acid (aluminum chloride or the like).

The compound [VI] ($Z^2$ is alkyl) can be also prepared by reacting the compound [VII] ($Z^5$ is dialkoxyboryl, dihydroxyboryl or trialkylstannyl) with the compound [VIII] ($Z^1$ is halogen atom, $Z^2$ is alkyl) in an appropriate solvent (THF, methylene chloride, dioxane, water, DMF, toluene, 1,2-dimethoxyethane or the like, or a mixture thereof) using a metal catalyst (for example, dichlorobis(triphenylphosphine)palladium, tetrakis(triphenylphosphine)palladium, tris(dibenzylideneacetone)dipalladium, dichloro[1,1'-bis(diphenylphosphino)ferrocene]palladium or the like), and the process preferably proceeds at −78° C. to 200° C.

Additionally, the compound [VI] ($Z^2$ is alkyl) can be also prepared by reacting the compound [VII] ($Z^5$ is lithio) with the compound [VIII] ($Z^1$ is alkoxy, $Z^2$ is alkyl) in an appropriate solvent (THF, dioxane, DMF, toluene, 1,2-dimethoxyethane or the like, or a mixture thereof), and the process can be preferably carried out at −78° C. to 200° C. Also, in case of using the compound [VII] (Zs is halogen atom), the compound [VI] ($Z^2$ is alkyl) can be prepared by converting the compound [VII] ($Z^5$ is halogen atom) into the compound [VII] ($Z^5$ is lithio) with an appropriate alkyllithium (n-butyllithium, sec-butyllithium, t-butyllithium or the like) in an appropriate solvent (THF, diethyl ether, toluene, 1,2-dimethoxyethane or the like, or a mixture thereof) to convert, followed by reacting with the compound [VIII] ($Z^1$ is alkoxy, $Z^2$ is alkyl) in the similar manner as the above-mentioned.

(2) The reaction of the compound [VI] ($Z^2$ is alkyl) with hydroxylamine or a salt thereof with an appropriate acid (hydrochloride, sulfate or the like) can be carried out in any conventional manner converting ketone into hydroxyimino. For example, the reaction can be carried out in an appropriate solvent (alcoholic solvent such as methanol, ethanol, or THF, dioxane, water or the like, or a mixed solvent thereof) in the presence or absence of a base. The base used in the reaction includes pyridine, picoline, lutidine, N,N-dimethylaniline, triethylamine or the like. An oxime generated in a cis-isomer or a mixture of cis- and trans-isomers can be converted into the desired trans-isomer by treating with acid (trifluoroacetic acid, acetic acid, hydrochloric acid, sulfuric acid, phosphoric acid or the like). Also an oxime generated in the reactions described below can also be converted into the desired trans-isomer by treating in the similar manner as the above.

(3) The reaction of the compound [IV] ($Z^2$ is alkyl) with the compound [V] wherein $Z^3$ is hydroxy can be carried out by using, in the presence of triphenylphosphine, an activating agent (diethyl azodicarboxylate, diisopropyl azodicarboxylate or the like), or, in absence of triphenylphosphine, cyanomethyl tri-n-butyl phosphorane or the like in an appropriate solvent (THF, methylene chloride or the like) (so-called Mitsunobu reaction). Also, the reaction with the compound [V] wherein $Z^3$ is halogen atom, arylsulfonyloxy or alkylsulfonyloxy can be carried out in an appropriate solvent (acetone, ethanol, THF, dimethyl sulfoxide, DMF, dioxane, N,N-dimethylacetamide, N-methylpyrrolidone or the like, or a mixed solvent thereof) in the presence of a base such as potassium carbonate, potassium tert-butoxide, sodium hydride, cesium carbonate or the like. A product resulted in this way can be converted into the compound [II] ($Z^2$ is hydrogen atom) in any conventional manner hydrolyzing alkoxycarbonyl to carboxyl, for example, by treating with lithium hydroxide, sodium hydroxide, potassium carbonate or the like in an appropriate solvent (alcoholic solvent such as methanol, ethanol, or THF, dioxane, water or the like, or a mixed solvent thereof) to hydrolyze $Z^2$ group.

(4) The reaction of the compound [II] ($Z^2$ is hydrogen atom) with the compound [III] can be carried out in an appropriate solvent in the presence or absence of a condensing agent by using any conventional method for amide formation usually used in peptide synthesis or the like. As the condensing agent, any of N-ethyl-N'-(3-diethylaminopropyl)carbodiimide, N,N'-dicyclohexylcarbodiimide, 1-methyl-2-bromopyridinium iodide, N,N'-carbonyldiimidazole, diphenyl phosphoryl azide, benzotriazol-1-yloxytris(dimethylamino)phosphonium hexafluorophosphate, 4-(4,6-dimethoxy-1,3,5-triazin-2-yl)-4-methylmorpholinium chloride, fluoro-N,N,N',N'-tetramethylformamidinium hexafluorophosphate or the like can be preferably used. As the solvent, any of a single solvent or a mixed solvent of water, methanol, isopropanol, ethanol, methylene chloride, TiF, dioxane, DMF, dimethylacetamide, chloroform or the like can be preferably used. The reaction preferably proceeds at −78° C. to 100° C., more preferably at −25° C. to 25° C. The proceed of the reaction can be accelerated by adding an inorganic base such as potassium carbonate, sodium carbonate, sodium bicarbonate or an organic base such as triethylamine, diisopropylethylamine, N-methylmorpholine, pyridine, N,N-dimethylaminopyridine, picoline, lutidine or the like as a base, and N-hydroxysuccinimide, 3-hydroxy-3,4-dihydro-4-oxo-1,2,3-benzotriazole, N,N-dimethylaminopyridine or N-hydroxybenzotriazole or the like as an additive.

The reaction from the compound [II] ($Z^2$ is hydrogen atom) to the compound [I] can be carried out by converting the compound [II] ($Z^2$ is hydrogen atom) into a reactive intermediate such as acid chloride or a mixed acid anhydride, followed by reacting with the compound [II]. The conversion into acid chloride can be preferably carried out by using thionyl chloride, oxalyl chloride, phosphorus oxychloride, phosphorus pentachloride, or triphenylphosphine in the presence of carbon tetrachloride, or the like, and the conversion into a mixed acid anhydride can be carried out by using diphenyl phosphoryl chloride, diethyl phosphorocyanidate, methanesulfonyl chloride, ethyl chloroformate, isobutyl chloroformate or the like in the presence of a base such as triethylamine. As the solvent, any of a single solvent or a mixed solvent of methylene chloride, chloroform, THF, DMF or the like can be preferably used. The reaction preferably proceeds at −78° C. to 100° C., more preferably −25° C. to 25° C. The reaction of an acid chloride or a mixed acid anhydride resulted in this way with the compound [III] proceeds in the presence of a base such as pyridine, triethylamine, N,N-dimethylaminopyridine, diisopropylethylamine or the like preferably at −78° C. to 100° C., more preferably −25° C. to 25° C. and as the solvent, any of a single solvent or a mixed solvent of methylene chloride, chloroform, THF, DMF or the like can be preferably used.

(5) The reaction of the compound [VI] ($Z^2$ is hydrogen atom or alkyl) with the compound [III] can be carried out in case that $Z^2$ is hydrogen atom in the similar manner as the reaction of the above (4), or in case that $Z^2$ is alkyl via the compound [VI'] and the compound [X'] below. The conversion from the compound [VI] ($Z^2$=alkyl) to the compound [VI] ($Z^2$ is hydrogen atom) can be carried out in any conventional manner reducing ketone to alcohol, for example, by treating with a reducing agent such as zinc borohydride, sodium triacetoxyborohydride, sodium borohydride or the like in an appropriate solvent (water, methanol, ethanol, chloroform, methylene chloride or the like, or a mixed solvent thereof), followed by hydrolysis in any conventional manner hydrolyzing alkoxycarbonyl to carboxyl, for example, by treating with lithium hydroxide, sodium hydroxide or the like in an appropriate solvent (methanol, ethanol, THF, dioxane, water or the like, or a mixed solvent thereof) to hydrolyze $Z^2$ group.

The reaction of the compound [VI'] ($Z^2$ is hydrogen atom) with the compound [III] can be carried out in the similar manner as the reaction of the above (4).

The conversion from the compound [X'] to the compound [X] can be carried out in any conventional manner oxidizing alcohol to ketone, for example, by dimethylsulfoxide oxidation using an activating agent such as oxalyl chloride (Swern oxidation), or by using an oxidizing agent (activated manganese dioxide, sulfur trioxide-pyridine complex, 1-hydroxy-1,2-benziodoxol-3(1H)-one 1-oxide, 1,1,1-triacetoxy-1,1-dihydro-1,2-benziodoxol-3(1H)-one, pyridinium chlorochromate, pyridinium dichromate or the like) in the presence or absence of a base (triethylamine or the like) in an appropriate solvent (dimethylsulfoxide, chloroform, methylene chloride or the like).

erocyclyl-oxyamine, benzyloxyamine or the like) as an alternative to hydroxylamine in the reaction of (2).

(9) The reaction of the compound [X] with the compound [XI] can be carried out in the similar manner as the reaction of the above (8).

(10) The reaction of the compound [XI] with the compound [VIII] (7' is halogen atom or hydroxy, 72 is alkyl) can be carried out in any conventional manner of amide formation usually used in peptide synthesis or the like, for example in the similar manner as the reaction of the above (4).

(11) The reaction from the compound [XIII] (72 is alkyl) to the compound [XII] ($Z^4$ is hydrogen atom) can be carried out by using any conventional method for converting amide into haloimino, preferably the manner of reference: WO9520569, for example, by using the compound [XIII] (72 is alkyl) with a halogenating agent (phosphorus oxychloride, phosphorus pentachloride or the like) in an appropriate solvent (acetonitrile, chloroform, methylene chloride, THF or the like, or a mixed solvent thereof). The reaction can be also carried out by using carbon tetrachloride, carbon tetrabromide, N-bromosuccinimide, N-chlorosuccinimide, iodine or the like in the presence of triphenylphosphine.

(12) The reaction from the compound [XII] (72 is alkyl) and the compound [VII], for example in case that 75 is dihydroxyboryl, to the compound [II] (72 is alkyl) can be carried out by using a metal catalyst (for example, dichlorobis (triphenylphosphine)palladium, tetrakis (triphenylphosphine) palladium, tris(dibenzylideneacetone)dipalladium, dichloro [1,1'-bis(diphenylphosphino) ferrocene]palladium or the like) in an appropriate solvent (for example, dioxane, toluene, THF, 1,2-dimethoxyethane, methanol, ethanol, DMF, N-methylpyrrolidone or

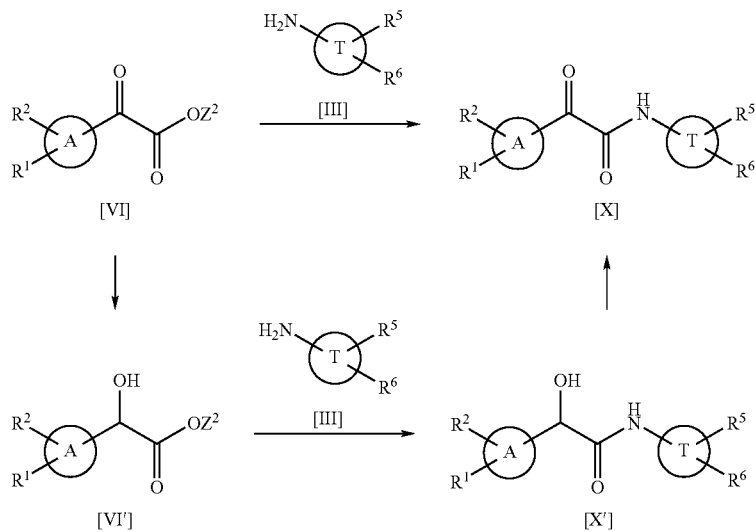

(6) The reaction from the compound [X] to the compound [IX] can be carried out in the similar manner as the reaction of the above (2).

(7) The reaction from the compound [IX] and the compound [V] to the compound [I] can be carried out in the similar manner as the reaction of the above (3).

(8) The reaction of the compound [VI] with the compound [XI] can be carried out in the similar manner as the reaction of the above (2) by using O-substituted hydroxylamine or a salt thereof (alkyloxyamine, cycloalkyloxyamine, hetthe like, or a mixed solvent thereof) in the presence of a base (sodium carbonate, potassium carbonate, triethylamine, diisopropylethylamine or the like). The reaction preferably proceeds under inert gas such as argon at room temperature to 200° C. or in the exposure of microwave.

The compound [I] can be converted further in the following methods.

(A) The compound containing sulfinyl (SO) or sulfonyl ($SO_2$) on $R^1$-$R^6$ among the objective compound [I] of the present invention can be prepared by oxidation using any conventional method for converting the corresponding sulfide compound into a sulfinyl or sulfonyl compound. For example, the oxidation can be carried out by treating with an oxidizing agent in an appropriate solvent (methylene chloride, chloroform, THF, methanol, water, or the like or a mixed solvent thereof. As the oxidizing agent, peracids such as hydrogen peroxide, m-chloroperbenzoic acid, peracetic acid or the like as well as Oxone™ ("a mixture of potassium peroxybisulfate, dipotassium sulfate and potassium bisulfate" manufactured by DuPont) can be preferably used, and the reaction can be preferably carried out at −78° C. to 100° C.

(B) The compound having a group of the formula:

—CH$_2$N(R$^{11}$)(R$^{12}$), wherein R$^{11}$ and R$^{12}$ are substituents of the substituted amino group described herein or R$^{11}$ and R$^{12}$ form together with N atom of said amino group a heterocycle having 1 to 3 heteroatoms independently selected from oxygen atom, sulfur atom and nitrogen atom wherein the heterocycle may be substituted,
on R$^1$-R$^6$ among the objective compound [I] can be also prepared by so-called "reductive amination", by reacting the compound wherein the corresponding site is formyl with a substituted or unsubstituted amine of the formula:

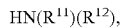
HN(R$^{11}$)(R$^{12}$), wherein the symbols have the same meanings as mentioned above (hereinafter, this compound is referred to as "a substituted or unsubstituted amine", and the group after removing of hydrogen atom from the substituted or unsubstituted amine is referred to as "a substituted or unsubstituted amino"), under reductive condition. The reaction can be carried out in any conventional manner of reductive amination. For example, the reaction can be preferably carried out by using a reducing agent (sodium borohydride, sodium triacetoxyborohydride, sodium cyanoborohydride or the like) in an appropriate solvent (methanol, methylene chloride, chloroform or the like) at −78° C. to 100° C.

(C) Among the objective compound [I], the compound wherein nitrogen atom on R$^1$-R$^6$ is substituted with a substituted or unsubstituted alkanoyl such as alkanoyl, cycloalkylcarbonyl, alkoxyalkanoyl, alkanoyloxyalkanoyl or the like, which is simply referred to as substituted or unsubstituted alkanoyl hereinafter, can be also prepared by alkanoylation of the compound wherein the corresponding N atom is unsubstituted (for example, the compound wherein R$^5$ is piperazinylmethyl, piperazinylcarbonyl or piperazinylsulfonyl or the like). The alkanoylation can be carried out by using any conventional method of amide formation usually used in peptide synthesis or the like. For example, the alkanoylation can be preferably carried out by using acid chloride, acid anhydride or ester in an appropriate solvent (methylene chloride, THF, DMF, N,N-dimethylacetamide, chloroform or a mixed solvent thereof) in the presence or absence of a base (triethylamine, pyridine or the like) at −78° C. to 100° C. The reaction can be also carried out, for example, in an appropriate solvent in the presence or absence of a condensing agent. As the condensing agent, any of N-ethyl-N'-(3-diethylaminopropyl)carbodiimide, N,N'-dicyclohexylcarbodiimide, 1-methyl-2-bromo-pyridinium iodide, N,N'-carbonyldiimidazole, diphenylphosphoryl azide, benzotriazol-1-yloxytris(dimethylamino)phosphonium hexafluorophosphate, 4-(4,6-dimethoxy[1.3.5]triazin-2-yl)-4-methylmorpholinium chloride, fluoro-N,N,N',N'-tetramethylformamidinium hexafluorophosphate or the like can be preferably used. As the solvent, any of a single solvent or a mixed solvent of water, methanol, isopropanol, ethanol, methylene chloride, THF, DMF, N,N-dimethylacetamide, chloroform or the like can be preferably used. The reaction preferably proceeds at −78° C. to 100° C., more preferably −25° C. to 25° C. The proceed of the reaction can be promoted by adding potassium carbonate, sodium carbonate, sodium bicarbonate or triethylamine, diisopropylethylamine, N-methylmorpholine, pyridine, N,N-dimethylaminopyridine, picoline, lutidine or the like as a base, and N-hydroxysuccinimide or 3-hydroxy-3,4-dihydro-4-oxo-1,2,3-benzotriazole, N,N-dimethylaminopyridine, N-hydroxybenzotriazole or the like as an additive.

(D) The compound having substituted or unsubstituted aminocarbonyl, i.e. substituted or unsubstituted carbamoyl, on R$^1$-R$^6$ among the objective compound [I] can be prepared by reacting the compound wherein the corresponding site is carboxy with a substituted or unsubstituted amine. The reaction can be carried out in the similar manner as the reaction of the above (C).

(E) The compound wherein R$^5$ or R$^6$ has substituted or unsubstituted alkoxymethyl, or substituted or unsubstituted heteroarylmethyl among the objective compound [I] can be also prepared by converting the compound wherein the corresponding site is hydroxymethyl into alkanoylmethyl, preferably acetyloxymethyl, in any conventional esterification manner, followed by condensing substituted or unsubstituted alkanol, cycloalkanol, alkylthio or a heterocycle compound having hydroxyl group, or substituted or unsubstituted heteroaryl compound having hydrogen atom on nitrogen atom, for example pyrazole or the like. The condensing reaction can be preferably carried out as neat or in an appropriate solvent (THF, dioxane, methylene chloride, chloroform, toluene, benzene or the like) in the presence or absence of an acid (p-toluenesulfonic acid, hydrochloric acid, sulfuric acid, trifluoroacetic acid or the like) at −78° C. to 200° C., more preferably 25° C. to 100° C.

(F) The compound having hydroxymethyl on R$^1$-R$^6$ among the objective compound [I] can be prepared by reducing the compound wherein the corresponding site is formyl in any conventional manner by reducing formyl to alcohol. For example, the reaction can be preferably carried out by using a reducing agent (sodium borohydride, sodium triacetoxyborohydride, diborane, diisobutylaluminum hydride, lithium aluminum hydride or the like) in an appropriate solvent (methanol, ethanol, methylene chloride, chloroform, dioxane, THE or the like) at −78° C. to 100° C.

(G) The compound having carboxyl on R$^1$-R$^6$ among the objective compound [I] can be prepared by oxidizing the compound wherein the corresponding site is formyl in any conventional manner by oxidizing formyl to carboxyl. The oxidation can be preferably carried out by, for example, using an oxidizing agent (sodium chlorite, potassium permanganate, pyridinium dichromate or the like) in an appropriate solvent (DMF, dimethylsulfoxide, acetone, tert-butanol, water, methylene chloride, chloroform or the like) at −78° C. to 100° C.

(H) The compound having alkoxycarbonyl on R$^1$-R$^6$ among the objective compound [I] can be also prepared by esterifying the compound wherein the corresponding site is carboxyl in any conventional manner by esterifying carboxyl to alkoxycarbonyl. The esterification can be preferably carried out by, for example, using an acid (sulfuric acid, hydrochloric acid, p-toluenesulfonic acid) in an appropriate solvent (methanol, ethanol, isopropanol, tert-butanol or the like) at −78° C. to 200° C., more preferably 0° C. to 100° C.

Additionally, the esterification can be also carried out by converting a carboxyl compound to a reactive intermediate such as an acid halide with a halogenating agent (oxalyl chloride, thionyl chloride or the like) in an appropriate solvent (methylene chloride, chloroform, THF, dioxane or the like), followed by using alkanol (methanol, ethanol, isopropanol or the like) at −78° C. to 200° C.

(I) The compound having carboxyl on $R^1$-$R^6$ among the objective compound [I] can be also prepared by hydrolyzing the compound wherein the corresponding site is alkoxycarbonyl in any conventional manner of ester hydrolysis. The hydrolysis can be preferably carried out by using a base (sodium hydroxide, potassium hydroxide, potassium carbonate, lithium hydroxide or the like) in an appropriate solvent (alcoholic solvent such as methanol, ethanol, or dioxane, THF, water or the like, or a mixed solvent thereof) at −78° C. to 200° C., more preferably 0° C. to 100° C.

Additionally, the hydrolysis can be also preferably carried out by using an acid (sulfuric acid, hydrochloric acid or the like) in an appropriate solvent (THF, dioxane, acetic acid, water or the like, or a mixed solvent thereof) at −78° C. to 200° C.

(J) The compound having formyl on $R^1$-$R^6$ among the objective compound [I] can be also prepared from the compound wherein the corresponding site is carboxyl in any conventional manner by reducing carboxyl to aldehyde. The reaction can be preferably carried out by using a halogenating agent (oxalyl chloride, thionyl chloride or the like) in an appropriate solvent (methylene chloride, chloroform, THF or the like, or a mixed solvent thereof to synthesize acid halide, followed by reducing the acid halide with a metal catalyst (palladium carbon, platinum dioxide or the like) under hydrogen at −78° C. to 200° C.

(K) The compound having hydroxymethyl on $R^1$-$R^6$ among the objective compound [I] can be prepared by using any conventional method of reduction of ester or carboxylic acid to alcohol. For example, the reaction can be preferably carried out by treating the corresponding carboxyl or alkoxycarbonyl with a reducing agent (sodium borohydride, diborane, lithium aluminum hydride, diisobutylaluminum hydride or the like) in an appropriate solvent (methylene chloride, chloroform, THF or the like) at −78° C. to 200° C.

(L) The compound having carboxyl on $R^1$-$R^6$ among the objective compound [I] can be prepared by using the conventional method of oxidation of primary alcohol to carboxylic acid. For example, the reaction can be preferably carried out by using the compound wherein the corresponding site is hydroxymethyl with an oxidizing agent (chromium trioxide, pyridinium dichromate or the like) in an appropriate solvent (methylene chloride, acetone, chloroform, DMF or the like) at, for example, 0° C. to 100° C.

(M) The compound having amino on $R^1$-$R^6$ among the objective compound [I] can be carried out by using any conventional method of reduction of nitro to amine. For example, the reaction can be carried out by treating the compound wherein the corresponding site is nitro with a metal catalyst (palladium carbon, platinum dioxide or the like) in an appropriate solvent (methanol, ethanol, DMF, THF, dioxane or the like) under hydrogen at 78° C. to 200° C.

Additionally, the process can be also preferably carried out by using a reducing agent (stannous chloride, iron, zinc or the like) in an appropriate solvent (alcoholic solvent such as methanol, ethanol, or methylene chloride, chloroform, THF, dioxane, acetic acid, water or the like, or a mixed solvent thereof at 78° C. to 200° C., more preferably 0° C. to 100° C.

(N) The compound having halogenosulfonyl on $R^1$-$R^6$ among the objective compound [X] can be prepared by reacting the compound wherein the corresponding site is amino under so-called Sandmayer reaction condition to halogenosulfonylate via a diazonium salt. The formation of a diazonium salt can be preferably carried out by, for example, using an oxidizing agent (sodium nitrite, isoamyl nitrite, tert-butyl nitrite or the like) in an appropriate solvent (water, methylene chloride, chloroform, THF or the like, or a mixed solvent thereof) in the presence or absence of an appropriate acid (hydrochloric acid, sulfuric acid or the like) and/or an additive (cupric chloride or the like) at −78° C. to 200° C. The following halogenosulfonylation can be carried out by adding a sulfonylating agent (sulfur dioxide, sodium bisulfite or the like) to the resulting reaction solution at −78° C. to 200° C.

(O) The compound having substituted or unsubstituted aminosulfonyl on $R^1$-$R^6$ among the objective compound [I] can be also prepared by reacting the compound wherein the corresponding site is halogenosulfonyl with a substituted or unsubstituted amine. The reaction can be preferably carried out in an appropriate solvent (methylene chloride, chloroform, THF, dioxane, water or the like) in the presence or absence of a base (pyridine, triethylamine, sodium hydroxide, sodium carbonate or the like) at −78° C. to 200° C.

(P) The compound having alkylthio, cycloalkylthio, heterocyclyl-thio on $R^1$-$R^6$ among the objective compound [I] can be also prepared by, for example, converting the compound wherein the corresponding site is methylsulfinyl into thiol in the same manner as described in a literature (Young R. N., et al., Tetrahedron Lett., 1984, 25(17), 1753.), followed by reacting with an alkylating agent (haloalkyl, halocycloalkyl, haloheterocycle compound, alkyl mesylate, cycloalkyl mesylate, heterocyclyl mesylate, alkyl tosylate, cycloalkyl tosylate, heterocyclyl tosylate or the like) in the presence or absence of a base (sodium hydride, cesium carbonate, potassium carbonate, potassium tert-butoxide, triethylamine, diazabicycloundecene or the like).

(Q) The compound having substituted or unsubstituted alkanoylamino on $R^1$-$R^6$ among the objective compound [I] can be also prepared by alkanoylating the compound wherein the corresponding site is amino. The alkanoylation can be carried out in a similar manner as in the reaction of the above (C). Also, the alkanoylation can be carried out in the compound wherein the corresponding site is secondary amine as well as primary amine.

(R) The compound having substituted sulfonylamino such as alkylsulfonylamino, heteroarylsulfonylamino, heterocyclylsulfonylamino or the like on $R^1$-$R^6$ among the objective compound [I] can be also prepared by sulfonylating the compound wherein the corresponding site is amino. The sulfonylation can be carried out in an appropriate solvent (water, THF, methylene chloride, chloroform or the like) in the presence or absence of a base (triethylamine, diisopropylethylamine, pyridine or the like) at −78° C. to 200° C. Also, the sulfonylation can be carried out in the compound wherein the corresponding site is secondary amine as well as primary amine.

(S) The compound having secondary alcohol on $R^1$-$R^6$ among the objective compound [I] can be prepared by using any conventional method for converting ketone into secondary alcohol. For example, the reaction can be carried out by using the compound having the corresponding oxo in the similar manner as the reaction of the above (K).

(T) The compound having oxo on $R^1$-$R^6$ among the objective compound [X] can be prepared by using any conventional method for converting secondary alcohol into ketone. For example, the reaction can be carried out by dimethylsulfoxide oxidation with an activating agent such as oxalyl chloride in an appropriate solvent (dimethylsulfoxide, chloroform, methylene chloride or the like) (Swern oxidation), or by using an oxidizing agent (activated manganese dioxide, sulfur trioxide-pyridine complex, 1-hydroxy-1,2-benziodoxol-3(1H)-one-1-oxide, 1,1,1-triacetoxy-1,1-dihydro-1,2-benziodoxol-3(1H)-one, pyridinium chlorochromate, pyridinium dichromate or the like) in the presence or absence of a base (triethylamine or the like).

(U) The compound having secondary alcohol on $R^1$-$R^6$ among the objective compound [I] can be prepared by using any conventional method for converting the compound having formyl into secondary alcohol. For example, the reaction can be preferably carried out by using the corresponding formyl and a metal reagent (alkylmagnesium halide, alkyllithium, dialkylzinc or the like) in an appropriate solvent. (THF, toluene, diethyl ether or the like) at −78° C. to 100° C.

(V) The compound having hydroxyamidino on $R^1$-$R^6$ among the objective compound [I] can be prepared by using any conventional method for converting cyano group into hydroxyamidino group. For example, the reaction can be preferably carried out by reacting the compound having the corresponding cyano with hydroxylamine (or a salt with an appropriate acid thereof) in the presence or absence of a base (sodium carbonate, potassium carbonate, sodium hydroxide, potassium hydroxide, potassium tert-butoxide, triethylamine, pyridine or the like) in an appropriate solvent (water, methanol, ethanol or the like, or a mixed solvent thereof) at 0° C. to 100° C.

(W) The compound having unsubstituted carbamoyl on $R^1$-$R^6$ among the objective compound [I] can be prepared by using any conventional method for converting cyano group into unsubstituted carbamoyl group. For example, the reaction can be preferably carried out by treating the compound having the corresponding cyano with a base (sodium hydroxide, potassium hydroxide, potassium tert-butoxide or the like) in an appropriate solvent (water, methanol, ethanol, isopropanol or the like, or a mixed solvent thereof) at −20° C. to 100° C.

(X) The compound having tertiary alcohol on $R^1$-$R^6$ among the objective compound [I] can be prepared by, for example, reacting the compound having the corresponding oxo under a condition of the above (U).

(Y) The preparation of the compound having optically-active secondary alcohol on $R^1$-$R^6$ among the objective compound [I] can be carried out by using any conventional method for resolution of secondary alcohol compound in enzymatic transesterification. For example, the preparation can be preferably carried out by treating the corresponding racemic secondary alcohol with acyl donor (vinyl acetate or the like) in the presence of enzyme (lipase PS or the like) in an appropriate solvent (tert-butylmethyl ether, hexane, diisopropyl ether, THF, diethyl ether, water or the like) at −78° C. to 100° C.

(Z) The preparation of the compound having alkyl on $R^1$-$R^6$ among the objective compound [I] can be carried out by using so-called catalytic hydrogenation. For example, the compound can be preferably prepared by treating the compound having the corresponding alkenyl with a metal catalyst (palladium carbon, platinum dioxide or the like) under hydrogen in an appropriate solvent (methanol, ethanol, DMF, THF, acetic acid or the like, or a mixed solvent thereof at 0° C. to 200° C.

(AA) The preparation of the compound having 1,2-diol on $R^1$-$R^6$ among the objective compound [I] can be preferably carried out by, for example, treating the compound having the corresponding alkenyl with an oxidizing agent (osmium tetroxide, ruthenium tetroxide, sodium periodate or the like) in an appropriate solvent (water, acetone, THF, acetonitrile, ethyl acetate or the like, or a mixed solvent thereof at 0° C. to 100° C.

(BB) The preparation of the compound having halogen atom on $R^1$-$R^6$ among the objective compound [I] can be carried out by using any conventional method for halogenation of alcohol. For example, the preparation can be preferably carried out by treating the corresponding alcohol with carbon tetrabromide in the presence of triphenylphosphine in an appropriate solvent (methylene chloride, chloroform or the like) at 0° C. to 100° C.

(CC) The preparation of the compound having unsubstituted and substituted alkylthio, heteroarylthio or arylthio on $R^1$, $R^2$, $R^5$ or $R^6$ among the objective compound [I] can be carried out by using any conventional method for coupling thiol with halogenated aryl, halogenated heteroaryl, aryl triflate or heteroaryl triflate. For example, the preparation can be preferably carried out by treating the compound having the corresponding haloaryl with thiol (hydroxyalkylthiol, dialkylaminoalkylthiol, or the like) in the presence of a metal catalyst (tetrakis(triphenylphosphine)palladium or the like) in an appropriate solvent (dioxane, toluene, THF, 1,2-dimethoxyethane or the like, or a mixed solvent thereof) in the presence or absence of a base (triethylamine, diisopropylamine or the like) at 0° C. to 200° C.

(DD) The preparation of the compound having mono-substituted or di-substituted alkylamino on $R^1$-$R^6$ among the objective compound [I] can be preferably carried out by, for example, treating the compound having the corresponding haloalkyl with mono-substituted or di-substituted alkylamine (dimethylamine, diethylamine, methylamine or the like) in an appropriate solvent (methanol, ethanol, dioxane, toluene, THF, 1,2-dimethoxyethane or the like) in the presence or absence of a base (triethylamine, diisopropylamine or the like) at 0° C. to 200° C. Also, the compound having dimethylamino can be preferably prepared by treating the compound having the corresponding haloalkyl with N-(trimethylsilyl)dimethylamine in an appropriate solvent (methanol, ethanol, dioxane, toluene, THF, 1,2-dimethoxyethane or the like) at 0° C. to 200° C.

(EE) The preparation of the compound having alkynyl on $R^1$, $R^2$, $R^5$ or $R^6$ among the objective compound [I] can be carried out by using any conventional method of so-called Sonogashira coupling reaction of halogenated aryl, halogenated heteroaryl, aryl triflate or heteroaryl triflate with the compound having alkyne. For example, the preparation can be preferably carried out by treating the compound having the corresponding halogen with alkyne (propargyl alcohol, N,N-dimethylpropargylamine or the like) in the presence of a metal catalyst (tetrakis(triphenylphosphine) palladium or the like) in an appropriate solvent (dioxane, toluene, THF, 1,2-dimethoxyethane or the like) in the presence or absence of a base (triethylamine, diisopropylamine or the like) and/or copper salt (for example, cuprous iodide) at 0° C. to 200° C.

(FF) The preparation of the compound having tetrazolyl on $R^1$-$R^6$ among the objective compound [I] can be carried out by using any conventional method for converting cyano group into tetrazolyl group. For example, the preparation can be preferably carried out by treating the compound having the corresponding cyano with metal azide (sodium azide, tributyltin azide, trimethylsilyl azide) in an appropriate solvent (methanol, ethanol, DMF, dioxane, toluene, THF, 1,2-dimethoxyethane or the like) in the presence or absence of a base (triethylamine, diisopropylamine or the like) or a salt (triethylamine hydrochloride or the like) at 0° C. to 200° C.

(GG) The preparation of the compound having O-alkoxycarbonylhydroxyimine on $R^1$-$R^6$ among the objective compound [I] can be preferably carried out by treating the compound having the corresponding hydroxyimine with alkyl chlorocarbonate (ethyl chlorocarbonate or the like) in an appropriate solvent (DMF, dioxane, toluene, THF, 1,2-dimethoxyethane or the like) or as neat in the presence or absence of a base (pyridine, triethylamine or the like) at 0° C. to 200° C.

(HH) The preparation of the compound having aryl or heteroaryl on $R^1$, $R^2$, $R^5$ or $R^6$ among the objective compound [I] can be carried out by using any conventional method of so-called Stille coupling or Suzuki coupling reaction. For example, the preparation can be preferably carried out by treating the compound having the corresponding haloaryl with aryltrialkyltin, heteroaryltrialkyltin, aryldihydroxyborane, heteroaryldihydroxyborane, arylcatecholborane, heteroarylcatecholborane or the like in the presence of a metal catalyst (for example, dichlorobis(triphenylphosphine)palladium, tetrakis(triphenylphosphine)palladium, tris(dibenzylideneacetone)dipalladium, dichloro [1,1'-bis(diphenylphosphino)ferrocene]palladium, palladium acetate or the like) in an appropriate solvent (dioxane, toluene, THF, 1,2-dimethoxyethane or the like, or a mixed solvent thereof in the presence or absence of a base (triethylamine, diisopropylamine, sodium tert-butoxide, sodium carbonate, cesium carbonate, potassium phosphate or the like) at 0° C. to 200° C.

(II) In the above each reaction, a protecting group can be optionally introduced or removed to give the desired compound [I] finally. The method for introduction and removal of the protecting group can be carried out according to the description of Protective Groups in Organic Synthesis Third Edition (Theodora W. Green and Peter G. Wuts).

(JJ) Alternatively, the compound [I] can be also synthesized by optionally carrying out any of the above reaction of (A) to (II) in the compound [II] to the compound [XIII] in an appropriate stage in each process of (1) to (13).

Example of Experiment

A Glucokinase Activation Effect
(Method)

A glucokinase activity was examined by measuring the amount of NADPH obtained in generating 6-phosphogluconic acid from glucose-6-phosphoric acid by a coupling enzyme glucose-6-phosphate dehydrogenase not by measuring directly the produced glucose-6-phosphoric acid. The glucokinase enzyme used in the examination is human-liver type GST-GK expressed in *E. Coli*. The measurement of GK activity was carried out by the following procedures.

Twenty five mM HEPES buffer (pH7.4) containing 25 mM $MgCl_2$, mM KCl, 1 mM DTT, 5 mM NADP (Roche), 16.64 μg/mL G6PDH (Roche 737-232 grade II from yeast) and 2.8 μg/mL GST-GK was prepared as a reaction solution. An evaluating compound dissolved in DMSO was added to the reaction solution to give final concentration of 0.001 to 100 μM (5% DMSO). Thereto was added glucose (final concentration of 5 mM) as a substrate and was added ATP (final concentration of 5 mM), and the reaction was started. The reaction temperature is 30° C. and a generation of NADPH was monitored by changes of absorbance of 340 nm. An increasing in absorbance for 15 minutes from starting reaction was measured and the blank-corrected value was used as GK activity (mOD/min). $EC_{50}$ level was calculated by a GK activity level in at each concentration of an evaluating compound.

(Results)

| EXAMPLE No. | $EC_{50}$ (μM) |
|---|---|
| 6 | 1.20 |
| 9 | 0.55 |
| 10 | 0.79 |
| 11 | 0.88 |
| 13-3 | 0.17 |
| 18-2 | 0.93 |
| 24-25 | 0.084 |
| 46-1 | 0.10 |
| 56 | 0.32 |
| 62-5 | 0.41 |
| 62-10 | 0.27 |
| 67-2 | 0.39 |
| 82-22 | 0.26 |
| 82-78 | 0.60 |
| 84-12 | 0.41 |
| 91-8 | 0.52 |
| 94-6 | 0.51 |
| 98-1 | 0.84 |
| 98-7 | 0.23 |
| 104-2 | 0.30 |
| 116 | 0.57 |
| 139-125 | 0.76 |
| 139-244 | 0.46 |
| 139-134 | 0.18 |
| 139-94 | 0.35 |
| 139-237 | 0.60 |
| 139-41 | 0.54 |
| 139-159 | 0.52 |
| 139-182 | 0.52 |
| 139-214 | 0.57 |
| 139-221 | 0.13 |

Another objective of the present invention is to provide an industrially advantageous method for preparing 5-substituted 2-aminothiazole and a salt thereof, and it has surprisingly been found that the desired 5-substituted 2-aminothiazole compound can be prepared in high yield by using 2-aminothiazole wherein the 5-position is not substituted as a starting material. The method of the present invention is an industrially very advantageous since the starting material, 2-aminothiazole, is commercially available at a low cost compared to 5-bromo-2-aminothiazole, which gives lowering of the production cost, and further various substituents can be introduced at 5-position of 2-aminothiazole.

Thus, the present invention includes the following embodiments of the method for preparing the desired compounds:

[1] A method for preparing 5-substituted 2-aminothiazole of the general formula:

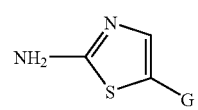

[XXI]

wherein the symbols have the same meanings as mentioned above, or a salt thereof by treating 2-aminothiazole wherein the amino group may be protected, or a salt thereof with a base, followed by treating the resultant with an electrophile of the general formula:

$$G\text{-}X \qquad [XII]$$

wherein X is a leaving group, G is halogen atom, formyl, alkoxycarbonyl, alkylthio, alkylsulfinyl, alkylsulfonyl, aminosulfonyl, dialkylsulforyl, alkylboryl or trialkylsilyl; and removing the protecting group where the amino group is protected.

[2] A method for preparing of [1] wherein 2-amino-1,3-thiazole wherein the amino group may be protected is 2-amino-1,3-thiazole wherein the amino group is protected.

[3] A method for preparing of [1] or [2] wherein G is halogen atom or formyl.

[4] A method for preparing of [1], [2] or [3] wherein the base is alkyl lithium.

[5] A method for preparing of [1], [2], [3] or [4] wherein the base is used in two or more equivalents to one equivalent of 2-amino-1,3-thiazole or a salt thereof.

5-Substituted 2-aminothiazole or a salt thereof to be prepared by the method of the present invention is preferably a compound wherein the substituent G is halogen atom or formyl. A compound wherein G is fluorine atom or formyl, particularly fluorine atom, is more preferable.

A conventional protecting group can be used as a protecting group of the amino group of the starting material, 2-aminothiazole. Said protecting group includes, for example, oxycarbonyl-type protecting group such as substituted or unsubstituted alkoxycarbonyl (for example, methoxycarbonyl, ethoxycarbonyl, 2,2,2-trichloroethoxycarbonyl, tert-butoxycarbonyl), substituted or unsubstituted aralkyloxycarbonyl (for example, benzyloxycarbonyl), or substituted or unsubstituted aryloxycarbonyl (for example, phenoxycarbonyl); formyl; carbonyl-type protecting group such as substituted or unsubstituted alkanoyl (for example, trifluoroacetyl, tert-butanoyl), or substituted or unsubstituted arylcarbonyl (for example, benzoyl); or alkyl-type protecting group such as substituted or unsubstituted alkyl (for example, tert-butyl), or substituted or unsubstituted aralkyl (for example, benzyl, benzhydryl, trityl).

A preferable protecting group among them is oxycarbonyl-type protecting group, carbonyl-type protecting group, alkyl-type protecting group, more preferably oxycarbonyl-type protecting group, carbonyl-type protecting group, particularly oxycarbonyl-type protecting group.

A preferable oxycarbonyl-type protecting group is substituted or unsubstituted alkoxycarbonyl, substituted or unsubstituted aralkyloxycarbonyl, particularly substituted or unsubstituted alkoxycarbonyl. A preferable carbonyl-type protecting group is substituted or unsubstituted alkanoyl. A preferable alkyl-type protecting group is substituted or unsubstituted aralkyl.

A preferable substituted or unsubstituted alkoxycarbonyl is tert-butoxycarbonyl. A preferable substituted or unsubstituted aralkyloxycarbonyl is benzyloxycarbonyl. A preferable substituted or unsubstituted alkanoyl is trifluoroacetyl. A preferable substituted or unsubstituted aralkyl is benzhydryl.

A salt of 2-aminothiazole wherein the amino group may be protected includes a salt with an inorganic acid such as hydrochloride, hydrobromide, hydroiodide, sulfate, nitrate or phosphate; or a salt with an organic acid such as formate, acetate, propionate, oxalate, malonate, succinate, fumarate, maleate, lactate, malate, tartarate, citrate, methanesulfonate, ethanesulfonate, benzenesulfonate or toluenesulfonate.

A strong base can be preferably used as a base of base-treatment. Such a strong base includes lithium compound such as alkyllithium, cycloalkyllithium, aryllithium, lithium amide or lithium cyclyl-amide. Among them, using alkyllithium or cycloalkyllithium is preferable, most preferably alkyllithium in particular.

Alkyllithium includes n-butyllithium, tert-butyllithium, sec-butyllithium or the like. Cycloalkyllithium includes cyclohexyllithium or the like. Aryllithium includes phenyllithium or the like. Lithium amide includes lithium dialkylamide (lithium diisopropylamide), lithium bis(trialkylsilyl)amide (lithium bis(trimethylsilyl)amide) or the like. Lithium cyclyl-amide includes lithium 2,2,6,6-tetraalkylpiperidide (lithium 2,2,6,6-tetramethylpiperidide) or the like.

The base-treatment can be carried out in an appropriate solvent under cooling. Any of aliphatic hydrocarbon-type solvent, aromatic hydrocarbon-type solvent, ether-type solvent, phosphoric amide-type solvent, urea-type solvent, amine-type solvent or a mixed solvent thereof can be preferably used as said solvent. A preferable solvent among them is ether-type solvent.

The aliphatic hydrocarbon-type solvent includes pentane, hexane, cyclohexane, preferably hexane or cyclohexane. The aromatic hydrocarbon-type solvent includes toluene, xylene, preferably toluene. The ether-type solvent includes anisole, dimethyl ether, diethyl ether, diisopropyl ether, tert-butylmethyl ether, cyclopentyl methyl ether, THE, 1,2-dimethoxyethane, preferably diethyl ether, THF, 1,2-dimethoxyethane, particularly THF. The phosphoric amide-type solvent includes hexaalkylphosphoric triamide, preferably hexamethylphosphoric triamide in particular. The urea-type solvent includes N,N'-dimethylpropyleneurea, N,N'-dimethylethyleneurea, preferably N,N'-dimethylpropyleneurea in particular. The amine-type solvent includes N,N,N',N'-tetramethylethylenediamine or the like.

The proceeding of the reaction can be promoted by adding a small portion of the phosphoric amide-type solvent, the urea-type solvent or the amine-type solvent as a co-solvent to the other solvent. For example, the co-solvent including hexamethylphosphoric triamide, N,N'-dimethylpropyleneurea, N,N'-dimethylethyleneurea or N,N,N',N'-tetramethylethylene diamine, or a mixed solvent comprising one or more kinds of these solvents can be added to the solvent including pentane, hexane, cyclohexane, toluene, xylene, anisole, dimethyl ether, diethyl ether, diisopropyl ether, tert-butylmethyl ether, cyclopentyl methyl ether, THF or 1,2-dimethoxyethane, or a mixed solvent comprising one or more kinds of these solvents. An amount of the co-solvent added in using in this way includes a range of 0.1% to 70%, preferably a range of 3% to 30% to an original solvent. In this case, the preferable original solvent among the above-mentioned is hexane, cyclohexane, toluene, diethyl ether, tert-butylmethyl ether, THF or 1,2-dimethoxyethane, or a mixed solvent comprising one or more kinds of these solvents, particularly hexane, toluene, diethyl ether, THF or 1,2-dimethoxyethane, or a mixed solvent comprising one or more kinds of these solvents. The most preferable one is THF.

The cooling condition in base-treatment includes a range of −100° C. to 25° C., preferably a range of −78° C. to 25° C. Particularly, a range of −78° C. to 0° C. is preferred.

The proceeding of the reaction can be promoted by using greater or equal to two equivalents of a base to one equivalent of 2-aminothiazole or a salt thereof in base-treatment.

An electrophile using in electrophile-treatment can include an electrophile of the general formula:

$$G\text{-}X \qquad [XXII]$$

wherein the symbols have the same meanings as mentioned above.

Any conventional leaving group can be preferably used as X of the electrophile G-X. Therefore, G-X can be, for example, halide-type electrophile using halogen atom as X, ester-type electrophile using alkoxy or the like as X, or amine-type electrophile using substituted or unsubstituted amino group as X. Also, in case that G is halogen atom or alkylthio, G-X can be dimer-type electrophile of G (in case X=G). Among them, amine-type electrophile is preferred.

The halide-type electrophile includes alkyl halocarbonate (ethyl chlorocarbonate, methyl chlorocarbonate or the like), alkylphosphoryl halide (ethylphosphoryl chloride or the like), trialkylsilyl halide (trialkylsilyl chloride, trialkylsilyl bromide or the like), alkylthio halide (methylthio chloride or the like), alkylsulfinyl halide (methylsulfinyl chloride or the like), or alkylsulfonyl chloride (methanesulfonyl chloride, ethanesulfonyl chloride or the like). Among them, alkylphosphoryl halide or trialkylsilyl halide is preferred, paricularly ethylphosphoryl chloride or trimethylsilyl chloride is most preferred. The ester-type electrophile includes dialkyl carbonate (diethyl carbonate, dimethyl carbonate or the like) or trialkyl borate (trimethyl borate, triisopropyl borate or the like). Among them, trialkyl borate is preferred, particularly trimethyl borate is most preferred. The amine-type electrophile includes N-chlorosuccinimide, N-bromosuccinimide, N-iodosuccinimide, N-fluoropyridinium, 1-fluoropyridin-2-one, N-fluoroquinuclidium, 1-chloromethyl-4-fluoro-1,4-diazoniabicyclo [2.2.2]octane bistetrafluoroborate, N-fluoroperfluoropiperidine, N-fluorobenzenesulfonylimide, N-fluorotrifluoromethanesulfonylimide, N-fluoro-N-methyl-p-toluenesulfonylamide or 2,3-dihydro-3,3-dimethyl-2-fluoro-1,2-benzothiazole-1,1-dione. Among them, N-fluorobenzenesulfonylimide or N-fluoro-N-methyl-p-toluenesulfonylamide is preferred, particularly N-fluorobenzenesulfonylimide is most preferred. The dimer-type electrophile includes dialkyl disulfide (dimethyl disulfide, bis(trifluoromethyl)disulfide or the like) or halogen molecule (fluorine, chlorine, bromine or iodine). Among them, dialkyl disulfide is preferred, particularly dimethyl disulfide is most preferred.

The electrophile-treatment can be carried out in an appropriate solvent under cooling. The solvent can preferably include the solvent of the above-mentioned in the base-treatment.

The base-treatment and the electrophile-treatment can be carried out in the same solvent by selecting an appropriate solvent. In this case, the electrophile-treatment can be carried out sequentially in the solvent used in the base-treatment. Such a solvent includes a mixed solvent of THF and hexane, a mixed solvent of diethyl ether and hexane, or the like.

The cooling condition of the electrophile-treatment includes a range of −100° C. to 25° C., preferably a range of −78° C. to 25° C.

The protecting group which protects the amino group of 5-substituted 2-aminothiazole compound or a salt thereof can be removed by the conventional method. A removing method of such a protecting group includes, for example, acidolysis, acid hydrolysis, alkali hydrolysis, catalytic reduction or the like.

The acidolysis can be carried out by using an acid such as trifluoroacetic acid, hydrochloric acid, sulfuric acid, titanium tetrachloride or stannic chloride in an appropriate solvent (for example, methylene chloride, chloroform, toluene, methanol, ethanol, THF, water or the like). The acid hydrolysis can be carried out by using an acid such as hydrochloric acid or sulfuric acid in an appropriate solvent (for example, water, or a mixed solvent of methanol, ethanol, THF or the like with water). Also, the alkali hydrolysis can be carried out by using sodium hydroxide, potassium hydroxide, potassium carbonate, sodium carbonate, sodium bicarbonate or the like in a solvent such as water, methanol, ethanol or THF.

The resulting 5-substituted 2-aminothiazole compound or a salt thereof can be the desired salt by the conventional method. The salt of 5-substituted 2-aminothiazole compound includes a salt with an inorganic acid such as hydrochloride, hydrobromide, hydroiodide, sulfate, nitrate, phosphate; or a salt with an organic acid such as formate, acetate, propionate, oxalate, malonate, succinate, fumarate, maleate, lactate, malate, tartarate, citrate, methanesulfonate, ethanesulfonate, benzenesulfonate, toluenesulfonate. Moreover, in case that substitutent at 5-position has an acidic group, the salt includes a salt with an inorganic base such as alkali metal including lithium, sodium or potassium, alkali earth metal including calcium or magnesium, or other metal including zinc or aluminum; or a salt with an organic base such as ammonium, choline, diethanolamine, lysine, ethylenediamine, tert-butylamine, tert-octylamine, tris(hydroxymethyl)aminomethane, N-methylglucosamine, triethanolamine or dehydroabiethylamine.

In the above method for preparing of the present invention, aryl and aryl in aralkyl include monocyclic, bicyclic or tricyclic aryl having 6 to 14 carbons, preferably 6 to 10 carbons, specifically phenyl, naphthyl, phenanthryl, anthranyl or the like. Alkyl, alkoxy, alkanoyl, aryl or aralkyl may be substituted with one or more groups selected from halogen atom, all, alkoxy or aryl.

The other groups are the same as the above-mentioned in the oxime derivative [I].

Meanwhile, thiazole includes 1,2-thiazole (isothiazole) and 1,3-thiazole, but in the above method for preparing of the present invention, it is described simply as "thiazole" in the meaning of 1,3-thiazole.

In the present specification, DMF repersents N,N-dimethylformamide and THF represents tetrahydrofuran.

EFFECT OF THE INVENTION

The compound [I] of the present invention or a pharmaceutically acceptable salt thereof is useful for preventing or treating diseases involving glucokinase, for example, diabetes, particularly type 2 diabetes, or chronic complications associated with diabetes such as retinopathy, nephropathy, neuropathy, ischemic heart disease or arteriosclerosis, additionally obesity, because of its excellent glucokinase activation effect.

On the other hand, 5-substituted 2-aminothiazole compound or a salt thereof can be prepared in a good yield by the method for the preparing of the present invention. Also, the method for the preparing of the present invention is an industrially advantageous method which can introduce various substituents at 5-position of 2-aminothiazole depending on the kinds of the electrophile used. Additionally, it is an industrially very advantageous method because 2-aminothiazole, the starting material of the method of the present invention, is low in price compared to 5-bromo-2-aminothiazole, which gives lowering of production cost.

BEST MODE FOR CARRYING OUT THE INVENTION

The present invention is explained in more detail in the following EXAMPLES and REFERENCE EXAMPLES, but the invention is not limited to these explanations.

In EXAMPLES, APCI is atmospheric pressure chemical ionization mass spectrum and ESI is electrospray ionization mass spectrum.

EXAMPLES

Example 1

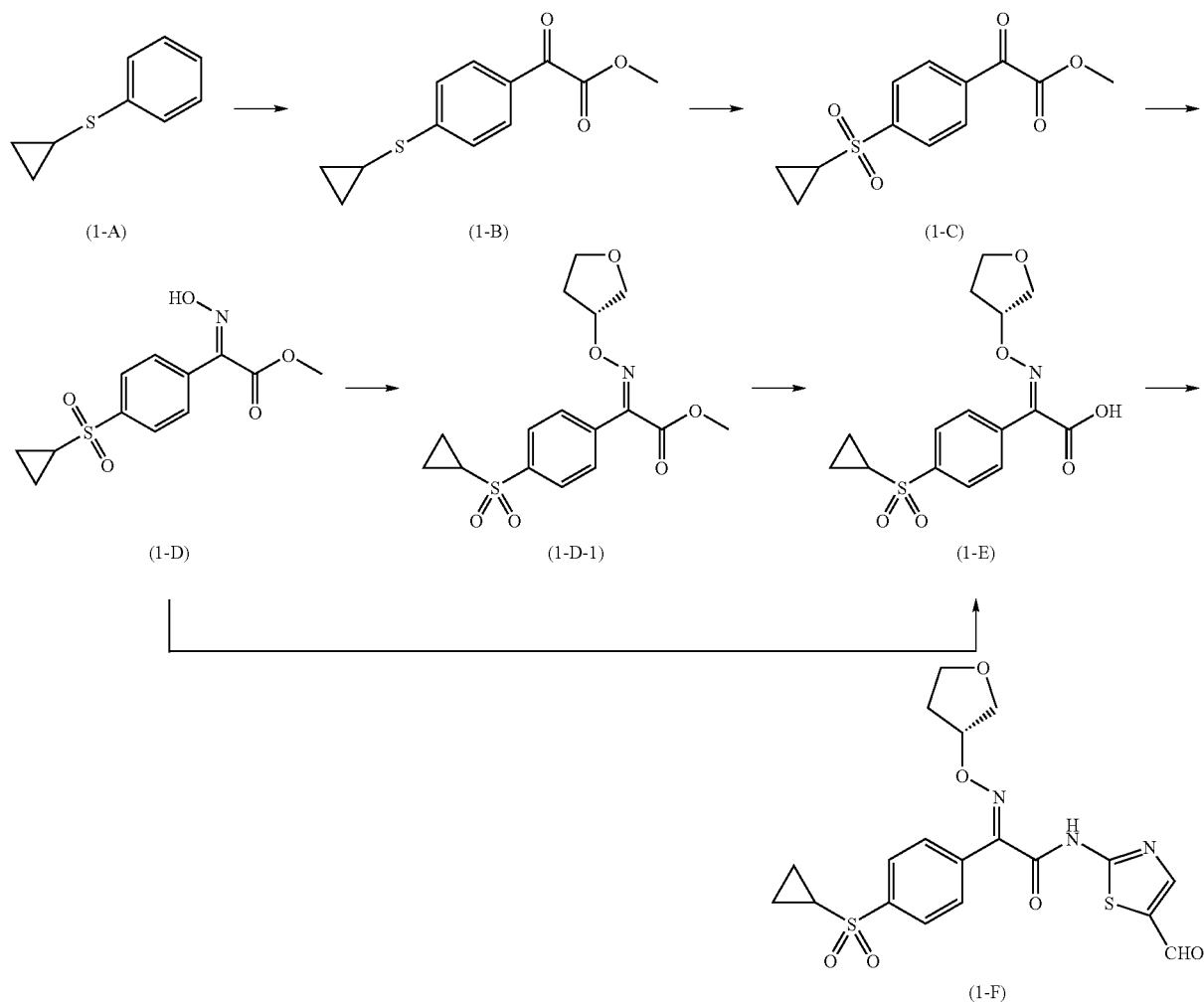

(1) To a solution of aluminum chloride (67.0 g, 503 mmol) in methylene chloride (380 ml) was added methyl chloroglyoxylate (48.9 g, 399 mmol) under ice-cooling, and the mixture was stirred for 30 minutes at the same temperature. To the mixture was added a solution of cyclopropyl phenyl sulfide (compound I-A) (50 g, 333 mmol) in methylene chloride (60 ml), and then the ice-cooling bath was removed and the mixture was stirred at room temperature for 1.5 hours. The reaction mixture was poured onto ice, and then the methylene chloride layer was separated and concentrated in vacuo. The residue was dissolved in ethyl acetate and then washed sequentially with water, a saturated aqueous sodium bicarbonate solution and brine, followed by drying over sodium sulfate and concentrated in vacuo. The residue was recrystallized from hexane to give the compound (1-B) (69.5 g, yield 88%) as pale yellow crystals.

(2) To a solution of the above compound (57.0 g, 241 mmol) in methanol-THF (1:1) (1480 ml) was added dropwise an aqueous solution (513 ml) of Oxone™ (177.9 g, 289 mmol) under ice-cooling over 1 hour, and then the mixture was stirred at room temperature for 12 hours after removing the ice bath. The insoluble materials were filtered off, and then the filtrate was concentrated in vacuo. The residue was dissolved in ethyl acetate, washed sequentially with water and brine, dried over sodium sulfate and concentrated in vacuo. The resulting residue was recrystallized from diethyl ether to give the compound (1-C) (44.3 g, yield 69%) as pale yellow crystals.

(3) To a solution of the above compound (65.0 g, 242 mmol) in methanol (450 ml) was added hydroxylamine hydrochloride (23.6 g, 339 mmol) at room temperature, and the mixture was heated to reflux for 3 hours. The reaction mixture was concentrated in vacuo and then the residue was dissolved in ethyl acetate and washed sequentially with water and brine, followed by drying over sodium sulfate and concentrated in vacuo. The residue was dissolved in trifluoroacetic acid (200 ml) and the mixture was stirred at room temperature for 12 hours. After concentration in vacuo, the residue was recrystallized from hexane-ethyl acetate to give the compound (1-D) (53.1 g, yield 78%) as colorless crystals.

(4)

(4-1) To a solution of the above compound (37.2 g, 130 mmol), triphenylphosphine (47.7 g, 182 mmol) and (S)-3-hydroxytetrahydrofuran (26.0 g, 294 mmol) in THF (400 ml) was added dropwise diisopropyl azodicarboxylate (36.8 g, 182 mmol) under ice-cooling, and the mixture was stirred at the same temperature for 3 hours and at room temperature for another 16 hours. The reaction mixture was ice-cooled again, and thereto were added water (55 ml) and a 5.4N sodium hydroxide solution (36 ml). The mixture was stirred at the same temperature for 1 hour and concentrated. Thereto was added water, and the mixture was washed with ethyl acetate twice and then the aqueous layer was acidified with 10% hydrochloric acid to pH 2 to 3 and extracted with chloroform. The organic layer was separated, followed by washing sequentially with water and brine and drying over sodium sulfate, and concentrated in vacuo. The residue was recrystallized from ethyl acetate to give the compound (1-E) (31.6 g, yield 72%) as colorless crystals.

(4-2) The above compound (1-E) was also synthesized by using the following alternative method.

(4-2-1) To a solution of the compound (1-D) (68.1 g, 241 mmol) and potassium carbonate (66.5 g, 482 mmol) in DMF (1200 ml) was added (S)-3-tetrahydrofuranol p-toluenesulfonate (synthesized from (S)-3-hydroxytetrahydrofuran and p-toluenesulfonyl chloride) (69.9 g, 289 mmol) under ice-cooling, and the ice bath was removed. The mixture was stirred at room temperature overnight, and then diluted with ethyl acetate, washed sequentially with water and brine, dried over sodium sulfate and concentrated in vacuo to give the compound (1-D-1) (94.7 g, quantitatively).

(4-2-2) To a solution of the above compound (94.7 g) in water-methanol (1:3.3) (365 ml) was added an aqueous solution (55 ml) of sodium hydroxide (12.5 g, 312 mmol) under ice-cooling, and the mixture was stirred at the same temperature for 30 minutes. To the reaction mixture was added ethyl acetate, and the aqueous layer was separated and then acidified with 10% hydrochloric acid and extracted with chloroform. The organic layer was separated and then washed sequentially with water and brine, dried over sodium sulfate and concentrated in vacuo to give the compound (1-E) (58.5 g, yield 71%).

(5) To a solution of the compound (1-B) (41.9 g, 123 mmol), 2-amino-5-formylthiazole hydrochloride (30.4 g, 184 mmol) and N,N-dimethylaminopyridine (22.5 g, 184 mmol) in methylene chloride (1270 ml) was added dropwise N-ethyl-N'-(3-dimethylaminopropyl)carbodiimide (28.6 g, 184 mmol) at room temperature. The mixture was stirred at the same temperature for 12 hours and concentrated in vacuo. The residue was purified by silica gel column chromatography (3% methanol-chloroform) to give the compound (1-F) (33.6 g, yield 61%) as pale yellow crystals.

MS (m/z) APCI: 450 [M+H]$^+$

Example 2

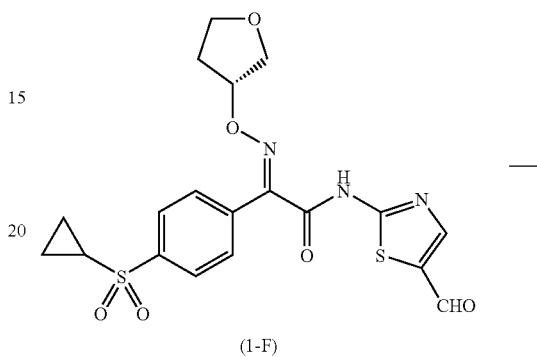

(1-F)

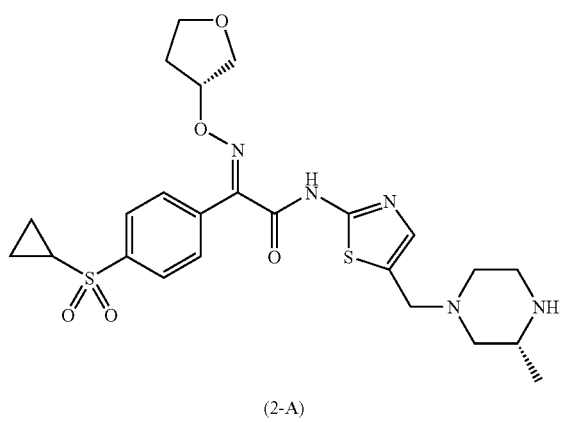

(2-A)

To a solution of the compound (1-F) (200 mg, 0.44 mmol) and (K)-2-methylpiperazine (223 mg, 2.65 mmol) in methylene chloride (4 ml) was added sodium triacetoxyborohydride (112 mg, 0.55 mmol) under ice-cooling, and the mixture was stirred at room temperature for 24 hours. To the reaction solution was added water, and the organic layer was separated, dried over magnesium sulfate and concentrated in vacuo. The residue was purified by silica gel column chromatography (NH-silica gel; 1 to 6% methanol-chloroform) to give the compound (2-A) (116.7 mg, yield 49%) as colorless crystals.

MS (m/z) APCI: 534 [M+H]$^+$

Examples 3 to 10

Corresponding starting compounds were treated in the similar manner as EXAMPLE 2 to give the following compounds.

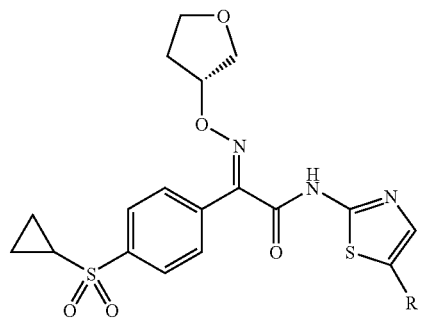
| EXAMPLE No. | No | Structure | MS (m/z) |
|---|---|---|---|
| 3 | | 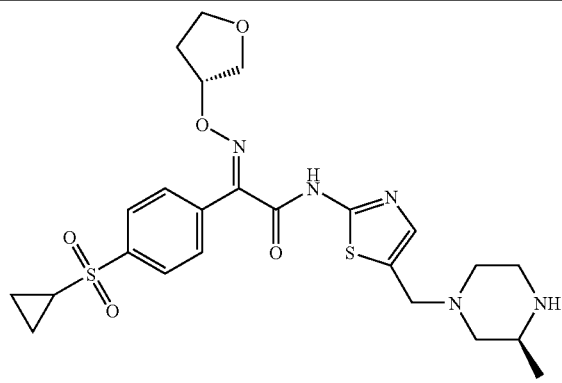 | 534 APCI [M + H]+ |
| 4 | | 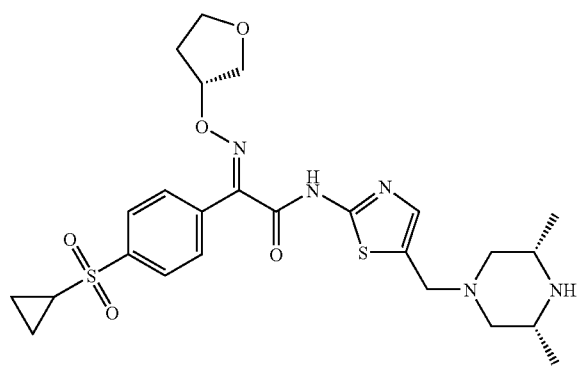 | 548 APCI [M + H]+ |
| 5 | | 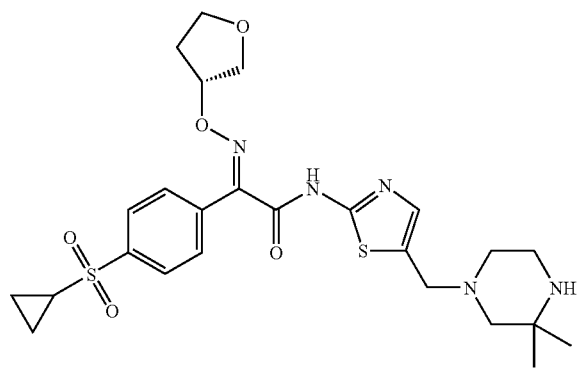 | 548 APCI [M + H]+ |

-continued
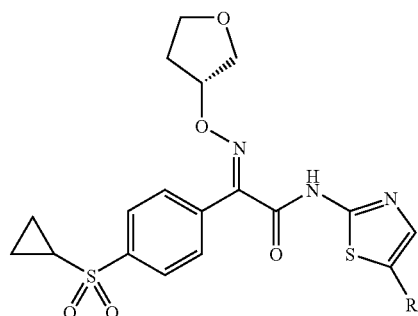
| EXAMPLE No. | No | Structure | MS (m/z) |
|---|---|---|---|
| 6 | | 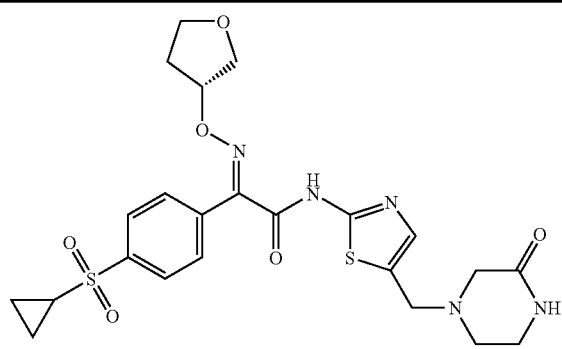 | 534 APCI [M + H]+ |
| 7 | | 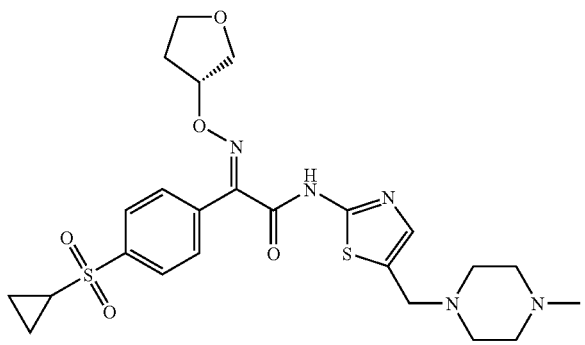 | 534 APCI [M + H]+ |
| 8 | | 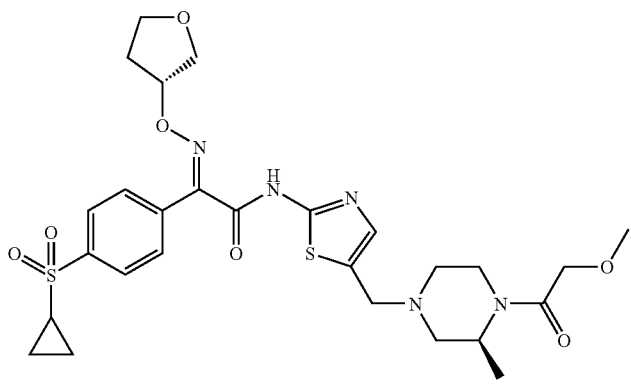 | 606 APCI [M + H]+ |

-continued

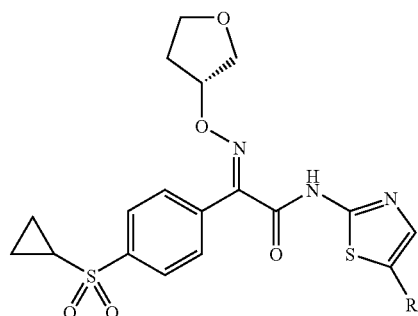

| EXAMPLE No. | No | Structure | MS (m/z) |
|---|---|---|---|
| 9 | | 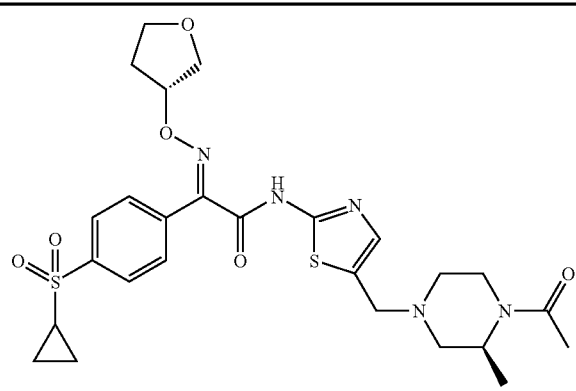 | 576 APCI [M + H]⁺ |
| 10 | | 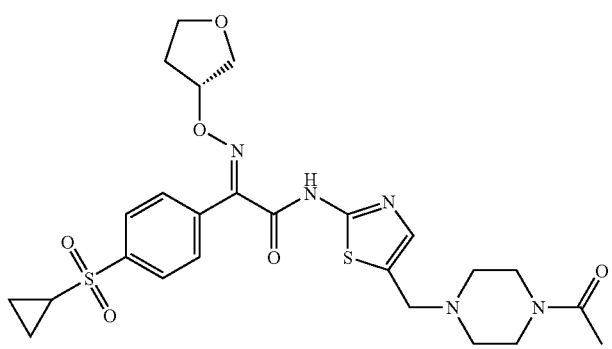 | 562 APCI [M + H]⁺ |

Example 11

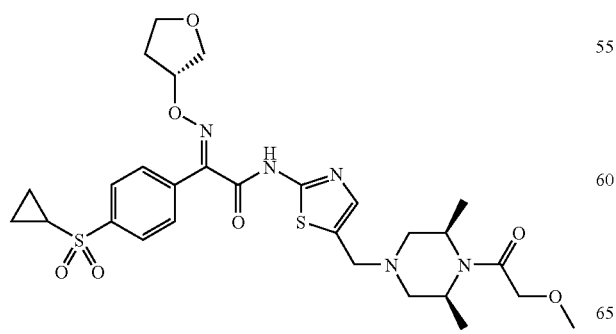

To a solution of the compound of EXAMPLE 4 (30 mg, 0.055 mmol) and diisopropylethylamine (21 mg, 0.165 mmol) in chloroform (1.5 ml) was added methoxyacetyl chloride (9.0 mg, 0.083 mmol) under ice-cooling, and the mixture was stirred at room temperature for 24 hours. To the reaction mixture was added an aqueous sodium bicarbonate solution. The organic layer was separated and concentrated in vacuo. The residue was purified by LC/MS (Xterra Prep MS C18 5 μm, 30×50 mm; MeOH-10 mM (NH$_4$)$_2$CO$_3$aq, 40:60 to 70:30) to give the above compound (13 mg, yield 43%) as colorless crystals.

MS (m/z) ESI: 620 [M+H]⁺

Example 12

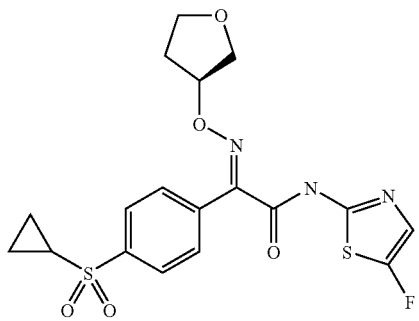

(1) An enantiomer ((S)-isomer) of the compound (1-E) was synthesized by reacting in the similar manner as EXAMPLE 1-(4) using the corresponding antipode ((R)-isomer) as an alternative to (S)-3-hydroxytetrahydrofuranol used in EXAMPLE 1-(4) or a tosylate thereof.

(2) The titled compound was obtained by reacting the above compound in the similar manner as EXAMPLE 1-(5).

MS (m/z) APCI: 440 [M+H]$^+$

Example 13

Corresponding starting compounds were reacted in the similar manner as EXAMPLE 1-(5) to give the following compounds.

| EXAMPLE No. | No | Structure | MS (m/z) |
|---|---|---|---|
| 13 | 1 | | 489 APCI [M + H]$^+$ |
| 13 | 2 | | 466 APCI [M + H]$^+$ |
| 13 | 3 | | 560 APCI [M + H]$^+$ |

| EXAMPLE No. | No | Structure | MS (m/z) |
|---|---|---|---|
| 13 | 4 | | 603 APCI [M + H]+ |
| 13 | 5 | | 546 APCI [M + H]+ |
| 13 | 6 | | 560 APCI [M + H]+ |

| EXAMPLE No. | No | Structure | MS (m/z) |
|---|---|---|---|
| 13 | 7 | 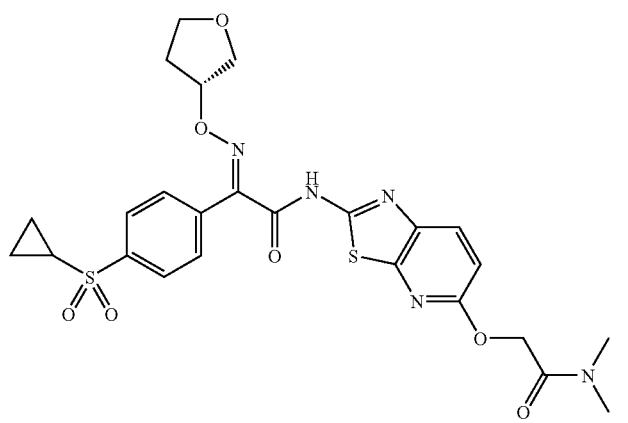 | 574 APCI [M + H]+ |
| 13 | 8 | 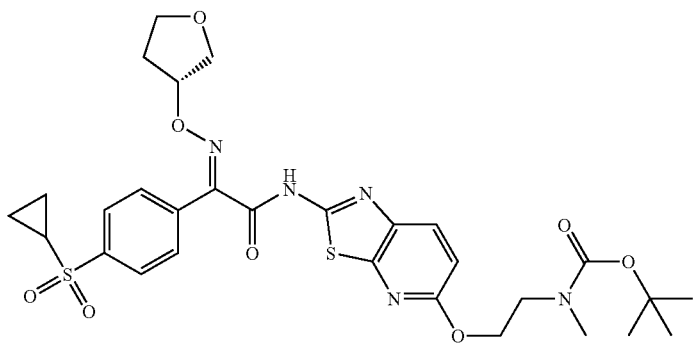 | 646 APCI [M + H]+ |
| 13 | 9 | 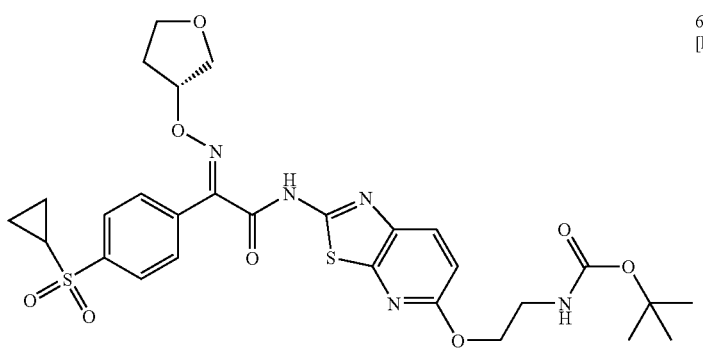 | 632 APCI [M + H]+ |

Example 14

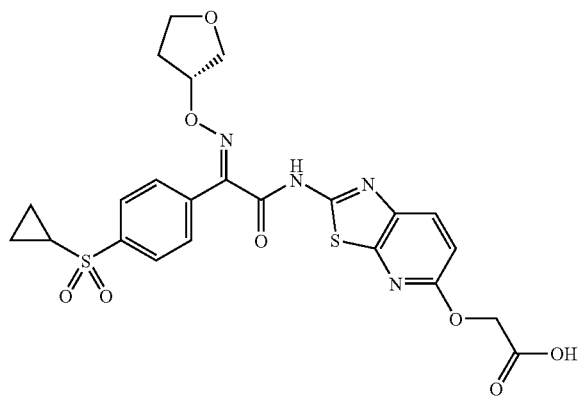

The compound of EXAMPLE 13-(4) (2.69 g, 4.46 mmol) was dissolved in formic acid (50 ml). The mixture was stirred at room temperature for 20 hours and concentrated in vacuo. The residue was chased with toluene and solidified with ethyl acetate-hexane to give the above compound (2.46 g, quantitatively)

MS (m/z) ESI: 545 [M−H]⁻

Example 15

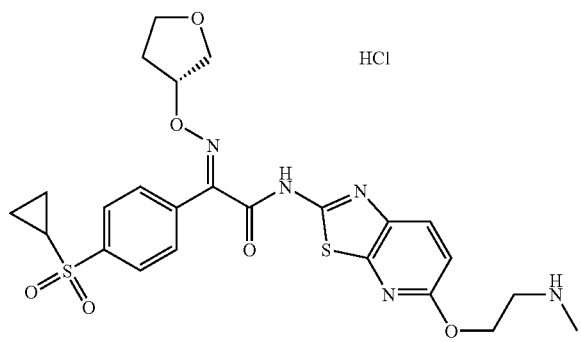

To a suspension of the compound of EXAMPLE 13-(8) (151 mg, 0.234 mmol) in ethyl acetate (3 ml) was added a 4M hydrogen chloride solution in dioxane (6 ml, 24 mmol) at room temperature. The mixture was stirred for 16 hours at the same temperature and then diluted with diethyl ether. The precipitated crystals were collected and dried to give the above compound (127 mg, yield 93%).

MS (m/z) APCI: 546 [M+H]⁺

Example 16

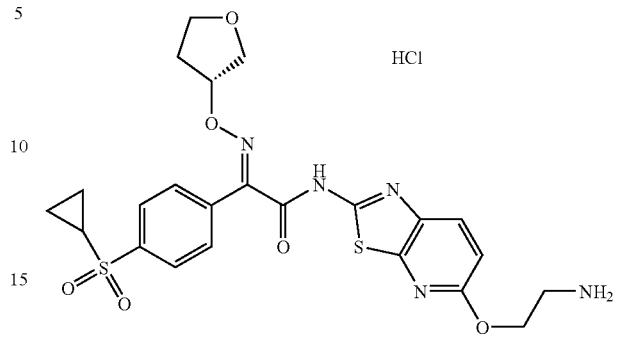

The compound of EXAMPLE 13-(9) was treated in the similar manner as EXAMPLE 15 to give the above compound.

MS (m/z) APCI: 532 [M+H]⁺

Example 17

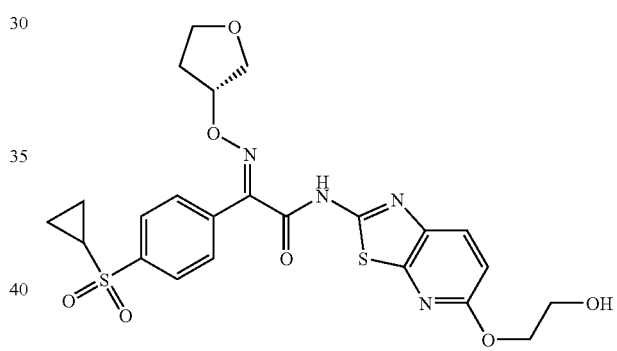

To a solution of the carboxylic acid (1-E) of EXAMPLE 1 (100 mg, 0.295 mmol) and the amine of REFERENCE EXAMPLE 8 (68.5 mg, 0.324 mmol) in THF—N-methylpyrrolidone (1:1) (6 ml) was added 4-(4,6-dimethoxy-1,3,5-triazin-2-yl)-4-methylmorpholinium chloride (hereinafter called DMT-MM) (90 mg, 0.325 mmol) at room temperature. The mixture was stirred for 20 hours at the same temperature and diluted with diisopropyl ether-hexane. The resulting precipitates were collected and purified by LC/MS (Xterra Prep MS C18 5 μm, 30×50 mm; MeOH-10 mM (NH₄)₂CO₃aq, 70:30) to give the above compound (8 mg, yield 6%) as colorless crystals.

MS (m/z) APCI: 533 [M+H]⁺

Example 18

Corresponding starting compounds were treated in the similar manner as EXAMPLE 2 to give the following compounds.

| EXAMPLE No. | No | Structure | MS (m/z) |
|---|---|---|---|
| 18 | 1 | | 537 APCI [M + H]⁺ |
| 18 | 2 | | 521 APCI [M + H]⁺ |
| 18 | 3 | | 548 APCI [M + H]⁺ |
| 18 | 4 | | 553 APCI [M + H]⁺ |

-continued

| EXAMPLE No. | No | Structure | MS (m/z) |
|---|---|---|---|
| 18 | 5 | | 569 APCI [M + H]⁺ |
| 18 | 6 | | 588 APCI [M + H]⁺ |
| 18 | 7 | | 562 APCI [M + H]⁺ |
| 18 | 8 | | 562 APCI [M + H]⁺ |

| EXAMPLE No. | No | Structure | MS (m/z) |
|---|---|---|---|
| 18 | 9 | 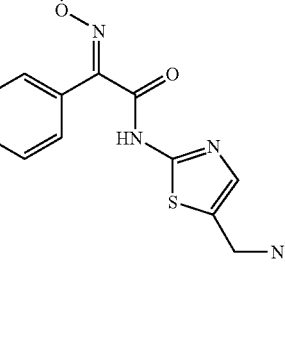 | 606 APCI [M + H]⁺ |
| 18 | 10 | 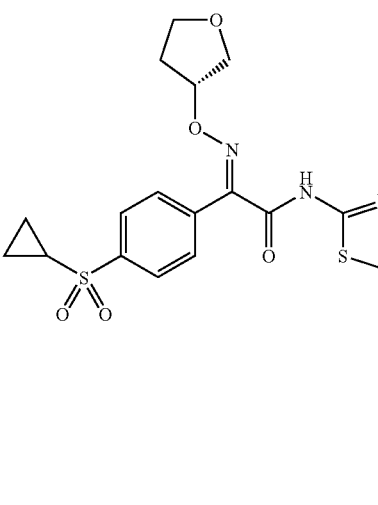 | 507 APCI [M + H]⁺ |
| 18 | 11 | 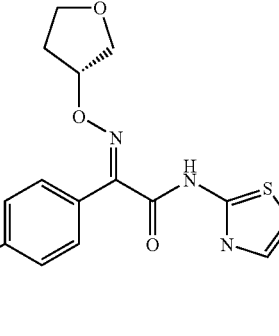 | 626 APCI [M + H]⁺ |

-continued

| EXAMPLE No. | No | Structure | MS (m/z) |
|---|---|---|---|
| 18 | 12 | | 634 APCI [M + H]+ |
| 18 | 13 | | 576 APCI [M + H]+ |
| 18 | 14 | | 548 APCI [M + H]+ |
| 18 | 15 | | 550 APCI [M + H]+ |

-continued

| EXAMPLE No. | No | Structure | MS (m/z) |
|---|---|---|---|
| 18 | 16 | | 536 APCI [M + H]+ |
| 18 | 17 | | 522 APCI [M + H]+ |
| 18 | 18 | | 548 APCI [M + H]+ |
| 18 | 19 | | 576 APCI [M + H]+ |

-continued
| EXAMPLE No. | No | Structure | MS (m/z) |
|---|---|---|---|
| 18 | 20 | 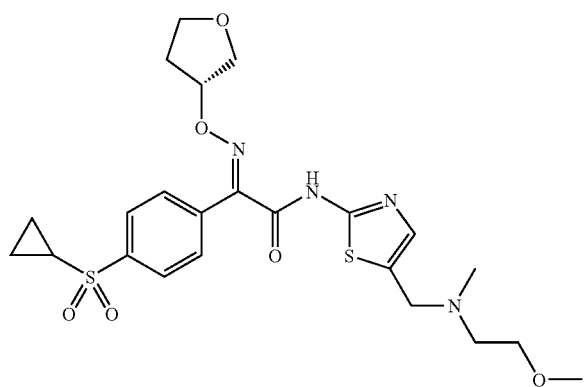 | 523 APCI [M + H]+ |
| 18 | 21 | 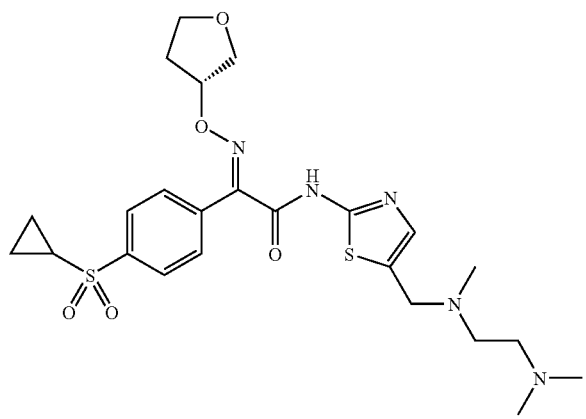 | 536 APCI [M + H]+ |
| 18 | 22 | 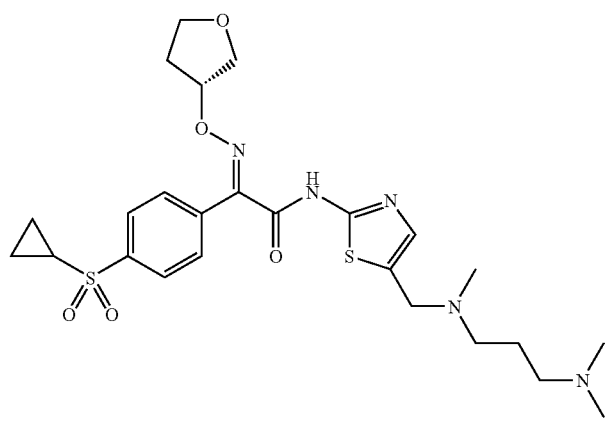 | 550 APCI [M + H]+ |

-continued

| EXAMPLE No. | No | Structure | MS (m/z) |
|---|---|---|---|
| 18 | 23 | | 567 APCI [M + H]⁺ |
| 18 | 24 | | 537 APCI [M + H]⁺ |
| 18 | 25 | | 548 APCI [M + H]⁺ |
| 18 | 26 | | 523 APCI [M + H]⁺ |

-continued
| EXAMPLE No. | No | Structure | MS (m/z) |
|---|---|---|---|
| 18 | 27 | 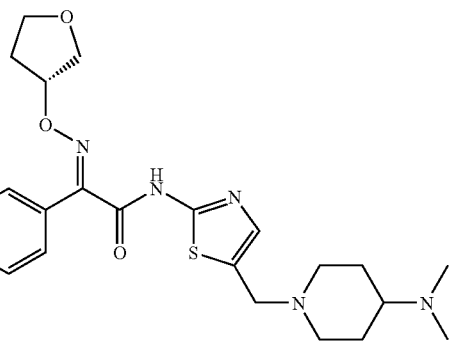 | 562 APCI [M + H]+ |
| 18 | 28 | 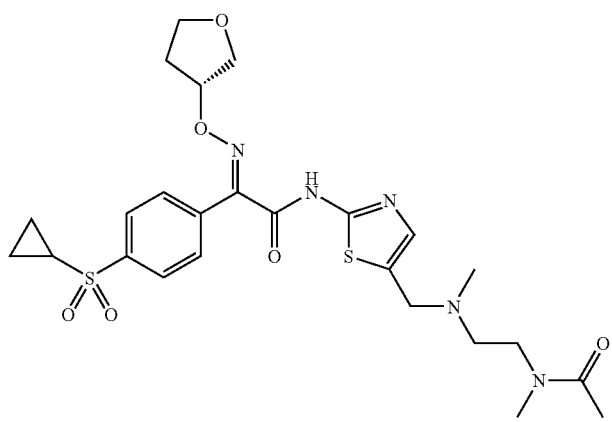 | 564 APCI [M + H]+ |
| 18 | 29 | 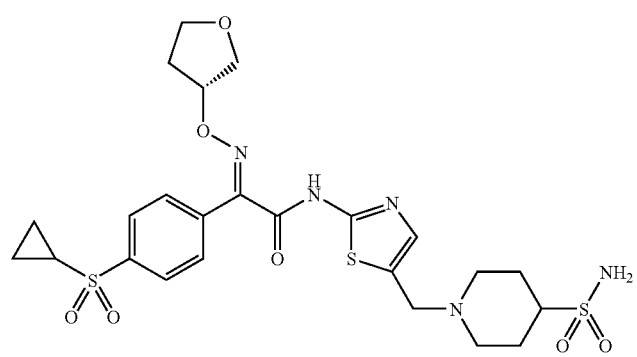 | 598 APCI [M + H]+ |
| 18 | 30 | 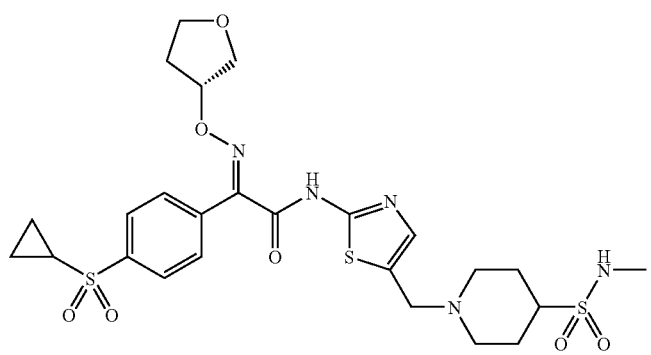 | 612 APCI [M + H]+ |

-continued

| EXAMPLE No. | No | Structure | MS (m/z) |
|---|---|---|---|
| 18 | 31 | | 626 APCI [M + H]+ |
| 18 | 32 | | 597 APCI [M + H]+ |
| 18 | 33 | | 598 APCI [M + H]+ |
| 18 | 34 | | 597 APCI [M + H]+ |

-continued
| EXAMPLE No. | No | Structure | MS (m/z) |
|---|---|---|---|
| 18 | 35 | 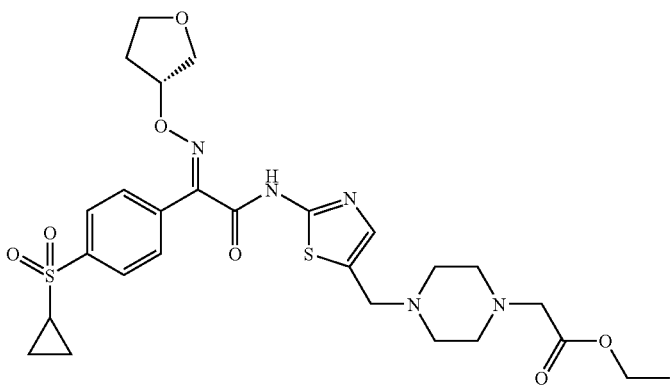 | 606 APCI [M + H]+ |
| 18 | 36 | 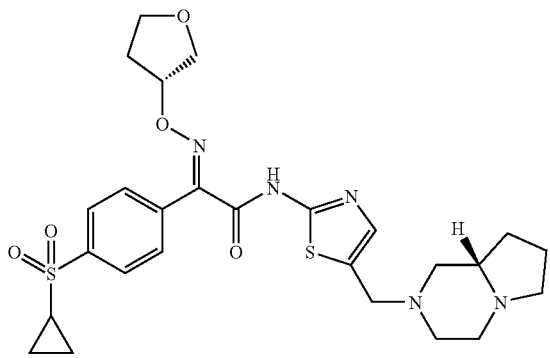 | 560 APCI [M + H]+ |
| 18 | 37 | 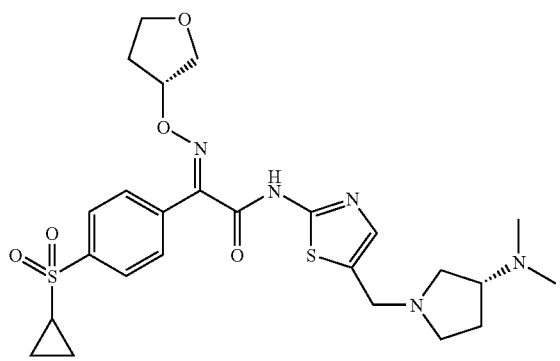 | 548 APCI [M + H]+ |
| 18 | 38 | 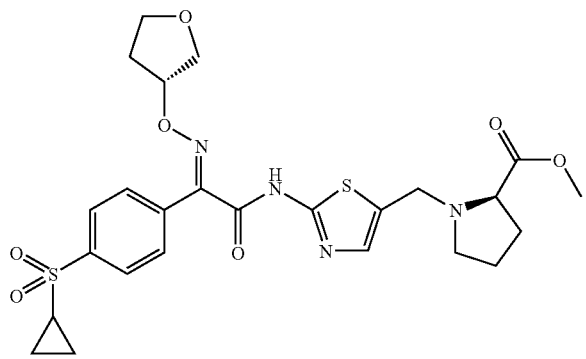 | 563 APCI [M + H]+ |

-continued
| EXAMPLE No. | No | Structure | MS (m/z) |
|---|---|---|---|
| 18 | 39 | 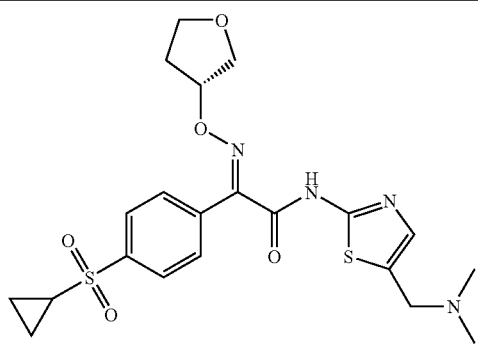 | 479 APCI [M + H]+ |
Example 19
Corresponding starting compounds were treated in the similar manner as EXAMPLE 11 to give the following compounds.
| EXAMPLE No. | No | Structure | MS (m/z) |
|---|---|---|---|
| 19 | 1 | 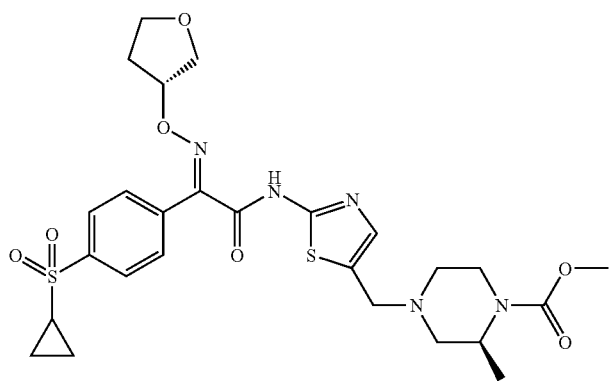 | 592 ESI+/UV [M + H]+ |
| 19 | 2 | 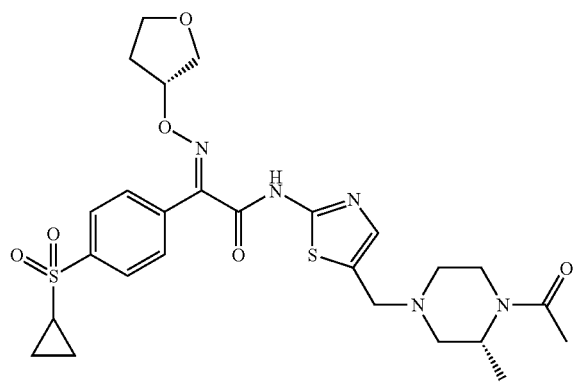 | 576 ESI+/UV [M + H]+ |

-continued

| EXAMPLE No. | No | Structure | MS (m/z) |
|---|---|---|---|
| 19 | 3 | | 606 ESI+/UV [M + H]+ |
| 19 | 4 | | 590 ESI+/UV [M + H]+ |
| 19 | 5 | | 590 ESI+/UV [M + H]+ |
| 19 | 6 | | 620 ESI+/UV [M + H]+ |

| EXAMPLE No. | No | Structure | MS (m/z) |
|---|---|---|---|
| 19 | 7 | 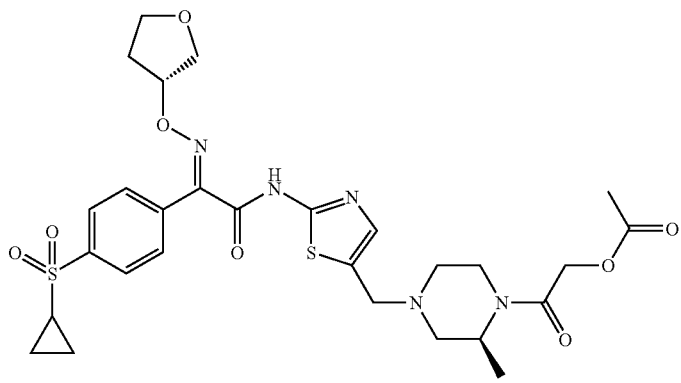 | 634 APCI [M + H]+ |
| 19 | 8 | 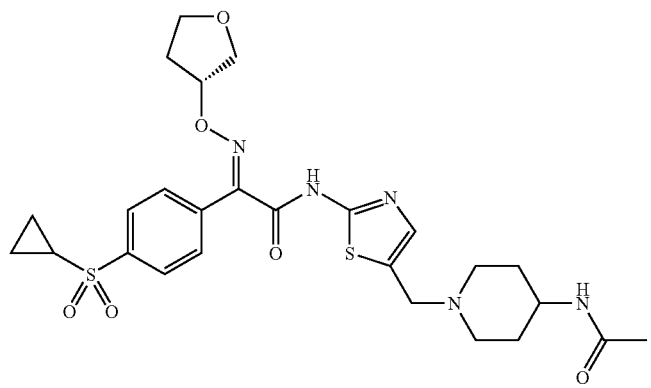 | 576 APCI [M + H]+ |
| 19 | 9 | 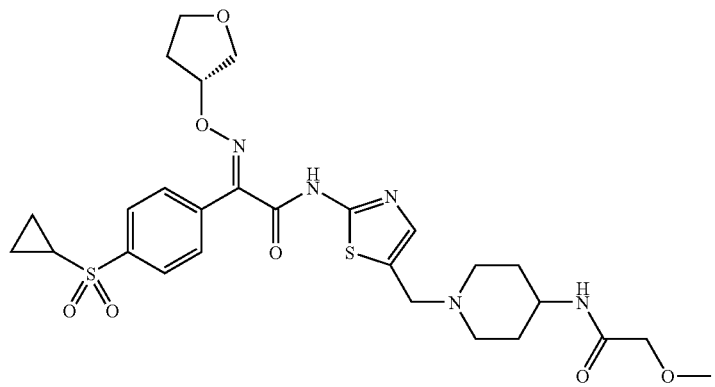 | 606 APCI [M + H]+ |
| 19 | 10 | 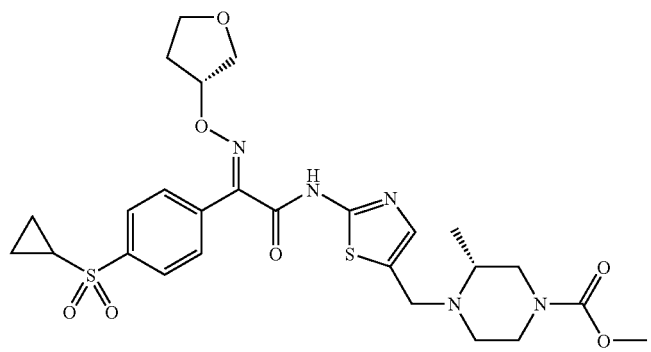 | 592 APCI [M + H]+ |

| EXAMPLE No. | No | Structure | MS (m/z) |
|---|---|---|---|
| 19 | 11 | | 576 APCI [M + H]+ |
| 19 | 12 | | 606 APCI [M + H]+ |
| 19 | 13 | | 592 APCI [M + H]+ |
| 19 | 14 | | 606 APCI [M + H]+ |

| EXAMPLE No. | No | Structure | MS (m/z) |
|---|---|---|---|
| 19 | 15 | | 592 APCI [M + H]+ |
| 19 | 16 | | 606 APCI [M + H]+ |
| 19 | 17 | | 604 APCI [M + H]+ |
| 19 | 18 | | 590 APCI [M + H]+ |

-continued

| EXAMPLE No. | No | Structure | MS (m/z) |
|---|---|---|---|
| 19 | 19 | | 606 APCI [M + H]+ |
| 19 | 20 | | 604 APCI [M + H]+ |
| 19 | 21 | | 620 APCI [M + H]+ |
| 19 | 22 | | 626 APCI [M + H]+ |

| EXAMPLE No. | No | Structure | MS (m/z) |
|---|---|---|---|
| 19 | 23 | 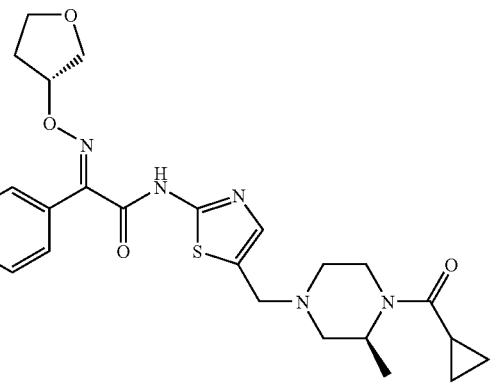 | 602 APCI [M + H]+ |
| 19 | 24 | 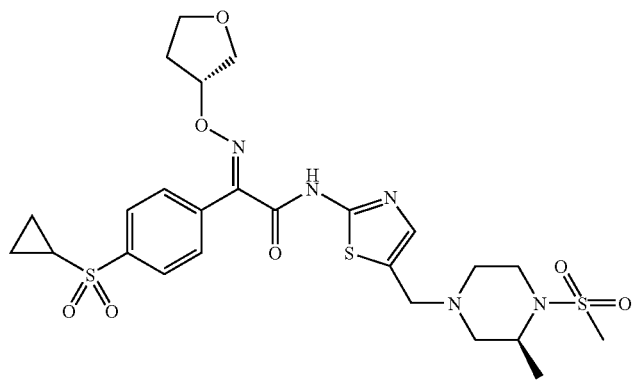 | 612 APCI [M + H]+ |
| 19 | 25 | 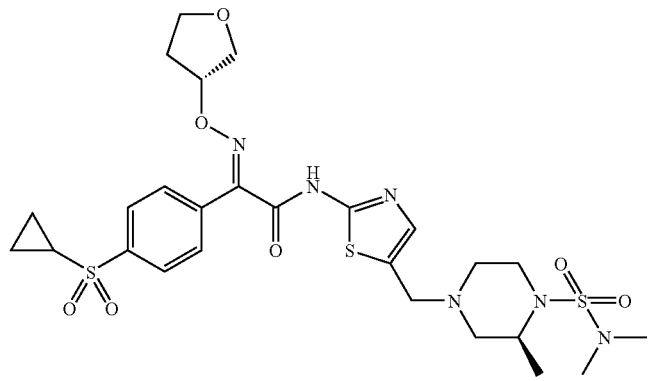 | 641 APCI [M + H]+ |
| 19 | 26 | 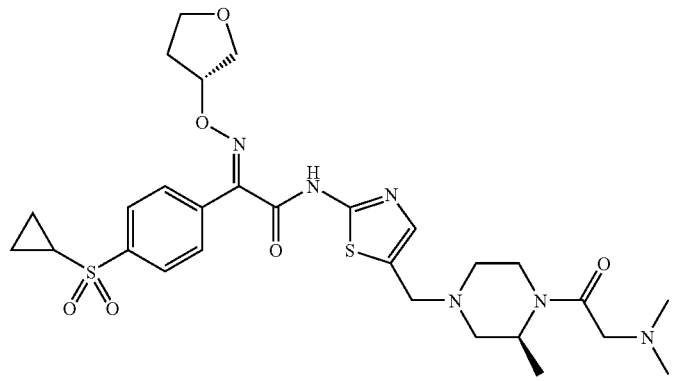 | 619 APCI [M + H]+ |

-continued

| EXAMPLE No. | No | Structure | MS (m/z) |
|---|---|---|---|
| 19 | 27 | | 630 APCI [M + H]+ |
| 19 | 28 | | 602 APCI [M + H]+ |
| 19 | 29 | | 592 APCI [M + H]+ |
| 19 | 30 | | 605 APCI [M + H]+ |

Example 20

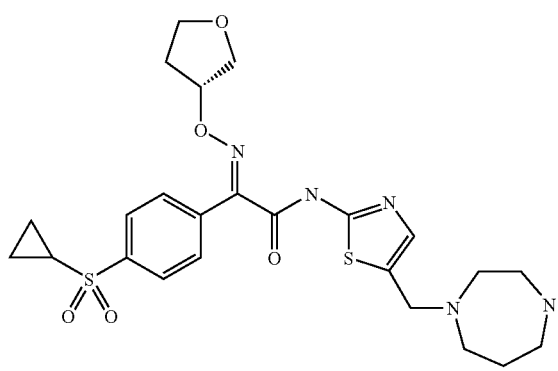

The compound of EXAMPLE (18-12) (640 mg, 1.01 mmol) was dissolved in formic acid (10 ml). The mixture was stirred at room temperature for 24 hours, concentrated, neutralized with a saturated aqueous sodium carbonate solution and extracted with methylene chloride. The organic layer was washed sequentially with water and brine, dried over magnesium sulfate and concentrated in vacuo. The residue was purified by NH-silica gel column chromatography (5% methanol-chloroform) to give the above compound (385 mg, yield 72%) as a colorless solid.

MS (m/z) APCI: 534 [M+H]$^+$

Corresponding starting compounds were converted in the similar manner as EXAMPLE 2 to the corresponding compounds having a tert-butoxycarbonyl group, and then the resulting starting compounds were treated in the similar manner as the above-mentioned to give the following compounds.

| EXAMPLE No. | No | Structure | MS (m/s) |
|---|---|---|---|
| 20 | 1 | | 534 APCI [M + H]$^+$ |
| 20 | 2 | | 534 APCI [M + H]$^+$ |
| 20 | 3 | | 534 APCI [M + H]$^+$ |

*The compound (20-3) was isolated as a dihydrochloride salt.

Example 21

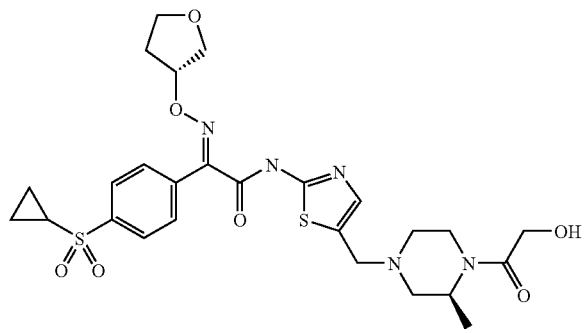

The compound of EXAMPLE 19-(7) (2.7 g, 4.26 mmol) was dissolved in methanol (30 ml), and thereto was added potassium carbonate (600 mg, 4.26 mmol) at room temperature. The mixture was stirred at room temperature for 4 hours and concentrated, and thereto was added water. The mixture was extracted with ethyl acetate, and the organic layer was washed sequentially with water and brine, dried over sodium sulfate and concentrated in vacuo. The residue was purified by silica gel column chromatography (1.5 to 10% methanol ethyl acetate) to give the above compound (1.7 g, yield 68%) as a colorless solid.

MS (m/z) APCI: 592[M+H]⁺

Example 22

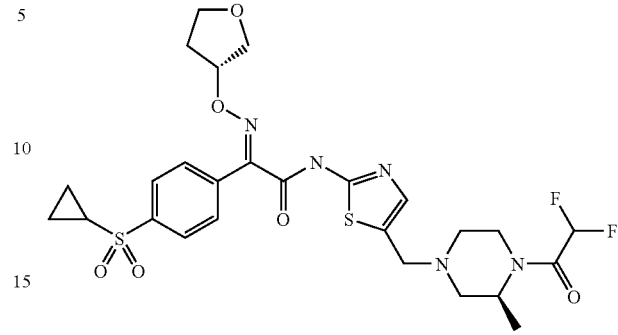

A solution of the compound of EXAMPLE 3 (80 mg, 0.15 mmol), difluoroacetic acid (0.028 ml, 0.45 mmol) and N-ethyl-N'-(3-dimethylaminopropyl)carbodiimide hydrochloride (116 mg, 0.60 mmol) in chloroform (3 ml) was stirred at room temperature for 7 hours. The reaction mixture was poured into a saturated aqueous sodium bicarbonate solution and the mixture was extracted with ethyl acetate. The organic layer was dried over sodium sulfate, concentrated in vacuo, and the residue was purified by silica gel chromatography (0 to 5% methanol-chloroform) to give the above compound (85.6 mg, yield 93%) as a colorless solid.

MS (m/z) APCI: 612[M+H]⁺

Corresponding compounds were reacted in the similar manner as the above-mentioned to give the following compounds.

| EXAMPLE No. | No | Structure | MS (m/z) |
|---|---|---|---|
| 22 | 1 | | 620 APCI [M + H]⁺ |
| 22 | 2 | | 646 APCI [M + H]⁺ |

| EXAMPLE No. | No | Structure | MS (m/z) |
|---|---|---|---|
| 22 | 3 | 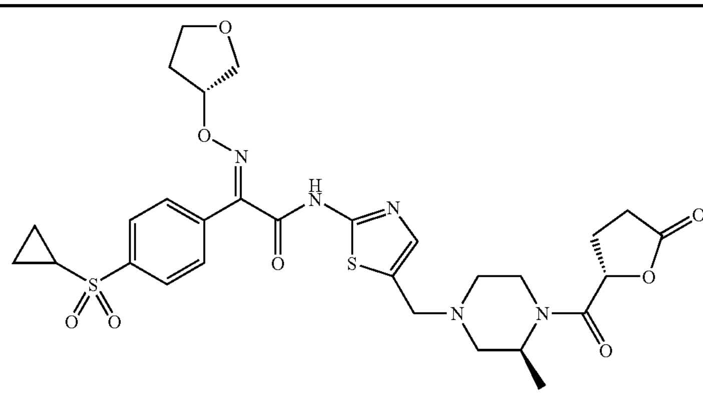 | 646 APCI [M + H]+ |

Example 23

The compound of EXAMPLE 3 (80 mg, 0.13 mmol) was dissolved in ethyl formate (3 ml), and the mixture was heated to reflux for 32 hours. The reaction mixture was concentrated and the residue was purified by silica gel column chromatography (0 to 8% methanolchloroform) to give the above compound (72.4 m g, yield 98%) as a colorless solid.

MS (m/z) APCI: 562[M+H]+

Corresponding starting compounds were reacted in the similar manner as the above-mentioned to give the following compounds.

| EXAMPLE No. | No | Structure | MS (m/z) |
|---|---|---|---|
| 23 | 1 | 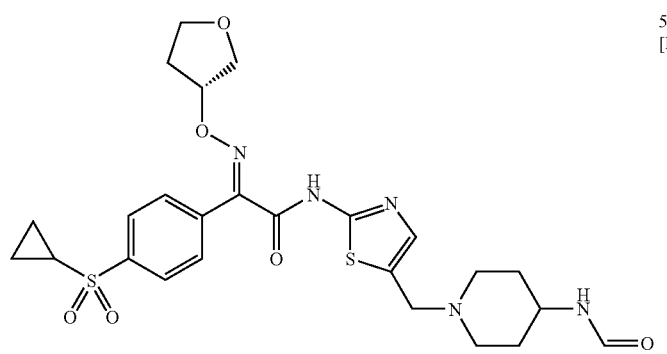 | 562 APCI [M + H]+ |

| EXAMPLE No. | No | Structure | MS (m/z) |
|---|---|---|---|
| 23 | 2 | 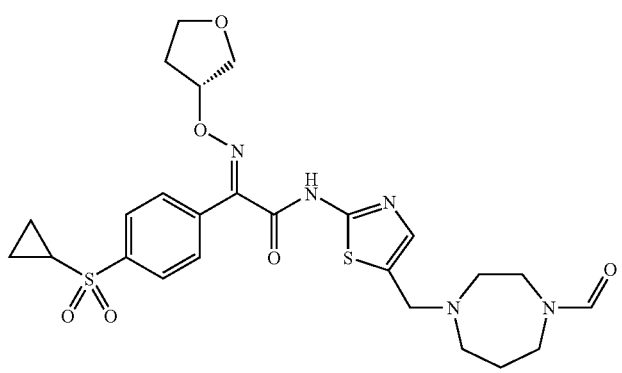 | 562 APCI [M + H]+ |
| 23 | 3 | 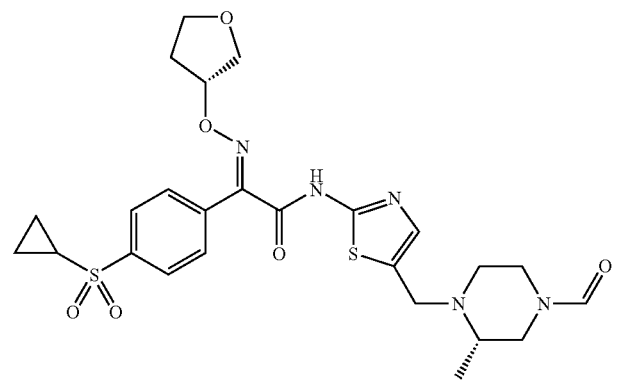 | 562 APCI [M + H]+ |
| 23 | 4 | 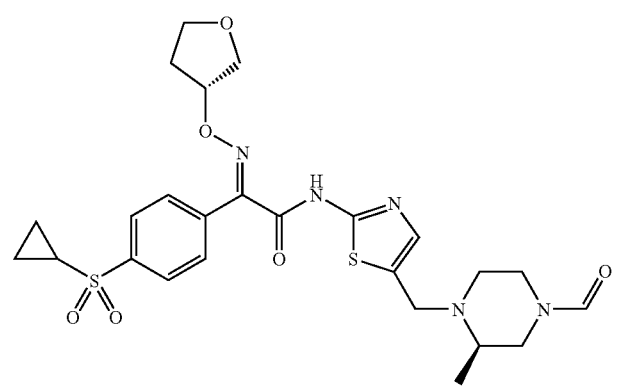 | 562 APCI [M + H]+ |

Example 24

Corresponding starting compounds were treated in the similar manner as EXAMPLE 1-(5) to give the following compounds.

| EXAMPLE No. | No | Structure | MS (m/z) |
|---|---|---|---|
| 24 | 1 | *(structure)* | 440 APCI [M + H]⁺ |
| 24 | 2 | *(structure)* | 456/458 APCI [M + H]⁺ |
| 24 | 3 | *(structure)* | 436 APCI [M + H]⁺ |
| 24 | 4 | *(structure)* | 529 APCI [M + H]⁺ |

-continued
| EXAMPLE No. | No | Structure | MS (m/z) |
|---|---|---|---|
| 24 | 5 | 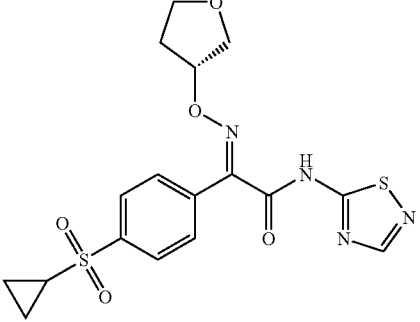 | 423 APCI [M + H]+ |
| 24 | 6 | 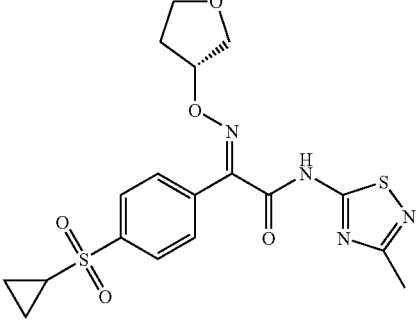 | 437 APCI [M + H]+ |
| 24 | 7 | 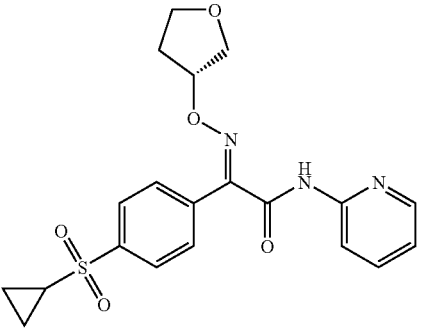 | 416 APCI [M + H]+ |
| 24 | 8 | 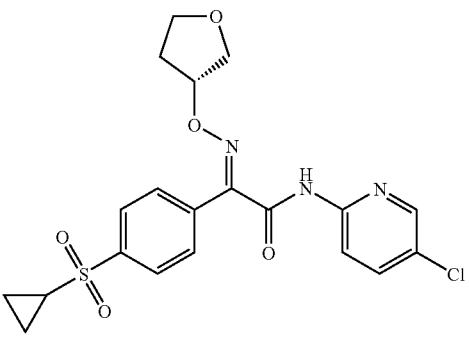 | 450/452 APCI [M + H]+ |

| EXAMPLE No. | No | Structure | MS (m/z) |
|---|---|---|---|
| 24 | 9 | 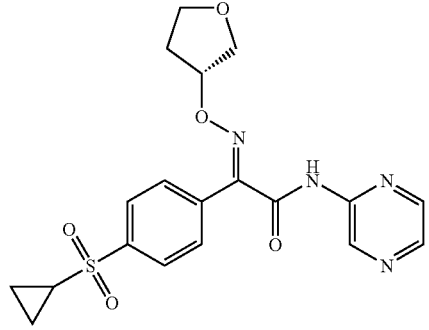 | 417 APCI [M + H]+ |
| 24 | 10 | 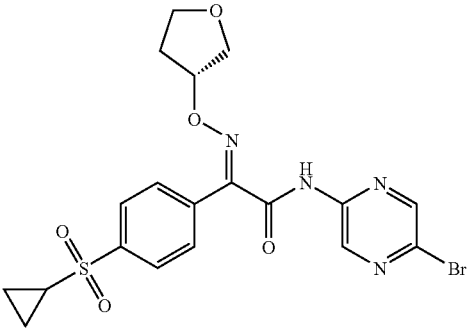 | 495/497 APCI [M + H]+ |
| 24 | 11 | 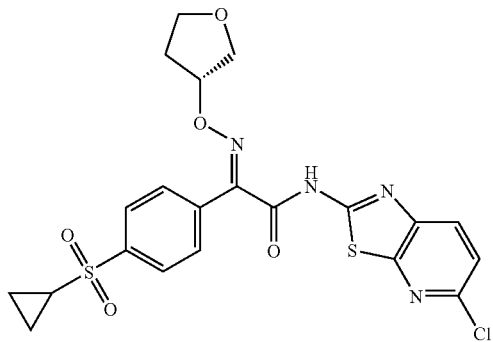 | 507/509 APCI [M + H]+ |
| 24 | 12 | 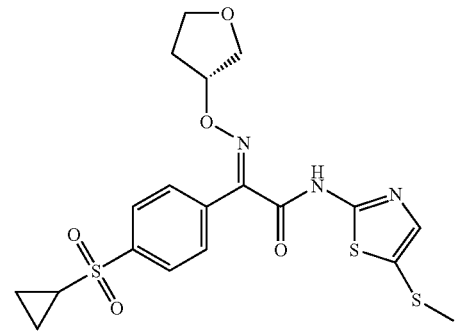 | 468 APCI [M + H]+ |

-continued
| EXAMPLE No. | No | Structure | MS (m/z) |
|---|---|---|---|
| 24 | 13 | 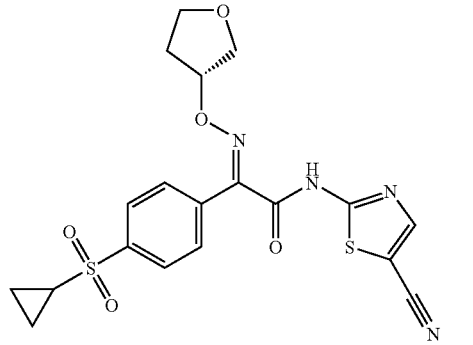 | 447 APCI [M + H]+ |
| 24 | 14 | 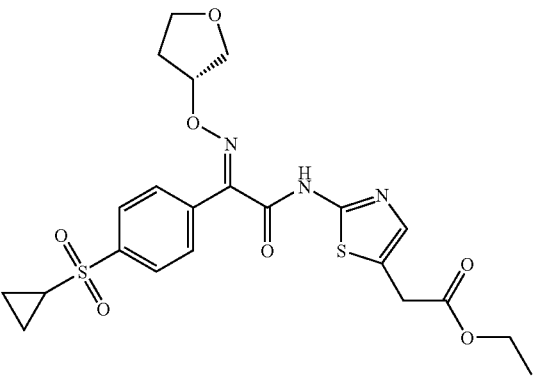 | 508 APCI [M + H]+ |
| 24 | 15 | 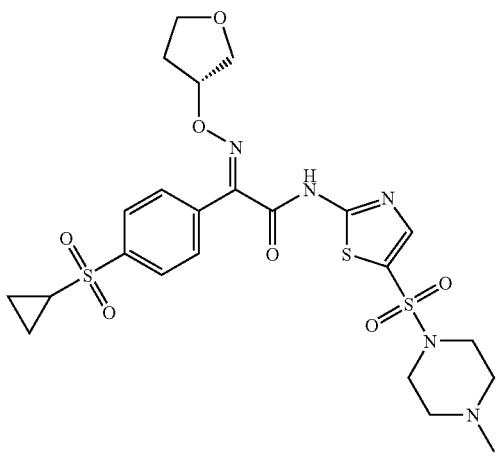 | 584 APCI [M + H]+ |
| 24 | 16 | 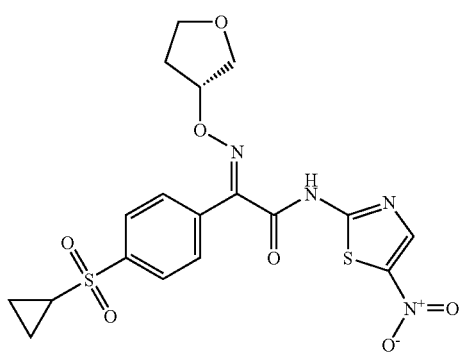 | 467 APCI [M + H]+ |

| EXAMPLE No. | No | Structure | MS (m/z) |
|---|---|---|---|
| 24 | 17 | 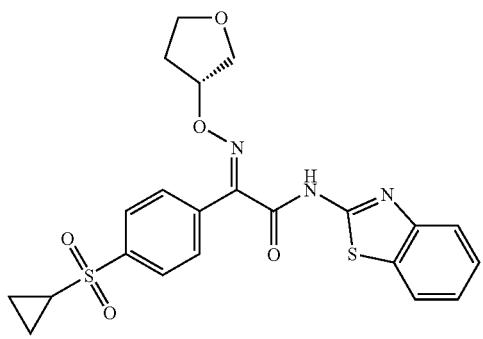 | 472 APCI [M + H]+ |
| 24 | 18 | 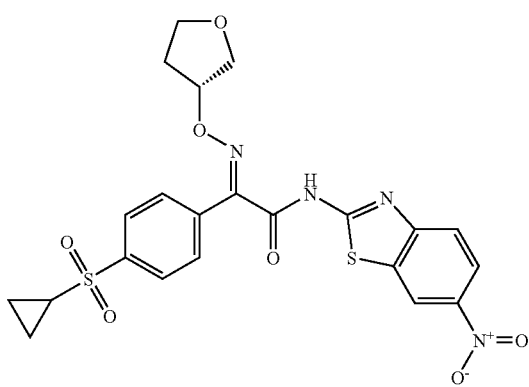 | 517 APCI [M + H]+ |
| 24 | 19 | 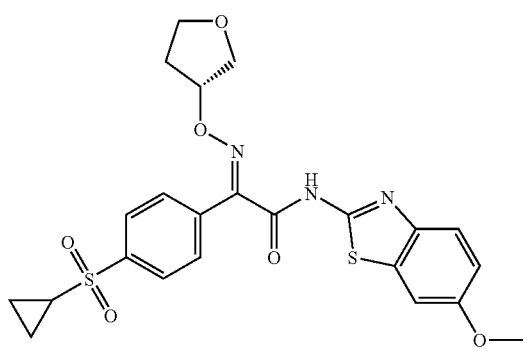 | 502 APCI [M + H]+ |
| 24 | 20 | 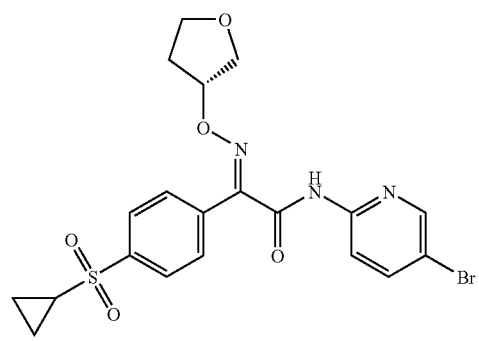 | 494/496 APCI [M + H]+ |

-continued
| EXAMPLE No. | No | Structure | MS (m/z) |
|---|---|---|---|
| 24 | 21 | 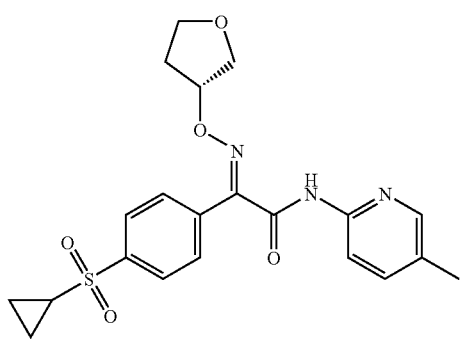 | 430 APCI [M + H]+ |
| 24 | 22 | 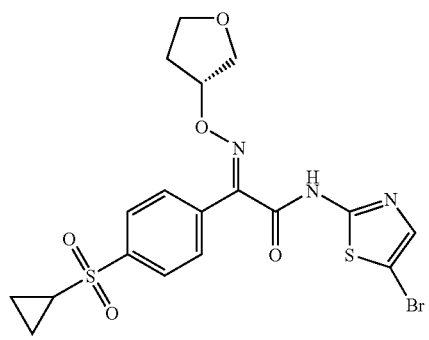 | 500/502 APCI [M + H]+ |
| 24 | 23 | 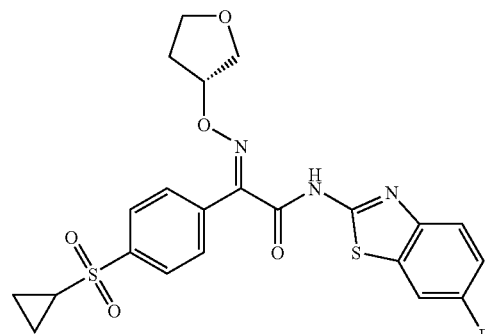 | 490 APCI [M + H]+ |
| 24 | 24 | 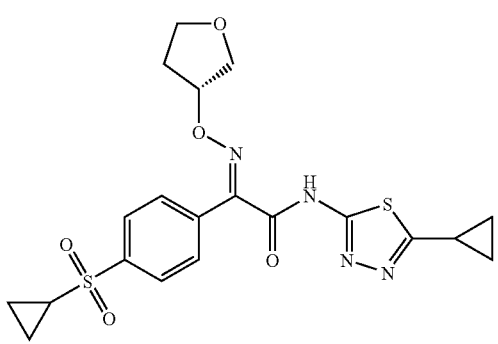 | 463 APCI [M + H]+ |

-continued
| EXAMPLE No. | No | Structure | MS (m/z) |
|---|---|---|---|
| 24 | 25 | 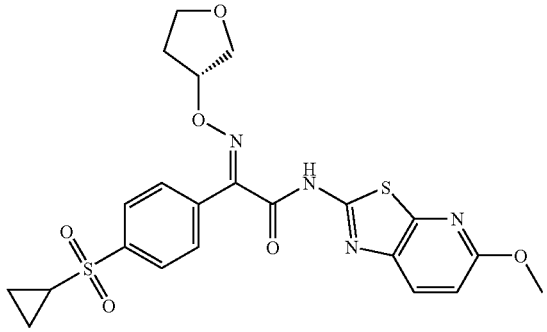 | 503 APCI [M + H]+ |
| 24 | 26 | 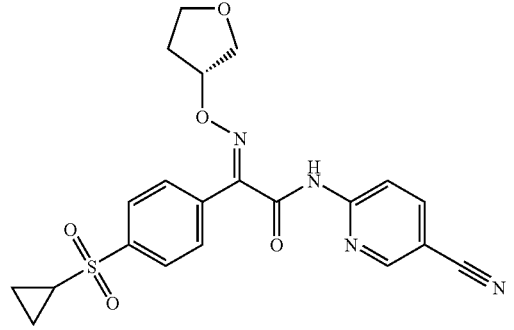 | 441 APCI [M + H]+ |
| 24 | 27 | 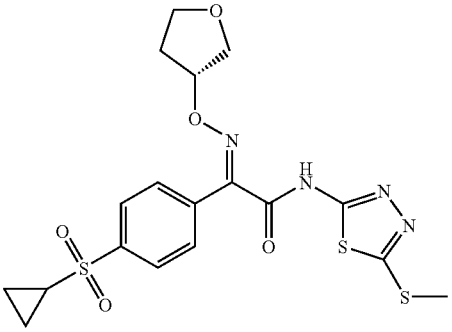 | 469 APCI [M + H]+ |
| 24 | 28 | 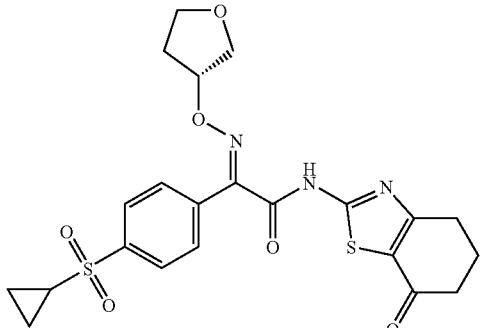 | 490 APCI [M + H]+ |

-continued

| EXAMPLE No. | No | Structure | MS (m/z) |
|---|---|---|---|
| 24 | 29 | | 434 APCI [M + H]+ |
| 24 | 30 | | 473 APCI [M + H]+ |
| 24 | 31 | | 494 APCI [M + H]+ |
| 24 | 32 | | 474 APCI [M + H]+ |

-continued
| EXAMPLE No. | No | Structure | MS (m/z) |
|---|---|---|---|
| 24 | 33 | 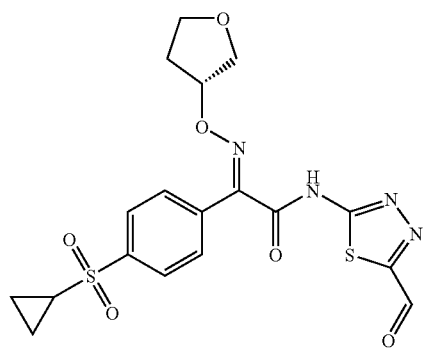 | 451 APCI [M + H]+ |
| 24 | 34 | 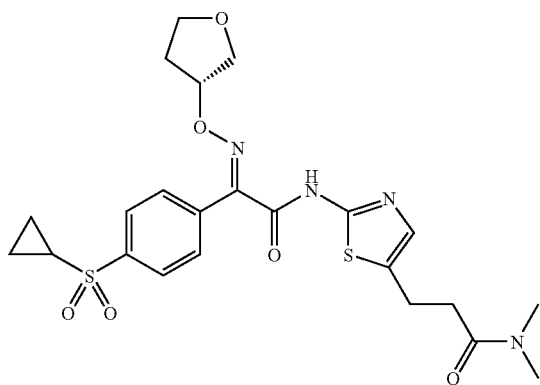 | 521 APCI [M + H]+ |
| 24 | 35 | 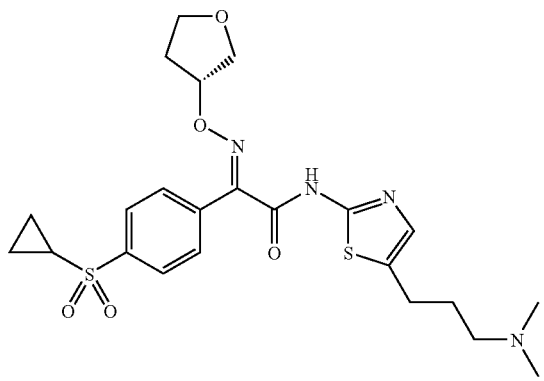 | 507 APCI [M + H]+ |
| 24 | 36 | 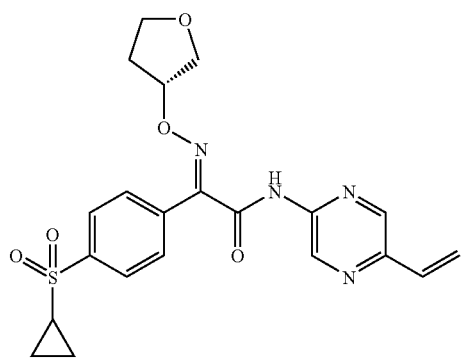 | 443 APCI [M + H]+ |

-continued
| EXAMPLE No. | No | Structure | MS (m/z) |
|---|---|---|---|
| 24 | 37 | 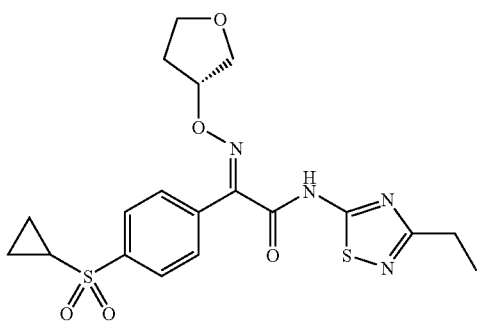 | 451 APCI [M + H]+ |
| 24 | 38 | 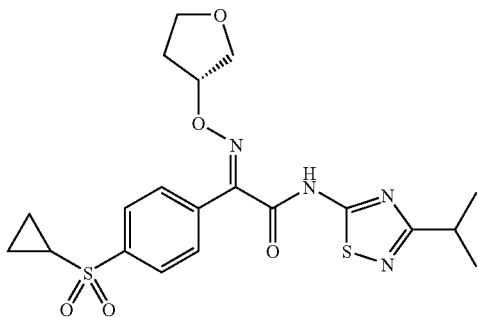 | 465 APCI [M + H]+ |
| 24 | 39 | 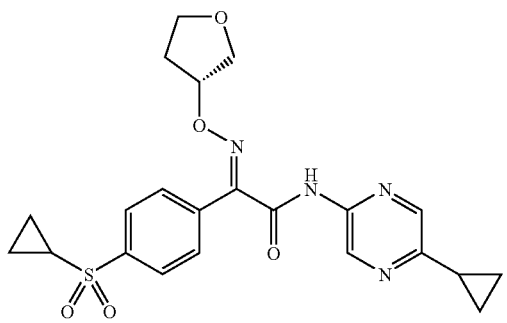 | 457 APCI [M + H]+ |
| 24 | 40 | 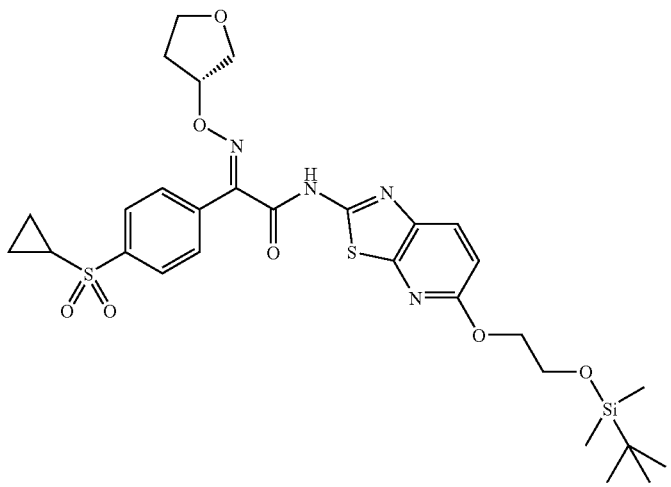 | 647 APCI [M + H]+ |

-continued

| EXAMPLE No. | No | Structure | MS (m/z) |
|---|---|---|---|
| 24 | 41 | | 471 APCI [M + H]+ |
| 24 | 42 | | 463 APCI [M + H]+ |
| 24 | 43 | | 522 APCI [M + NH4]+ |
| 24 | 44 | Chiral | 466 APCI [M + H]+ |

Example 25

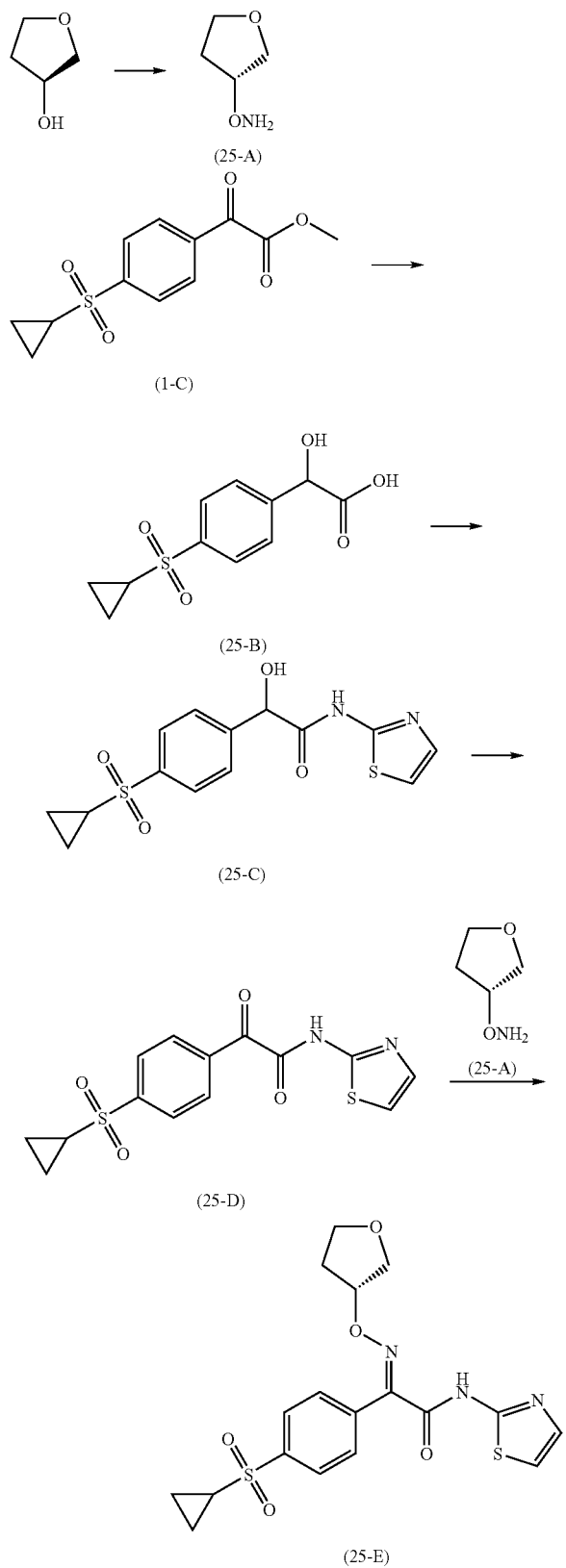

(1) To a solution of N-hydroxyphthalimide (142 g, 868 mmol), triphenylphosphine (252.9 g, 964 mmol) and (S)-3-hydroxytetrahydrofuran (70.7 g, 804 mmol) in THF (2800 ml) was added dropwise diisopropyl azodicarboxylate (195.0 g, 964 mmol) over 1.5 hours under ice-cooling. The mixture was stirred at room temperature for 16 hours and concentrated in vacuo. The residue was dissolved in ethanol (800 ml), and thereto was added hydrazine monohydrate (43.4 g, 867 mmol) at room temperature, and the mixture was heated to reflux for 4 hours and stirred at room temperature for another 40 hours. To the reaction mixture were added ethanol (500 ml) and a 4N hydrogen chloride solution in dioxane (300 ml, 1200 mmol). The precipitated crystals were filtered off. The filtrate was concentrated, and the residue was recrystallized from ethyl acetate to give the compound (25-A, monohydrochloride) (92.6 g, yield 83%) as colorless crystals.

MS (m/z) APCI: 104 [M+H]$^+$ (2) To a solution of the compound (1-C) (3.7 g, 13.8 mmol) in methanol (70 ml) was added sodium triacetoxyborohydride (7.33 g, 34.6 mmol) under ice-cooling. The mixture was stirred at the same temperature for 20 minutes, then the ice bath was removed. The reaction mixture was stirred at room temperature for another 3 hours, concentrated in vacuo, and then the residue was dissolved in ethyl acetate, washed sequentially with water and brine, dried over sodium sulfate and concentrated. The resulting crude ester (4.2 g) was dissolved in a mixed solvent of methanol (40 ml) and water (10 ml), and thereto was added a 2N aqueous sodium hydroxide solution (10.4 ml) under ice-cooling. The mixture was stirred at room temperature for 14 hours, concentrated, acidified with 10% hydrochloric acid and extracted with ethyl acetate. The organic layer was washed sequentially with water and brine, dried over sodium sulfate and concentrated. The residue was recrystallized from ethyl acetate-hexane to give the compound (25-B) (3.30 g, yield 93%) as colorless crystals.

MS (m/z) ESI: 255 [M−H]$^-$ (3) A solution of the above compound (1.58 g, 6.15 mmol), 2-aminothiazole (1.23 g, 12.3 mmol) and N,N-dimethylaminopyridine (1.13 g, 9.25 mmol) in chloroform (30 ml) was ice-cooled, and thereto was added N-ethyl-N'-(3-dimethylaminopropyl)carbodiimide hydrochloride (1.77 g, 9.23 mmol). The reaction mixture was stirred at room temperature for 20 hours, diluted with ethyl acetate, washed sequentially with a 10% aqueous citric acid solution, brine, a saturated aqueous sodium bicarbonate solution and brine, dried over sodium sulfate and then concentrated in vacuo. The residue was purified by silica gel chromatography (0 to 10% methanol-chloroform) to give crude crystals. The resulting crude crystals were washed with diethyl ether to give the compound (25-C) (1.15 g, yield 55%) as colorless crystals.

MS (m/z) APCI: 339 [M+H]$^+$ (4) To a solution of the above compound (957 mg, 2.83 mmol) in dimethylsulfoxide (30 ml) were added sequentially triethylamine (3.94 ml, 28.3 mmol) and sulfur trioxide-pyridine complex (2.25 g, 14.2 mmol) at room temperature, and the mixture was stirred at the same temperature for 1.5 hours. To the reaction mixture was added water, and the mixture was extracted with ethyl acetate. The organic layer was washed sequentially with water and brine, dried over sodium sulfate and concentrated. The residue was solidified with diisopropyl ether to give the compound (25-D) (690 mg, yield 73%) as a colorless solid.
MS (m/z) APCI: 337 [M+H]+

(5) To a solution of the above compound (107 mg, 0.31 mmol) and the compound (25-A, monohydrochloride) (89 mg, 0.64 mmol) in methanol-THF (1:1) (4 ml) was added pyridine (0.068 ml, 0.80 mmol), and the mixture was stirred at room temperature for 16 hours and then heated to reflux for 2 hours. To the reaction mixture was added water, and the mixture was extracted with ethyl acetate. The organic layer was washed sequentially with a 10% citric acid solution, water and brine, dried over sodium sulfate and concentrated. The residue was purified by silica gel column chromatography (0 to 10% methanolchloroform) to give the compound (25-E) (76 mg, (E)-isomer, yield 32%) and the corresponding (Z)-isomer (76 mg, yield 56%) as a colorless solid each.
MS (m/z) APCI: 422 [M+H]+

Example 26

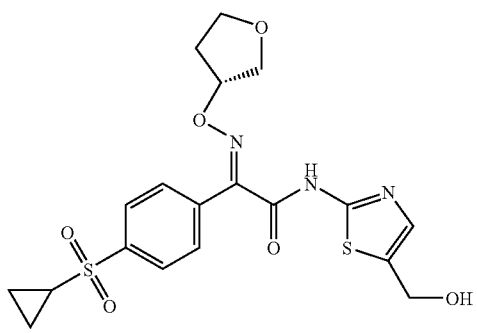

To a solution of the compound of EXAMPLE 1 (958 mg, 2.13 mmol) in methanol (40 ml) was added sodium borohydride (160 mg, 4.26 mmol) under ice-cooling, and the mixture was stirred for 2 hours at the same temperature. Acetone (1 ml) was added and the mixture was concentrated in vacuo. The resulting residue was purified by silica gel column chromatography (3 to 10% methanol-chloroform) to give the above compound (976 mg, yield 100%) as a colorless solid.
MS (m/z) APCI: 452 [M+H]+

Example 27

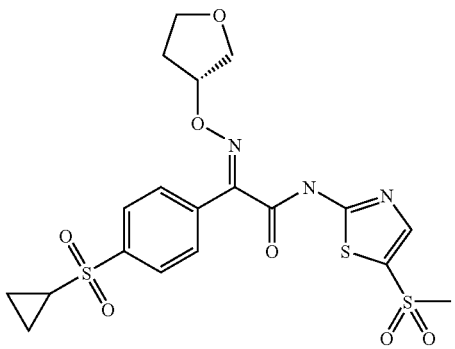

To a solution of the compound of EXAMPLE 24-(12) (150 mg, 0.32 mmol) in methylene chloride (3 ml) was added m-chloroperbenzoic acid (110 mg, 0.48 mmol) under ice-cooling. The mixture was stirred for 2 hours at the same temperature and concentrated in vacuo. The resulting residue was purified by silica gel column chromatography (1 to 8% methanol-chloroform) to give the above compound (61 mg, yield 38%) as a colorless solid.
MS (m/z) APCI: 500 [M+H]+

Example 28

The following compounds were synthesized by treating the compounds of EXAMPLE 24-(33) in the similar manner as EXAMPLE 2.

| EXAMPLE No. | No | Structure | MS (m/z) |
|---|---|---|---|
| 28 | 1 | 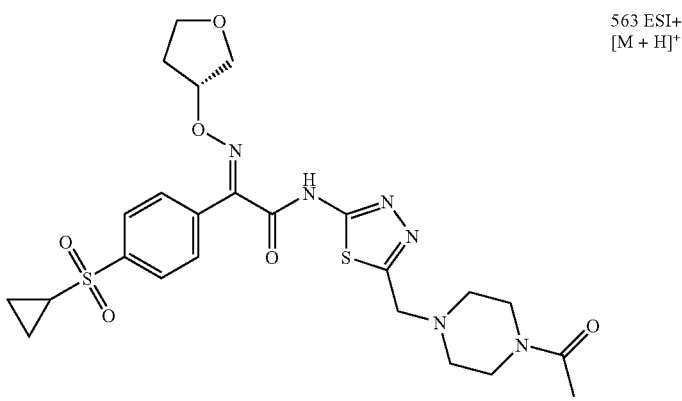 | 563 ESI+ [M + H]+ |

| EXAMPLE No. | No | Structure | MS (m/z) |
|---|---|---|---|
| 28 | 2 | | 549 ESI+ [M + H]+ |
| 28 | 3 | | 522 ESI [M + H]+ |

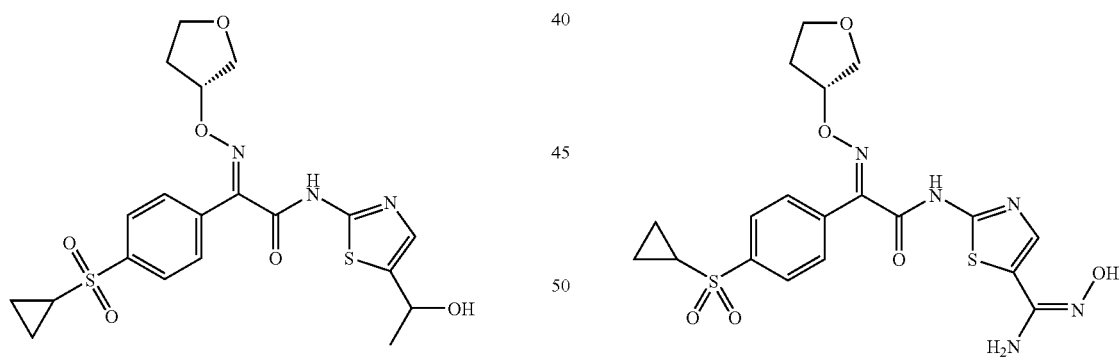

Example 29

Example 30

To a solution of the compound of EXAMPLE 1 (1.28 g, 2.85 mmol) in THF (30 ml) was added a 3M solution of methyl magnesium bromide in diethyl ether (2 ml, 5.98 mmol) at −78° C., and then the mixture was warmed to 0° C. and stirred for 1 hour at the same temperature. To the reaction mixture was added a saturated aqueous ammonium chloride solution, and the mixture was extracted with ethyl acetate. The organic layer was washed sequentially with water and brine, dried over magnesium sulfate and concentrated in vacuo. The resulting residue was purified by silica gel column chromatography (2 to 10% methanolchloroform) to give the above compound (1.03 g, yield 78%) as a colorless solid.

MS (m/z) APCI: 466 [M+H]+

To a solution of the compound of EXAMPLE 24-(13) (100 mg, 0.224 mmol) in ethanol-water (1.1) (6 ml) were added sodium carbonate (40.4 mg, 0.38 mmol) and hydroxylamine hydrochloride (57.6 mg, 0.83 mmol) at room temperature. The reaction mixture was heated to reflux for 3 hours and extracted with chloroform, and the organic layer was washed sequentially with water and brine, dried over sodium sulfate and concentrated in vacuo. The resulting residue was purified by silica gel column chromatography (5 to 10% methanol-chloroform) to give the above compound (30 mg, yield 28%) as a colorless solid.

MS (m/z) APCI: 480 [M+H]+

Example 31

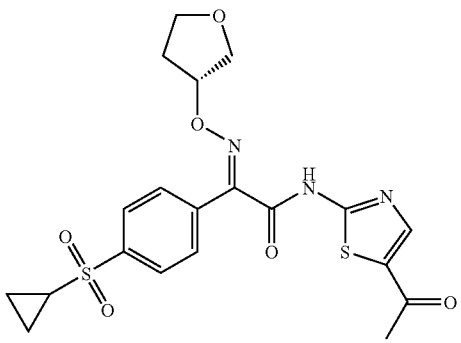

To a solution of the compound of EXAMPLE 29 (100 mg, 0.21 mmol) in methylene chloride (7 ml) was added manganese dioxide (1 g) at room temperature. The mixture was stirred for 12 hours at the same temperature and filtered through Celite. The filtrate was concentrated in vacuo, and the resulting residue was purified by silica gel column chromatography (2 to 5% methanol-chloroform) to give the above compound (77.6 mg, yield 78%) as a colorless solid.

MS (m/z) APCI: 464 [M+H]$^+$

Example 32

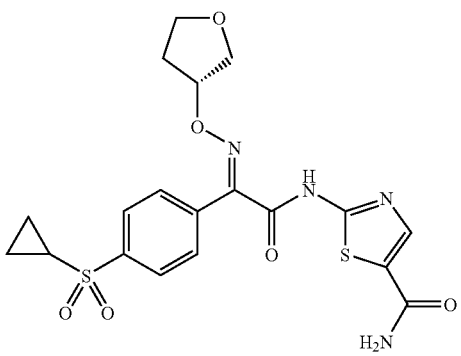

To a solution of the compound of EXAMPLE 24-(13) (100 mg, 0.22 mmol) in acetone-water (4:1) (5 ml) were added potassium carbonate (31 mg, 0.22 mmol) and a 30% aqueous hydrogen peroxide solution (0.2 ml) under ice-cooling, and the mixture was stirred at room temperature for 38 hours. To the reaction mixture was added a 10% aqueous sodium sulfite solution, and then the mixture was extracted with a mixed solvent of 10% methanol-chloroform. The organic layer was dried over sodium sulfate and concentrated in vacuo, and the resulting residue was purified by silica gel column chromatography (10% methanolchloroform) to give the above compound (74 mg, yield 71%) as a colorless solid.

MS (m/z) APCI: 465 [M+H]$^+$

Example 33

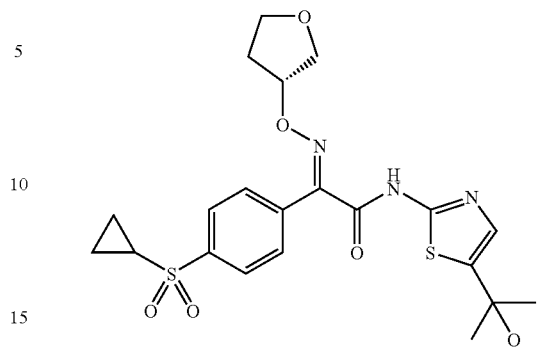

The above compound was obtained as a colorless solid by reacting the compound of EXAMPLE 31 in the similar manner as EXAMPLE 29.

MS (m/z) APCI: 480 [M+H]$^+$

Example 34

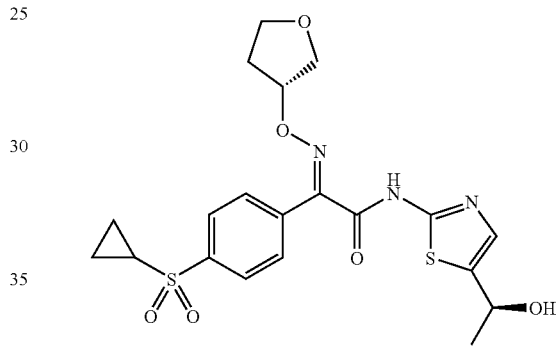

To a solution of the compound of EXAMPLE 29 (100 mg, 0.21 mmol) and vinyl acetate (0.4 ml, 4.30 mmol) in ethyl acetate (5 ml) was added Lipase PS (manufactured by Amano Pharmaceutical Co., Ltd.) (1.0 g) at room temperature, and the mixture was stirred at the same temperature for 3 days. The reaction mixture was filtered through Celite and the filtrate was concentrated in vacuo. The resulting residue was purified by silica gel column chromatography (0 to 5% methanolethyl acetate) to give the above compound (36.5 mg, yield 37%) as a colorless solid.

MS (m/z) APCI: 466 [M+H]$^+$

Example 35

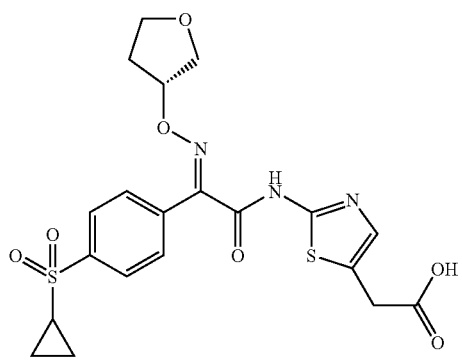

To a solution of the compound of EXAMPLE 24-(14) (1.06 g, 2.09 mmol) in ethanol (30 ml) was added a 2N aqueous sodium hydroxide solution (2.09 ml, 4.18 mmol) under ice-cooling. The mixture was stirred at room temperature for 5 hours, acidified with 2N hydrochloric acid and extracted with methylene chloride. The organic layer was washed sequentially with water and brine, dried over magnesium sulfate and concentrated in vacuo. The resulting residue was solidified with diethyl ether to give the compound (920 mg, yield 92%) as a colorless solid.

MS (m/z) ESI: 478 [M−H]⁻

Example 36

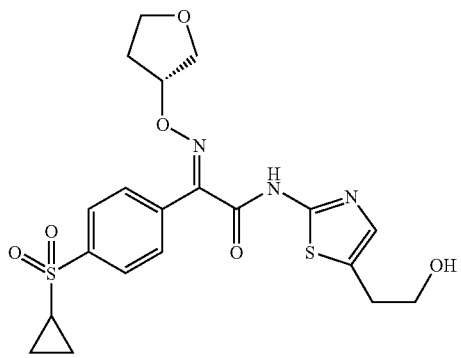

To a solution of the compound of EXAMPLE 24-(14) (100 mg, 0.20 mmol) in THF (4 ml) was added lithium borohydride (17.2 mg, 0.79 mmol) under ice-cooling, and then the mixture was stirred at room temperature for 24 hours. To the reaction mixture was added methanol (4 ml) and oxalic acid (100 mg), and the mixture was stirred at room temperature for another 24 hours, and thereto was added ethyl acetate. The organic layer was separated, washed sequentially with a saturated aqueous sodium carbonate solution, water and brine, dried over magnesium sulfate and concentrated in vacuo. The residue was purified by silica gel column chromatography (1 to 7% methanolchloroform) to give the above compound (27.6 mg, yield 30%) as a colorless solid.

MS (m/z) APCI: 466 [M+H]⁺

Example 37

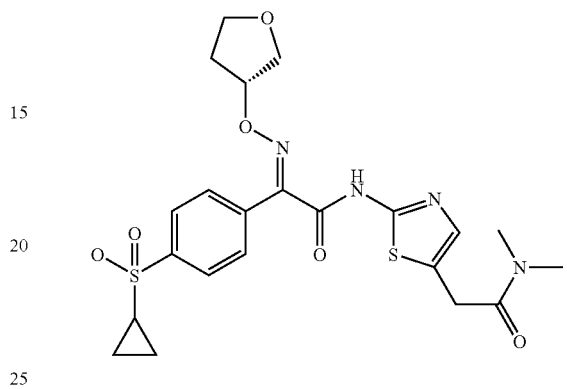

To a solution of the compound of EXAMPLE 35 (200 mg, 0.42 mmol), dimethylamine hydrochloride (102 mg, 1.25 mmol) and 1-hydroxybenzotriazole (169 mg, 1.25 mmol) in methylene chloride (6 ml) was added dropwise N-ethyl-N'-(3-diethylaminopropyl)carbodiimide (0.226 ml, 1.25 mmol) at room temperature. The mixture was stirred at the same temperature for 24 hours, diluted with methylene chloride, washed sequentially with a saturated aqueous sodium carbonate solution, water and brine, dried over magnesium sulfate and concentrated in vacuo. The residue was purified by NH-silica gel column chromatography (5% methanol-chloroform) to give the above compound (212 mg, yield 100%) as a colorless solid.

MS (m/z) APCI: 507 [M+H]⁺

The following compounds were synthesized by reacting the corresponding starting compounds in the similar manner as the above-mentioned.

| EXAMPLE No. | No | Structure | MS (m/z) |
|---|---|---|---|
| 37 | 1 | 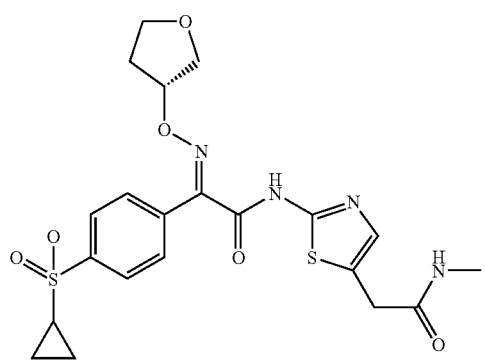 | 493 APCI [M + H]⁺ |

| EXAMPLE No. | No | Structure | MS (m/z) |
|---|---|---|---|
| 37 | 2 | 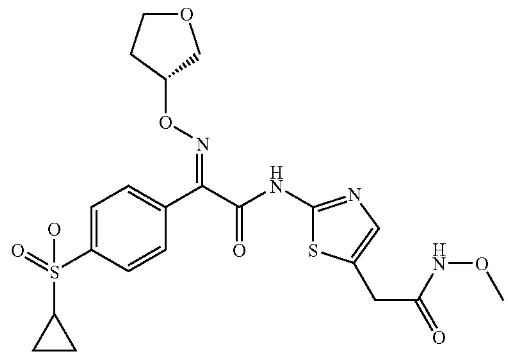 | 509 APCI [M + H]+ |

Example 38

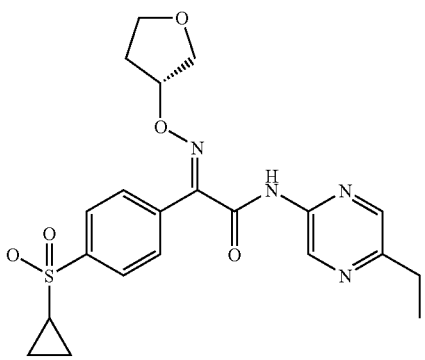

To a solution of the compound of EXAMPLE 24-(36) (66 mg, 0.15 mmol) in ethanol-THF (1:1) (6 ml) was added 10% Pd/C (60 mg). The mixture was stirred at room temperature for 12 under hydrogen at normal pressure, filtered through Celite and then the filtrate was concentrated in vacuo to give the above compound (67 mg, yield 100%) as a colorless solid.

MS (m/z) APCI: 445 [M+H]+

Example 39

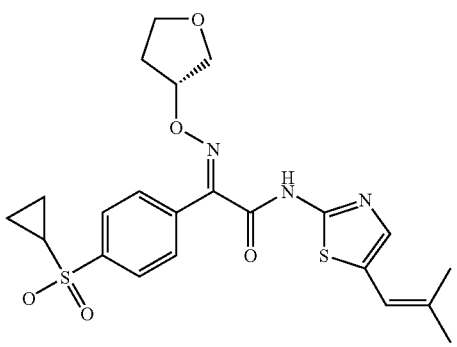

To a solution of the compound of EXAMPLE 24-(22) (500 mg, 1.0 mmol) in DMF (15 ml) were added tributyl(2-methyl-1-propenyl)tin (690 mg, 2.0 mmol), diisopropylethylamine (0.87 ml, 5.0 mmol), lithium chloride (296 mg, 7.0 mmol) and tetrakis(triphenylphosphine)palladium (58 mg, 0.05 mmol) under argon. The mixture was stirred at 120° C. for 4 hours, diluted with ethyl acetate, and thereto was added water and then filtered through Celite. The filtrate was washed sequentially with water and brine, dried over sodium sulfate and concentrated in vacuo. The resulting residue was purified by NH-silica gel column chromatography (50 to 100% chloroform-hexane) to give the above compound (268 mg, yield 56%) as a colorless solid.

MS (m/z) APCI: 476 [M+H]+

Example 40

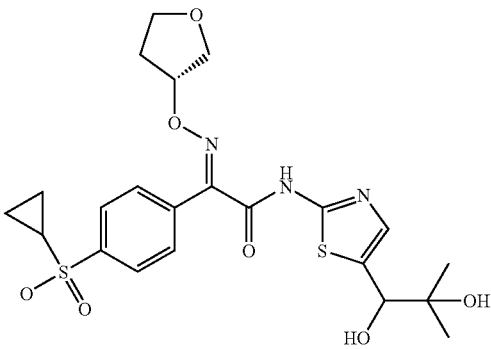

To a solution of the compound of EXAMPLE 39 (95 mg, 0.20 mmol) in acetone-acetonitrile-water (1:1:1) (6 ml) were added N-methylmorpholine N-oxide (59 mg, 0.50 mmol) and 10% microencapsulated osmium tetroxide (Osmium (VIII) Oxide, Microencapsulate™, Wako Pure Chemical Industries, Ltd., 102 mg, 0.04 mmol). The mixture was stirred at room temperature for 2 days, diluted with ethyl acetate and filtered through Celite, and then the filtrate was concentrated in vacuo. The residue was purified by silica gel column chromatography (3-10% methanol-chloroform) to give the above compound (96 mg, yield 94%) as a colorless solid.

MS (m/z) APCI: 510 [M+H]+

The following compound was synthesized by treating the corresponding starting compound in the similar manner as the above-mentioned.

| EXAMPLE No. | No | Structure | MS (m/z) |
|---|---|---|---|
| 40 | 1 | 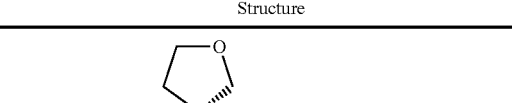 | 505 APCI [M + H]+ |

Example 41

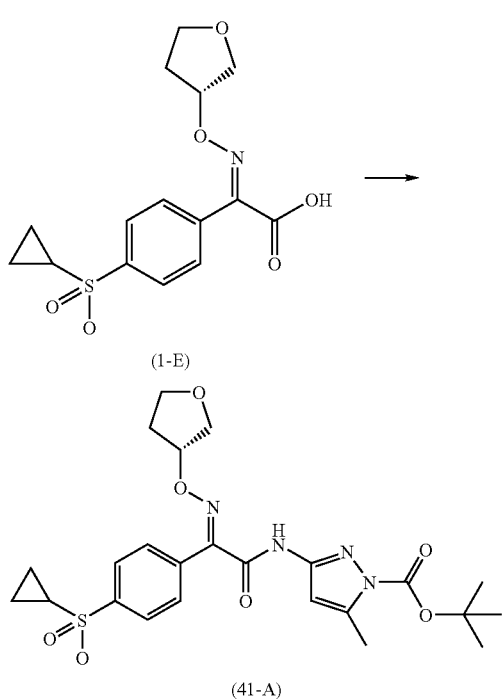

(1) A corresponding starting compound and the compound (1-E) were treated in the similar manner as EXAMPLE 1-(5) to give the compound (41-A).
MS (m/z) APCI: 519 [M+H]+

(2) The above compound (72 mg, 0.14 mmol) was dissolved in formic acid (3 ml) at room temperature. The mixture was stirred at the same temperature for 24 hours and concentrated. The residue was purified by silica gel column chromatography (0 to 8% methanol-chloroform) to give the compound (41-B) (50.7 mg, yield 87%) as a colorless solid.
MS (m/z) APCI: 419 [M+H]+

The following compound was synthesized by treating the corresponding starting compound in the similar manner as the above-mentioned.

| EXAMPLE No. | No | Structure | MS (m/z) |
|---|---|---|---|
| 41 | 1 | 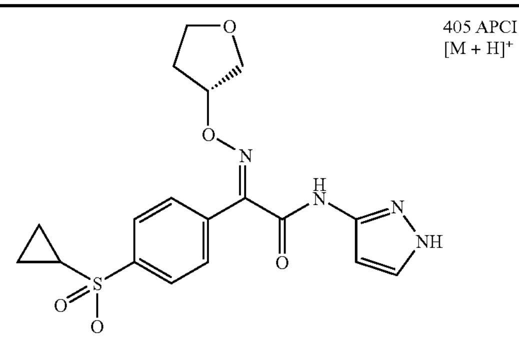 | 405 APCI [M + H]+ |

Example 42

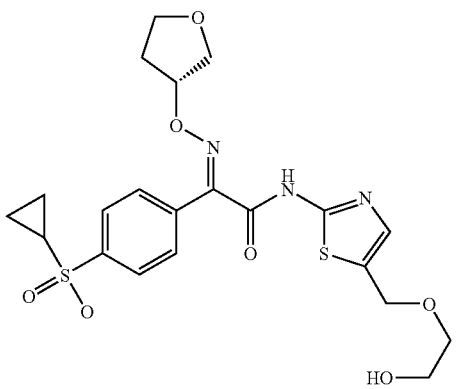

To a solution of the compound of EXAMPLE 26 (300 mg, 0.66 mmol) in methylene chloride (10 ml) were added sequentially triethylamine (0.28 ml, 1.99 mmol) and acetic anhydride (0.095 ml, 1.0 mmol) at room temperature. The mixture was stirred at room temperature for 16 hours, concentrated in vacuo and then to the residue was added ethylene glycol (15 ml). The mixture was heated to reflux for 8 hours, diluted with ethyl acetate, and then washed sequentially with water and brine, dried over sodium sulfate and concentrated in vacuo. The resulting residue was purified by silica gel column chromatography (0 to 5% methanol-ethyl acetate) to the above compound (166 mg, yield 50%) as a colorless solid.

MS (m/z) APCI: 496 [M+H]$^+$

The following compounds were synthesized by treating the corresponding starting compounds in the similar manner as the above-mentioned.

| EXAMPLE No. | No | Structure | MS (m/z) |
|---|---|---|---|
| 42 | 1 | 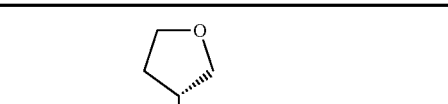 | 510 APCI [M + H]$^+$ |
| 42 | 2 | | 510 APCI [M + H]$^+$ |

-continued
| EXAMPLE No. | No | Structure | MS (m/z) |
|---|---|---|---|
| 42 | 3 | 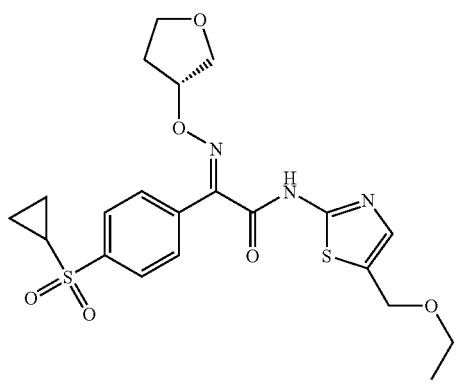 | 480 APCI [M + H]+ |
| 42 | 4 | 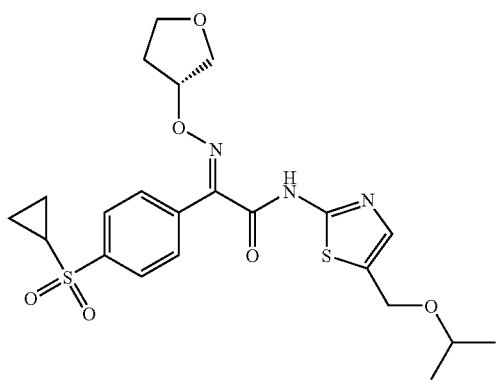 | 494 APCI [M + H]+ |
| 42 | 5 | 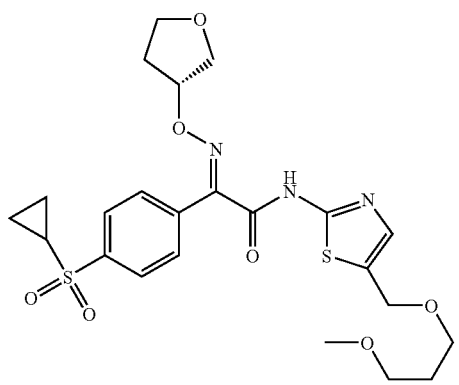 | 524 APCI [M + H]+ |

Example 43

Corresponding starting compounds were treated in the similar manner as EXAMPLE 1-(5) to give the following compounds.

| EXAMPLE No. | No | Structure | MS (m/z) |
|---|---|---|---|
| 43 | 1 | | 431 APCI [M + H]+ |
| 43 | 2 | | 525 APCI [M + H]+ |
| 43 | 3 | | 535 APCI [M + H]+ |
| 43 | 4 | | 597 APCI [M + H]+ |

| EXAMPLE No. | No | Structure | MS (m/z) |
|---|---|---|---|
| 43 | 5 | | 463 APCI [M + H]⁺ |
| 43 | 6 | | 474 APCI [M + H]⁺ |
| 43 | 7 | | 550/552 ESI [M − H]⁻ |
| 43 | 8 | | 504 APCI [M + H]⁺ |

-continued
| EXAMPLE No. | No | Structure | MS (m/z) |
|---|---|---|---|
| 43 | 9 | 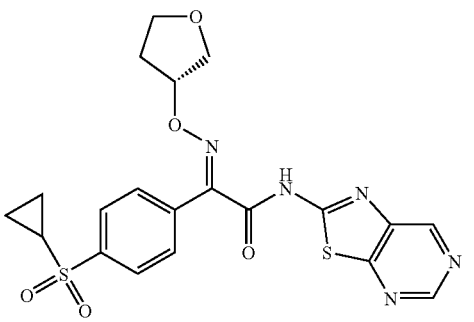 | 474 APCI [M + H]+ |
| 43 | 10 | 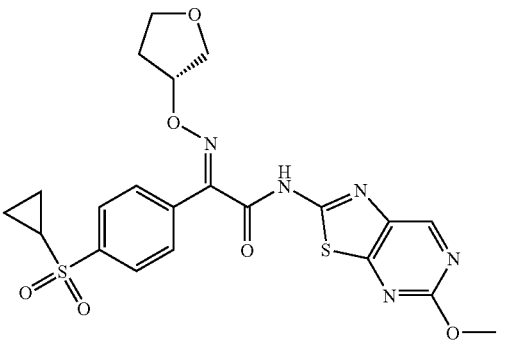 | 504 APCI [M + H]+ |
| 43 | 11 | 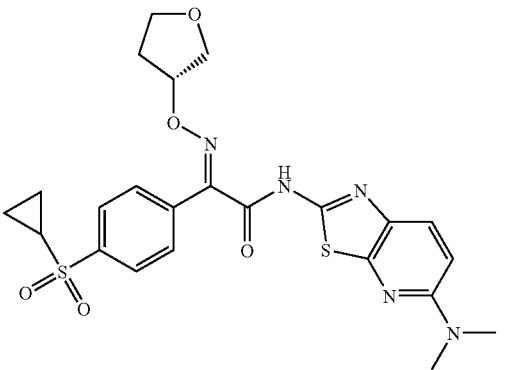 | 516 APCI [M + H]+ |
| 43 | 12 | 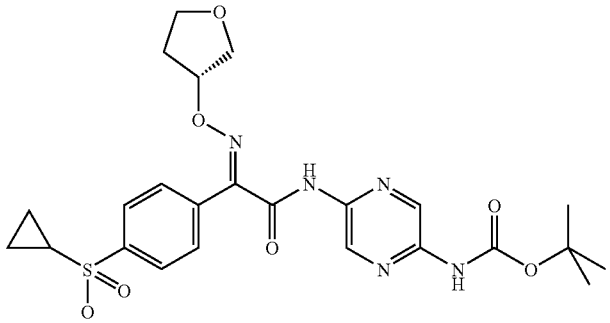 | 532 APCI [M + H]+ |

| EXAMPLE No. | No | Structure | MS (m/z) |
|---|---|---|---|
| 43 | 13 | 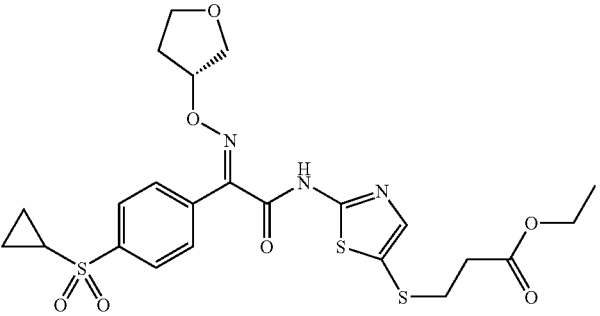 | 554 APCI [M + H]+ |
| 43 | 14 | 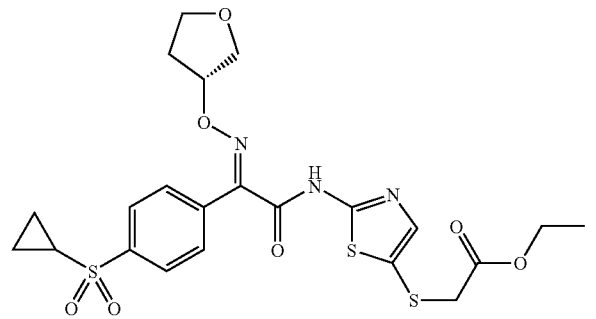 | 540 APCI [M + H]+ |
| 43 | 15 | 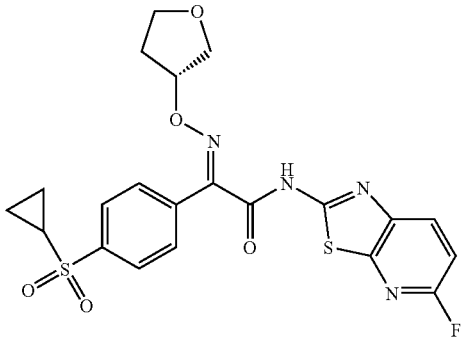 | 491 APCI [M + H]+ |
| 43 | 16 | 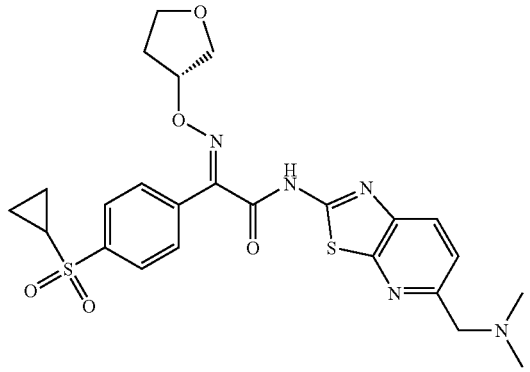 | 530 APCI [M + H]+ |

-continued

| EXAMPLE No. | No | Structure | MS (m/z) |
|---|---|---|---|
| 43 | 17 | | 571 APCI [M + H]+ |
| 43 | 18 | | 447 APCI [M + H]+ |
| 43 | 19 | | 460 APCI [M + H]+ |
| 43 | 20 | | 490 APCI [M + H]+ |

| EXAMPLE No. | No | Structure | MS (m/z) |
|---|---|---|---|
| 43 | 21 | 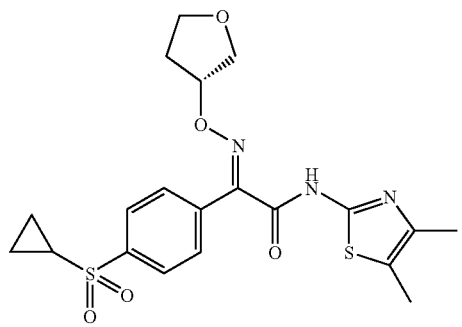 | 450 APCI [M + H]+ |
| 43 | 22 | 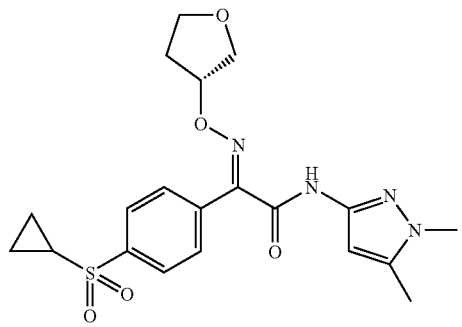 | 433 APCI [M + H]+ |
| 43 | 23 | 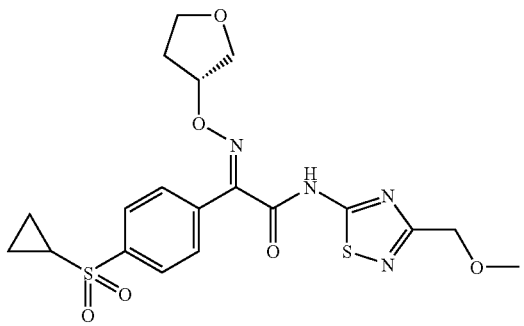 | 467 APCI [M + H]+ |
| 43 | 24 | 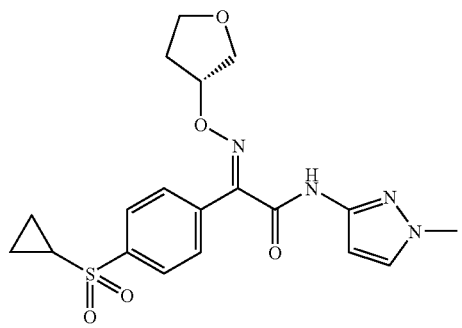 | 419 APCI [M + H]+ |

Example 44

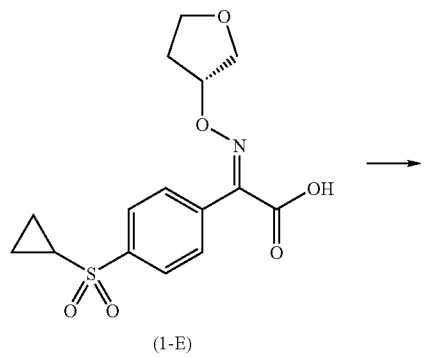

(1-E)

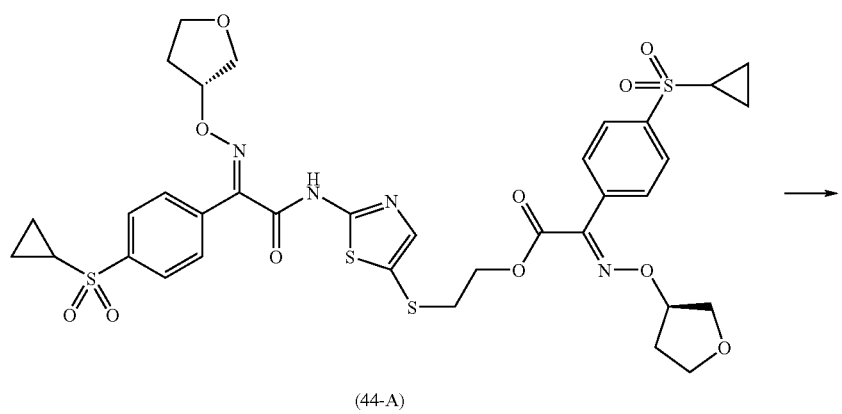

(44-A)

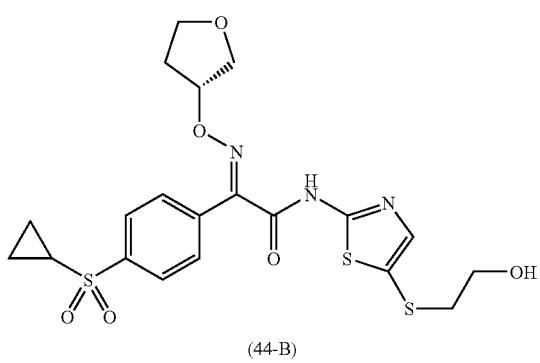

(44-B)

(1) To a solution of the compound (1-E) (200 mg, 0.59 mmol) and 2-(2-aminothiazol-5-ylsulfanyl)ethanol (104 mg, 0.59 mmol) in THF (4 ml) was added DMT-MM (4-(4,6-dimethoxy-1,3,5-triazin-2-yl)-4-methylmorpholinium chloride) (240 mg, 0.87 mmol) at room temperature. The mixture was stirred at the same temperature for 20 hours, diluted with ethyl acetate, and then washed sequentially with water and brine, dried over magnesium sulfate and concentrated in vacuo. The residue was purified by NH-silica gel column chromatography (0 to 1% methanol-chloroform) to give the compound (44-A) (82 mg, yield 17%) as a pale yellow solid.

MS (m/z) APCI: 819 [M+H]$^+$ (2) To a solution of the above compound (78 mg, 0.095 mmol) in THF-methanol-water (10:3:3) (1.6 ml) was added a 2N aqueous sodium hydroxide solution (0.12 ml, 0.24 mmol) under ice-cooling. The mixture was stirred at the same temperature for 2.5 hours, diluted with ethyl acetate, and then washed sequentially with water and brine, dried over magnesium sulfate and concentrated in vacuo. The residue was purified by silica gel chromatography (80 to 100% ethyl acetate-hexane) to give the compound (44-B) (31 mg, yield 66%).

MS (m/z) APCI: 498 [M+H]$^+$

A corresponding starting compound was treated in the similar manner as the above-mentioned to give the following compound.

| EXAMPLE No. | No | Structure | MS (m/z) |
|---|---|---|---|
| 44 | 1 | 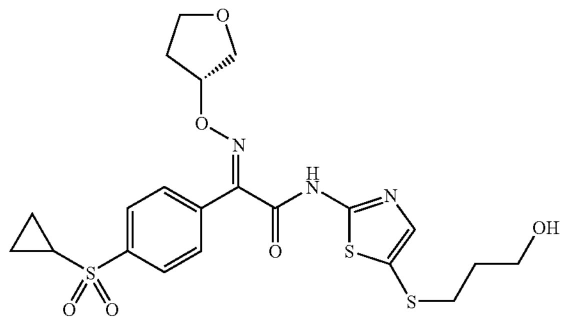 | 512 APCI [M + H]+ |

Example 45

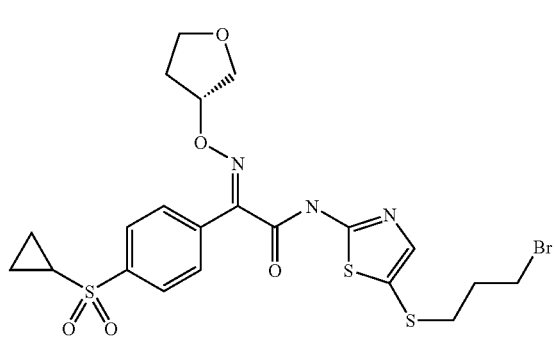

To a solution of the compound of EXAMPLE 44-(1) (100 mg, 0.20 mmol) and carbon tetrabromide (321 mg, 0.97 mmol) in THF (4 ml) was added triphenylphosphine (256 mg, 0.97 mmol) at −10° C., and the mixture was stirred at room temperature for 38 hours, and then concentrated in vacuo. The residue was purified by NH-silica gel column chromatography (50 to 90% ethyl acetate-hexane) to give the above compound (176 mg, quantitatively).

MS (m/z) APCI: 574/576 [M+H]+

Example 46

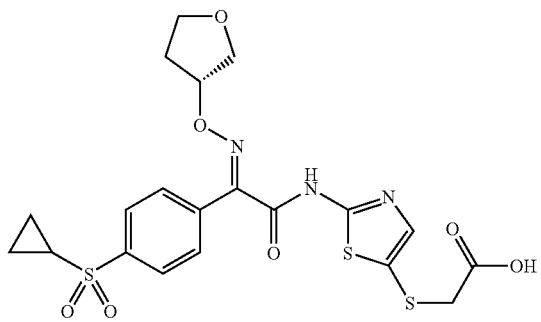

To a solution of the compound of EXAMPLE 43-(14) (1800 mg, 3.34 mmol) in ethanol-THF (1:3) (26 ml) was added a 2N aqueous sodium hydroxide solution (5.0 ml, 10 mmol) under ice-cooling. The mixture was stirred at the same temperature for 2 hours, concentrated in vacuo, and then the residue was acidified with 2N hydrochloric acid. After diluting with ethyl acetate, the mixture was washed sequentially with water and brine, dried over sodium sulfate and concentrated in vacuo. The residue was solidified with ethyl acetate-hexane to give the above compound (1631 mg, yield 96%) as colorless crystals.

MS (m/z) APCI: 510 [M−H]−

A corresponding starting compound was treated in the similar manner as the above-mentioned to give the following compound.

| EXAMPLE No. | No | Structure | MS (m/z) |
|---|---|---|---|
| 46 | 1 | 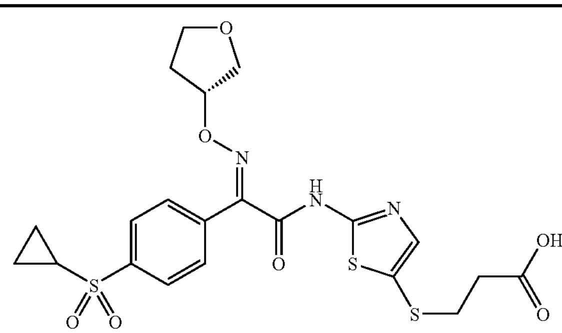 | 524 ESI [M − H]− |

Example 47

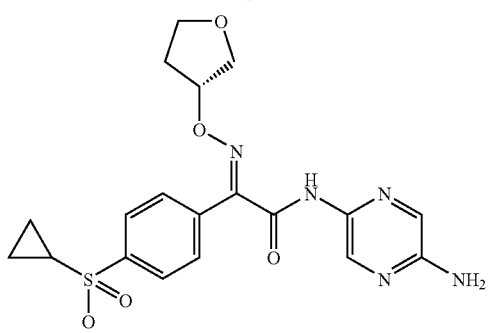

The compound of EXAMPLE 43-(12) (287 mg, 0.54 mmol) was dissolved in formic acid (3 ml). The mixture was stirred at room temperature for 24 hours at the same temperature and concentrated in vacuo. The residue was dissolved in chloroform, washed sequentially with a saturated aqueous sodium bicarbonate solution, water and brine, dried over sodium sulfate and concentrated in vacuo. The residue was purified by silica gel column chromatography (0 to 5% methanol-ethyl acetate) to give the above compound (180 mg, yield 77%) as a colorless solid.

MS (m/z) APCI: 432 [M+H]$^+$

Corresponding starting compounds were treated in the similar manner as the above-mentioned to give the following compounds.

| EXAMPLE No. | No | Structure | MS (m/z) |
|---|---|---|---|
| 47 | 1 | | 497 APCI [M + H]$^+$ |
| 47 | 2 | | 511 APCI [M + H]$^+$ |

Example 48

Corresponding starting compounds were treated in the similar manner as EXAMPLE 37 to give the following compounds.

| EXAMPLE No. | No | Structure | MS (m/z) |
|---|---|---|---|
| 48 | 1 | 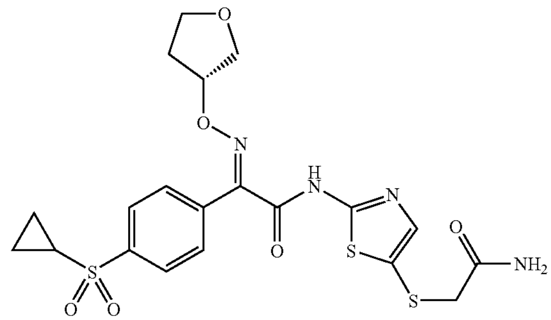 | 511 APCI [M + H]$^+$ |

| EXAMPLE No. | No | Structure | MS (m/z) |
|---|---|---|---|
| 48 | 2 | 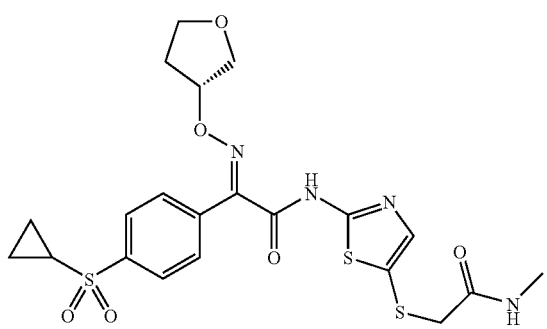 | 525 APCI [M + H]+ |
| 48 | 3 | 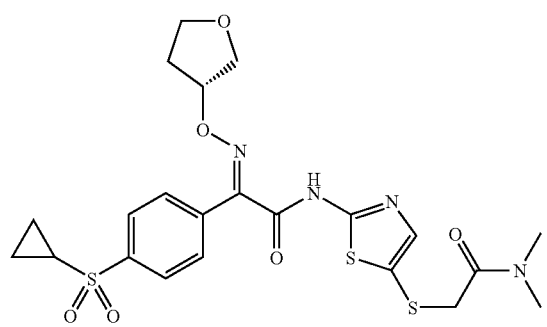 | 539 APCI [M + H]+ |
| 48 | 4 | 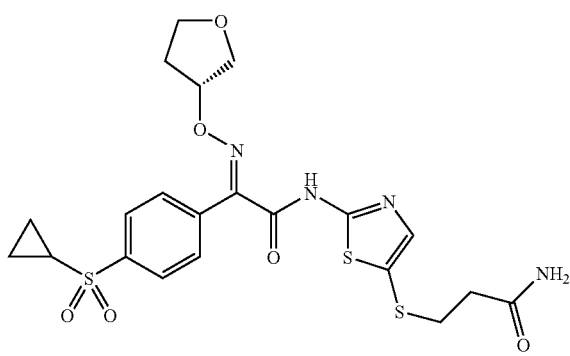 | 525 APCI [M + H]+ |
| 48 | 5 | 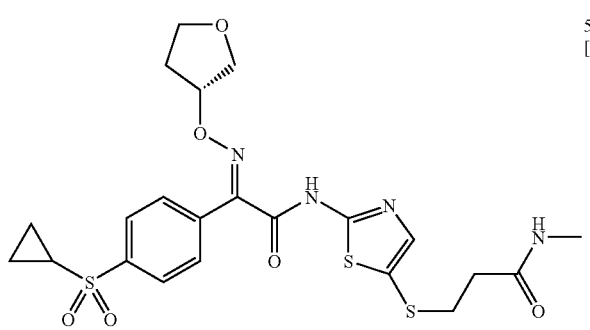 | 539 APCI [M + H]+ |

-continued

| EXAMPLE No. | No | Structure | MS (m/z) |
|---|---|---|---|
| 48 | 6 | 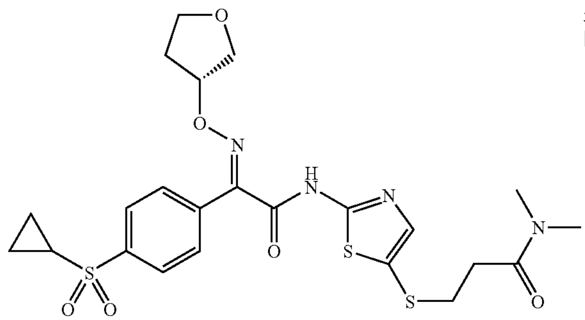 | 553 APCI [M + H]+ |

Example 49

To a solution of the compound of EXAMPLE 24-(10) (248 mg, 0.50 mmol) in DMF (3 ml) were added tetrakis(triphenylphosphine)palladium (57 mg, 0.05 mmol) and 2-mercaptoethanol (98 mg, 1.25 mmol) under argon. The mixture was stirred at 120° C. for 3 hours, diluted with ethyl acetate, and then washed sequentially with water and brine, dried over sodium sulfate and concentrated in vacuo. The residue was purified by silica gel column chromatography (50 to 100% ethyl acetate-hexane) to give the above compound (72.1 mg, yield 29%) as a colorless solid.

MS (m/z) APCI: 493 [M+H]+

A corresponding starting compound was treated in the similar manner as the above-mentioned to give the following compound.

| EXAMPLE No. | No | Structure | MS (m/z) |
|---|---|---|---|
| 49 | 1 | 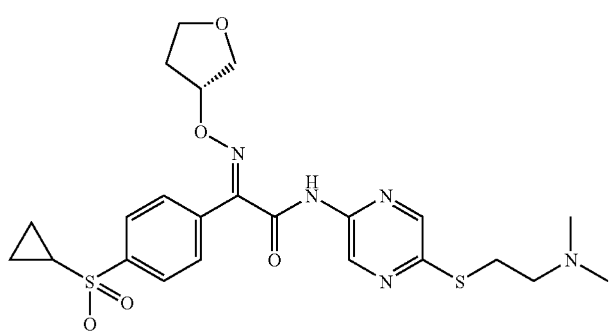 | 520 APCI [M + H]+ |

Example 50

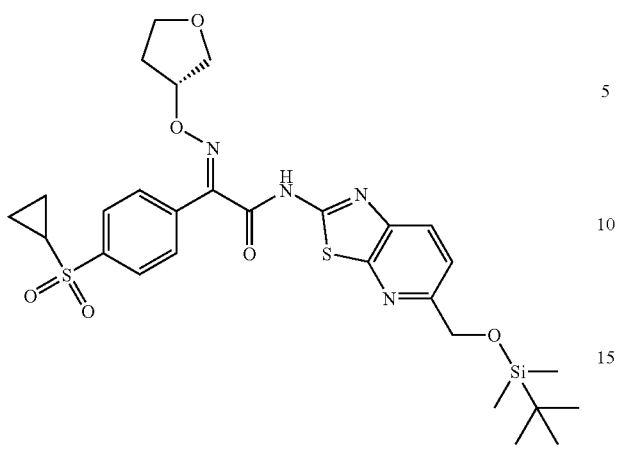

A corresponding starting compound was treated in the similar manner as EXAMPLE 1-(5) to give the above compound.
MS (m/z) APCI: 617 [M+H]$^+$

Example 51

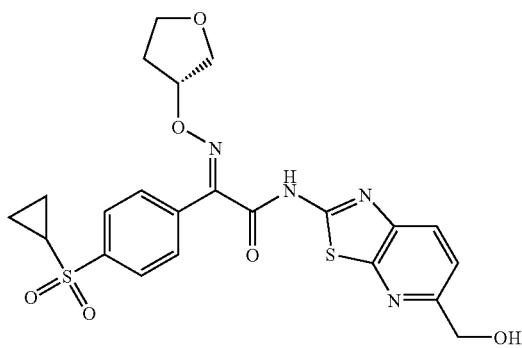

To a solution of the compound of EXAMPLE 50 (810 mg, 1.31 mmol) in THF (10 ml) was added a 1.0 M solution of tetrabutylammonium fluoride in THF (3.9 ml, 3.9 mmol) under ice-cooling. The mixture was stirred at room temperature for 3 hours, diluted with ethyl acetate, washed sequentially with water and brine, dried over sodium sulfate and concentrated in vacuo. The residue was purified by silica gel column chromatography (0 to 8% methanolchloroform) to give the above compound (646 mg, yield 98%).
MS (m/z) APCI: 503 [M+H]$^+$

Example 52

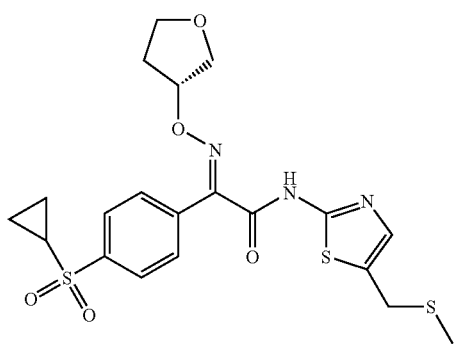

To a solution of the compound of EXAMPLE 26 (296 mg, 0.66 mmol) in chloroform (3 ml) were added trifluoroacetic acid (2 ml) and sodium thiomethoxide (183 mg, 2.61 mmol). The mixture was stirred at 60° C. in a sealed tube under microwave irradiation for 3 hours, diluted with ethyl acetate, washed sequentially with a saturated aqueous sodium bicarbonate solution, water and brine, dried over sodium sulfate and concentrated in vacuo. The residue was purified by silica gel column chromatography (ethyl acetate) to give the above compound (281 mg, yield 89%).
MS (m/z) APCI: 482 [M+H]+

Example 53

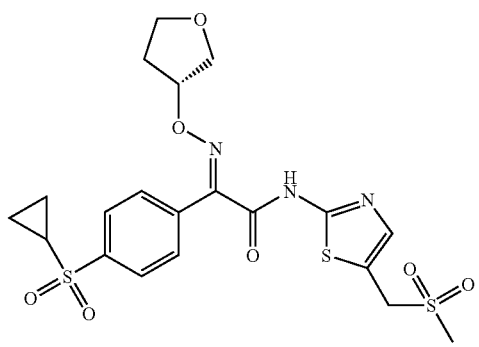

To a solution of the compound of EXAMPLE 52 (176 mg, 0.365 mmol) in chloroform (5 ml) was added 70% m-chloroperbenzoic acid (225 mg, 0.913 mmol) under ice-cooling, and the mixture was stirred at the same temperature for 1 hour and at room temperature for another 3 hours. To the reaction mixture was added a 10% sodium sulfite solution, and the organic layer was separated, dried over sodium sulfate and concentrated in vacuo. The residue was purified by silica gel column chromatography (0 to 5% methanol-chloroform) to give the above compound (148 mg, yield 79%).
MS (m/z) APCI: 514 [M+H]$^+$

Example 54

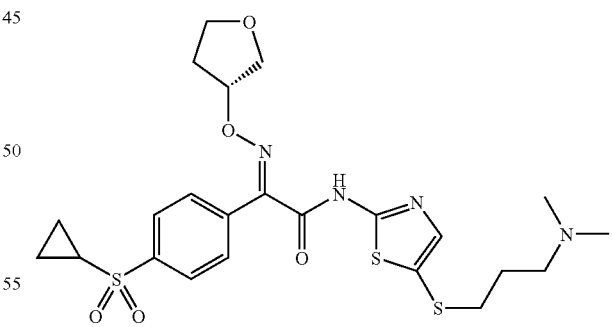

To a solution of the compound of EXAMPLE 45 (50 mg, 0.087 mmol) in methanol (1.5 ml) was added N,N-dimethyltrimethylsilylamine (459 mg, 3.92 mmol) under ice-cooling. The mixture was stirred at the same temperature for 30 minutes and at room temperature for another 18 hours, and concentrated in vacuo. The residue was purified by silica gel column chromatography (0 to 6% methanol-chloroform) to give the above compound (41.2 mg, yield 88%).
MS (m/z) APCI: 539 [M+H]$^+$

Example 55

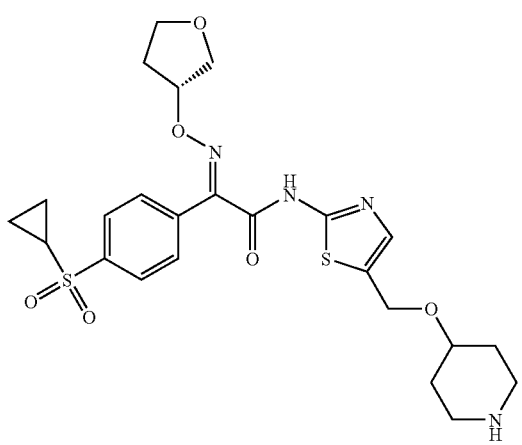

To a solution of the compound of EXAMPLE 26 (908 mg, 2.01 mmol) and 4-hydroxypiperidine (610 mg, 6.03 mmol) in toluene (60 ml) was added p-toluenesulfonic acid monohydrate (3.65 g, 19.2 mmol) at room temperature, and the mixture was heated to reflux for 1 hour using a Dean-Stark apparatus for azeotropic removal of the resulting water. After standing to cool, to the reaction mixture was added a saturated aqueous sodium bicarbonate solution, and the mixture was extracted with chloroform. The organic layer was dried over sodium sulfate and concentrated in vacuo. The residue was purified by silica gel column chromatography (aqueous ammonia-methanol-chloroform, 1:10:100) to give the above compound (461 mg, yield 43%).

MS (m/z) APCI: 535 [M+H]$^+$

A corresponding starting compound was treated in the similar manner as the above-mentioned to give the following compound.

Example 56

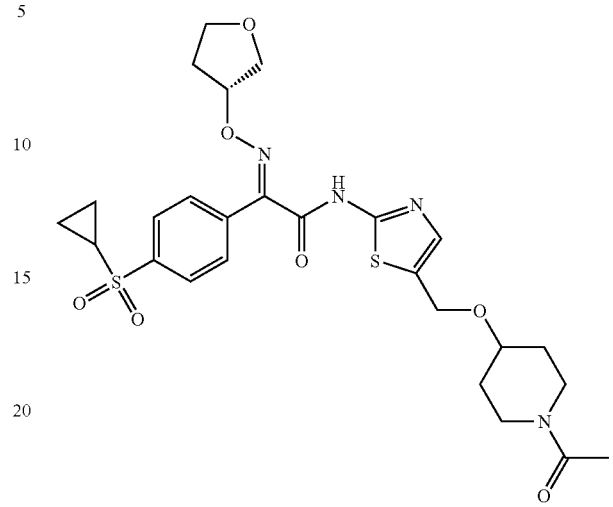

To a solution of the compound of EXAMPLE 55 (107 mg, 0.2 mmol) and pyridine (0.081 ml, 1.0 mmol) in chloroform (5 ml) was added acetic anhydride (0.0284 ml, 0.3 mmol) at room temperature, and the mixture was stirred at the same temperature for 3 hours. To the reaction mixture was added a saturated aqueous sodium bicarbonate solution, and the mixture was extracted with chloroform. The organic layer was dried over sodium sulfate, and concentrated in vacuo, and then the residue was purified by silica gel column chromatography (0 to 10% methanol-chloroform) to give the above compound (105 mg, yield 91%).

MS (m/z) APCI: 577 [M+H]$^+$

A corresponding starting compound was treated in the similar manner as the above-mentioned to give the following compound.

| EXAMPLE No. | No | Structure | MS (m/z) |
|---|---|---|---|
| 55 | 1 | 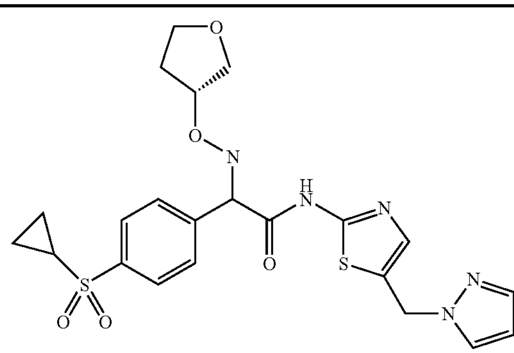 | 502 APCI [M + H]$^+$ |

| EXAMPLE No. | No | Structure | MS (m/z) |
|---|---|---|---|
| 56 | 1 | 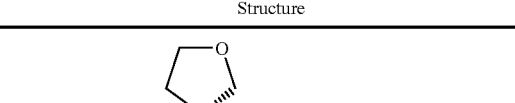 | 474 APCI [M + H]+ |

Example 57

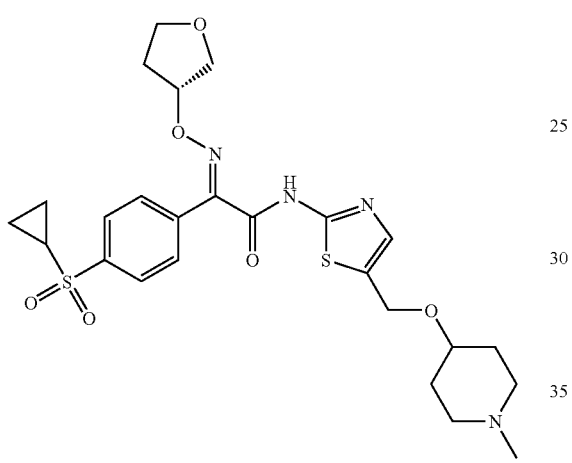

To a mixture of the compound of EXAMPLE 55 (111 mg, 0.208 mmol) and a 38% aqueous formalin solution (1 ml) in chloroform (3 ml) was added sodium triacetoxyborohydride (132 mg, 0.603 mmol) under ice-cooling, and the mixture was stirred at room temperature for 3 hours. To the reaction mixture was added a saturated aqueous sodium bicarbonate solution, and the organic layer was separated, dried over magnesium sulfate and concentrated. The residue was purified by silica gel column chromatography (0 to 20% methanol-chloroform) to give the above compound (106 mg, yield 93%).
MS (m/z) APCI: 549 [M+H]+

Example 58

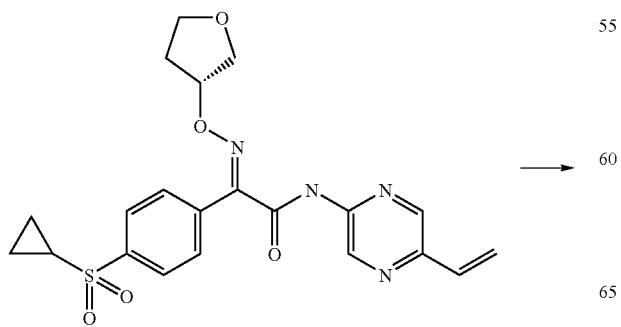

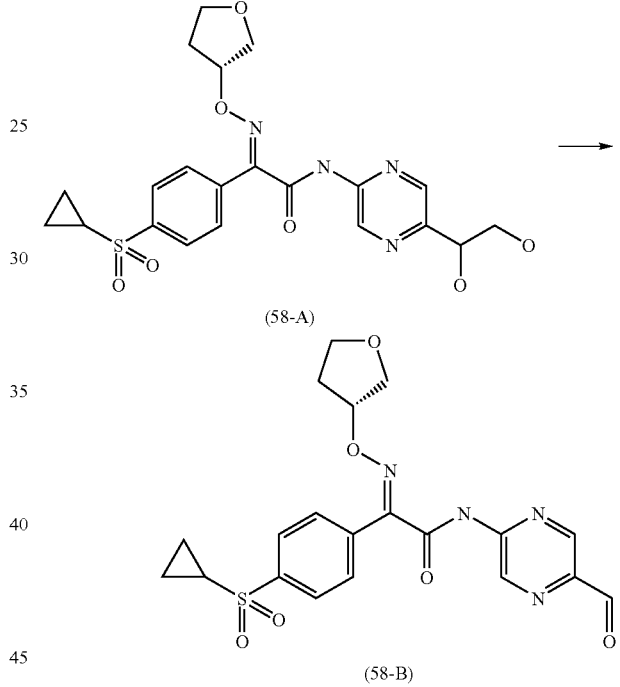

(1) The compound of EXAMPLE 24-(36) was treated in the similar manner as EXAMPLE 40 to give the compound (58-A).
MS (m/z) APCI: 477 [M+H]+
(2) To a solution of the above compound (477 mg, 1.0 mmol) in acetone (10 ml) was added an aqueous solution of sodium periodate (235 mg, 1.10 mmol) (10 ml) under ice-cooling. The mixture was stirred at the same temperature for 2 hours, diluted with ethyl acetate, and then washed sequentially with a 1M aqueous sodium sulfite solution, water and brine, dried over sodium sulfate and concentrated in vacuo. The resulting residue was purified by silica gel column chromatography (0 to 5% methanol-ethyl acetate) to give the compound (58-B) (401 mg, yield 90%).
MS (m/z) APCI: 445 [M+H]+

Example 59

A corresponding starting compound was treated in the similar manner as EXAMPLE 29 to give the following compound.

| EXAMPLE No. | No | Structure | MS (m/z) |
|---|---|---|---|
| 59 | | 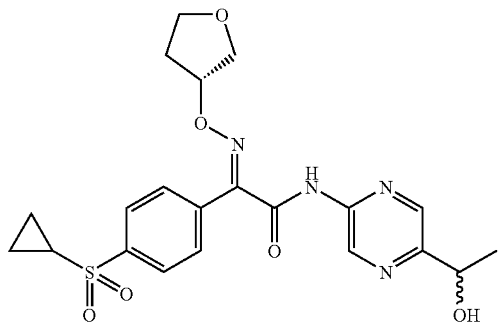 | 461 APCI [M + H]+ |

Example 60

A corresponding starting compound was treated in the similar manner as EXAMPLE 31 to give the following compound.

| EXAMPLE No. | No | Structure | MS (m/z) |
|---|---|---|---|
| 60 | | 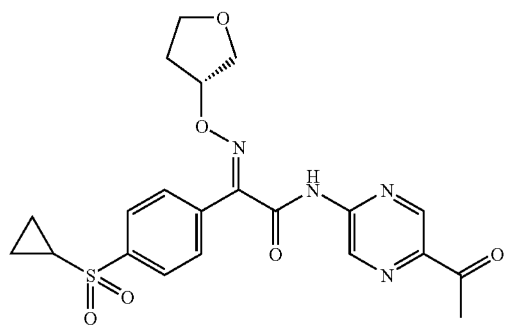 | 459 APCI [M + H]+ |

Example 61

Corresponding starting compounds were treated in the similar manner as EXAMPLE 2 to give the following compounds.

| EXAMPLE No. | No | Structure | MS (m/z) |
|---|---|---|---|
| 61 | 1 | 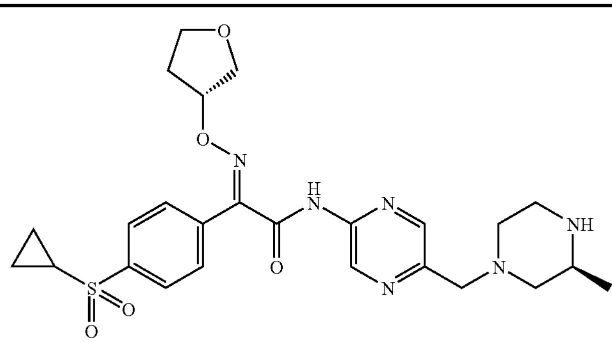 | 529 APCI [M + H]+ |

| EXAMPLE No. | No | Structure | MS (m/z) |
|---|---|---|---|
| 61 | 2 | 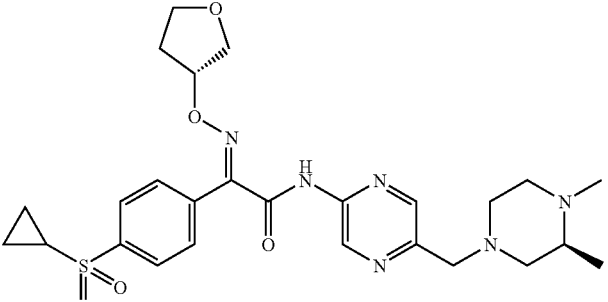 | 543 APCI [M + H]+ |

Example 62

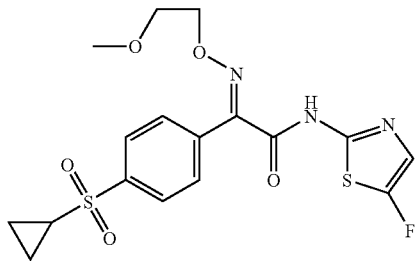

The compound (1-D), 2-methoxyethanol and the corresponding starting compound were reacted in the similar manner as EXAMPLE 1 to give the above compound.

MS (m/z) APCI: 428 [M+H]+

Corresponding starting compounds were reacted in the similar manner as the above-mentioned to give the following compounds.

| EXAMPLE No. | No | Structure | MS (m/z) |
|---|---|---|---|
| 62 | 1 | 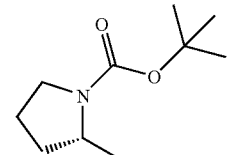 | 553 APCI [M + H]+ |
| 62 | 2 | 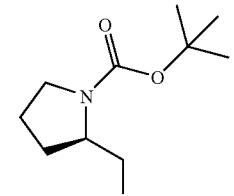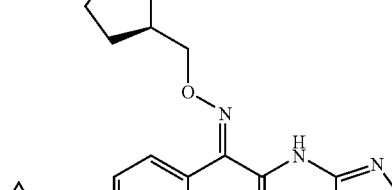 | 553 APCI [M + H]+ |
| 62 | 3 | 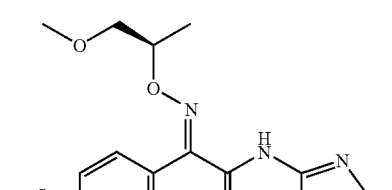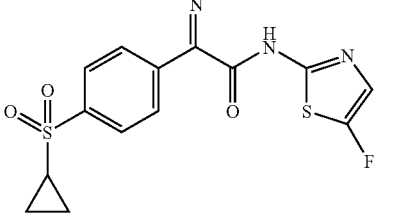 | 442 ESI+ [M + H]+ |
| 62 | 4 | 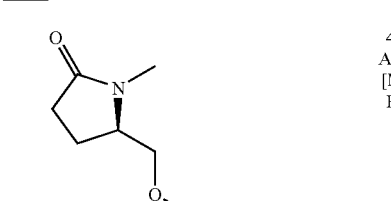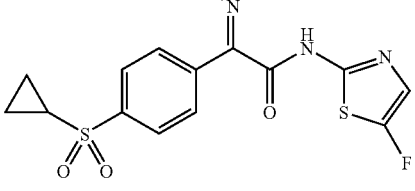 | 481 APCI [M + H]+ |

-continued
| EXAMPLE No. | No | Structure | MS (m/z) |
|---|---|---|---|
| 62 | 5 | 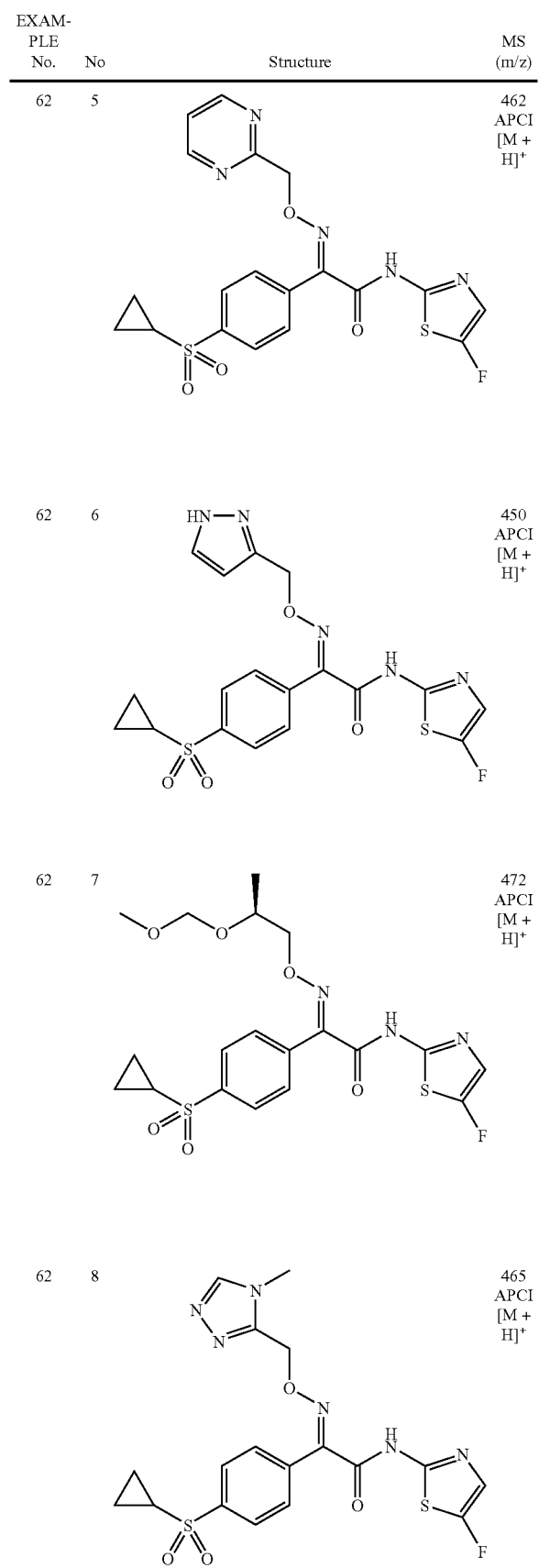 | 462 APCI [M+H]+ |
| 62 | 6 | | 450 APCI [M+H]+ |
| 62 | 7 | | 472 APCI [M+H]+ |
| 62 | 8 | | 465 APCI [M+H]+ |
-continued
| EXAMPLE No. | No | Structure | MS (m/z) |
|---|---|---|---|
| 62 | 9 | 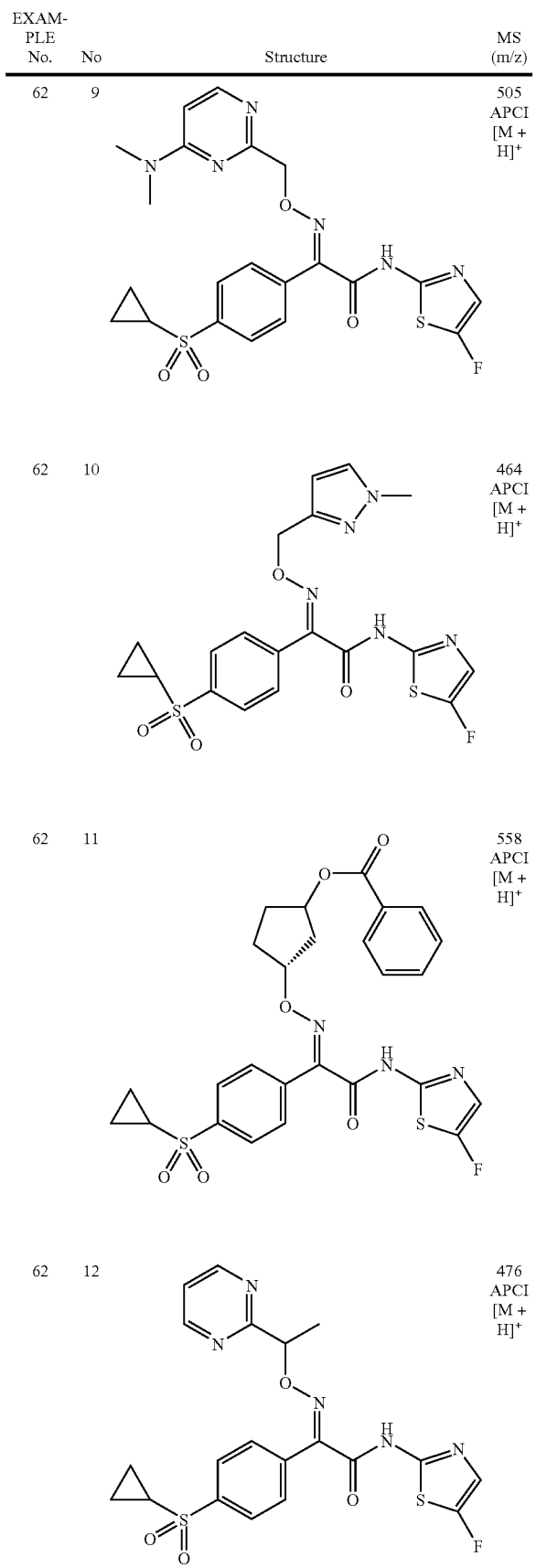 | 505 APCI [M+H]+ |
| 62 | 10 | | 464 APCI [M+H]+ |
| 62 | 11 | | 558 APCI [M+H]+ |
| 62 | 12 | | 476 APCI [M+H]+ |

-continued

| EXAMPLE No. | No | Structure | MS (m/z) |
|---|---|---|---|
| 62 | 13 | 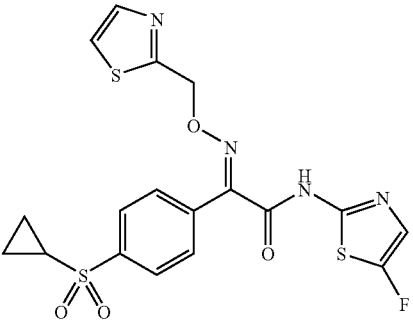 | 467 APCI [M + H]+ |
| 62 | 14 | 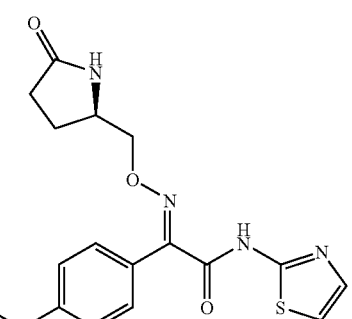 | 467 APCI [M + H]+ |

Example 63

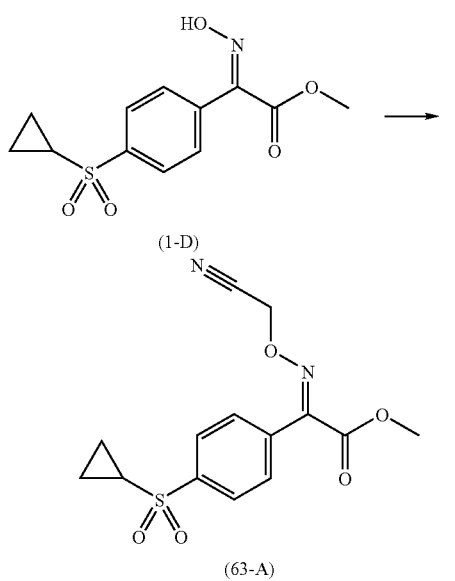

-continued

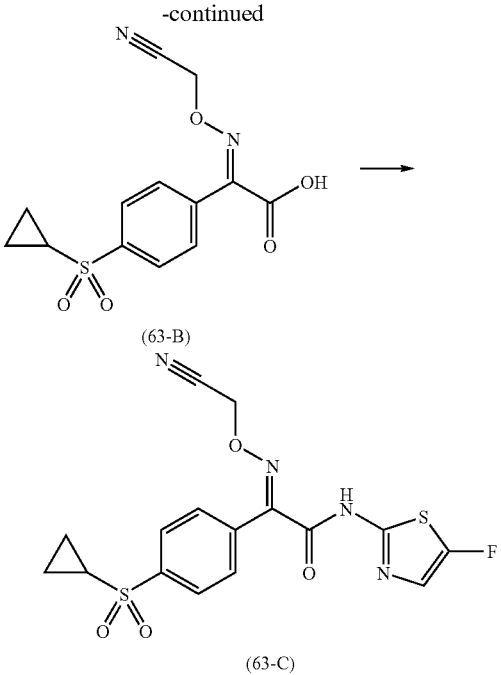

(1) To a solution of the compound (1-D) (2.5 g, 8.8 mmol) and potassium carbonate (2.44 g, 17.7 mmol) in DMF (50 ml) was added bromoacetonitrile (0.737 ml, 10.6 mmol) at room temperature. The mixture was stirred at the same temperature for 15 hours, diluted with ethyl acetate, and then washed sequentially with water and brine, dried over sodium sulfate and concentrated in vacuo. The resulting residue was purified by silica gel column chromatography (40% ethyl acetatehexane) to give the compound (63-A) (2.65 g, yield 93%).
MS (m/z) APCI: 340 [M+H]+

(2) To a solution of the above compound (2.8 g, 8.8 mmol) in methanol-THF (3:1) (20 ml) was added a 2N aqueous sodium hydroxide solution (4.4 ml, 8.8 mmol) under ice-cooling, and the ice bath was removed. The mixture was stirred at the same temperature for 30 minutes, and extracted with methylene chloride. The organic layer was washed sequentially with water and brine, dried over magnesium sulfate and concentrated in vacuo to give the compound (63-B) (2.8 g, quantitatively).

(3) A corresponding starting compound was reacted with the above compound in the similar manner as EXAMPLE 1-(5) to give the compound (63-C).
MS (m/z) APCI: 409 [M+H]+

Example 64

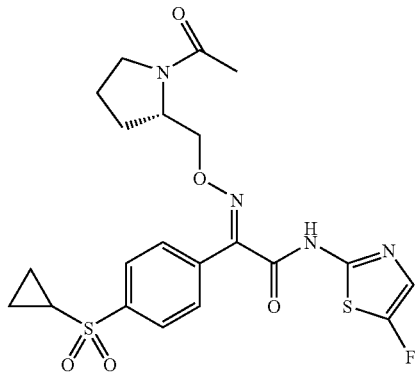

(1) The compound of EXAMPLE 62-(1) (332 mg, 0.601 mmol) was dissolved in formic acid (9 ml) The mixture was stirred at room temperature for 24 hours and concentrated in vacuo. The residue was dissolved in ethyl acetate and thereto was added a 4N hydrogen chloride solution in dioxane, and the precipitated crystals were collected to give a crude amine (308 mg) as a monohydrochloride.

(2) To a solution of the above crude amine (60 mg) and pyridine (0.046 ml, 0.545 mmol) in chloroform (1 ml) was added acetic anhydride (0.015 ml, 0.163 mmol) at room temperature, and the mixture was stirred at the same temperature for 20 hours and then concentrated in vacuo. The resulting residue was purified by NH-silica gel column chromatography (0 to 10% methanol-chloroform) to give the titled compound (50.4 mg, yield 87% in 2 steps).

MS (m/z) APCI: 495 [M+H]$^+$

A corresponding starting compound was treated in the similar manner as the above-mentioned to give the following compound.

| EXAMPLE No. | No | Structure | MS (m/z) |
|---|---|---|---|
| 64 | 1 | 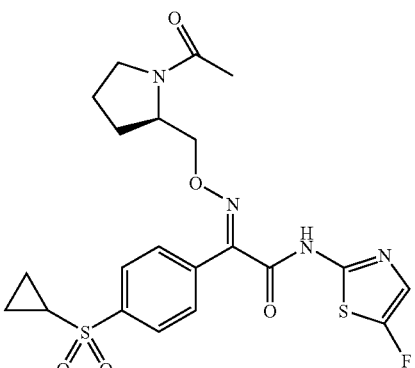 | 495 APCI [M+H]$^+$ |

Example 65

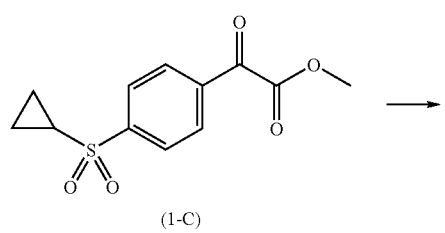

(1-C)

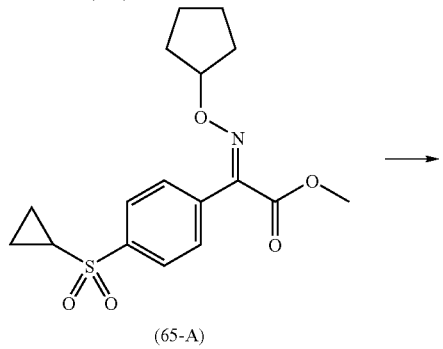

(65-A)

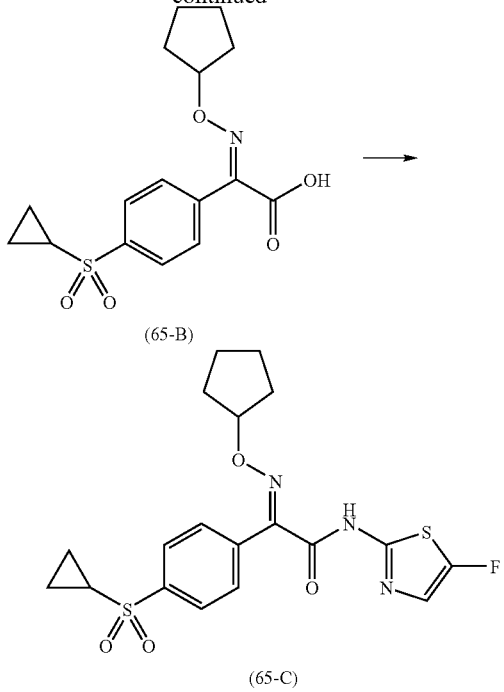

(1) To a solution of the compound (1-C) (10 g, 37.2 mmol) and cyclopentyloxyamine (8.4 g, 83.0 mmol) in methanol (100 ml) was added pyridinium p-toluenesulfonate (10 mg, 0.04 mmol). The mixture was stirred at room temperature for 36 hours and concentrated in vacuo. The residue was purified by silica gel column chromatography (25 to 33% ethyl acetate-hexane) to give (E)-ester (65-A) (3.05 g, yield 23%) and the corresponding (Z)-ester (6.17 g, yield 47%) as a colorless solid each.

(2) The above compound (65-A) was reacted in the similar manner as EXAMPLE 1-(4-2-2) to give the compound (65-B).

MS (m/z) ESI: 336 [M−H]$^-$ (3) The above compound and the corresponding starting compound were reacted in the similar manner as EXAMPLE 1-(S) to give the compound (65-C).

MS (m/z) APCI: 438 [M+H]$^+$

Corresponding starting compounds were treated in the similar manner as the above-mentioned to give the following compounds.

| EXAMPLE No. | No | Structure | MS (m/z) |
|---|---|---|---|
| 65 | 1 | 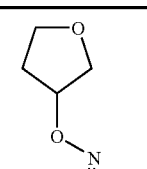 | 440 APCI [M+H]$^+$ |

-continued

| EXAMPLE No. | No | Structure | MS (m/z) |
|---|---|---|---|
| 65 | 2 | 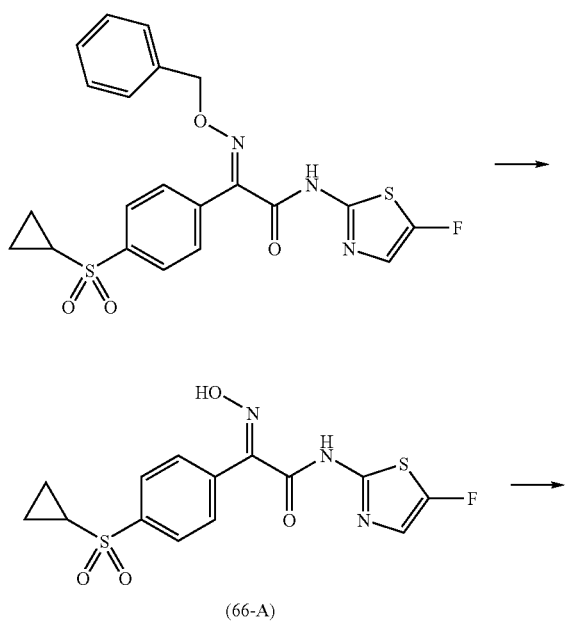 | 460 APCI [M+H]+ |

Example 66

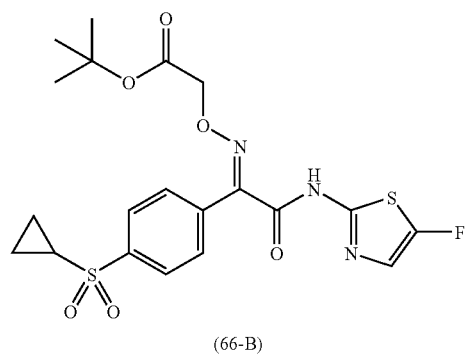

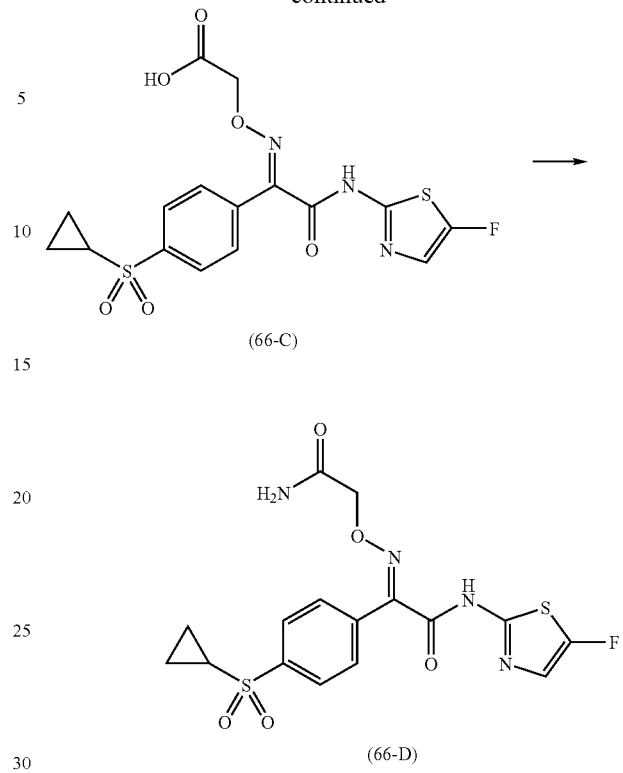

(1) To a solution of the compound of EXAMPLE 65-(2) (4.59 g, 9.99 mmol) in methylene chloride (200 ml) was added dropwise a 1.0M solution of boron tribromide in methylene chloride (50 ml, 50 mmol) over 30 minutes at −78° C., and then the mixture was stirred at the same temperature for 2 hours. To the reaction mixture was added water, and the mixture was warmed to room temperature and then extracted with chloroform. The organic layer was washed sequentially with water and brine, dried over sodium sulfate and concentrated in vacuo. The residue was solidified with a mixture of ethyl acetate-hexane (1:1) to give the comopund (66-A) (2.97 g, yield 81%).
MS (m/z) APCI: 370 [M+H]+

(2) To a solution of the above compound (500 mg, 1.35 mmol) in THF-N,N-dimethylacetamide (1:1) (4 ml) were added potassium tert-butoxide (379 mg, 3.38 mmol) and tert-butyl bromoacetate (0.22 ml, 1.49 mmol) under ice-cooling. The mixture was stirred at the same temperature for 40 minutes, diluted with ethyl acetate, and then washed sequentially with a saturated aqueous ammonium chloride solution, water and brine, dried over sodium sulfate and concentrated in vacuo. The residue was purified by silica gel column chromatography (20 to 50% ethyl acetate-hexane) to give the compound (66-B) (477 mg, yield 73%).
MS (m/z) APCI: 484 [M+H]+

(3) The above compound (448 mg, 0.927 mmol) was dissolved in formic acid (10 ml) at room temperature. The mixture was stirred at the same temperature for 70 hours and concentrated in uacuo, and then the residue was solidified with diisopropyl ether to give the carboxylic acid (66-C) (359 mg, yield 91%).
MS (m/z) ESI: 426 [M−H]−

(4) To a solution of the above compound (70 mg, 0.164 mmol) and 1-hydroxybenzotriazole (33.2 mg, 0.246 mmol) in DMF (2 ml) was added N-ethyl-N'-(3-dimethylaminopropyl)carbodiimide hydrochloride (63 mg, 0.328 mmol) under ice-cooling. The mixture was stirred at the same temperature for 1 hour. Then, thereto was added a 28% aqueous ammonia solution (1 ml), and the mixture was stirred at the same temperature for 30 minutes, diluted with ethyl acetate, washed sequentially with water and brine, dried over sodium sulfate and concentrated in vacuo. The residue was purified by silica gel column chromatography (0 to 7% methanol-chloroform) to give the compound (66-D) (24.7 mg, yield 35%).

MS (m/z) APCI: 427 [M+H]+

Corresponding starting compounds were treated in the similar manner as the above-mentioned to give the following compounds.

| EXAMPLE No. | No | Structure | MS (m/z) |
|---|---|---|---|
| 66 | 1 | | 441 APCI [M+H]+ |
| 66 | 2 | | 455 APCI [M+H]+ |

Example 67

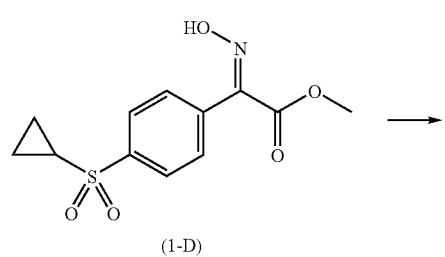

(1-D)

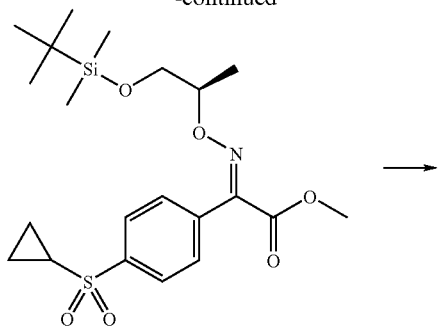

(67-A)

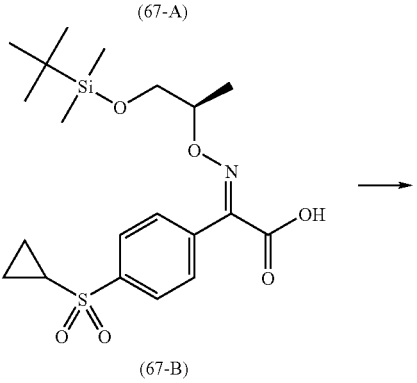

(67-B)

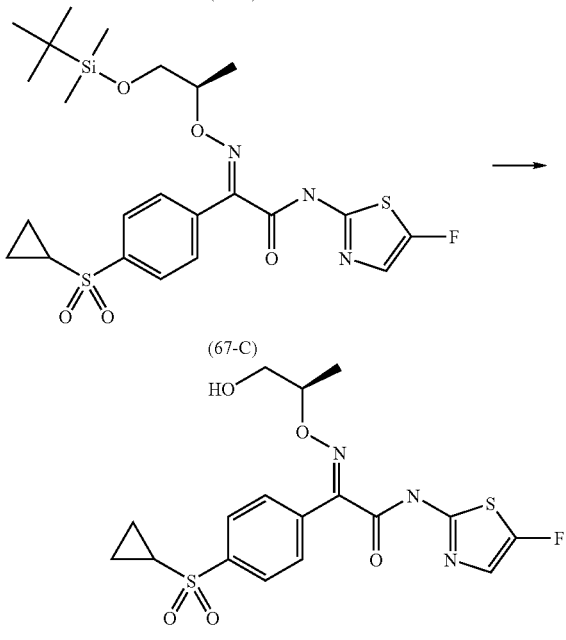

(67-C)

(67-D)

(1) The compound (1-D), (S)-1-(tert-butyldimethylsilyloxy)-2-propanol and the corresponding starting compound were reacted in the similar manner as EXAMPLE 1-(4-1) to give the compound (67-A).
MS (m/z) APCI: 473 [M+NH4]+

(2) The above compound was treated in the similar manner as EXAMPLE 1-(4-2-2) to give the compound (67-B).
MS (m/z) ESI: 440 [M−H]−

(3) The above compound was treated in the similar manner as EXAMPLE 1-(5) to give the compound (67-C).
MS (m/z) APCI: 542 [M+H]+

(4) To a solution of the above compound (73.7 mg, 0.136 mmol) in THF (3 ml) was added a 1.0M solution of tetrabutylammonium fluoride in THF (0.54 ml, 0.54 mmol) under ice-cooling. The mixture was stirred at room temperature for 24 hours, diluted with ethyl acetate, washed sequentially with water and brine, dried over magnesium sulfate and concentrated in vacuo. The residue was purified by silica gel column chromatography (0 to 5% methanol-ethyl acetate) to give the compound (67-D) (38 mg, yield 65%).

MS (m/z) APCI: 428 [M+H]$^+$

Corresponding starting compounds were treated in the similar manner as the above-mentioned to give the following compounds.

| EXAMPLE No. | No | Structure | MS (m/z) |
|---|---|---|---|
| 67 | 1 | | 414 APCI [M+H]$^+$ |
| 67 | 2 | | 428 APCI [M+H]$^+$ |
| 67 | 3 | | 454 APCI [M+H]$^+$ |
| 67 | 4 | | 454 APCI [M+H]$^+$ |
| 67 | 5 | | 428 APCI [M+H]$^+$ |
| 67 | 6 | | 454 APCI [M+H]$^+$ |
| 67 | 7 | | 453 APCI [M+H]$^+$ |
| 67 | 8 | | 468 APCI [M+H]$^+$ |

183
-continued
| EXAMPLE No. | No | Structure | MS (m/z) |
|---|---|---|---|
| 67 | 9 | 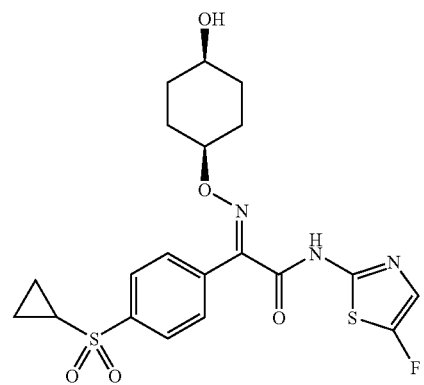 | 468 APCI [M+H]+ |
Example 68
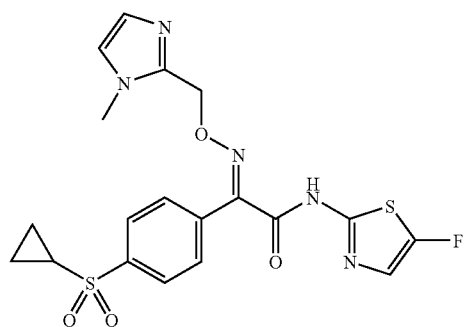
The compound (66-A) and the corresponding starting compound were reacted in the similar manner as EXAMPLE 66-(2) to give the above compound.
MS (m/z) APCI: 464 [M+H]+
Example 69
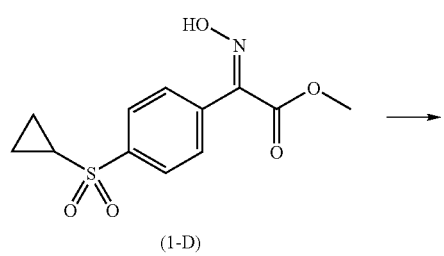
(1-D)
184
-continued
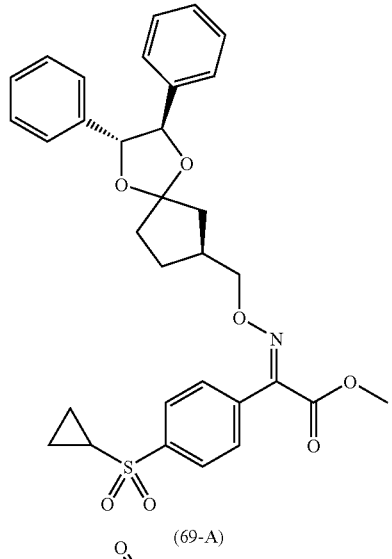
(69-A)
(69-B)
(69-C)
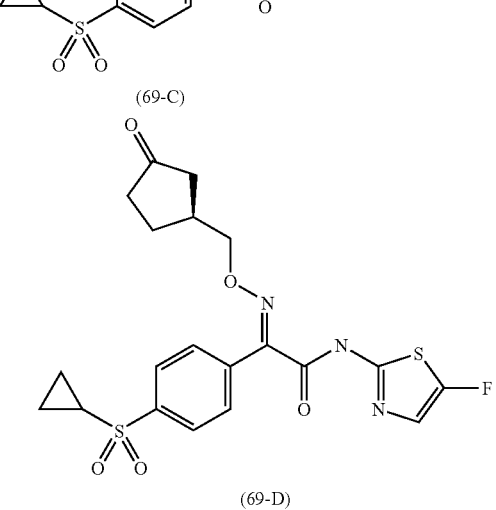
(69-D)

185

(1) To a solution of the compound (1-D) (858 mg, 3.03 mmol) in dimethylacetamide (5 ml) was added potassium tert-butoxide (374 mg, 3.33 mmol) under ice-cooling, and thereto was added (7S)-iodomethyl-(2R,3R)-diphenyl-1,4-dioxaspiro[4.4]nonane (WO2003095438) (1.40 g, 3.33 mmol). The mixture was stirred at room temperature overnight, diluted with ethyl acetate, washed sequentially with a 10% aqueous ammonium chloride solution, water and brine, dried over sodium sulfate and concentrated in vacuo. The residue was purified by silica gel column chromatography (30% ethyl acetate-hexane) to give the compound (69-A) (856 mg, yield 49%).

MS (m/z) APCI: 593 [M+NH$_4$]$^+$ (2) To a solution of the above compound (1.05 g, 1.83 mmol) in dioxane (60 ml) was added 5N hydrochloric acid (30 ml) at room temperature. The mixture was stirred at the same temperature for 15 hours, diluted with ethyl acetate, washed sequentially with water and brine, dried over sodium sulfate and concentrated in vacuo. The residue was purified by silica gel column chromatography (50% ethyl acetate-hexane) to give the compound (69-B) (512 mg, yield 74%).

MS (m/z) APCI: 380 [M+H]$^+$ (3) The above compound was reacted in the similar manner as EXAMPLE 1-(4-2-2) to give the compound (69-C).

MS (m/z) ESI: 751 [2M+Na−2H]$^-$ (4) The above compound and the corresponding starting compound were reacted in the similar manner as EXAMPLE 1-(5) to give the compound (69-D).

MS (m/z) APCI: 466 [M+H]$^+$

Example 70

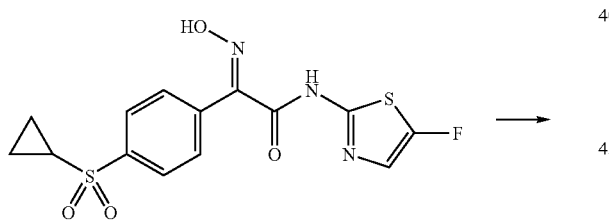

(66-A)

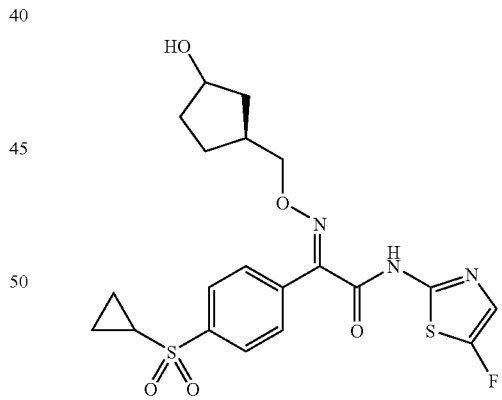

(70-A)

186

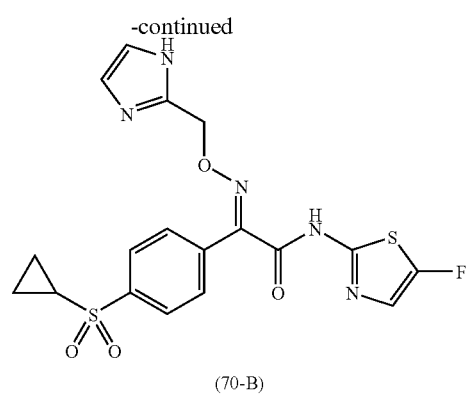

(70-B)

(1) The compound (66-A) and the corresponding starting compound were reacted in the similar manner as EXAMPLE 66-(2) to give the compound (70-A).

MS (m/z) APCI: 534 [M+H]$^+$ (2) The above compound (48.5 mg, 0.091 mmol) was dissolved in a mixed solvent of water-trifluoroacetic acid (1:3) (4 ml). The mixture was stirred at room temperature for 4 days, concentrated in vacuo, and then the residue was diluted with ethyl acetate, washed sequentially with a saturated aqueous sodium bicarbonate solution, water and brine, dried over sodium sulfate and concentrated in vacuo. The residue was purified by gel-filtration (column: JAI-GEL, solvent: chloroform) to give the compound (70-B) (7 mg, yield 17%).

MS (m/z) APCI: 450 [M+H]$^+$

Example 71

The compound (69-D) (84.3 mg, 0.181 mmol) was dissolved in a mixture of methanol-THF (2:1) (6 ml), and thereto was added sodium borohydride (33.8 mg, 0.89 mmol) under ice-cooling. The mixture was stirred at room temperature for 90 minutes, diluted with ethyl acetate, washed sequentially with water and brine, dried over sodium sulfate and concentrated in vacuo. The residue was purified by silica gel column chromatography (0 to 7% methanol-chloroform) to give the above compound (79.8 mg, yield 94%).

MS (m/z) APCI: 468 [M+H]$^+$

Example 72

A corresponding starting compound was treated in the similar manner as EXAMPLE 62 and EXAMPLE 64 to give the following compound.

| EXAMPLE No. | No | Structure | MS (m/z) |
|---|---|---|---|
| 72 | | 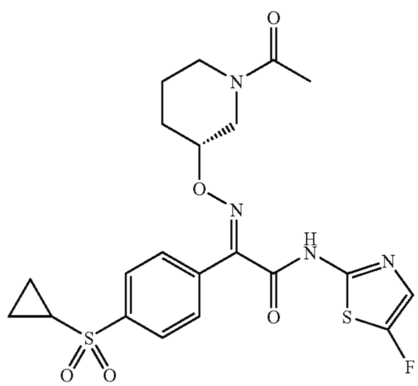 | 495 APCI [M + H]⁺ |

Example 73

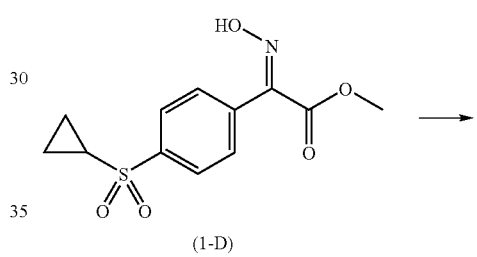

To a solution of the compound of EXAMPLE 62-(7) (100 mg, 0.21 mmol) in methanol (3 ml) was added a 4N solution of hydrogen chloride in dioxane at room temperature, and the mixture was stirred for 3 days. To the reaction mixture was added a saturated aqueous sodium carbonate solution, and then the mixture was extracted with chloroform. The organic layer was washed sequentially with water and brine, dried over magnesium sulfate and concentrated in vacuo. The residue was purified by silica gel column chromatography (2 to 10% methanolchloroform) to give the above compound (54.1 mg, yield 60%).

MS (m/z) APCI: 428 [M+H]⁺

A corresponding starting compound was treated in the similar manner as the above-mentioned to give the following compound.

| EXAMPLE No. | No | Structure | MS (m/z) |
|---|---|---|---|
| 73 | 1 | 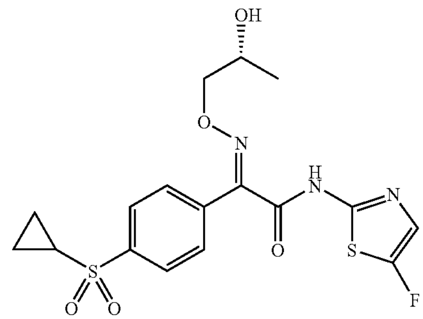 | 428 APCI [M + H]⁺ |

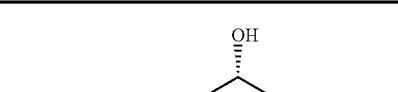

Example 74

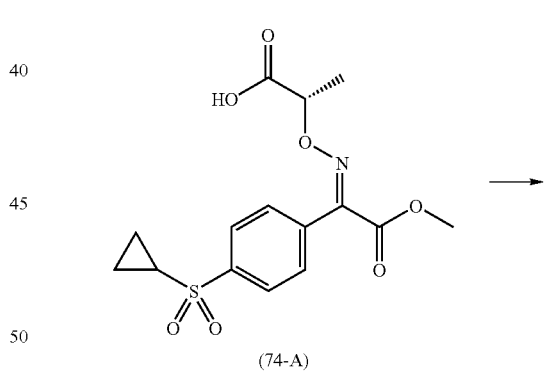

(1-D)

(74-A)

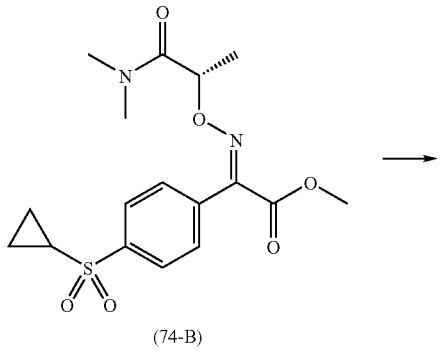

(74-B)

189

-continued

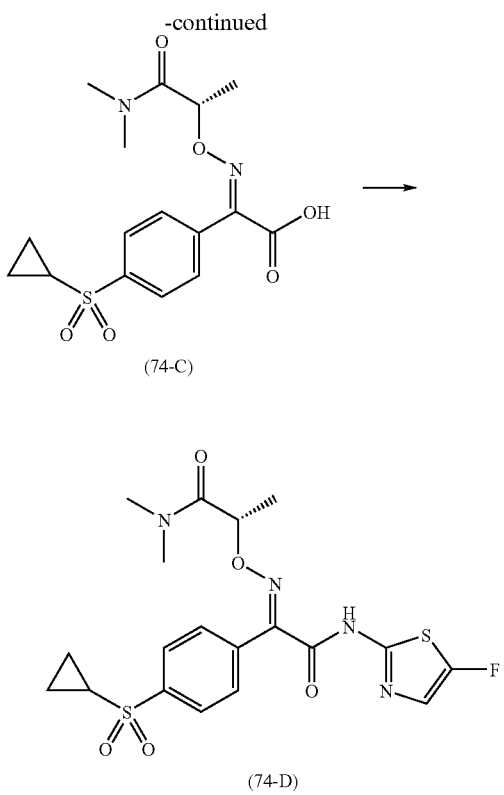

(74-C)

(74-D)

(1) To a solution of the compound (1-D) (1.0 g, 3.53 mmol) in THF (40 ml) was added sodium hydride (60%, 353 mg, 8.83 mmol) under ice-cooling, and thereto was added (R)-2-bromopropionic acid (702 mg, 4.59 mmol) and the ice bath was removed. The mixture was stirred at room temperature for 3 hours, diluted with ethyl acetate, and then washed sequentially with 10% hydrochloric acid, water and brine, dried over magnesium sulfate and concentrated in vacuo. The resulting crude carboxylic acid (74-A) was used in the next reaction directly.

(2) To a solution of the above crude carboxylic acid in DMF (15 ml) were added sequentially 1-hydroxybenzotriazole (1.25 g, 9.29 mmol) and N-ethyl-N'-(3-dimethylaminopropyl)carbodiimide hydrochloride (2.97 g, 15.5 mmol) under ice-cooling, and the mixture was stirred at the same temperature for 4 hours. Then, thereto was added an aqueous solution of dimethylamine (50%) (5.0 ml) and the ice bath was removed and the mixture was stirred at room temperature for 30 minutes. The reaction mixture was diluted with ethyl acetate, and then washed sequentially with water and brine, dried over magnesium sulfate and concentrated in vacuo. The residue was purified by NH-silica gel column chromatography (50% ethyl acetate-hexane) to give the compound (74-B) (594 mg, yield 44%).

MS (m/z) APCI: 383 [M+H]⁺

(3) The above compound was treated in the similar manner as EXAMPLE 1-(4-2-2) to give the compound (74-C).

(4) The above compound and the corresponding starting compound were reacted in the similar manner as EXAMPLE 1-(5) to give the compound (74-D).

MS (m/z) APCI: 469 [M+H]⁺

190

Example 75

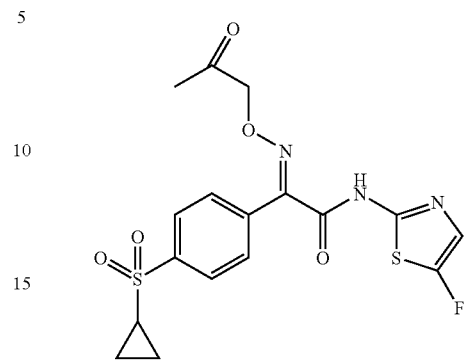

To a solution of the compound of EXAMPLE 73 (100 mg, 0.23 mmol) and triethylamine (0.326 ml, 2.34 mmol) in dimethylsulfoxide (3 ml) was added sulfur trioxide-pyridine complex (186 mg, 1.17 mmol) at room temperature. The mixture was stirred at the same temperature for 18 hours, diluted with ethyl acetate, and then washed sequentially with water and brine, dried over magnesium sulfate and concentrated in vacuo. The residue was purified by silica gel column chromatography (30 to 100% ethyl acetate-hexane) to give the above compound (27.9 mg, yield 28%).

MS (m/z) APCI: 426 [M+H]⁺

A corresponding starting compound was treated in the similar manner as the above-mentioned to give the following compound.

| EXAMPLE No. | No | Structure | MS (m/z) |
|---|---|---|---|
| 75 | 1 | 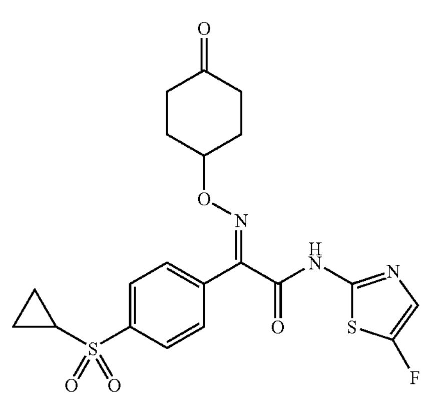 | 466 APCI [M+H]⁺ |

Example 76

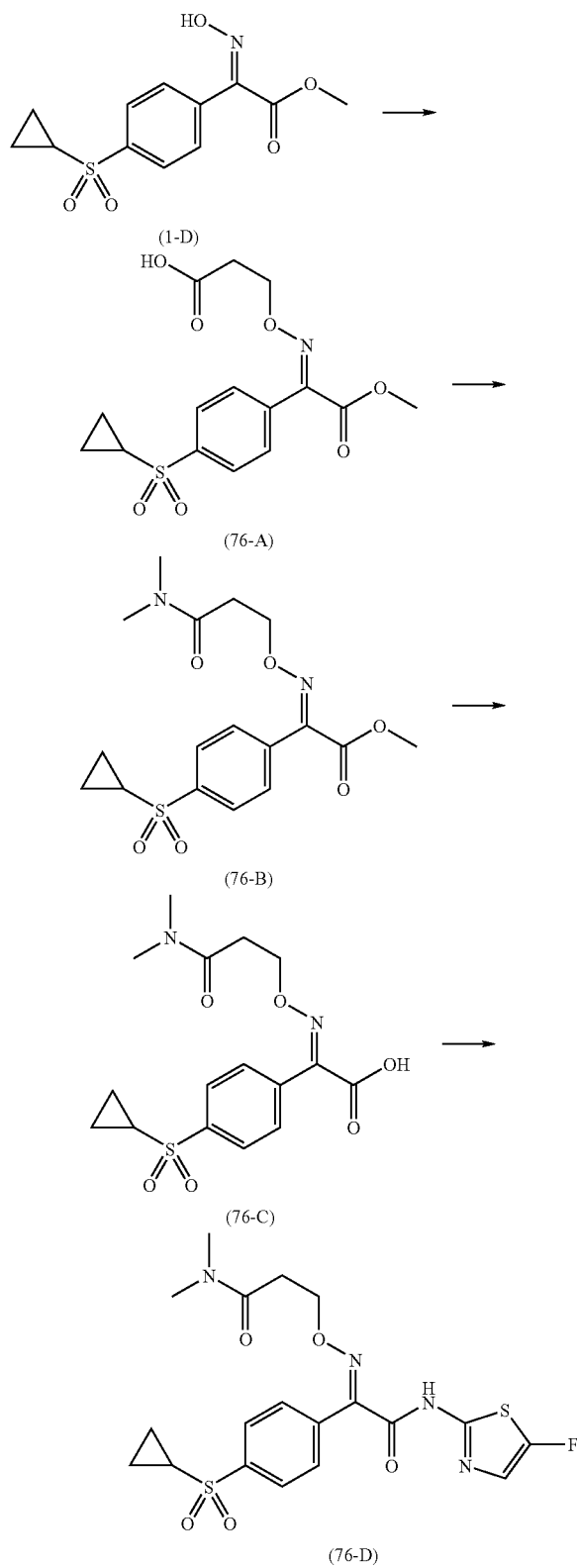

(1) To a solution of the compound (1-D) (1.0 g, 3.53 mmol) in THF (15 ml) were added sequentially potassium tert-bu-toxide (396 mg, 3.53 mmol) and then β-propiolactone (382 mg, 5.30 mmol) under ice-cooling, and the mixture was stirred at the same temperature for 2 hours and at room temperature for another 2 hours, and further at 50° C. for 2 hours. To the reaction mixture was added 10% hydrochloric acid, and then the mixture was diluted with ethyl acetate, washed sequentially with water and brine, dried over magnesium sulfate and concentrated in vacuo. The resulting crude carboxylic acid (76-A) was used in the next reaction directly.

(2) The above crude carboxylic acid and the corresponding starting compound were reacted in the similar manner as EXAMPLE 74-(2) to give the compound (76-B).

MS (m/z) APCI: 383 [M+H]$^+$ (3) The above compound was treated in the similar manner as EXAMPLE 1-(4-2-2) to give the compound (76-C).

(4) The above compound was reacted in the similar manner as EXAMPLE 1-(5) to give the compound (76-D).

MS (m/z) APCI: 469 [M+H]$^+$

Example 77

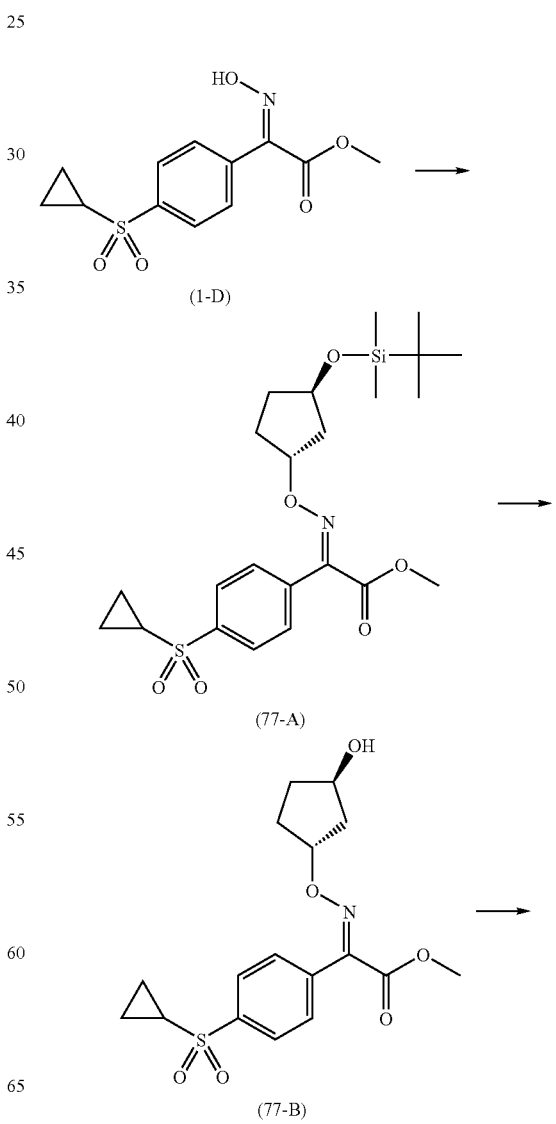

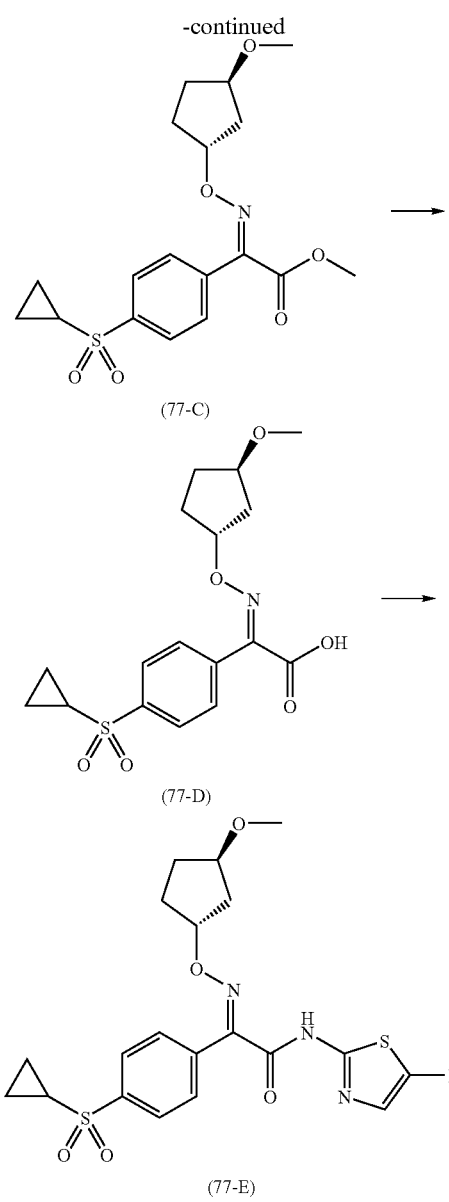

(77-C)

(77-D)

(77-E)

(1) To a solution of the compound (77-A) (1.77 g, 3.67 mmol) obtained from the compound (1-D) in the method of EXAMPLE 1-(4-2-1) in THF (10 ml) was added acetic acid (0.631 ml, 11.0 mmol) under ice-cooling, and thereto was added a 1.0M solution of tetrabutylammonium fluoride in THF (11.0 ml, 11.0 mmol), and the mixture was warmed to 50° C. and then stirred for 3 hours, diluted with ethyl acetate, washed sequentially with water and brine, dried over magnesium sulfate and concentrated in vacuo. The residue was purified by silica gel column chromatography (50 to 80% ethyl acetate-hexane) to give the compound (77-B) (1.21 g, yield 90%).

MS (m/z) APCI: 368 [M+H]+

(2) To a solution of the above compound (1.05 g, 2.86 mmol) in DMF (10 ml) were added silver (I) oxide (2.99 g, 12.7 mmol) and then methyl iodide (1.60 ml, 25.7 mmol) at room temperature, and the mixture was stirred at 40 to 50° C. for 24 hours, diluted with ethyl acetate, and then filtered through Celite and the filtrate was washed sequentially with water and brine, dried over sodium sulfate and concentrated in vacuo. The residue was purified by silica gel column chromatography (30% ethyl acetate-hexane) to give the compound (77-C) (617 mg, yield 57%).

MS (m/z) APCI: 382 [M+H]+

(3) The above compound was reacted in the similar manner as EXAMPLE 1-(4-2-2) to give the compound (77-D).

MS (m/z) ESI: 366 [M−H]−

(4) The above compound was reacted in the similar manner as EXAMPLE 1-(5) to give the compound (77-E).

MS (m/z) APCI: 468 [M+H]+

Example 78

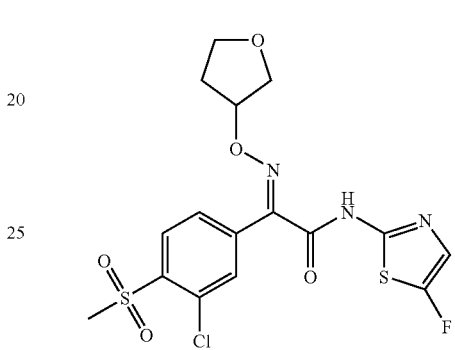

(3-Chloro-4-methanesulfonylphenyl)oxoacetic acid ethyl ester and the corresponding starting compound were reacted in the similar manner as EXAMPLE 65 to give the above compound.

MS (m/z) APCI: 448/450 [M+H]+

Example 79

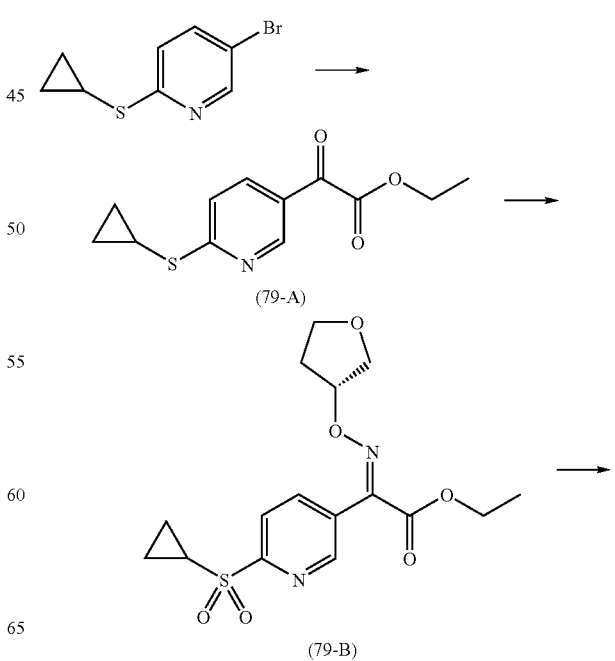

(79-A)

(79-B)

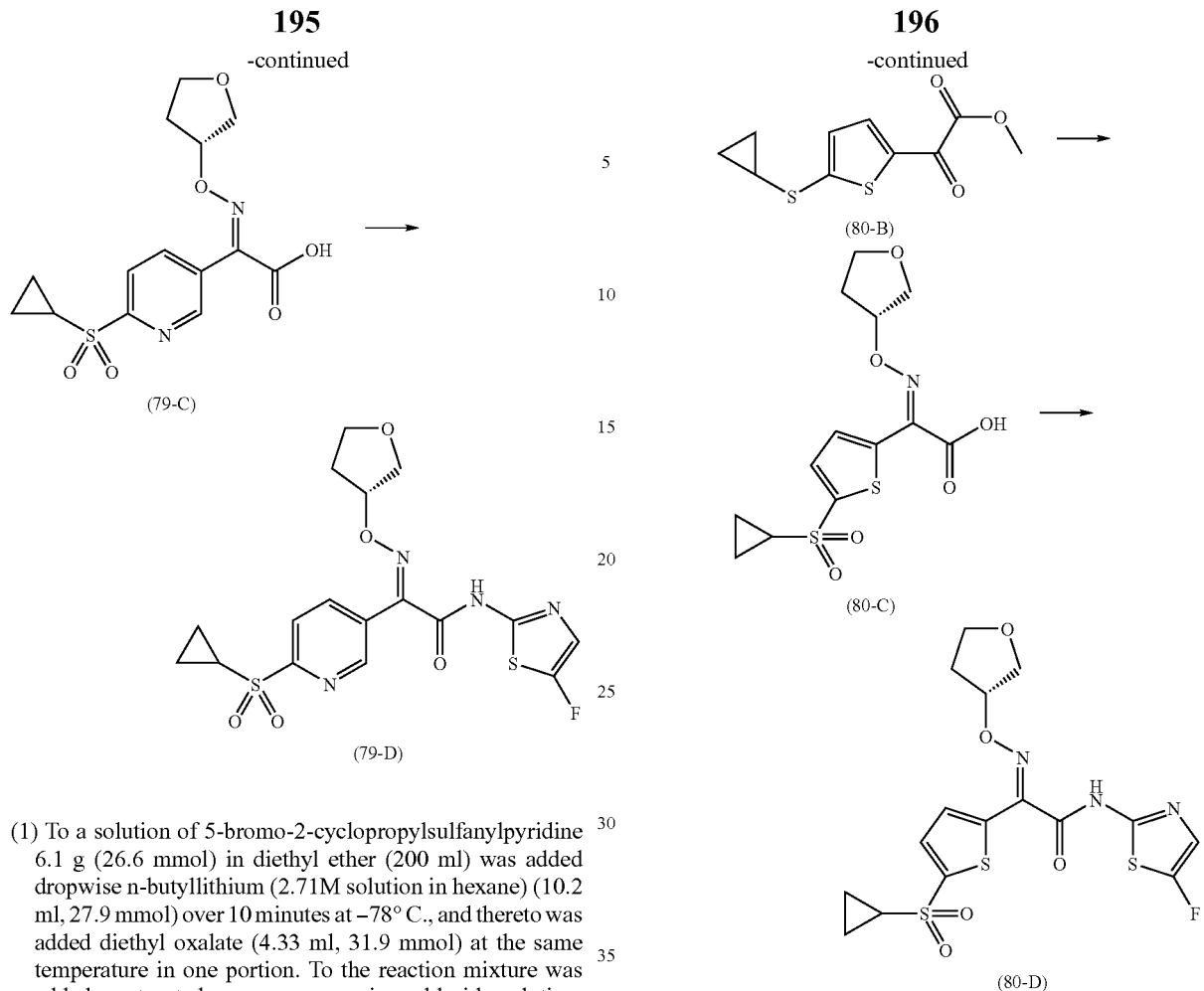

(1) To a solution of 5-bromo-2-cyclopropylsulfanylpyridine 6.1 g (26.6 mmol) in diethyl ether (200 ml) was added dropwise n-butyllithium (2.71M solution in hexane) (10.2 ml, 27.9 mmol) over 10 minutes at −78° C., and thereto was added diethyl oxalate (4.33 ml, 31.9 mmol) at the same temperature in one portion. To the reaction mixture was added a saturated aqueous ammonium chloride solution, and the mixture was extracted with ethyl acetate. The organic layer was separated and then washed sequentially with water and brine, dried over magnesium sulfate and concentrated in vacuo. The residue was purified by silica gel column chromatography (14% ethyl acetate-hexane) to give the above compound (79-A) (2.64 g, yield 40%).

MS (m/z) APCI: 252 [M+H]⁺

(2) The above compound and the corresponding starting compound were reacted in the similar manner as EXAMPLE 65-(1) and 27 to give the compound (79-B).

MS (m/z) APCI: 369 [M+H]⁺

(3) The above compound was reacted in the similar manner as EXAMPLE 1-(4-2-2) to give the compound (79-C).

MS (m/z) ESI: 339 [M−H]⁻

(4) The above compound was reacted in the similar manner as EXAMPLE 1-(5) to give the compound (79-D).

MS (m/z) APCI: 441 [M+H]⁺

Example 80

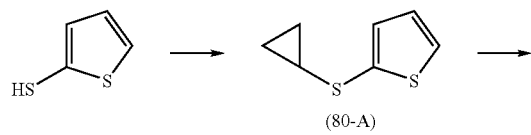

(1) To a solution of thiophene-2-thiol (23.39 g, 200.4 mmol) in DMF (150 ml) was added potassium tert-butoxide (24.74 g, 220 mmol) under ice-cooling, and the mixture was stirred at the same temperature for 30 minutes and at room temperature for another 1 hour. To the above reaction mixture was added cyclopropyl bromide (17.8 ml, 222 mmol), and the mixture was stirred at 60° C. for 30 hours and at 80° C. for another 5 hours. The reaction mixture was diluted with ethyl acetate, washed sequentially with a saturated aqueous sodium bicarbonate solution, water and brine, dried over sodium sulfate and concentrated in vacuo. The residue was purified by NH-silica gel chromatography (ethyl acetate) and further purified by distillation under reduced pressure to give 2-cyclopropylsulfanylthiophene (80-A) (18.5 g, yield 59%) as a colorless oil.

bp 70 to 100° C. (19 mmHg), MS (m/z) APCI: 157 [M+H]⁺

(2) The above compound and the corresponding starting compound were reacted in the similar manner as EXAMPLE 1-(1) to give the above compound (80-B).

MS (m/z) APCI: 257 [M+H]⁺

(3) The above compound and the corresponding starting compound were reacted in the similar manner as EXAMPLE 1-(2) to (4) to give the above compound (80-C).

MS (m/z) ESI: 344 [M−H]⁻

(4) The above compound and the corresponding starting compound were reacted in the similar manner as EXAMPLE 1-(5) to give the above compound (80-D).

MS (m/z) APCI: 446 [M+H]⁺

Example 81

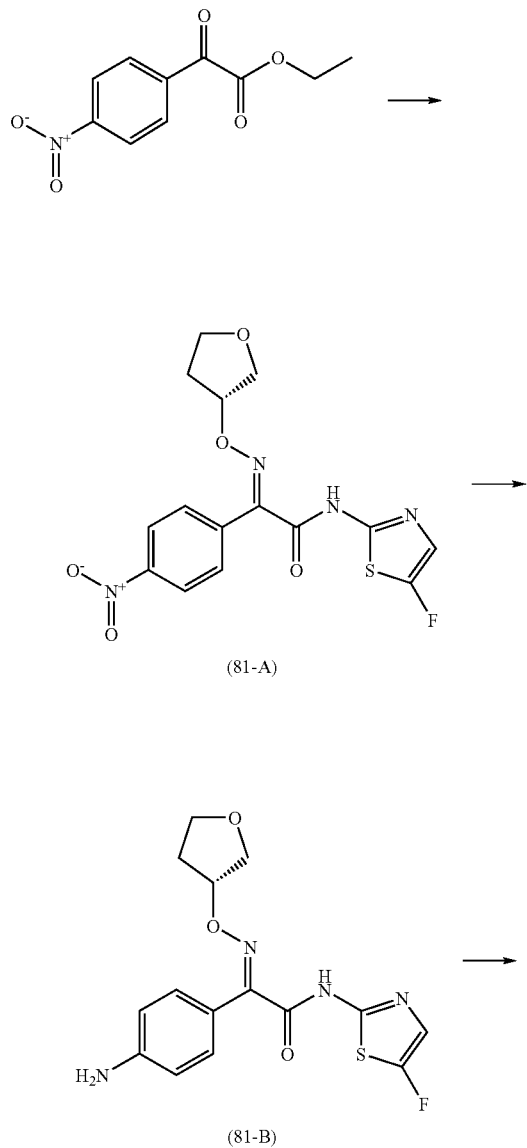

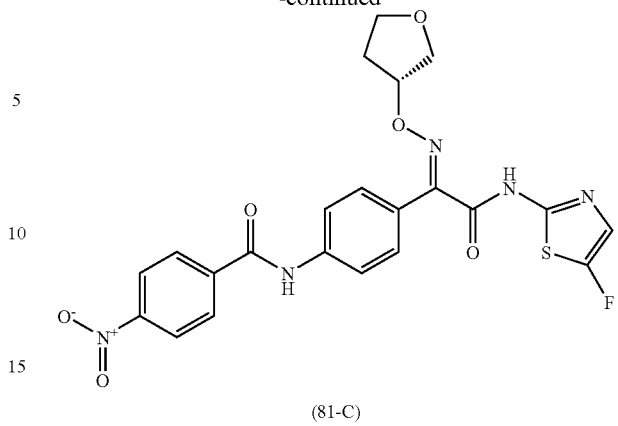

(1) (4-Nitrophenyl)oxoacetic acid ethyl ester and the corresponding starting compounds were reacted in the similar manner as EXAMPLE 1-(3) to (5) to give the compound (81-A).

MS (m/z) APCI: 381 [M+H]$^+$ (2) To a solution of the above compound (3.0 g, 7.89 mmol) in ethanol (150 ml) was added stannous chloride dihydrate (8.9 g, 39.4 mmol) at room temperature, and the mixture was stirred at the same temperature for 16 hours. The reaction mixture was concentrated, and thereto was added ethyl acetate. The mixture was washed sequentially with a saturated aqueous sodium bicarbonate solution, water and brine, dried over magnesium sulfate and concentrated in vacuo. The residue was purified by silica gel chromatography (5% methanol-chloroform) to give the compound (81-B) 2.47 g, yield 89%).

MS (m/z) APCI: 351 [M+H]$^+$ (3) To a solution of the above compound (100 mg, 0.29 mmol) and diisopropylethylamine (0.060 ml, 0.34 mmol) in THF (5 ml) was added p-nitrobenzoyl chloride (58 mg, 0.31 mmol) under ice-cooling, and then the ice bath was removed and the mixture was stirred at room temperature overnight. The reaction mixture was concentrated in vacuo and the residue was purified by NH-silica gel chromatography (0 to 3% methanol-chloroform) to give the compound (81-C) (160 mg, yield 57%).

MS (m/z) APCI: 500 [M+H]$^+$

Corresponding starting compounds were treated in the similar manner as the above-mentioned to give the following compounds.

| EXAMPLE No. | No | Structure | MS (m/z) |
|---|---|---|---|
| 81 | 1 | 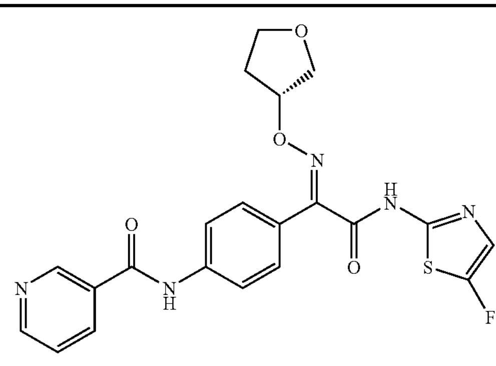 | 456 APCI [M + H]$^+$ |

| EXAMPLE No. | No | Structure | MS (m/z) |
|---|---|---|---|
| 81 | 2 | | 475 APCI [M + H]+ |
| 81 | 3 | | 419 APCI [M + H]+ |
| 81 | 4 | | 456 APCI [M + H]+ |
| 81 | 5 | | 437 APCI [M + H]+ |

-continued
| EXAMPLE No. | No | Structure | MS (m/z) |
|---|---|---|---|
| 81 | 6 | 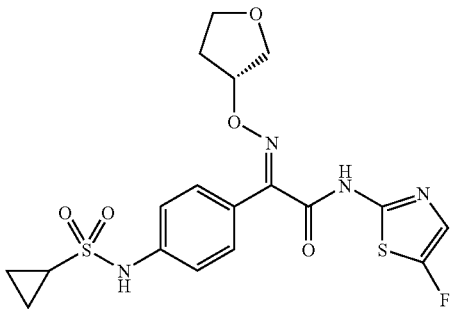 | 455 APCI [M + H]+ |
| 81 | 7 | 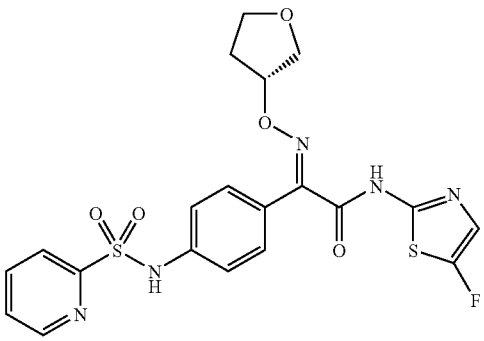 | 492 APCI [M + H]+ |
| 81 | 8 | 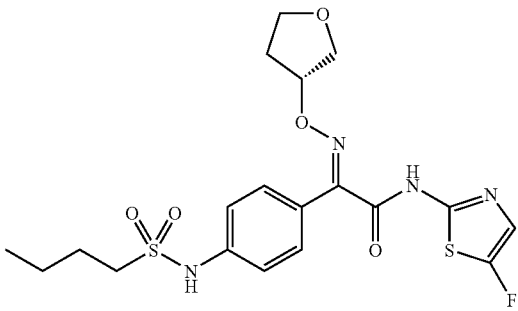 | 471 APCI [M + H]+ |
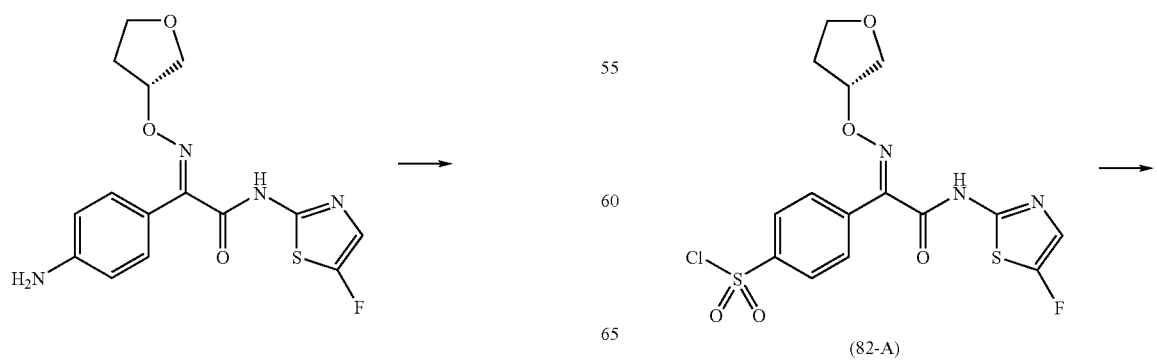

-continued

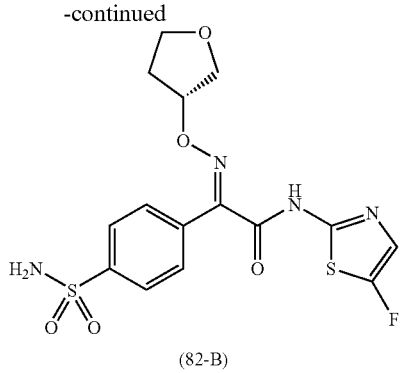

(82-B)

(1) The compound (81-B) (1.0 g, 2.9 mmol) was dissolved in a mixture of acetic acid (5 ml) and concentrated hydrochloric acid (14 ml), and thereto was added dropwise an aqueous solution (4 ml) of sodium nitrite (217 mg, 3.14 mmol) under ice-cooling, and the mixture was stirred at the same temperature for 30 minutes. To the above reaction mixture were added sequentially copper (II) chloride dihydrate (243 mg, 1.43 mmol) and a solution of sodium bisulfite (4.45 g, 42.8 mmol) in 5.5M hydrochloric acid (22 ml), and the mixture was stirred at the same temperature for 10 minutes, and then the ice bath was removed. The mixture was stirred at room temperature for 3 hours and poured onto ice and extracted with ethyl acetate. The organic layer was dried over magnesium sulfate and concentrated in vacuo to give a crude sulfonyl chloride (82-A), which was used in the next reaction directly.

(2) To a solution of the above compound (142 mg) in THF (2 ml) was added a 28% aqueous ammonia solution (0.1 ml) at −5° C. The mixture was warmed to room temperature and stirred for 1 hour, diluted with ethyl acetate, washed sequentially with 2N hydrochloric acid, water and brine, dried over magnesium sulfate and concentrated in vacuo. The residue was purified by silica gel chromatography (40 to 60% ethyl acetate-hexane) to give the compound (82-B) (54 mg, yield 46% in 2 steps).

MS (m/z) APCI: 415 [M+H]$^+$

Corresponding starting compounds were treated in the similar manner as the above-mentioned to give the following compounds.

| EXAMPLE No. | No | Structure | MS (m/z) |
|---|---|---|---|
| 82 | 1 |  | 429 APCI [M + H]$^+$ |
| 82 | 2 |  | 443 APCI [M + H]$^+$ |
| 82 | 3 |  | 443 APCI [M + H]$^+$ |

-continued

| EXAMPLE No. | No | Structure | MS (m/z) |
|---|---|---|---|
| 82 | 4 | | 457 APCI [M + H]+ |
| 82 | 5 | | 455 APCI [M + H]+ |
| 82 | 6 | | 455 APCI [M + H]+ |
| 82 | 7 | | 471 APCI [M + H]+ |

-continued
| EXAMPLE No. | No | Structure | MS (m/z) |
|---|---|---|---|
| 82 | 8 | 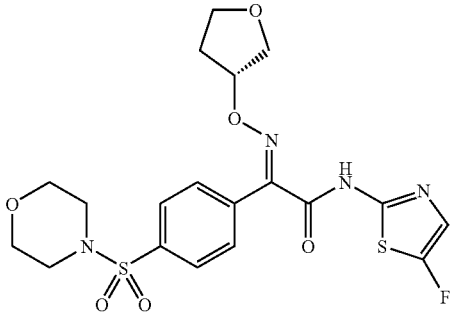 | 485 APCI [M + H]+ |
| 82 | 9 | 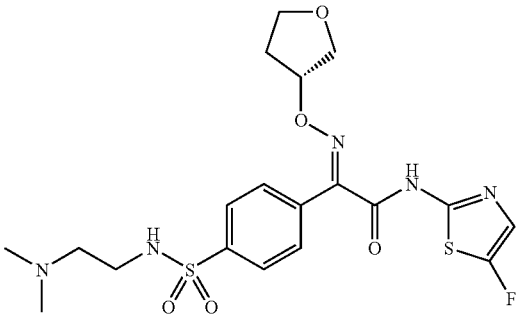 | 486 APCI [M + H]+ |
| 82 | 10 | 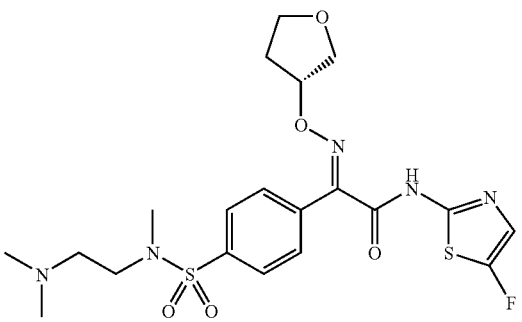 | 500 APCI [M + H]+ |
| 82 | 11 | 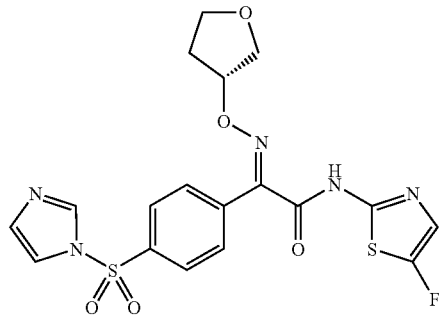 | 466 APCI [M + H]+ |

| EXAMPLE No. | No | Structure | MS (m/z) |
|---|---|---|---|
| 82 | 12 | | 457 APCI [M + H]+ |
| 82 | 13 | | 459 APCI [M + H]+ |
| 82 | 14 | | 473 APCI [M + H]+ |
| 82 | 15 | | 473 APCI [M + H]+ |

| EXAMPLE No. | No | Structure | MS (m/z) |
|---|---|---|---|
| 82 | 16 | 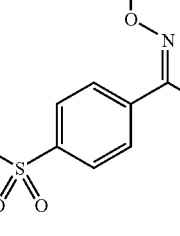 | 487 APCI [M + H]+ |
| 82 | 17 |  | 484 APCI [M + H]+ |
| 82 | 18 |  | 498 APCI [M + H]+ |
| 82 | 19 | 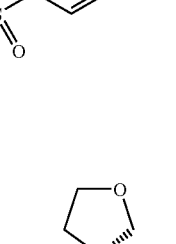 | 498 APCI [M + H]+ |

-continued

| EXAMPLE No. | No | Structure | MS (m/z) |
|---|---|---|---|
| 82 | 20 | | 526 APCI [M + H]+ |
| 82 | 21 | | 499 APCI [M + H]+ |
| 82 | 22 | | 499 APCI [M + H]+ |
| 82 | 23 | | 498 APCI [M + H]+ |

-continued

| EXAMPLE No. | No | Structure | MS (m/z) |
|---|---|---|---|
| 82 | 24 | | 512 APCI [M + H]⁺ |
| 82 | 25 | | 499 APCI [M + H]⁺ |
| 82 | 26 | | 499 APCI [M + H]⁺ |
| 82 | 27 | | 506 APCI [M + H]⁺ |

| EXAMPLE No. | No | Structure | MS (m/z) |
|---|---|---|---|
| 82 | 28 | | 520 APCI [M + H]+ |
| 82 | 29 | | 584 APCI [M + H]+ |
| 82 | 30 | | 512 APCI [M + H]+ |
| 82 | 31 | | 526 APCI [M + H]+ |

-continued

| EXAMPLE No. | No | Structure | MS (m/z) |
|---|---|---|---|
| 82 | 32 | | 555 APCI [M + H]+ |
| 82 | 33 | | 561 APCI [M + H]+ |
| 82 | 34 | | 562 APCI [M + H]+ |
| 82 | 35 | | 576 APCI [M + H]+ |

| EXAMPLE No. | No | Structure | MS (m/z) |
|---|---|---|---|
| 82 | 36 | | 590 APCI [M + H]+ |
| 82 | 37 | | 512 APCI [M + H]+ |
| 82 | 38 | | 540 APCI [M + H]+ |
| 82 | 39 | | 485 APCI [M + H]+ |

-continued

| EXAMPLE No. | No | Structure | MS (m/z) |
|---|---|---|---|
| 82 | 40 | | 485 APCI [M + H]⁺ |
| 82 | 41 | | 512 APCI [M + H]⁺ |
| 82 | 42 | | 512 APCI [M + H]⁺ |
| 82 | 43 | | 469 APCI [M + H]⁺ |

-continued

| EXAMPLE No. | No | Structure | MS (m/z) |
|---|---|---|---|
| 82 | 44 | | 487 APCI [M + H]+ |
| 82 | 45 | | 487 APCI [M + H]+ |
| 82 | 46 | | 501 APCI [M + H]+ |
| 82 | 47 | | 517 APCI [M + H]+ |

-continued
| EXAMPLE No. | No | Structure | MS (m/z) |
|---|---|---|---|
| 82 | 48 | 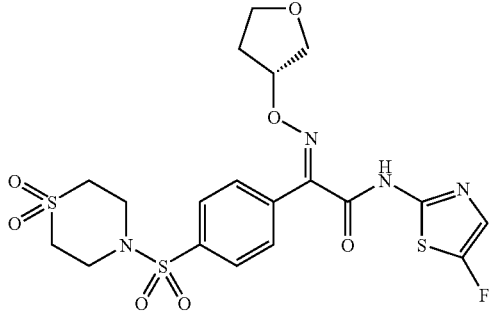 | 533 APCI [M + H]+ |
| 82 | 49 | 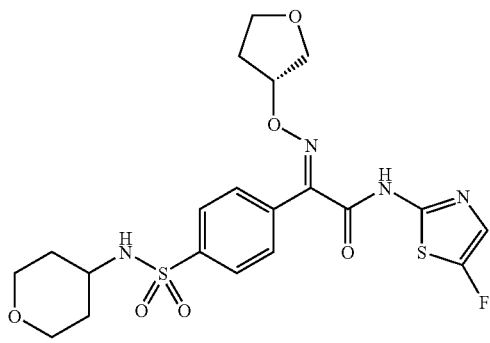 | 499 APCI [M + H]+ |
| 82 | 50 | 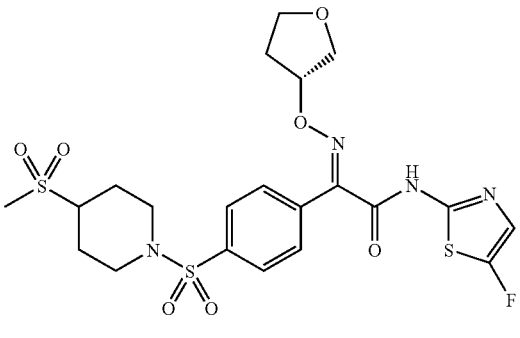 | 561 APCI [M + H]+ |
| 82 | 51 | 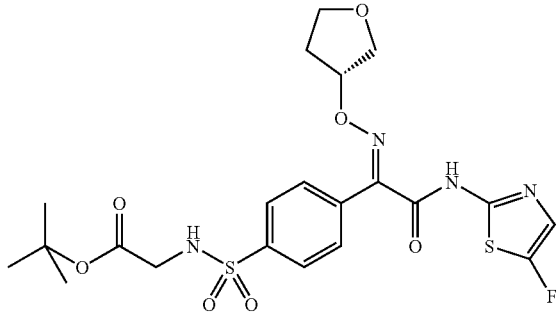 | 529 APCI [M + H]+ |

-continued
| EXAMPLE No. | No | Structure | MS (m/z) |
|---|---|---|---|
| 82 | 52 | 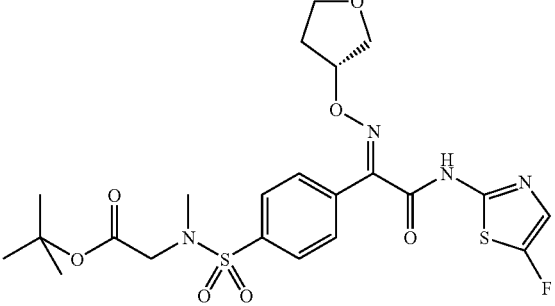 | 560 APCI [M + NH$_4$]$^+$ |
| 82 | 53 | 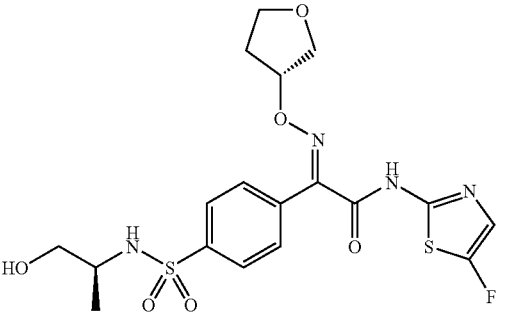 | 473 APCI [M + H]$^+$ |
| 82 | 54 | 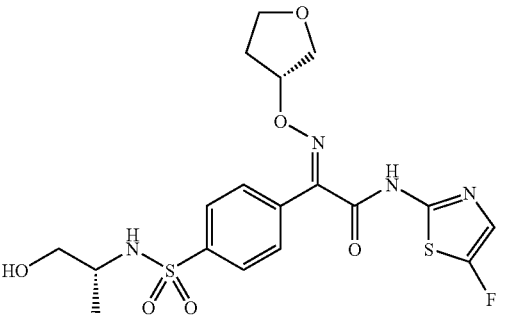 | 473 APCI [M + H]$^+$ |
| 82 | 55 | 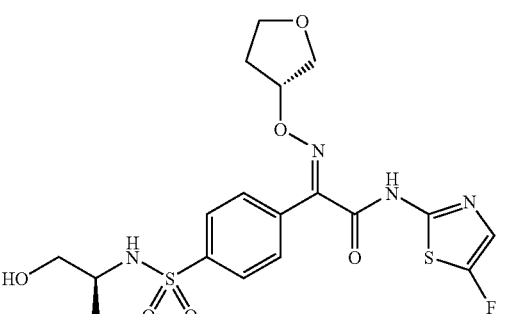 | 487 APCI [M + H]$^+$ |

-continued

| EXAMPLE No. | No | Structure | MS (m/z) |
|---|---|---|---|
| 82 | 56 | | 487 APCI [M + H]+ |
| 82 | 57 | | 501 APCI [M + H]+ |
| 82 | 58 | | 501 APCI [M + H]+ |
| 82 | 59 | | 473 APCI [M + H]+ |

-continued

| EXAMPLE No. | No | Structure | MS (m/z) |
|---|---|---|---|
| 82 | 60 | | 473 APCI [M + H]+ |
| 82 | 61 | | 487 APCI [M + H]+ |
| 82 | 62 | | 487 APCI [M + H]+ |
| 82 | 63 | | 513 APCI [M + H]+ |

| EXAMPLE No. | No | Structure | MS (m/z) |
|---|---|---|---|
| 82 | 64 | | 526 APCI [M + H]+ |
| 82 | 65 | | 513 APCI [M + H]+ |
| 82 | 66 | | 513 APCI [M + H]+ |
| 82 | 67 | | 507 APCI [M + H]+ |

-continued

| EXAMPLE No. | No | Structure | MS (m/z) |
|---|---|---|---|
| 82 | 68 | | 509 APCI [M + H]+ |
| 82 | 69 | | 487 APCI [M + H]+ |
| 82 | 70 | | 501 APCI [M + H]+ |
| 82 | 71 | | 503 APCI [M + H]+ |

-continued

| EXAMPLE No. | No | Structure | MS (m/z) |
|---|---|---|---|
| 82 | 72 | | 531 APCI [M + H]+ |
| 82 | 73 | | 487 APCI [M + H]+ |
| 82 | 74 | | 487 APCI [M + H]+ |
| 82 | 75 | | 503 APCI [M + H]+ |

-continued

| EXAMPLE No. | No | Structure | MS (m/z) |
|---|---|---|---|
| 82 | 76 | | 499 APCI [M + H]+ |
| 82 | 77 | | 499 APCI [M + H]+ |
| 82 | 78 | | 461 APCI [M + H]+ |
| 82 | 79 | | 479 APCI [M + H]+ |

-continued

| EXAMPLE No. | No | Structure | MS (m/z) |
|---|---|---|---|
| 82 | 80 | | 489 APCI [M + H]+ |
| 82 | 81 | | 469 APCI [M + H]+ |
| 82 | 82 | | 514 APCI [M + H]+ |
| 82 | 83 | | 514 APCI [M + H]+ |

-continued

| EXAMPLE No. | No | Structure | MS (m/z) |
|---|---|---|---|
| 82 | 84 | | 528 APCI [M + H]+ |
| 82 | 85 | | 500 APCI [M + H]+ |
| 82 | 86 | | 472 APCI [M + H]+ |
| 82 | 87 | | 486 APCI [M + H]+ |

| EXAMPLE No. | No | Structure | MS (m/z) |
|---|---|---|---|
| 82 | 88 | | 500 APCI [M + H]+ |
| 82 | 89 | | 486 APCI [M + H]+ |
| 82 | 90 | | 528 APCI [M + H]+ |
| 82 | 91 | | 528 APCI [M + H]+ |

-continued

| EXAMPLE No. | No | Structure | MS (m/z) |
|---|---|---|---|
| 82 | 92 | | 542 APCI [M + H]+ |
| 82 | 93 | | 512 APCI [M + H]+ |
| 82 | 94 | | 512 APCI [M + H]+ |
| 82 | 95 | | 540 APCI [M + H]+ |

-continued
| EXAMPLE No. | No | Structure | MS (m/z) |
|---|---|---|---|
| 82 | 96 | 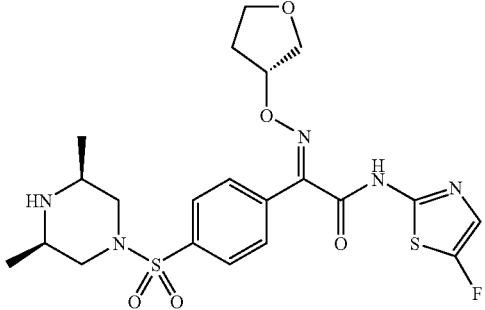 | 512 APCI [M + H]+ |
| 82 | 97 | 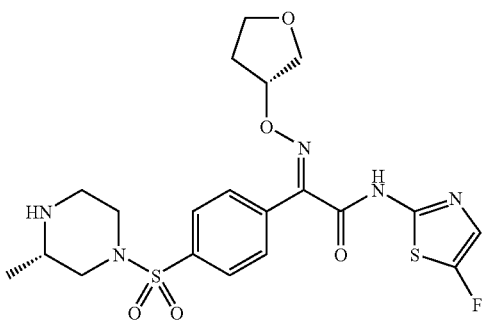 | 498 APCI [M + H]+ |
| 82 | 98 | 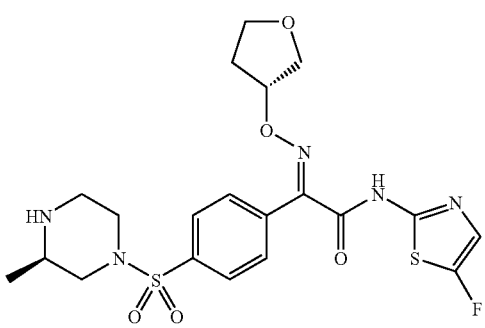 | 498 APCI [M + H]+ |
| 82 | 99 | 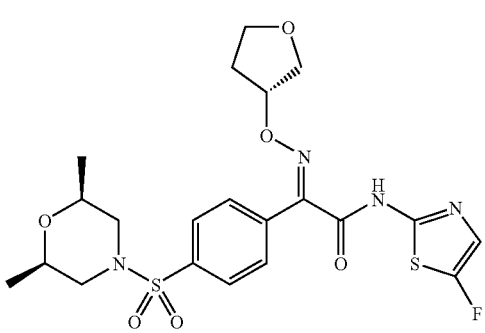 | 513 APCI [M + H]+ |

-continued
| EXAMPLE No. | No | Structure | MS (m/z) |
|---|---|---|---|
| 82 | 100 | | 526 APCI [M + H]+ |
| 82 | 101 | | 459 APCI [M + H]+ |
| 82 | 102 | | 459 APCI [M + H]+ |
Example 83
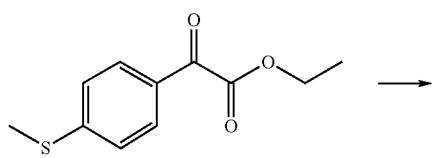
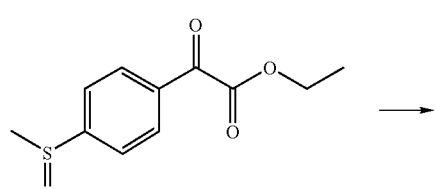
(83-A)
-continued
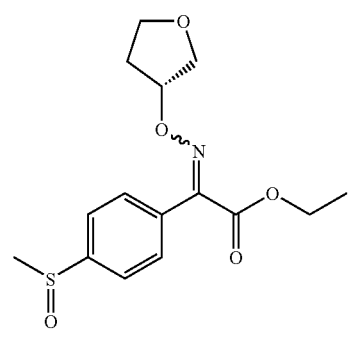
(83-B)

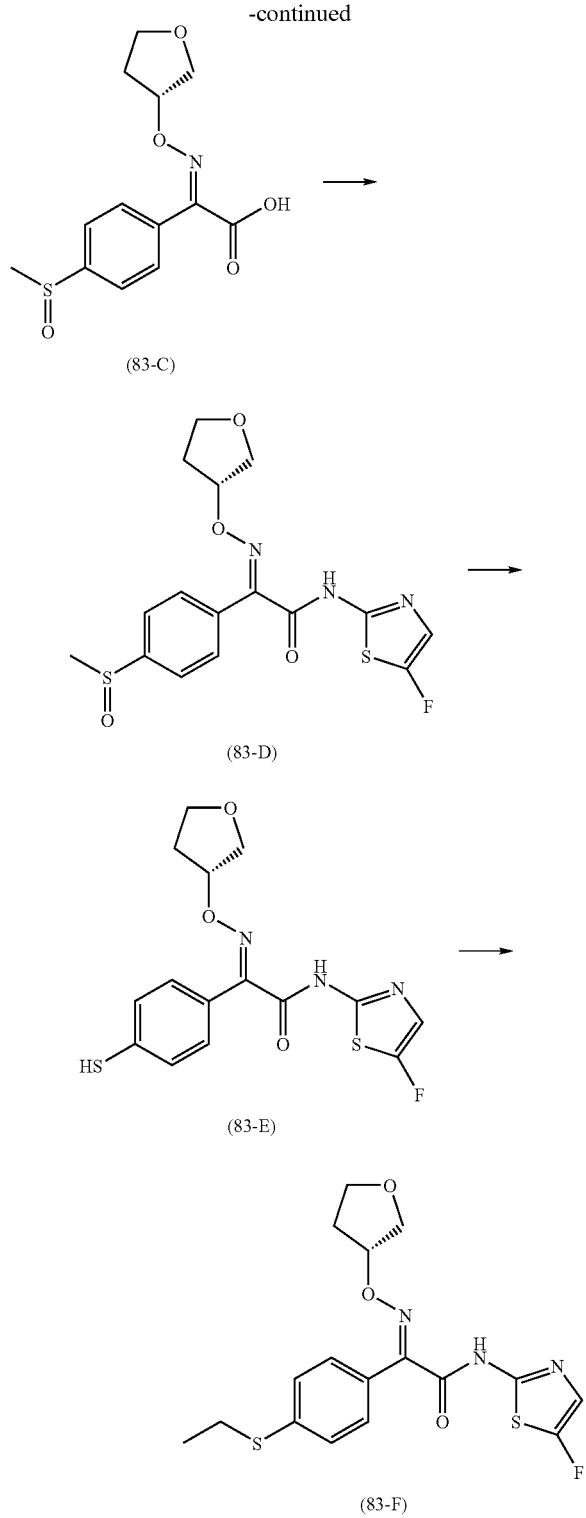

(83-C)

(83-D)

(83-E)

(83-F)

(1) To a solution of (4-methylthiophenyl)oxoacetic acid ethyl ester (44.9 g, 200 mmol) in chloroform (500 ml) was added 65% m-chloroperbenzoic acid (50 g, 188 mmol) over 30 minutes under ice-cooling, and the mixture was stirred at the same temperature for another 1 hour. The precipitated insoluble was filtered off, and then to the filtrate was added a saturated aqueous sodium bicarbonate solution, and the mixture was extracted with chloroform. The organic layer was dried over sodium sulfate and concentrated in vacuo. The residue was purified by silica gel chromatography (50 to 100% ethyl acetate-hexane) to give the compound (83-A) (41.1 g, yield 85%) as a pale yellow oil.

MS (m/z) APCI: 241 [M+H]+

(2) To a solution of the above compound (41.1 g, 171 mmol) in ethanol (400 ml) was added hydroxylamine hydrochloride (15.5 g, 222 mmol). The mixture was stirred at 50° C. for 2 hours, concentrated in vacuo, and then the residue was dissolved in ethyl acetate, washed sequentially with water and brine, dried over sodium sulfate and concentrated in vacuo. To a solution of the resulting crude oxime (45.7 g) and potassium carbonate (49.4 g, 358 mmol) in DMF (325 ml) was added 3-(S)-tetrahydrofuranol p-toluenesulfonate (56.1 g, 232 mmol) at room temperature. The mixture was stirred for 2 days, diluted with ethyl acetate, washed sequentially with water and brine, dried over sodium sulfate and concentrated in vacuo. The residue was purified by silica gel chromatography (ethyl acetate) to give the compound (83-B) (20.9 g, (E)-isomer:(Z)-isomer=72:28).

MS (m/z) APCI: 326 [M+H]+

(3) The above compound (20.35 g) was dissolved in THF-ethanol-water (3:1:1) (350 ml), and thereto was added potassium carbonate (8.63 g, 62.5 mmol), and the mixture was stirred at room temperature for 23 hours. To the reaction mixture was added water, and the aqueous layer was washed with ethyl acetate, acidified with concentrated hydrochloric acid, saturated with sodium chloride and extracted with ethyl acetate several times. The extract was dried over sodium sulfate and concentrated in vacuo to give the compound (83-C, (E)-isomer) (10.9 g, yield 59%) as a pale yellow oil.

MS (m/z) APCI: 298 [M+H]+

(4) The above compound and the corresponding starting compound were reacted in the similar manner as EXAMPLE 1-(5) to give the compound (83-D).

MS (m/z) APCI: 398 [M+H]+

(5) To a solution of the above compound (2.85 g, 7.17 mmol) in chloroform (40 ml) was added trifluoroacetic anhydride (2.03 ml, 14.3 mmol) at room temperature, and the mixture was stirred at the same temperature for 3 hours and concentrated in vacuo. The residue was dissolved in methanol (15 ml), and thereto was added triethylamine (15 ml) at room temperature. The mixture was stirred at the same temperature for 30 minutes and concentrated in vacuo to give the crude thiol (83-E) (2.62 g).

(6) The above compound (150 mg, 0.41 mmol) was dissolved in DMF (2 ml), and thereto was added potassium tert-butoxide (36.6 mg, 0.33 mmol) under ice-cooling, and the mixture was stirred at the same temperature for 10 minutes. Then, thereto was added ethyl iodide (0.026 ml, 0.33 mmol). The mixture was stirred at the same temperature for 2 hours and at room temperature overnight, diluted with ethyl acetate, washed sequentially with water and brine, dried over sodium sulfate, concentrated in vacuo. The residue was purified by silica gel chromatography (25 to 75% ethyl acetate-hexane) to give the compound (83-F) (96.8 mg, yield 65% in 2 steps).

MS (m/z) APCI: 396 [M+H]+

Corresponding starting compounds were treated in the similar manner as the above-mentioned to give the following compounds.

| EXAMPLE No. | No | Structure | MS (m/z) |
|---|---|---|---|
| 83 | 1 | | 426 APCI [M + H]⁺ |
| 83 | 2 | | 410 APCI [M + H]⁺ |
| 83 | 3 | | 422 APCI [M + H]⁺ |
| 83 | 4 | | 541 APCI [M + H]⁺ |
| 83 | 5 | | 499 APCI [M + NH₄]⁺ |

-continued

| EXAMPLE No. | No | Structure | MS (m/z) |
|---|---|---|---|
| 83 | 6 | | 422 APCI [M + H]+ |
| 83 | 7 | | 438 APCI [M + H]+ |
| 83 | 8 | | 438 APCI [M + H]+ |
| 83 | 9 | | 456 APCI [M + H]+ |
| 83 | 10 | | 440 APCI [M + H]+ |

-continued

| EXAMPLE No. | No | Structure | MS (m/z) |
|---|---|---|---|
| 83 | 11 | | 426 APCI [M + H]⁺ |
| 83 | 12 | | 440 APCI [M + H]⁺ |
| 83 | 13 | | 440 APCI [M + H]⁺ |
| 83 | 14 | | 435 APCI [M + H]⁺ |
| 83 | 15 | | 421 APCI [M + H]⁺ |

-continued

| EXAMPLE No. | No | Structure | MS (m/z) |
|---|---|---|---|
| 83 | 16 | 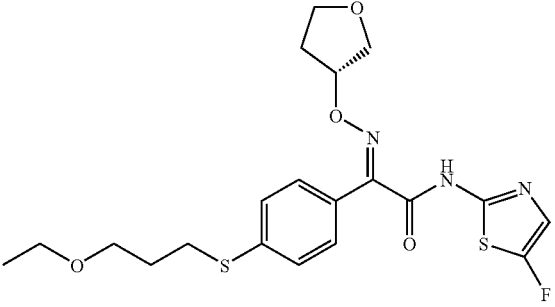 | 454 APCI [M + H]+ |
| 83 | 17 | 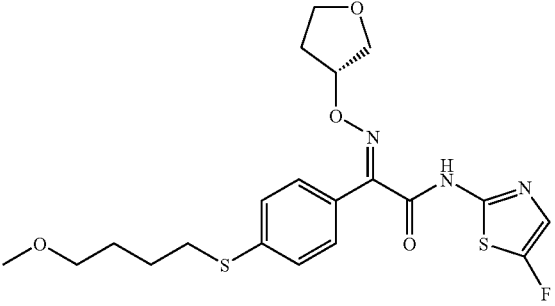 | 454 APCI [M + H]+ |

Example 84

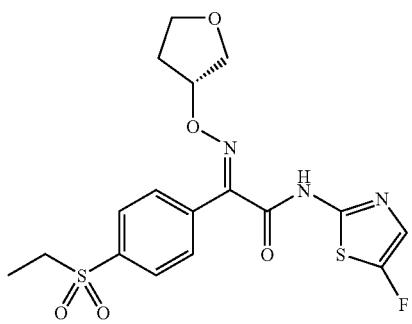

To a solution of the compound (83-F) (88.8 mg, 0.23 mmol) in chloroform (3 ml) was added 70% m-chloroperbenzoic acid (166 mg, 0.68 mmol) at room temperature, and the mixture was stirred at the same temperature for 6 hours and concentrated in vacuo. The residue was purified by NH-silica gel chromatography (0 to 5% methanolchloroform) to give the above compound (76.8 mg, yield 80%).

MS (m/z) APCI: 428 [M+H]+

Corresponding starting compounds were reacted in the similar manner as EXAMPLE 83 and/or the above-mentioned to give the following compounds.

| EXAMPLE No. | No | Structure | MS (m/z) |
|---|---|---|---|
| 84 | 1 | 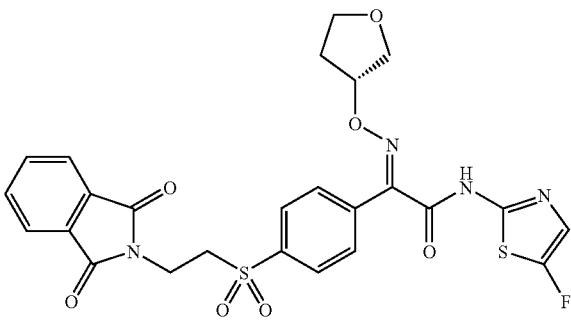 | 573 APCI [M + H]+ |

| EXAMPLE No. | No | Structure | MS (m/z) |
| --- | --- | --- | --- |
| 84 | 2 | | 514 APCI [M + H]⁺ |
| 84 | 3 | | 442 APCI [M + H]⁺ |
| 84 | 4 | | 442 APCI [M + H]⁺ |
| 84 | 5 | | 458 APCI [M + H]⁺ |

| EXAMPLE No. | No | Structure | MS (m/z) |
|---|---|---|---|
| 84 | 6 | | 454 APCI [M + H]$^+$ |
| 84 | 7 | | 444 APCI [M + H]$^+$ |
| 84 | 8 | | 456 APCI [M + H]$^+$ |
| 84 | 9 | | 454 APCI [M + H]$^+$ |

-continued
| EXAMPLE No. | No | Structure | MS (m/z) |
|---|---|---|---|
| 84 | 10 | 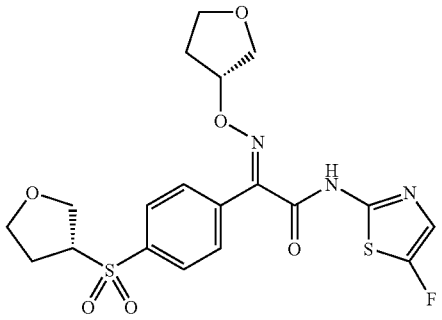 | 470 APCI [M + H]+ |
| 84 | 11 | 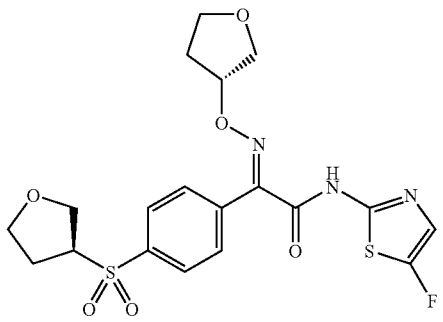 | 470 APCI [M + H]+ |
| 84 | 12 | 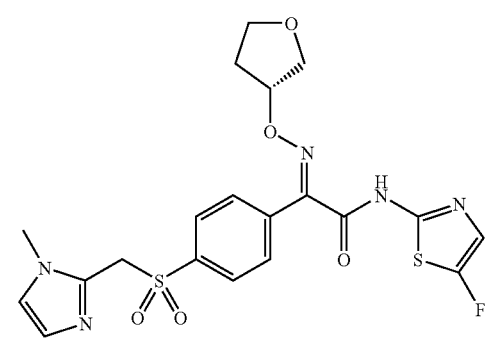 | 494 APCI [M + H]+ |
| 84 | 13 | 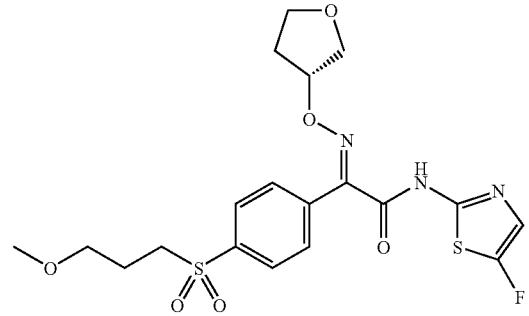 | 472 APCI [M + H]+ |

|EXAMPLE No.|No|Structure|MS (m/z)|
|---|---|---|---|
|84|14||458 APCI [M + H]+|
|84|15||427 APCI [M + H]+|
|84|16||472 APCI [M + H]+|
|84|17||506 APCI [M + H]+|

| EXAMPLE No. | No | Structure | MS (m/z) |
|---|---|---|---|
| 84 | 18 | | 467 APCI [M + H]+ |
| 84 | 19 | | 453 APCI [M + H]+ |
| 84 | 20 | | 486 APCI [M + H]+ |
| 84 | 21 | | 486 APCI [M + H]+ |

Example 85

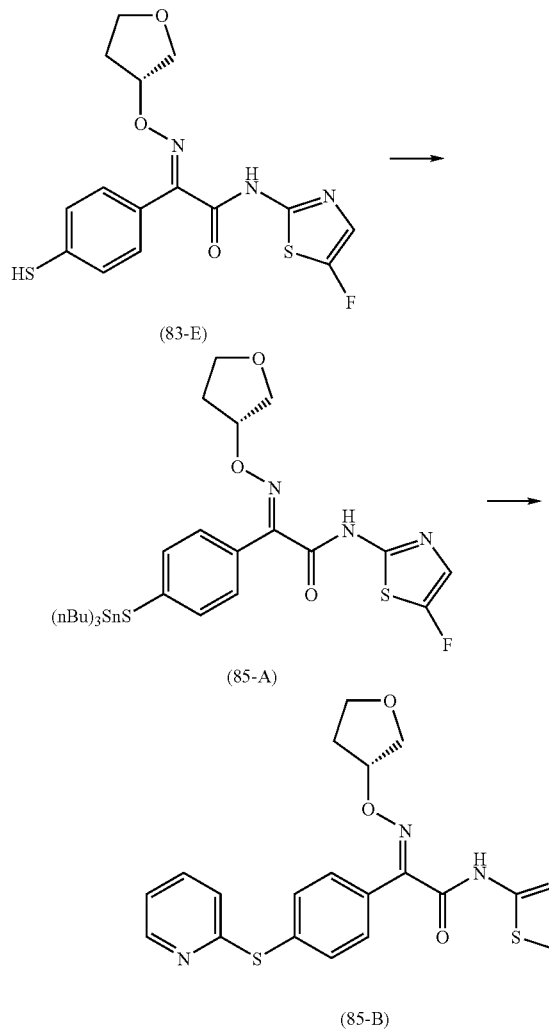

Example 86

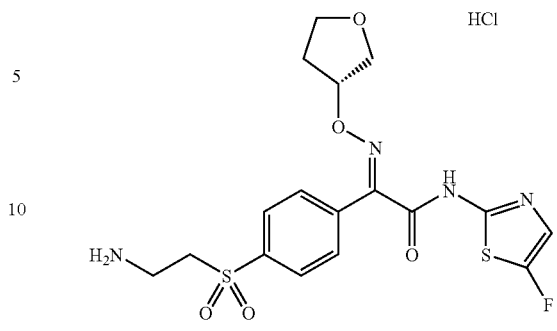

To a solution of the compound of EXAMPLE 84-(1) (264 mg, 0.46 mmol) in ethanol-THF (1:1) (12 ml) was added hydrazine hydrate (92.2 mg, 1.98 mmol) at room temperature. The mixture was stirred at the same temperature for 24 hours, and thereto was added a saturated aqueous sodium bicarbonate solution. The mixture was extracted with chloroform, and the organic layer was dried over sodium sulfate and concentrated in vacuo. The residue was dissolved in ethyl acetate, and thereto was added a 4N solution of hydrogen chloride in dioxane (0.5 ml) at room temperature, and the precipitated crystals were collected to give the above compound (242 mg, quantitatively) as a hydrochloride.

MS (m/z) APCI: 443 [M+H]$^+$

Example 87

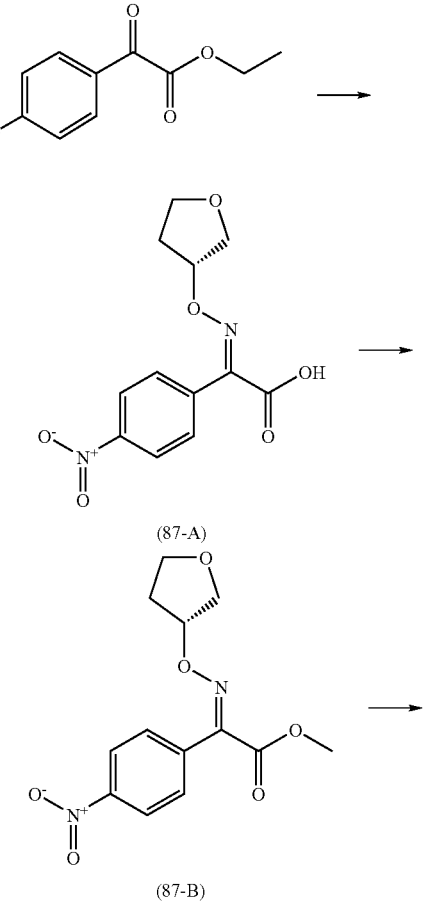

(1) To a solution of the compound (83-E) (300 mg, 0.82 mmol) in chloroform (10 ml) were added sequentially triethylamine (0.17 ml, 1.2 mmol) and then tri-n-butyltin chloride (0.18 ml, 0.65 mmol) under ice-cooling. The mixture was stirred at the same temperature for 1 hour and at room temperature for another 4 hours, diluted with ethyl acetate, washed sequentially with water and brine, dried over sodium sulfate and concentrated in vacuo. The residue was purified by silica gel chromatography (10 to 60% ethyl acetate-hexane) to give the compound (85-A) (294 mg, yield 55%).

MS (m/z) APCI: 654/656 [M+H]$^+$ (2) To a solution of the above compound in toluene (3 ml) were added 2-bromopyridine (0.087 ml, 0.91 mmol) and tetrakis(triphenylphosphine)palladium (71 mg, 0.061 mmol) under argon. The mixture was heated to reflux for 5 hours, diluted with ethyl acetate, washed sequentially with water and brine, dried over sodium sulfate and concentrated in vacuo. The residue was purified by silica gel chromatography (20 to 80% ethyl acetate-hexane) to give the compound (85-B) (76.7 mg, yield 79%).

MS (m/z) APCI: 445 [M+H]$^+$

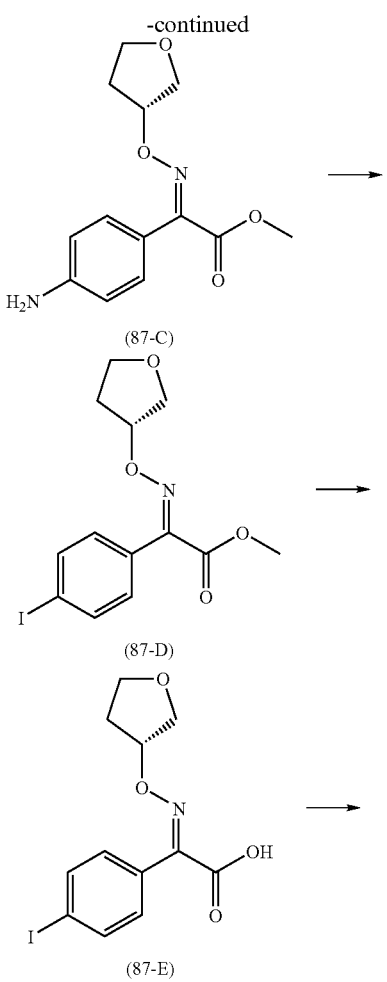

(87-C)

(87-D)

(87-E)

(87-F)

(1) (4-Nitrophenyl)oxoacetic acid ethyl ester and the corresponding starting compound were reacted in the similar manner as EXAMPLE 1-(3) and 1-(4-1) to give the compound (87-A).

MS (m/z) ESI: 279 [M−H]⁻

(2) A solution of the above compound (21.5 g, 76.7 mmol) in DMF (358 ml) was ice-cooled and thereto were added potassium carbonate (15.9 g, 115 mmol) and methyl iodide (5.75 ml, 92.1 mmol). The mixture was stirred at room temperature for 4 hours, diluted with ethyl acetate, washed sequentially with water and brine, dried over sodium sulfate and concentrated in vacuo to give the compound (87-B) (23.9 g, quantitatively).

MS (m/z) APCI: 295 [M+H]⁺

(3) The above compound was treated in the similar manner as EXAMPLE 81-(2) to give the compound (87-C).

MS (m/z) APCI: 265 [M+H]⁺

(4) To a solution of the above compound (3.0 g, 11.4 mmol) in a mixture of concentrated hydrochloric acid (30 ml) and water (10 ml) was added an aqueous solution (8 ml) of sodium nitrite (875 mg, 12.5 mmol) under ice-cooling, and the mixture was stirred at the same temperature for 30 minutes. Then, thereto was added an aqueous solution (12 ml) of potassium iodide (5.68 g, 34.1 mmol), and the ice bath was removed. The mixture was stirred at room temperature for another 1 hour, poured onto ice and extracted with ethyl acetate. The organic layer was filtered through Celite, and then the filtrate was washed sequentially with water and brine, dried over magnesium sulfate and concentrated in vacuo. The residue was purified by silica gel chromatography (30% ethyl acetate-hexane) to give the compound (87-D) (2.57 g, yield 60%).

MS (m/z) APCI: 376 [M+H]⁺

(5) The above compound was reacted in the similar manner as EXAMPLE 1-(4-2-2) to give the compound (87-E).

MS (m/z) EST: 360 [M−H]⁻

(6) The above compound and the corresponding starting compound were reacted in the similar manner as EXAMPLE 1-(5) to give the compound (87-F).

MS (m/z) APCI: 462 [M+H]⁺

Example 88

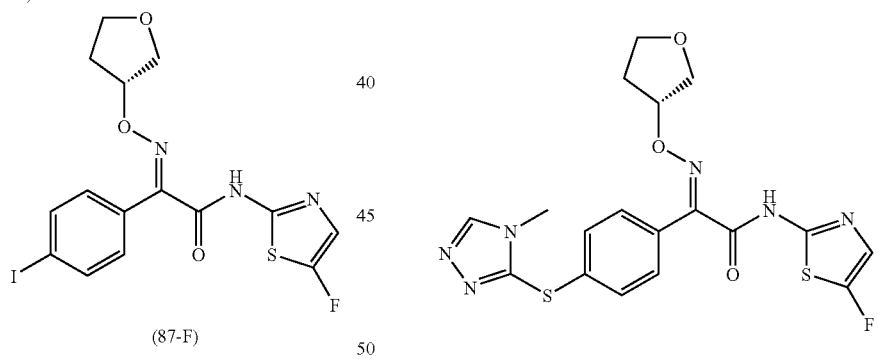

To a suspension of the compound (87-F) (200 mg, 0.43 mmol), potassium tert-butoxide (53.5 mg, 0.48 mmol), 3-mercapto-4-methyl-4H-1,2,4-triazole (50 mg, 0.43 mmol) and bis(2-diphenylphosphinophenyl)ether (23.4 mg, 0.043 mmol) in toluene (5 ml) was added tris(dibenzylideneacetone)dipalladium (20 mg, 0.022 mmol) at room temperature under argon. The mixture was heated to reflux for 2 hours, diluted with ethyl acetate, and then filtered through Celite and concentrated in vacuo. The residue was purified by NH-silica gel chromatography (0 to 3% methanol-chloroform) to give the above compound (79 mg, yield 41%).

MS (m/z) APCI: 449 [M+H]⁺

A corresponding starting compound was treated in the similar manner as the above-mentioned to give the following compound.

| EXAMPLE No. | No | Structure | MS (m/z) |
|---|---|---|---|
| 88 | 1 | 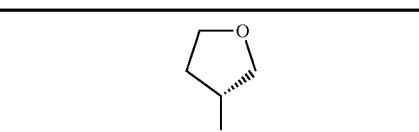 | 448 APCI [M + H]+ |

Example 89

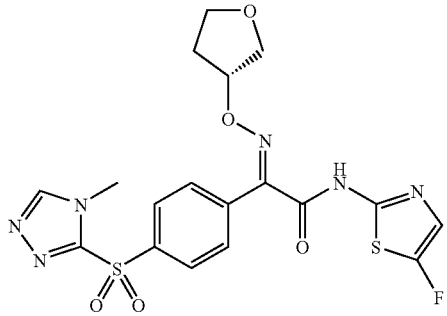

To a solution of the compound of EXAMPLE 88 (80 mg, 0.18 mmol) in methylene chloride (3 ml) was added 65% m-chloroperbenzoic acid (189 mg, 0.71 mmol) under ice-cooling, and then the ice bath was removed and the mixture was stirred at room temperature for another 2 hours. To the reaction mixture was added a 10% aqueous sodium thiosulfate solution, and then the mixture was extracted with chloroform. The organic layer was dried over magnesium sulfate and concentrated in vacuo. The residue was purified by NH-silica gel chromatography (0 to 3% methanol-chloroform) to give the above compound (7.8 mg, yield 9%).

MS (m/z) APCI: 481 [M+H]+

Example 90

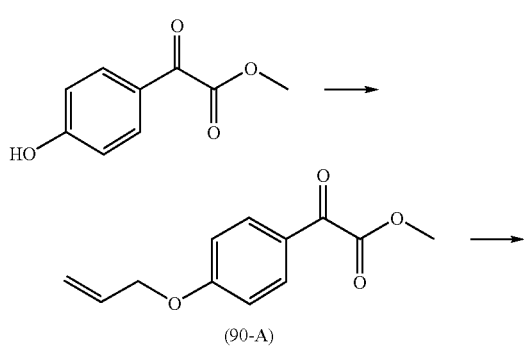

(90-A)

-continued (90-B)

(90-C)

(1) To a solution of 4-hydroxyphenyloxoacetic acid ethyl ester (19.4 g, 108 mmol) in acetone (300 ml) were added sequentially potassium carbonate (44.1 g, 319 mmol) and then alkyl bromide (15.4 g, 127 mmol) under ice-cooling, and then the ice bath was removed. The mixture was stirred at room temperature for 16 hours and heated to reflux for another 6 hours, filtered through Celite, and then concentrated in vacuo. The resulting residue was purified by silica gel chromatography (17% ethyl acetate-hexane) to give the compound (90-A) (3.38 g, yield 14%).

(2) The above compound was reacted in the similar manner as EXAMPLE 1-(3) and 1-(4-2) to give the compound (90-B).

MS (m/z) ESI: 290 [M−H]−

(3) The above compound and the corresponding starting compound were reacted in the similar manner as EXAMPLE 1-(5) to give the compound (90-C).
MS (m/z) APCI: 392 [M+H]⁺
Corresponding starting compounds were treated in the similar manner as the above-mentioned to give the following compounds.
| EXAMPLE No. | No | Structure | MS (m/z) |
|---|---|---|---|
| 90 | 1 | | 394 APCI [M + H]⁺ |
| 90 | 2 | | 406 APCI [M + H]⁺ |
Example 91
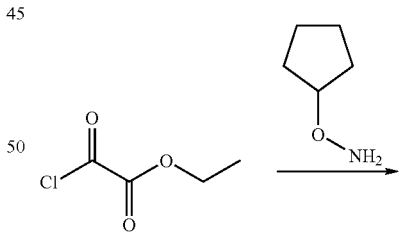
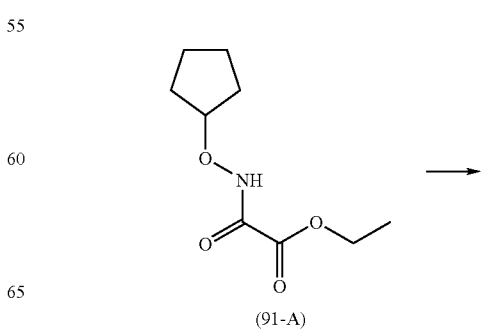
(91-A)

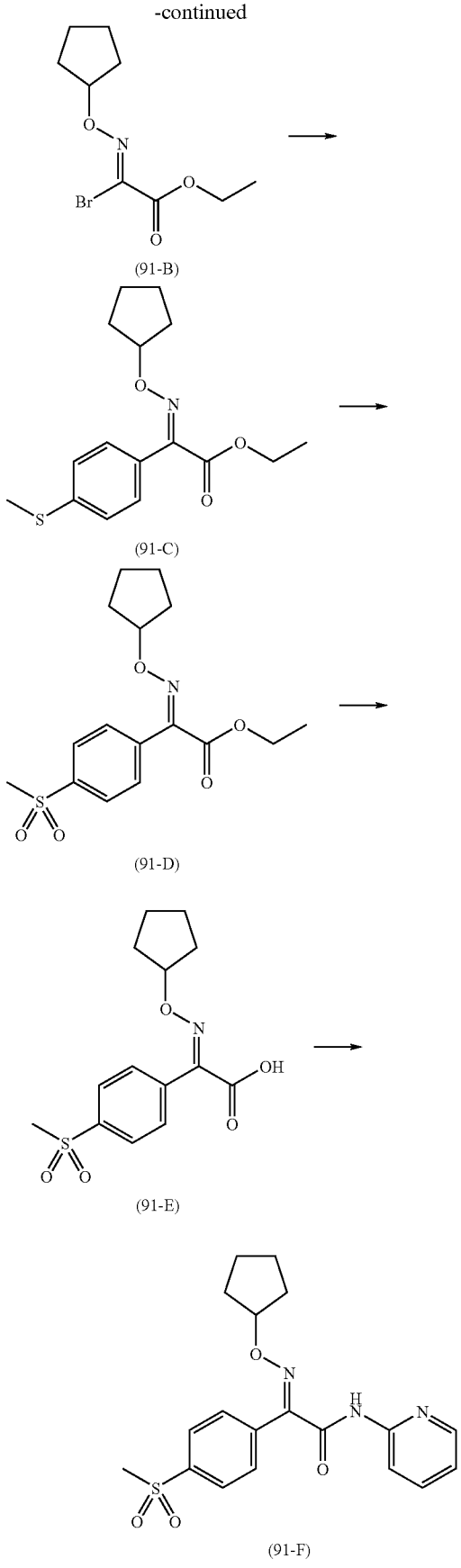

(1) To a solution of cyclopentyloxyamine (5.0 g, 49 mmol) and triethylamine (8.15 ml, 59 mmol) in THF (50 ml) was added dropwise a solution of ethyl chloroglyoxylate (6.1 g, 45 mmol) in THF (25 ml) under ice-cooling, and the mixture was stirred at the same temperature for 30 minutes and at room temperature for another 1 hour. The insoluble was filtered off through Celite, and then the filtrate was concentrated in vacuo, and the resulting residue was purified by silica gel column chromatography (25% ethyl acetate-hexane) to give the compound (91-A) (7.97 g, yield 88%) as a pale yellow oil.

MS (m/z) APCI: 202 [M+H]$^+$ (2) To a solution of the above compound (2.0 g, 10 mmol) in acetonitrile (80 ml) were added sequentially triphenylphosphine (3.93 g, 15 mmol) and carbon tetrabromide (4.97 g, 15 mmol) at room temperature, and the mixture was heated to reflux for 3 hours. After cooling to room temperature, the mixture was concentrated and the residue was purified by silica gel column chromatography (3% ethyl acetate-hexane) to give the compound (91-B) (1.87 g, yield 71%) as a colorless oil.

(3) To a solution of the above compound (5.28 g, 20 mmol), 4-methylthiophenylboronic acid (5.04 g, 30 mmol) in 1,2-dimethoxyethane (120 ml) were added a 1N aqueous sodium carbonate solution (60 ml) and dichlorobis(triphenylphosphine)palladium (1.4 g, 2.0 mmol) under argon, and the mixture was heated at 80° C. for 30 minutes using a microwave reactor. After cooling to room temperature, the reaction mixture was diluted with ethyl acetate, washed sequentially with water and brine, dried over sodium sulfate and concentrated in vacuo. The residue was purified by silica gel column chromatography (2 to 3% ethyl acetate-hexane) to give the compound (91-C) (4.20 g, yield 68%) as a pale yellow oil.

(4) To a solution of the above compound (20 g, 65 mmol) in methylene chloride (320 ml) was added dropwise a solution of 75% m-chloroperbenzoic acid (32.9 g, 143 mmol) in methylene chloride (80 ml) under ice-cooling, and then the mixture was stirred at the same temperature for 30 minutes and at room temperature for 2 hours. The precipitate was filtered off through Celite, and then to the filtrate was added a 10% aqueous sodium sulfite solution and the mixture was stirred for a while. The organic layer was separated, and then washed sequentially with a saturated aqueous sodium carbonate solution, water and brine, dried over sodium sulfate and concentrated in vacuo. The residue was purified by silica gel column chromatography (25% ethyl acetate-hexane) to give the compound (91-D) (19.35 g, yield 88%).

MS (m/z) APCI: 340[M+H]$^+$ (5) The above compound was reacted in the similar manner as EXAMPLE 1-(4-2-2) to give the compound (91-B).

(6) The above compound and the corresponding starting compound were reacted in the similar manner as EXAMPLE 1-(5) to give the compound (91-F).

MS (m/z) APCI: 388 [M+H]$^+$

The above compounds of EXAMPLE (91-C), (91-D) or (91-E) and the corresponding starting compounds were reacted in the similar manner as a combination of any or some of the above EXAMPLEs to give the following compounds.

| EXAMPLE No. | No | Structure | MS (m/z) |
|---|---|---|---|
| 91 | 1 | | 394 APCI [M + H]+ |
| 91 | 2 | | 466 APCI [M + H]+ |
| 91 | 3 | | 436 ESI [M − H]− |
| 91 | 4 | | 419 APCI [M + H]+ |

-continued
| EXAMPLE No. | No | Structure | MS (m/z) |
|---|---|---|---|
| 91 | 5 | 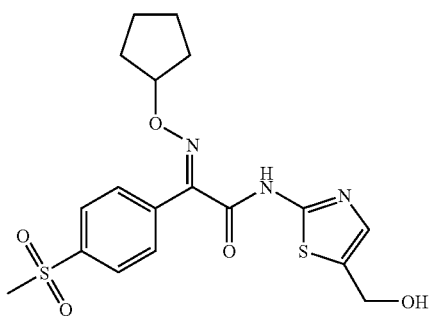 | 424 APCI [M + H]+ |
| 91 | 6 | 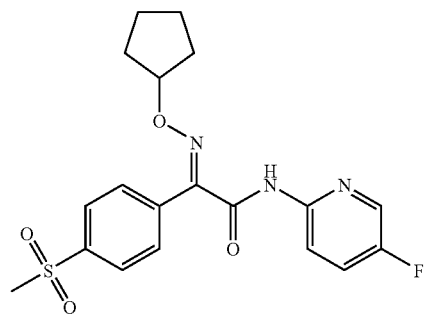 | 406 APCI [M + H]+ |
| 91 | 7 | 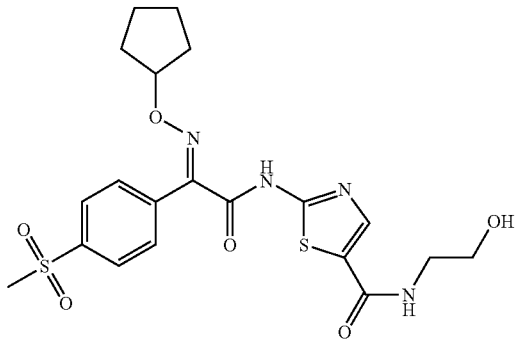 | 479 ESI [M − H]− |
| 91 | 8 | 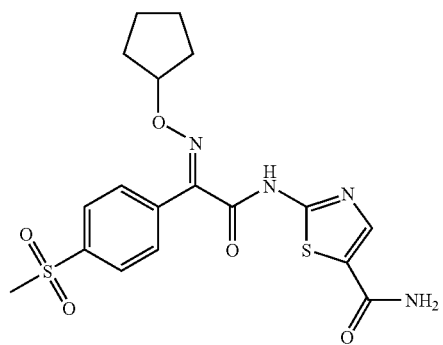 | 435 ESI [M − H]− |

-continued

| EXAMPLE No. | No | Structure | MS (m/z) |
|---|---|---|---|
| 91 | 9 | | 422 APCI [M + H]+ |
| 91 | 10 | | 528 APCI [M + H]+ |
| 91 | 11 | | 428/430 APCI [M + H]+ |
| 91 | 12 | | 462 APCI [M + H]+ |

-continued

| EXAMPLE No. | No | Structure | MS (m/z) |
|---|---|---|---|
| 91 | 13 | | 412 APCI [M + H]+ |
| 91 | 14 | | 466 APCI [M + H]+ |
| 91 | 15 | | 424 APCI [M + H]+ |
| 91 | 16 | | 395 APCI [M + H]+ |
| 91 | 17 | | 480 APCI [M + H]+ |

-continued

| EXAMPLE No. | No | Structure | MS (m/z) |
|---|---|---|---|
| 91 | 18 | | 506 APCI [M + H]+ |
| 91 | 19 | | 493 APCI [M + H]+ |
| 91 | 20 | | 535 APCI [M + H]+ |
| 91 | 21 | | 477 APCI [M + H]+ |

-continued

| EXAMPLE No. | No | Structure | MS (m/z) |
|---|---|---|---|
| 91 | 22 | | 495 APCI [M + H]+ |
| 91 | 23 | | 507 APCI [M + H]+ |
| 91 | 24 | | 521 APCI [M + H]+ |
| 91 | 25 | | 520 APCI [M + H]+ |

-continued

| EXAMPLE No. | No | Structure | MS (m/z) |
|---|---|---|---|
| 91 | 26 | | 550 APCI [M + H]+ |
| 91 | 27 | | 521 APCI [M + H]+ |
| 91 | 28 | | 509 APCI [M + H]+ |
| 91 | 29 | | 508 APCI [M + H]+ |

-continued

| EXAMPLE No. | No | Structure | MS (m/z) |
|---|---|---|---|
| 91 | 30 | | 507 APCI [M + H]+ |
| 91 | 31 | | 528 APCI [M + H]+ |
| 91 | 32 | | 506 ESI+ [M + H]+ |
| 91 | 33 | | 500 ESI+ [M + H]+ |

| EXAMPLE No. | No | Structure | MS (m/z) |
|---|---|---|---|
| 91 | 34 | | 514 ESI+ [M + H]+ |
| 91 | 35 | | 528 ESI+ [M + H]+ |
| 91 | 36 | | 494 ESI+ [M + H]+ |
| 91 | 37 | | 480 ESI+ [M + H]+ |

| EXAMPLE No. | No | Structure | MS (m/z) |
|---|---|---|---|
| 91 | 38 | | 514 APCI [M + H]+ |
| 91 | 39 | | 451 APCI [M + H]+ |
| 91 | 40 | | 465 APCI [M + H]+ |

Example 92

Corresponding starting compounds were treated in the similar manner as EXAMPLE 65 to give the following compounds.

| EXAMPLE No. | No | Structure | MS (m/z) |
|---|---|---|---|
| 92 | 1 | | 380 APCI [M + H]$^+$ |
| 92 | 2 | | 444/446 APCI [M + H]$^+$ |
| 92 | 3 | | 382 APCI [M + H]$^+$ |

Example 93

Corresponding starting compounds were treated in the similar manner as EXAMPLE 65 to give the following compounds.

| EXAMPLE No. | No | Structure | MS (m/z) |
|---|---|---|---|
| 93 | 1 | | 428/430 APCI [M + H]$^+$ |
| 93 | 2 | | 462/464 APCI [M + H]$^+$ |
| 93 | 3 | | 430/432 APCI [M + H]$^+$ |

Example 94

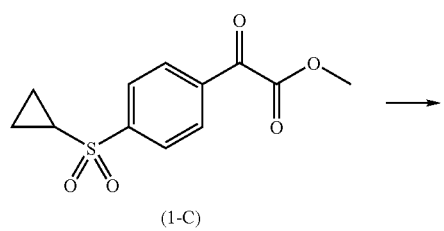

(1-C)

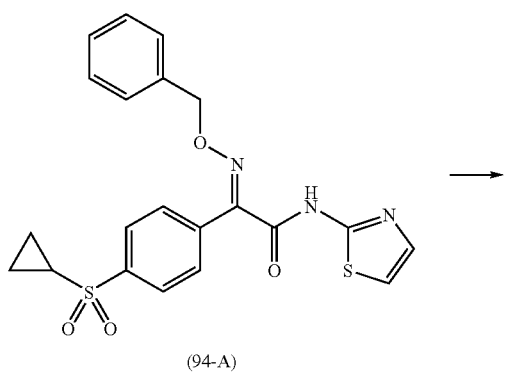

(94-A)

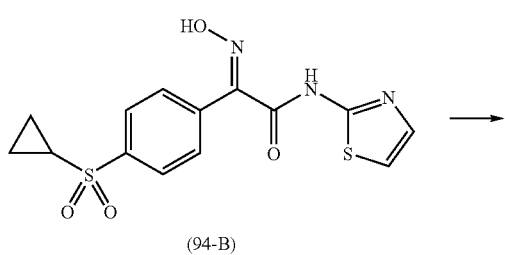

(94-B)

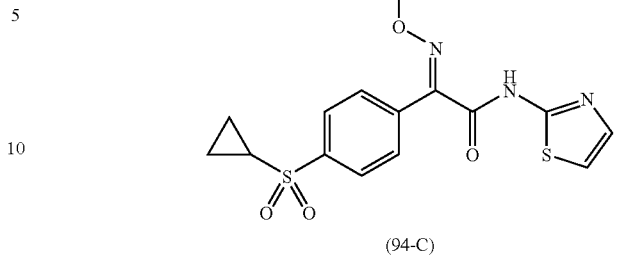

(94-C)

(1) The compound (1-C) was treated in the similar manner as EXAMPLE 65 to give the compound (94-A).

MS (m/z) APCI: 442 [M+H]$^+$ (2) The above compound was reacted in the similar manner as EXAMPLE 66-(I) to give the compound (94-B).

MS (m/z) APCI: 352 [M+H]$^+$ (3) To a solution of the above compound (95.0 mg, 0.27 mmol), triphenylphosphine (127 mg, 0.487 mmol) and cyclopropylmethanol (58.4 mg, 0.810 mmol) in THF (6 ml) was added dropwise diisopropyl azodicarboxylate (0.096 ml, 0.487 mmol) under ice-cooling. The mixture was stirred at the same temperature for 3 hours, concentrated in vacuo, and the residue was purified by gel-filtration (column: JAIGEL, solvent: chloroform) to give the compound (94-C) (82.8 mg, yield 78%) as a colorless solid.

MS (m/z) APCI: 406 [M+H]$^+$

Corresponding starting compounds were treated in the similar manner as one or more combinations selected from the above methods, EXAMPLE 66-(2), EXAMPLE 64 and EXAMPLE 53 to give the following compounds.

| EXAMPLE No. | No | Structure | MS (m/z) |
|---|---|---|---|
| 94 | 1 | 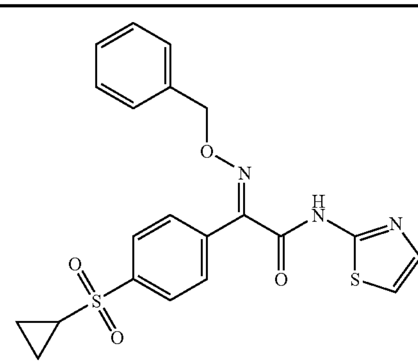 | 442 APCI [M + H]$^+$ |

-continued
| EXAMPLE No. | No | Structure | MS (m/z) |
|---|---|---|---|
| 94 | 2 | 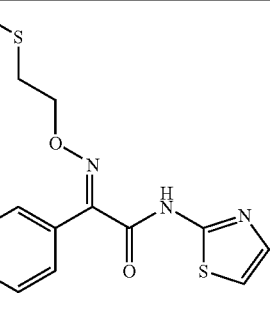 | 426 APCI [M + H]+ |
| 94 | 3 | 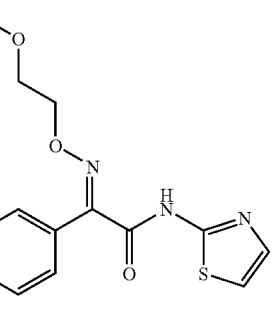 | 410 APCI [M + H]+ |
| 94 | 4 | 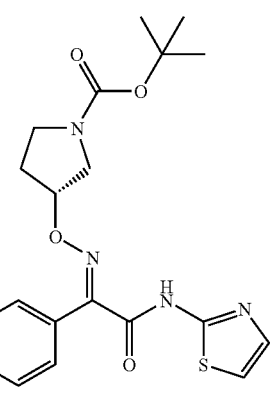 | 521 APCI [M + H]+ |
| 94 | 5 | 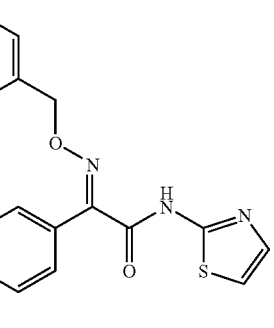 | 467 APCI [M + H]+ |

-continued

| EXAMPLE No. | No | Structure | MS (m/z) |
|---|---|---|---|
| 94 | 6 | | 443 APCI [M + H]+ |
| 94 | 7 | | 456 APCI [M + H]+ |
| 94 | 8 | | 463 APCI [M + H]+ |
| 94 | 9 | | 447 APCI [M + H]+ |

-continued

| EXAMPLE No. | No | Structure | MS (m/z) |
|---|---|---|---|
| 94 | 10 | | 461 APCI [M + H]+ |
| 94 | 11 | | 467 APCI [M + H]+ |
| 94 | 12 | | 434 ESI+ [M + H]+ |
| 94 | 13 | | 472 ESI+ [M + H]+ |

-continued

| EXAMPLE No. | No | Structure | MS (m/z) |
|---|---|---|---|
| 94 | 14 | | 443 ESI+ [M + H]+ |
| 94 | 15 | | 448 ESI+ [M + H]+ |
| 94 | 16 | | 424 ESI+ [M + H]+ |
| 94 | 17 | | 408 ESI+ [M + H]+ |

-continued
| EXAMPLE No. | No | Structure | MS (m/z) |
|---|---|---|---|
| 94 | 18 | 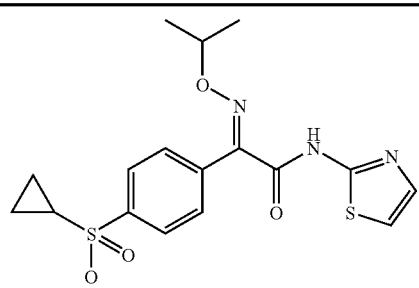 | 394 ESI+ [M + H]+ |
| 94 | 19 | 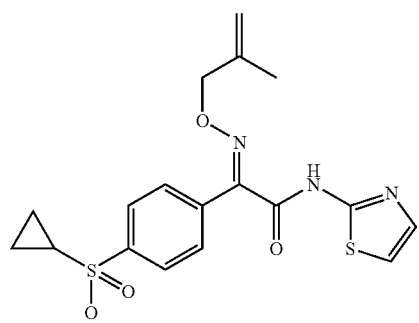 | 406 ESI+ [M + H]+ |
| 94 | 20 | 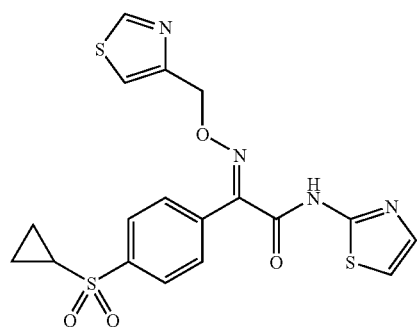 | 449 APCI [M + H]+ |
| 94 | 21 | 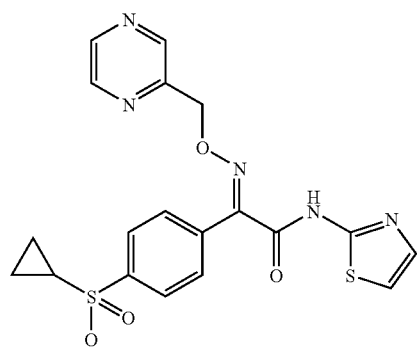 | 444 ESI+ [M + H]+ |

-continued

| EXAMPLE No. | No | Structure | MS (m/z) |
|---|---|---|---|
| 94 | 22 | | 476 ESI+ [M + H]+ |
| 94 | 23 | | 436 ESI+ [M + H]+ |
| 94 | 24 | | 436 APCI [M + H]+ |
| 94 | 25 | | 467 APCI [M + H]+ |

-continued
| EXAMPLE No. | No | Structure | MS (m/z) |
|---|---|---|---|
| 94 | 26 | 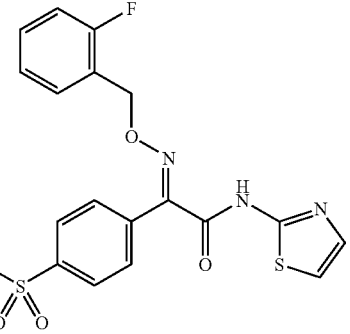 | 460 ESI+ [M + H]+ |
| 94 | 27 | 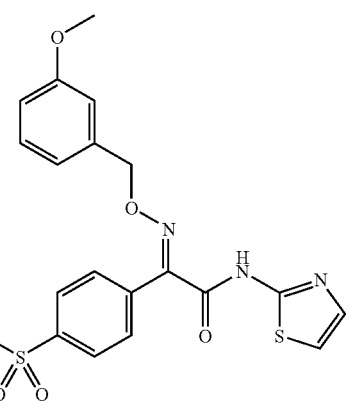 | 472 ESI+ [M + H]+ |
| 94 | 28 | 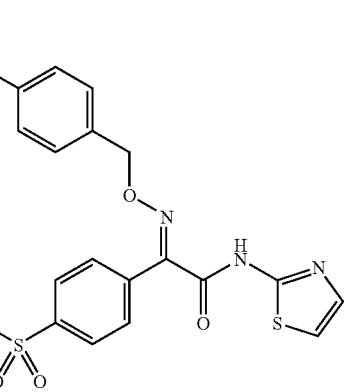 | 472 ESI+ [M + H]+ |
| 94 | 29 | 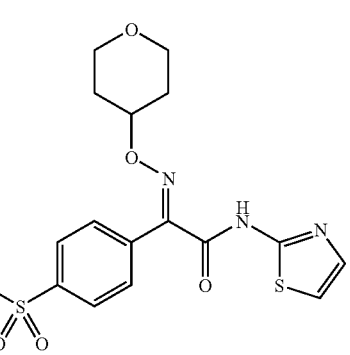 | 436 APCI [M + H]+ |

-continued

| EXAMPLE No. | No | Structure | MS (m/z) |
| --- | --- | --- | --- |
| 94 | 30 | | 424 APCI [M + H]⁺ |
| 94 | 31 | | 424 APCI [M + H]⁺ |
| 94 | 32 | | 463 APCI [M + H]⁺ |
| 94 | 33 | | 430 APCI [M + H]⁺ |

-continued

| EXAMPLE No. | No | Structure | MS (m/z) |
|---|---|---|---|
| 94 | 34 | | 449 APCI [M + H]+ |
| 94 | 35 | | 424 APCI [M + H]+ |
| 94 | 36 | | 457 APCI [M + H]+ |
| 94 | 37 | | 452 APCI [M + H]+ |

-continued
| EXAMPLE No. | No | Structure | MS (m/z) |
|---|---|---|---|
| 94 | 38 | 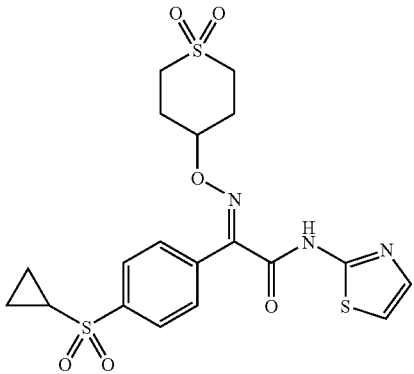 | 484 APCI [M + H]+ |
| 94 | 39 | 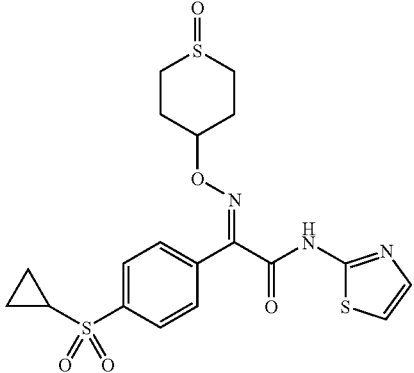 | 468 APCI [M + H]+ |
| 94 | 40 | 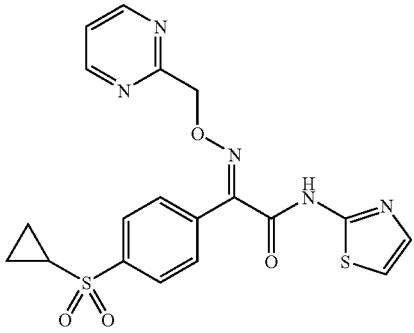 | 444 APCI [M + H]+ |
| 94 | 41 | 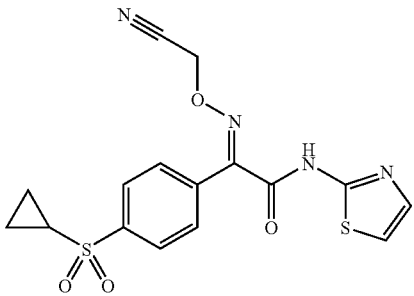 | 391 APCI [M + H]+ |

-continued

| EXAMPLE No. | No | Structure | MS (m/z) |
|---|---|---|---|
| 94 | 42 | | 410 ESI+ [M + H]+ |
| 94 | 43 | | 410 ESI+ [M + H]+ |
| 94 | 44 | | 535 APCI [M + H]+ |
| 94 | 45 | | 432 APCI [M + H]+ |

Example 95

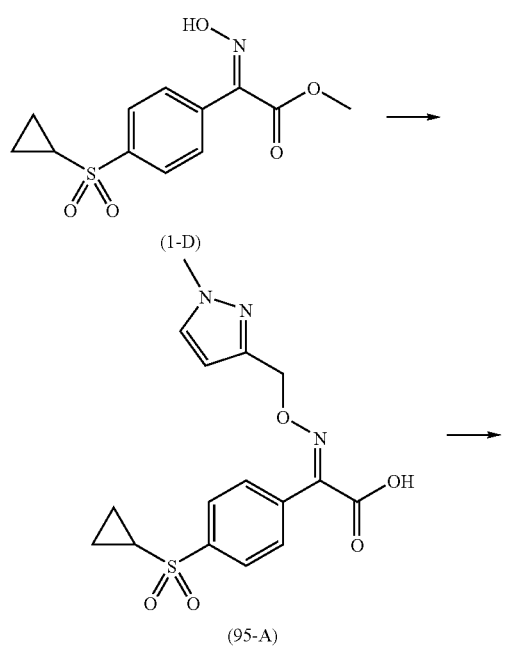

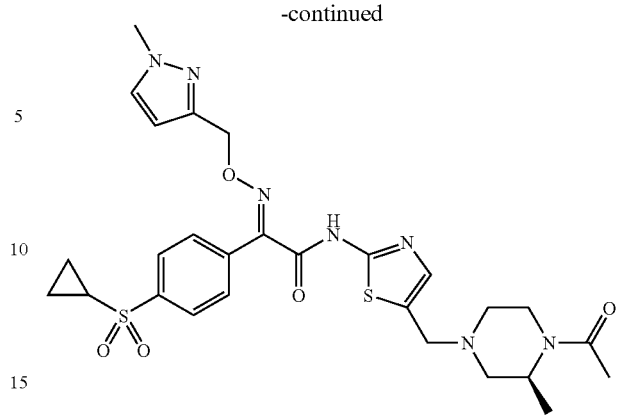

(95-B)

(1) The compound (1-D) and the corresponding starting compound were reacted in the similar manner as EXAMPLE 1-(4-1) to give the compound (95-A).
MS (m/z) ESI: 362 [M−H]⁻

(2) The above compound and the corresponding starting compound were reacted in the similar manner as EXAMPLE 1-(5) to give the compound (95-B).
MS (m/z) APCI: 600 [M+H]⁺

A corresponding starting compound was treated in the similar manner as the above-mentioned to give the following compound.

| EXAMPLE No. | No | Structure | MS (m/z) |
|---|---|---|---|
| 95 | 1 | (structure) | 490 APCI [M + H]⁺ |

Example 96

The compound (80-C) and the corresponding starting compounds were reacted in the similar manner as EXAMPLE 1-(5) to give the following compounds.

| EXAMPLE No. | No | Structure | MS (m/z) |
|---|---|---|---|
| 96 | 1 | (structure) | 442 APCI [M + H]⁺ |

-continued

| EXAMPLE No. | No | Structure | MS (m/z) |
|---|---|---|---|
| 96 | 2 | 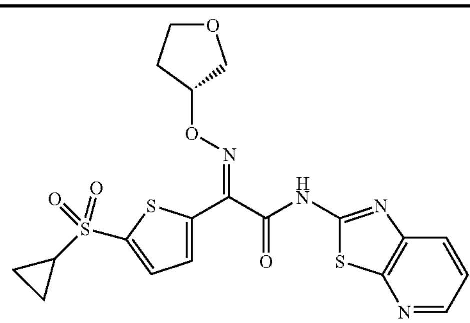 | 479 APCI [M + H]⁺ |

Example 97

Corresponding starting compounds were treated in the similar manner as a combination of the method of EXAMPLE 91 and the above-mentioned method to give the following compounds.

| EXAMPLE No. | No | Structure | MS (m/z) |
|---|---|---|---|
| 97 | 1 | | 450 APCI [M + H]⁺ |
| 97 | 2 | | 390 APCI [M + H]⁺ |
| 97 | 3 | | 362 APCI [M + H]⁺ |

| EXAMPLE No. | No | Structure | MS (m/z) |
|---|---|---|---|
| 97 | 4 | 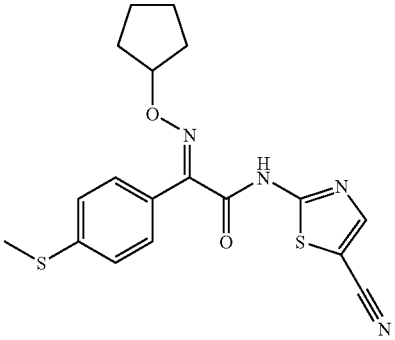 | 387 APCI [M + H]+ |
| 97 | 5 | 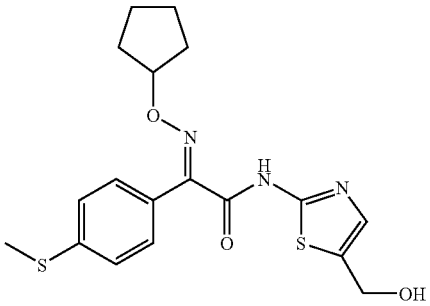 | 392 APCI [M + H]+ |
| 97 | 6 | 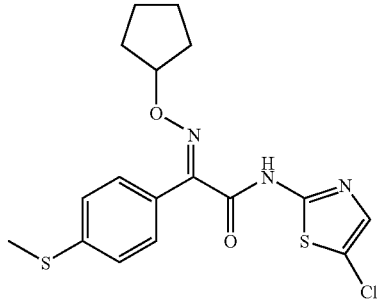 | 396/398 APCI [M + H]+ |
| 97 | 7 | 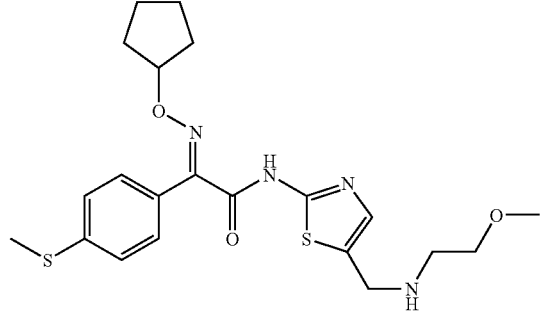 | 449 APCI [M + H]+ |

-continued

| EXAMPLE No. | No | Structure | MS (m/z) |
|---|---|---|---|
| 97 | 8 | 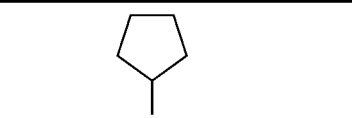 | 380 APCI [M + H]+ |

Example 98

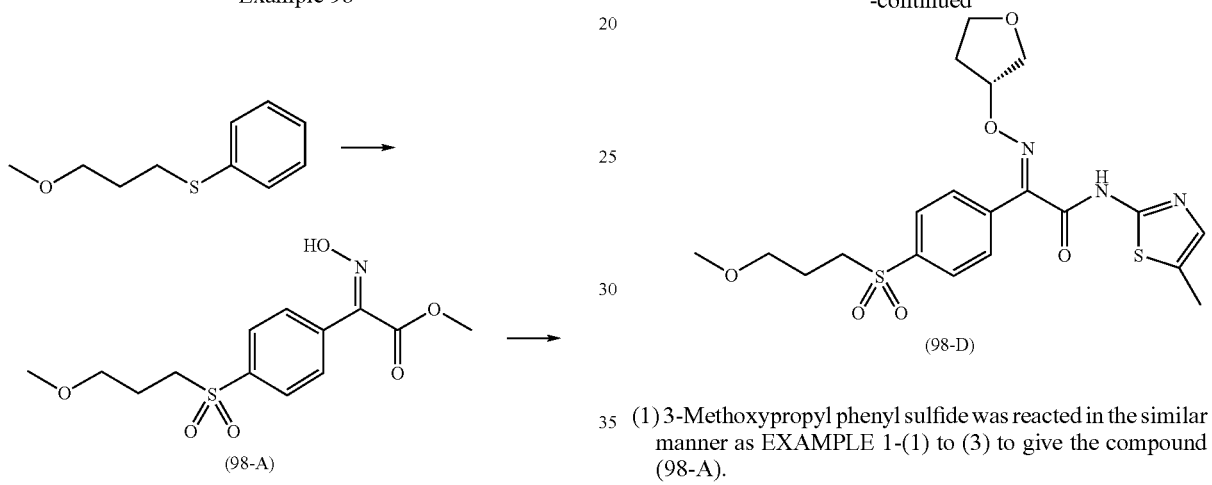

(1) 3-Methoxypropyl phenyl sulfide was reacted in the similar manner as EXAMPLE 1-(1) to (3) to give the compound (98-A).
MS (m/z) APCI: 316 [M+H]+

(2) The above compound and the corresponding starting compound were treated in the similar manner as EXAMPLE 1-(4-2-1) to give the compound (98-B).
MS (m/z) APCI: 386 [M+H]+

(3) The above compound was treated in the similar manner as EXAMPLE 1-(4-2-2) to give the compound (98-C).
MS (m/z) ESI: 741 [2M−H]−

(4) The above compound was treated in the similar manner as EXAMPLE 1-(5) to give the compound (98-D).
MS (m/z) APCI: 468 [M+H]+

The compound (98-B) was also synthesized in the following alternative method.

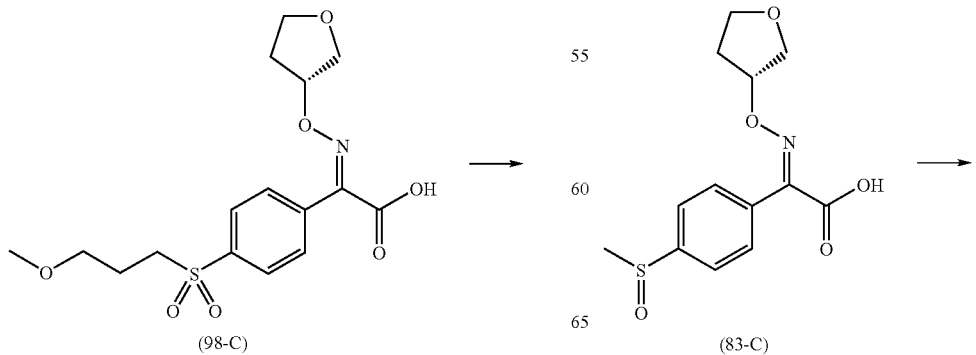

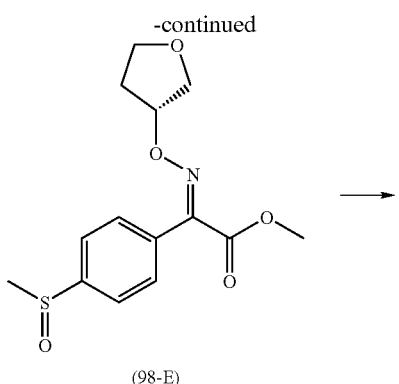

(98-E)

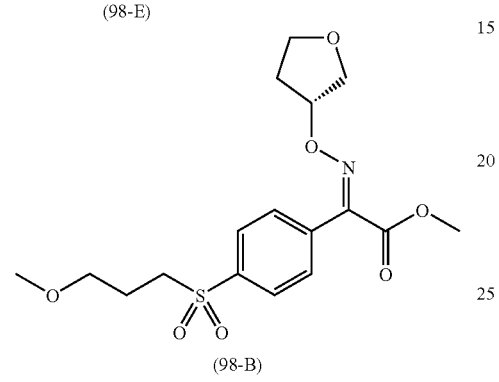

(98-B)

(1) A solution of the compound (83-C) (1.00 g, 3.36 mmol) in DMF (15 ml) was ice-cooled, and thereto were added potassium carbonate (697 mg, 5.04 mmol) and methyl iodide (0.0251 ml, 4.03 mmol). The mixture was stirred at room temperature for 3 hours, diluted with ethyl acetate, washed sequentially with water and brine, dried over sodium sulfate and concentrated in vacuo, and then the residue was purified by silica gel chromatography (0 to 10% methanol-ethyl acetate) to give the compound (98-E) (1.04 g, yield 99%) as a colorless oil.
MS (m/z) APCI: 312 [M+H]$^+$ (2) The above compound (98-E) was reacted with the corresponding starting compound in the similar manner as EXAMPLE 83-(5), (6) and EXAMPLE 84 to give the compound (98-B).
MS (m/z) APCI: 386 [M+H]$^+$ Corresponding starting compounds were treated in the similar manner as the above-mentioned to give the following compounds.

| EXAMPLE No. | No | Structure | MS (m/z) |
|---|---|---|---|
| 98 | 1 | 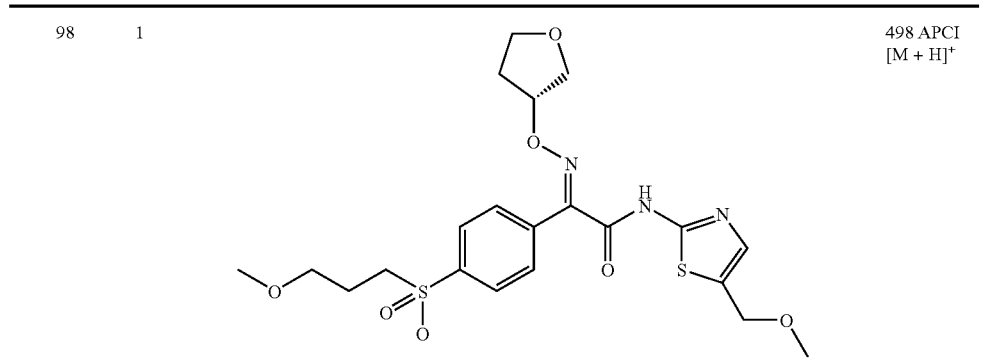 | 498 APCI [M + H]$^+$ |
| 98 | 2 | 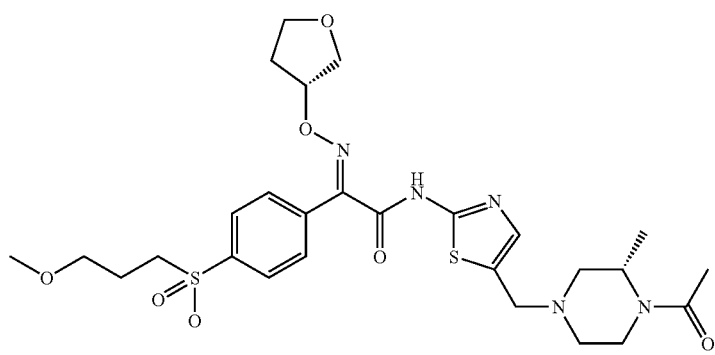 | 608 APCI [M + H]$^+$ |

-continued
| EXAMPLE No. | No | Structure | MS (m/z) |
|---|---|---|---|
| 98 | 3 | 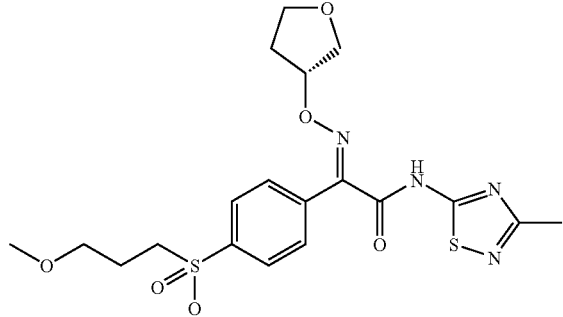 | 469 APCI [M + H]+ |
| 98 | 4 | 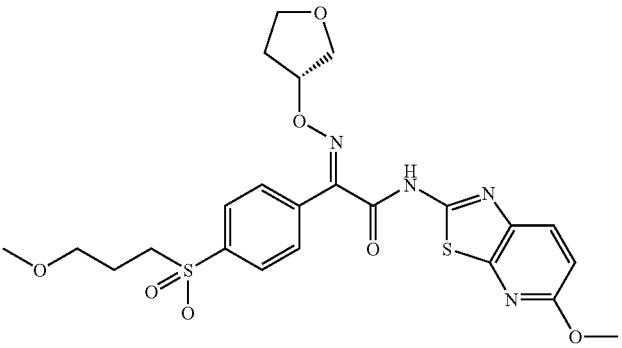 | 535 APCI [M + H]+ |
| 98 | 5 | 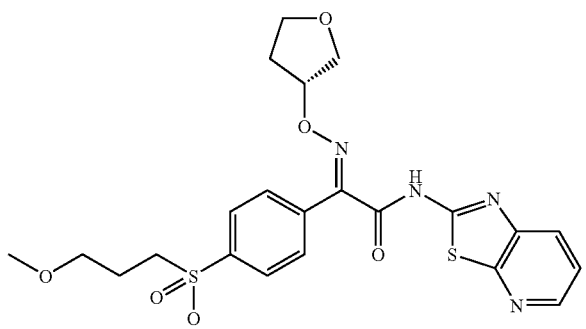 | 505 APCI [M + H]+ |
| 98 | 6 | 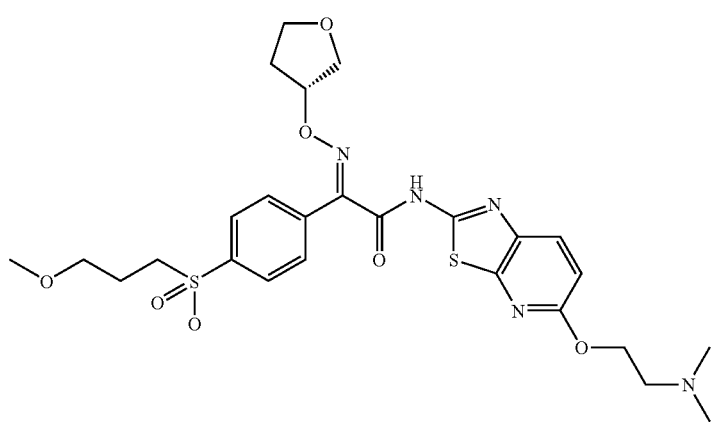 | 592 APCI [M + H]+ |

| EXAMPLE No. | No | Structure | MS (m/z) |
|---|---|---|---|
| 98 | 7 | 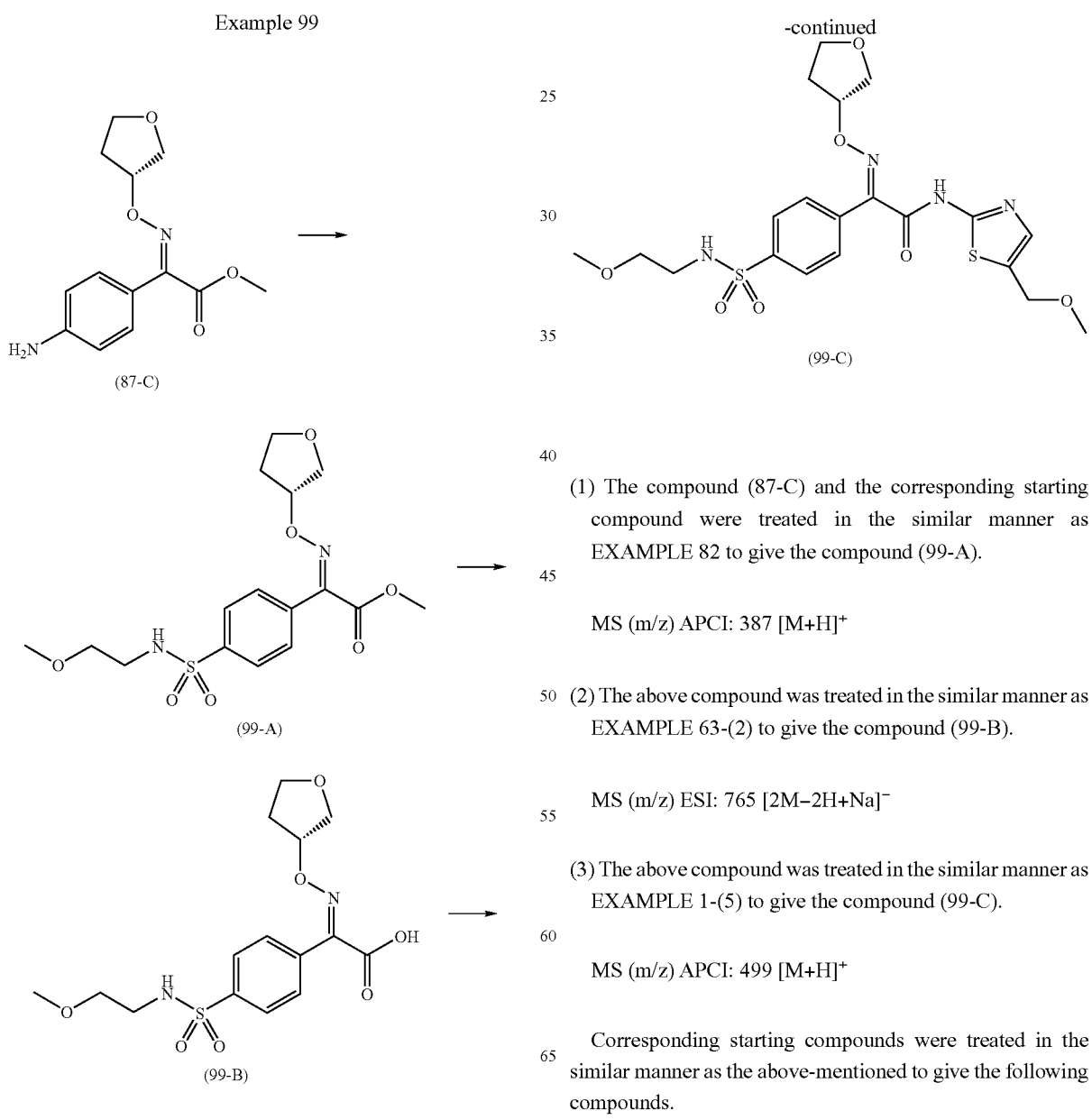 | 565 APCI [M + H]+ |

Example 99

(1) The compound (87-C) and the corresponding starting compound were treated in the similar manner as EXAMPLE 82 to give the compound (99-A).

MS (m/z) APCI: 387 [M+H]+

(2) The above compound was treated in the similar manner as EXAMPLE 63-(2) to give the compound (99-B).

MS (m/z) ESI: 765 [2M−2H+Na]−

(3) The above compound was treated in the similar manner as EXAMPLE 1-(5) to give the compound (99-C).

MS (m/z) APCI: 499 [M+H]+

Corresponding starting compounds were treated in the similar manner as the above-mentioned to give the following compounds.

| EXAMPLE No. | No | Structure | MS (m/z) |
|---|---|---|---|
| 99 | 1 | | 470 APCI [M + H]+ |
| 99 | 2 | | 469 APCI [M + H]+ |
| 99 | 3 | | 609 APCI [M + H]+ |
| 99 | 4 | | 506 APCI [M + H]+ |

| EXAMPLE No. | No | Structure | MS (m/z) |
|---|---|---|---|
| 99 | 5 | 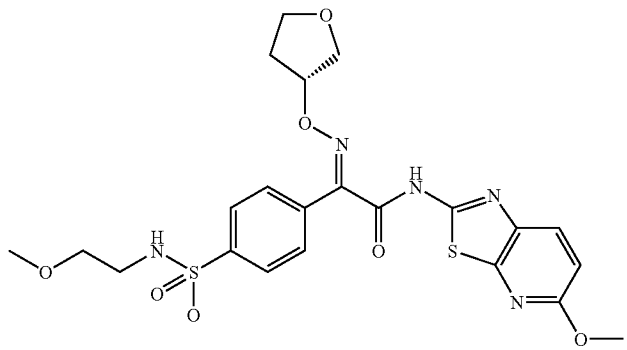 | 536 APCI [M + H]+ |
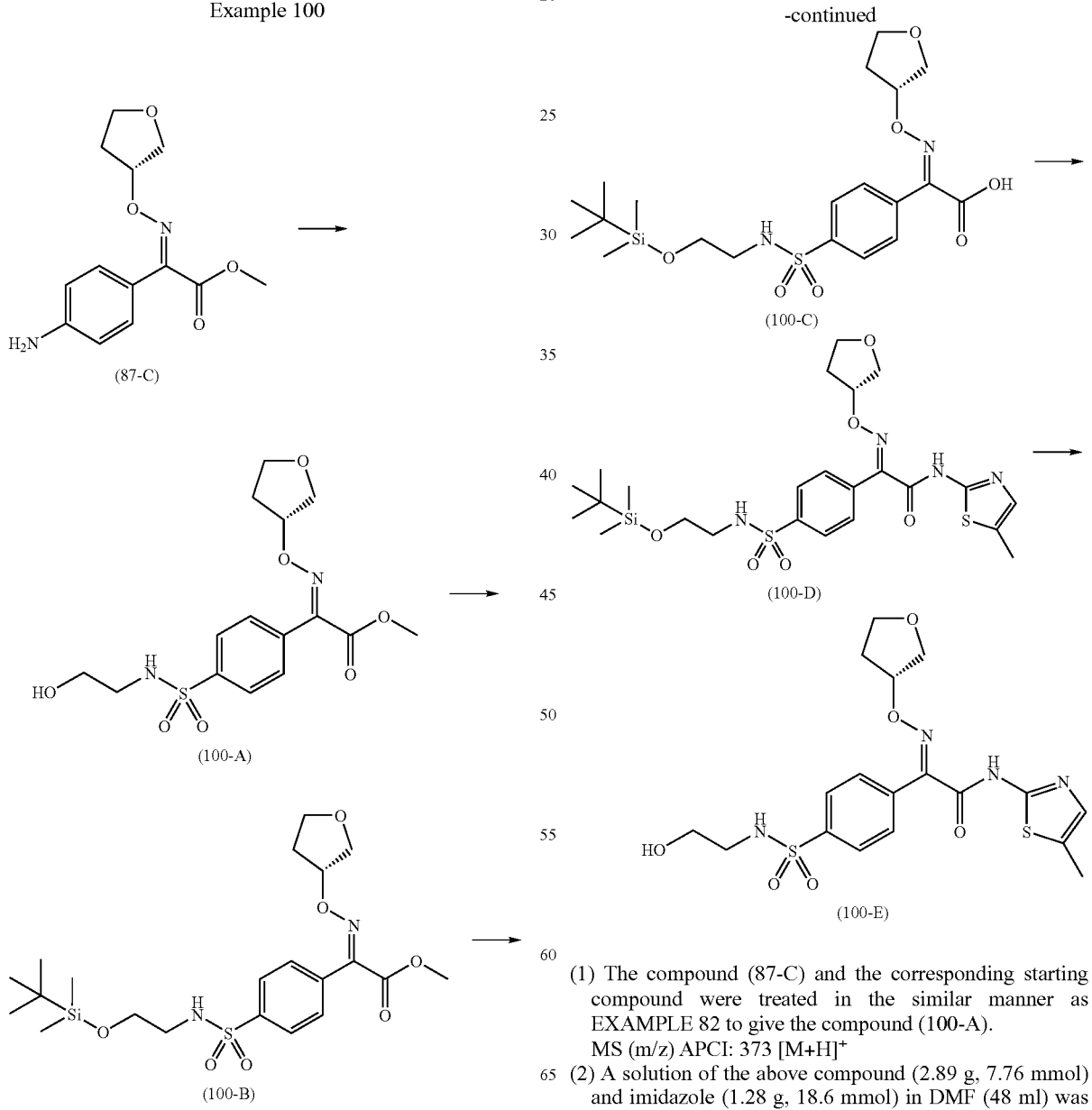
Example 100
(1) The compound (87-C) and the corresponding starting compound were treated in the similar manner as EXAMPLE 82 to give the compound (100-A).
MS (m/z) APCI: 373 [M+H]+
(2) A solution of the above compound (2.89 g, 7.76 mmol) and imidazole (1.28 g, 18.6 mmol) in DMF (48 ml) was ice-cooled, and thereto was added tert-butyldimethylchlorosilane (1.45 g, 9.3 mmol). The mixture was stirred at room temperature for 2 hours, diluted with ethyl acetate, and washed with water and brine, dried over sodium sulfate and concentrated in vacuo, and the resulting residue was purified by silica gel chromatography (33% ethyl acetate-hexane) to give the compound (100-B) (3.58 g, yield 95%) as a colorless oil.

MS (m/z) APCI: 487 [M+H]$^+$ (3) The above compound was treated in the similar manner as EXAMPLE 63-(2) to give the compound (100-C).

(4) The above compound was treated in the similar manner as EXAMPLE 1-(5) to give the compound (100-D).

MS (m/z) APCI: 569 [M+H]

(5) The above compound was treated in the similar manner as EXAMPLE 67-(4) to give the compound (100-E).

MS (m/z) APCI: 455 [M+H]$^+$

Corresponding starting compounds were treated in the similar manner as the above-mentioned to give the following compounds.

| EXAMPLE No. | No | Structure | MS (m/z) |
|---|---|---|---|
| 100 | 1 | | 485 APCI [M + H]$^+$ |
| 100 | 2 | | 492 APCI [M + H]$^+$ |
| 100 | 3 | | 522 APCI [M + H]$^+$ |

Example 101

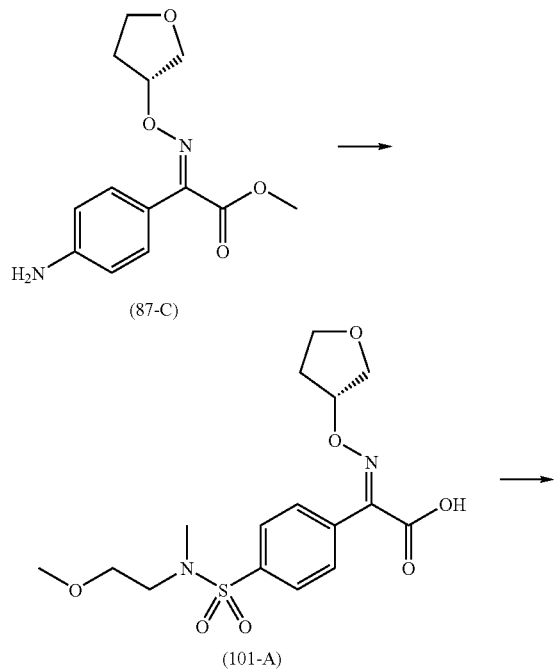

(87-C)

(101-A)

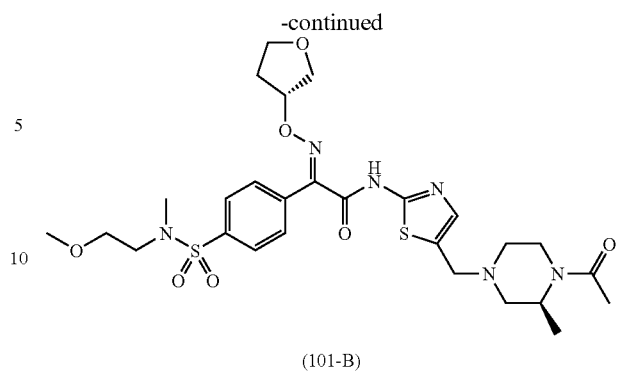

(101-B)

(1) The compound (87-C) was treated in the similar manner as EXAMPLE 82-(1) and 1-(4-2-2) to give the compound (101-A).

MS (m/z) ESI: 793 [2M−2H+Na]−

(2) The above compound was reacted in the similar manner as EXAMPLE 1-(5) to give the compound (101-B).

MS (m/z) APCI: 623 [M+H]+

Corresponding starting compounds were treated in the similar manner as the above-mentioned to give the following compounds.

| EXAMPLE No. | No | Structure | MS (m/z) |
|---|---|---|---|
| 101 | 1 | 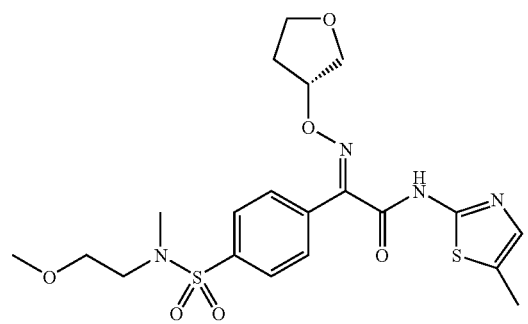 | 483 APCI [M + H]+ |
| 101 | 2 | 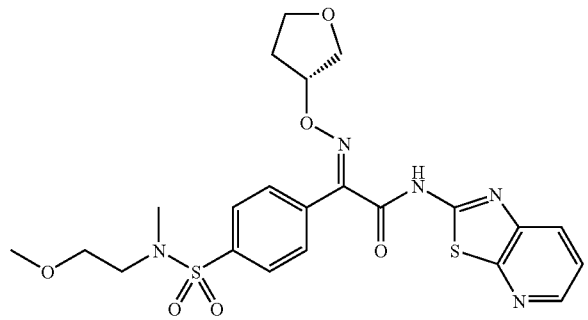 | 520 APCI [M + H]+ |

| EXAMPLE No. | No | Structure | MS (m/z) |
|---|---|---|---|
| 101 | 3 | 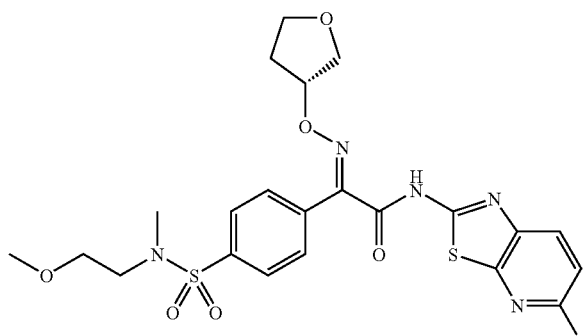 | 550 APCI [M + H]+ |
Example 102
Corresponding starting compounds were treated in a combination of the above-mentioned methods to give the following compounds.
| EXAMPLE No. | No | Structure | MS (m/z) |
|---|---|---|---|
| 102 | 1 | 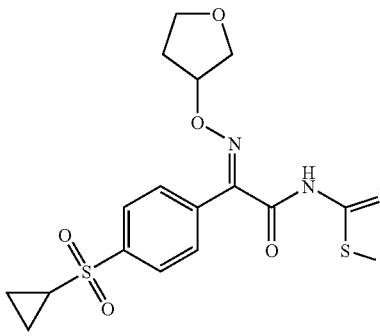 | 423 APCI [M + H]+ |
| 102 | 2 | 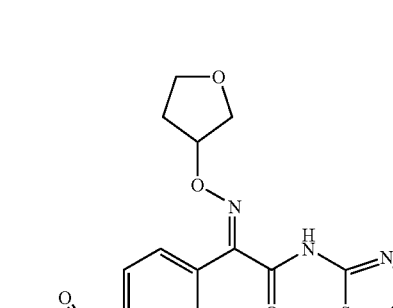 | 422 APCI [M + H]+ |

| EXAMPLE No. | No | Structure | MS (m/z) |
|---|---|---|---|
| 102 | 3 | 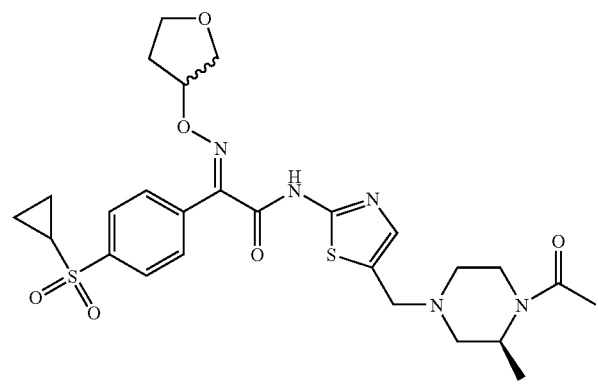 | 576 APCI [M + H]+ |
| 102 | 4 | 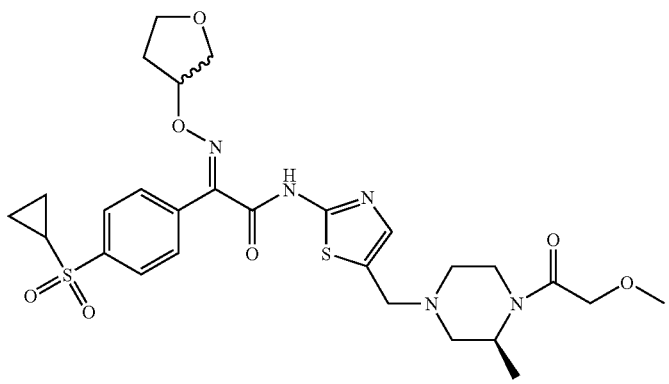 | 606 APCI [M + H]+ |
| 102 | 5 | 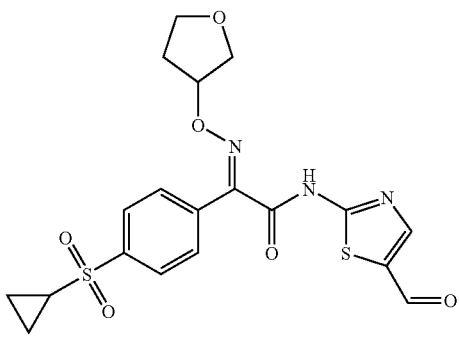 | 450 APCI [M + H]+ |
| 102 | 6 | 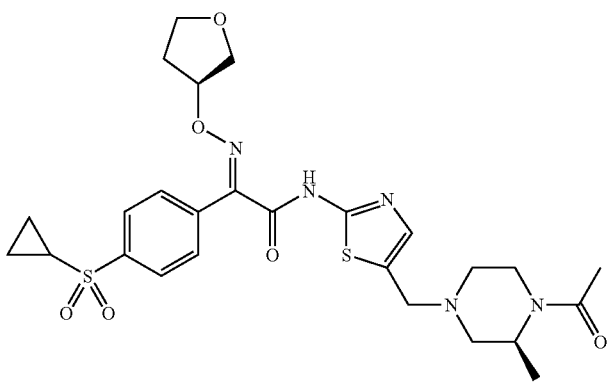 | 576 APCI [M + H]+ |

-continued

| EXAMPLE No. | No | Structure | MS (m/z) |
|---|---|---|---|
| 102 | 7 | | 532 APCI [M + H]+ |
| 102 | 8 | | 560 APCI [M + H]+ |
| 102 | 9 | | 532 APCI [M + H]+ |
| 102 | 10 | | 519 APCI [M + H]+ |

-continued
| EXAMPLE No. | No | Structure | MS (m/z) |
|---|---|---|---|
| 102 | 11 | 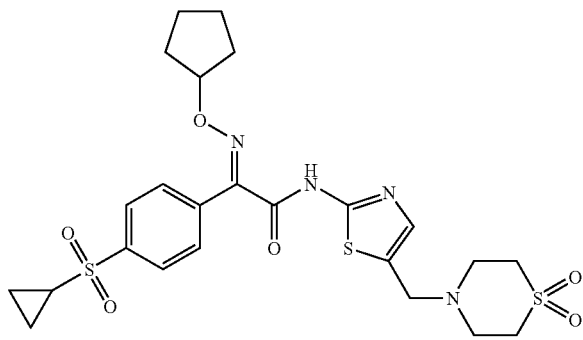 | 567 APCI [M + H]+ |
| 102 | 12 | 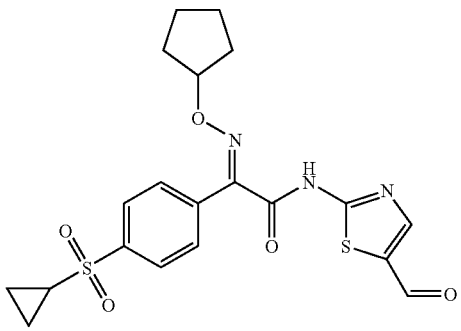 | 448 APCI [M + H]+ |
| 102 | 13 | 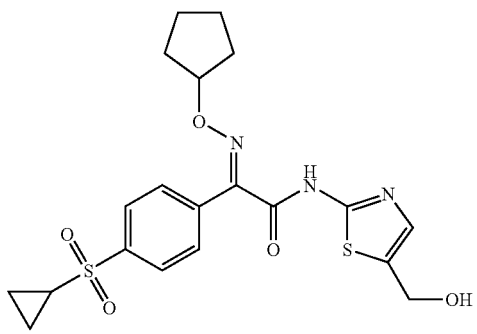 | 450 APCI [M + H]+ |
| 102 | 14 | 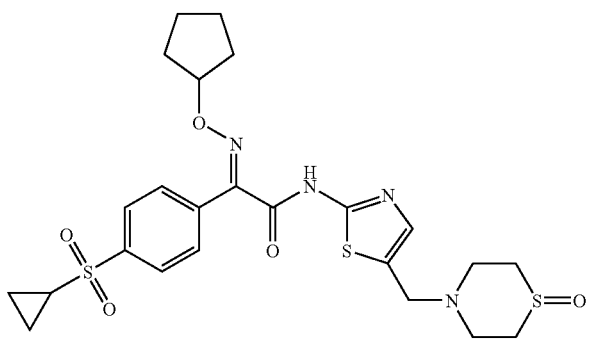 | 551 APCI [M + H]+ |

| EXAMPLE No. | No | Structure | MS (m/z) |
|---|---|---|---|
| 102 | 15 | 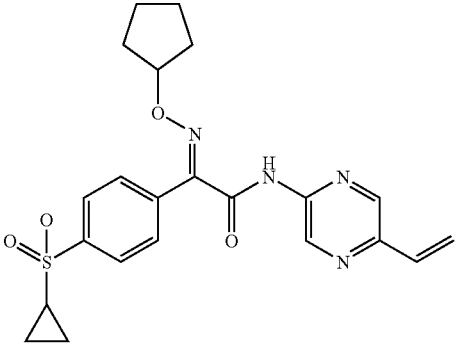 | 441 APCI [M + H]+ |
| 102 | 16 | 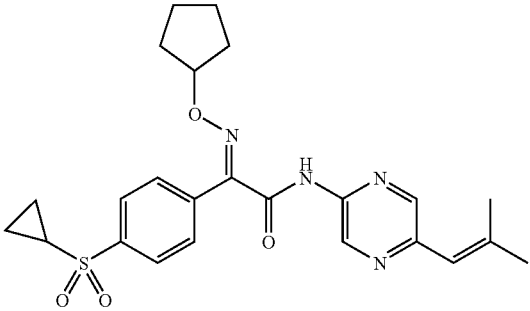 | 469 APCI [M + H]+ |
| 102 | 17 | 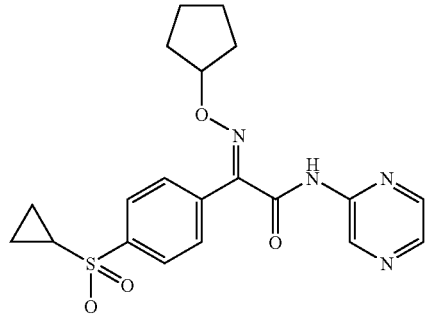 | 415 APCI [M + H]+ |
| 102 | 18 | 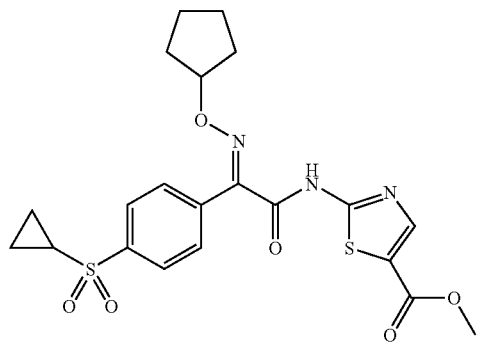 | 478 APCI [M + H]+ |

-continued
| EXAMPLE No. | No | Structure | MS (m/z) |
|---|---|---|---|
| 102 | 19 | 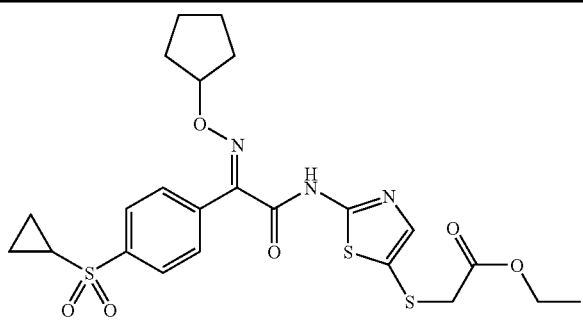 | 538 APCI [M + H]+ |
| 102 | 20 | 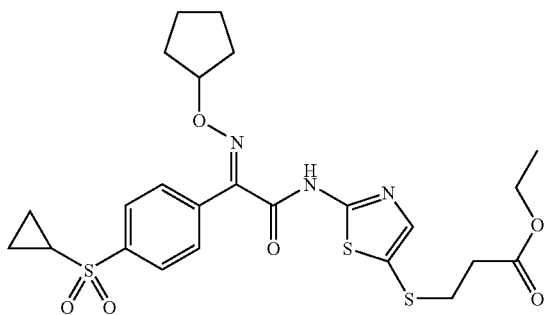 | 552 APCI [M + H]+ |
| 102 | 21 | 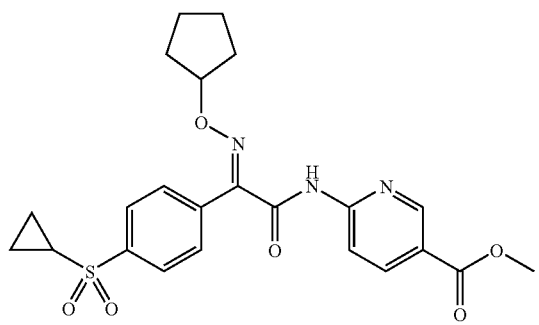 | 472 APCI [M + H]+ |
| 102 | 22 | 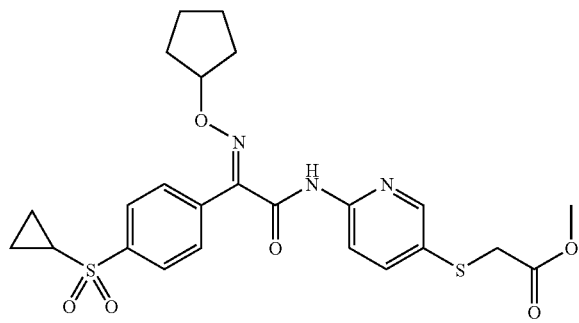 | 518 APCI [M + H]+ |

-continued

| EXAMPLE No. | No | Structure | MS (m/z) |
|---|---|---|---|
| 102 | 23 | | 580 ESI [M − H]− |
| 102 | 24 | | 493/495 APCI [M + H]+ |
| 102 | 25 | | 569 APCI [M + H]+ |
| 102 | 26 | | 366 ESI [M + H]+ |

Example 103

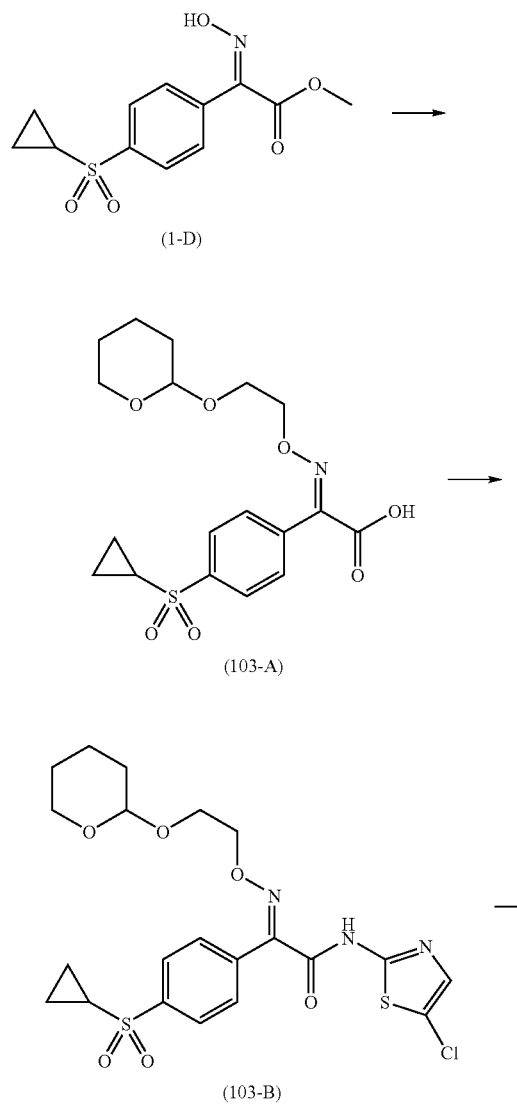

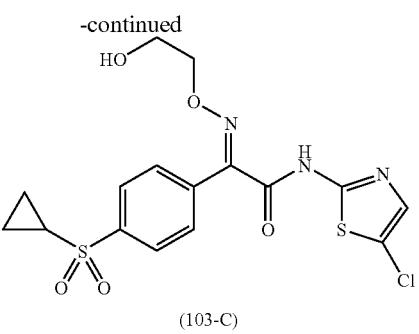

(1) The compound (1-D) and the corresponding starting compound were reacted in the similar manner as EXAMPLE 1-(4-1) to give the compound (103-A).

(2) The above compound and the corresponding starting compound were reacted in the similar manner as EXAMPLE 1-(5) to give the compound (103-B).

MS (m/z) APCI: 536/538 [M+H]$^+$ (3) The above compound (107 mg, 0.21 mmol) was dissolved in methanol (2 ml), and thereto were added two drops of a 4N solution of hydrogen chloride in dioxane. The mixture was stirred at room temperature for 24 hours, diluted with ethyl acetate, washed with water and brine, dried over magnesium sulfate and concentrated in uacuo, and the resulting residue was purified by silica gel chromatography (0 to 3% methanol-ethyl acetate) to give the compound (103-C).

MS (m/z) APCI: 430/432 [M+H]$^+$

Corresponding starting compounds were treated in the similar manner as the above-mentioned to give the following compounds.

| EXAMPLE No. | No | Structure | MS (m/z) |
|---|---|---|---|
| 103 | 1 | ![structure] | 477 APCI [M + H]$^+$ |

-continued

| EXAMPLE No. | No | Structure | MS (m/z) |
|---|---|---|---|
| 103 | 2 | (structure) | 410 APCI [M + H]+ |

Example 104

Corresponding starting compounds were treated in the similar manner as EXAMPLE 67 using the compound 67-B or the corresponding enantiomer synthesized in the method of EXAMPLE 67 to give the following compounds.

| EXAMPLE No. | No | Structure | MS (m/z) |
|---|---|---|---|
| 104 | 1 | (structure) | 550 ESI+ [M + H]+ |
| 104 | 2 | (structure) | 444 ESI+ [M + H]+ |

-continued
| EXAMPLE No. | No | Structure | MS (m/z) |
|---|---|---|---|
| 104 | 3 | 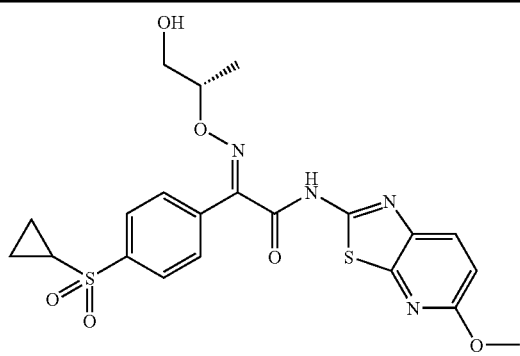 | 491 ESI+ [M + H]+ |
| 104 | 4 | 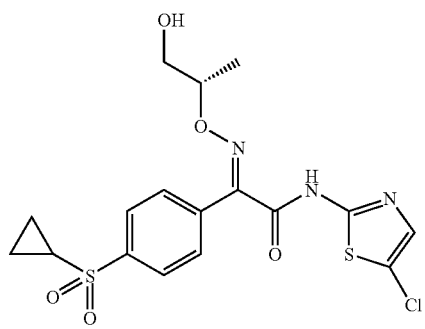 | 444 ESI+ [M + H]+ |
| 104 | 5 | 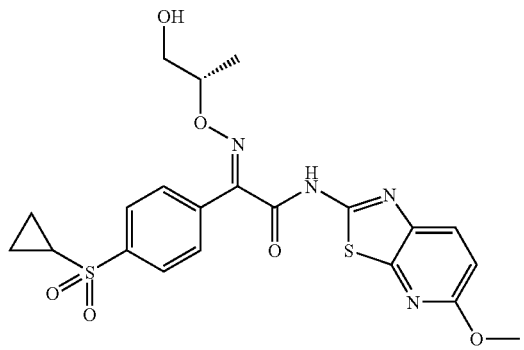 | 491 ESI+ [M + H]+ |
| 104 | 6 | 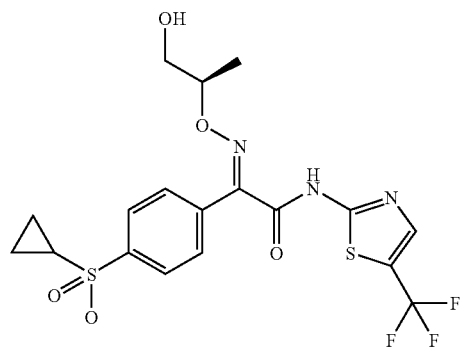 | 478 APCI [M + H]+ |

-continued
| EXAMPLE No. | No | Structure | MS (m/z) |
|---|---|---|---|
| 104 | 7 | 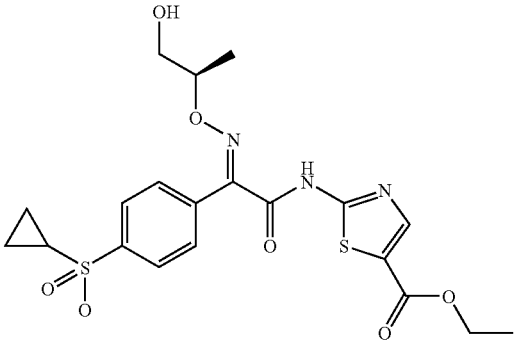 | 482 APCI [M + H]+ |
| 104 | 8 | 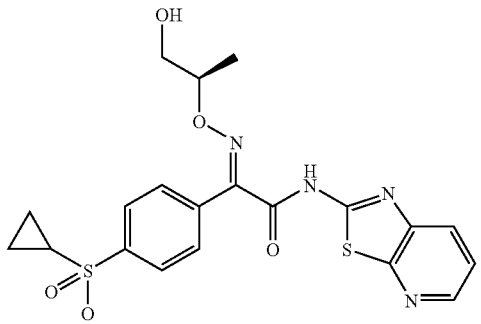 | 461 APCI [M + H]+ |
| 104 | 9 | 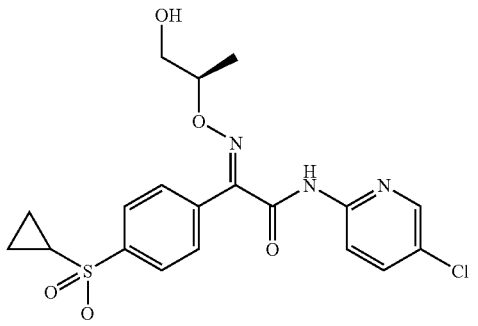 | 438/440 APCI [M + H]+ |
| 104 | 10 | 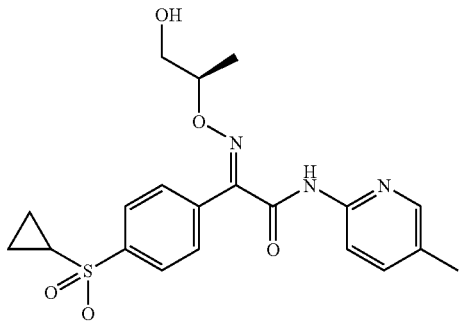 | 418 APCI [M + H]+ |

-continued
| EXAMPLE No. | No | Structure | MS (m/z) |
|---|---|---|---|
| 104 | 11 | 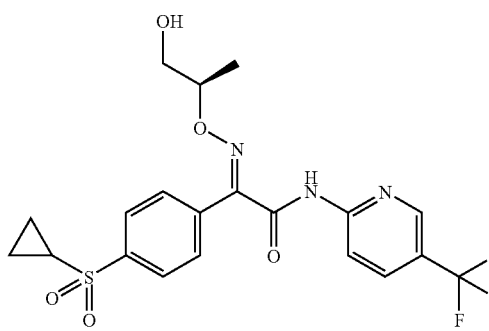 | 472 APCI [M + H]+ |
| 104 | 12 | 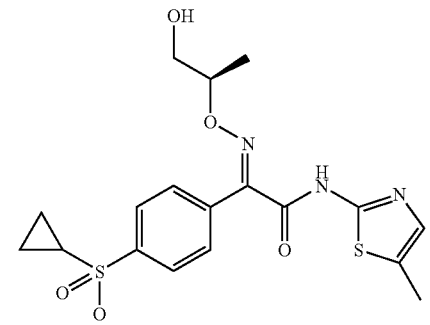 | 424 APCI [M + H]+ |
| 104 | 13 | 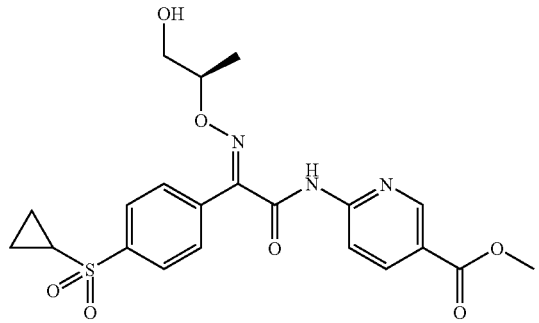 | 462 APCI [M + H]+ |
| 104 | 14 | 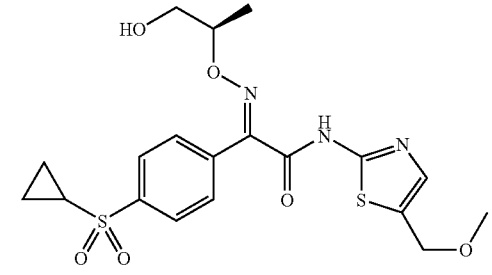 | 454 APCI [M + H]+ |

Example 105

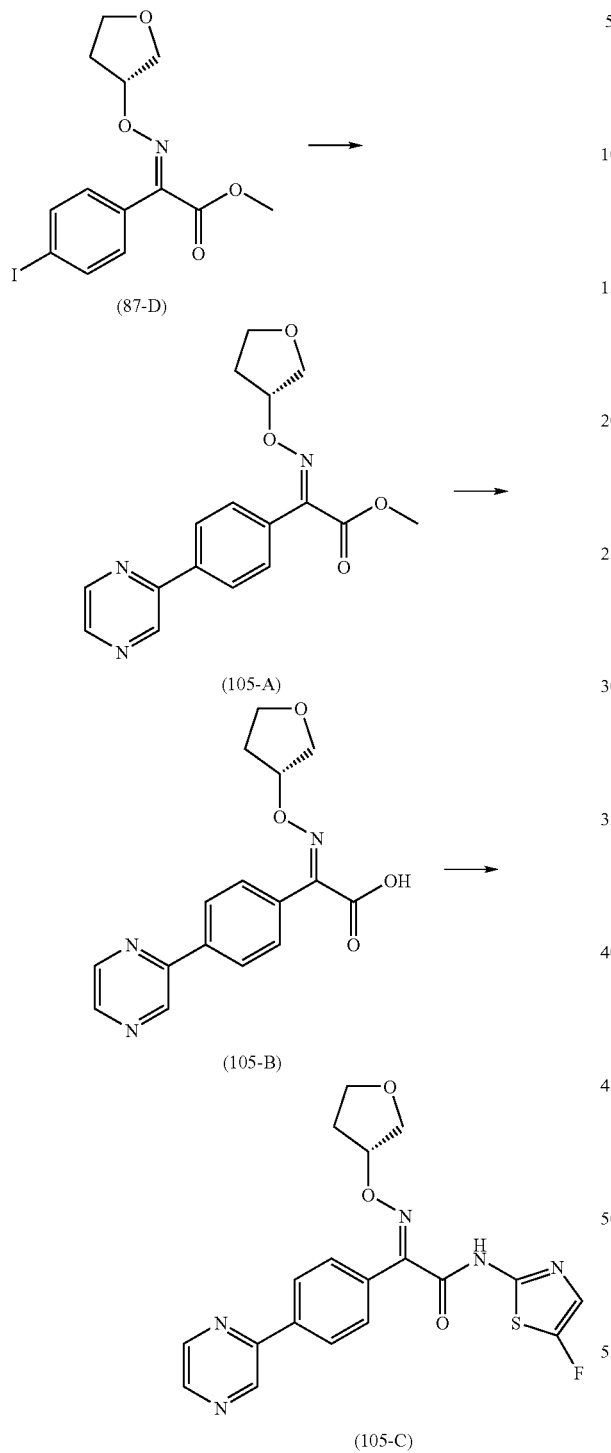

(1) To a solution of the compound (87-D) (300 mg, 0.80 mmol), 2-tributylstannylpyrazine (384 mg, 1.04 mmol) and copper (I) iodide (15.2 mg, 0.08 mmol) in THF (6 ml) was added tetrakis(triphenylphosphine)palladium (92.4 mg, 0.08 mmol) at room temperature under argon, and the mixture was heated to reflux for 6 hours. After cooling, thereto was added a 10% aqueous potassium fluoride solution and the mixture was diluted with ethyl acetate, and then the precipitated insoluble was filtered off through Celite. The filtrate was washed with brine, dried over magnesium sulfate and concentrated in vacuo. The residue was purified by silica gel chromatography (30 to 60% ethyl acetate-hexane) to give the compound (105-A) (206 mg, yield 79%).
MS (m/z) APCI: 328 [M+H]$^+$ (2) The above compound was reacted in the similar manner as EXAMPLE 1-(4-2-2) to give the compound (105-B).
MS (m/z) ESI: 312 [M−H]$^−$ (3) The above compound and the corresponding starting compound were reacted in the similar manner as EXAMPLE 1-(5) to give the compound (105-C).
MS (m/z) APCI: 414 [M+H]+

Example 106

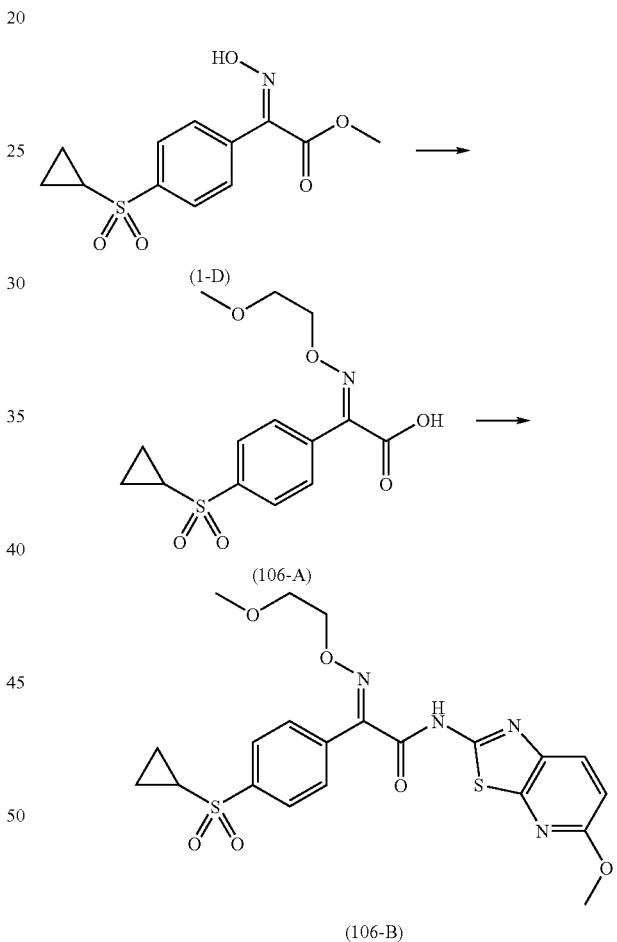

(1) The compound (1-D) and the corresponding starting compound were reacted in the similar manner as EXAMPLE 1-(4-1) to give the compound (106-A).
MS (m/z) ESI: 326 [M−H]$^−$ (2) The above compound and the corresponding starting compound were reacted in the similar manner as EXAMPLE 1-(5) to give the compound (103-B).
MS (m/z) ESI: 491 [M+H]$^+$ Corresponding starting compounds were treated in the similar manner as the above-mentioned to give the following compounds.

| EXAMPLE No. | No | Structure | MS (m/z) |
|---|---|---|---|
| 106 | 1 | | 444 ESI+ [M + H]⁺ |
| 106 | 2 | | 424 ESI+ [M + H]⁺ |
| 106 | 3 | | 454 APCI [M + H]⁺ |

Example 107

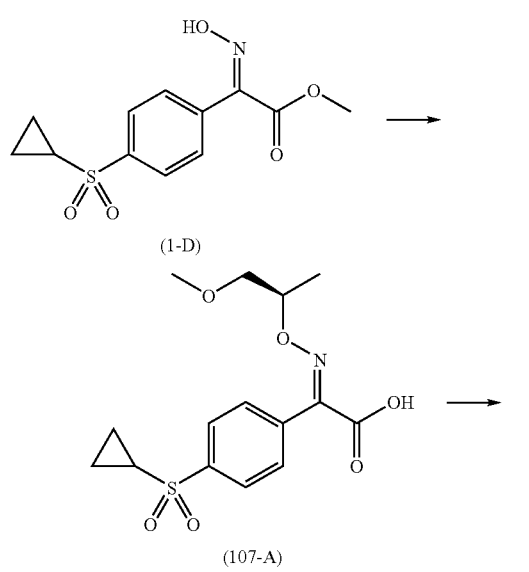

(1-D)

(107-A)

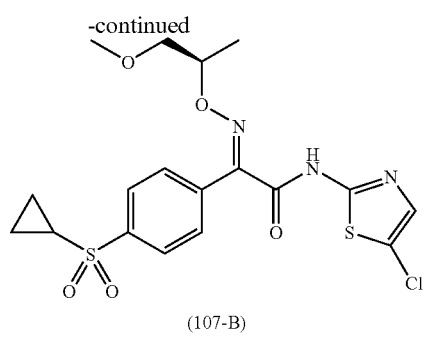

(107-B)

(1) The compound (1-D) and the corresponding starting compound were reacted in the similar manner as EXAMPLE 1-(4-1) to give the compound (107-A).

MS (m/z) ESI: 340 [M−H]⁻

(2) The above compound and the corresponding starting compound were reacted in the similar manner as EXAMPLE 1-(5) to give the compound (107-B).

MS (m/z) ESI: 458/460 [M+H]⁺

Corresponding starting compounds were treated in the similar manner as the above-mentioned to give the following compounds.

| EXAMPLE No. | No | Structure | MS (m/z) |
|---|---|---|---|
| 107 | 1 | 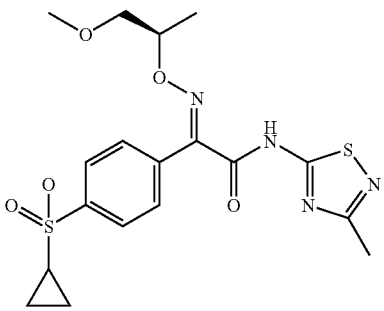 | 439 ESI+ [M + H]+ |
| 107 | 2 | 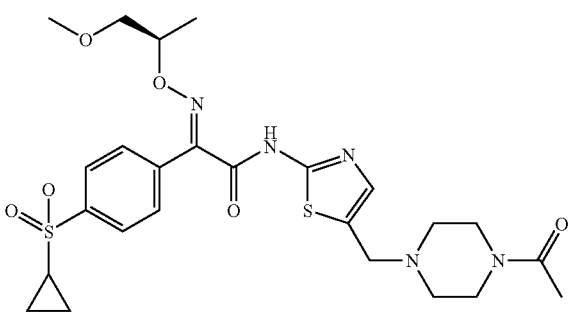 | 564 ESI+ [M + H]+ |
| 107 | 3 | 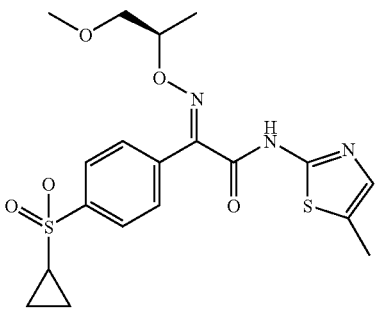 | 438 ESI+ [M + H]+ |
| 107 | 4 | 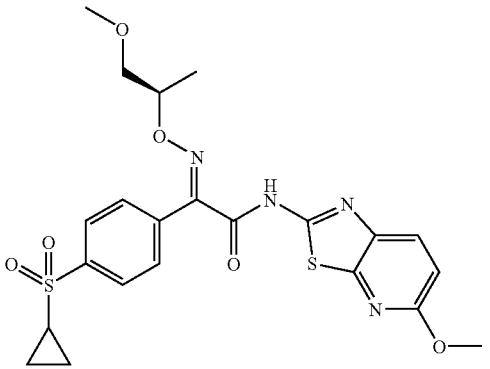 | 505 APCI [M + H]+ |

-continued

| EXAMPLE No. | No | Structure | MS (m/z) |
|---|---|---|---|
| 107 | 5 | 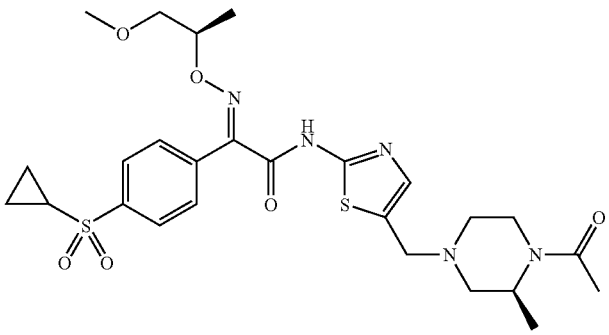 | 578 APCI [M + H]⁺ |
| 107 | 6 | 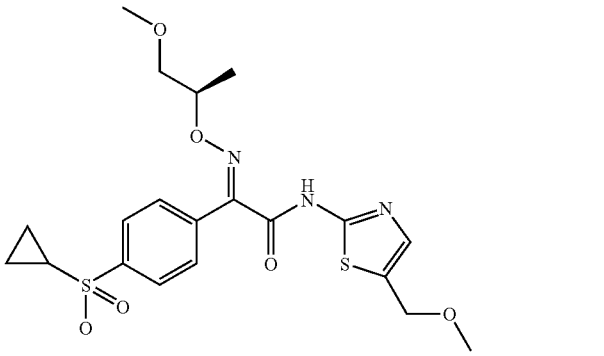 | 468 APCI [M + H]⁺ |

Example 108

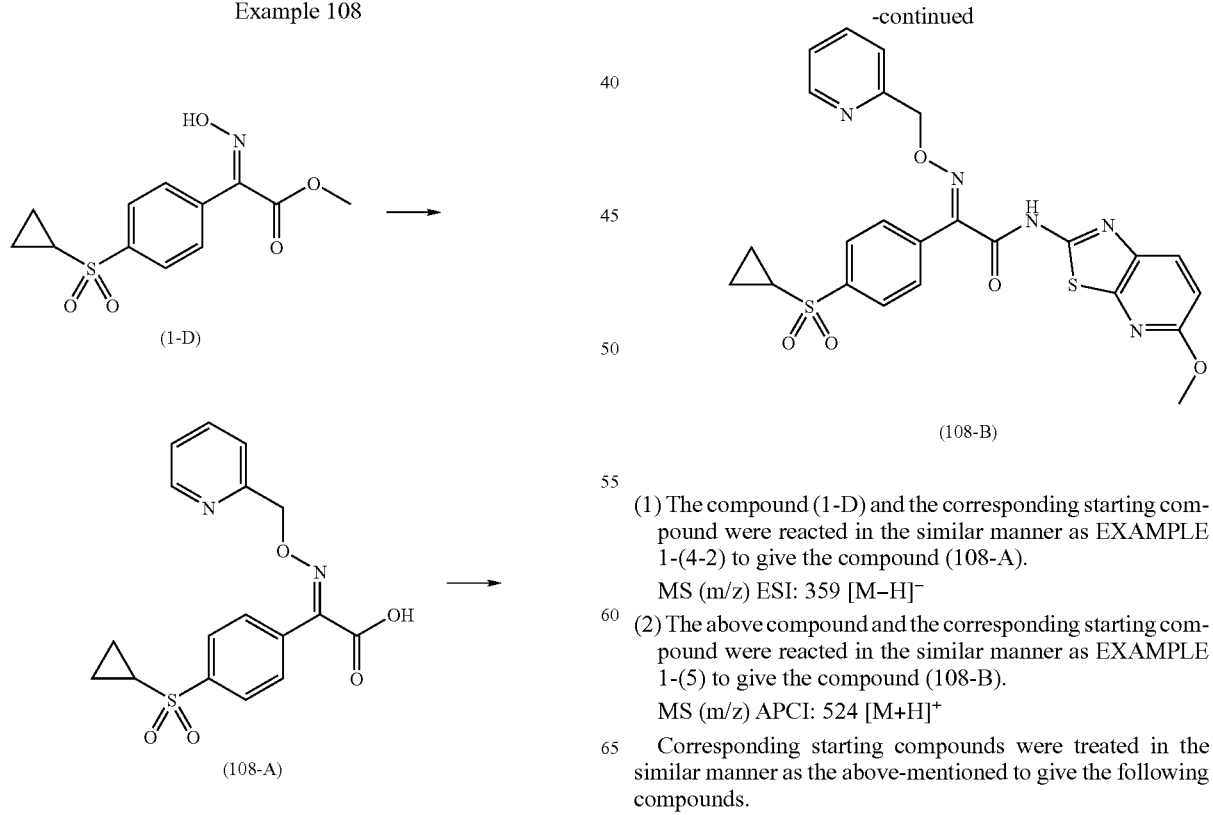

(1) The compound (1-D) and the corresponding starting compound were reacted in the similar manner as EXAMPLE 1-(4-2) to give the compound (108-A).

MS (m/z) ESI: 359 [M−H]⁻

(2) The above compound and the corresponding starting compound were reacted in the similar manner as EXAMPLE 1-(5) to give the compound (108-B).

MS (m/z) APCI: 524 [M+H]⁺

Corresponding starting compounds were treated in the similar manner as the above-mentioned to give the following compounds.

| EXAMPLE No. | No | Structure | MS (m/z) |
|---|---|---|---|
| 108 | 1 | 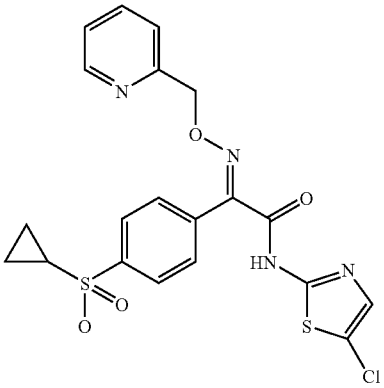 | 477/479 APCI [M + H]+ |
| 108 | 2 | 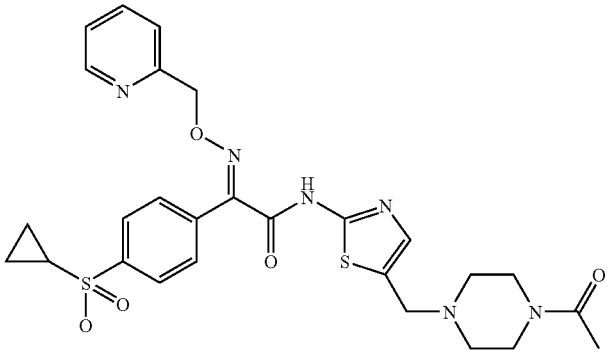 | 583 APCI [M + H]+ |
| 108 | 3 | 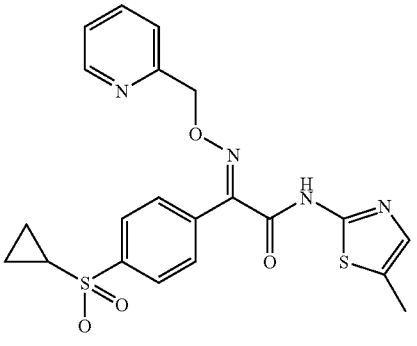 | 457 APCI [M + H]+ |
| 108 | 4 | 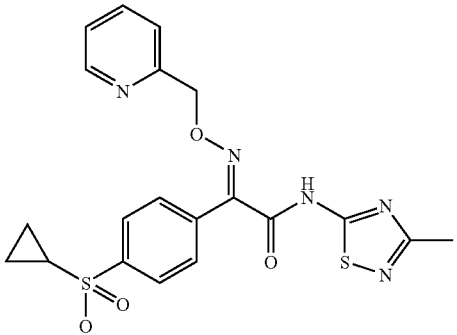 | 458 APCI [M + H]+ |

-continued
| EXAMPLE No. | No | Structure | MS (m/z) |
|---|---|---|---|
| 108 | 5 | 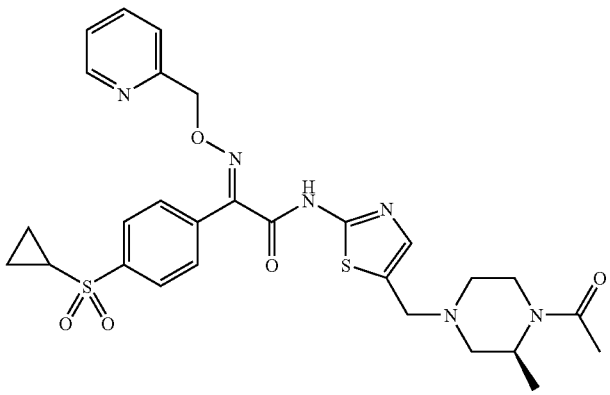 | 597 APCI [M + H]+ |
| 108 | 6 | 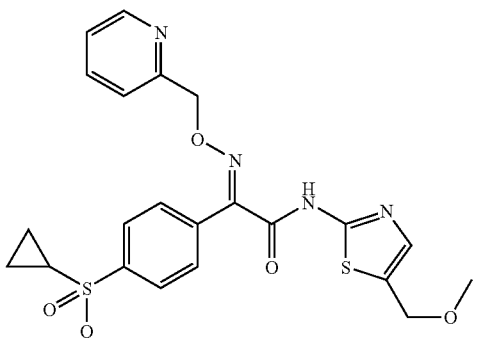 | 487 APCI [M + H]+ |
| 108 | 7 | 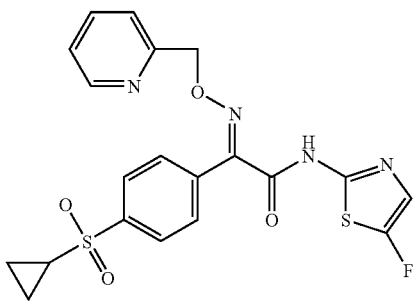 | 461 APCI [M + H]+ |
Example 109
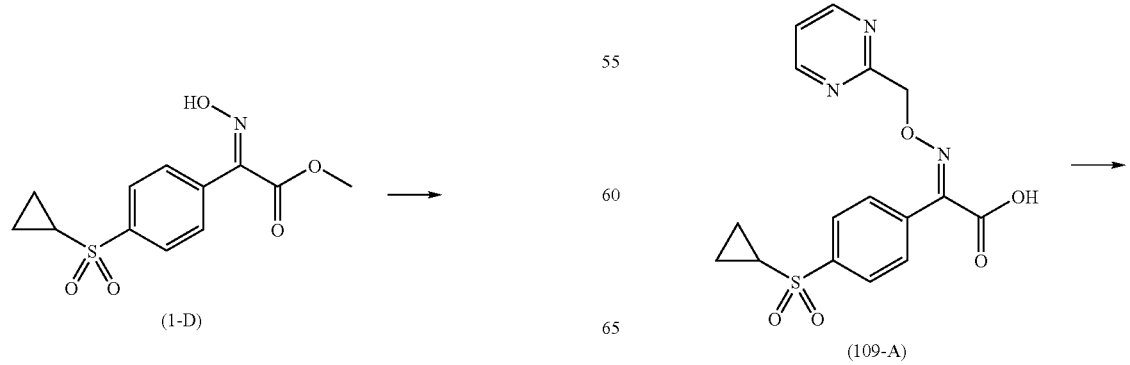

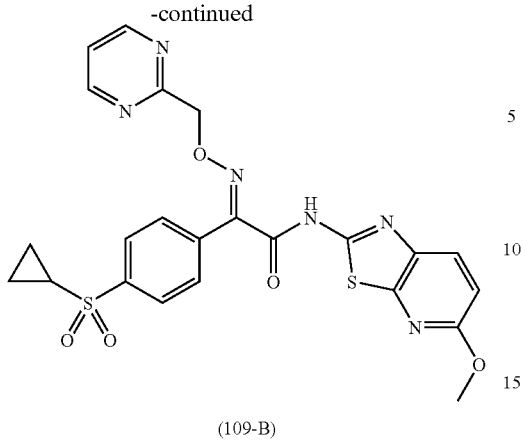

(109-B)

(1) The compound (1-D) and the corresponding starting compound were reacted in the similar manner as EXAMPLE 1-(4-2) to give the compound (109-A).

MS (m/z) ESI: 360 [M−H]⁻

(2) The above compound and the corresponding starting compound were reacted in the similar manner as EXAMPLE 1-(5) to give the compound (109-B).

MS (m/z) APCI: 525 [M+H]⁺

Corresponding starting compounds were treated in the similar manner as the above-mentioned to give the following compounds.

| EXAMPLE No. | No | Structure | MS (m/z) |
|---|---|---|---|
| 109 | 1 | | 478/480 APCI [M + H]⁺ |
| 109 | 2 | 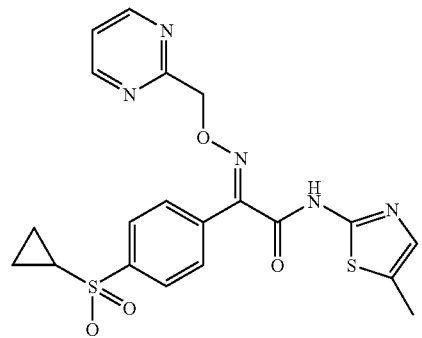 | 458 APCI [M + H]⁺ |

-continued
| EXAMPLE No. | No | Structure | MS (m/z) |
|---|---|---|---|
| 109 | 3 | 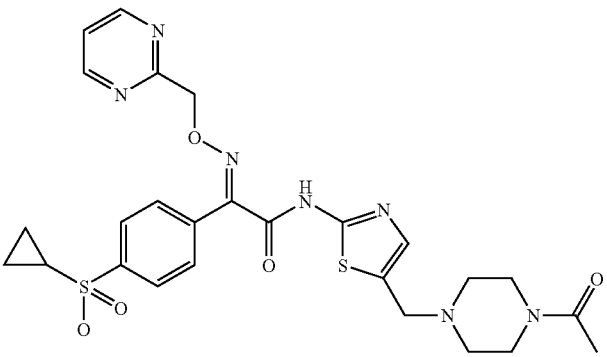 | 584 APCI [M + H]+ |
| 109 | 4 | 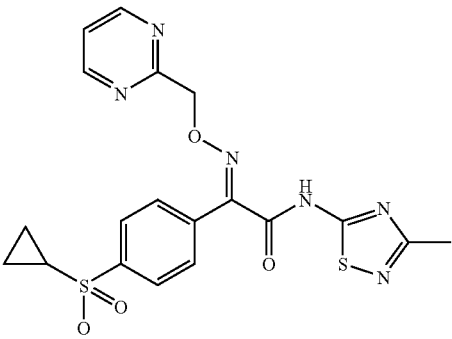 | 459 APCI [M + H]+ |
| 109 | 5 | 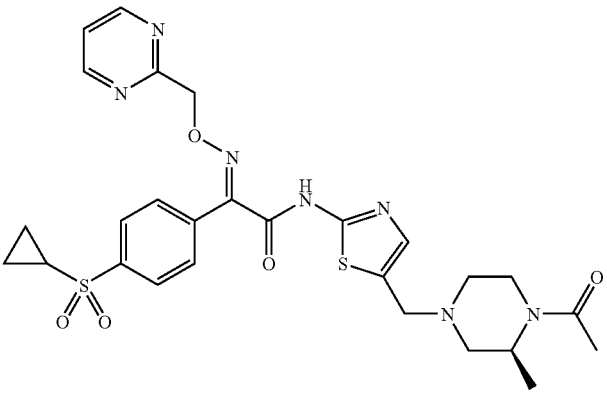 | 598 APCI [M + H]+ |
| 109 | 6 | 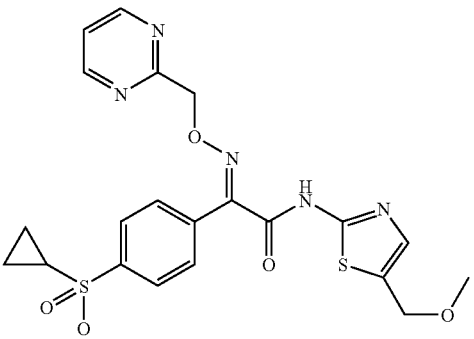 | 488 APCI [M + H]+ |

Example 110

Corresponding starting compounds were reacted in the similar manner as EXAMPLE 1 using (R)-(−)-2,2-dimethyl-1,3-dioxolan-4-methanol or the corresponding (S)-isomer to give the following compounds.

| EXAMPLE No. | No | Structure | MS (m/z) |
|---|---|---|---|
| 110 | 1 | | 547 APCI [M + H]$^+$ |
| 110 | 2 | | 547 APCI [M + H]$^+$ |

Example 111

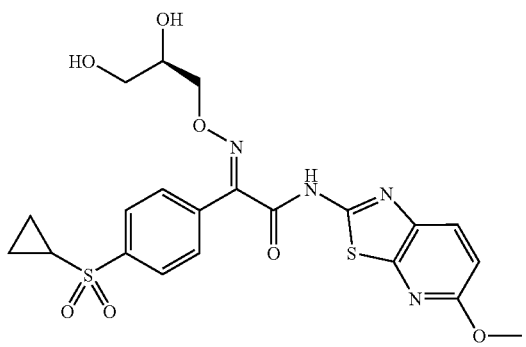

To a solution of the compound of EXAMPLE 110-(1) (300 mg, 0.55 mmol) in THF (4 ml) was added 1N hydrochloric acid (2 ml, 2 mmol) at room temperature, and the mixture was stirred at the same temperature for 16 hours. The mixture was extracted with chloroform, and the organic layer was dried over sodium sulfate and concentrated in vacuo. The residue was purified by silica gel column chromatography (10% methanol-chloroform) to give the above compound (230 mg, yield 83%).

MS (m/z) APCI: 507 [M+H]$^+$

The compound of EXAMPLE 110-(2) was reacted in the similar manner as the above-mentioned to give the following compound.

| EXAMPLE No. | No | Structure | MS (m/z) |
|---|---|---|---|
| 111 | 1 | 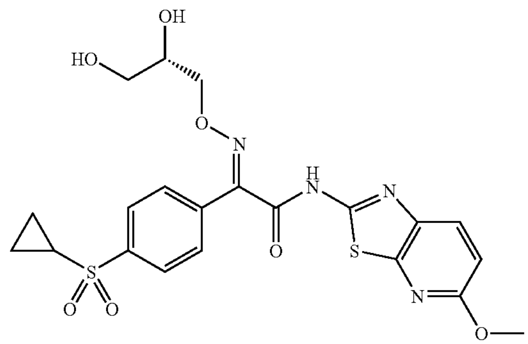 | 507 APCI [M + H]+ |
Example 112
A corresponding starting compound was reacted in the similar manner as EXAMPLE 1-(5) to give the following compound.
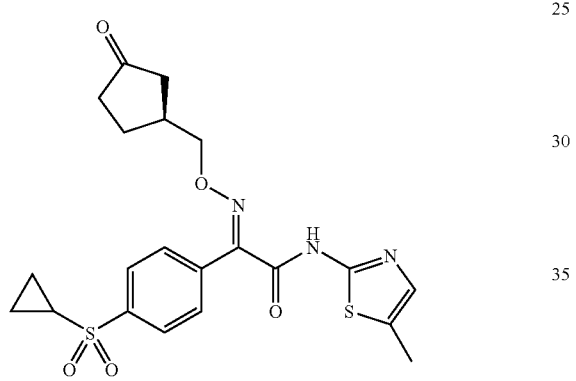
MS (m/z) APCI: 462 [M+H]+
Example 113
Corresponding starting compounds were reacted in the similar manner as EXAMPLE 40 to give the following compounds.
| EXAMPLE No. | No | Structure | MS (m/z) |
|---|---|---|---|
| 113 | 1 | 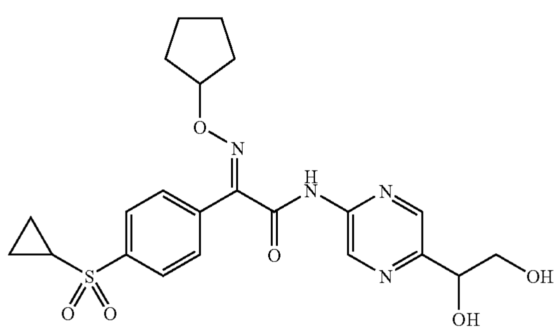 | 475 APCI [M + H]+ |

| EXAMPLE No. | No | Structure | MS (m/z) |
|---|---|---|---|
| 113 | 2 | 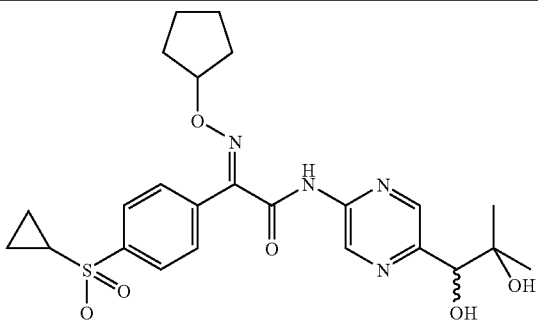 | 503 APCI [M + H]+ |

Example 114

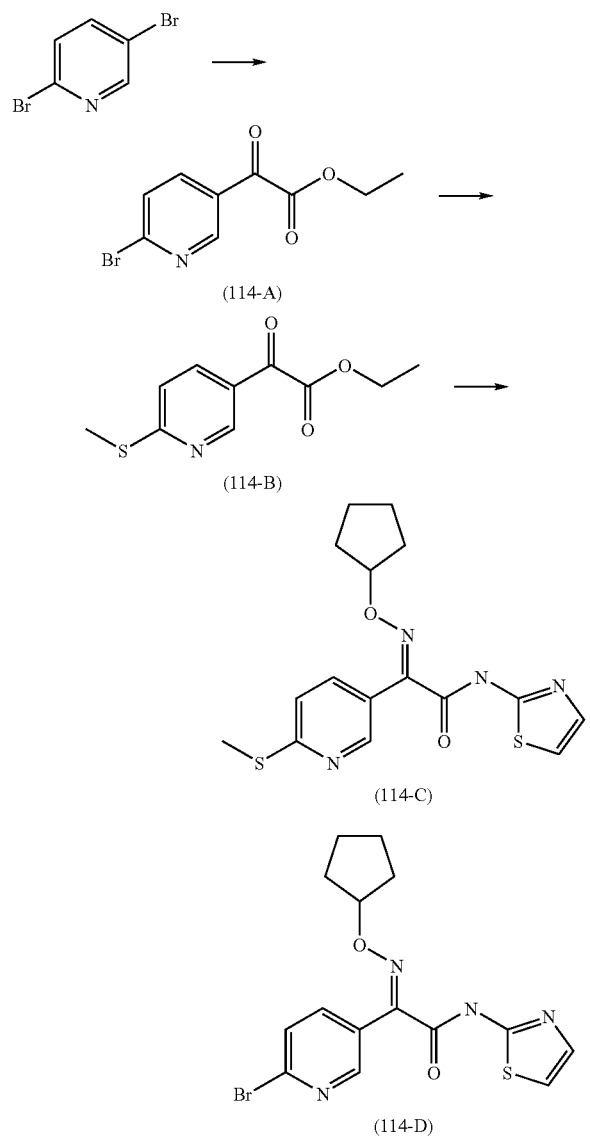

(1) To a solution of 2,5-dibromopyridine (23.7 g, 100 mmol) in diethyl ether (800 ml) was added dropwise a 2.6 M solution of n-butyllithium in hexane (39.2 ml, 102 mmol) over 15 minutes at 78° C. under argon, and the mixture was stirred at the same temperature for 20 minutes. Then, thereto was added dropwise diethyl oxalate (16.4 ml, 120 mmol) over 15 minutes. The mixture was stirred at the same temperature for 30 minutes and warmed to 0° C. over another 3 hours, poured into a saturated aqueous ammonium chloride solution, and thereto was added diethyl ether. The organic layer was separated, washed sequentially with water and brine, dried over magnesium sulfate and concentrated in vacuo. The residue was purified by silica gel chromatography (14% ethyl acetate-hexane) to give the compound (114-A) (11.6 g, yield 51%).
MS (m/z) APCI: 276 [M+H+H$_2$O]+

(2) To a solution of the above compound (11.6 g, 44.9 mmol) in DMF (200 ml) was added sodium thiomethoxide (3.15 g, 44.9 mmol) at room temperature. The mixture was stirred at the same temperature overnight, diluted with ethyl acetate, and then washed sequentially with water and brine, dried over magnesium sulfate and concentrated in vacuo. The residue was purified by silica gel chromatography (9% ethyl acetate-hexane) to give the compound (114-B) (11.2 g, yield 69%).
MS (m/z) APCI: 226 [M+H]+

(3) The above compound and the corresponding starting compound were reacted in the similar manner as EXAMPLE 65-(1) and 1-(5) to give the compound (114-C).
MS (m/z) APCI: 363 [M+H]+

(4) In this case, the compound (114-D) which was believed to be derived from (114-A) remaining unreacted in the reaction of the above (3) was also obtained.
MS (m/z) APCI: 395/397 [M+H]+

A corresponding starting compound was treated in the similar manner as the above-mentioned method and EXAMPLE 27 to synthesize the following compound.

| EXAMPLE No. | No | Structure | MS (m/z) |
|---|---|---|---|
| 114 | 1 | 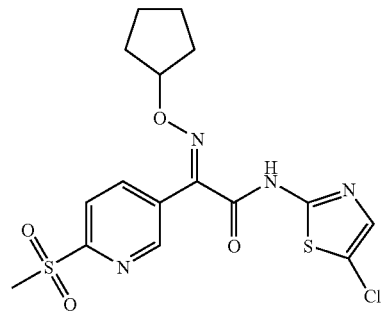 | 429/431 APCI [M + H]+ |
Example 115
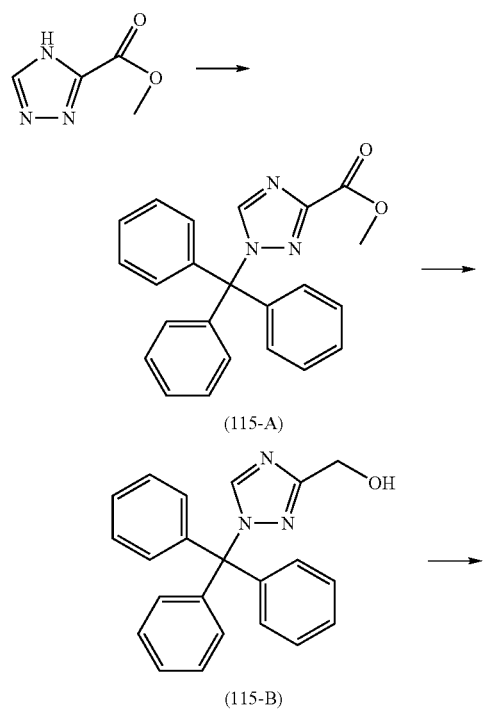
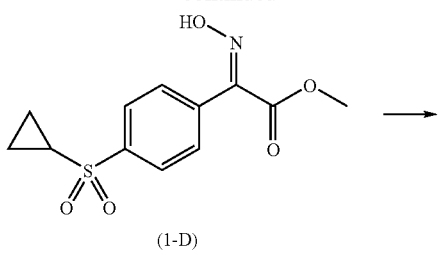
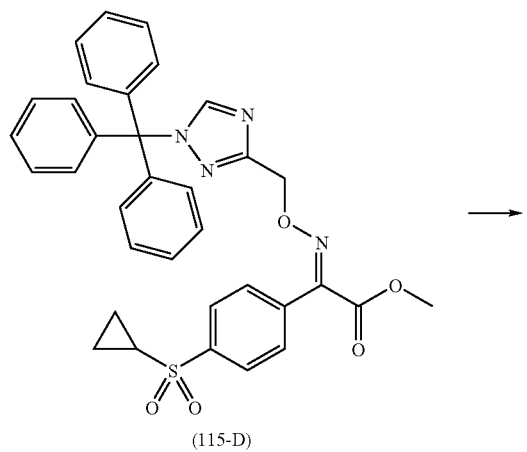
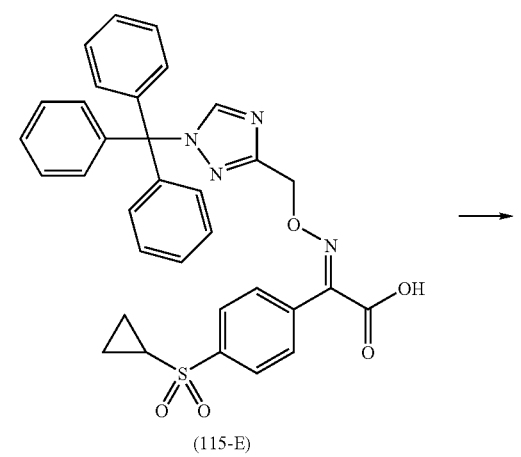
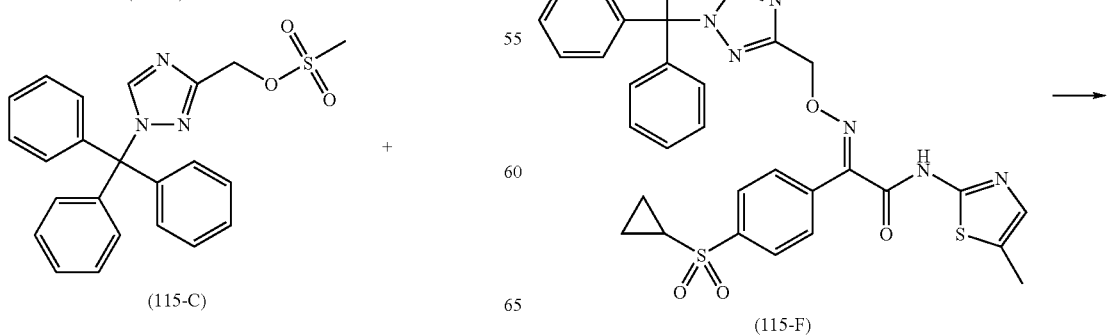

-continued

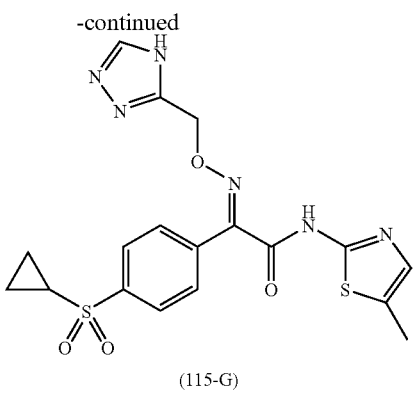

(115-G)

(1) To a solution of 4H-[1,2,4]triazole-3-carboxylic acid methyl ester (25.0 g, 197 mmol) in pyridine (350 ml) was added trityl chloride (65.8 g, 236 mmol) under ice-cooling. The mixture was stirred at room temperature 90 minutes and at 100° C. for 2 hours and concentrated in vacuo, and then the residue was solidified with isopropanol to give the compound (115-A) (68.8 g, yield 95%).
(2) To a solution of the above compound (64.6 g, 175 mmol) in THF (1000 ml) was added gradually lithium aluminum hydride (10.8 g, 284 mmol) under ice-cooling, and the ice bath was removed. After stirring at room temperature for 3 hours, thereto was added a 10% aqueous sodium hydroxide solution, and the suspension was filtered. The filtrate was concentrated, and then the residue was solidified with diethyl ether to give the compound (115-B) (34.8 g, yield 58%).
MS (m/z) ESI: 364 [M+Na]$^+$
(3) To a solution of the above compound (17.4 g, 50.8 mmol) and diisopropylethylamine (9.9 g, 76.2 mmol) in methylene chloride (250 ml) was added methanesulfonyl chloride (7.76 g, 67.8 mmol) under ice-cooling, and the mixture was stirred at the same temperature for 30 minutes. To the reaction mixture was added water and the organic layer was separated, and dried over sodium sulfate, and concentrated in vacuo to give the crude methanesulfonate (115-C) (23.6 g).
(4) To a solution of the compound (1-D) (12.0 g, 42.4 mmol) and potassium carbonate (17.6 g, 127 mmol) in DMF (250 ml) was added dropwise a solution of the above sulfonate (115-C) in DMF (50 ml) under ice-cooling, and the ice bath was removed. After stirring at room temperature for 16 hours, the mixture was diluted with ethyl acetate, washed sequentially with water and brine, dried over sodium sulfate and concentrated in vacuo to give the crude ester (31.7 g, 115-D).
(5) The above compound was reacted in the similar manner as EXAMPLE 1-(4-2-2) to give the compound (115-E).
MS (m/z) ESI: 591 [M−H]$^-$
(6) The above compound and the corresponding starting compound were reacted in the similar manner as EXAMPLE 1-(5) to give the compound (115-F).
MS (m/z) ESI: 689 [M+H]$^+$
(7) The above compound (191 mg, 0.28 mmol) was dissolved in formic acid (3 ml). The mixture was stirred at room temperature for 18 hours and concentrated in vacuo, and then the residue was purified by silica gel chromatography (2 to 6% methanol-chloroform) to give the compound (115-G) (75 g, yield 61%).
MS (m/z) APCI: 447 [M+H]$^+$ Corresponding starting compounds were treated in the similar manner as the above-mentioned to give the following compounds.

| EXAMPLE No. | No | Structure | MS (m/z) |
|---|---|---|---|
| 115 | 1 | 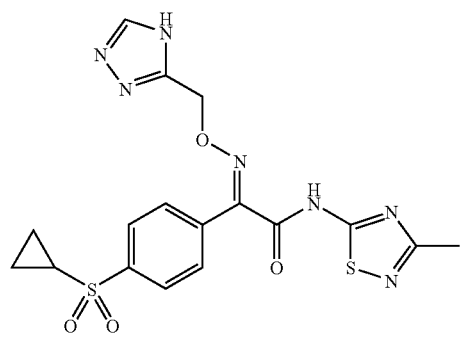 | 448 APCI [M + H]$^+$ |
| 115 | 2 | 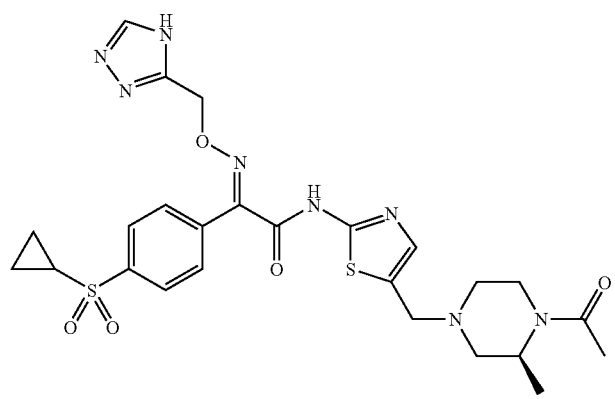 | 587 APCI [M + H]$^+$ |

| EXAMPLE No. | No | Structure | MS (m/z) |
|---|---|---|---|
| 115 | 3 | 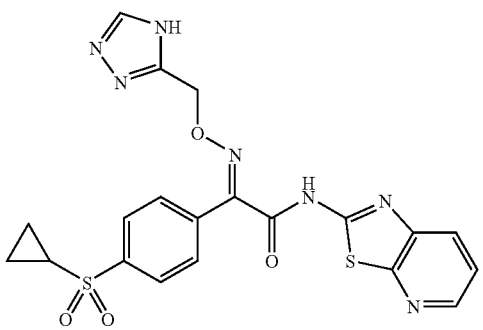 | 484 APCI [M + H]+ |
| 115 | 4 | 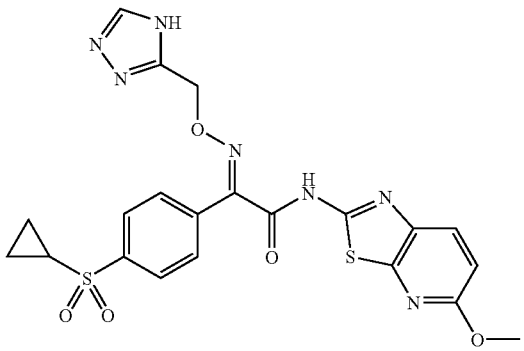 | 514 APCI [M + H]+ |
| 115 | 5 | 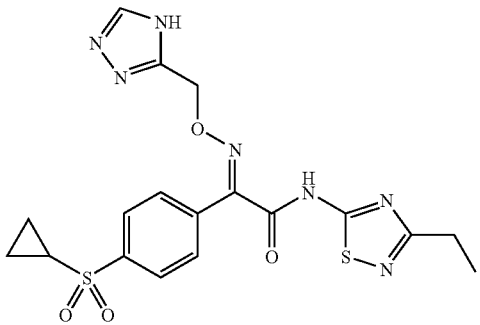 | 462 APCI [M + H]+ |

| EXAMPLE No. | No | Structure | MS (m/z) |
|---|---|---|---|
| 115 | 6 | | 477 APCI [M + H]+ |
| 115 | 8 | | 451 APCI [M + H]+ |
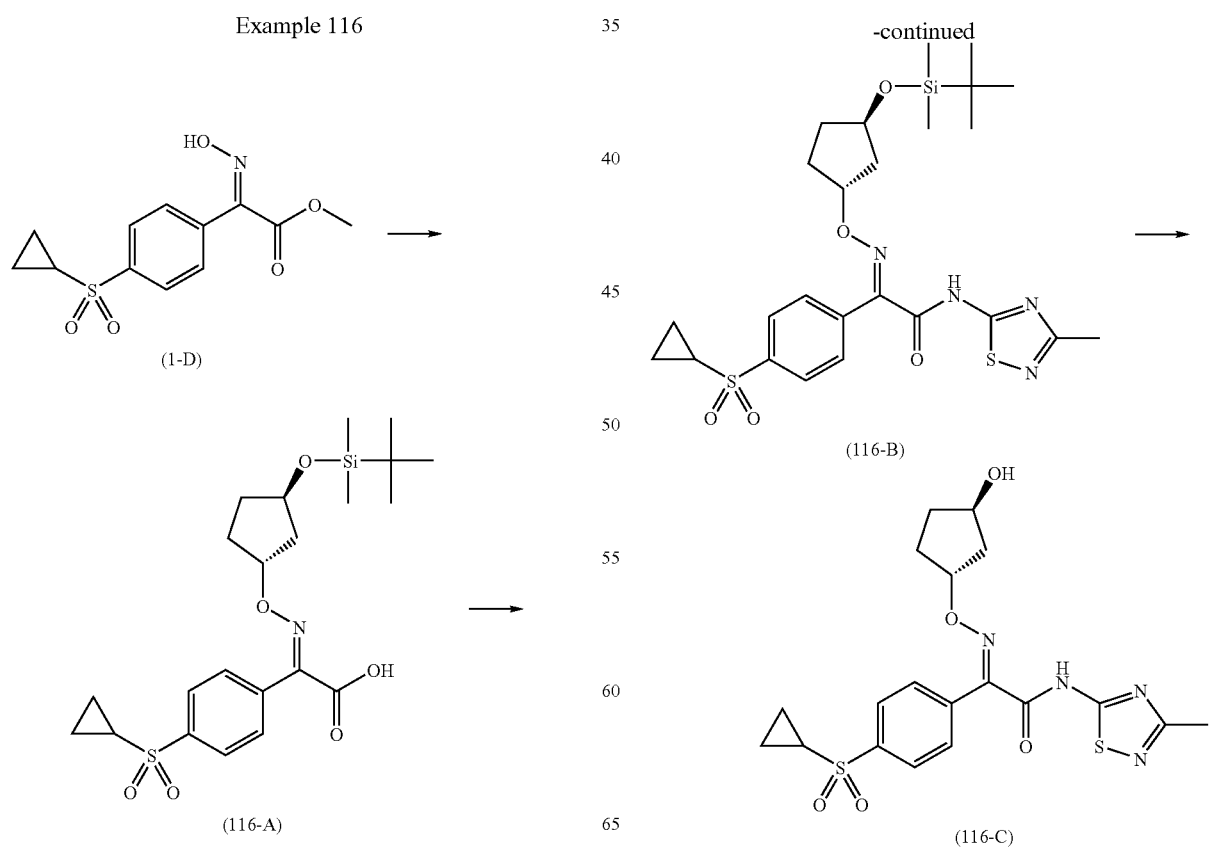
Example 116

(1) The compound (1-D) and tert-butyldimethylsilyl-protected corresponding starting compound were reacted in the similar manner as EXAMPLE 67-(1), (2) to give the compound (116-A).
MS (m/z) ESI: 466 [M−H]−

(2) The above compound and the corresponding starting compound were reacted in the similar manner as EXAMPLE 1-(5) to give the compound (116-B).

(3) The above compound was reacted in the similar manner as EXAMPLE 67-(4) to give the compound (116-C).
MS (m/z) APCI: 451 [M+H]+

Corresponding starting compounds were treated in the similar manner as the above-mentioned to give the following compounds.

| EXAMPLE No. | No | Structure | MS (m/z) |
|---|---|---|---|
| 116 | 1 | | 487 APCI [M + H]+ |
| 116 | 2 | | 590 APCI [M + H]+ |
| 116 | 3 | | 480 APCI [M + H]+ |

| EXAMPLE No. | No | Structure | MS (m/z) |
|---|---|---|---|
| 116 | 4 | 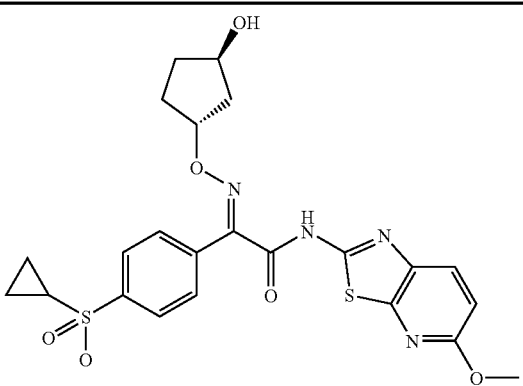 | 517 APCI [M + H]+ |
| 116 | 5 | 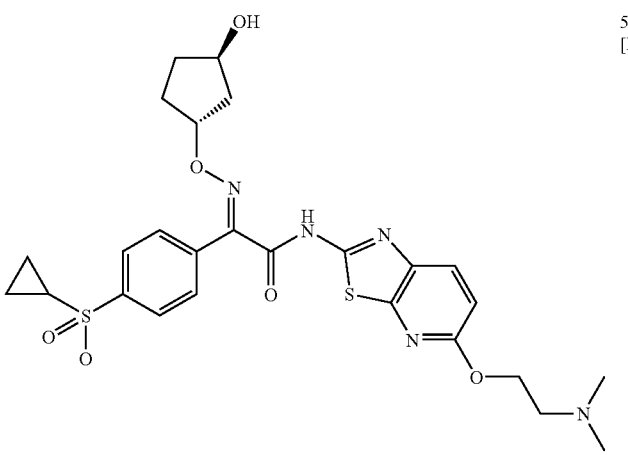 | 574 APCI [M + H]+ |
| 116 | 6 | 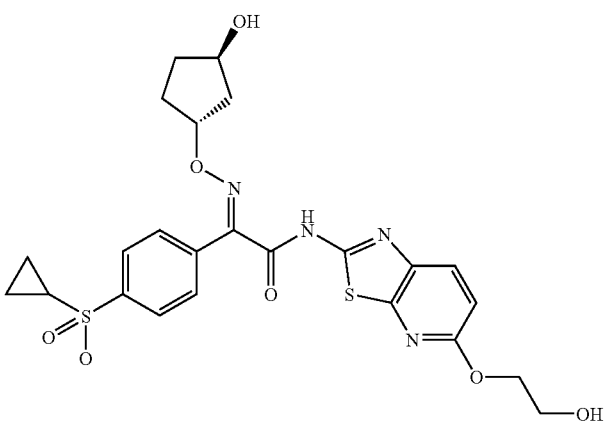 | 547 APCI [M + H]+ |
Example 117
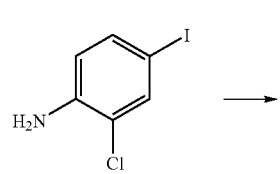
-continued
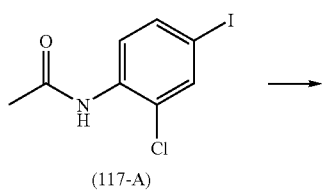
(117-A)

-continued

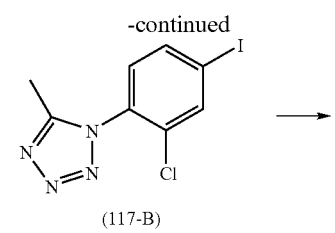
(117-B)

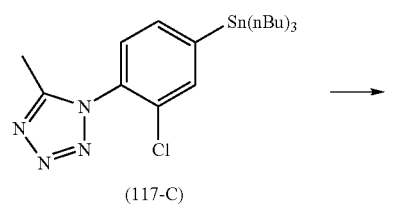
(117-C)

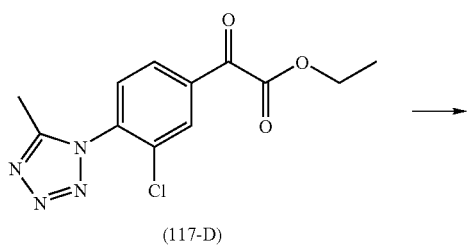
(117-D)

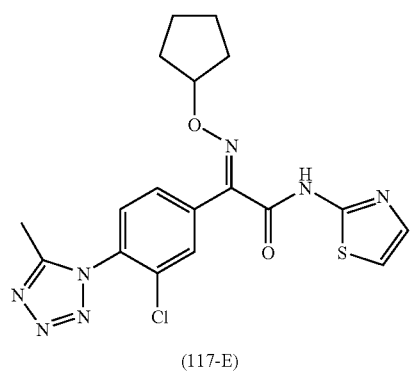
(117-E)

(1) To a solution of 2-chloro-4-iodoaniline (25 g, 96.7 mmol) in THF (100 ml) was added acetic anhydride (47 ml, 473 mmol) under ice-cooling. The mixture was stirred at the same temperature for 10 minutes and at room temperature for another 18 hours, and concentrated in vacuo. The residue was recrystallized from a mixture of ethyl acetate-hexane (11) to give the compound (117-A) (28.6 g, quantitatively).
MS (m/z) APCI: 296/298 [M+H]$^+$ (2) To a solution of the above compound (2.4 g, 8.1 mmol) and sodium azide (1.1 g, 16 mmol) in acetonitrile (40 ml) and methylene chloride (5 ml) was added trifluoromethanesulfonic anhydride (3.4 g, 12 mmol) under ice-cooling, and the ice bath was removed. The mixture was stirred at room temperature for 20 hours and concentrated in vacuo, and then to the residue was added ethyl acetate. The mixture was washed sequentially with water and brine, dried over magnesium sulfate and concentrated in vacuo. The residue was purified by silica gel chromatography (20% ethyl acetate-hexane) to give the compound (117-B) (2.07 g, yield 80%).
MS (m/z) APCI: 321/323 [M+H]$^+$ (3) To a solution of the above compound (4.8 g, 15 mmol), bis(tributyltin) (17.5 g, 30 mmol) in toluene (70 ml) was added dichlorobis(triphenylphosphine)palladium (1.06 g, 1.5 mmol) at room temperature under argon. The mixture was stirred at 100° C. for 3 hours. After air-cooling, thereto was added a 10% aqueous potassium fluoride solution, and the mixture was stirred at room temperature for 1 hour, and the precipitated insoluble was filtered off through Celite. The filtrate was dried over sodium sulfate and concentrated in vacuo and the residue was purified by silica gel chromatography (0 to 20% ethyl acetate-hexane) to give the compound (117-C) (4.8 g, yield 66%).
MS (m/z) APCI: 481/483/485 [M+H]$^+$ (4) To a solution of the above compound (7.6 g, 16 mmol), diisopropylethylamine (3.6 ml, 20 mmol), potassium carbonate (130 mg, 0.94 mmol) and tris(dibenzylideneacetone)dipalladium (720 mg, 0.78 mmol) in THF (70 ml) was added ethyl chlorooxalate (2.64 ml, 24 mmol) at room temperature under argon, and the mixture was stirred at the same temperature for 3 hours. To the reaction mixture was added a 10% aqueous potassium fluoride solution, and the mixture was stirred at the same temperature for 3 hours and diluted with diethyl ether. The insoluble was filtered off and the organic layer of the filtrate was separated, washed sequentially with water and brine, dried over magnesium sulfate and concentrated in vacuo. The residue was purified by silica gel chromatography (30% ethyl acetate-hexane) to give the compound (117-D) (1.04 g, yield 22%).
MS (m/z) APCI: 295/297 [M+H]$^+$ (5) The above compound and the corresponding starting compound were reacted in the similar manner as EXAMPLE 1-(3), 65-(1), 1-(4-2-2) and (5) to give the compound (117-E).
MS (m/z) APCI: 432/434 [M+H]$^+$ Example 118

The compound (79° C.) and the corresponding starting compounds were treated in the similar manner as EXAMPLE 1-(5) to give the following compounds.

| EXAMPLE No. | No | Structure | MS (m/z) |
|---|---|---|---|
| 118 | 1 | | 504 APCI [M + H]⁺ |
| 118 | 2 | | 563 APCI [M + H]⁺ |

Example 119

Corresponding starting compounds were treated in the similar manner as EXAMPLE 1-(3), (4-1), (5) to give the following compounds.

| EXAMPLE No. | No | Structure | MS (m/z) |
|---|---|---|---|
| 119 | 1 | 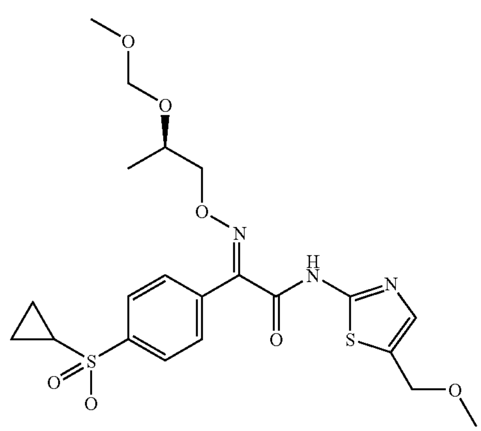 | 498 APCI [M + H]⁺ |

| EXAMPLE No. | No | Structure | MS (m/z) |
|---|---|---|---|
| 119 | 2 | 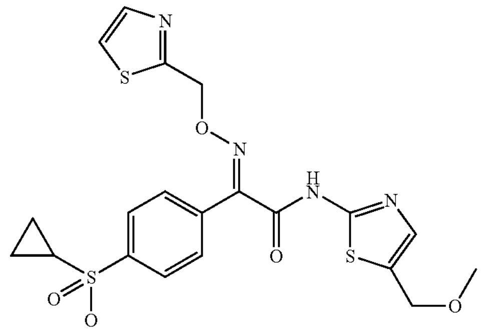 | 493 APCI [M + H]+ |
Example 120
A corresponding starting compound was treated in the similar manner as EXAMPLE 73 to give the following compound.
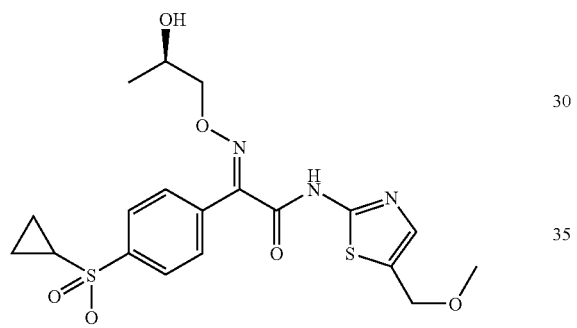
MS (m/z) APCI: 454 [M+H]+
Example 121
Corresponding starting compounds were treated in the similar manner as EXAMPLE 1-(4-1), (5) to give the following compounds.
| EXAMPLE No. | No | Structure | MS (m/z) |
|---|---|---|---|
| 121 | 1 | 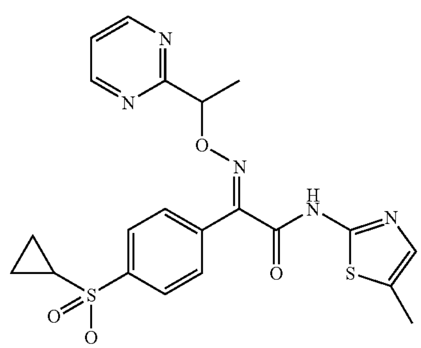 | 472 APCI [M + H]+ |

-continued

| EXAMPLE No. | No | Structure | MS (m/z) |
|---|---|---|---|
| 121 | 2 | 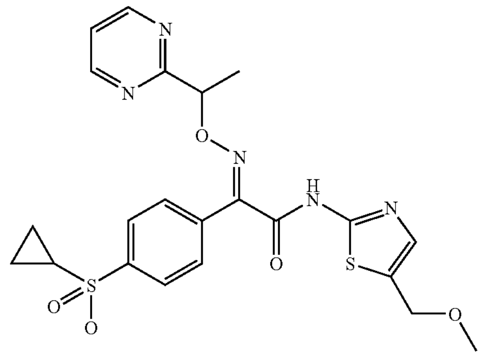 | 502 APCI [M + H]+ |

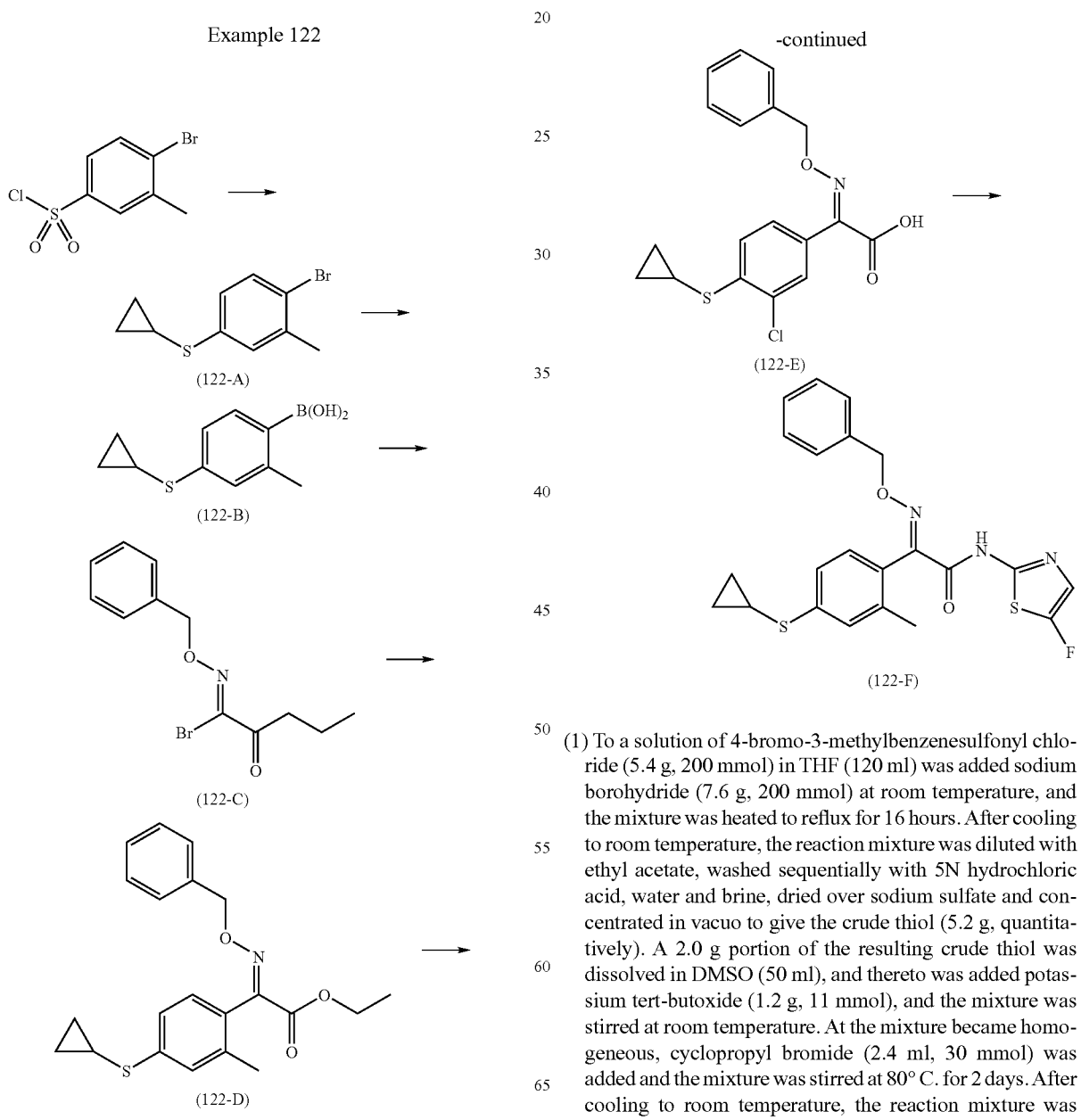

Example 122

(1) To a solution of 4-bromo-3-methylbenzenesulfonyl chloride (5.4 g, 200 mmol) in THF (120 ml) was added sodium borohydride (7.6 g, 200 mmol) at room temperature, and the mixture was heated to reflux for 16 hours. After cooling to room temperature, the reaction mixture was diluted with ethyl acetate, washed sequentially with 5N hydrochloric acid, water and brine, dried over sodium sulfate and concentrated in vacuo to give the crude thiol (5.2 g, quantitatively). A 2.0 g portion of the resulting crude thiol was dissolved in DMSO (50 ml), and thereto was added potassium tert-butoxide (1.2 g, 11 mmol), and the mixture was stirred at room temperature. At the mixture became homogeneous, cyclopropyl bromide (2.4 ml, 30 mmol) was added and the mixture was stirred at 80° C. for 2 days. After cooling to room temperature, the reaction mixture was poured into water and the mixture was extracted with ethyl acetate (200 ml) twice. The organic layers were combined, washed sequentially with water and brine, dried over sodium sulfate, concentrated in vacuo, and then the residue was purified by silica gel column chromatography (hexane) to give the compound (122-A) (155 mg, yield 8% in 2 steps) as an oil.

(2) To a solution of the above compound (150 mg, 0.62 mmol) in diethyl ether (15 ml) was added dropwise a 1.59 M solution (0.81 ml, 1.3 mmol) of tert-butyllithium in pentane at −70° C. over 4 minutes, and thereto was added trimethyl borate (0.076 ml, 0.68 mmol) after 10 minutes in one portion, and the mixture was warmed to 0° C. Thereto was added a saturated aqueous ammonium chloride solution, and the mixture was stirred at room temperature for 15 minutes, and then was extracted with ethyl acetate (20 ml). The organic layer was dried over sodium sulfate and concentrated in vacuo to give the crude boronic acid (122-B).

(3) The above crude boronic acid was suspended in 1,2-dimethoxyethane (3 ml), and thereto were added the compound (122-C) (114 mg, 0.40 mmol), which was synthesized by reacting a corresponding starting compound in the similar manner as EXAMPLE 91, a 1M aqueous sodium carbonate solution (1.2 ml, 1.2 mmol) and dichlorobis(triphenylphosphine)palladium (28 mg, 0.04 mmol). After stirring at 80° C. for 4 hours, the mixture was cooled to room temperature, poured into water and extracted with ethyl acetate (15 ml). The organic layer was washed with brine, dried over sodium sulfate and concentrated in vacuo. The resulting residue was purified by silica gel column chromatography (5% to 25% hexane-ethyl acetate) to give the compound (122-D) (30 mg, yield 20%) as an oil.
MS (m/z) APCI: 370 [M+H]$^+$ (4) The above compound was treated in the similar manner as EXAMPLE 1-(4-2-2) to give the compound (122-E).
MS (m/z) ESI: 681 [2M−H]$^-$ (5) The above compound and the corresponding starting compound were reacted in the similar manner as EXAMPLE 1-(5) to give the compound (122-F).
MS (m/z) APCI: 442 [M+H]$^+$ (6) The above compound was treated in the similar manner as EXAMPLE 84 to give the compound (122-G).
MS (m/z) APCI: 474 [M+H]$^+$ Example 123

Corresponding starting compounds were treated in a combination of the methods of EXAMPLE 1-(5), EXAMPLE 15, EXAMPLE 17 using the compound (77-D) to give the following compounds.

| EXAMPLE No. | No | Structure | MS (m/z) |
|---|---|---|---|
| 123 | 1 | | 494 APCI [M + H]$^+$ |
| 123 | 2 | | 604 APCI [M + H]$^+$ |

| EXAMPLE No. | No | Structure | MS (m/z) |
|---|---|---|---|
| 123 | 3 | 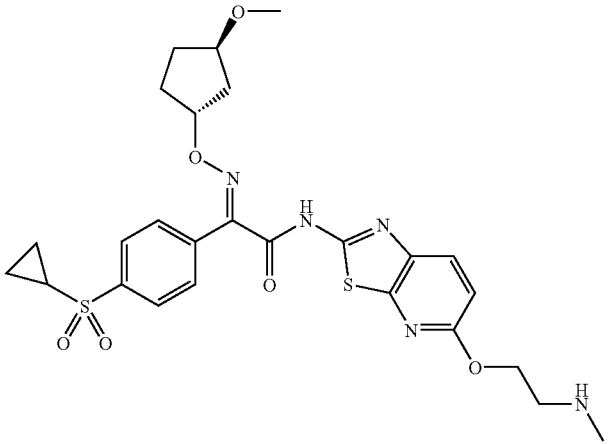 | 574 APCI [M + H]+ |
| 123 | 4 | 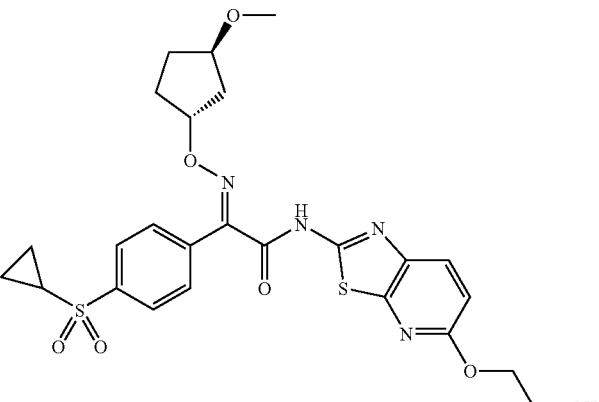 | 561 APCI [M + H]+ |

Example 124

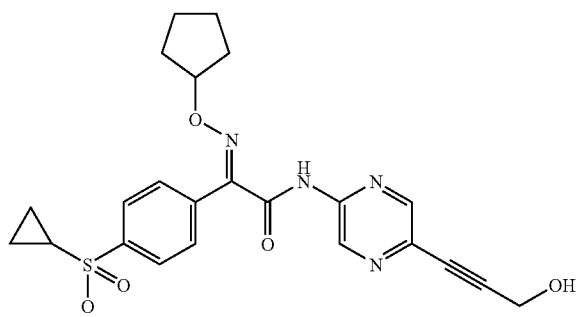

To a suspension of the compound of EXAMPLE 102-(24) (80 mg, 0.162 mmol), propargyl alcohol (0.047 ml, 0.81 mmol), copper (I) iodide (6.2 mg, 0.03 mmol) and triethylamine (0.5 ml, 3.6 mmol) in THF (2 ml) was added dichlorobis(triphenylphosphine)palladium (22.7 mg, 0.03 mmol) at room temperature under argon, and the mixture was heated to reflux for 8 hours. After cooling to room temperature, the mixture was concentrated in vacuo and the resulting residue was purified by silica gel chromatography (50 to 100% ethyl acetate-hexane) to give the above compound (25 mg, yield 33%).

MS (m/z) APCI: 469 [M+H]+

A corresponding starting compound was treated in the similar manner as the above-mentioned to give the following compound.

| EXAMPLE No. | No | Structure | MS (m/z) |
|---|---|---|---|
| 124 | 1 | 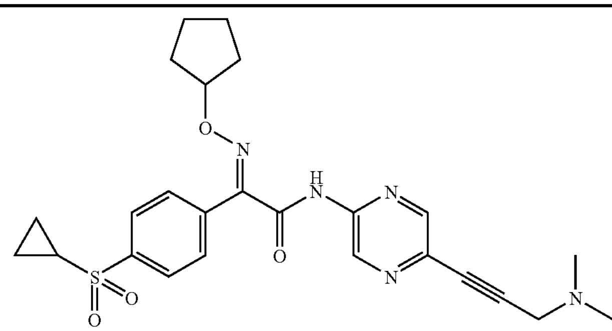 | 496 APCI [M + H]+ |

Example 125

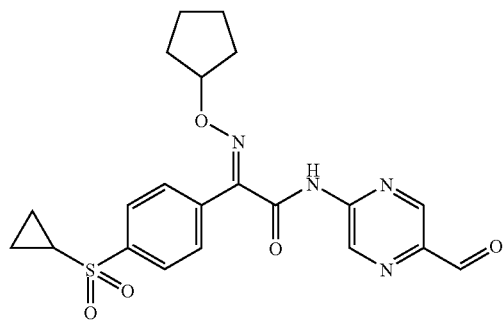

A corresponding starting compound was treated in the similar manner as EXAMPLE 58 to give the above compound.

MS (m/z) APCI: 443 [M+H]+

Example 126

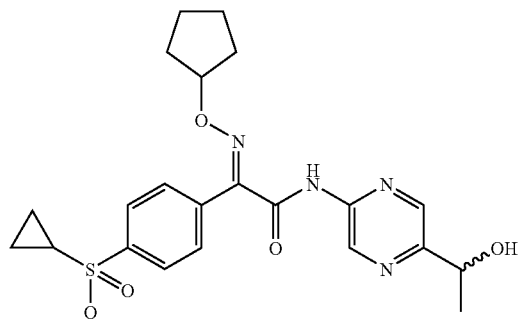

A corresponding starting compound was treated in the similar manner as EXAMPLE 29 to give the above compound.

MS (m/z) APCI: 459 [M+H]+

Example 127

A corresponding starting compound was treated in the similar manner as EXAMPLE 26 to give the above compound.

MS (m/z) APCI: 445 [M+H]+

Example 128

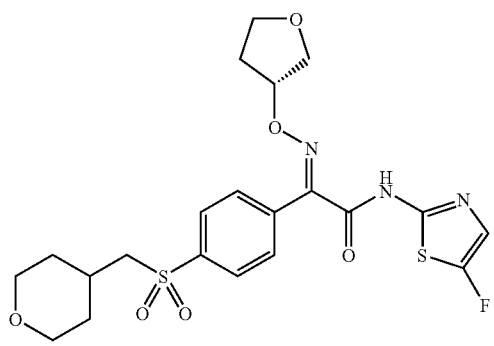

A corresponding starting compound was treated in the similar manner as EXAMPLE 83 and 84 to give the above compound.

MS (m/z) APCI: 498 [M+H]+

Example 129

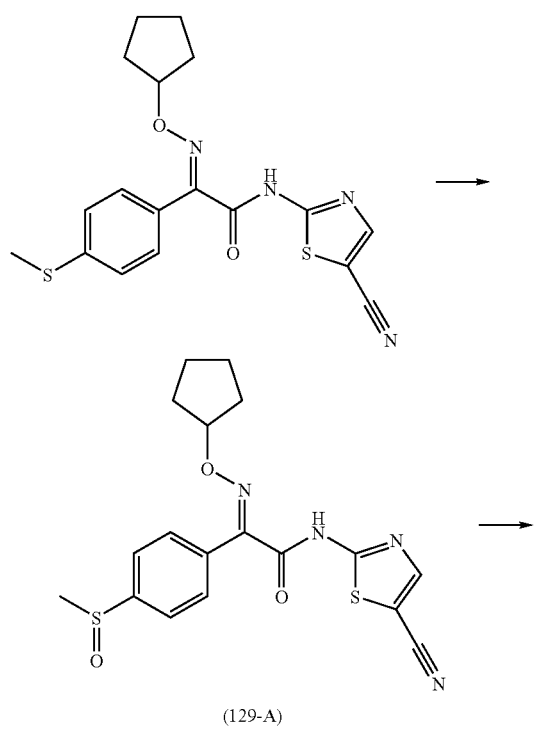

(129-A)

(129-B)

(1) The compound of EXAMPLE 97-(4) was reacted in the similar manner as EXAMPLE 83-(1) to give the compound (129-A).

MS (m/z) APCI: 403 [M+H]+

(2) To a solution of the above compound (100 mg, 0.25 mmol) in DMF (2 ml) were added sequentially ammonium chloride (134 mg, 2.5 mmol) and sodium azide (162 mg, 2.5 mmol), and the mixture was stirred at 115° C. for 3 hours. After cooling to room temperature, the mixture was acidified with 10% hydrochloric acid, diluted with ethyl acetate, washed sequentially with water and brine, dried over magnesium sulfate and concentrated in vacuo to give the compound (129-B).

MS (m/z) ESI: 444 [M−H]−

Example 130

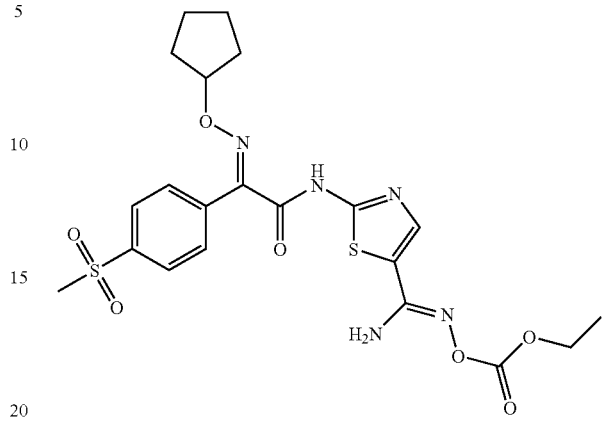

To a solution of the compound of EXAMPLE (134) (100 mg, 0.22 mml) in pyridine (5 ml) was added ethyl chlorocarbonate (0.023 ml, 0.24 mmol), and the mixture was stirred at 120° C. for 3 hours. After cooling to room temperature, the reaction mixture was concentrated in vacuo and the residue was purified by silica gel chromatography (0 to 5% methanol-chloroform) to give the above compound (44 mg, yield 38%).

MS (m/z) ESI: 522 [M−H]−

Example 131

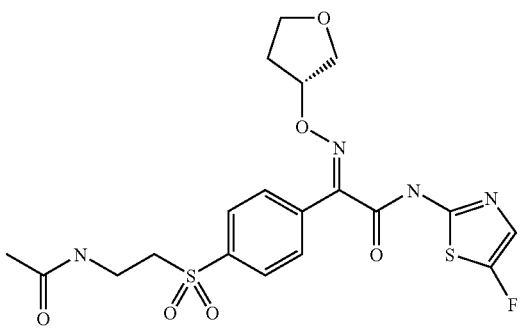

To a solution of the compound of EXAMPLE 86 (58 mg, 0.11 mmol) and diisopropylethylamine (0.098 ml, 0.57 mmol) in chloroform (2 ml) was added acetic anhydride (0.021 ml, 0.22 mmol) under ice-cooling, and the mixture was stirred at room temperature overnight. To the reaction mixture was added a saturated aqueous sodium bicarbonate solution, and the mixture was extrated with chloroform. The organic layer was washed sequentially with water and brine, dried over sodium sulfate and concentrated in vacuo. The resulting residue was purified by silica gel chromatography (0 to 5% methanol-chloroform) to give the above compound (42 mg, yield 77%).

MS (m/z) APCI: 485 [M+H]+

Example 132

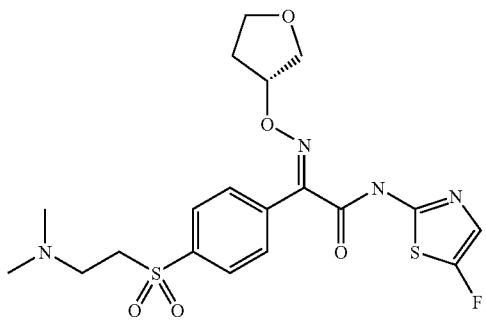

Example 133

To a mixture of the compound of EXAMPLES 86 (59 mg, 0.11 mmol) and diisopropylethylamine (0.060 ml, 0.0.34 mmol) in a 38% aqueous formalin solution (1 ml) and chloroform (2 ml) was added sodium triacetoxyborohydride (73 mg, 0.34 mmol) under ice-cooling, and the mixture was stirred at the same temperature for 1 hour and at room temperature for 3 hours. Then, to the reaction mixture was added a saturated aqueous sodium bicarbonate solution, and the mixture was extracted with chloroform. The organic layer was washed sequentially with water and brine, dried over sodium sulfate and concentrated in vacuo. The resulting residue was purified by NH-silica gel chromatography (0 to 15% methanol-ethyl acetate) to give the above compound (29 mg, yield 54%).

MS (m/z) APCI: 471 [M+H]$^+$

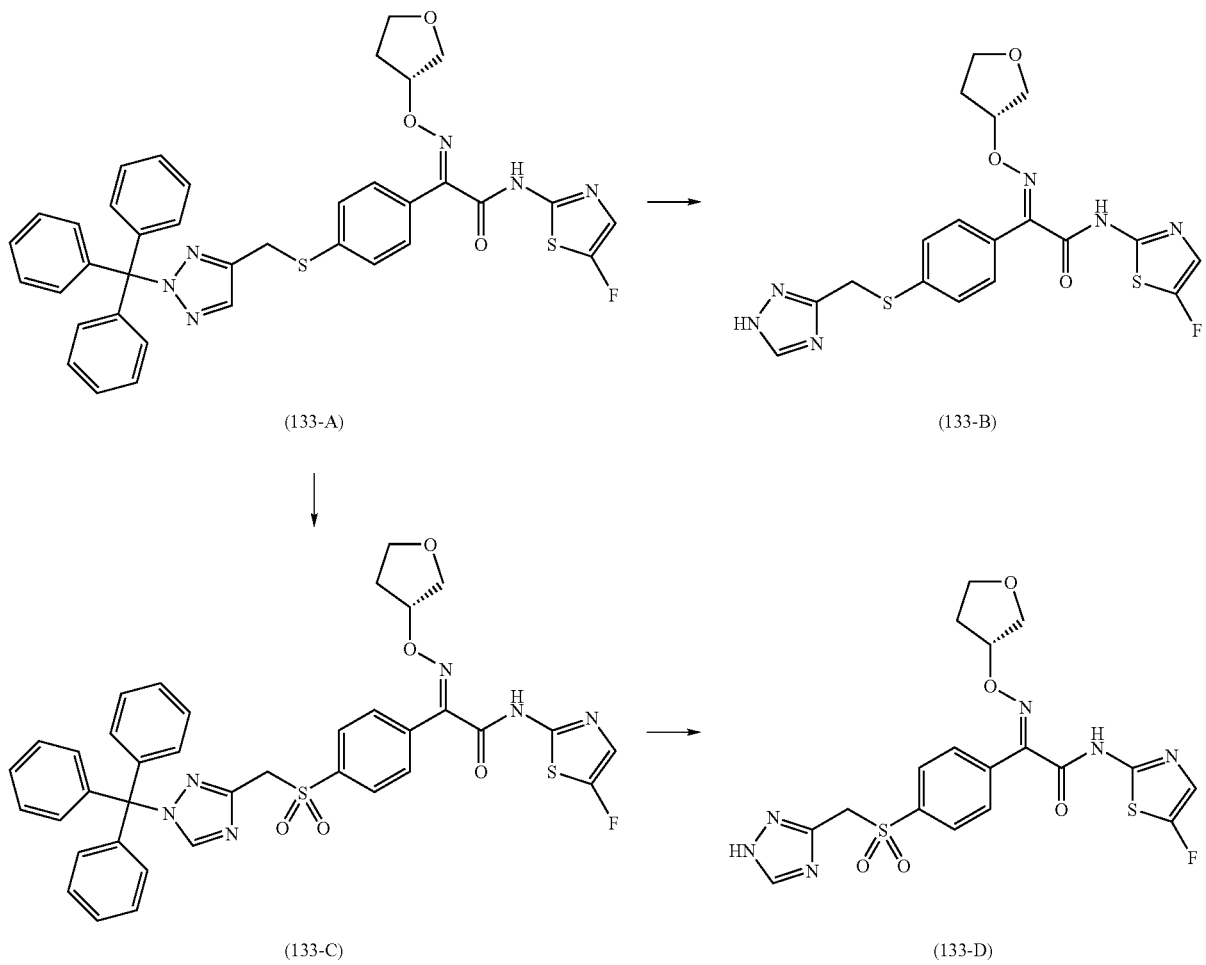

(1) The compound (83-E) was treated in the similar manner as EXAMPLE 83 to give the compound (133-A).
(2) The above compound was treated in the similar manner as EXAMPLE 115-(7) to give the compound (133-B).
   MS (m/z) APCI: 449 [M+H]$^+$
(3) The compound (133-A) was treated in the similar manner as EXAMPLE 84 to give the compound (133-C).
(4) The above compound was treated in the similar manner as the above (2) to give the compound (133-D).
   MS (m/z) APCI: 481 [M+H]$^+$

Example 134

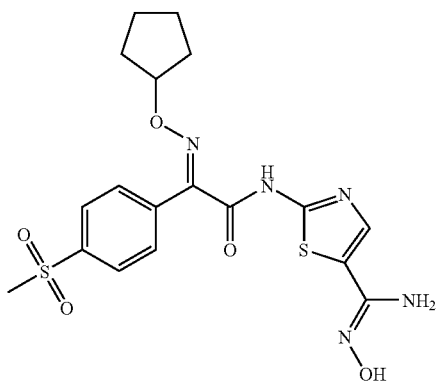

The compound of EXAMPLE 91-(4) was treated in the similar manner as EXAMPLE 30 to give the above compound.
MS (m/z) APCI: 452 [M+H]+

Example 135

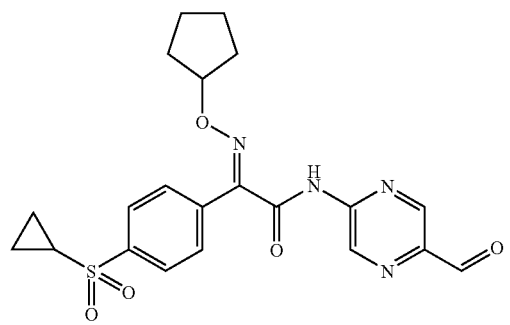

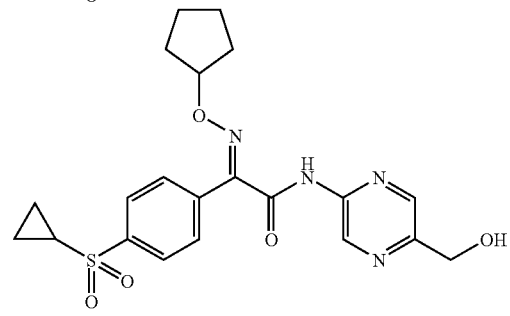

(135-A)

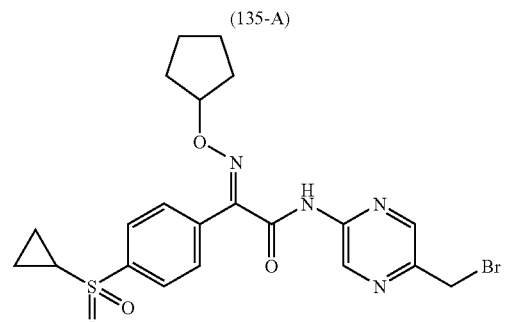

(135-B)

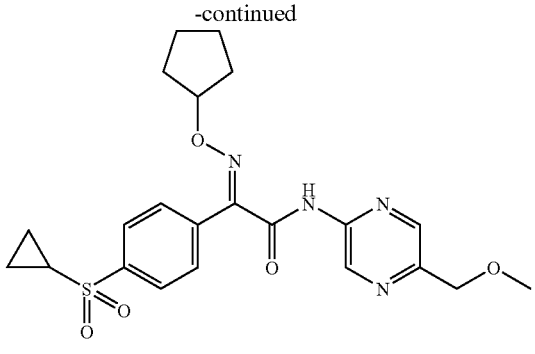

(135-C)

(1) The compound of EXAMPLE 125 was treated in the similar manner as EXAMPLE 26 to give the compound (135-A).
MS (m/z) APCI: 445 [M+H]+

(2) To a solution of the compound obtained in the above (1) (78 mg, 0.18 mmol) and triphenylphosphine (92 mg, 0.35 mmol) in THF (2 ml) was added carbon tetrabromide (116 mg, 0.35 mmol) at room temperature, and the mixture was stirred at the same temperature for 6 hours and concentrated in vacuo. The residue was purified by silica gel column chromatography (30 to 80% ethyl acetate-hexane) to give the compound (135-B) (73 mg, yield 80%).
MS (m/z) APCI: 507/509 [M+H]+

(3) To a solution of the compound obtained in the above (2) (70 mg, 0.14 mmol) in methanol (3 ml) was added silver (II) oxide (34 mg, 0.28 mmol) at room temperature. The mixture was stirred at the same temperature for 16 hours and filtered. The filtrate was concentrated in vacuo, and the resulting residue was purified by silica gel column chromatography (30 to 100% ethyl acetate-hexane) to give the compound (135-C) (10 mg, yield 16%).
MS (m/z) APCI: 459 [M+H]+

Example 136

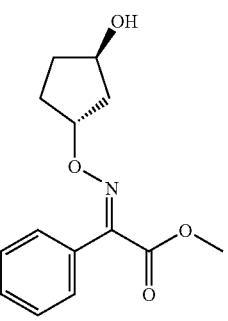

(77-B)

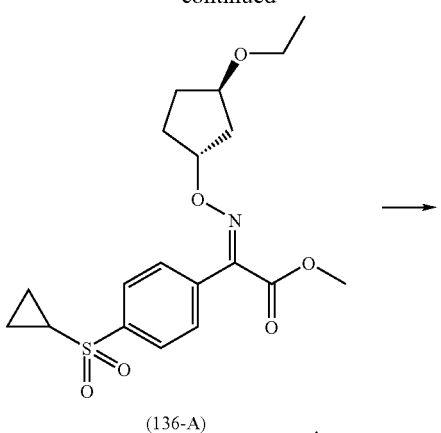

(136-A)

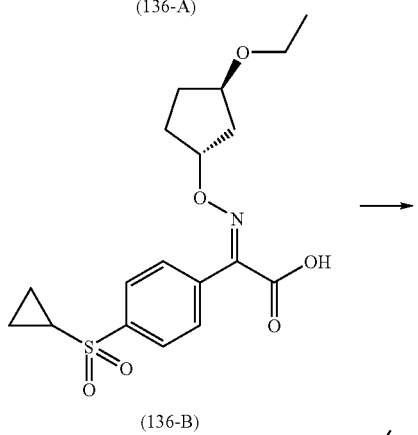

(136-B)

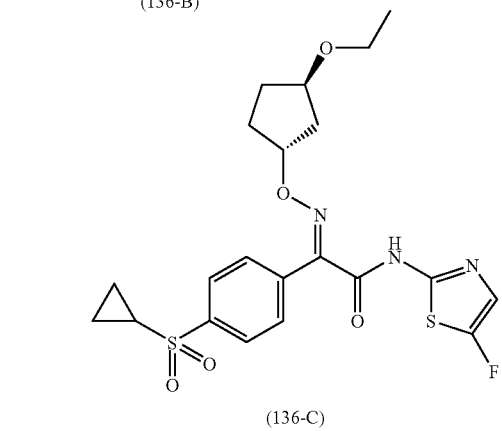

(136-C)

(1) A suspension of the compound (77-B) of EXAMPLE 77 (1.95 g, 5.31 mmol) and molecular sieves (4 Å, powder) (1.95 g) in 1,2-dichloroethane (38 ml) was ice-cooled and thereto were added sequentially 1,8-bis(dimethylamino)naphthalene (3.35 g, 15.6 mmol) and triethyloxonium tetrafluoroborate (2.97 g, 15.6 mmol). The mixture was stirred at room temperature for 18 hours and filtered. To the filtrate was added ethyl acetate. The mixture was washed with brine, dried over sodium sulfate and then concentrated in vacuo, and the residue was purified by silica gel column chromatography (33 to 50% ethyl acetate-hexane) to give the compound (136-A) (1.54 g, yield 73%).
MS (m/z) APCI: 396 [M+H]$^+$ (2) The compound obtained in the above (1) was treated in the similar manner as EXAMPLE 1-(4-2-2) to give the compound (136-B).
MS (m/z) APCI: 783 [2M−2H+Na]$^-$ (3) The compound obtained in the above (2) was treated in the similar manner as EXAMPLE 1-(5) to give the compound (136-C).
MS (m/z) APCI: 482 [M+H]$^+$ Example 137

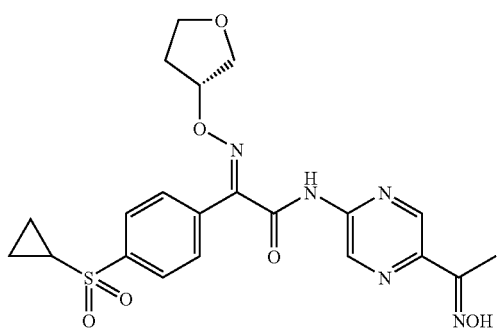

To a solution of the compound of EXAMPLE 60 (49 mg, 0.11 mmol) and pyridine (0.50 ml) in methanol (1.0 ml) was added hydroxylamine hydrochloride (15 mg, 0.21 mmol), and the mixture was stirred at room temperature for 16 hours. To the reaction mixture was added chloroform, and the mixture was washed with water and brine, dried over sodium sulfate and concentrated in vacuo. The residue was purified by silica gel column chromatography (0 to 5% methanolchloroform) to give the titled compound (52 mg, quantitatively).
MS (m/z) APCI: 474 [M+H]$^+$ Example 138

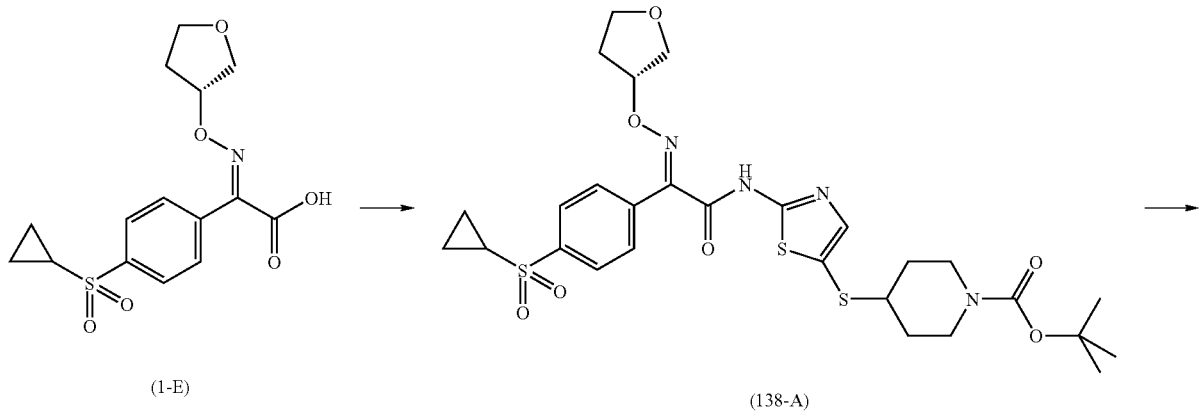

(1-E)          (138-A)

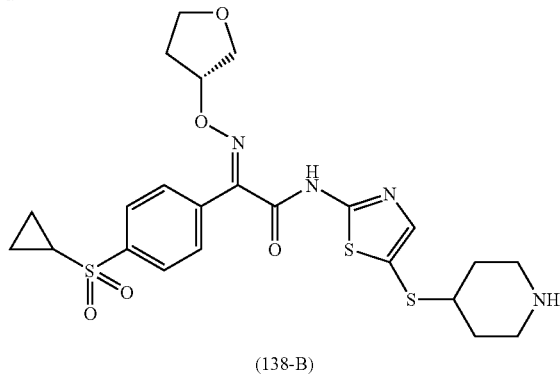

(138-B)

(1) The compound (1-E) of EXAMPLE 1 was treated in the similar manner as EXAMPLE 1-(5) to give the compound (138-A).

MS (m/z) APCI: 637 [M+H]+

(2) A solution of the compound obtained in the above (1) (3.20 g, 5.03 mmol) in chloroform-trifluoroacetic acid (1:1) (80 ml) was stirred at room temperature for 2 days. The reaction mixture was concentrated in vacuo and the residue was chased with toluene, and then to the residue was added a saturated aqueous sodium bicarbonate solution. The mixture was extracted with chloroform. The extract was dried over sodium sulfate and concentrated in vacuo. The residue was then purified by silica gel column chromatography (methanol-chloroform-ammonia water 200:10:1 to 100:10:1) to give the compound (138-B) (2.06 g, yield 77%).

MS (m/z) APCI: 537 [M+H]+

Example 139

Corresponding starting compounds were treated in the similar manner as any of the above EXAMPLEs to give the following compounds.

| EXAMPLE No. | No. | Structure | MS (m/z) |
|---|---|---|---|
| 139 | 1 | | 582 APCI [M + H]+ |
| 139 | 2 | | 568 APCI [M + H]+ |

-continued

| EXAMPLE No. | No. | Structure | MS (m/z) |
|---|---|---|---|
| 139 | 3 | | 430 APCI [M + H]+ |
| 139 | 4 | | 457 APCI [M + H]+ |
| 139 | 5 | | 462 ESI [M − H]− |
| 139 | 6 | | 522 ESI [M − H]− |

|EXAMPLE No.|No.|Structure|MS (m/z)|
|---|---|---|---|
| 139 | 7 | 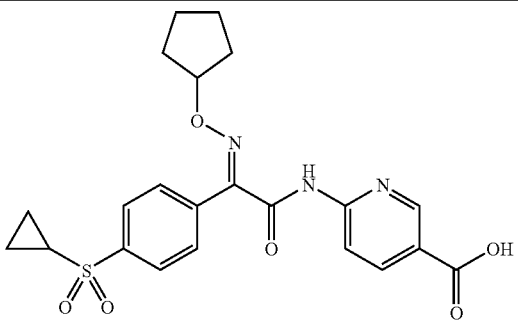 | 456 ESI [M − H]− |
| 139 | 8 | 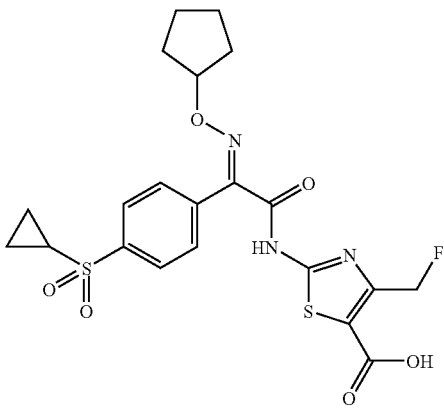 | 494 ESI [M − H]− |
| 139 | 9 | 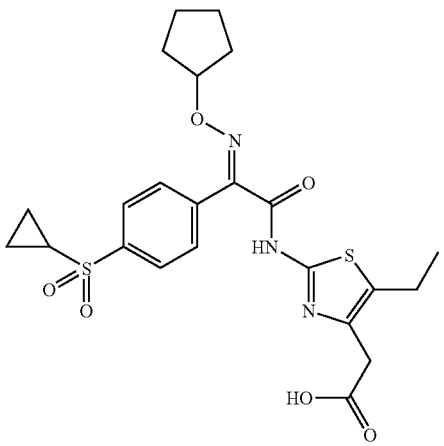 | 504 ESI [M − H]− |
| 139 | 10 | 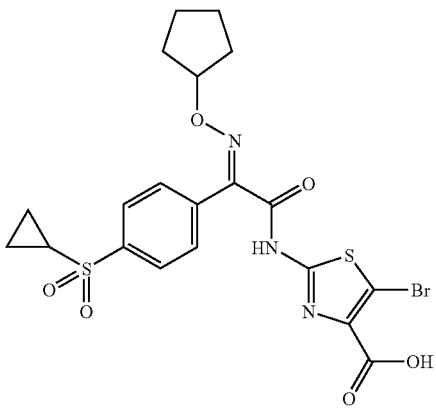 | 540/542 ESI [M − H]− |

-continued

| EXAMPLE No. | No. | Structure | MS (m/z) |
|---|---|---|---|
| 139 | 11 | | 476 ESI [M − H]− |
| 139 | 12 | | 476 ESI [M − H]− |
| 139 | 13 | | ESI 512 [M − H]− |
| 139 | 14 | | 530 ESI [M − H]− |

-continued

| EXAMPLE No. | No. | Structure | MS (m/z) |
|---|---|---|---|
| 139 | 15 | | 506 APCI [M + H]+ |
| 139 | 16 | | 506 APCI [M + H]+ |
| 139 | 17 | | 556/558 APCI [M + H]+ |
| 139 | 18 | | 506 APCI [M + H]+ |

-continued
| EXAMPLE No. | No. | Structure | MS (m/z) |
|---|---|---|---|
| 139 | 19 | 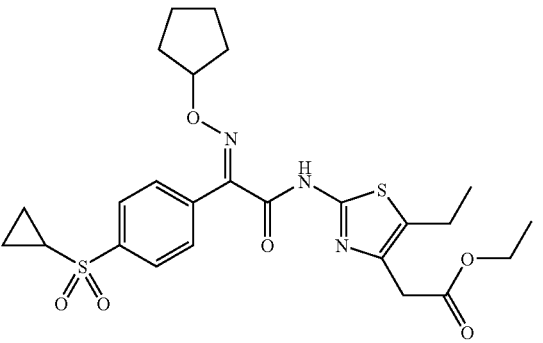 | 534 APCI [M + H]+ |
| 139 | 20 | 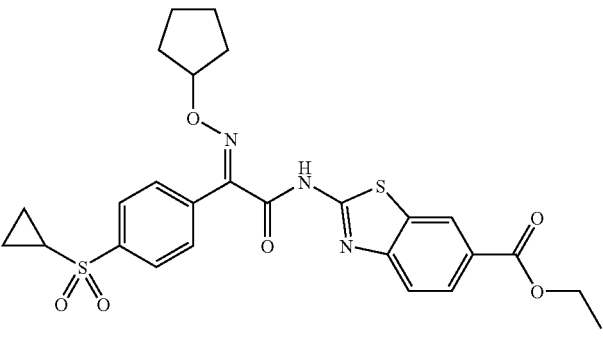 | 542 APCI [M + H]+ |
| 139 | 21 | 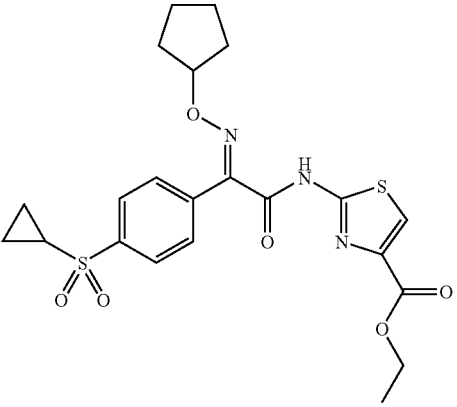 | 492 APCI [M + H]+ |
| 139 | 22 | 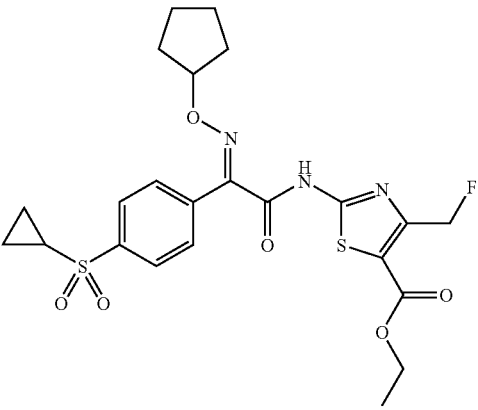 | 524 APCI [M + H]+ |

| EXAMPLE No. | No. | Structure | MS (m/z) |
|---|---|---|---|
| 139 | 23 | | 459 APCI [M + H]+ |
| 139 | 24 | | 502 ESI [M − H]− |
| 139 | 25 | | 561 APCI [M + H]+ |
| 139 | 26 | | 601 APCI [M + H]+ |

| EXAMPLE No. | No. | Structure | MS (m/z) |
|---|---|---|---|
| 139 | 27 | 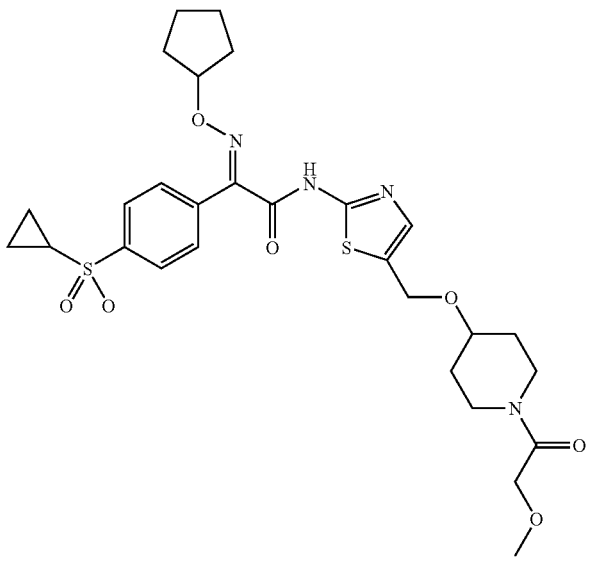 | 605 APCI [M + H]+ |
| 139 | 28 | 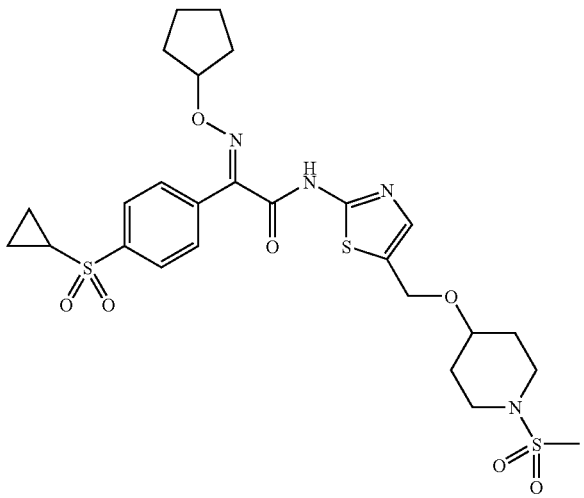 | 611 APCI [M + H]+ |
| 139 | 29 | 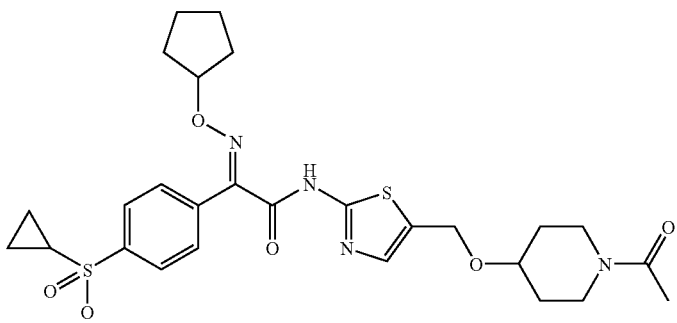 | 575 APCI [M + H]+ |

-continued

| EXAMPLE No. | No. | Structure | MS (m/z) |
|---|---|---|---|
| 139 | 30 | | 475 APCI [M + H]+ |
| 139 | 31 | | 558 APCI [M + H]+ |
| 139 | 32 | | 572 APCI [M + H]+ |
| 139 | 33 | | 482 APCI [M + H]+ |

| EXAMPLE No. | No. | Structure | MS (m/z) |
|---|---|---|---|
| 139 | 34 | 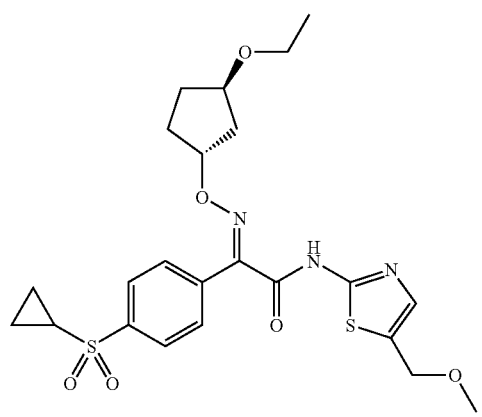 | 508 APCI [M + H]+ |
| 139 | 35 | 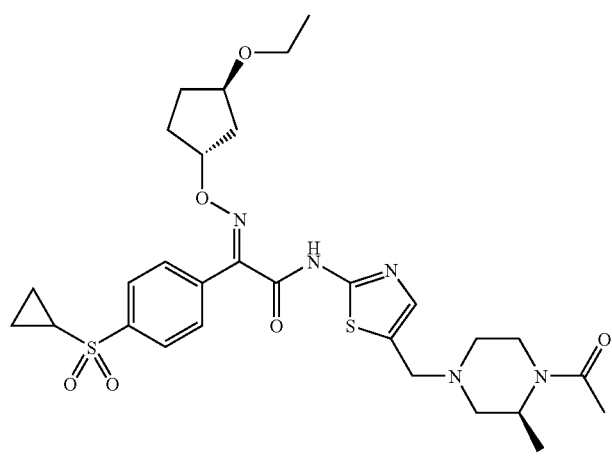 | 618 APCI [M + H]+ |
| 139 | 36 | 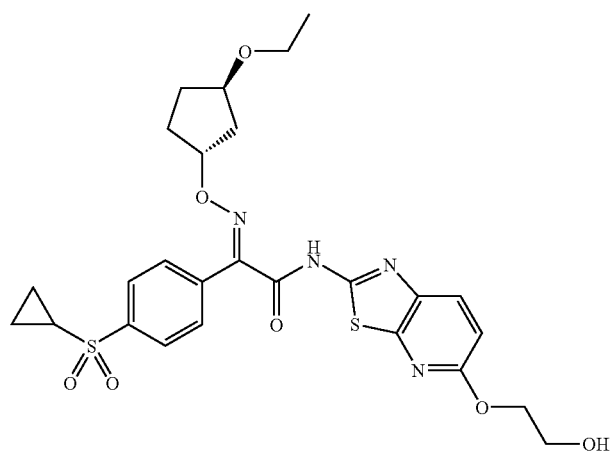 | 575 APCI [M + H]+ |

| EXAMPLE No. | No. | Structure | MS (m/z) |
|---|---|---|---|
| 139 | 37 | 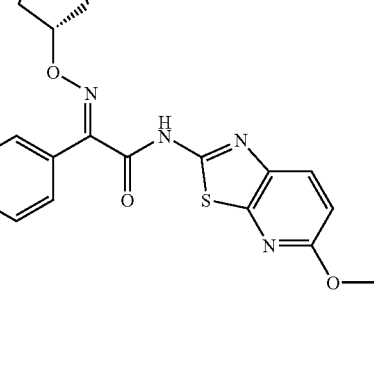 | 588 APCI [M + H]+ |
| 139 | 38 | 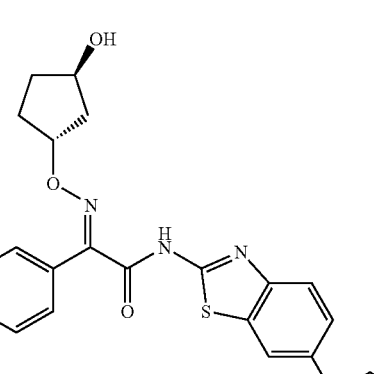 | 559 APCI [M + H]+ |
| 139 | 39 | 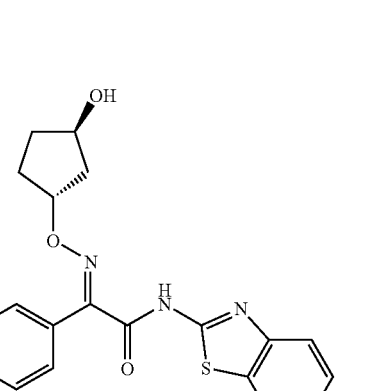 | 546 APCI [M + H]+ |

| EXAMPLE No. | No. | Structure | MS (m/z) |
|---|---|---|---|
| 139 | 40 | 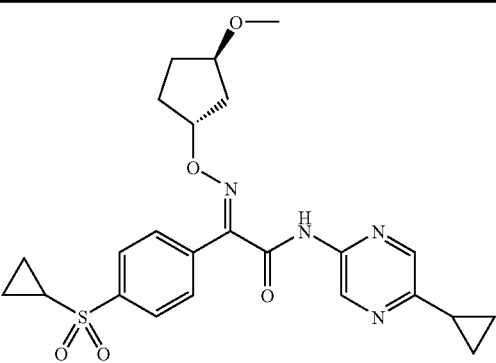 | 485 APCI [M + H]+ |
| 139 | 41 | 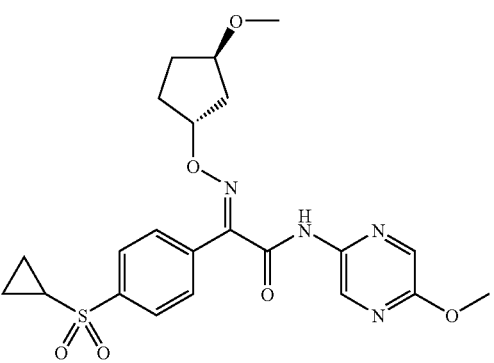 | 475 APCI [M + H]+ |
| 139 | 42 | 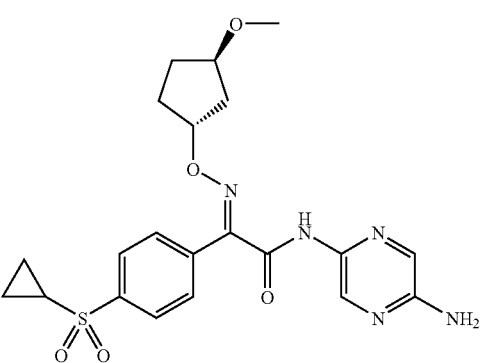 | 460 APCI [M + H]+ |
| 139 | 43 | 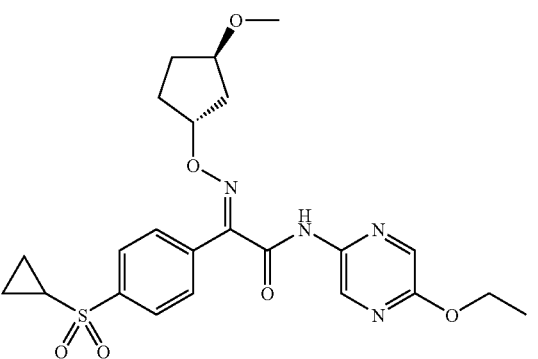 | 489 APCI [M + H]+ |

-continued

| EXAMPLE No. | No. | Structure | MS (m/z) |
|---|---|---|---|
| 139 | 44 | | 474 APCI [M + H]+ |
| 139 | 45 | | 516 APCI [M + H]+ |
| 139 | 46 | | 528 APCI [M + H]+ |
| 139 | 47 | | 602 APCI [M + H]+ |

| EXAMPLE No. | No. | Structure | MS (m/z) |
|---|---|---|---|
| 139 | 48 | | 588 APCI [M + H]+ |
| 139 | 49 | | 450 APCI [M + H]+ |
| 139 | 50 | | 570 APCI [M + H]+ |
| 139 | 51 | | 498 APCI [M + H]+ |

| EXAMPLE No. | No. | Structure | MS (m/z) |
|---|---|---|---|
| 139 | 52 | 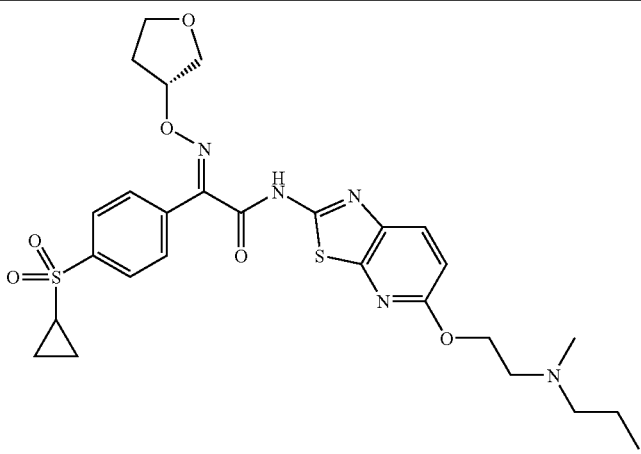 | 588 APCI [M + H]+ |
| 139 | 53 | 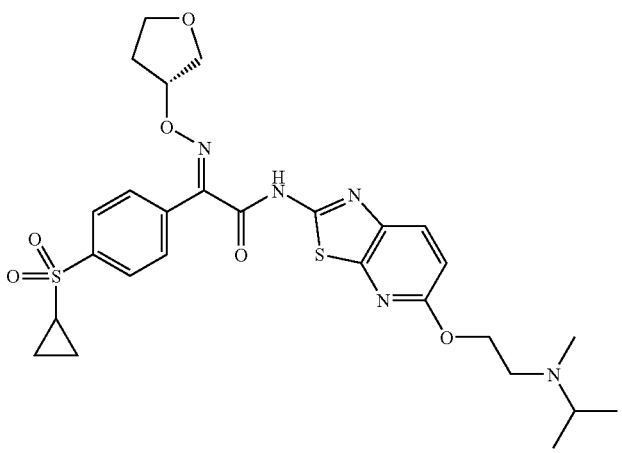 | 588 APCI [M + H]+ |
| 139 | 54 | 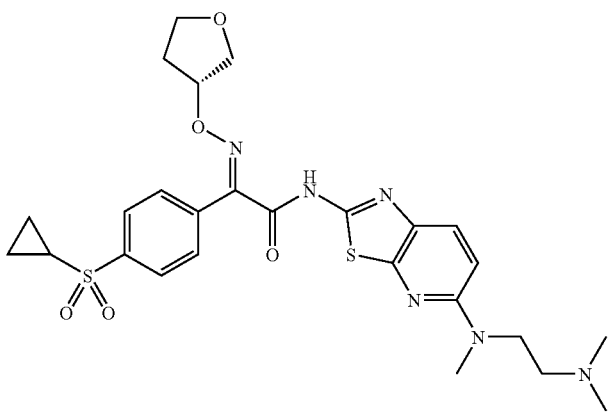 | 573 APCI [M + H]+ |

| EXAMPLE No. | No. | Structure | MS (m/z) |
|---|---|---|---|
| 139 | 55 | | 474 APCI [M + H]+ |
| 139 | 56 | | 436 APCI [M + H]+ |
| 139 | 57 | | 478 APCI [M + H]+ |
| 139 | 58 | | 586 APCI [M + H]+ |

| EXAMPLE No. | No. | Structure | MS (m/z) |
|---|---|---|---|
| 139 | 59 | 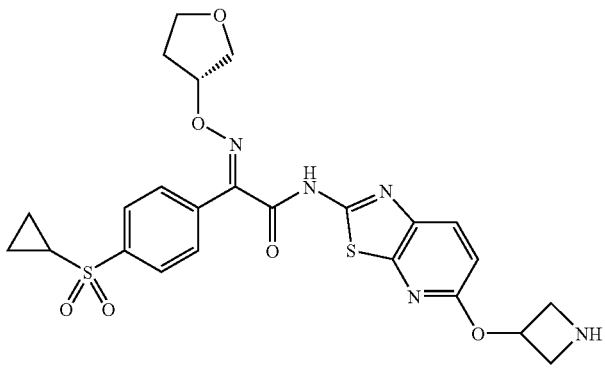 | 544 APCI [M + H]+ |
| 139 | 60 | 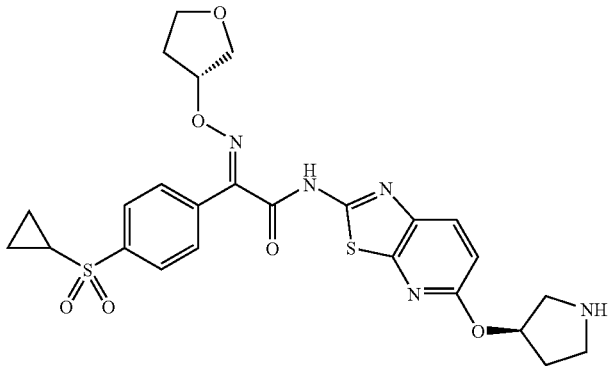 | 558 APCI [M + H]+ |
| 139 | 61 | 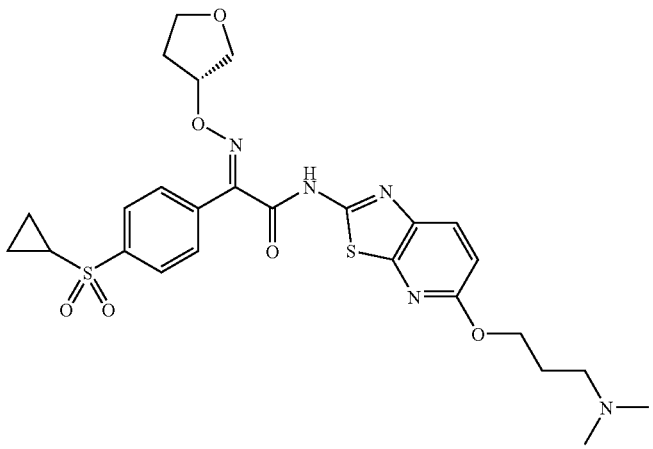 | 574 APCI [M + H]+ |
| 139 | 62 | 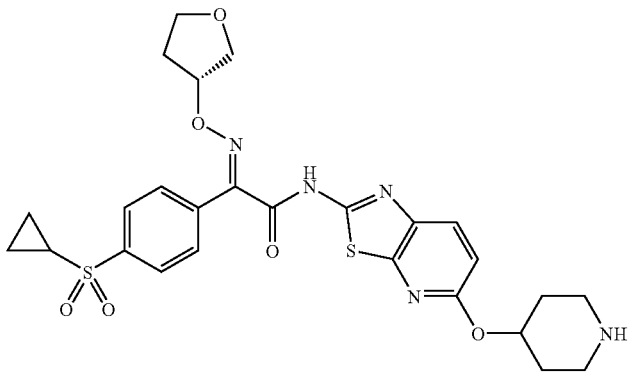 | 572 APCI [M + H]+ |

-continued
| EXAMPLE No. | No. | Structure | MS (m/z) |
|---|---|---|---|
| 139 | 63 | 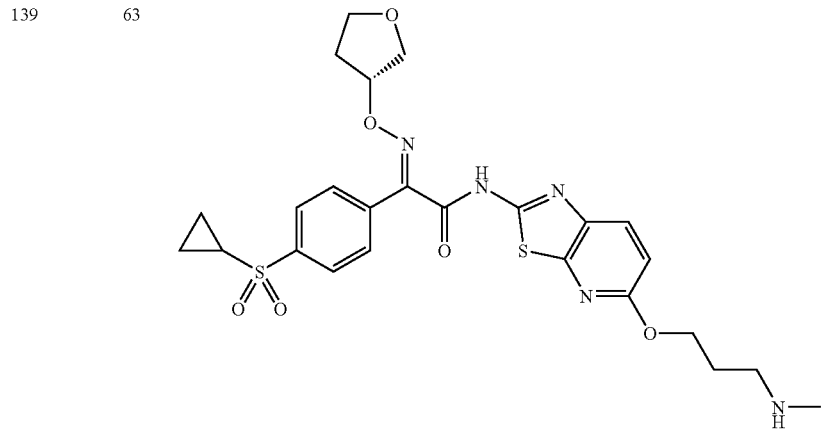 | 560 APCI [M + H]+ |
| 139 | 64 | 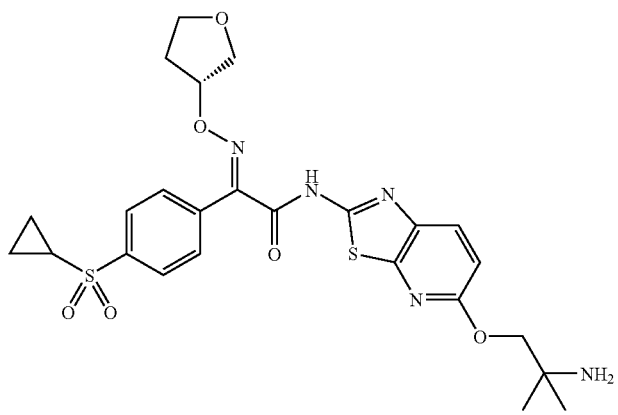 | 560 APCI [M + H]+ |
| 139 | 65 | 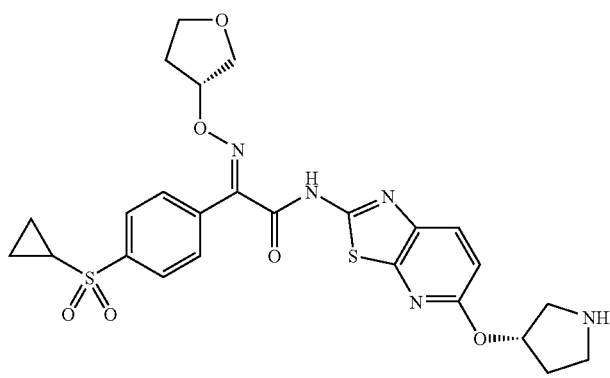 | 558 APCI [M + H]+ |

-continued
| EXAMPLE No. | No. | Structure | MS (m/z) |
|---|---|---|---|
| 139 | 66 | 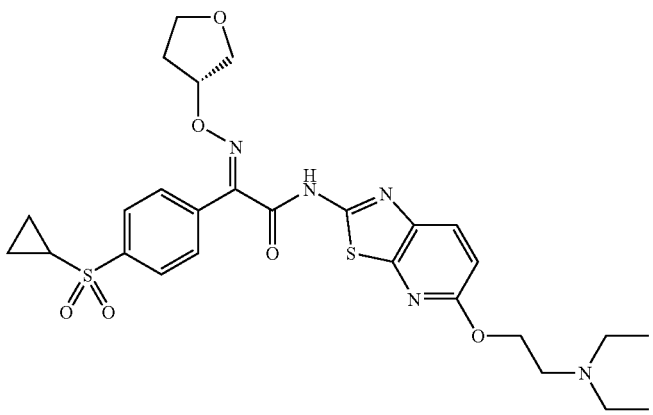 | 588 APCI [M + H]+ |
| 139 | 67 | 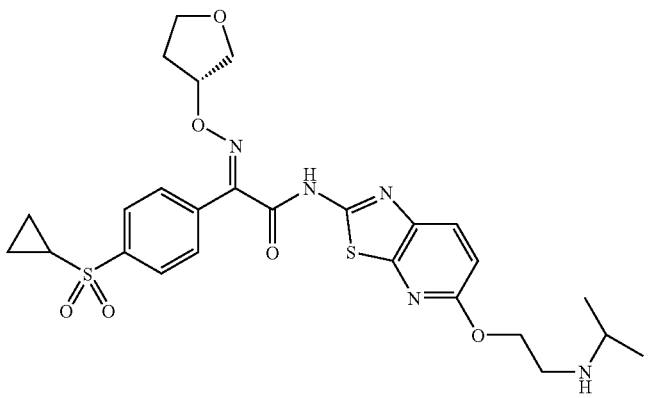 | 574 APCI [M + H]+ |
| 139 | 68 | 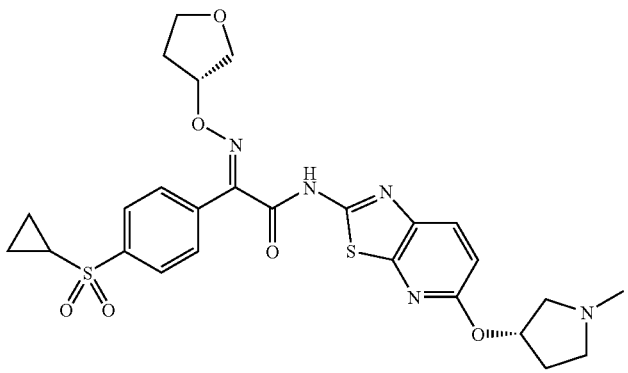 | 572 APCI [M + H]+ |
| 139 | 69 | 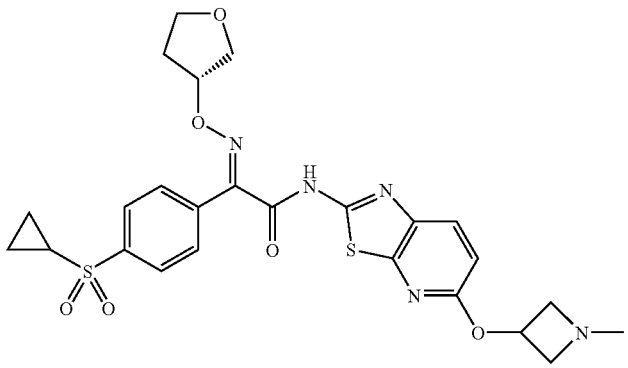 | 558 APCI [M + H]+ |

-continued
| EXAMPLE No. | No. | Structure | MS (m/z) |
|---|---|---|---|
| 139 | 70 | 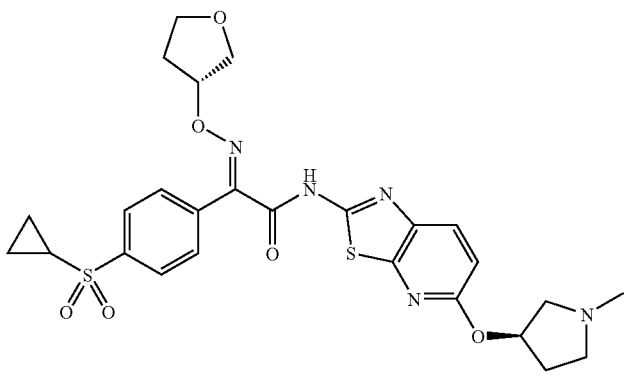 | 572 APCI [M + H]+ |
| 139 | 71 | 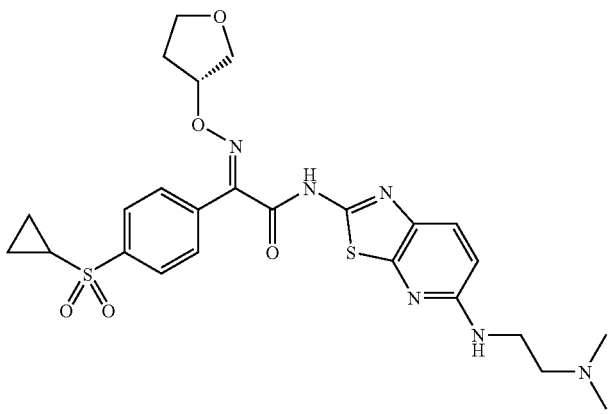 | 559 APCI [M + H]+ |
| 139 | 72 | 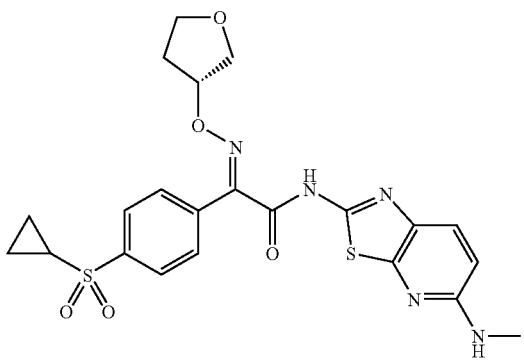 | 502 APCI [M + H]+ |
| 139 | 73 | 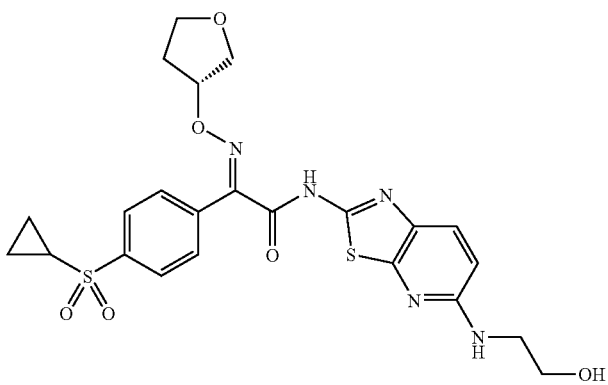 | 532 APCI [M + H]+ |

-continued
| EXAMPLE No. | No. | Structure | MS (m/z) |
|---|---|---|---|
| 139 | 74 | 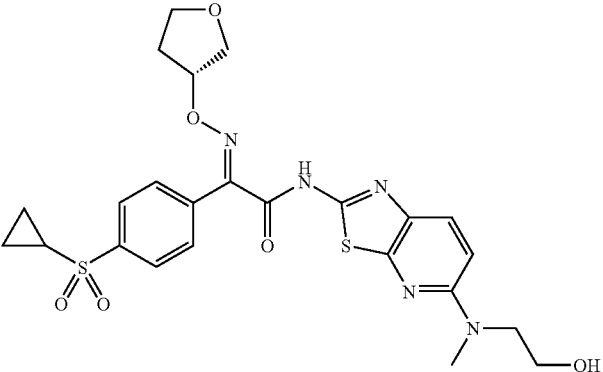 | 546 APCI [M + H]+ |
| 139 | 75 | 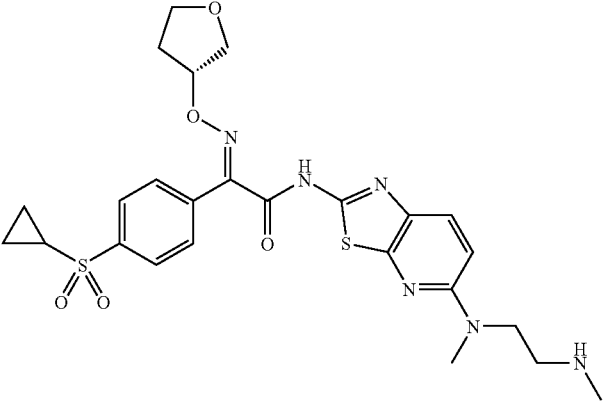 | 559 APCI [M + H]+ |
| 139 | 76 | 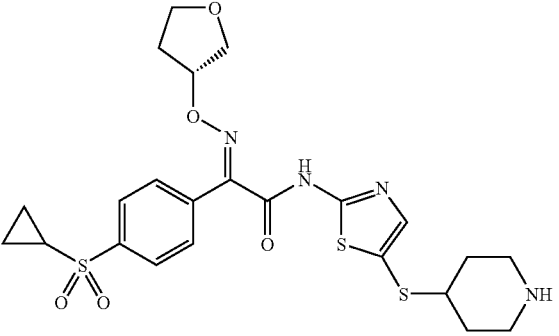 | APCI 537 [M + H]+ |
| 139 | 77 | 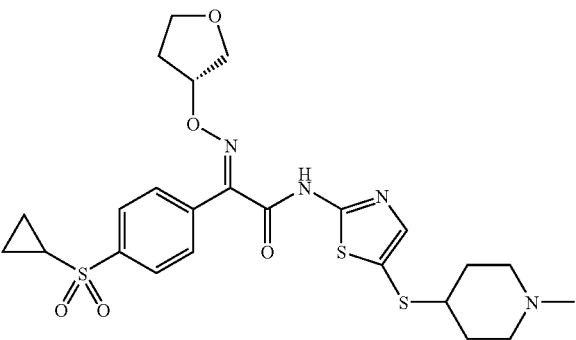 | APCI 551 [M + H]+ |

-continued
| EXAMPLE No. | No. | Structure | MS (m/z) |
|---|---|---|---|
| 139 | 78 | 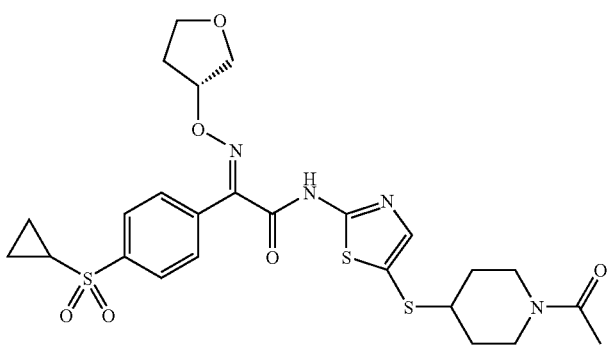 | APCI 579 [M + H]+ |
| 139 | 79 | 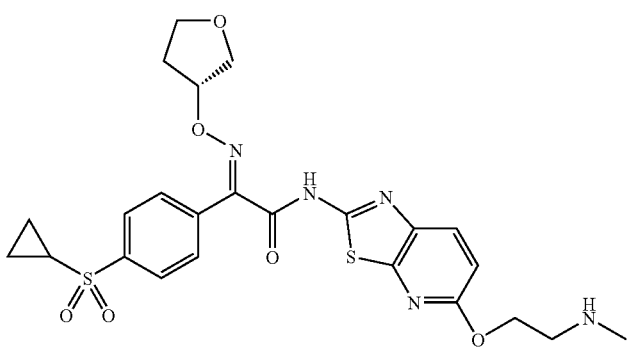 | 545 [M + H]+ |
| 139 | 80 | 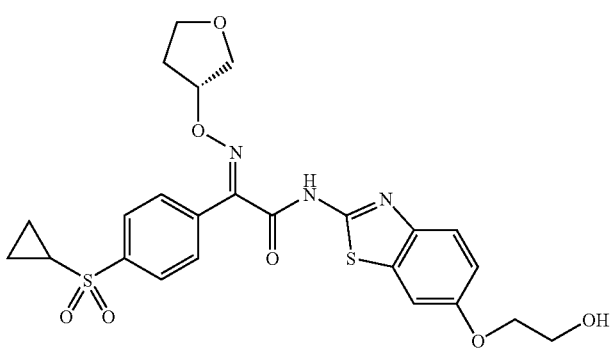 | 532 [M + H]+ |
| 139 | 81 | 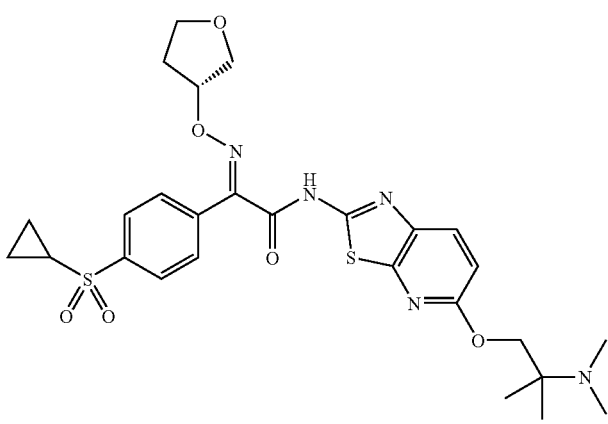 | 588 [M + H]+ |

-continued
| EXAMPLE No. | No. | Structure | MS (m/z) |
|---|---|---|---|
| 139 | 82 | 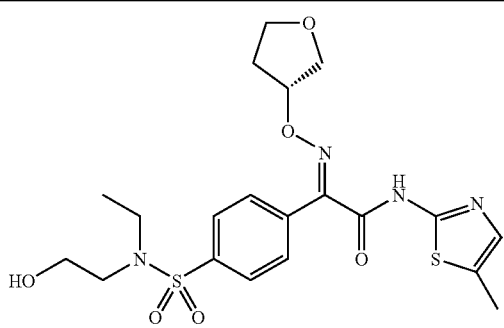 | 483 APCI [M + H]+ |
| 139 | 83 | 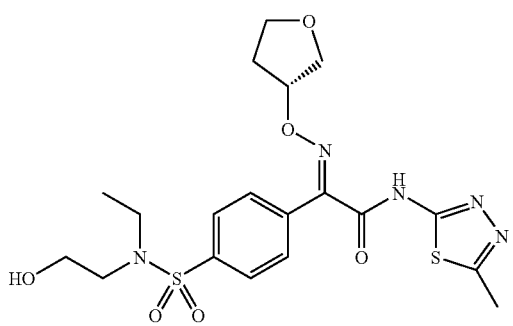 | 484 APCI [M + H]+ |
| 139 | 84 | 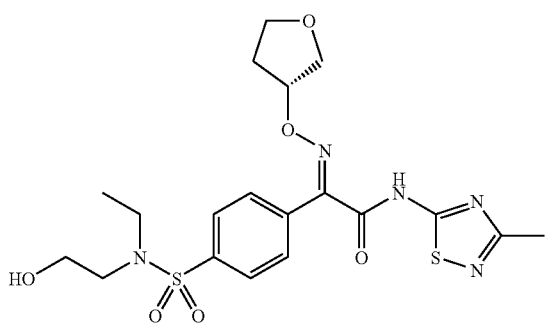 | 484 APCI [M + H]+ |
| 139 | 85 | 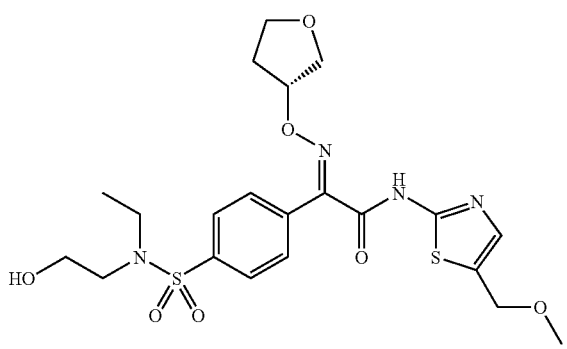 | 513 APCI [M + H]+ |

-continued

| EXAMPLE No. | No. | Structure | MS (m/z) |
|---|---|---|---|
| 139 | 86 | | 623 APCI [M + H]+ |
| 139 | 87 | | 550 APCI [M + H]+ |
| 139 | 88 | | 464 APCI [M + H]+ |
| 139 | 89 | | 514 APCI [M + H]+ |

-continued

| EXAMPLE No. | No. | Structure | MS (m/z) |
|---|---|---|---|
| 139 | 90 | | 494 APCI [M + H]+ |
| 139 | 91 | | 508 APCI [M + H]+ |
| 139 | 92 | | 503 APCI [M + H]+ |
| 139 | 93 | | 522 APCI [M + H]+ |

-continued

| EXAMPLE No. | No. | Structure | MS (m/z) |
|---|---|---|---|
| 139 | 94 | | 504 APCI [M + H]+ |
| 139 | 95 | | 609 APCI [M + H]+ |
| 139 | 96 | | 469 APCI [M + H]+ |
| 139 | 97 | | 506 APCI [M + H]+ |

-continued
| EXAMPLE No. | No. | Structure | MS (m/z) |
|---|---|---|---|
| 139 | 98 | 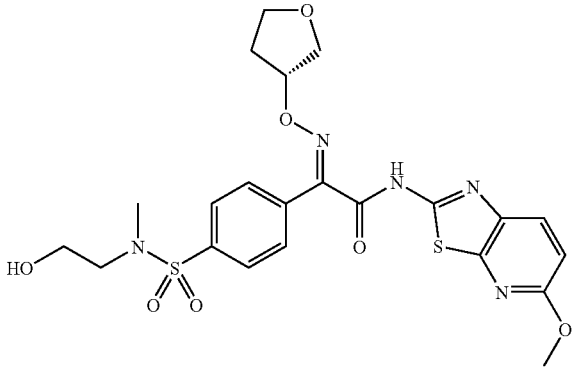 | 536 APCI [M + H]+ |
| 139 | 99 | 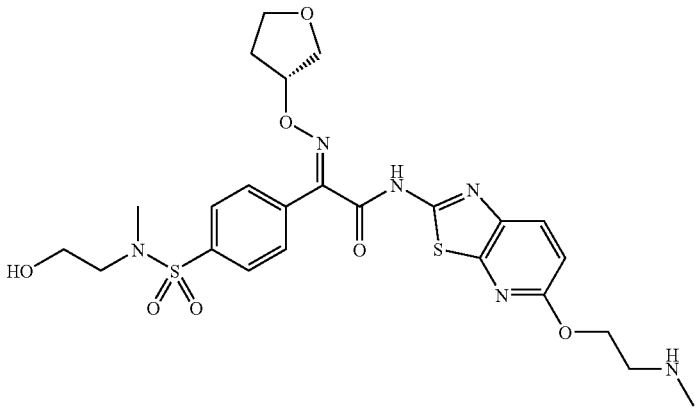 | 579 APCI [M + H]+ |
| 139 | 100 | 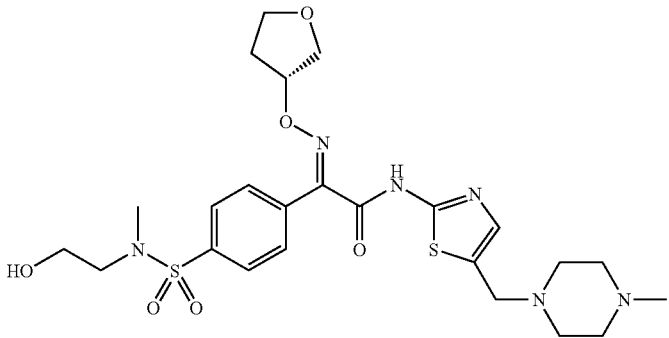 | 567 APCI [M + H]+ |
| 139 | 101 | 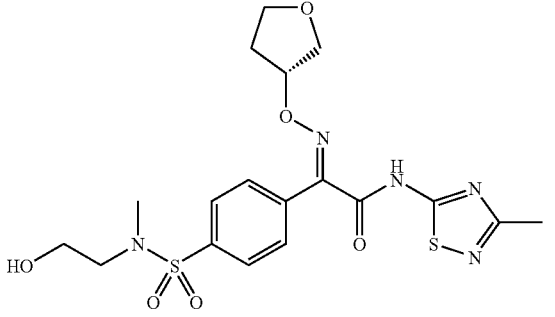 | 470 APCI [M + H]+ |

| EXAMPLE No. | No. | Structure | MS (m/z) |
|---|---|---|---|
| 139 | 102 | 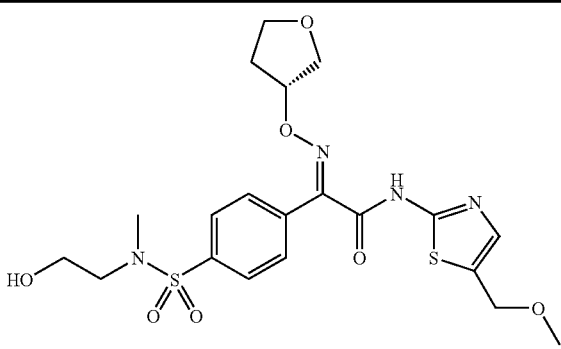 | 499 APCI [M + H]+ |
| 139 | 103 | 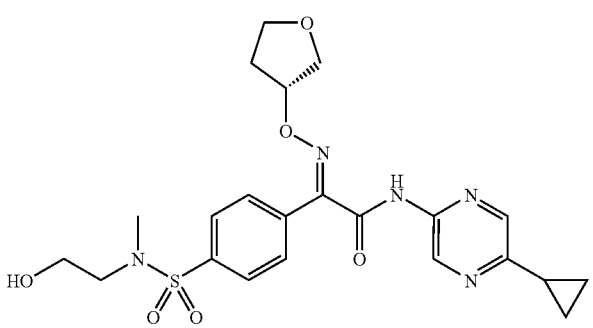 | 490 APCI [M + H]+ |
| 139 | 104 | 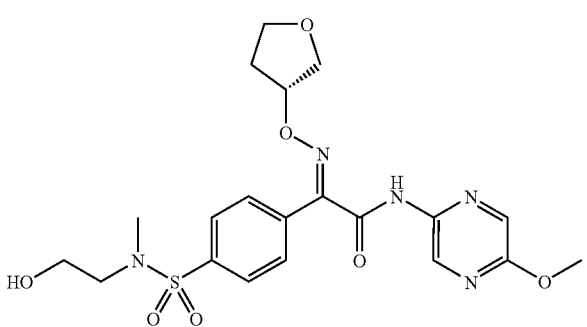 | 480 APCI [M + H]+ |
| 139 | 105 | 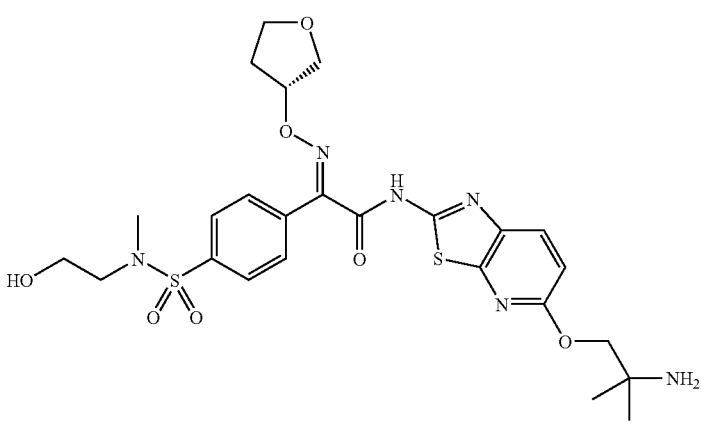 | 593 ESI [M + H]+ |

| EXAMPLE No. | No. | Structure | MS (m/z) |
|---|---|---|---|
| 139 | 106 | 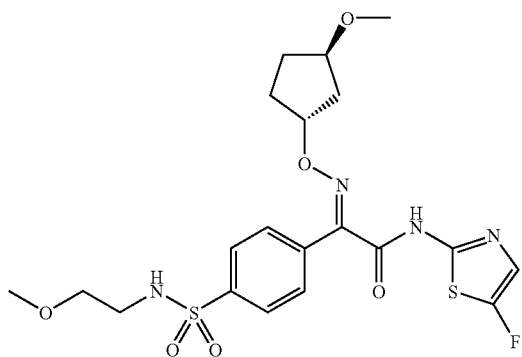 | 501 APCI [M + H]+ |
| 139 | 107 | 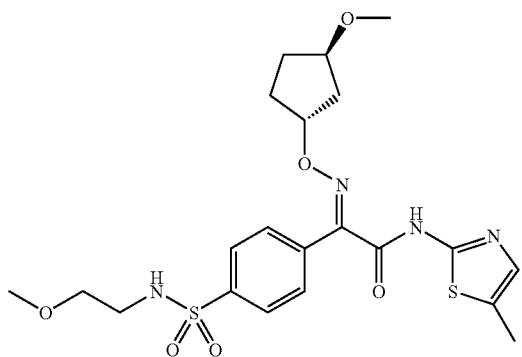 | 497 APCI [M + H]+ |
| 139 | 108 | 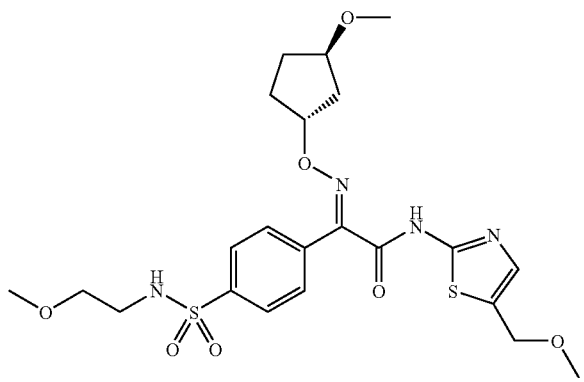 | 527 APCI [M + H]+ |
| 139 | 109 | 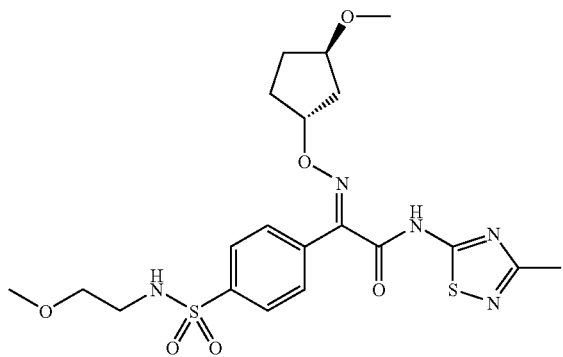 | 498 APCI [M + H]+ |

US 8,119,626 B2

-continued

| EXAMPLE No. | No. | Structure | MS (m/z) |
|---|---|---|---|
| 139 | 110 | | 564 APCI [M + H]+ |
| 139 | 111 | | 508 APCI [M + H]+ |
| 139 | 112 | | 518 APCI [M + H]+ |
| 139 | 113 | | 567 APCI [M + H]+ |

-continued
| EXAMPLE No. | No. | Structure | MS (m/z) |
|---|---|---|---|
| 139 | 114 | 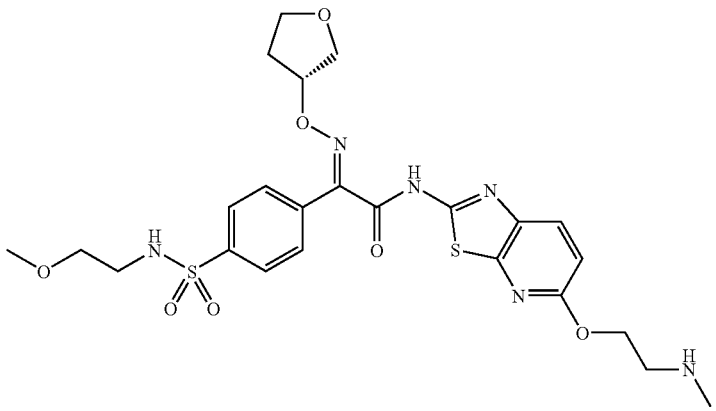 | 579 APCI [M + H]+ |
| 139 | 115 | 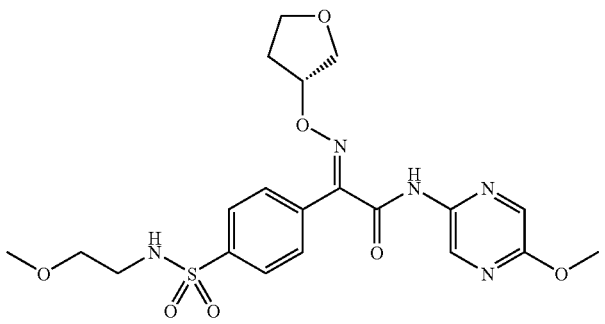 | 480 APCI [M + H]+ |
| 139 | 116 | 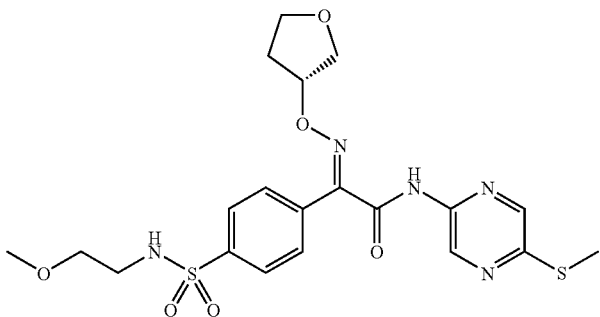 | 496 APCI [M + H]+ |
| 139 | 117 | 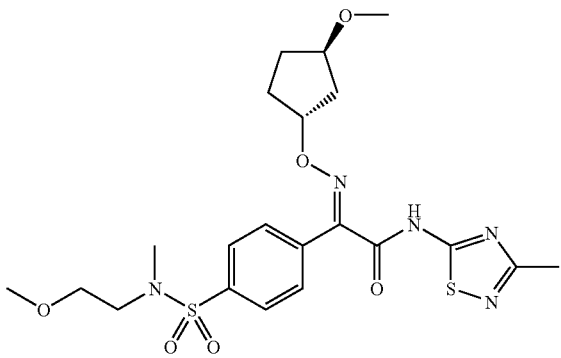 | 512 APCI [M + H]+ |

| EXAMPLE No. | No. | Structure | MS (m/z) |
|---|---|---|---|
| 139 | 118 | 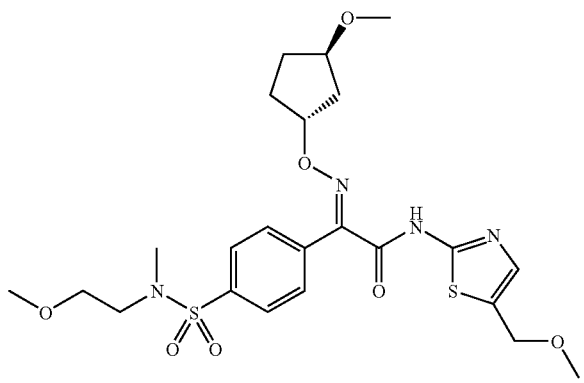 | 541 APCI [M + H]+ |
| 139 | 119 | 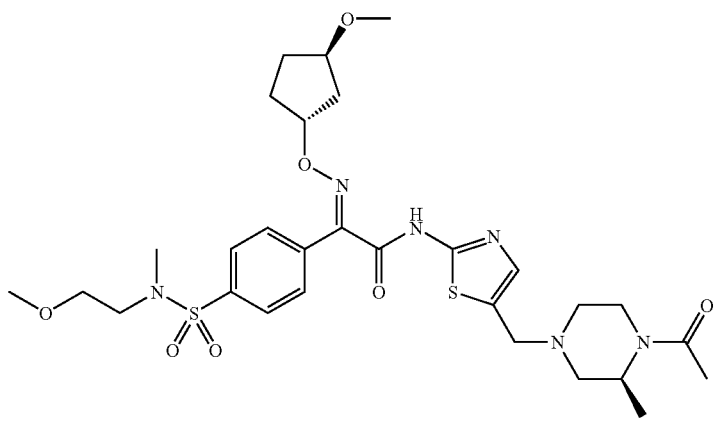 | 651 APCI [M + H]+ |
| 139 | 120 | 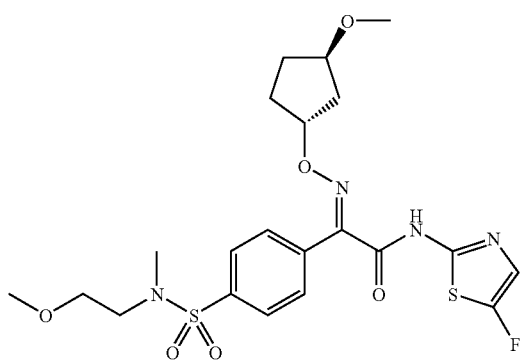 | 515 APCI [M + H]+ |
| 139 | 121 | 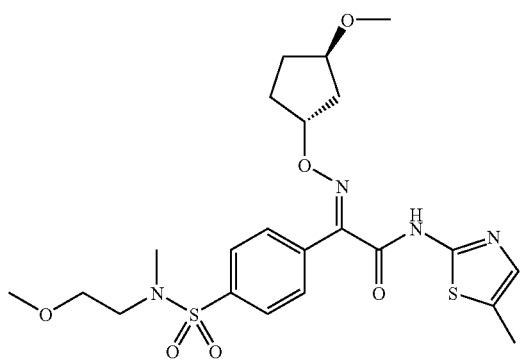 | 511 APCI [M + H]+ |

| EXAMPLE No. | No. | Structure | MS (m/z) |
|---|---|---|---|
| 139 | 122 | 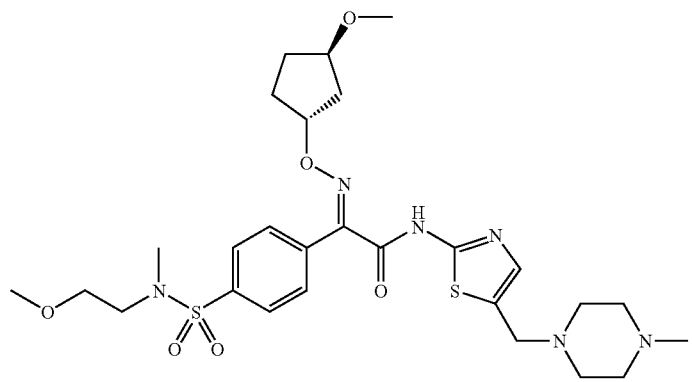 | 609 APCI [M + H]+ |
| 139 | 123 | 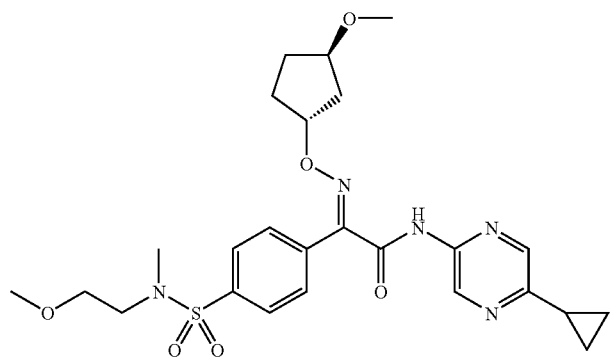 | 532 APCI [M + H]+ |
| 139 | 124 | 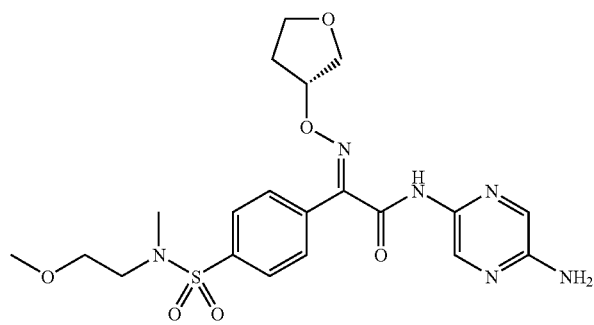 | 479 APCI [M + H]+ |
| 139 | 125 | 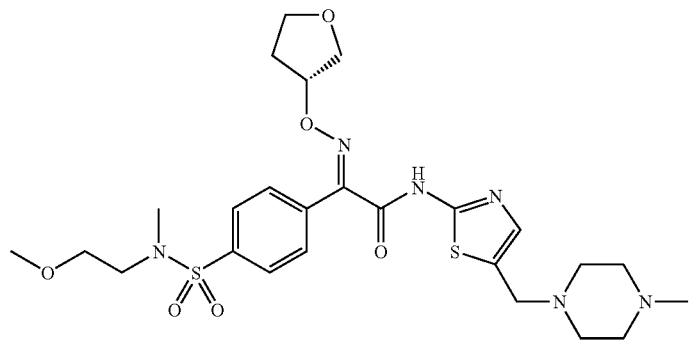 | 581 APCI [M + H]+ |

-continued

| EXAMPLE No. | No. | Structure | MS (m/z) |
|---|---|---|---|
| 139 | 126 | | 593 APCI [M + H]+ |
| 139 | 127 | | 484 APCI [M + H]+ |
| 139 | 128 | | 513 APCI [M + H]+ |
| 139 | 129 | | 494 APCI [M + H]+ |

-continued
| EXAMPLE No. | No. | Structure | MS (m/z) |
|---|---|---|---|
| 139 | 130 | 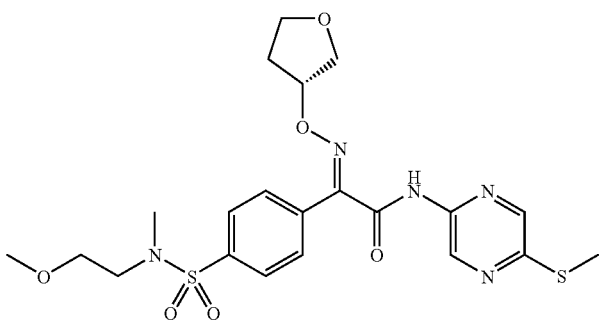 | 510 APCI [M + H]+ |
| 139 | 131 | 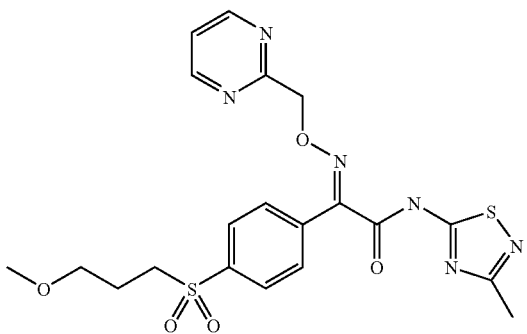 | 491 APCI [M + H]+ |
| 139 | 132 | 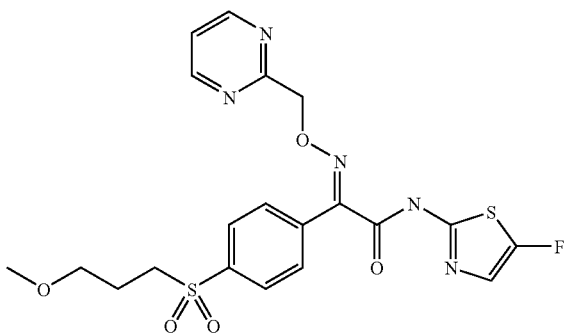 | 495 APCI [M + H]+ |
| 139 | 133 | 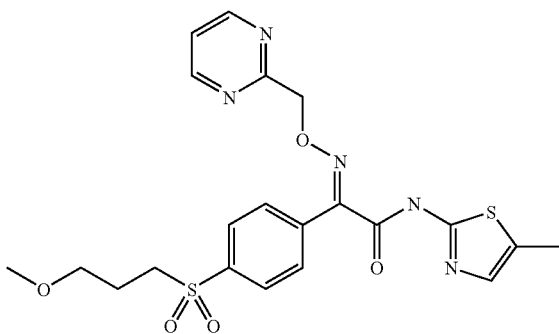 | 490 APCI [M + H]+ |

| EXAMPLE No. | No. | Structure | MS (m/z) |
|---|---|---|---|
| 139 | 134 | 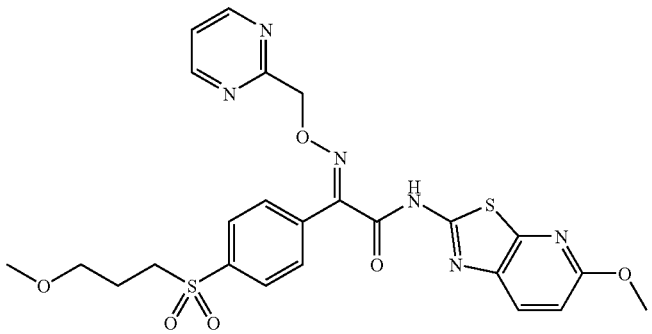 | 557 APCI [M + H]+ |
| 139 | 135 | 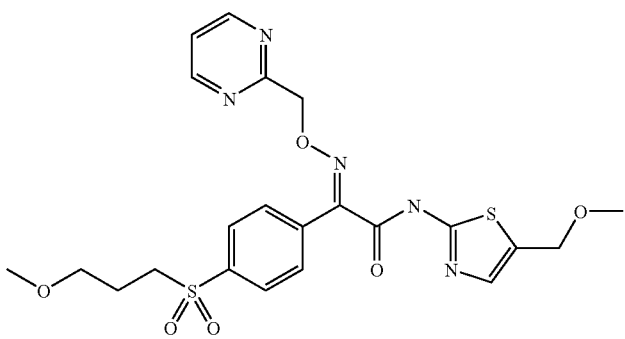 | 520 APCI [M + H]+ |
| 139 | 136 | 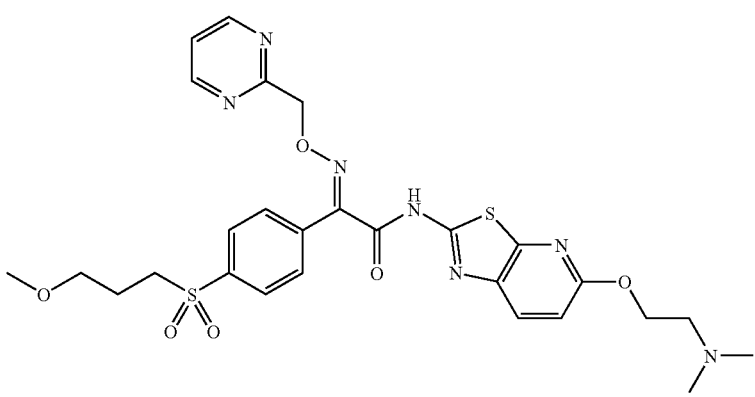 | 614 APCI [M + H]+ |
| 139 | 137 | 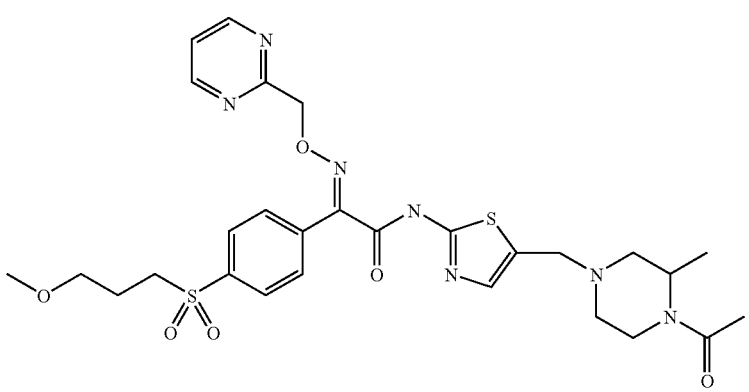 | 630 APCI [M + H]+ |

| EXAMPLE No. | No. | Structure | MS (m/z) |
|---|---|---|---|
| 139 | 138 | 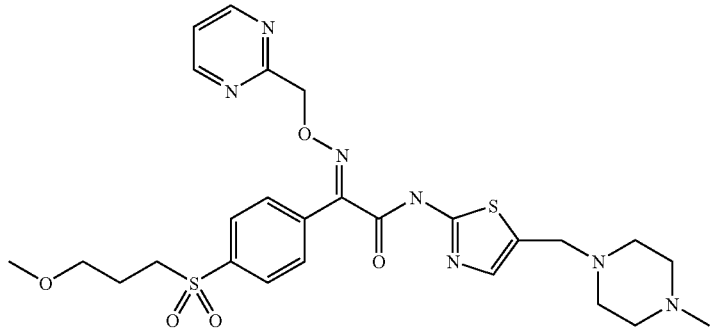 | 588 APCI [M + H]+ |
| 139 | 139 | 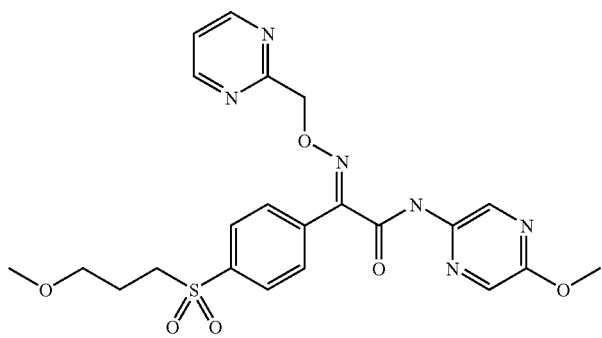 | 501 APCI [M + H]+ |
| 139 | 140 | 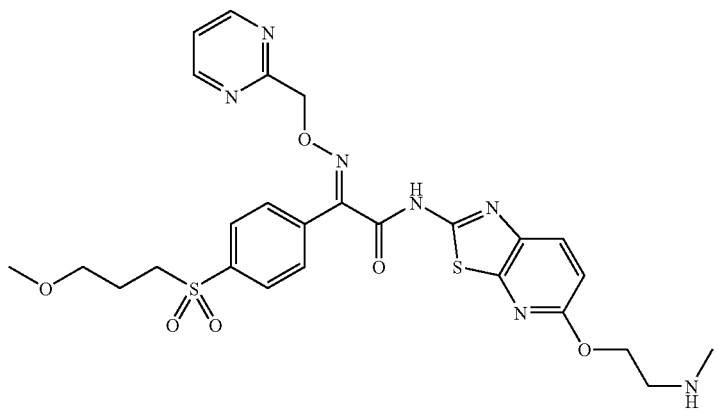 | 600 APCI [M + H]+ |
| 139 | 141 | 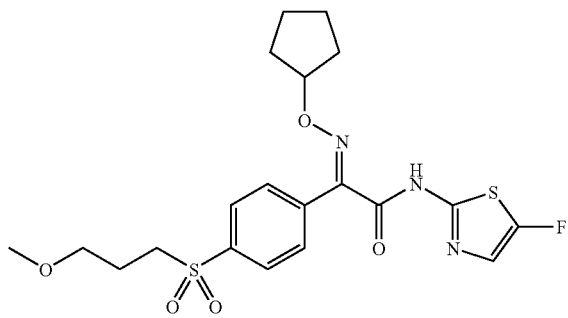 | 470 APCI [M + H]+ |

-continued
| EXAMPLE No. | No. | Structure | MS (m/z) |
|---|---|---|---|
| 139 | 142 | 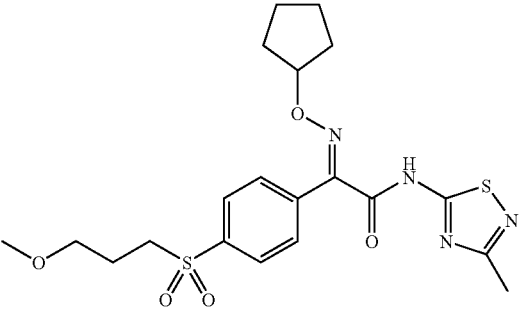 | 467 APCI [M + H]+ |
| 139 | 143 |  | 496 APCI [M + H]+ |
| 139 | 144 | 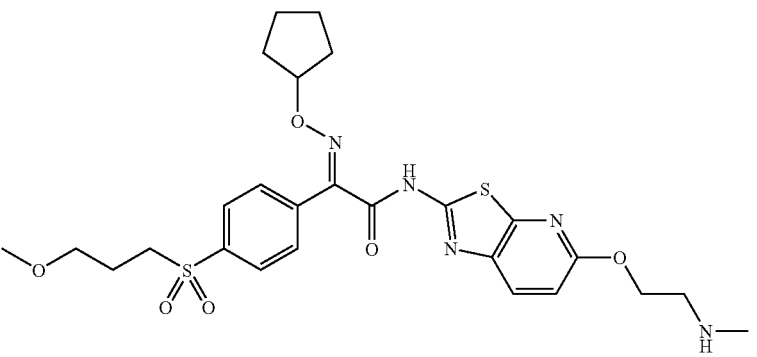 | 576 APCI [M + H]+ |
| 139 | 145 |  | 563 APCI [M + H]+ |

-continued

| EXAMPLE No. | No. | Structure | MS (m/z) |
|---|---|---|---|
| 139 | 146 | | 604 APCI [M + H]+ |
| 139 | 147 | | 590 APCI [M + H]+ |
| 139 | 148 | | 564 APCI [M + H]+ |
| 139 | 149 | | 603 APCI [M + H]+ |

-continued

| EXAMPLE No. | No. | Structure | MS (m/z) |
|---|---|---|---|
| 139 | 150 | | 589 APCI [M + H]+ |
| 139 | 151 | | 532 APCI [M + H]+ |
| 139 | 152 | | 518 APCI [M + H]+ |
| 139 | 153 | | 562 APCI [M + H]+ |

-continued
| EXAMPLE No. | No. | Structure | MS (m/z) |
|---|---|---|---|
| 139 | 154 | 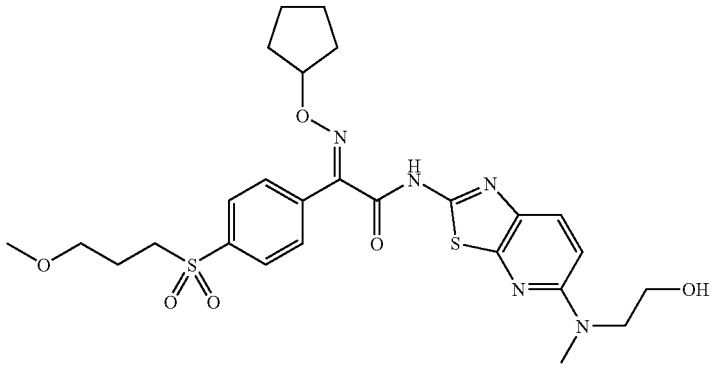 | 576 APCI [M + H]+ |
| 139 | 155 | 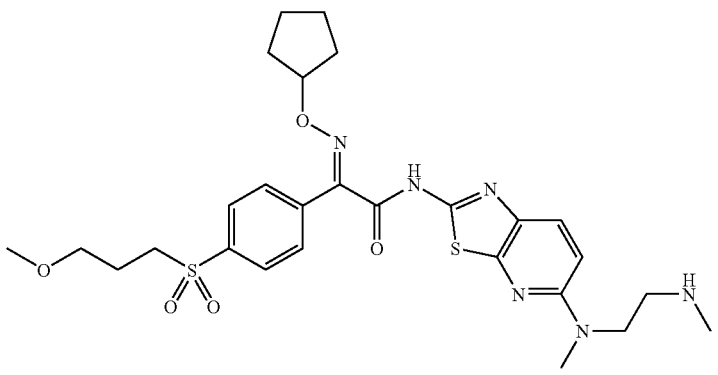 | 589 APCI [M + H]+ |
| 139 | 156 | 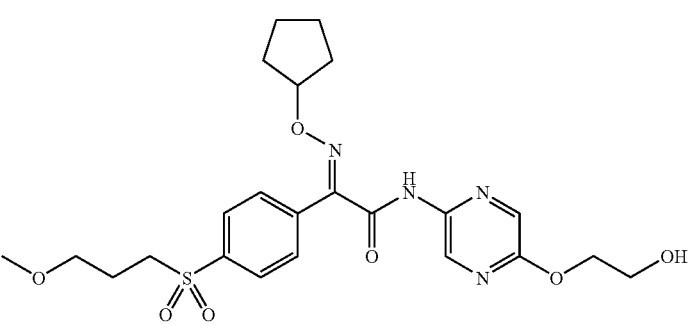 | 507 APCI [M + H]+ |
| 139 | 157 | 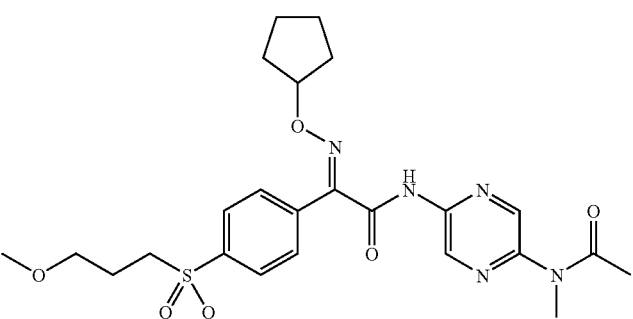 | 518 APCI [M + H]+ |

| EXAMPLE No. | No. | Structure | MS (m/z) |
|---|---|---|---|
| 139 | 158 | 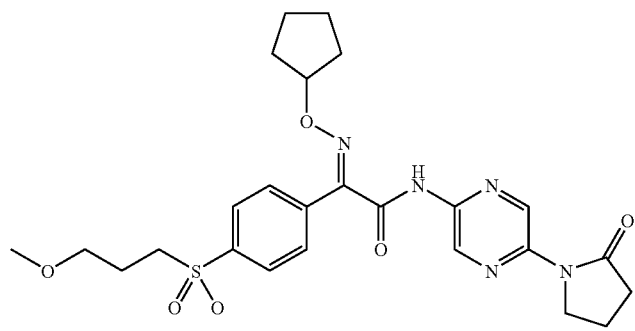 | 530 APCI [M + H]+ |
| 139 | 159 | 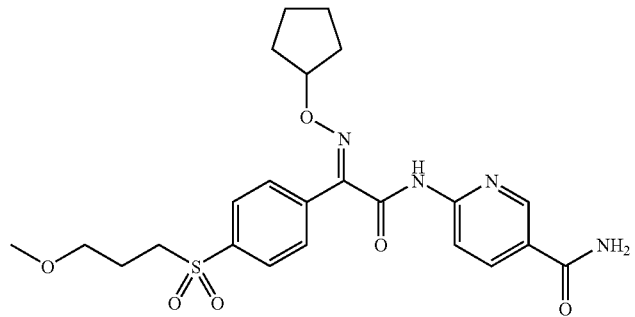 | 489 APCI [M + H]+ |
| 139 | 160 | 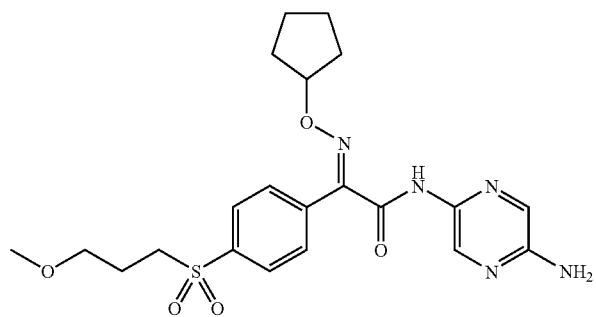 | 462 APCI [M + H]+ |
| 139 | 161 | 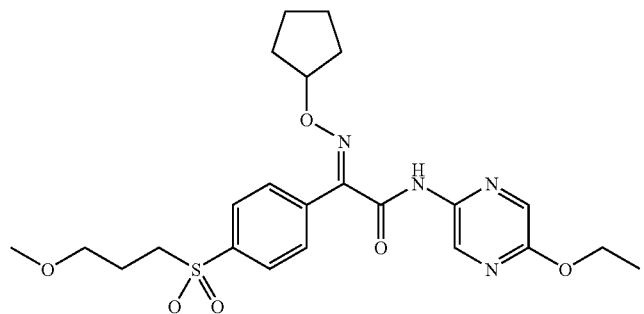 | 491 APCI [M + H]+ |

-continued

| EXAMPLE No. | No. | Structure | MS (m/z) |
|---|---|---|---|
| 139 | 162 | | 505 APCI [M + H]+ |
| 139 | 163 | | 521 APCI [M + H]+ |
| 139 | 164 | | 486 APCI [M + H]+ |
| 139 | 166 | | 493 APCI [M + H]+ |
| 139 | 167 | | 487 APCI [M + H]+ |

| EXAMPLE No. | No. | Structure | MS (m/z) |
|---|---|---|---|
| 139 | 168 | | 590 APCI [M + H]+ |
| 139 | 169 | | 588 APCI [M + H]+ |
| 139 | 170 | | 602 APCI [M + H]+ |
| 139 | 171 | | 476 APCI [M + H]+ |

| EXAMPLE No. | No. | Structure | MS (m/z) |
|---|---|---|---|
| 139 | 172 | 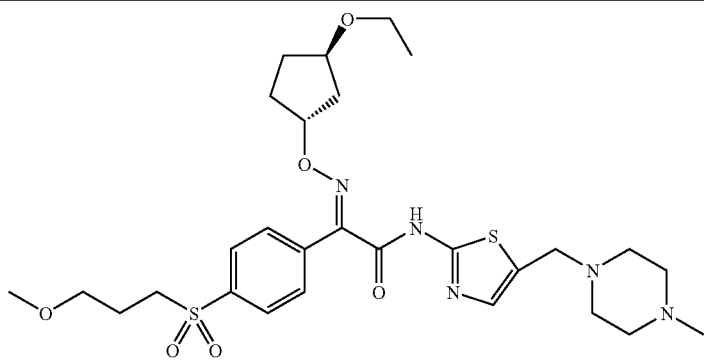 | 608 APCI [M + H]+ |
| 139 | 173 | 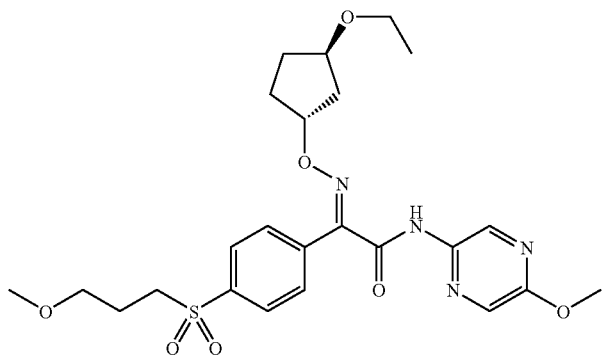 | 521 APCI [M + H]+ |
| 139 | 174 | 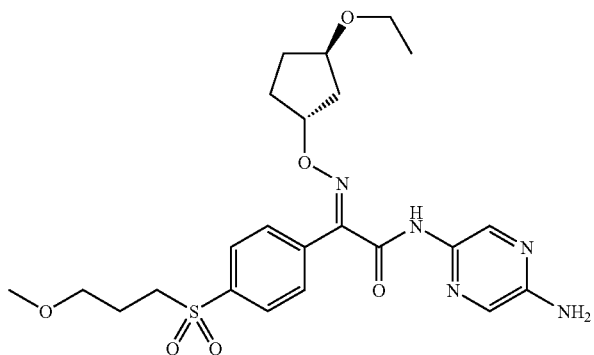 | 506 APCI [M + H]+ |
| 139 | 175 | 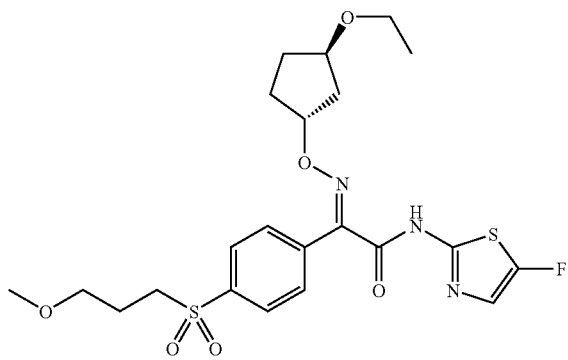 | 514 APCI [M + H]+ |

-continued
| EXAMPLE No. | No. | Structure | MS (m/z) |
|---|---|---|---|
| 139 | 176 | 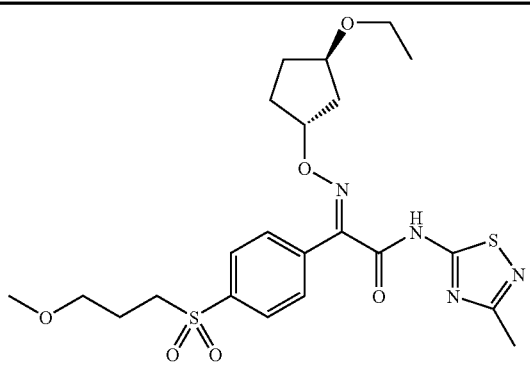 | 511 APCI [M + H]+ |
| 139 | 177 | 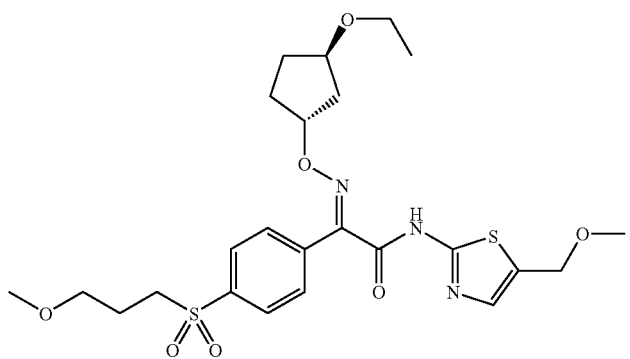 | 540 APCI [M + H]+ |
| 139 | 178 | 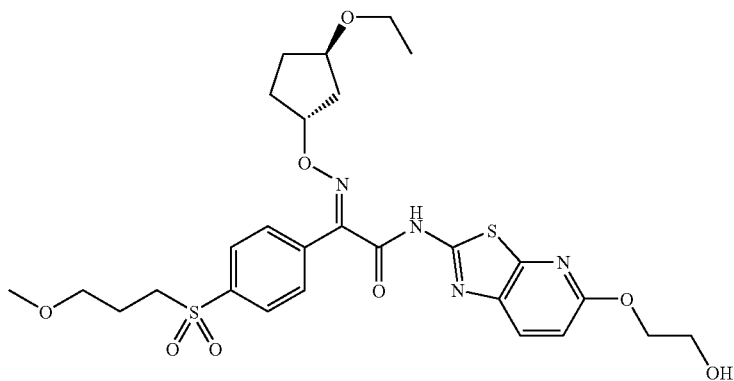 | 607 APCI [M + H]+ |
| 139 | 179 | 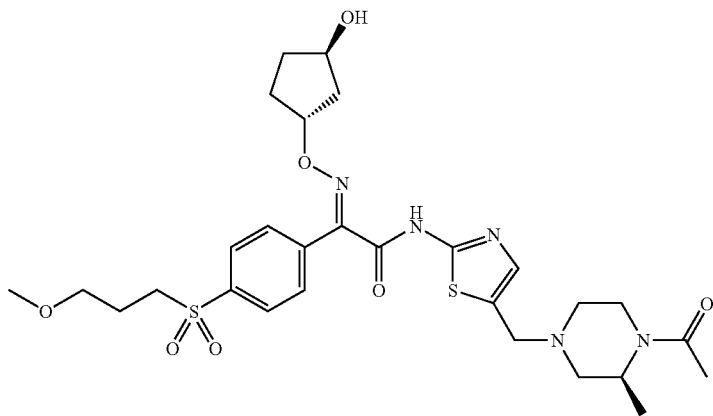 | 622 APCI [M + H]+ |

-continued

| EXAMPLE No. | No. | Structure | MS (m/z) |
|---|---|---|---|
| 139 | 180 | | 580 APCI [M + H]+ |
| 139 | 181 | | 493 APCI [M + H]+ |
| 139 | 182 | | 482 APCI [M + H]+ |
| 139 | 183 | | 512 APCI [M + H]+ |

-continued
| EXAMPLE No. | No. | Structure | MS (m/z) |
|---|---|---|---|
| 139 | 184 | 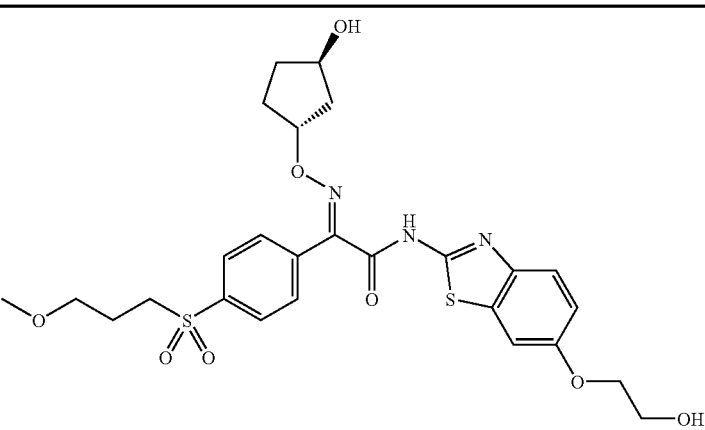 | 578 APCI [M + H]+ |
| 139 | 185 | 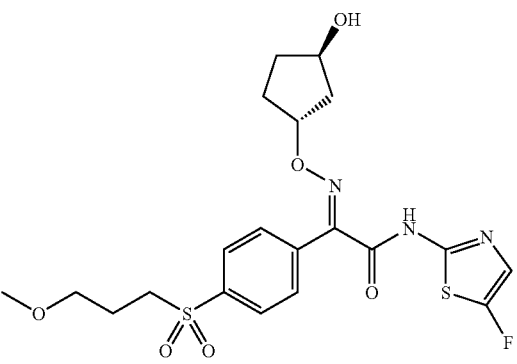 | 486 APCI [M + H]+ |
| 139 | 186 | 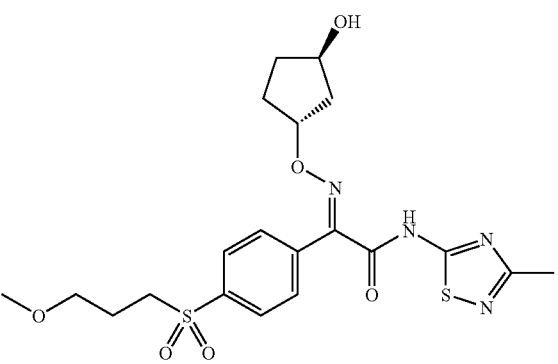 | 483 APCI [M + H]+ |
| 139 | 187 | 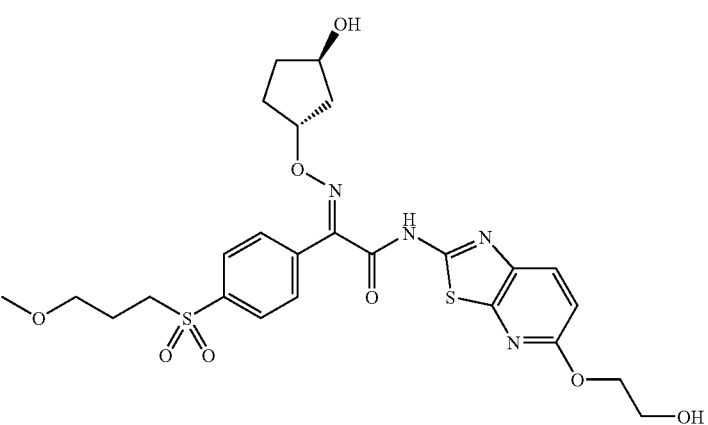 | 579 APCI [M + H]+ |

| EXAMPLE No. | No. | Structure | MS (m/z) |
|---|---|---|---|
| 139 | 188 | | 592 APCI [M + H]+ |
| 139 | 189 | | 606 APCI [M + H]+ |
| 139 | 190 | | 519 APCI [M + H]+ |

-continued

| EXAMPLE No. | No. | Structure | MS (m/z) |
|---|---|---|---|
| 139 | 191 | | 549 APCI [M + H]+ |
| 139 | 192 | | 618 APCI [M + H]+ |
| 139 | 193 | | 500 APCI [M + H]+ |
| 139 | 194 | | 496 APCI [M + H]+ |

| EXAMPLE No. | No. | Structure | MS (m/z) |
|---|---|---|---|
| 139 | 195 | 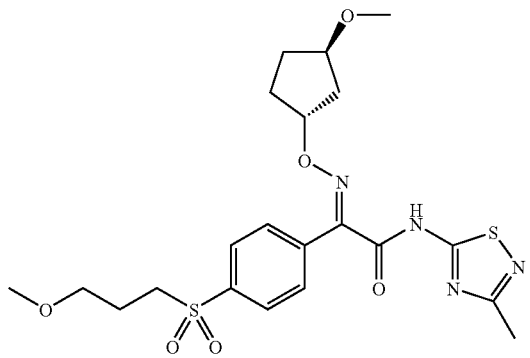 | 497 APCI [M + H]+ |
| 139 | 196 | 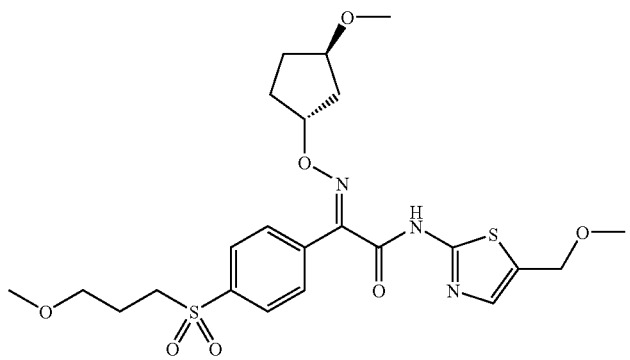 | 526 APCI [M + H]+ |
| 139 | 197 | 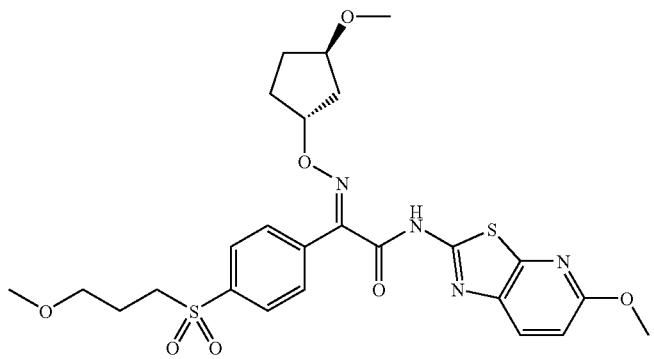 | 563 APCI [M + H]+ |
| 139 | 199 | 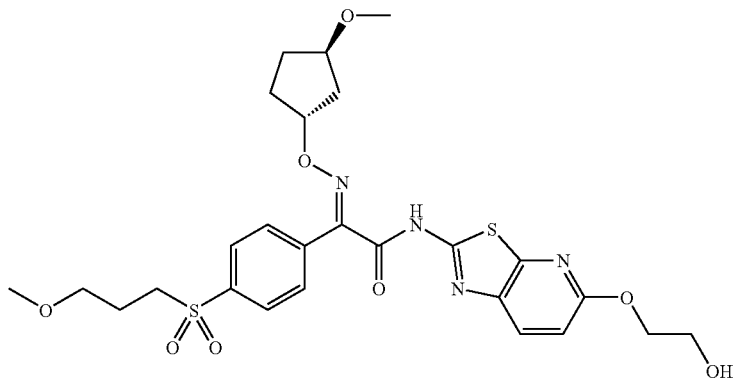 | 593 APCI [M + H]+ |

-continued
| EXAMPLE No. | No. | Structure | MS (m/z) |
|---|---|---|---|
| 139 | 200 | 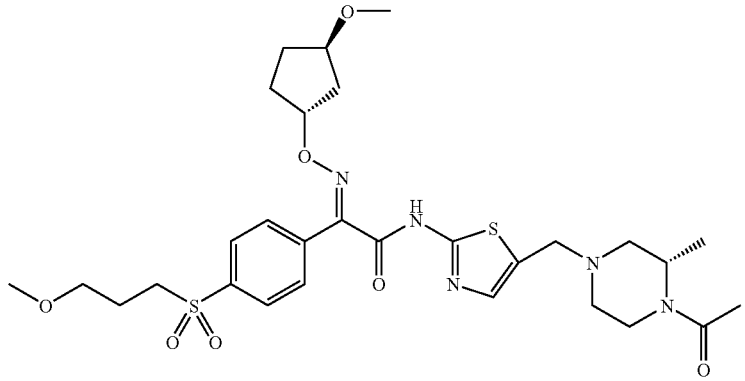 | 636 APCI [M + H]+ |
| 139 | 201 | 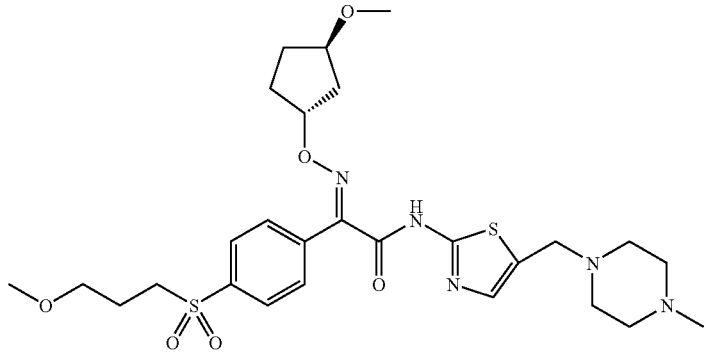 | 594 APCI [M + H]+ |
| 139 | 202 | 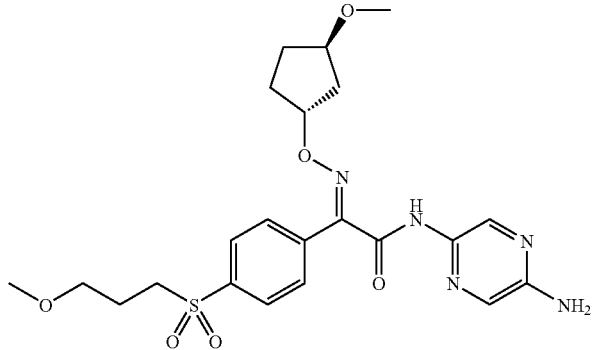 | 492 APCI [M + H]+ |
| 139 | 203 | 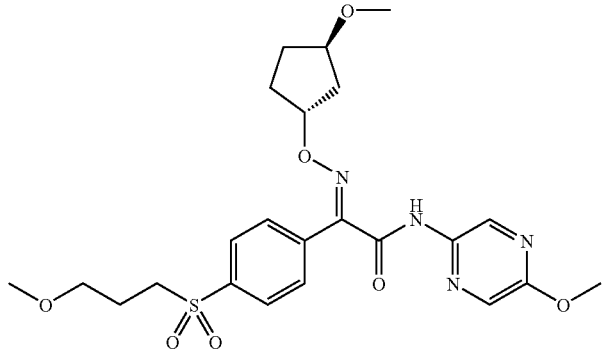 | 507 APCI [M + H]+ |

| EXAMPLE No. | No. | Structure | MS (m/z) |
|---|---|---|---|
| 139 | 204 | | 523 APCI [M + H]+ |
| 139 | 205 | | 517 APCI [M + H]+ |
| 139 | 206 | HCl | 618 APCI [M + H]+ |
| 139 | 207 | | 632 APCI [M + H]+ |

-continued

| EXAMPLE No. | No. | Structure | MS (m/z) |
|---|---|---|---|
| 139 | 208 | | 578 APCI [M + H]+ |
| 139 | 209 | | 566 APCI [M + H]+ |
| 139 | 210 | | 479 APCI [M + H]+ |
| 139 | 211 | | 464 APCI [M + H]+ |

| EXAMPLE No. | No. | Structure | MS (m/z) |
|---|---|---|---|
| 139 | 212 | | 495 APCI [M + H]+ |
| 139 | 213 | | 577 APCI [M + H]+ |
| 139 | 214 | | 564 APCI [M + H]+ |
| 139 | 215 | | 536 APCI [M + H]+ |

| EXAMPLE No. | No. | Structure | MS (m/z) |
|---|---|---|---|
| 139 | 216 | 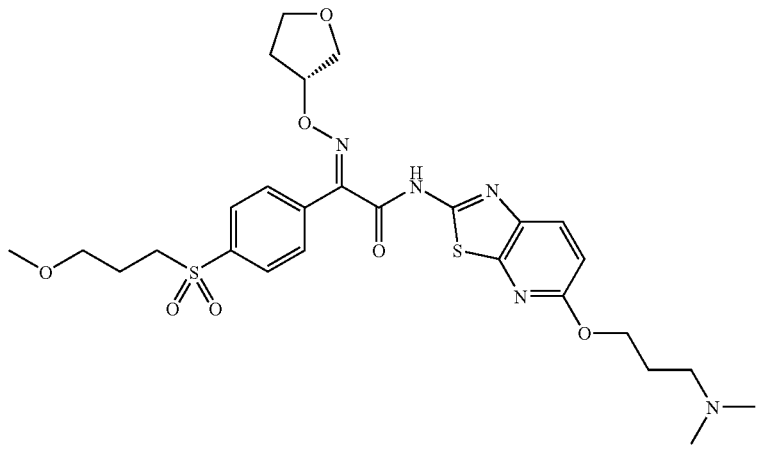 | 606 APCI [M + H]+ |
| 139 | 217 | 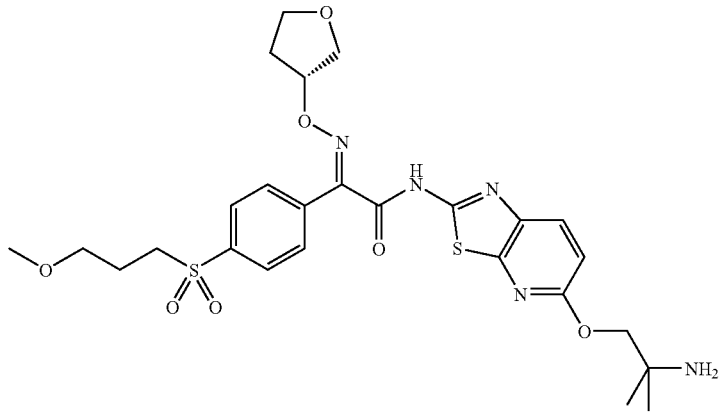 | 592 APCI [M + H]+ |
| 139 | 218 | 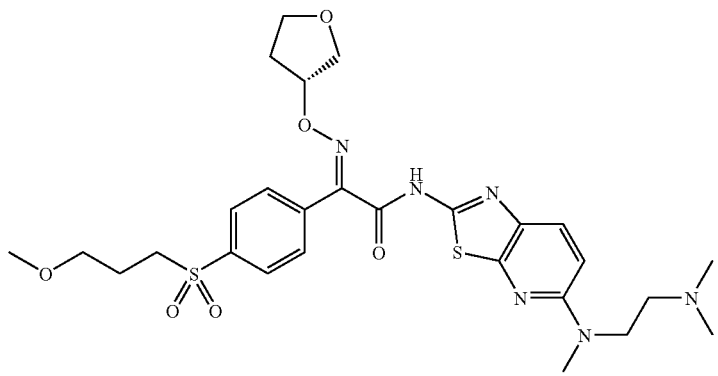 | 605 APCI [M + H]+ |
| 139 | 219 | 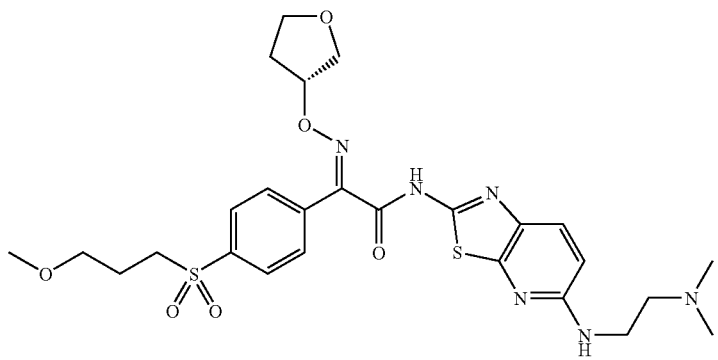 | 591 APCI [M + H]+ |

| EXAMPLE No. | No. | Structure | MS (m/z) |
|---|---|---|---|
| 139 | 220 | 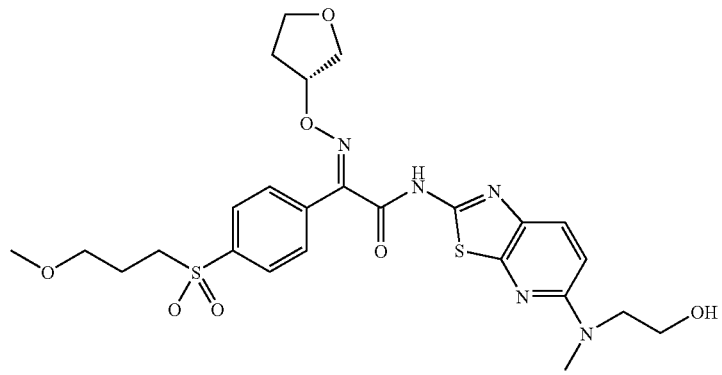 | 578 APCI [M + H]+ |
| 139 | 221 | 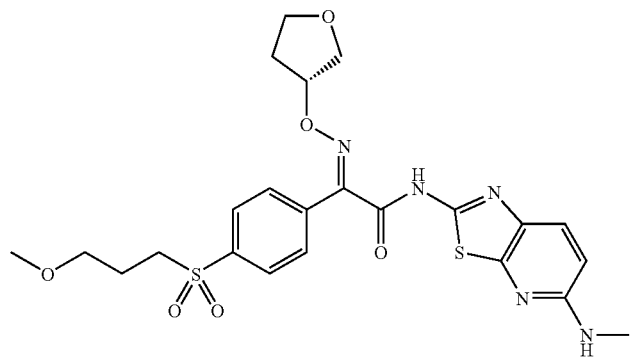 | 534 APCI [M + H]+ |
| 139 | 222 | 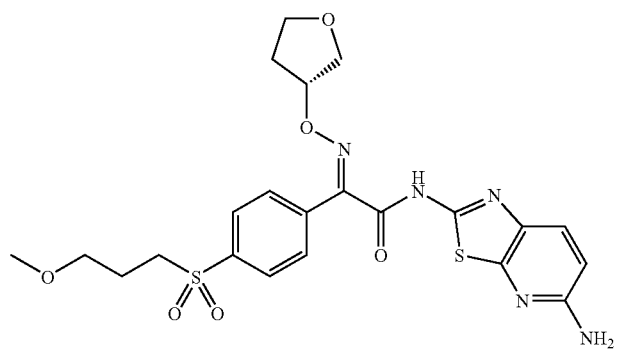 | 520 APCI [M + H]+ |
| 139 | 223 | 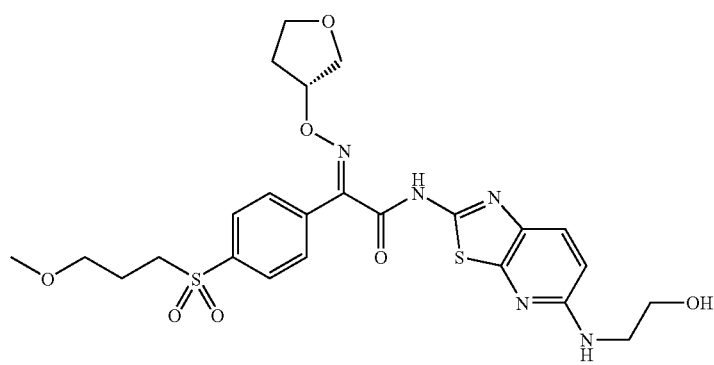 | 564 APCI [M + H]+ |

| EXAMPLE No. | No. | Structure | MS (m/z) |
|---|---|---|---|
| 139 | 224 | 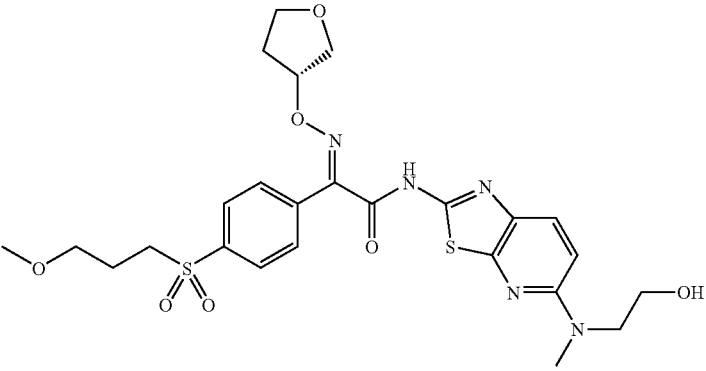 | 578 APCI [M + H]+ |
| 139 | 225 | 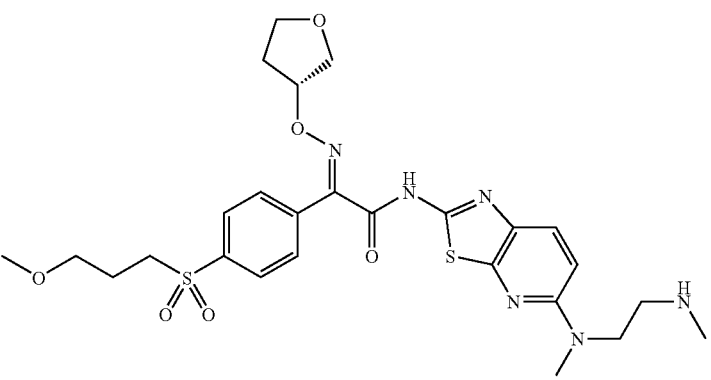 | 591 APCI [M + H]+ |
| 139 | 226 | 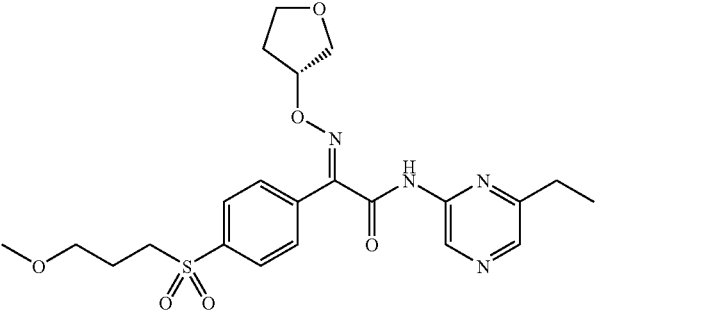 | 477 APCI [M + H]+ |
| 139 | 227 | 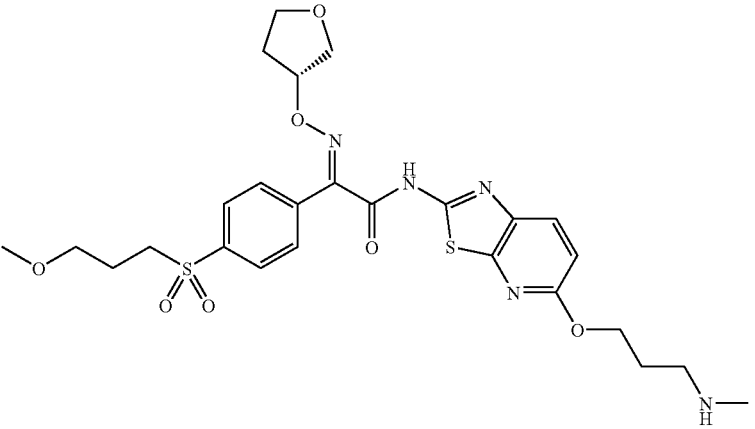 | 592 APCI [M + H]+ |

-continued
| EXAMPLE No. | No. | Structure | MS (m/z) |
|---|---|---|---|
| 139 | 228 | 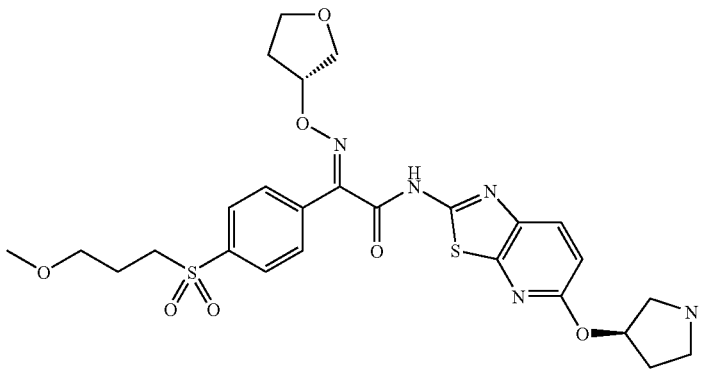 | 590 APCI [M + H]+ |
| 139 | 229 | 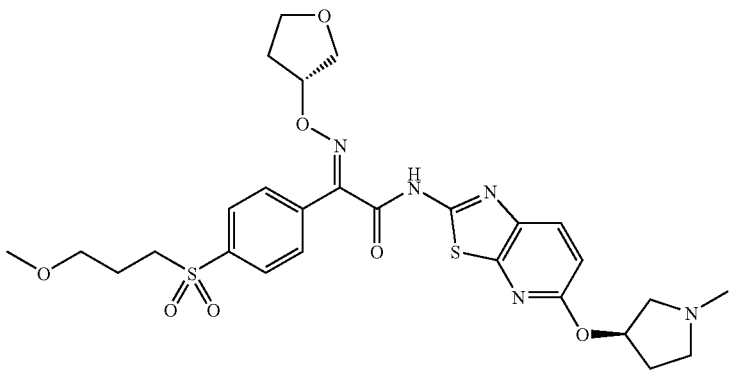 | 604 APCI [M + H]+ |
| 139 | 230 | 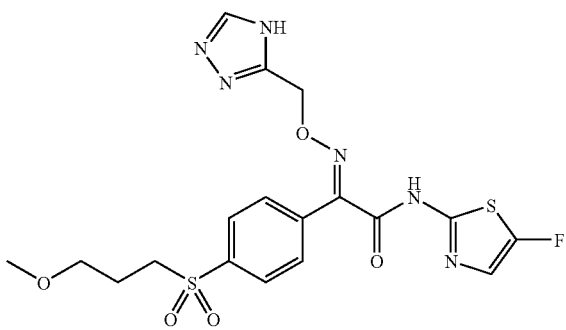 | 483 APCI [M + H]+ |
| 139 | 231 | 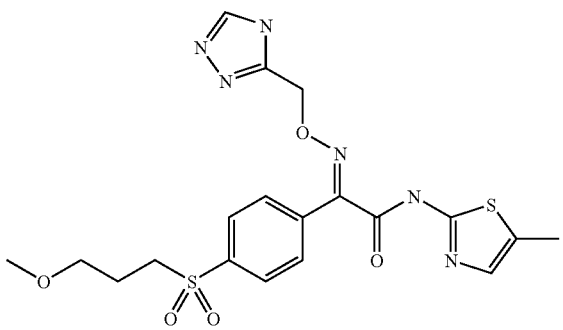 | 479 APCI [M + H]+ |

-continued

| EXAMPLE No. | No. | Structure | MS (m/z) |
|---|---|---|---|
| 139 | 232 | | 480 APCI [M + H]+ |
| 139 | 233 | | 509 APCI [M + H]+ |
| 139 | 234 | | 546 APCI [M + H]+ |
| 139 | 235 | | 577 APCI [M + H]+ |

-continued
| EXAMPLE No. | No. | Structure | MS (m/z) |
|---|---|---|---|
| 139 | 236 | 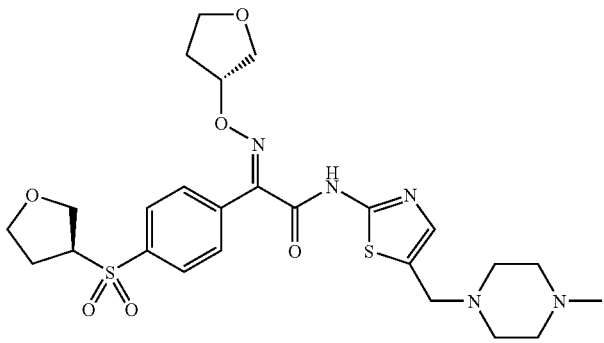 | 564 APCI [M + H]+ |
| 139 | 237 | 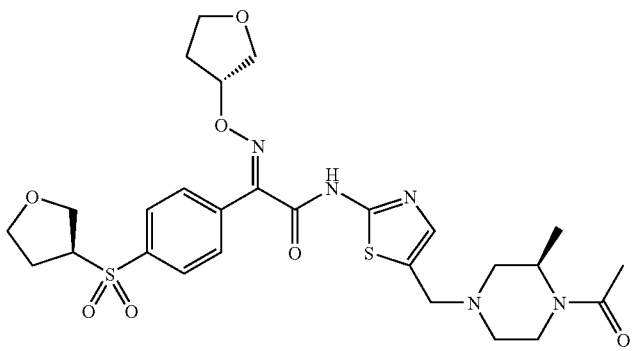 | 606 APCI [M + H]+ |
| 139 | 238 | 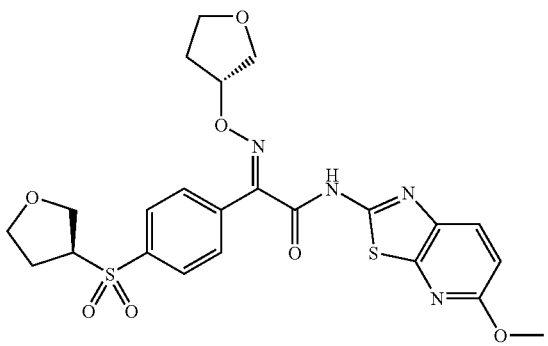 | 533 APCI [M + H]+ |
| 139 | 239 | 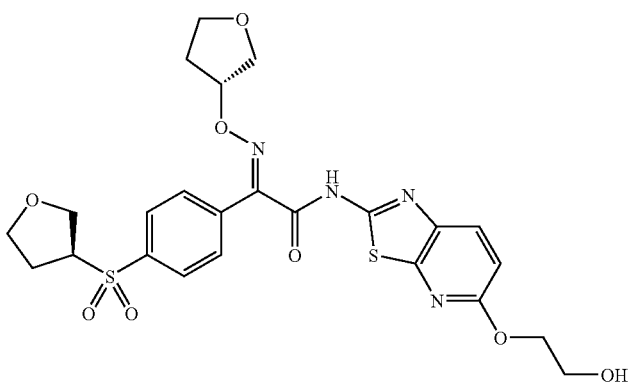 | 563 APCI [M + H]+ |

-continued

| EXAMPLE No. | No. | Structure | MS (m/z) |
|---|---|---|---|
| 139 | 240 | | 496 APCI [M + H]+ |
| 139 | 241 | | 462 APCI [M + H]+ |
| 139 | 242 | | 590 APCI [M + H]+ |
| 139 | 243 | | 595 APCI [M + H]+ |

-continued
| EXAMPLE No. | No. | Structure | MS (m/z) |
|---|---|---|---|
| 139 | 244 | 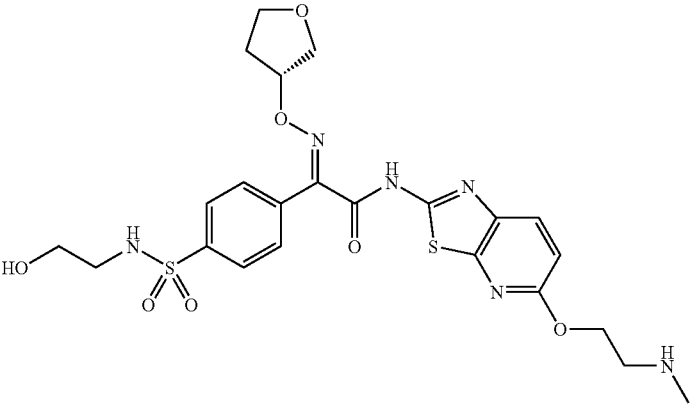 | 565 APCI [M + H]+ |
| 139 | 245 | 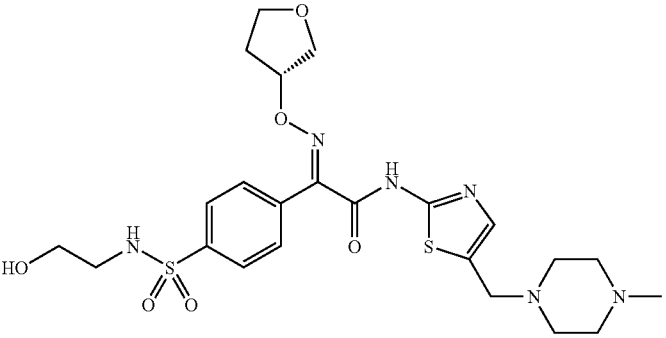 | 553 APCI [M + H]+ |
| 139 | 246 | 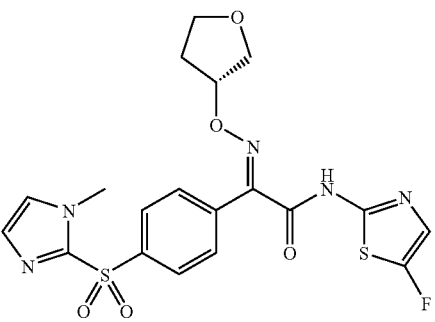 | 480 APCI [M + H]+ |
Example 140
Corresponding starting compounds are treated in the similar manner as any of the above EXAMPLEs to give the following compounds.

| EXAMPLE No. | No. | Structure |
|---|---|---|
| 140 | 1 | 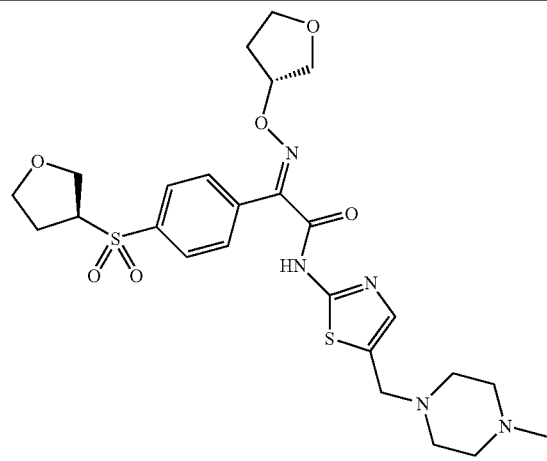 |
| 140 | 2 | 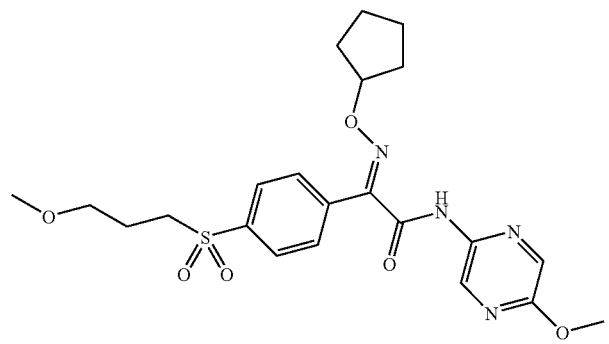 |
| 140 | 3 | 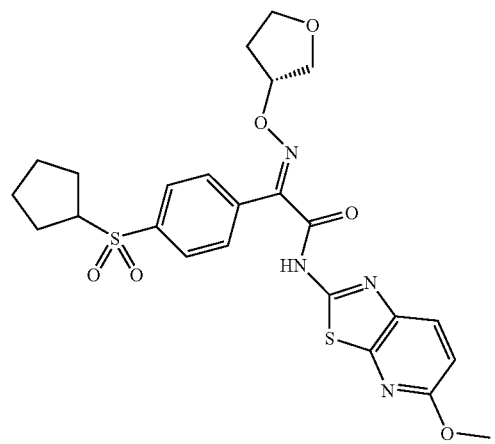 |

| EXAMPLE No. | No. | Structure |
|---|---|---|
| 140 | 4 | 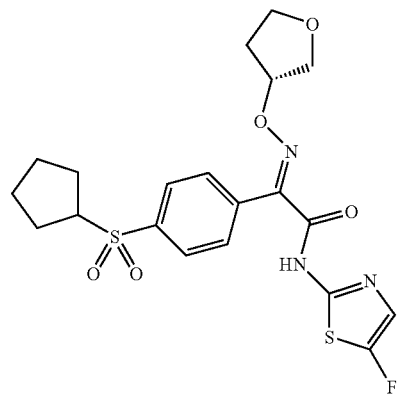 |
| 140 | 5 | 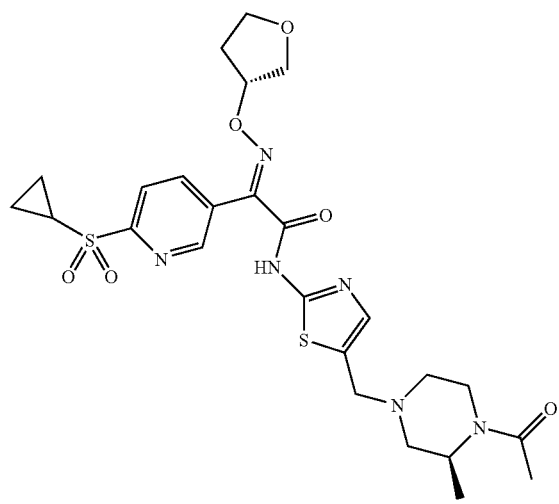 |
| 140 | 6 | 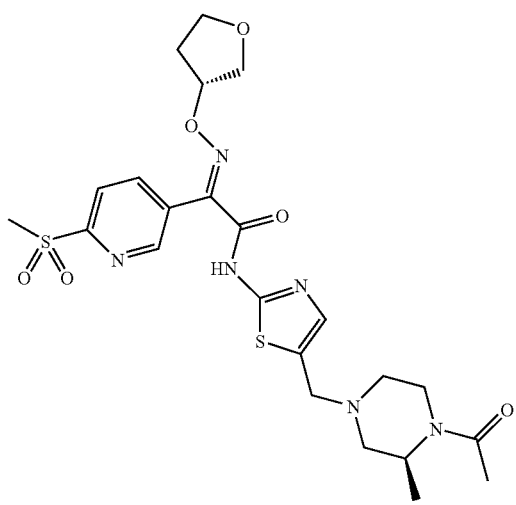 |

| EXAMPLE No. | No. | Structure |
|---|---|---|
| 140 | 7 | 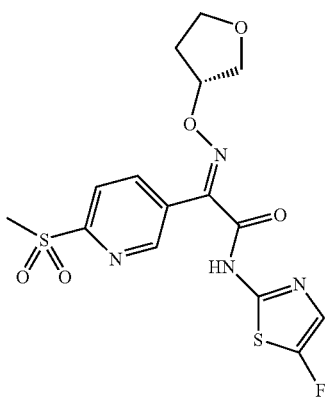 |
| 140 | 8 | 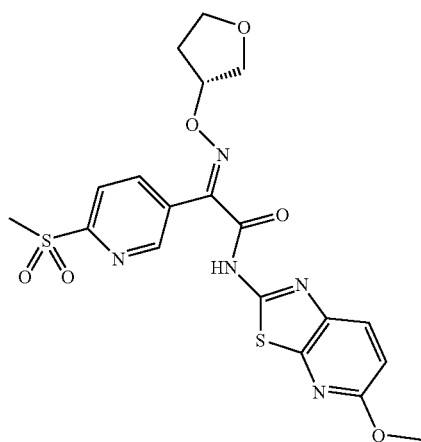 |
| 140 | 9 | 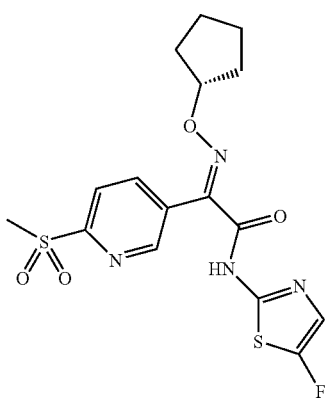 |

| EXAMPLE No. | No. | Structure |
|---|---|---|
| 140 | 10 | 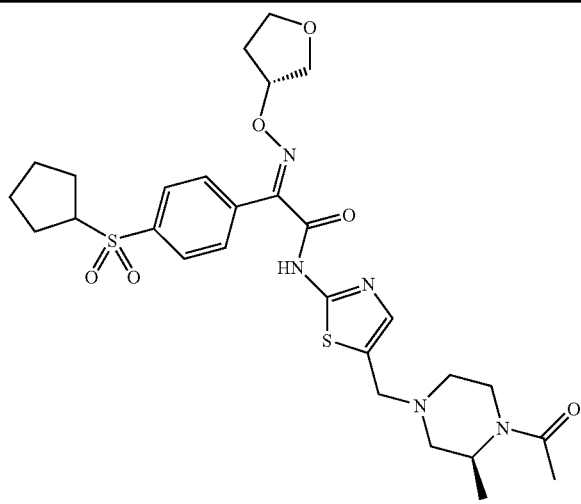 |
| 140 | 11 | 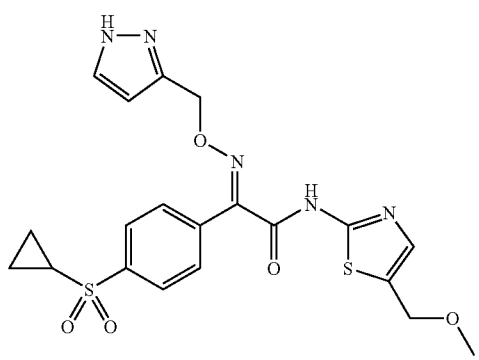 |
| 140 | 12 | 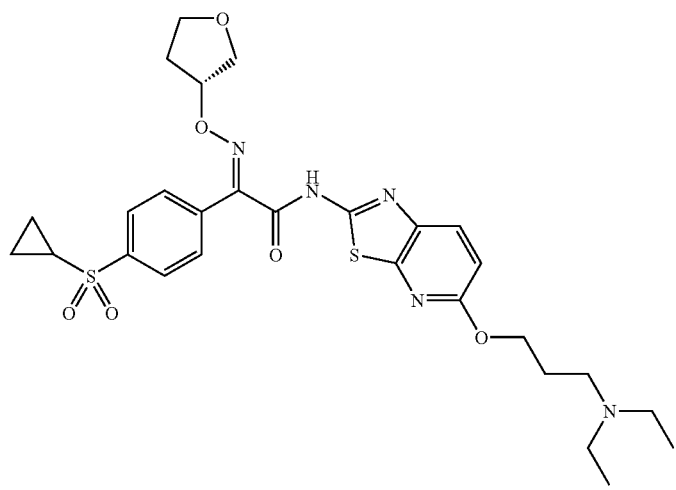 |

-continued
| EXAMPLE No. | No. | Structure |
|---|---|---|
| 140 | 13 | 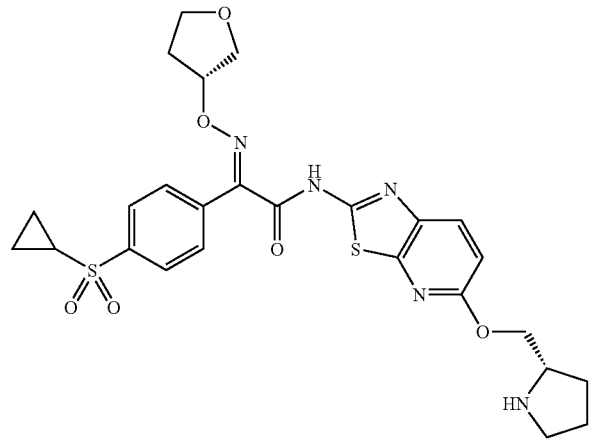 |
| 140 | 14 | 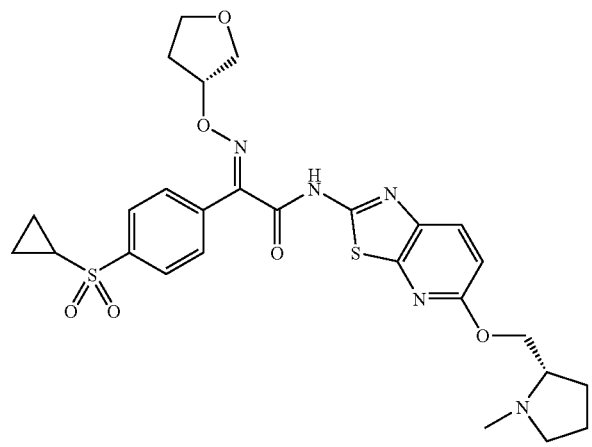 |
| 140 | 15 | 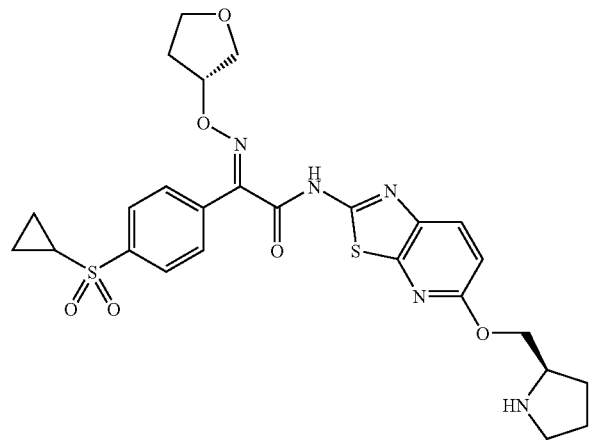 |

| EXAMPLE No. | No. | Structure |
|---|---|---|
| 140 | 16 | 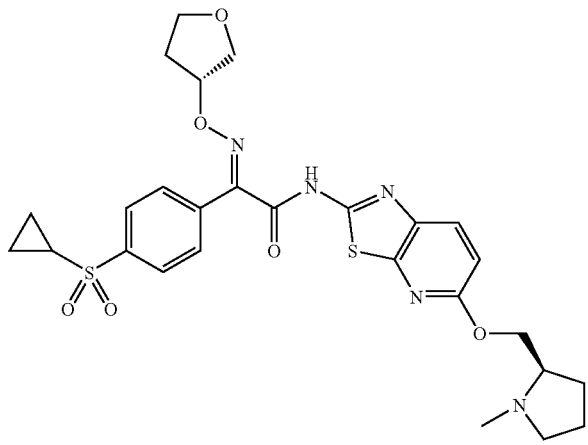 |
| 140 | 17 | 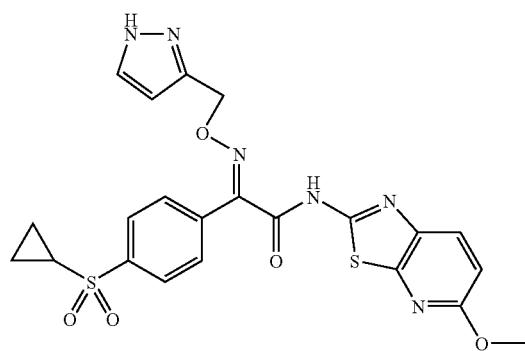 |
| 140 | 18 | 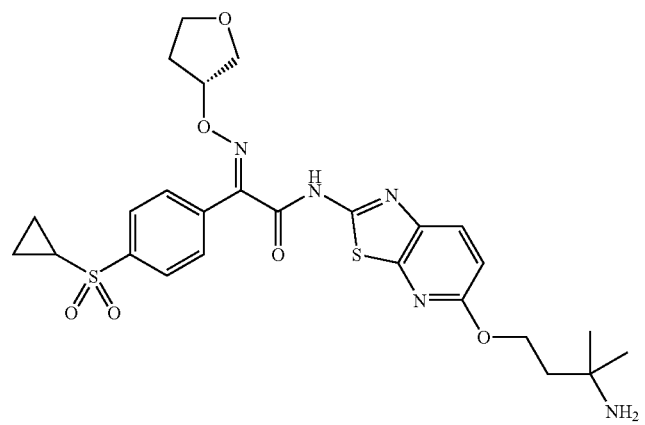 |

| EXAMPLE No. | No. | Structure |
|---|---|---|
| 140 | 19 | 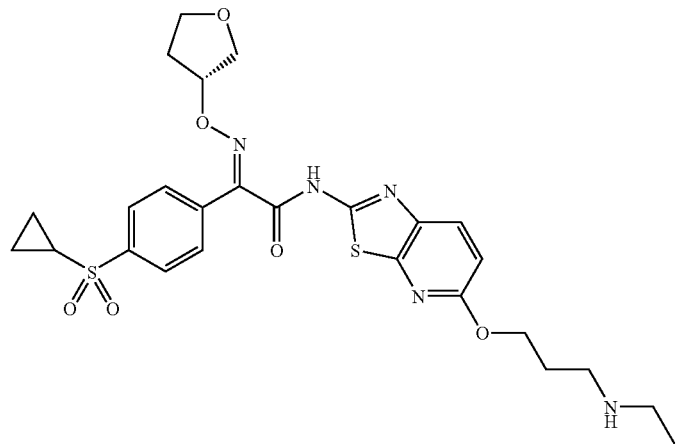 |
| 140 | 20 | 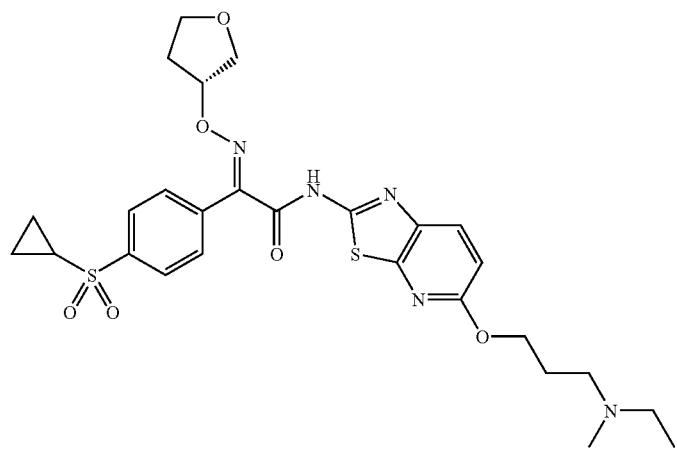 |
| 140 | 21 | 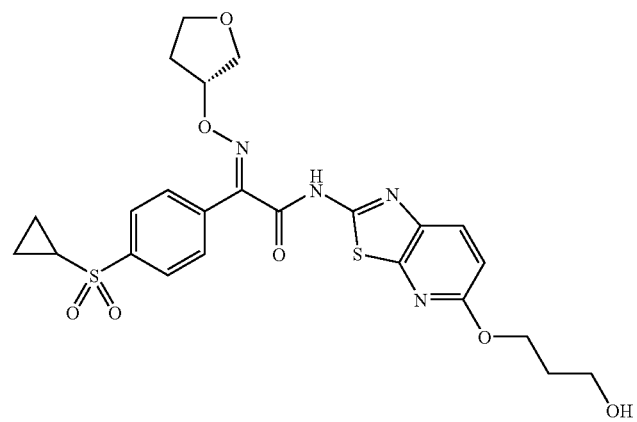 |

US 8,119,626 B2
573                                                                 574
-continued
| EXAMPLE No. | No. | Structure |
|---|---|---|
| 140 | 22 | 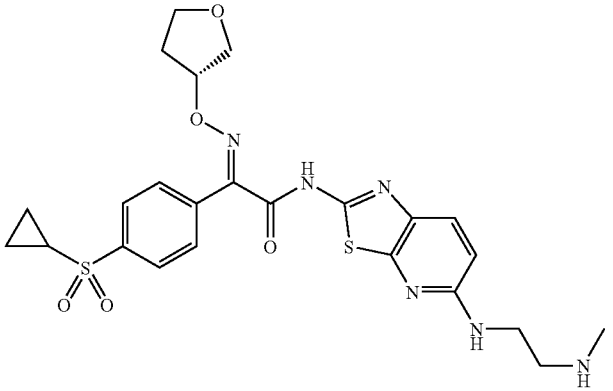 |
| 140 | 23 | 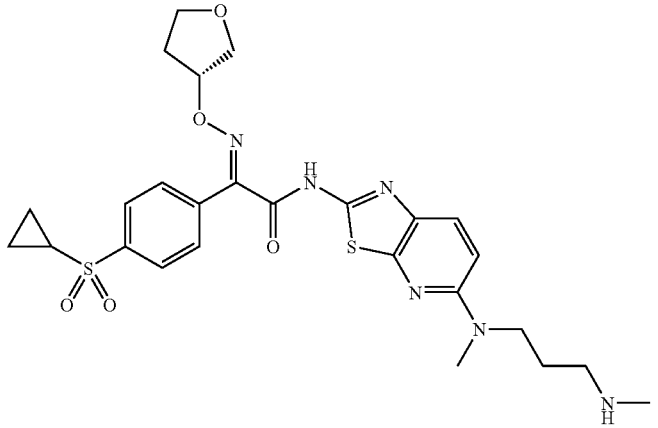 |
| 140 | 24 | 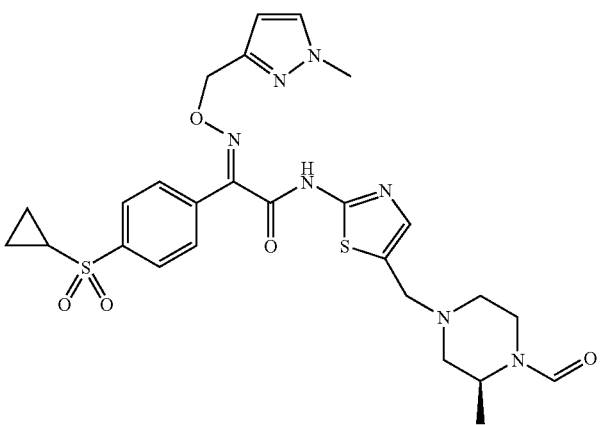 |

| EXAMPLE No. | No. | Structure |
|---|---|---|
| 140 | 25 | 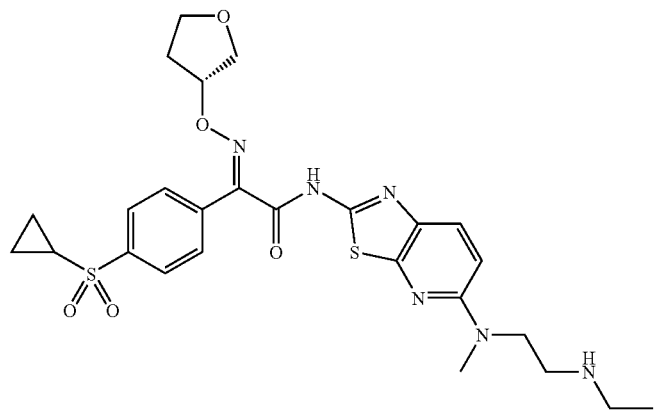 |
| 140 | 26 | 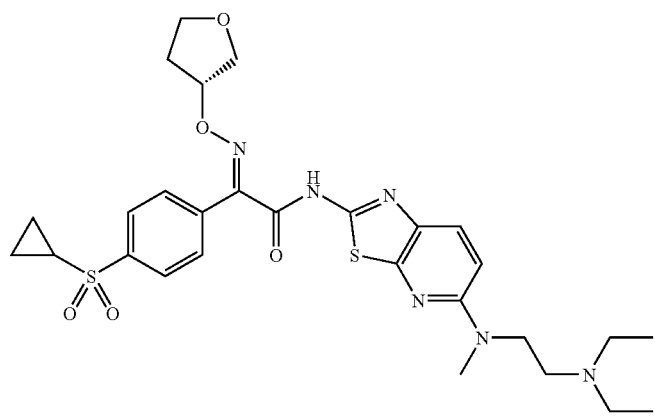 |
| 140 | 27 | 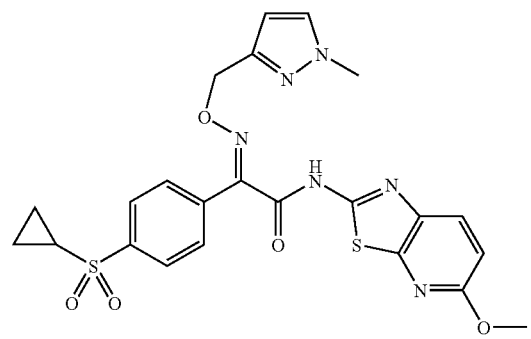 |
| 140 | 28 | 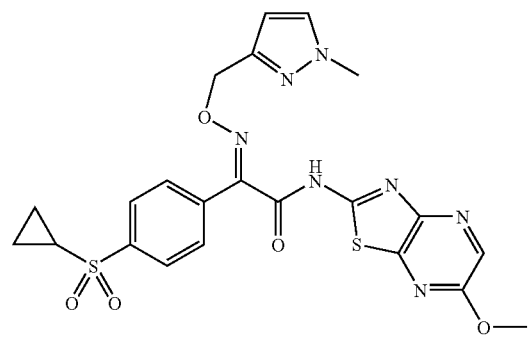 |

| EXAMPLE No. | No. | Structure |
|---|---|---|
| 140 | 29 | 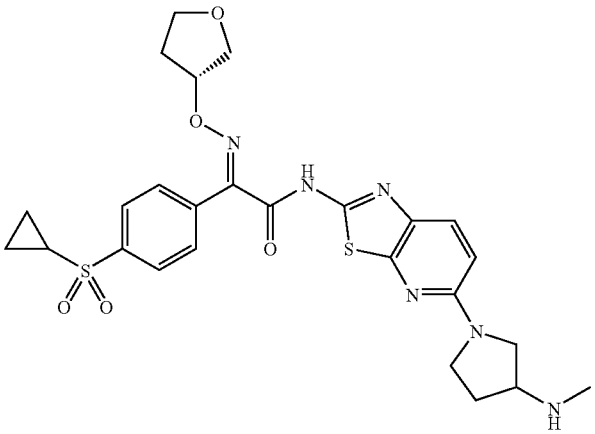 |
| 140 | 30 | 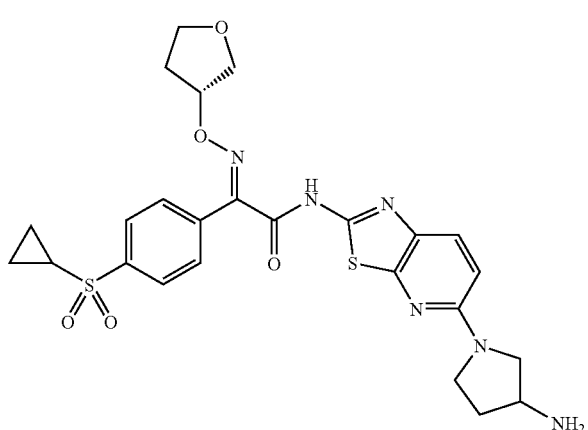 |
| 140 | 31 | 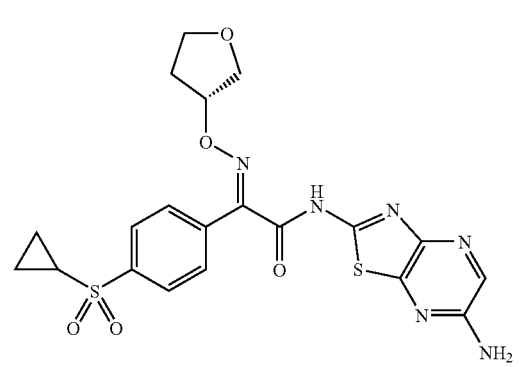 |
| 140 | 32 | 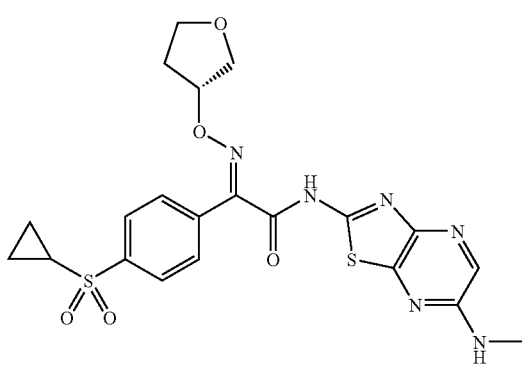 |

| EXAMPLE No. | No. | Structure |
|---|---|---|
| 140 | 33 | |
| 140 | 34 | |
| 140 | 35 | |
| 140 | 36 | |

| EXAMPLE No. | No. | Structure |
|---|---|---|
| 140 | 37 | 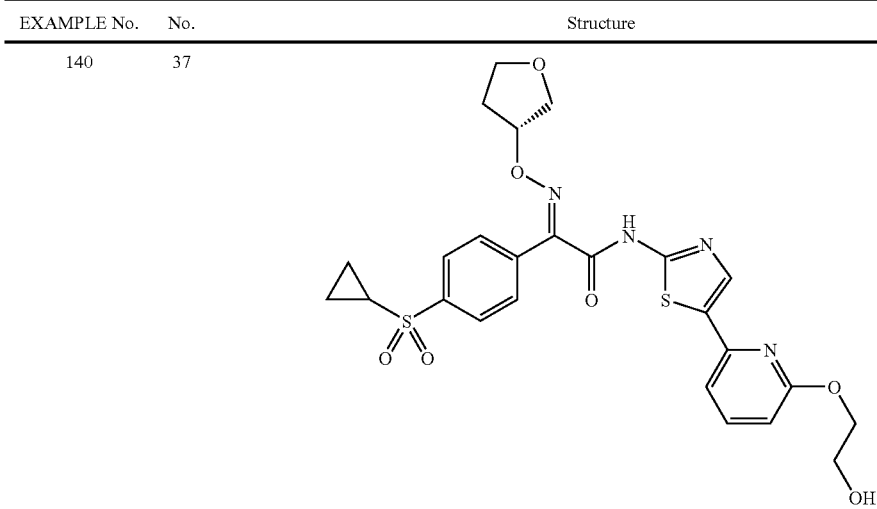 |
| 140 | 38 | 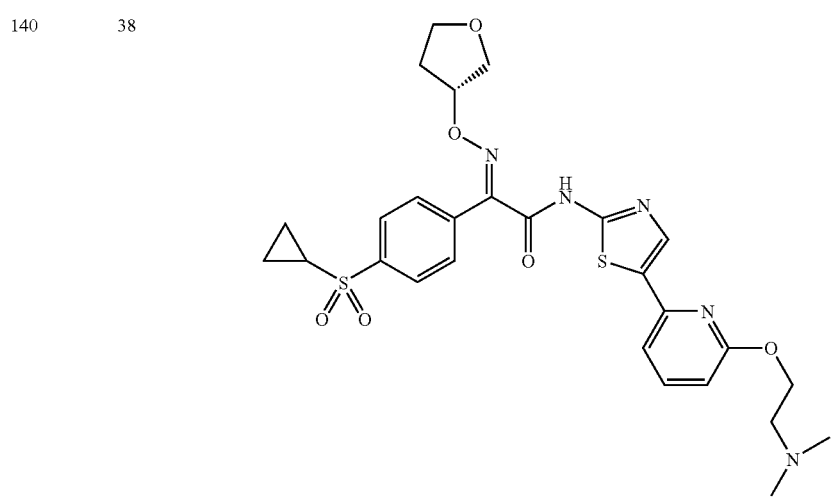 |
| 140 | 39 | 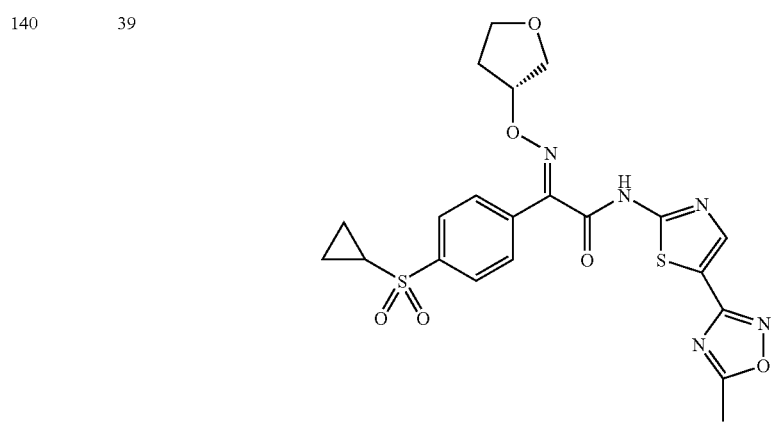 |

-continued
| EXAMPLE No. | No. | Structure |
|---|---|---|
| 140 | 40 | 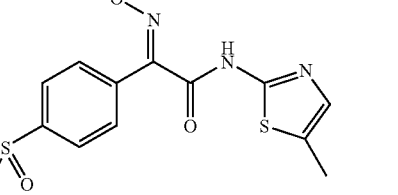 |
| 140 | 41 | 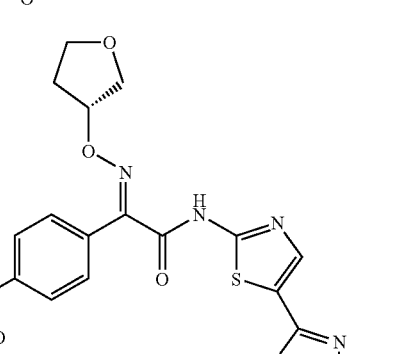 |
| 140 | 42 | 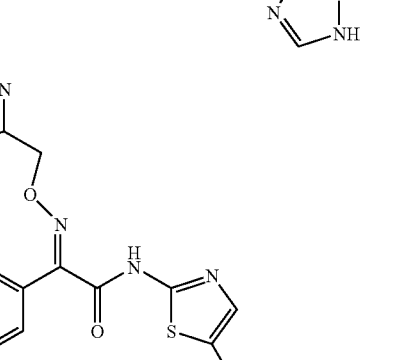 |
| 140 | 43 | 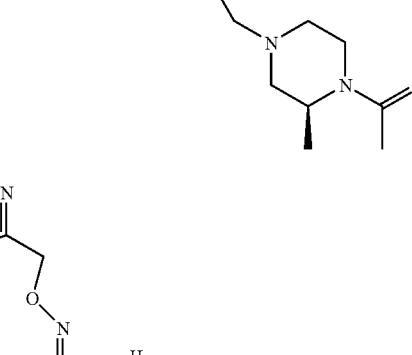 |

| EXAMPLE No. | No. | Structure |
|---|---|---|
| 140 | 44 | 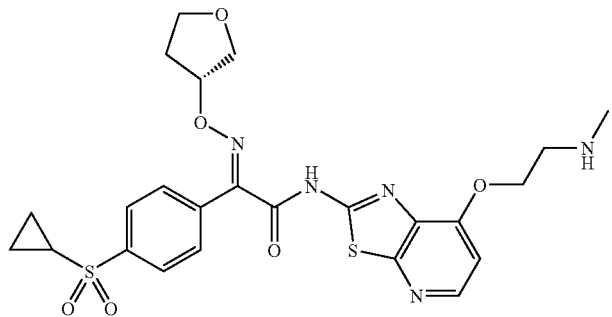 |
| 140 | 45 | 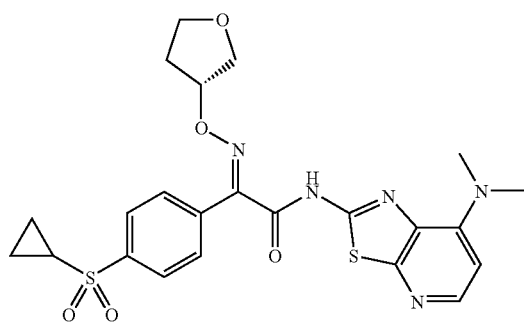 |
| 140 | 46 | 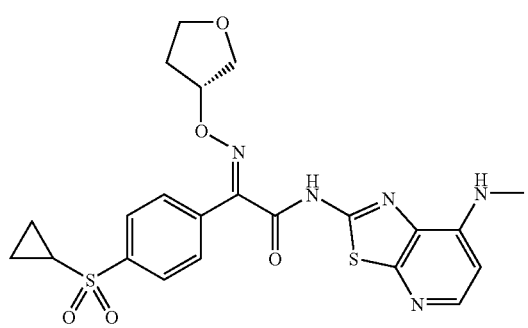 |
| 140 | 47 | 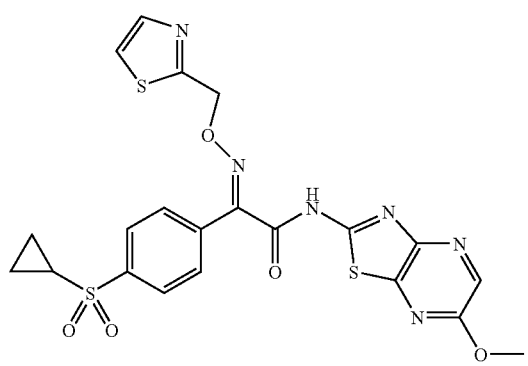 |

| EXAMPLE No. | No. | Structure |
|---|---|---|
| 140 | 48 | 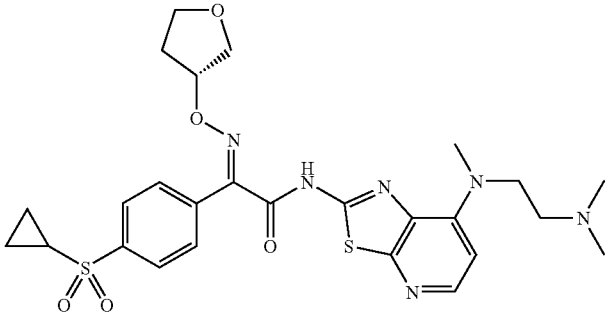 |
| 140 | 49 | 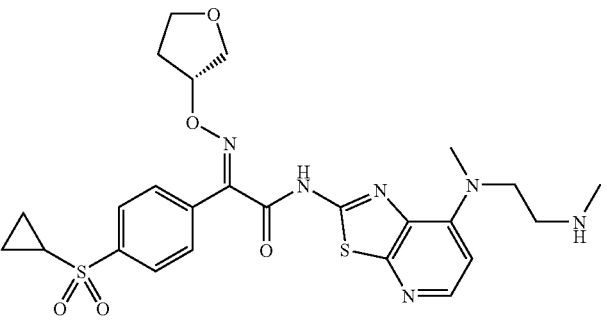 |
| 140 | 50 | 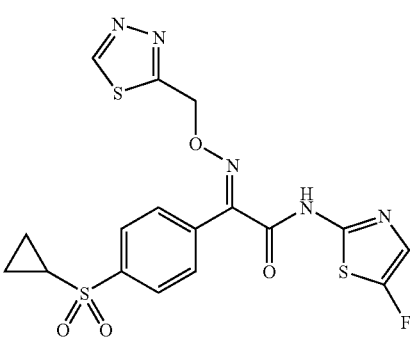 |
| 140 | 51 | 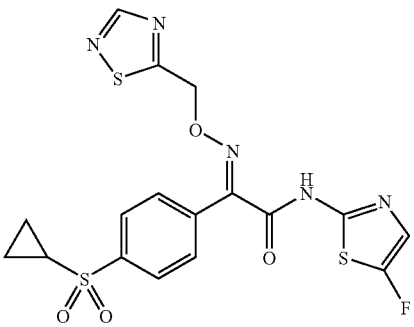 |

| EXAMPLE No. | No. | Structure |
|---|---|---|
| 140 | 52 | 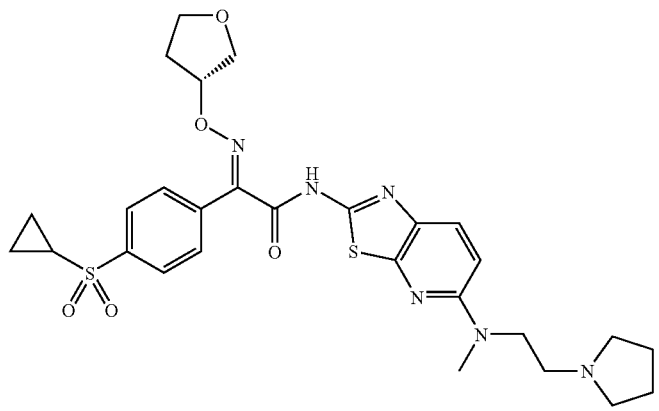 |
| 140 | 53 | 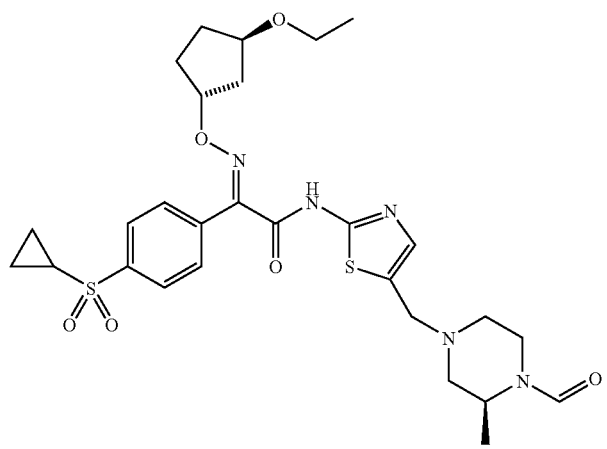 |
| 140 | 54 | 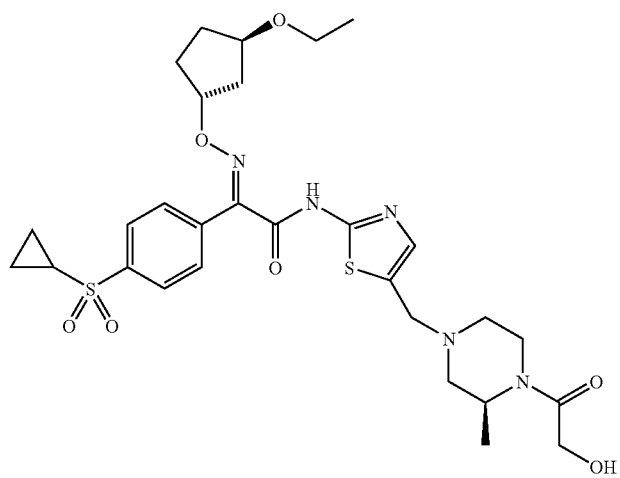 |

-continued
| EXAMPLE No. | No. | Structure |
|---|---|---|
| 140 | 55 | 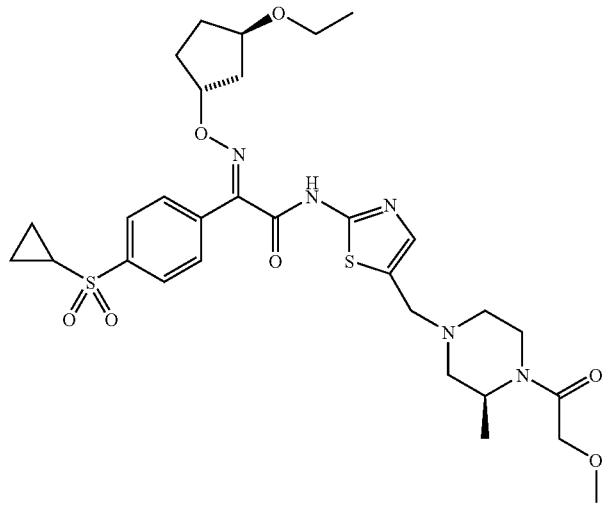 |
| 140 | 56 | 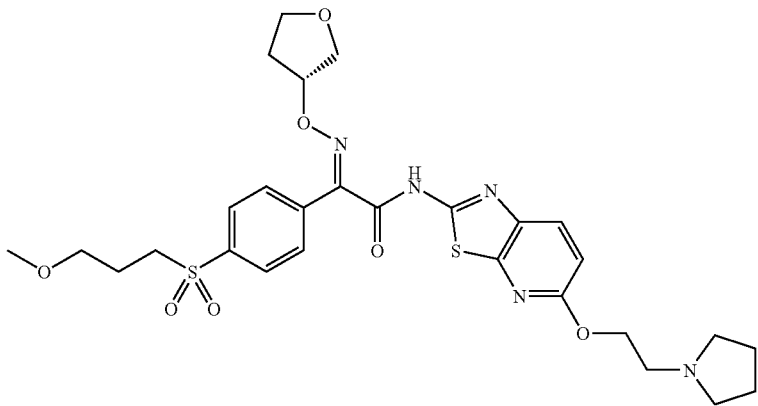 |
| 140 | 57 | 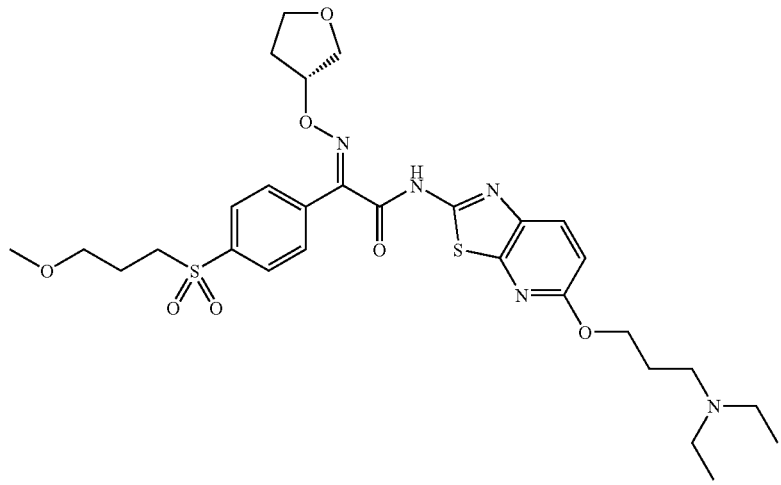 |

| EXAMPLE No. | No. | Structure |
|---|---|---|
| 140 | 58 | 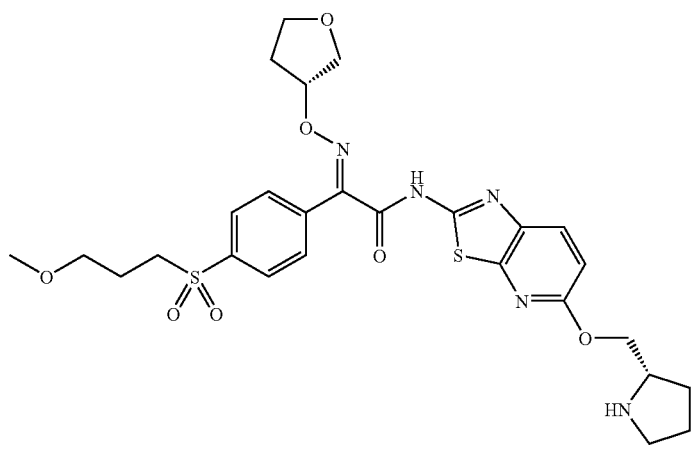 |
| 140 | 59 | 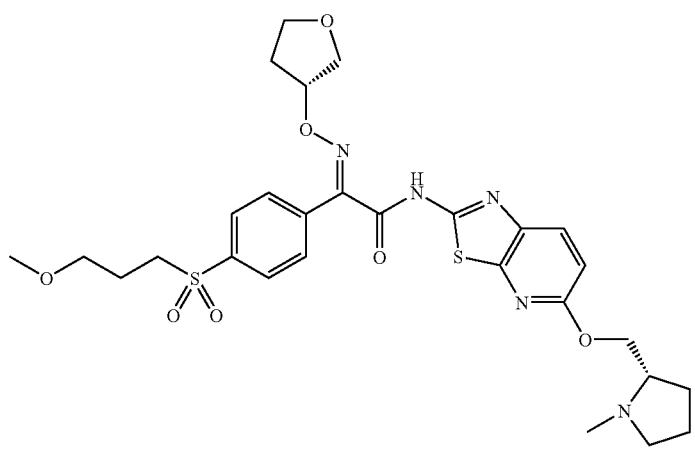 |
| 140 | 60 | 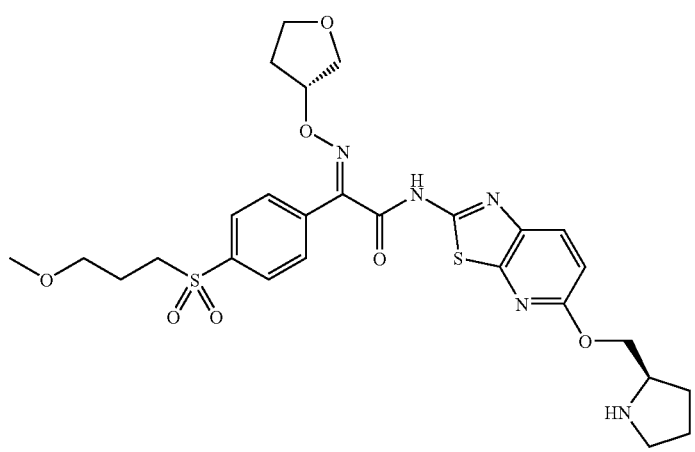 |

| EXAMPLE No. | No. | Structure |
|---|---|---|
| 140 | 61 | 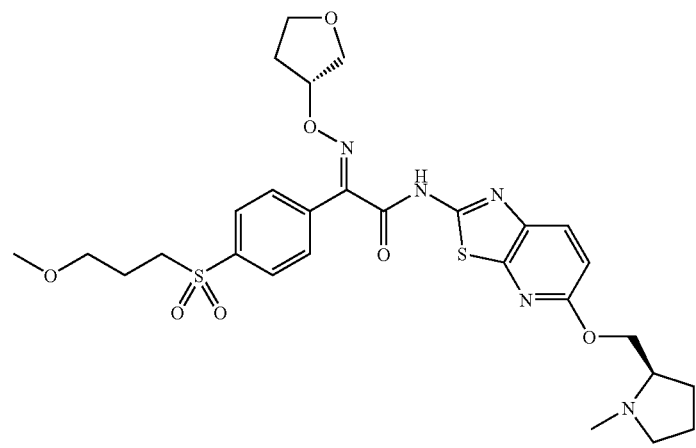 |
| 140 | 62 | 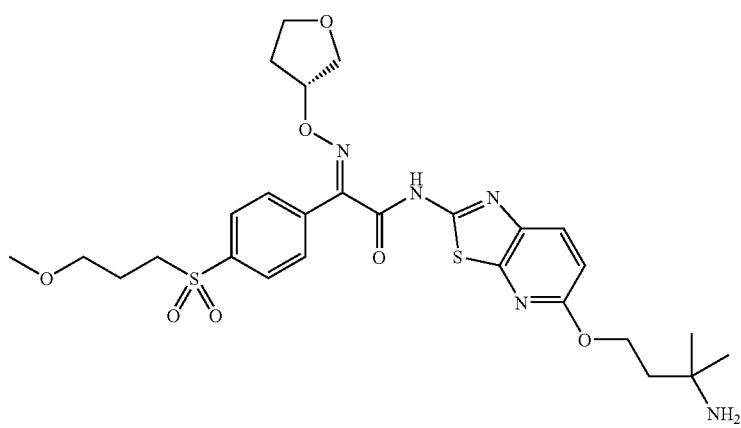 |
| 140 | 63 | 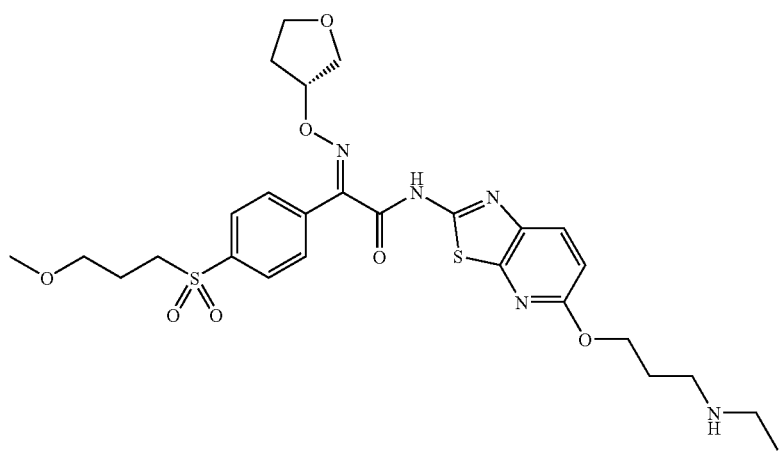 |

| EXAMPLE No. | No. | Structure |
|---|---|---|
| 140 | 64 | 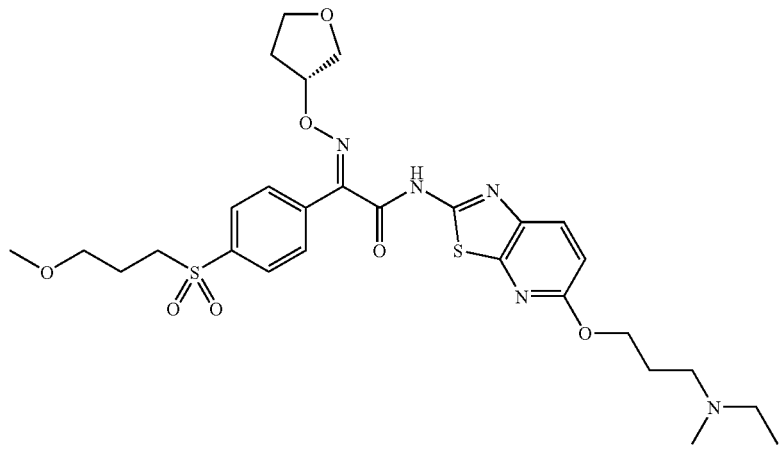 |
| 140 | 65 | 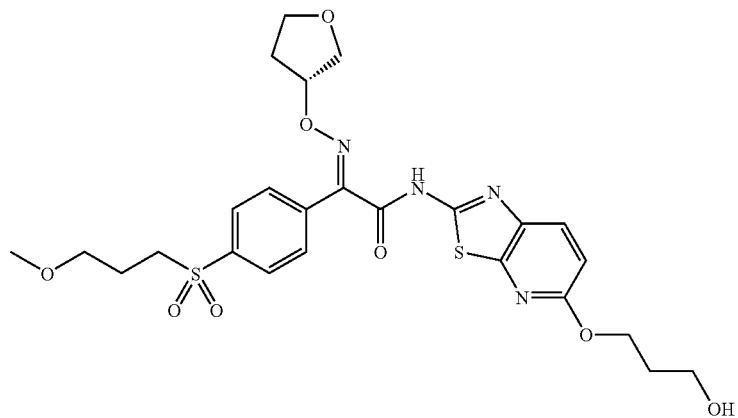 |
| 140 | 66 | 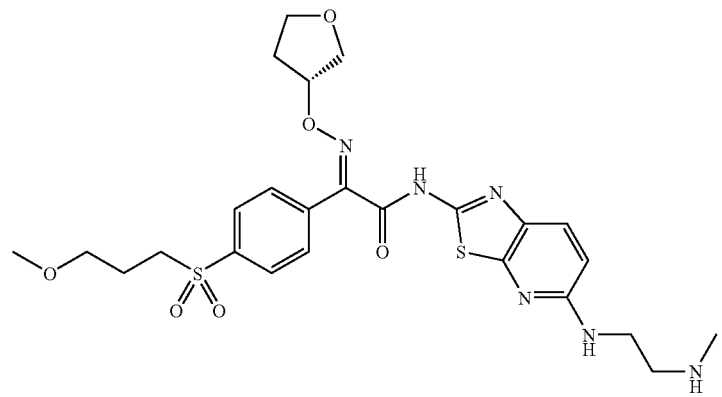 |

| EXAMPLE No. | No. | Structure |
|---|---|---|
| 140 | 67 | 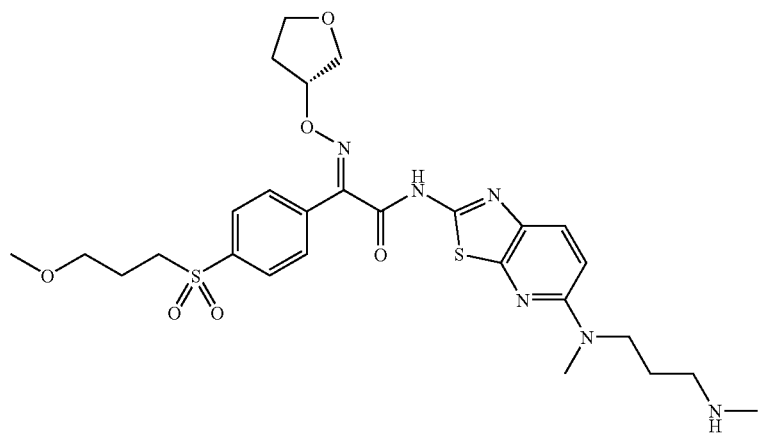 |
| 140 | 68 | 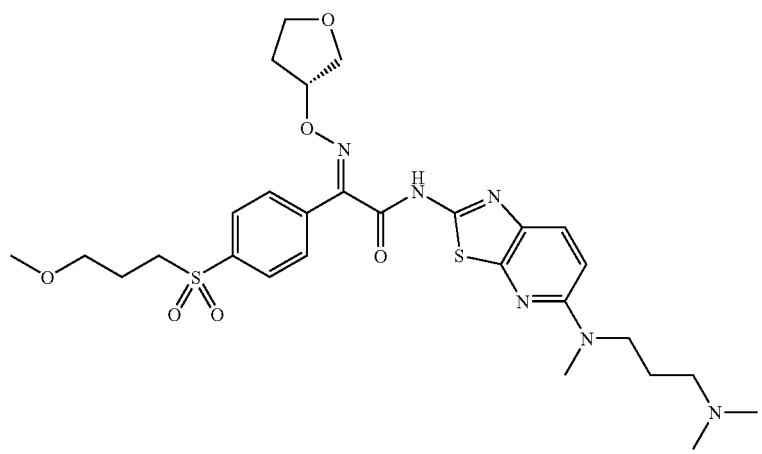 |
| 140 | 69 | 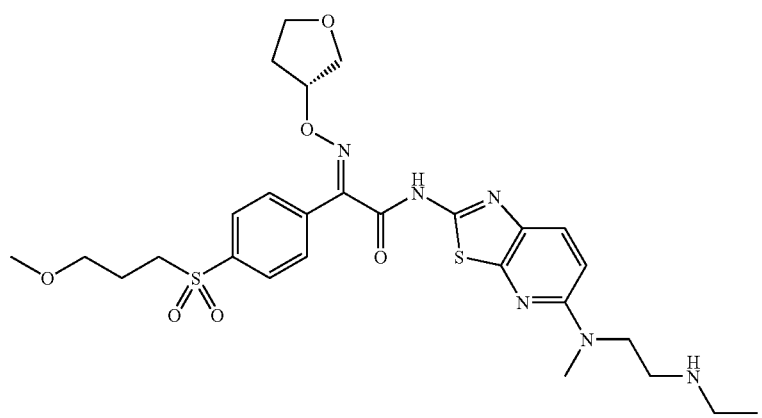 |

| EXAMPLE No. | No. | Structure |
|---|---|---|
| 140 | 70 | 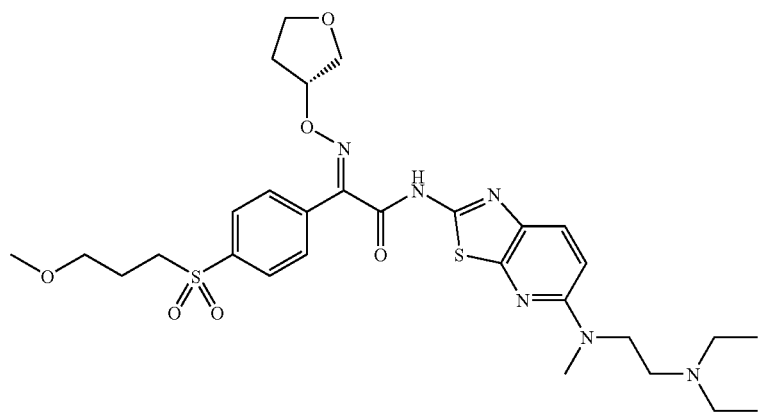 |
| 140 | 71 | 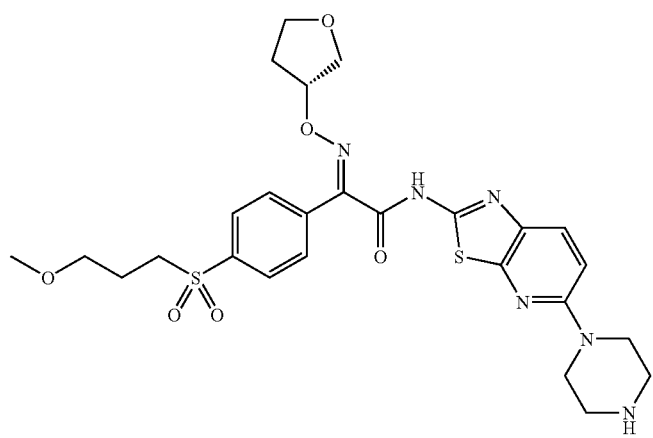 |
| 140 | 72 | 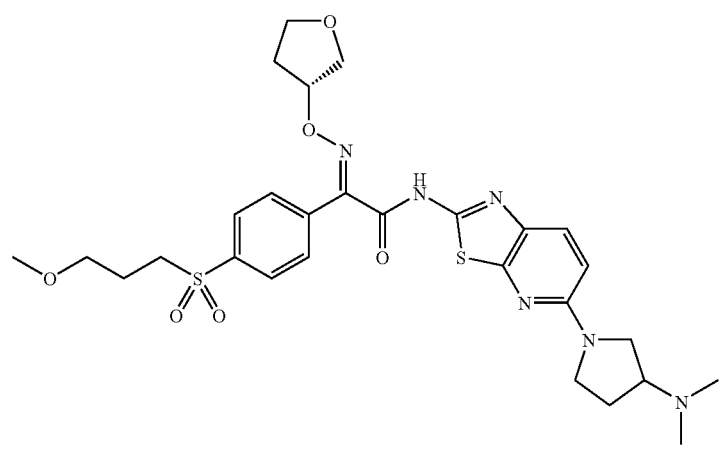 |

| EXAMPLE No. | No. | Structure |
|---|---|---|
| 140 | 73 | 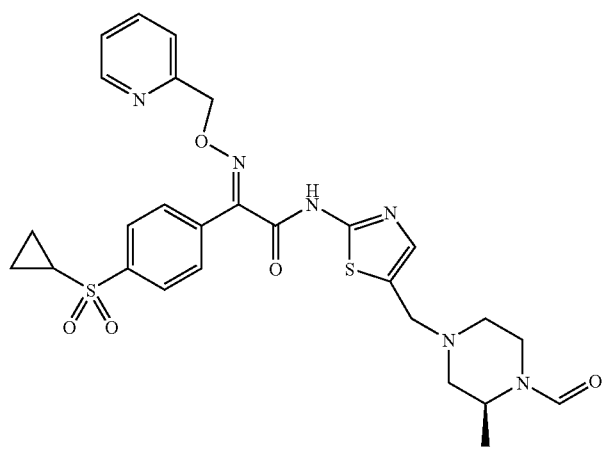 |
| 140 | 74 | 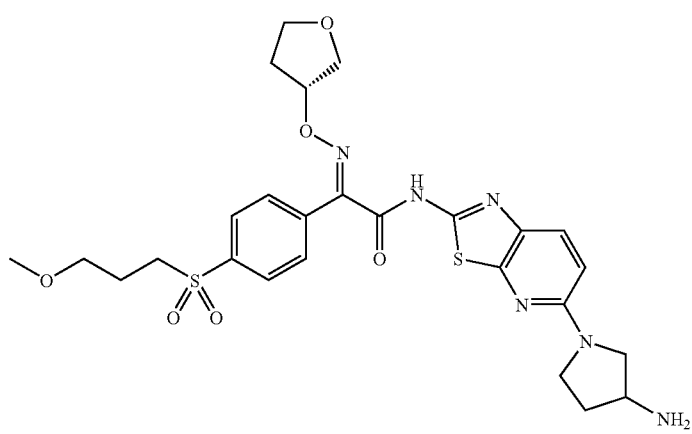 |
| 140 | 75 | 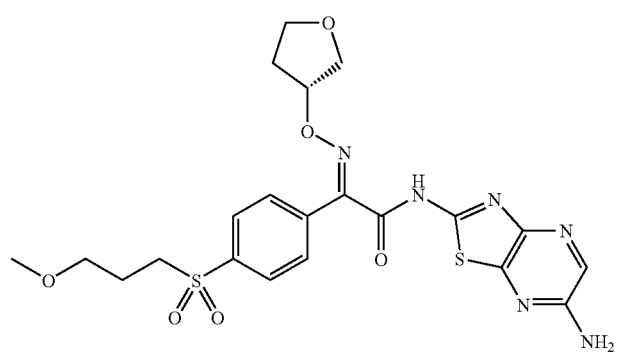 |
| 140 | 76 | 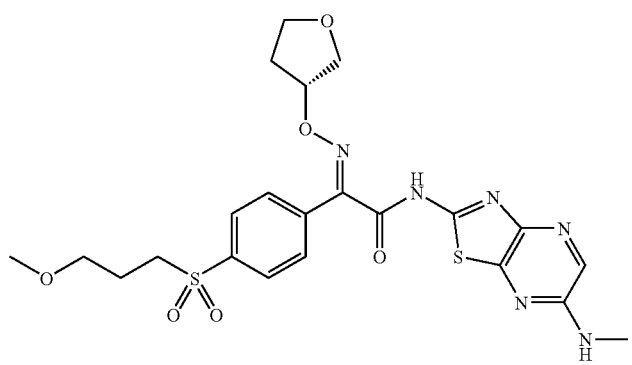 |

-continued
| EXAMPLE No. | No. | Structure |
|---|---|---|
| 140 | 77 | 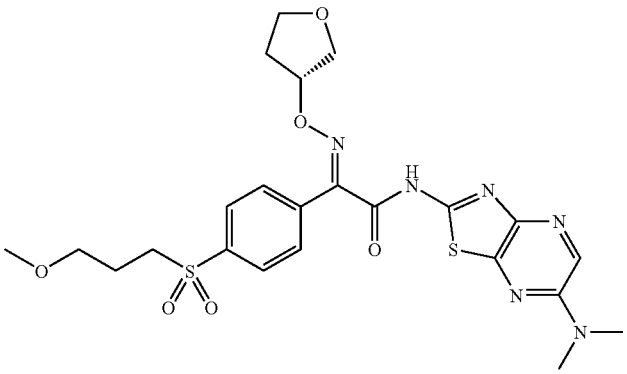 |
| 140 | 78 | 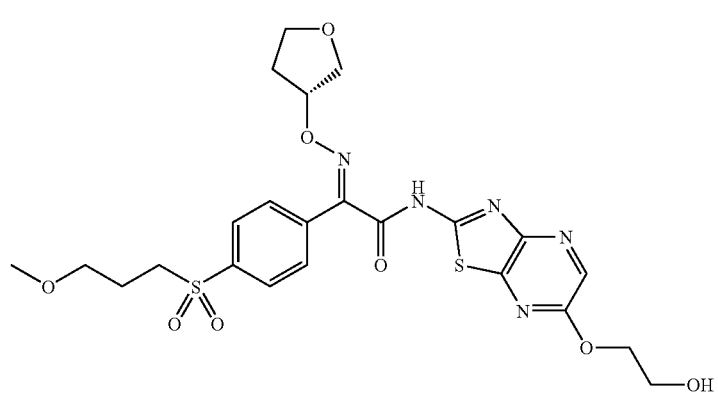 |
| 140 | 79 | 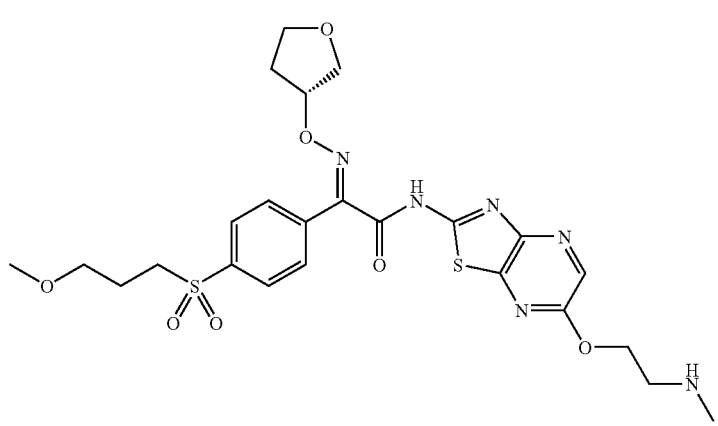 |
| 140 | 80 | 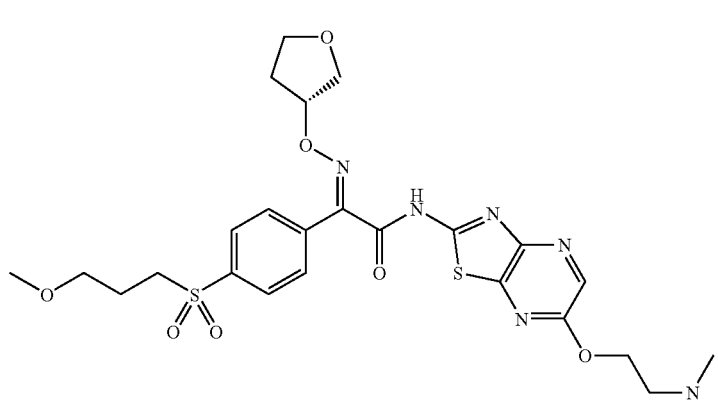 |

| EXAMPLE No. | No. | Structure |
|---|---|---|
| 140 | 81 | 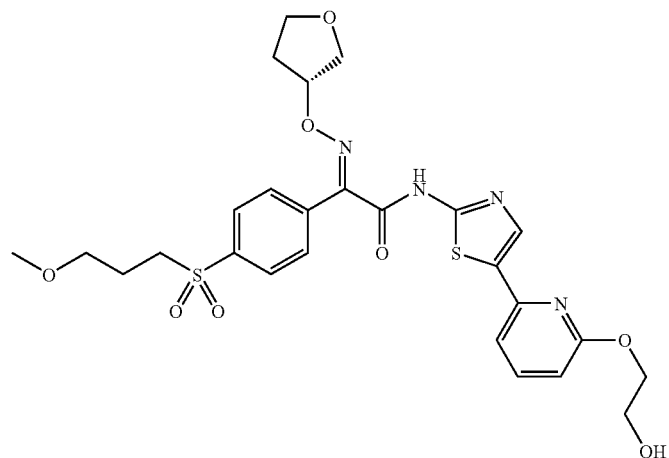 |
| 140 | 82 | 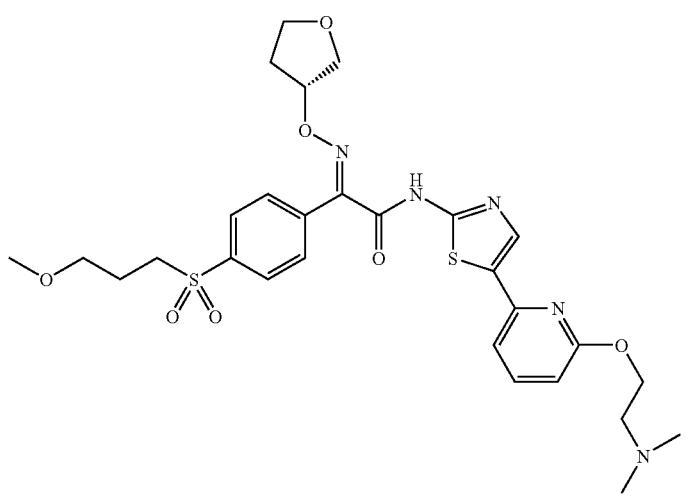 |
| 140 | 83 | 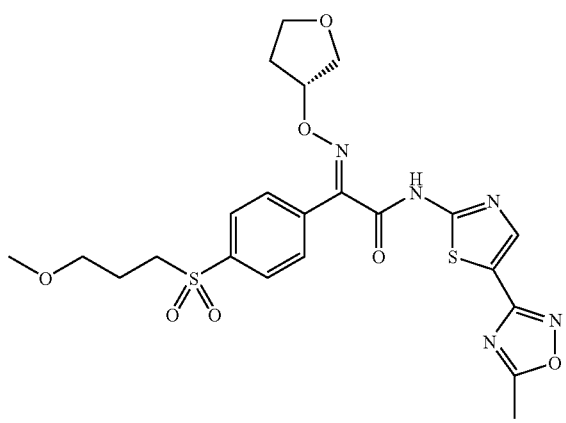 |

| EXAMPLE No. | No. | Structure |
|---|---|---|
| 140 | 84 | 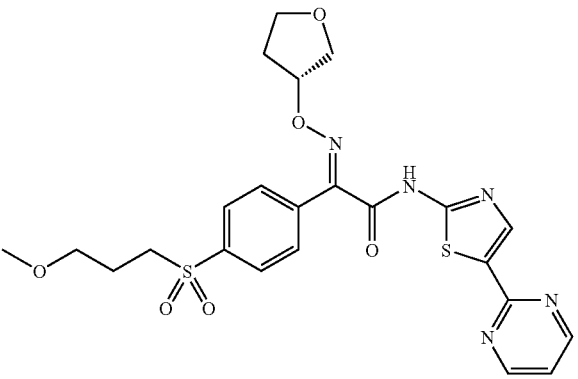 |
| 140 | 85 | 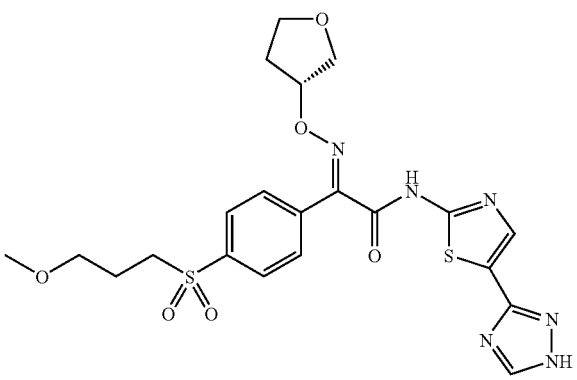 |
| 140 | 86 | 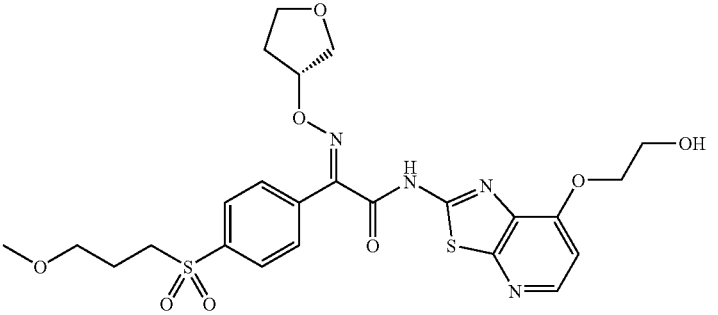 |
| 140 | 87 | 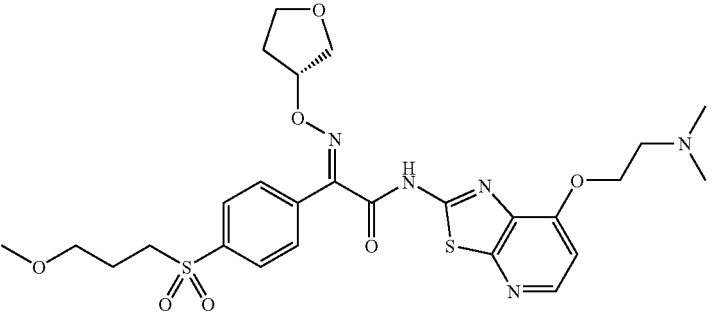 |

-continued
| EXAMPLE No. | No. | Structure |
|---|---|---|
| 140 | 88 | 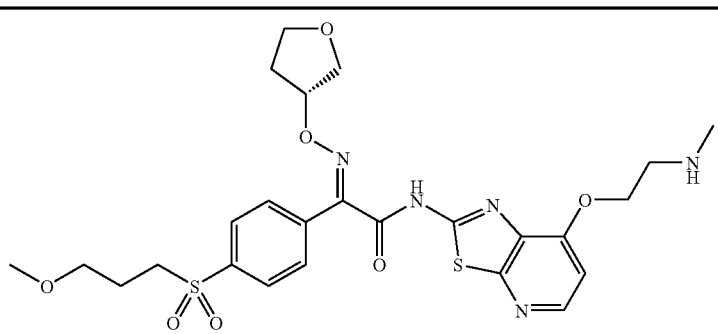 |
| 140 | 89 | 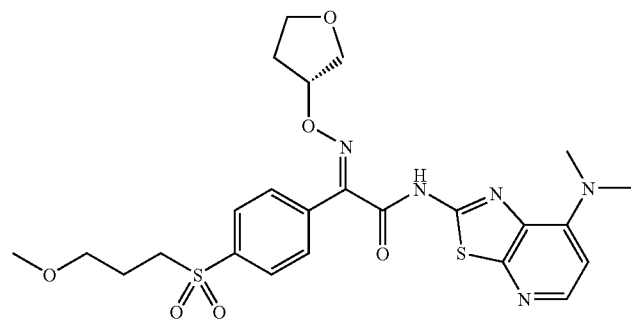 |
| 140 | 90 | 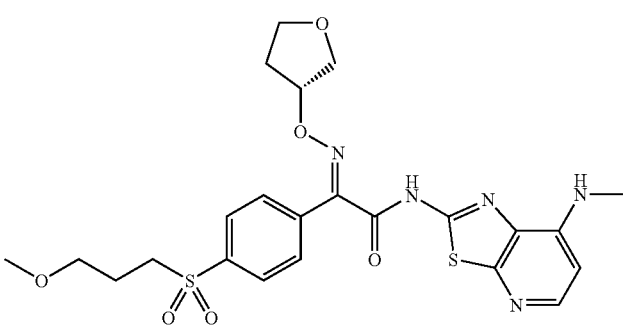 |
| 140 | 91 | 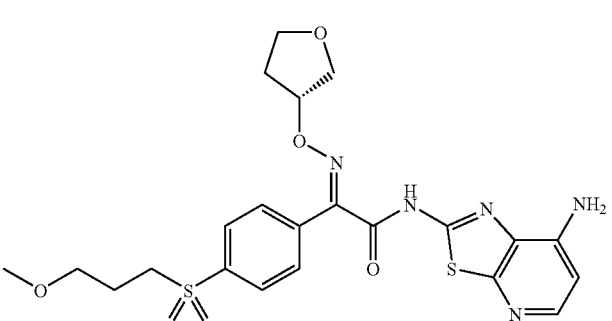 |

| EXAMPLE No. | No. | Structure |
|---|---|---|
| 140 | 92 | 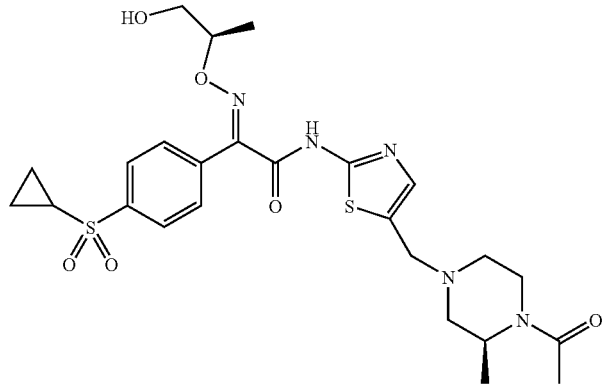 |
| 140 | 93 | 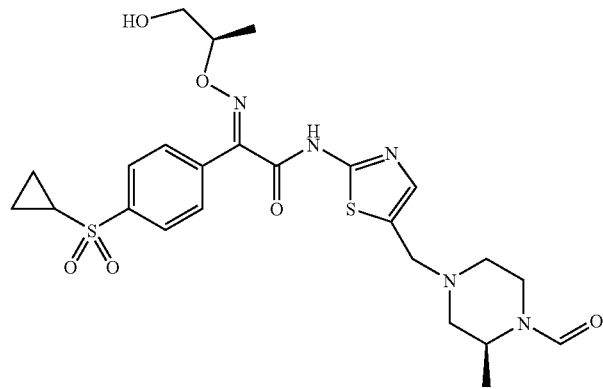 |
| 140 | 94 | 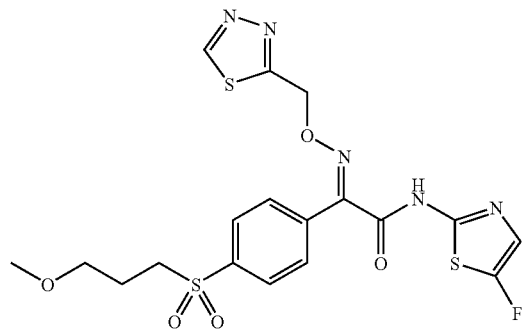 |
| 140 | 95 | 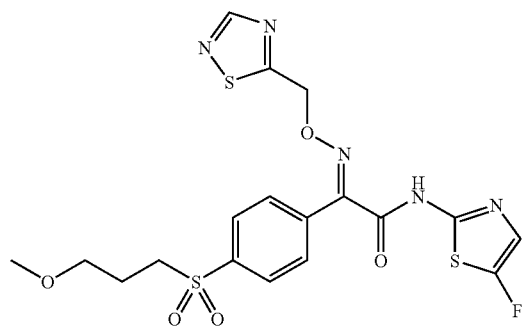 |

| EXAMPLE No. | No. | Structure |
|---|---|---|
| 140 | 96 | 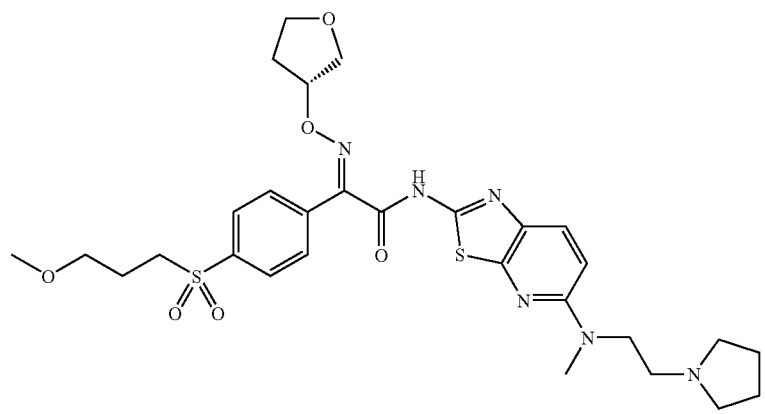 |
| 140 | 97 | 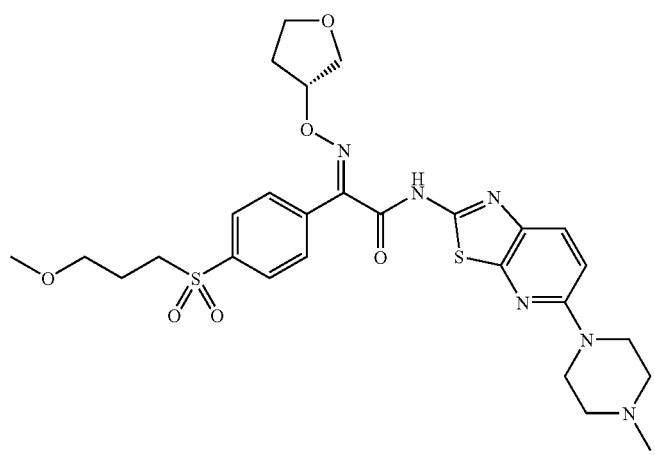 |
| 140 | 98 | 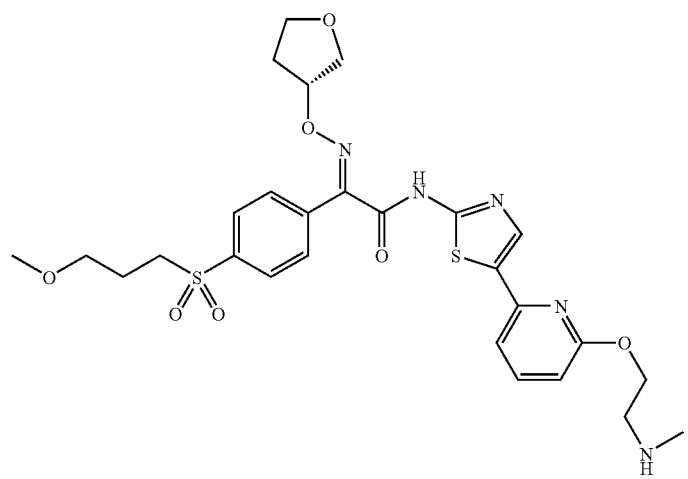 |

| EXAMPLE No. | No. | Structure |
|---|---|---|
| 140 | 99 | |
| 140 | 100 | |
| 140 | 101 | |
| 140 | 102 | |

-continued

| EXAMPLE No. | No. | Structure |
|---|---|---|
| 140 | 103 | |
| 140 | 104 | |
| 140 | 105 | |
| 140 | 106 | |

-continued
| EXAMPLE No. | No. | Structure |
|---|---|---|
| 140 | 107 | 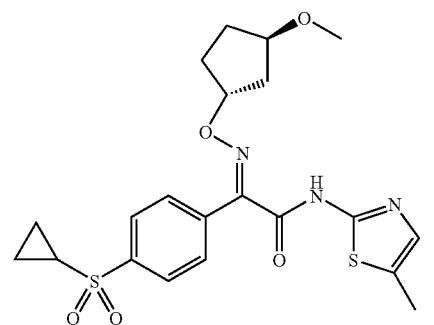 |
| 140 | 108 | 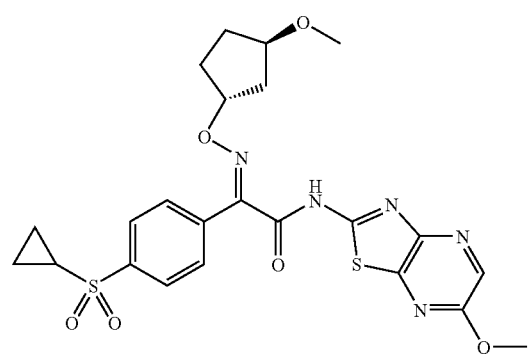 |
| 140 | 109 | 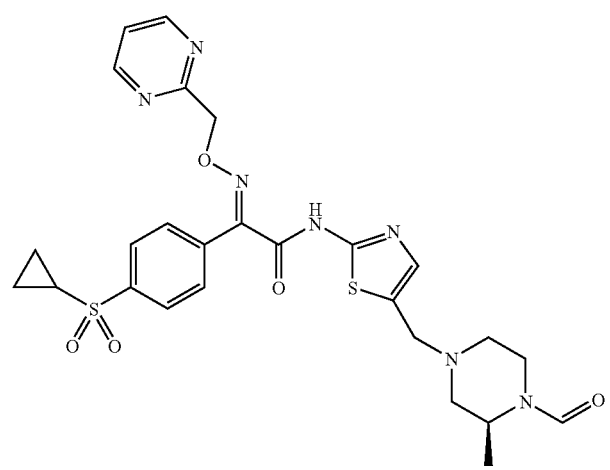 |
| 140 | 110 | 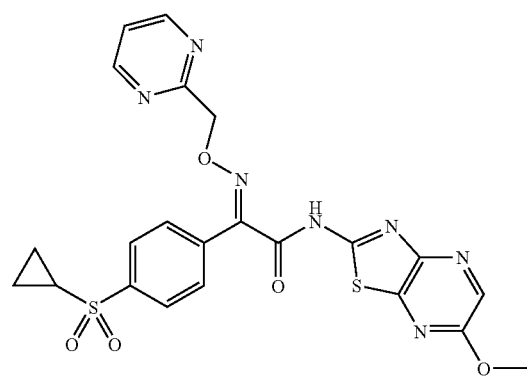 |

| EXAMPLE No. | No. | Structure |
|---|---|---|
| 140 | 111 | 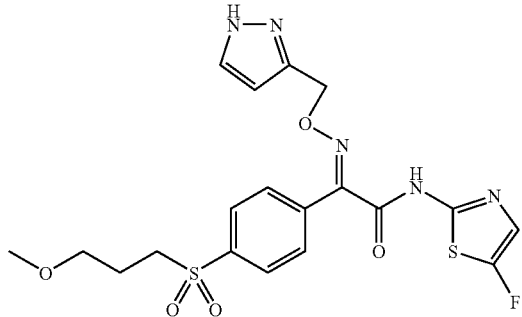 |
| 140 | 112 | 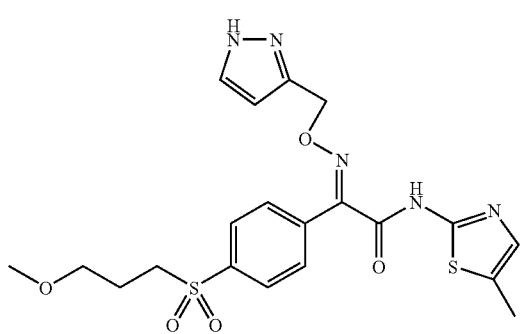 |
| 140 | 113 | 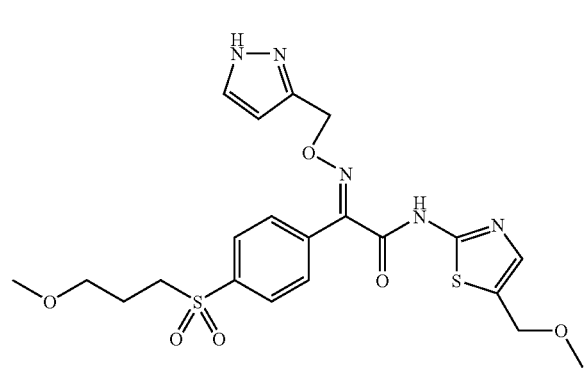 |
| 140 | 114 | 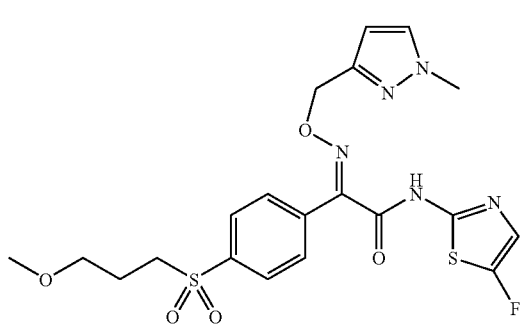 |

| EXAMPLE No. | No. | Structure |
|---|---|---|
| 140 | 115 | 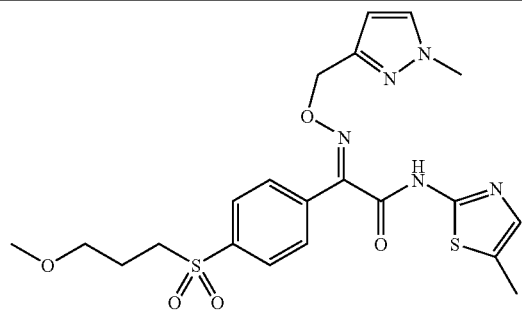 |
| 140 | 116 | 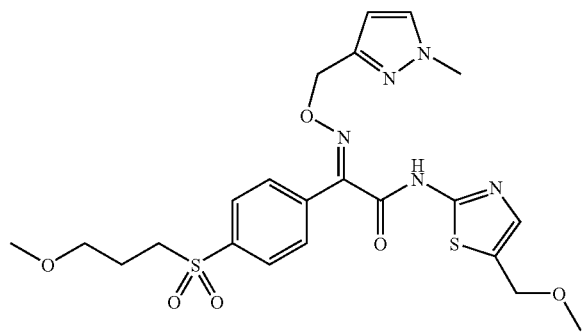 |
| 140 | 117 | 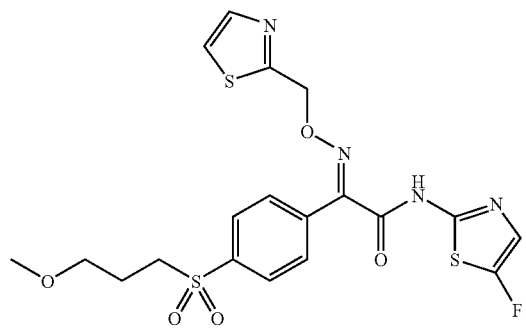 |
| 140 | 118 | 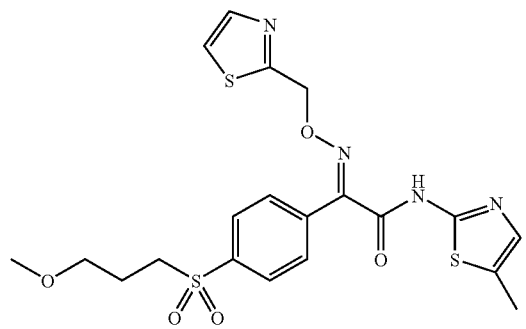 |

-continued
| EXAMPLE No. | No. | Structure |
|---|---|---|
| 140 | 119 | 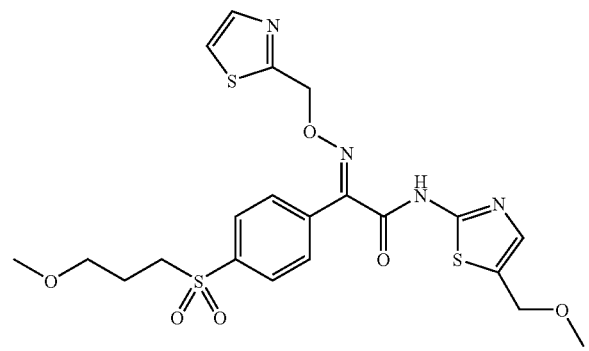 |
| 140 | 120 | 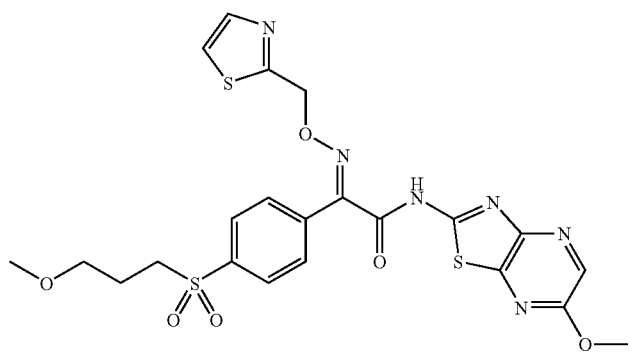 |
| 140 | 121 | 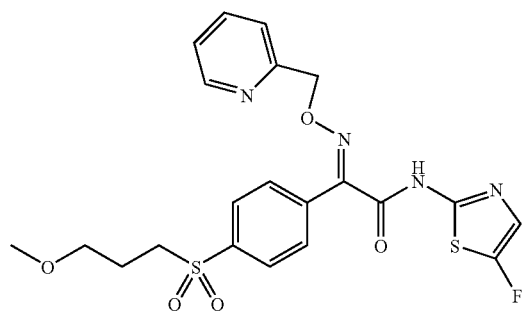 |
| 140 | 122 | 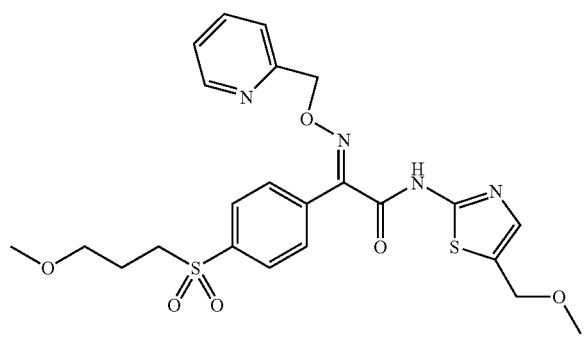 |

| EXAMPLE No. | No. | Structure |
|---|---|---|
| 140 | 123 | 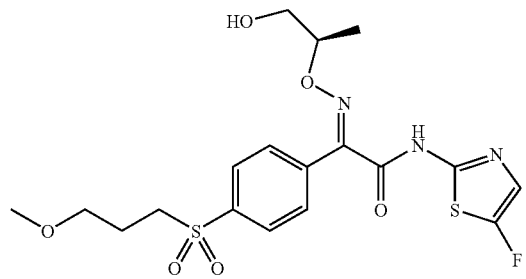 |
| 140 | 124 | 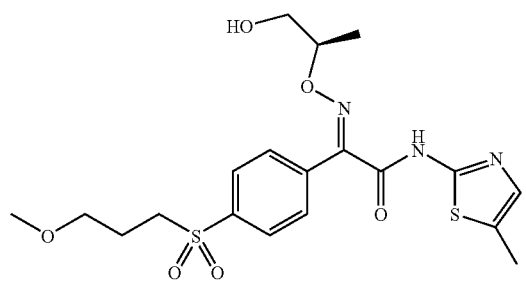 |
| 140 | 125 | 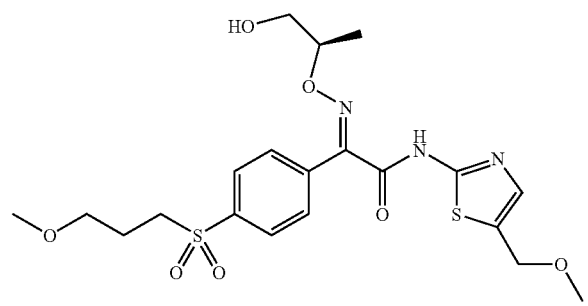 |
| 140 | 126 | 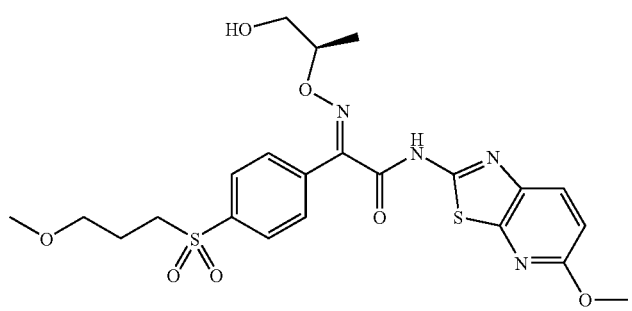 |
| 140 | 127 | 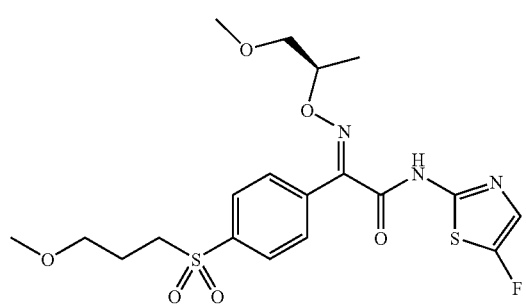 |

| EXAMPLE No. | No. | Structure |
|---|---|---|
| 140 | 128 | 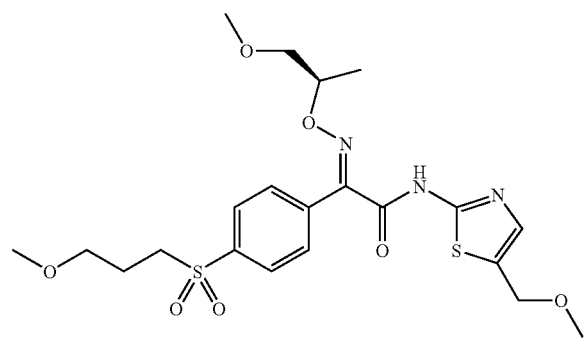 |
| 140 | 129 | 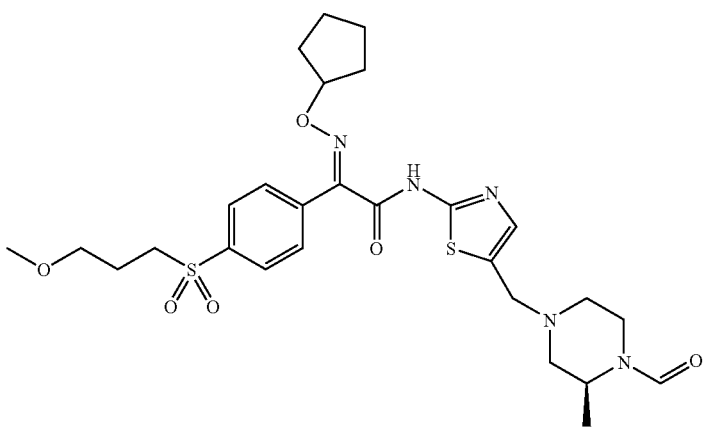 |
| 140 | 130 | 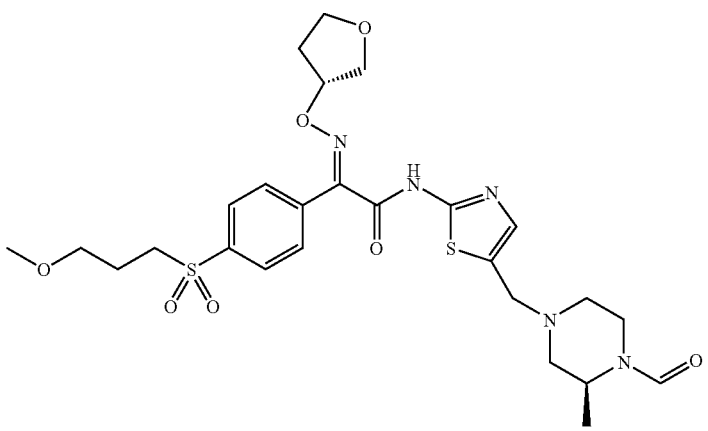 |
| 140 | 131 | 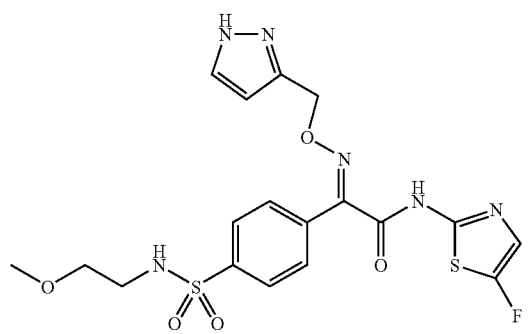 |

| EXAMPLE No. | No. | Structure |
|---|---|---|
| 140 | 132 | 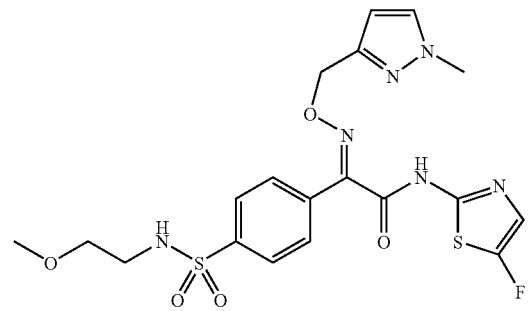 |
| 140 | 133 | 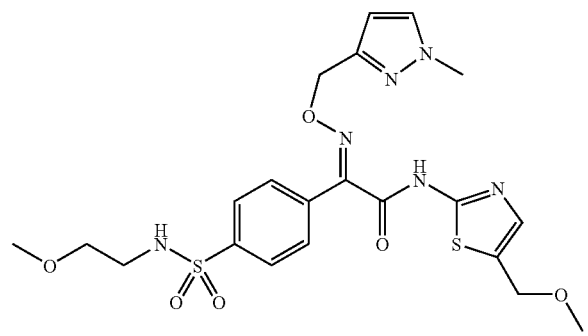 |
| 140 | 134 | 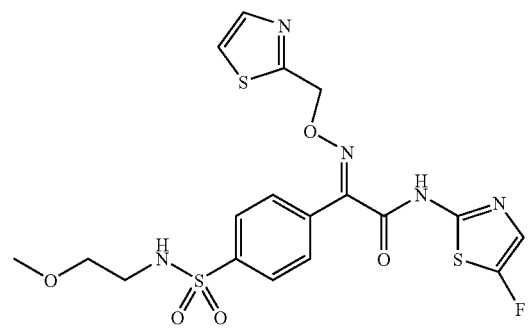 |
| 140 | 135 | 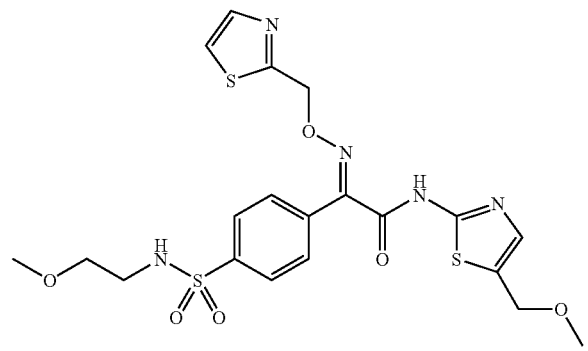 |

-continued
| EXAMPLE No. | No. | Structure |
|---|---|---|
| 140 | 136 | 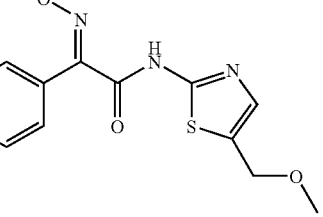 |
| 140 | 137 | 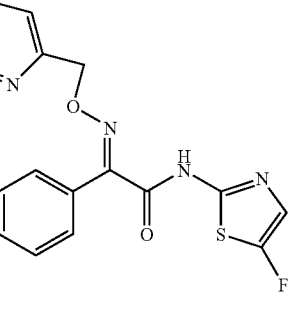 |
| 140 | 138 | 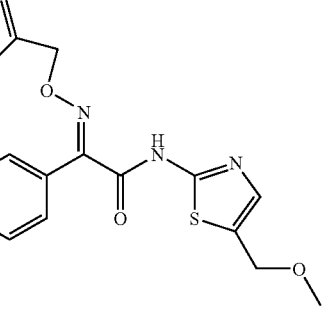 |
| 140 | 139 | 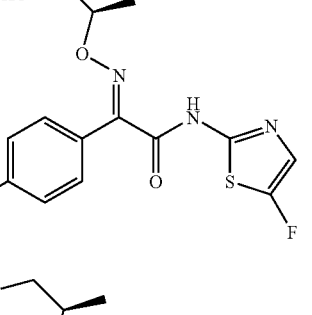 |
| 140 | 140 | 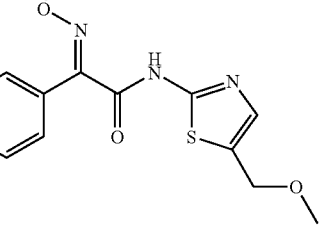 |

-continued
| EXAMPLE No. | No. | Structure |
|---|---|---|
| 140 | 141 | 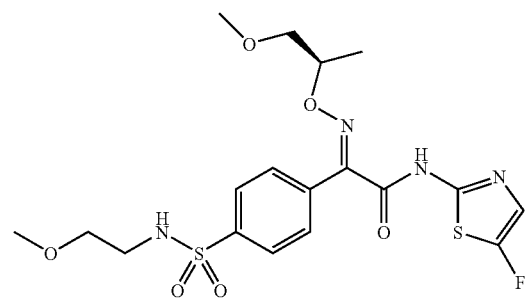 |
| 140 | 142 | 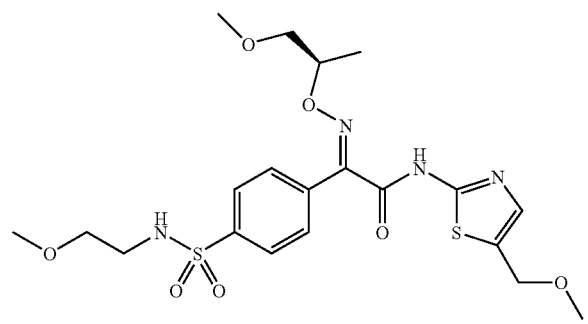 |
| 140 | 143 | 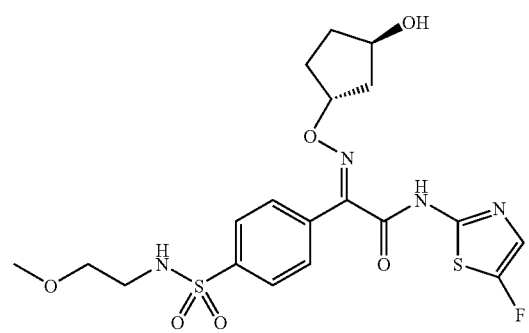 |
| 140 | 144 | 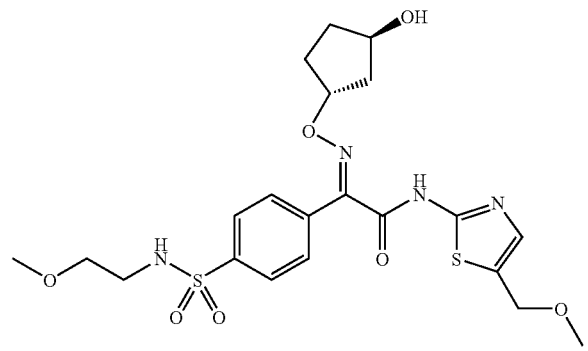 |

| EXAMPLE No. | No. | Structure |
|---|---|---|
| 140 | 145 | 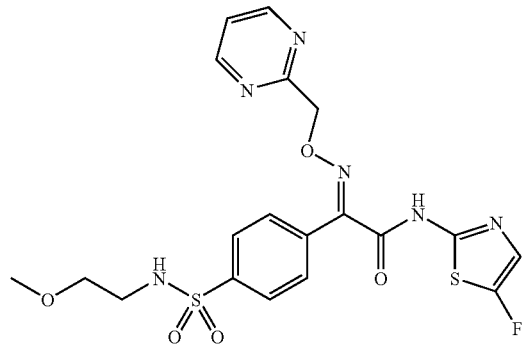 |
| 140 | 146 | 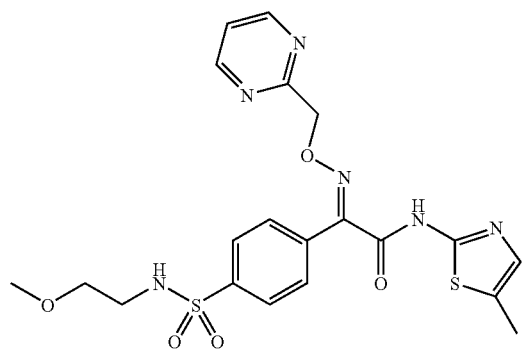 |
| 140 | 147 | 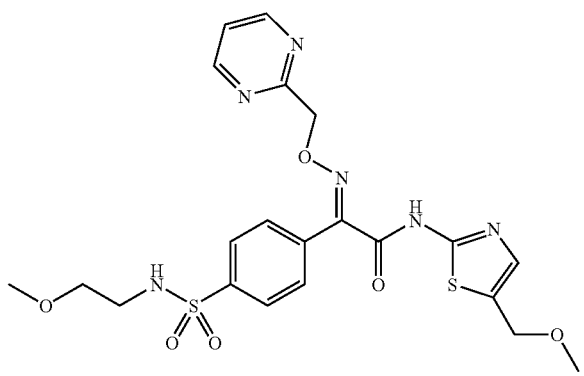 |
| 140 | 148 | 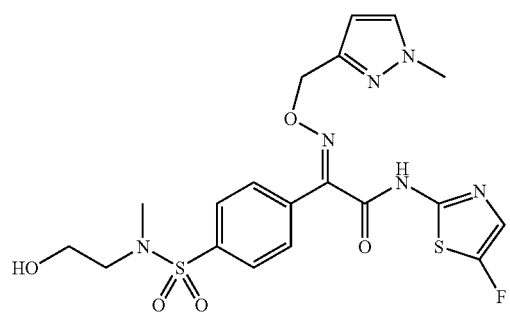 |

| EXAMPLE No. | No. | Structure |
|---|---|---|
| 140 | 149 | 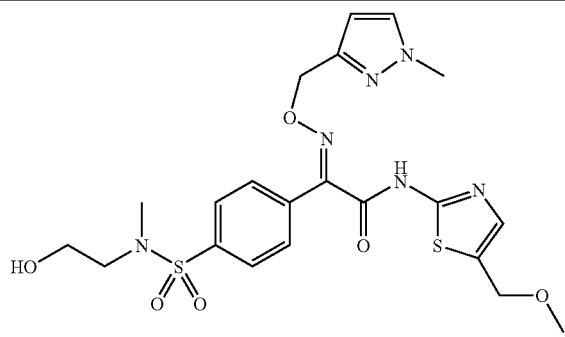 |
| 140 | 150 | 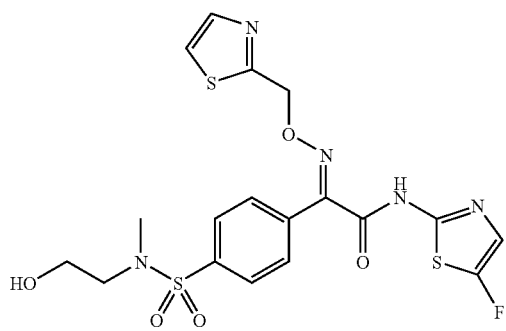 |
| 140 | 151 | 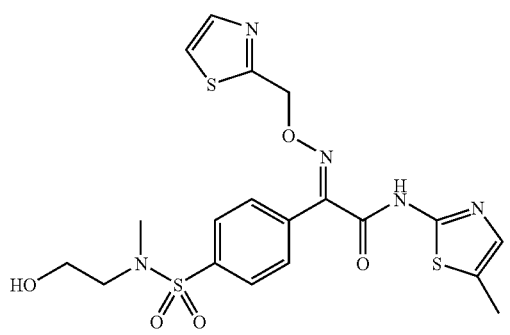 |
| 140 | 152 | 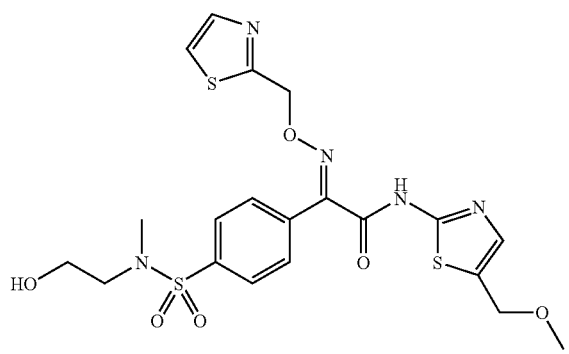 |

| EXAMPLE No. | No. | Structure |
|---|---|---|
| 140 | 153 | 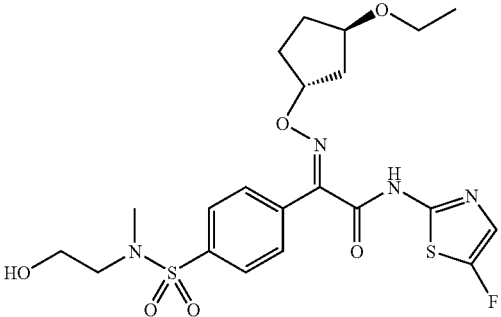 |
| 140 | 154 | 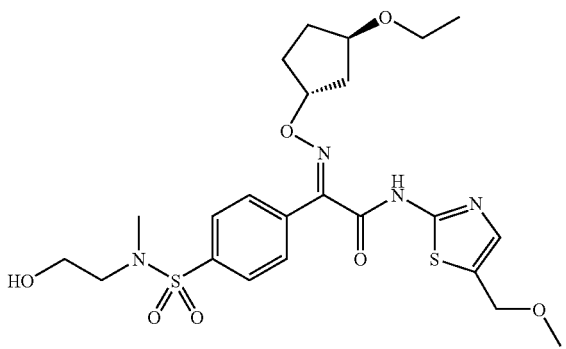 |
| 140 | 155 | 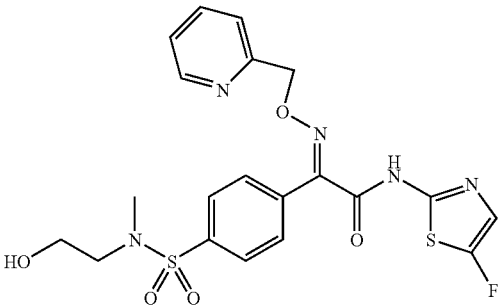 |
| 140 | 156 | 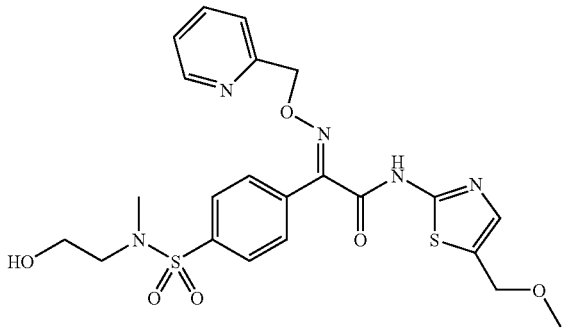 |
| 140 | 157 | 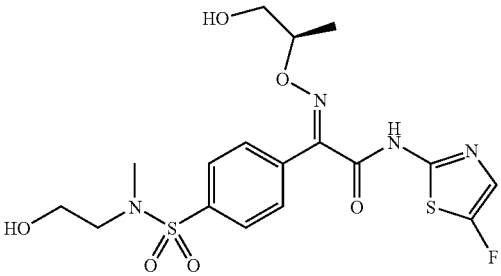 |

| EXAMPLE No. | No. | Structure |
|---|---|---|
| 140 | 158 | 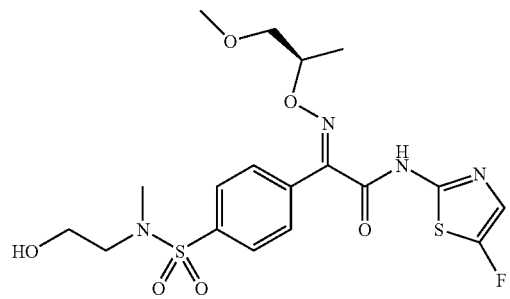 |
| 140 | 159 | 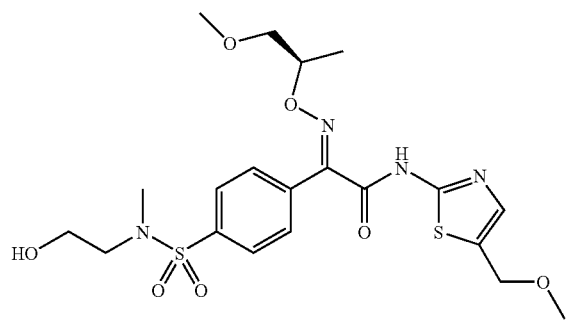 |
| 140 | 160 | 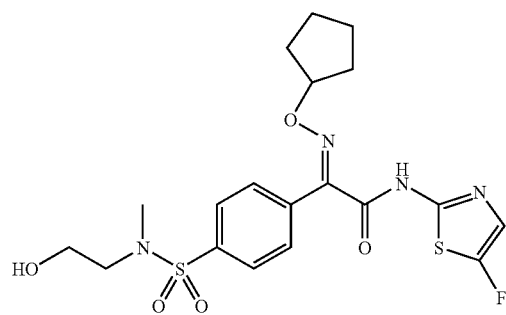 |
| 140 | 161 | 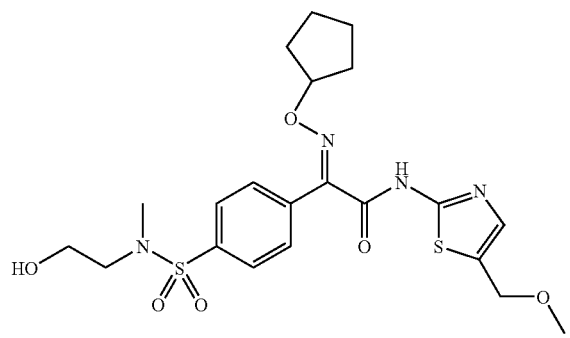 |

-continued
| EXAMPLE No. | No. | Structure |
|---|---|---|
| 140 | 162 | 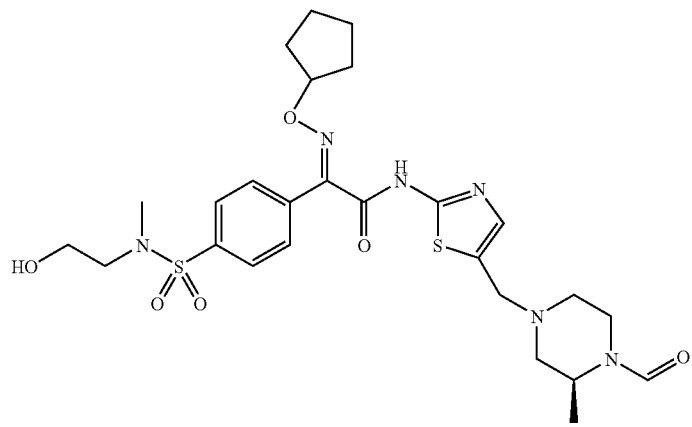 |
| 140 | 163 | 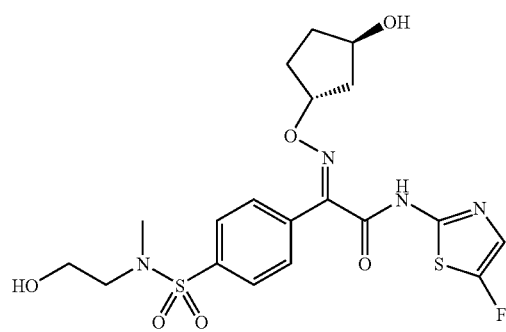 |
| 140 | 164 | 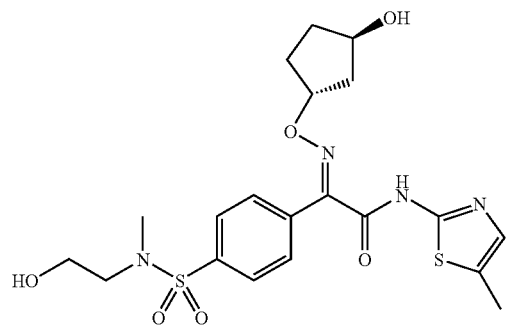 |
| 140 | 165 | 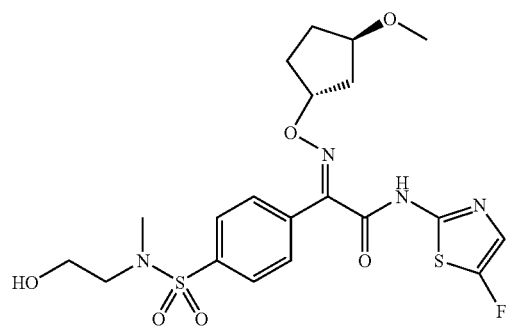 |

| EXAMPLE No. | No. | Structure |
|---|---|---|
| 140 | 166 | 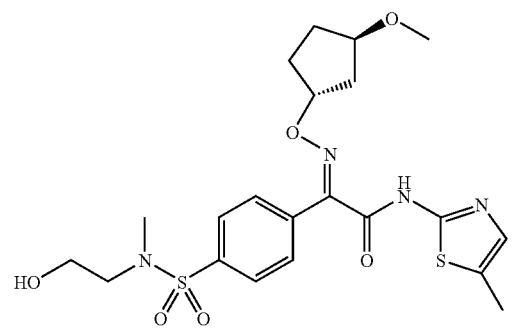 |
| 140 | 167 | 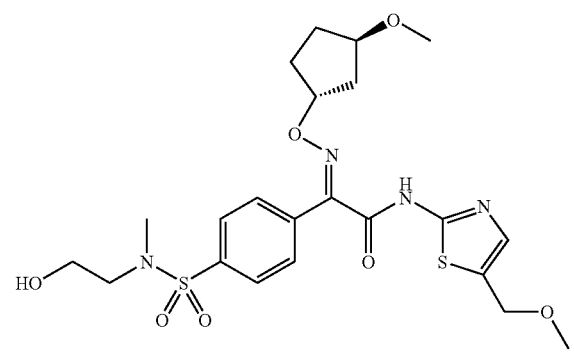 |
| 140 | 168 | 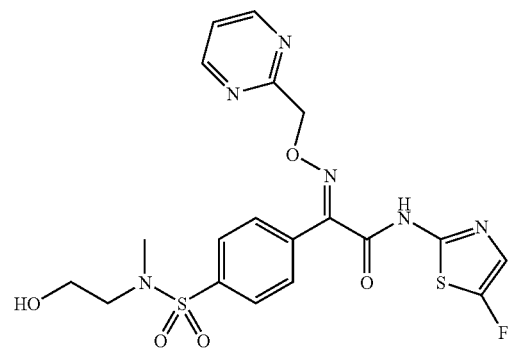 |
| 140 | 169 | 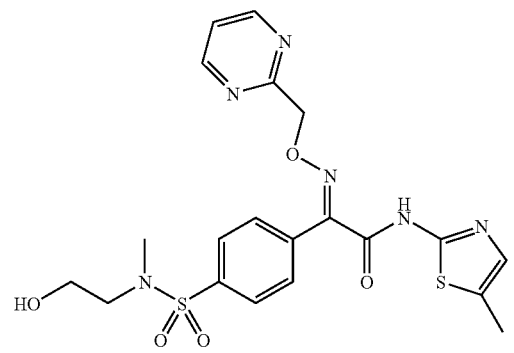 |

| EXAMPLE No. | No. | Structure |
|---|---|---|
| 140 | 170 | 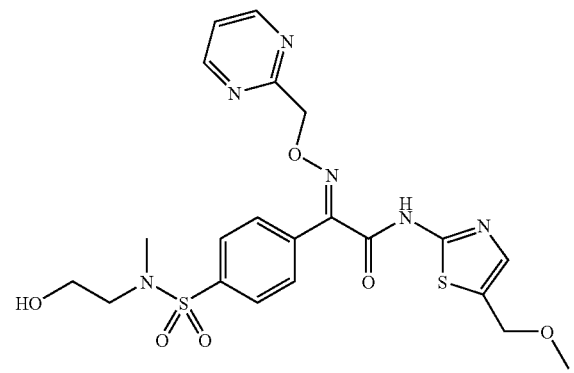 |
| 140 | 171 | 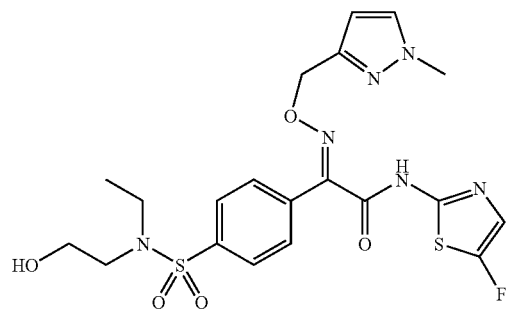 |
| 140 | 172 | 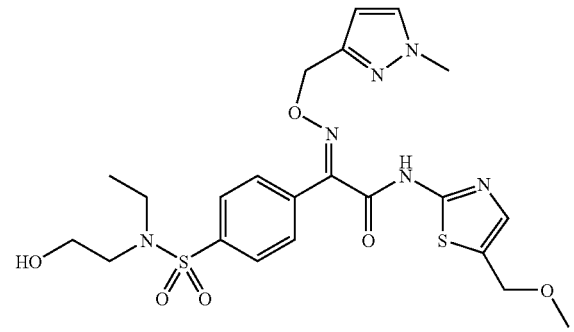 |
| 140 | 173 | 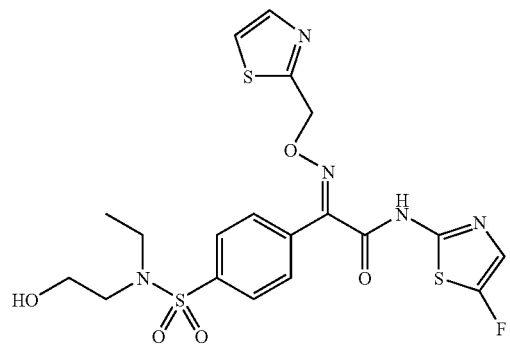 |

| EXAMPLE No. | No. | Structure |
|---|---|---|
| 140 | 174 | 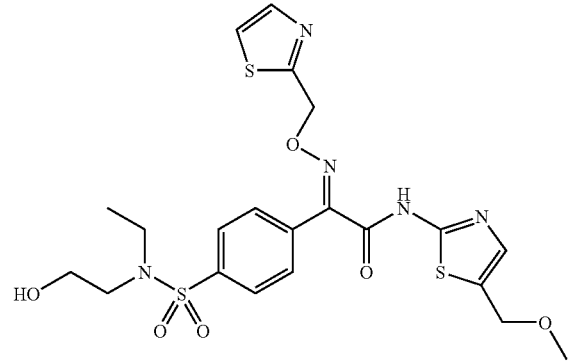 |
| 140 | 175 | 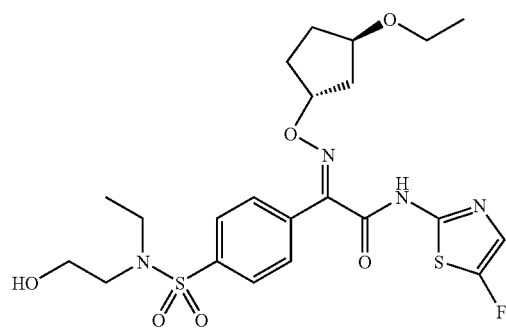 |
| 140 | 176 | 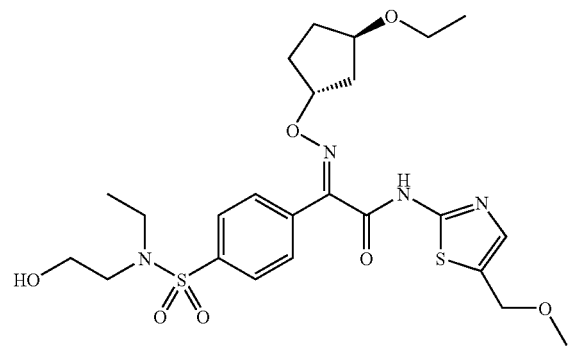 |
| 140 | 177 | 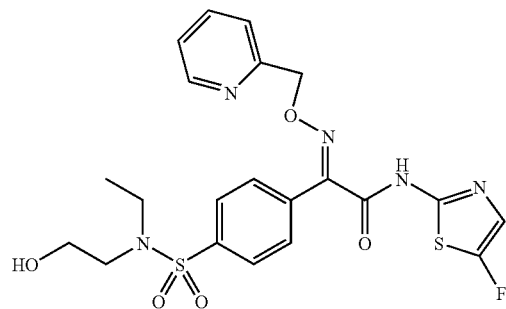 |

| EXAMPLE No. | No. | Structure |
|---|---|---|
| 140 | 178 | |
| 140 | 179 | |
| 140 | 180 | |
| 140 | 181 | |
| 140 | 182 | |

| EXAMPLE No. | No. | Structure |
|---|---|---|
| 140 | 183 | 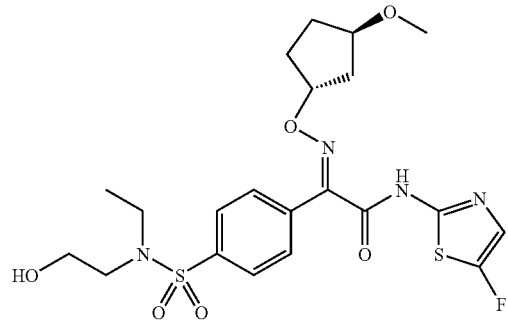 |
| 140 | 184 | 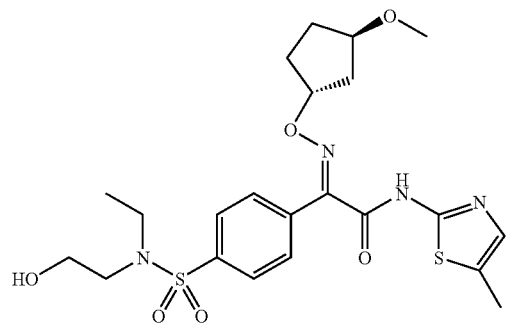 |
| 140 | 185 | 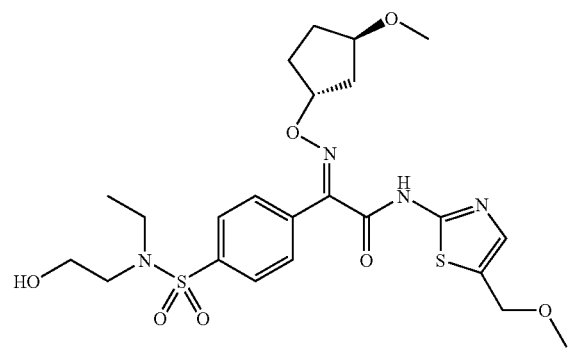 |
| 140 | 186 | 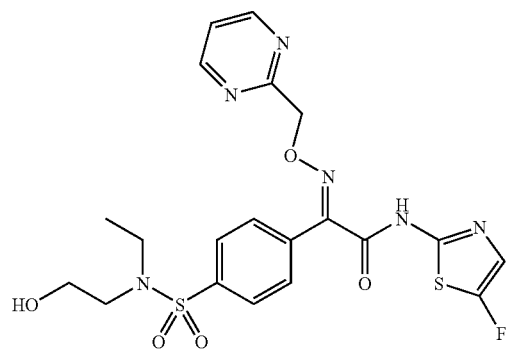 |

-continued
| EXAMPLE No. | No. | Structure |
|---|---|---|
| 140 | 187 | 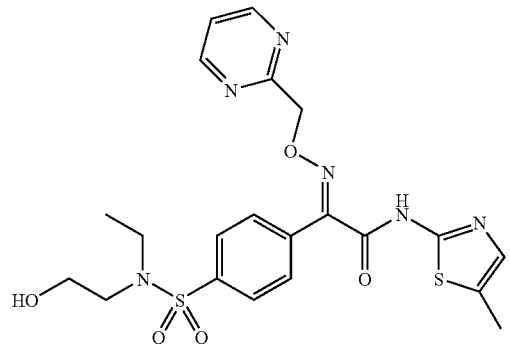 |
| 140 | 188 | 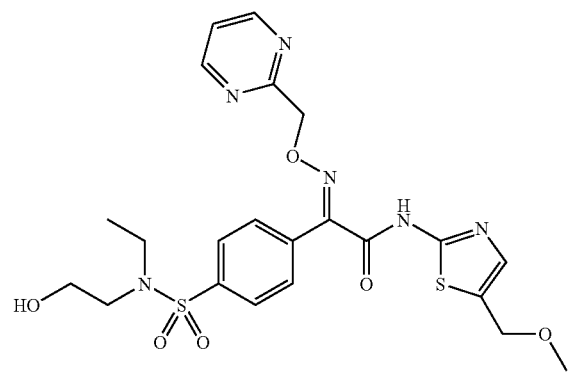 |
| 140 | 189 | 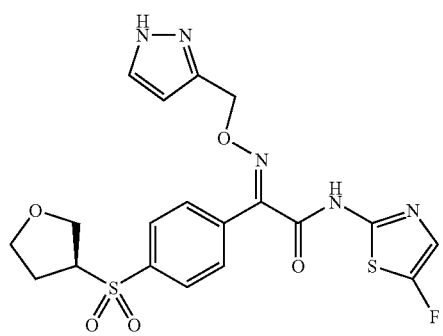 |
| 140 | 190 | 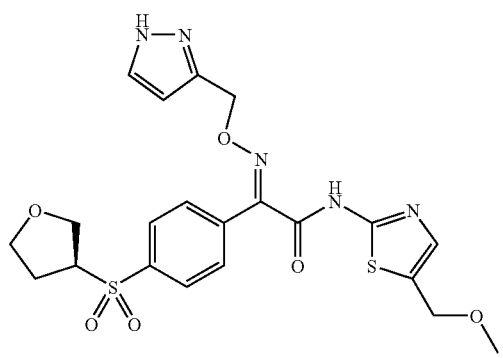 |

| EXAMPLE No. | No. | Structure |
|---|---|---|
| 140 | 191 | 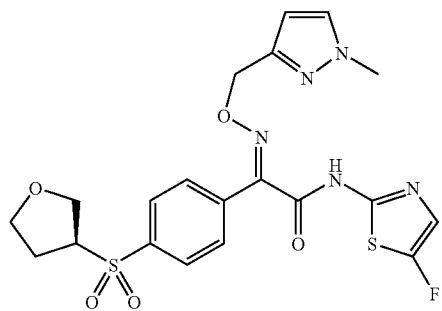 |
| 140 | 192 | 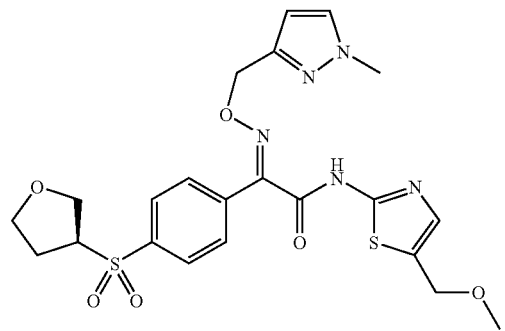 |
| 140 | 193 | 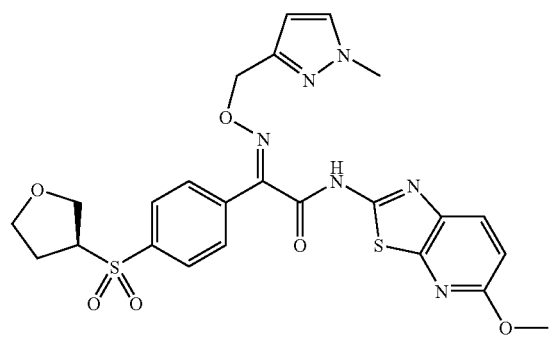 |
| 140 | 194 | 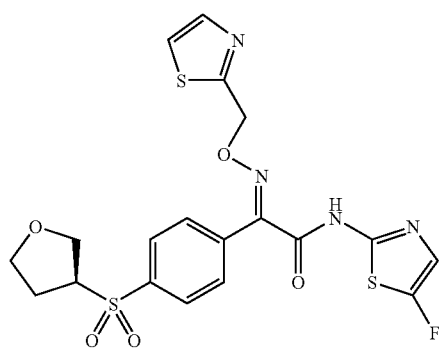 |

-continued
| EXAMPLE No. | No. | Structure |
|---|---|---|
| 140 | 195 | 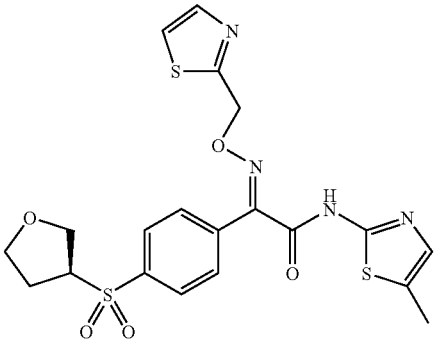 |
| 140 | 196 | 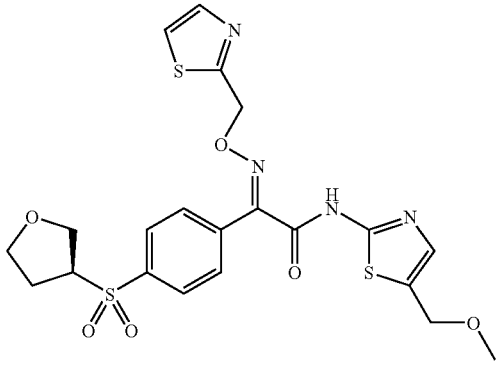 |
| 140 | 197 | 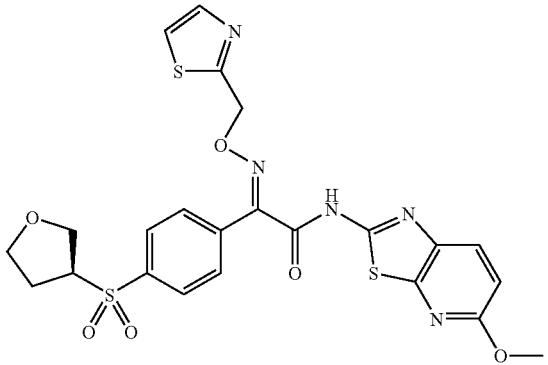 |
| 140 | 198 | 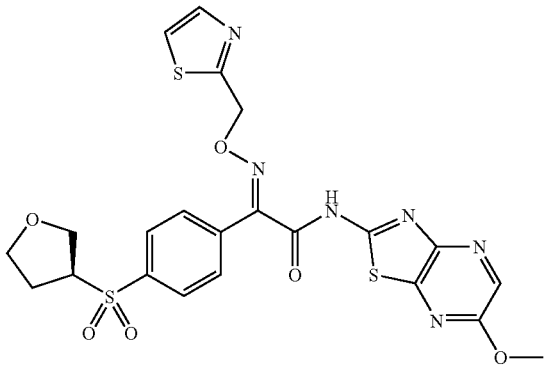 |

| EXAMPLE No. | No. | Structure |
|---|---|---|
| 140 | 199 | 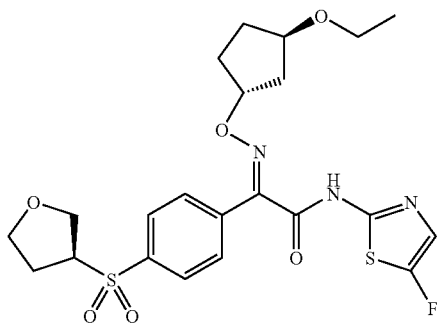 |
| 140 | 200 | 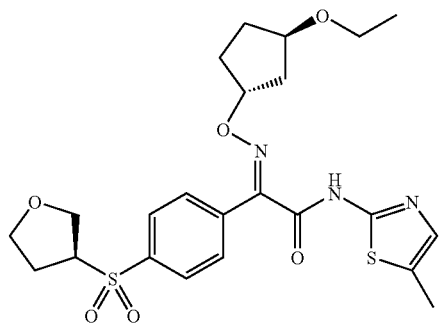 |
| 140 | 201 | 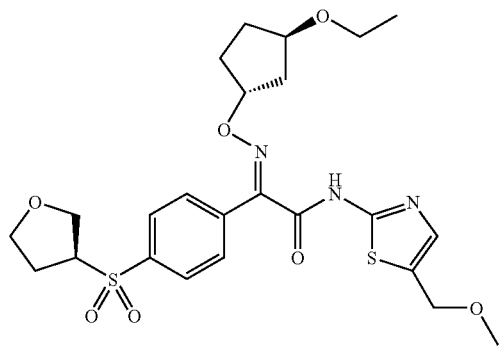 |
| 140 | 202 | 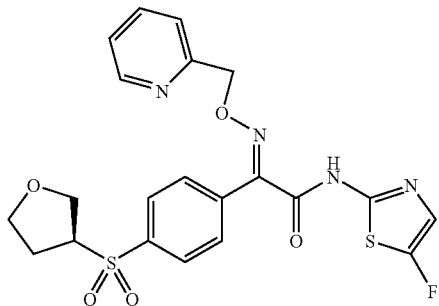 |

| EXAMPLE No. | No. | Structure |
|---|---|---|
| 140 | 203 | 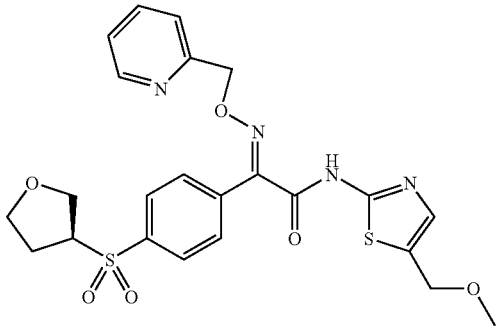 |
| 140 | 204 | 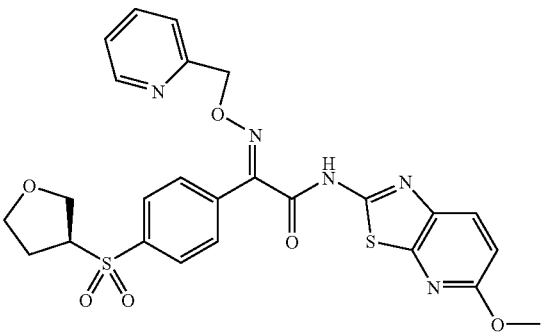 |
| 140 | 205 | 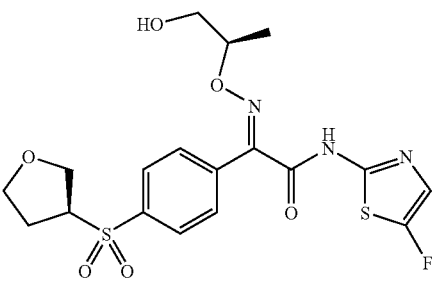 |
| 140 | 206 | 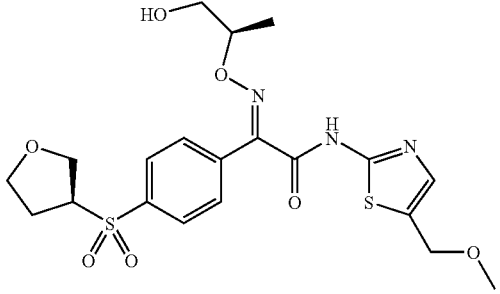 |
| 140 | 207 | 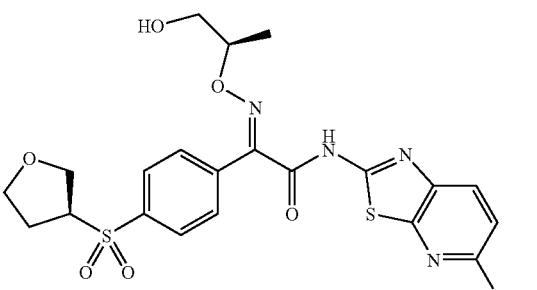 |

-continued
| EXAMPLE No. | No. | Structure |
|---|---|---|
| 140 | 208 | 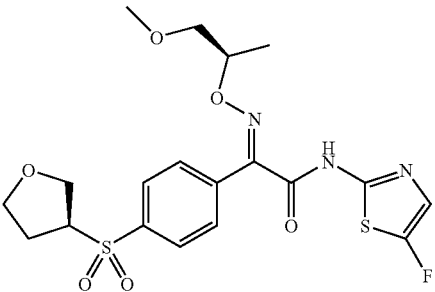 |
| 140 | 209 | 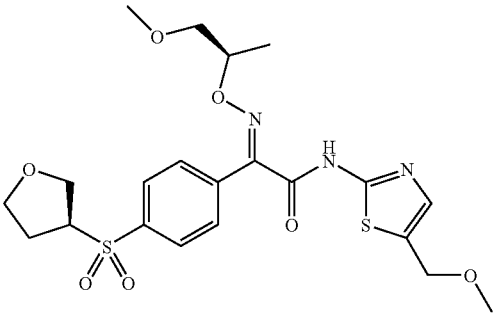 |
| 140 | 210 | 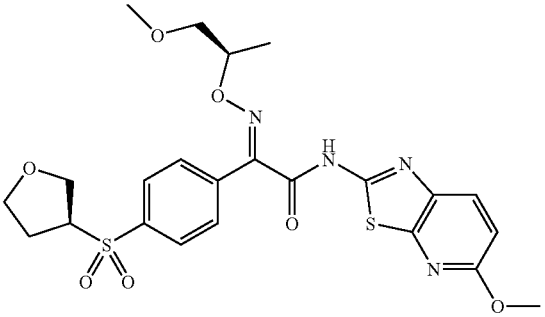 |
| 140 | 211 | 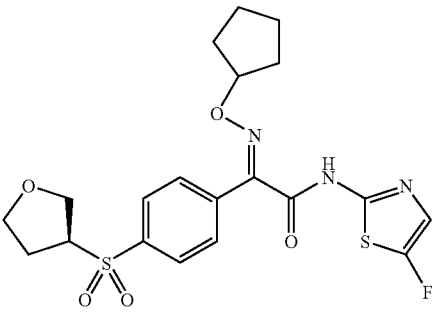 |
| 140 | 212 | 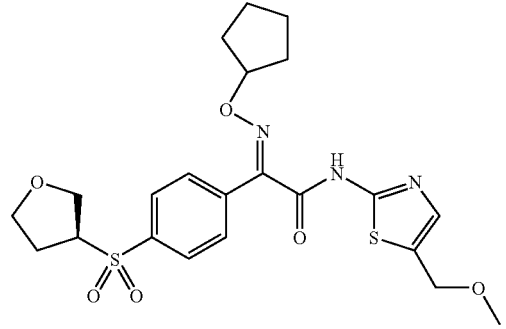 |

| EXAMPLE No. | No. | Structure |
|---|---|---|
| 140 | 213 | 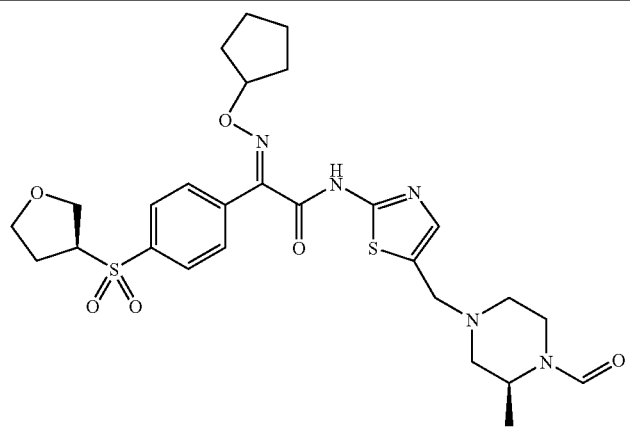 |
| 140 | 214 | 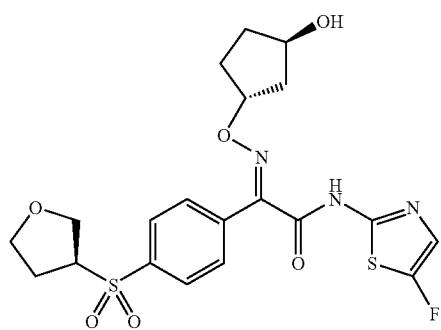 |
| 140 | 215 | 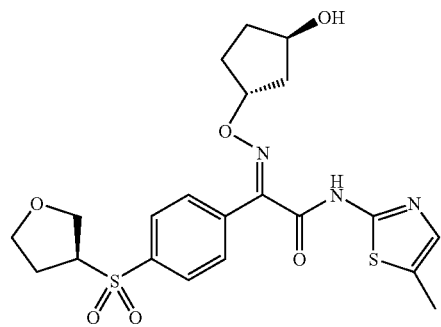 |
| 140 | 216 | 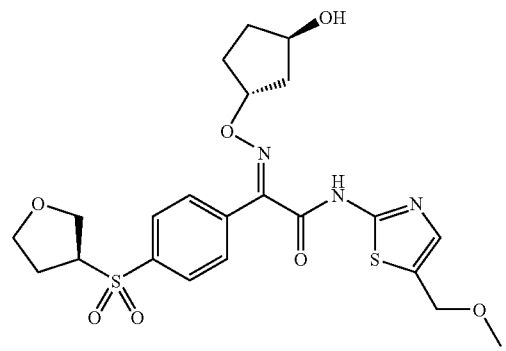 |

| EXAMPLE No. | No. | Structure |
|---|---|---|
| 140 | 217 | 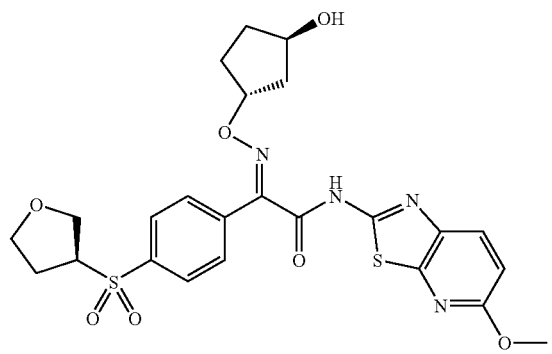 |
| 140 | 218 | 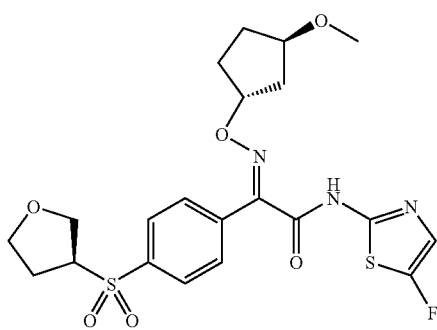 |
| 140 | 219 | 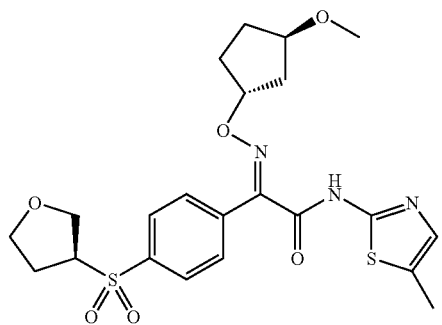 |
| 140 | 220 | 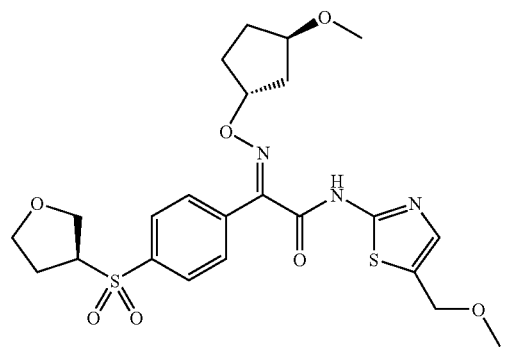 |

-continued
| EXAMPLE No. | No. | Structure |
|---|---|---|
| 140 | 221 | 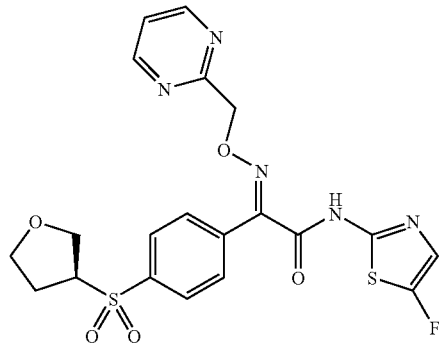 |
| 140 | 222 | 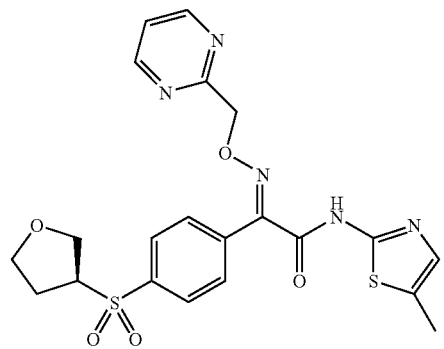 |
| 140 | 223 | 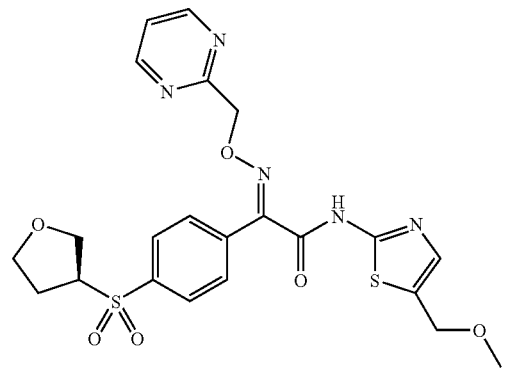 |
| 140 | 224 | 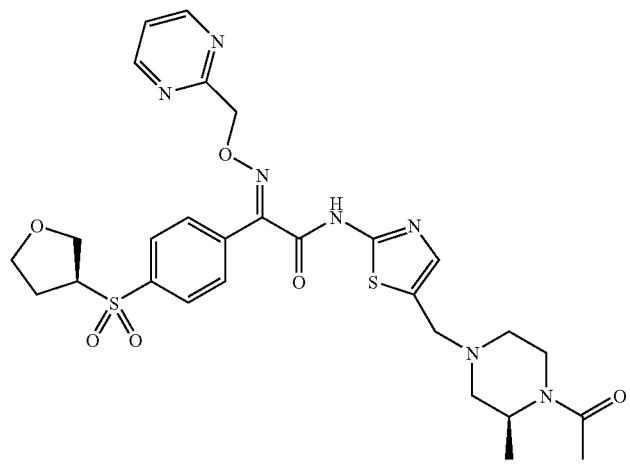 |

-continued

| EXAMPLE No. | No. | Structure |
|---|---|---|
| 140 | 225 | |
| 140 | 226 | |
| 140 | 227 | |
| 140 | 228 | |

| EXAMPLE No. | No. | Structure |
|---|---|---|
| 140 | 229 | 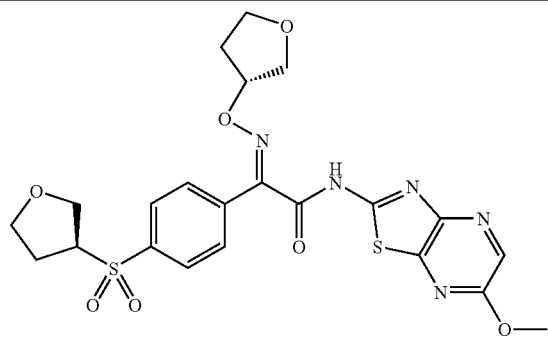 |
| 140 | 230 | 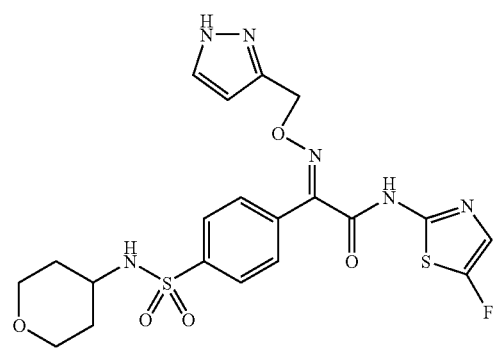 |
| 140 | 231 | 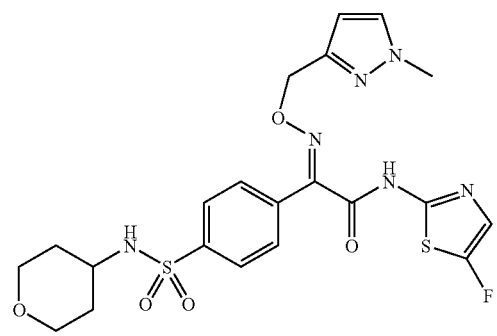 |
| 140 | 232 | 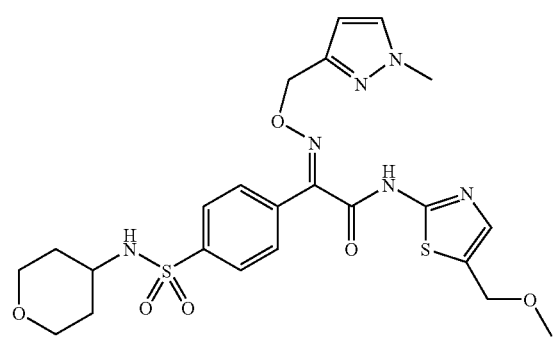 |

| EXAMPLE No. | No. | Structure |
|---|---|---|
| 140 | 233 | 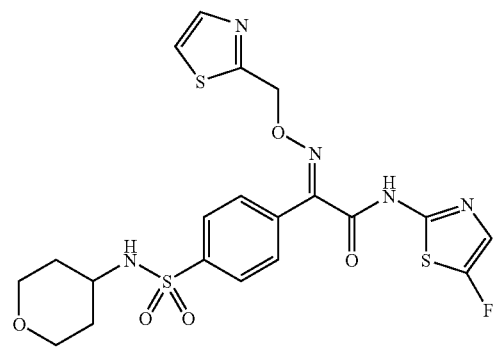 |
| 140 | 234 | 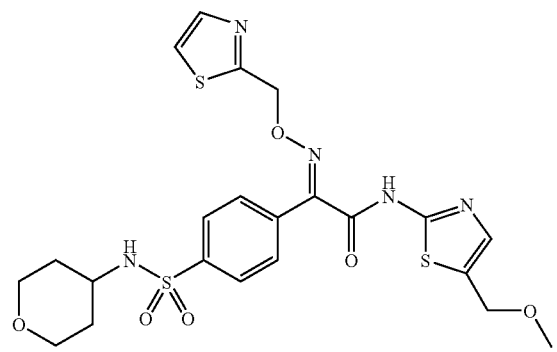 |
| 140 | 235 | 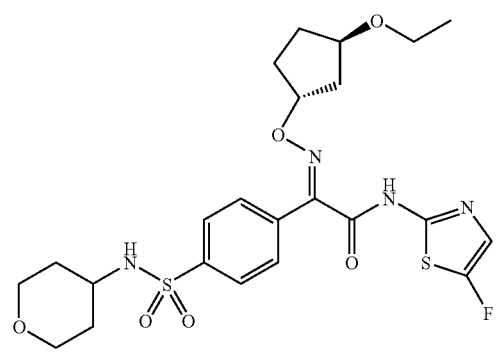 |
| 140 | 236 | 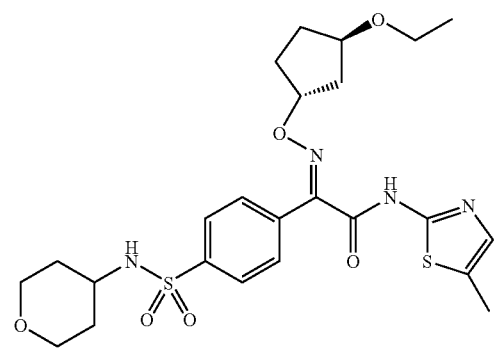 |

-continued
| EXAMPLE No. | No. | Structure |
|---|---|---|
| 140 | 237 | 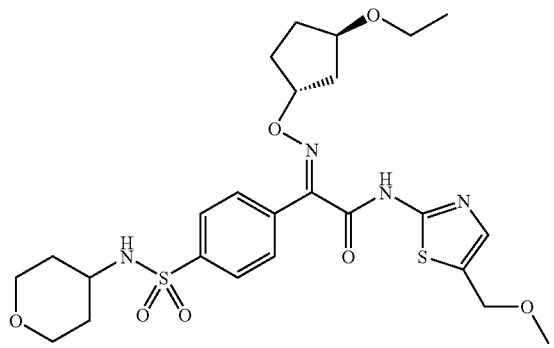 |
| 140 | 238 | 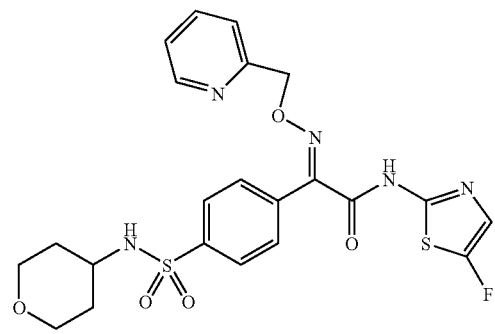 |
| 140 | 239 | 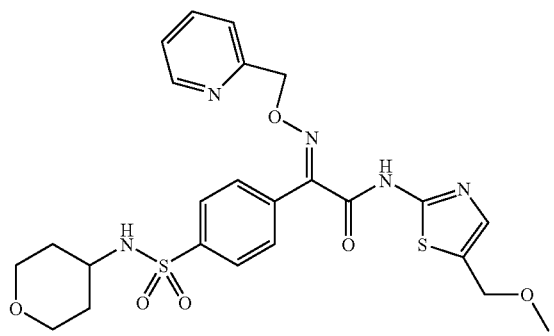 |
| 140 | 240 | 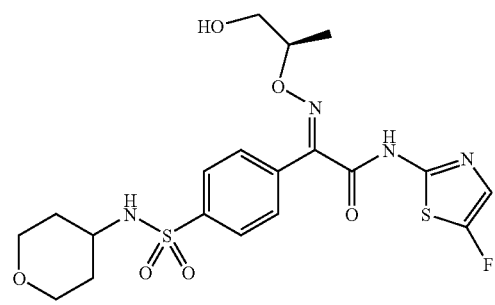 |

-continued
| EXAMPLE No. | No. | Structure |
|---|---|---|
| 140 | 241 | 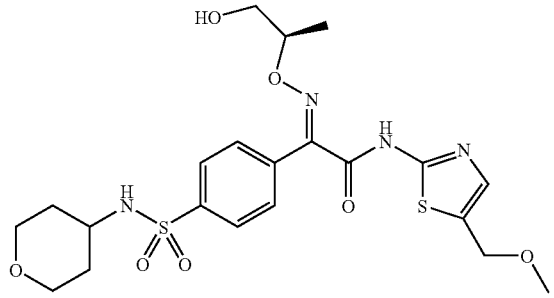 |
| 140 | 242 | 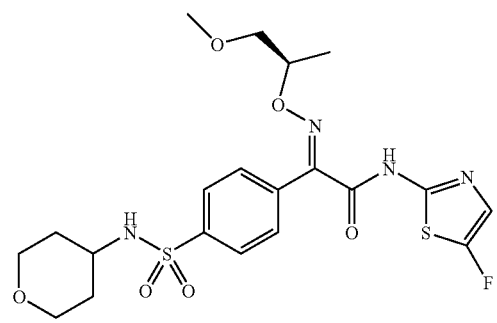 |
| 140 | 243 | 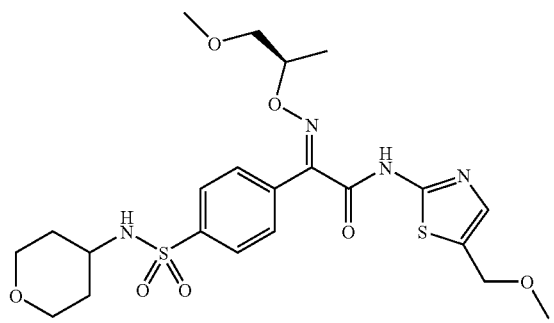 |
| 140 | 244 | 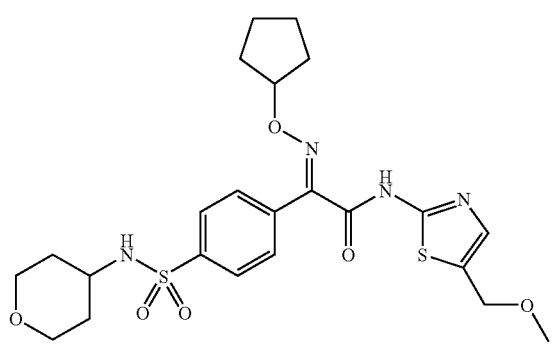 |

| EXAMPLE No. | No. | Structure |
|---|---|---|
| 140 | 245 | 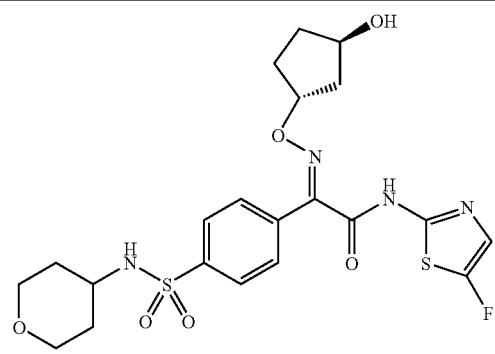 |
| 140 | 246 | 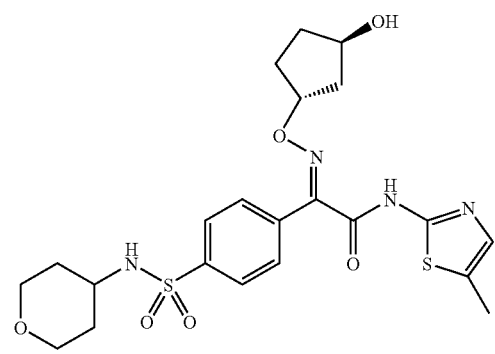 |
| 140 | 247 | 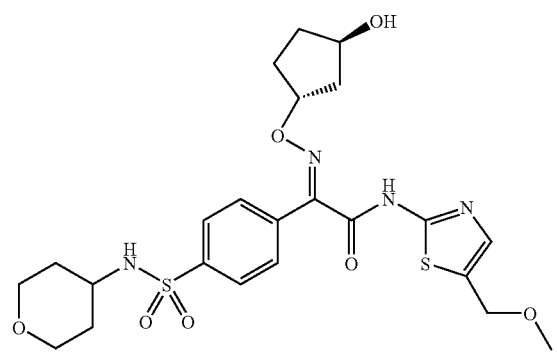 |
| 140 | 248 | 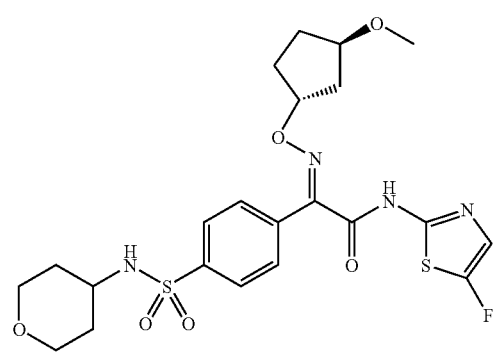 |

| EXAMPLE No. | No. | Structure |
|---|---|---|
| 140 | 249 | |
| 140 | 250 | |
| 140 | 251 | |
| 140 | 252 | |

-continued
| EXAMPLE No. | No. | Structure |
|---|---|---|
| 140 | 253 | 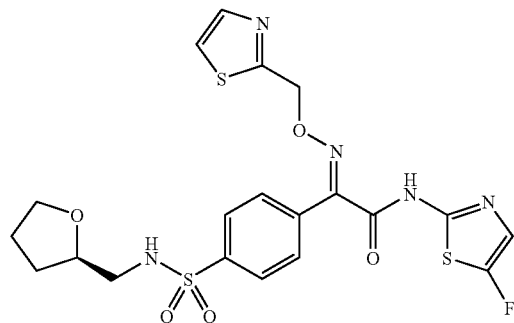 |
| 140 | 254 | 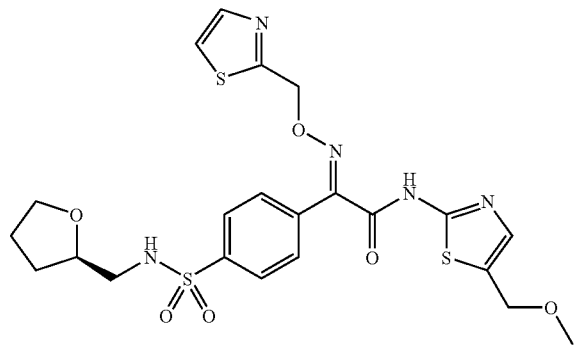 |
| 140 | 255 | 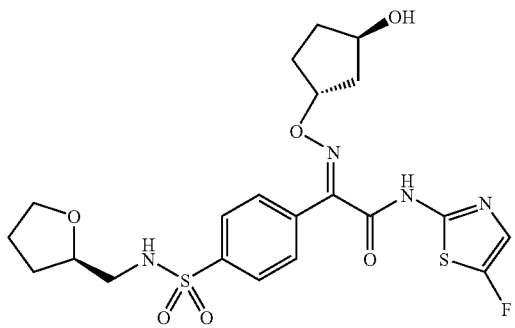 |
| 140 | 256 | 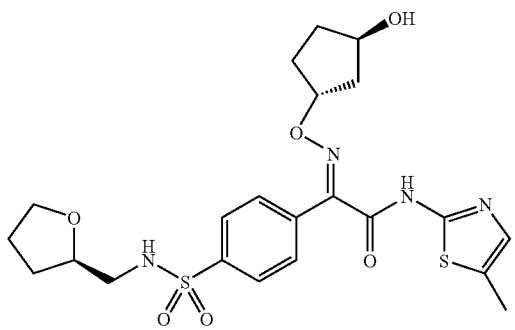 |

-continued
| EXAMPLE No. | No. | Structure |
|---|---|---|
| 140 | 257 | 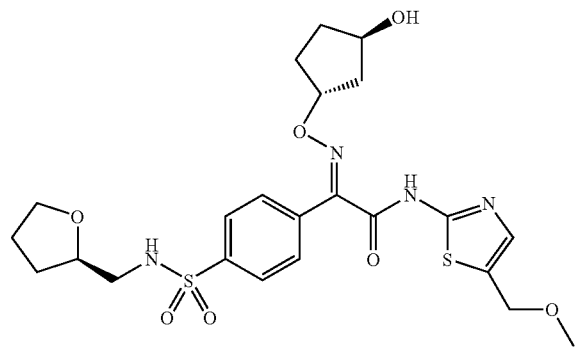 |
| 140 | 258 | 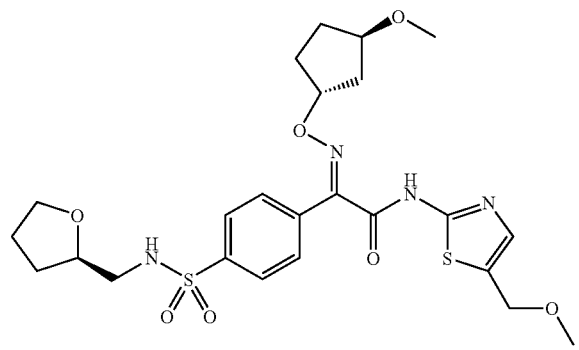 |
| 140 | 259 | 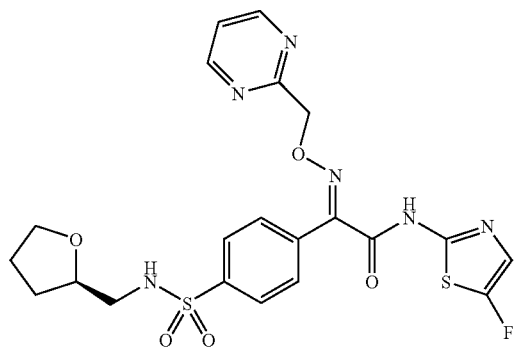 |
| 140 | 260 | 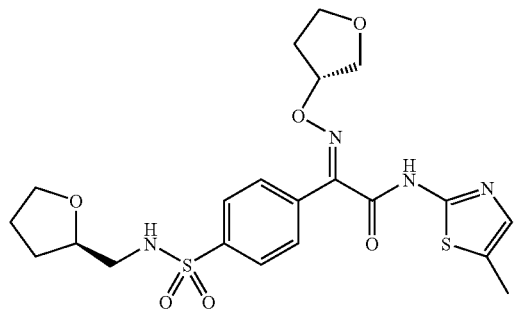 |

-continued
| EXAMPLE No. | No. | Structure |
|---|---|---|
| 140 | 261 | 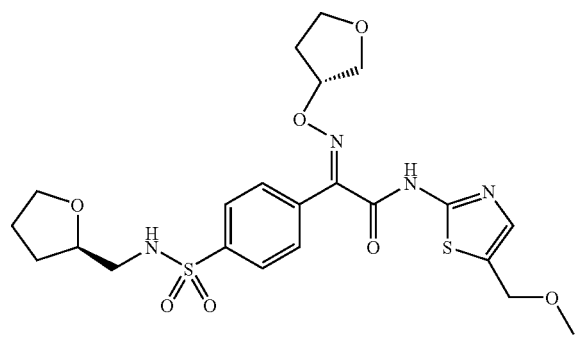 |
| 140 | 262 | 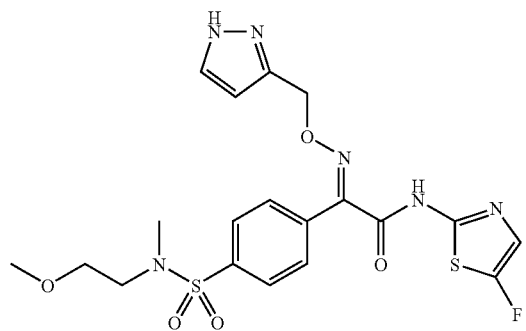 |
| 140 | 263 | 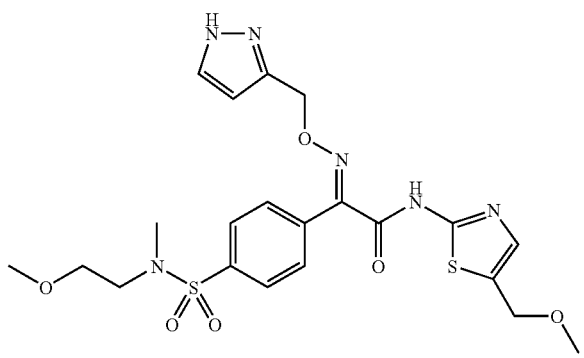 |
| 140 | 264 | 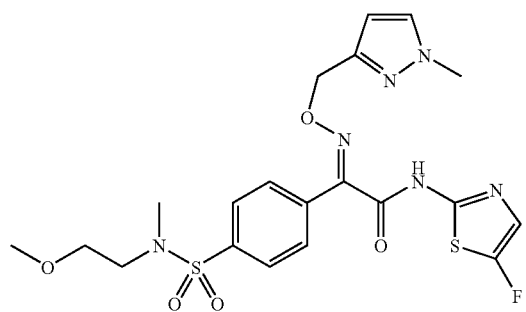 |

-continued
| EXAMPLE No. | No. | Structure |
|---|---|---|
| 140 | 265 | 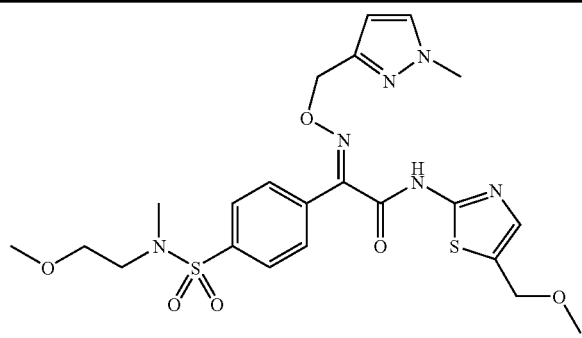 |
| 140 | 266 | 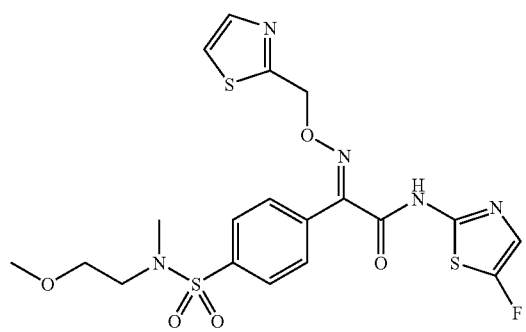 |
| 140 | 267 | 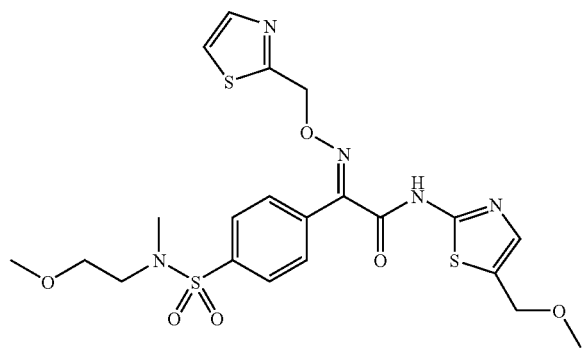 |
| 140 | 268 | 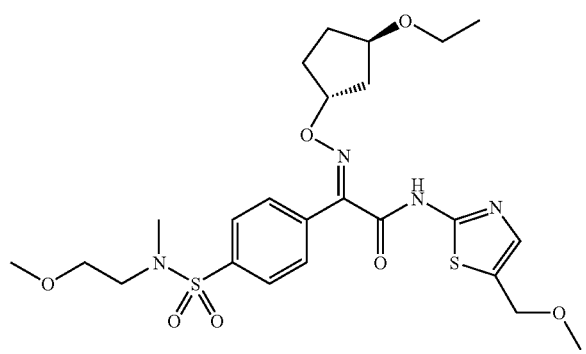 |

| EXAMPLE No. | No. | Structure |
|---|---|---|
| 140 | 269 | 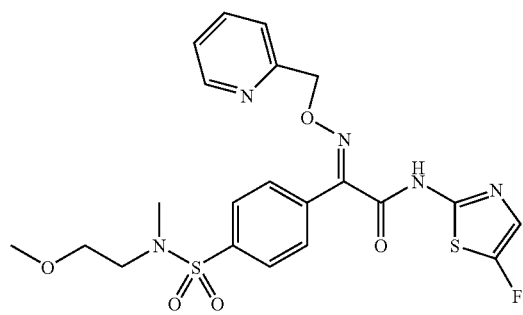 |
| 140 | 270 | 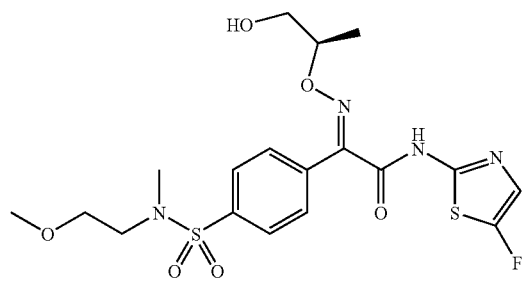 |
| 140 | 271 | 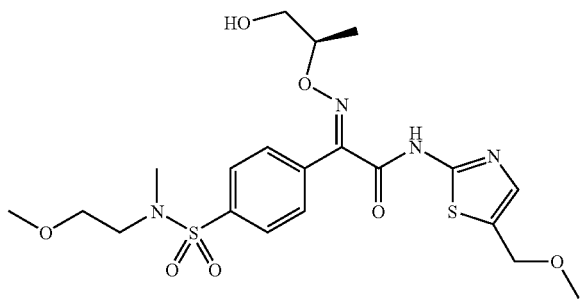 |
| 140 | 272 | 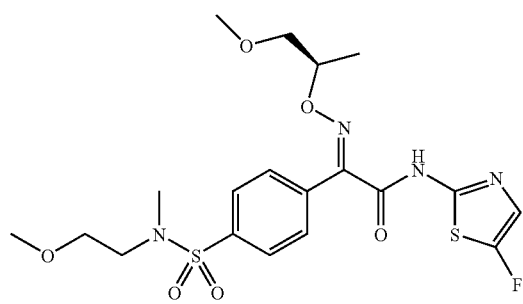 |
| 140 | 273 | 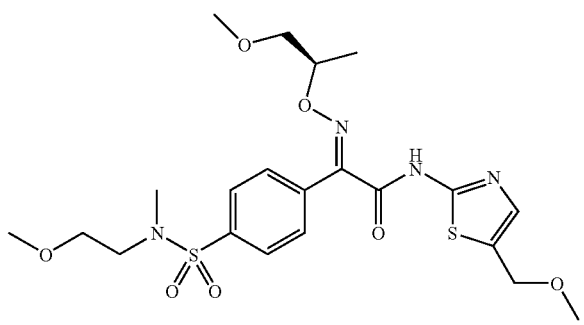 |

| EXAMPLE No. | No. | Structure |
|---|---|---|
| 140 | 274 | 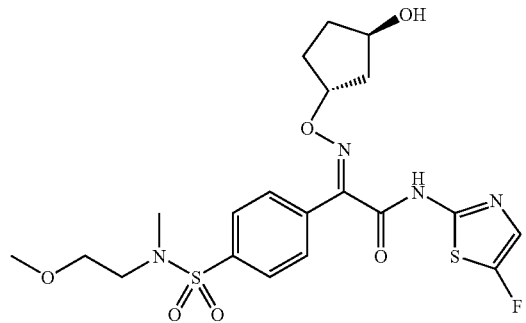 |
| 140 | 275 | 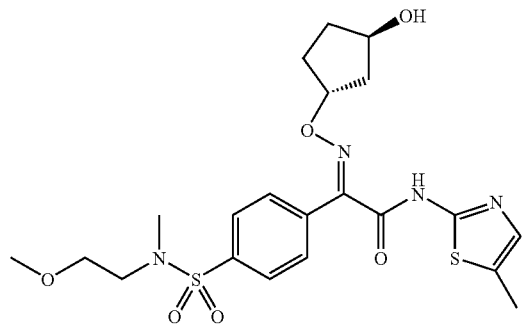 |
| 140 | 276 | 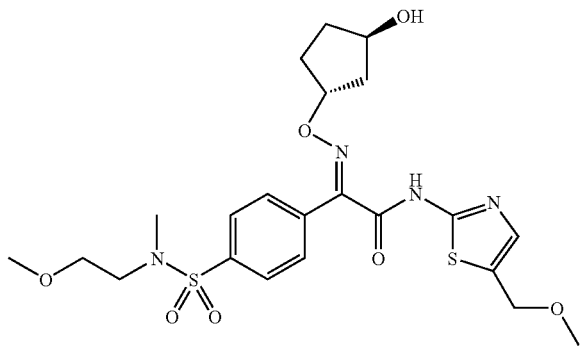 |
| 140 | 277 | 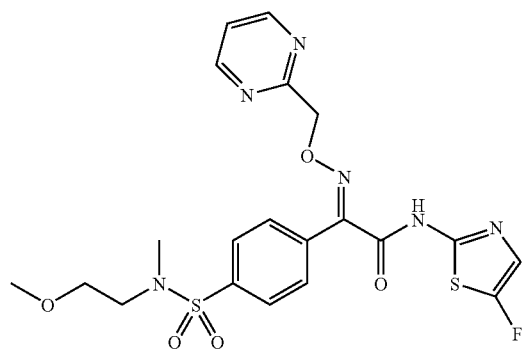 |

| EXAMPLE No. | No. | Structure |
|---|---|---|
| 140 | 278 | 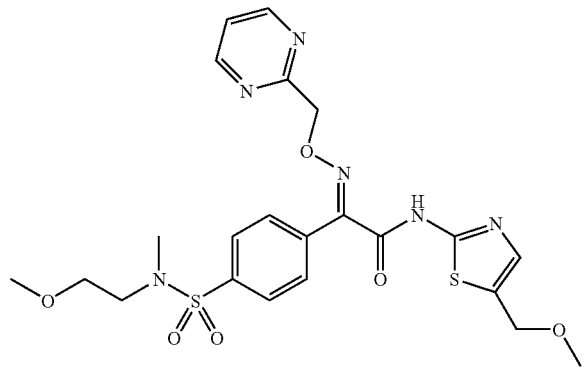 |
| 140 | 279 | 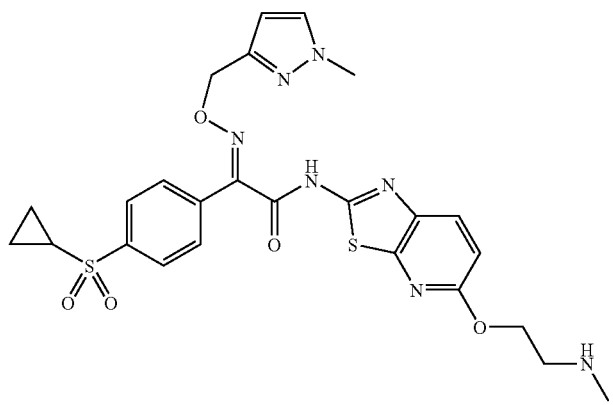 |
| 140 | 280 | 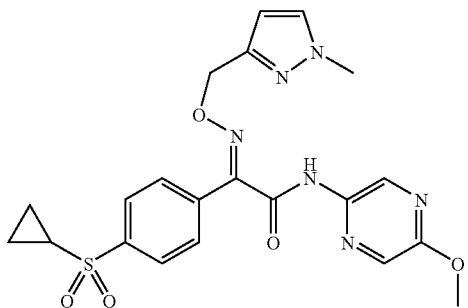 |
| 140 | 281 | 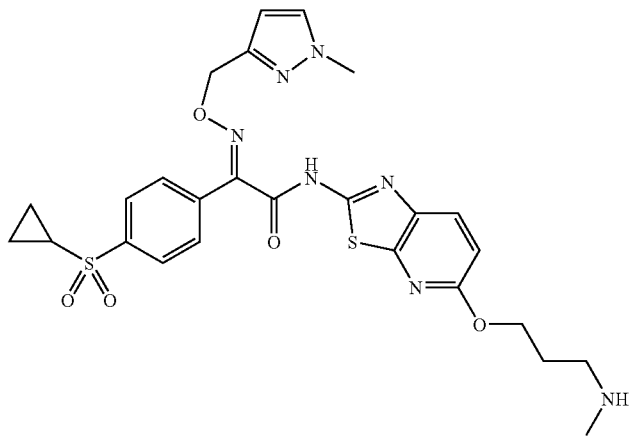 |

-continued
| EXAMPLE No. | No. | Structure |
|---|---|---|
| 140 | 282 | 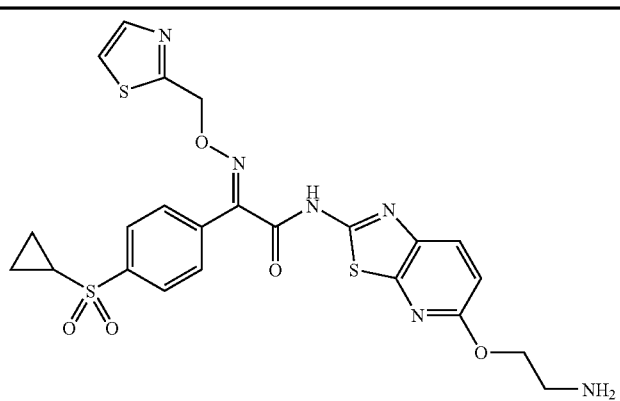 |
| 140 | 283 | 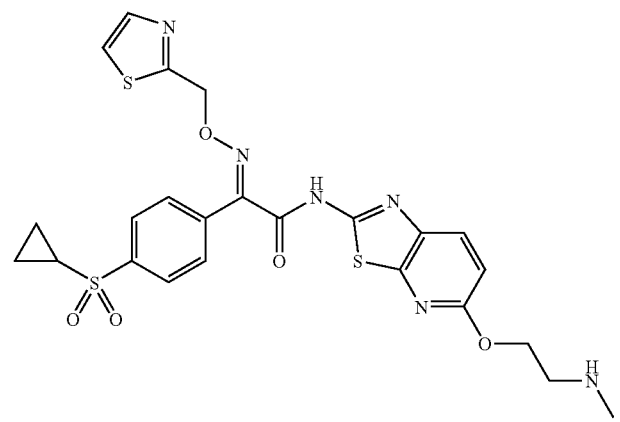 |
| 140 | 284 | 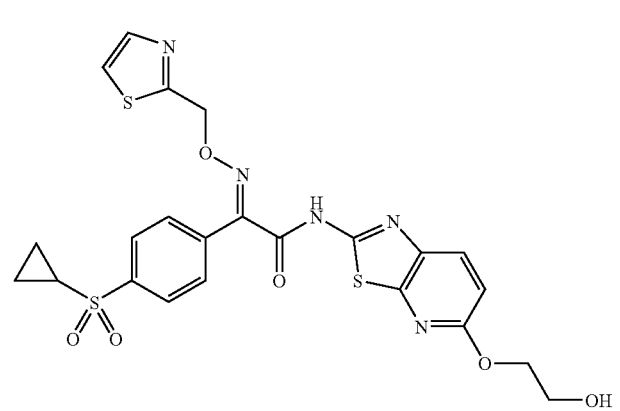 |
| 140 | 285 | 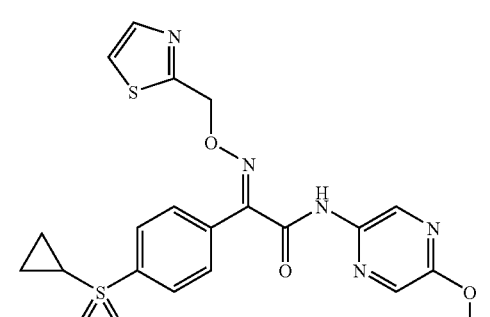 |

| EXAMPLE No. | No. | Structure |
|---|---|---|
| 140 | 286 | 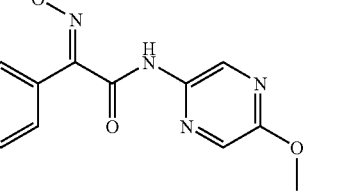 |
| 140 | 287 |  |
| 140 | 288 | 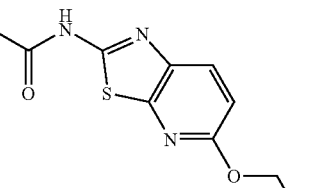 |
| 140 | 289 |  |

-continued

| EXAMPLE No. | No. | Structure |
|---|---|---|
| 140 | 290 | |
| 140 | 291 | |
| 140 | 292 | |
| 140 | 293 | |

| EXAMPLE No. | No. | Structure |
|---|---|---|
| 140 | 294 | 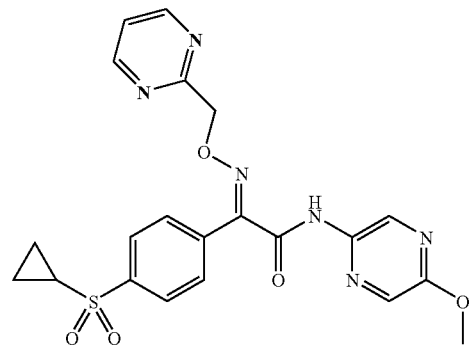 |
| 140 | 295 | 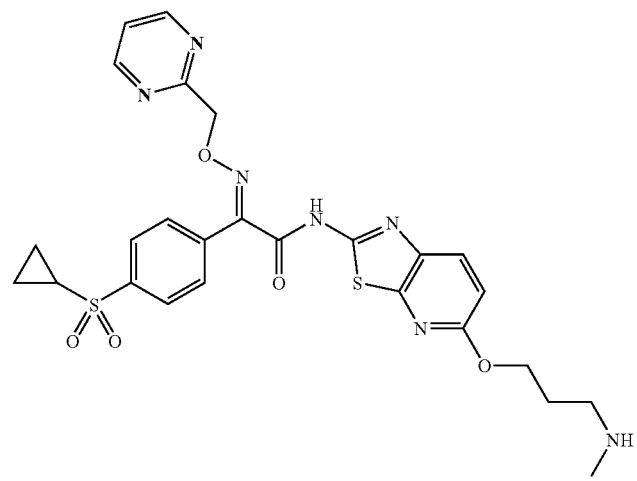 |
| 140 | 296 | 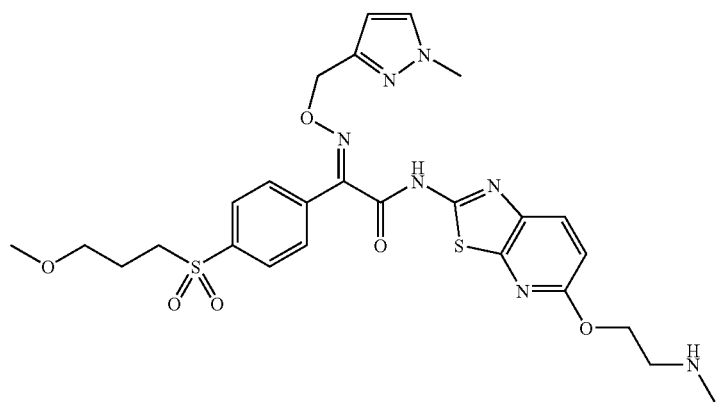 |
| 140 | 297 | 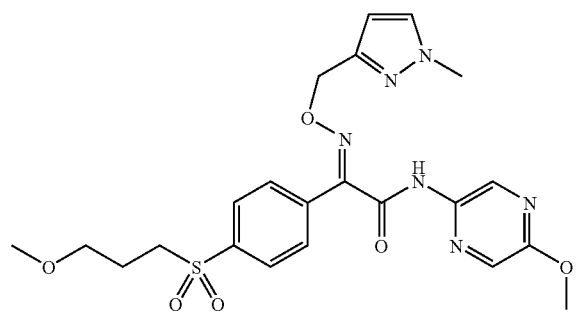 |

-continued
| EXAMPLE No. | No. | Structure |
|---|---|---|
| 140 | 298 | 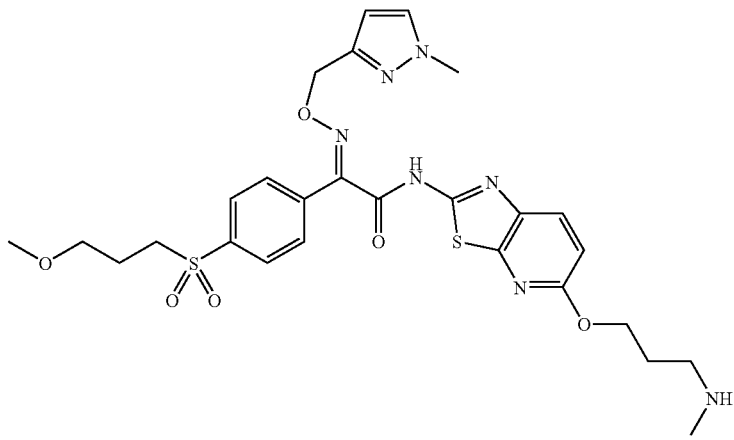 |
| 140 | 299 | 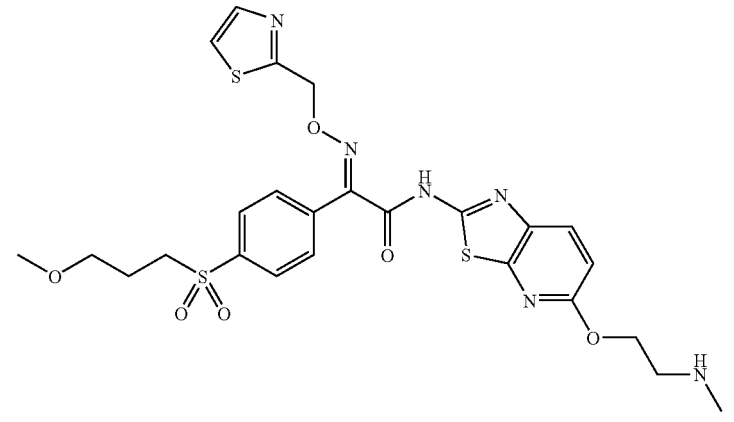 |
| 140 | 300 | 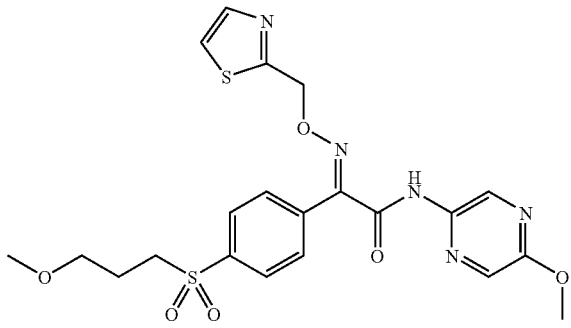 |
| 140 | 301 | 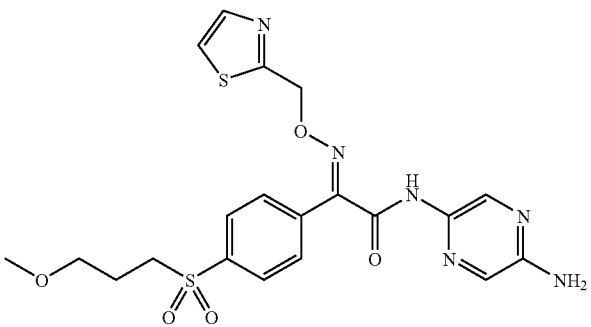 |

-continued
| EXAMPLE No. | No. | Structure |
|---|---|---|
| 140 | 302 | 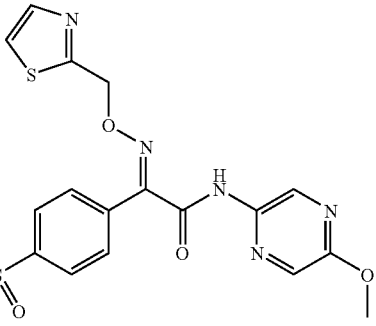 |
| 140 | 303 | 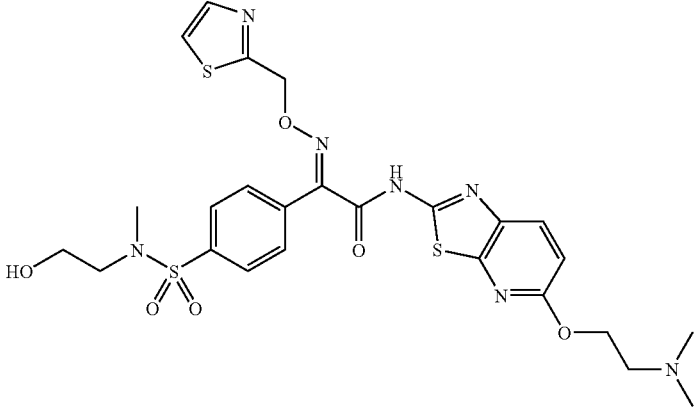 |
| 140 | 304 | 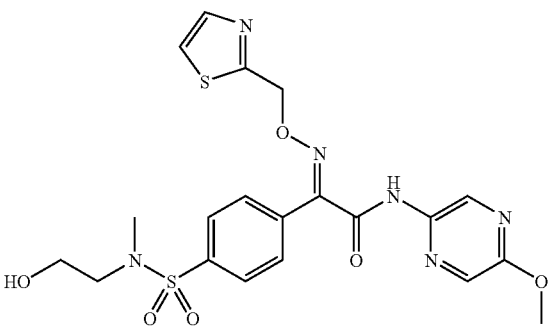 |
| 140 | 305 | 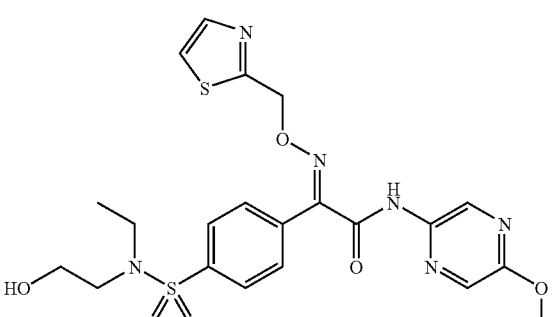 |

| EXAMPLE No. | No. | Structure |
|---|---|---|
| 140 | 306 | 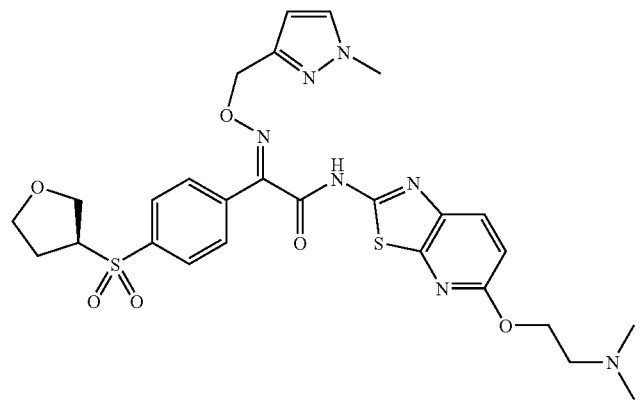 |
| 140 | 307 | 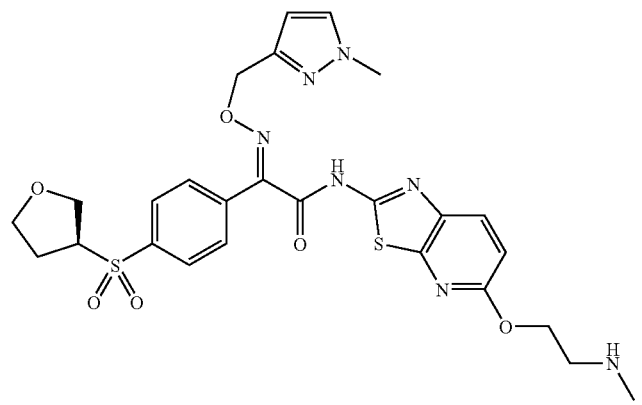 |
| 140 | 308 | 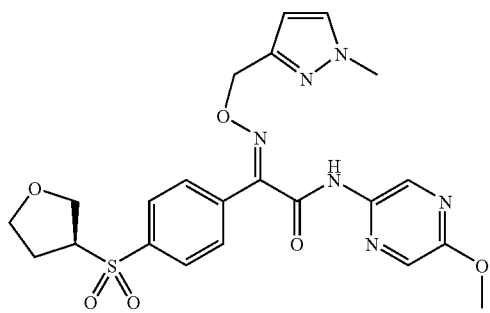 |
| 140 | 309 | 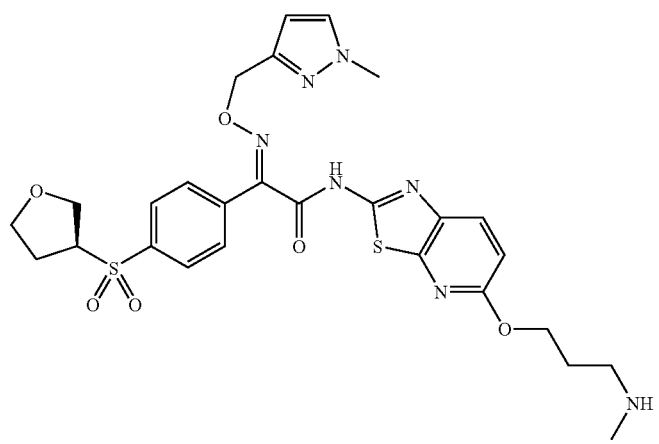 |

-continued
| EXAMPLE No. | No. | Structure |
|---|---|---|
| 140 | 310 | 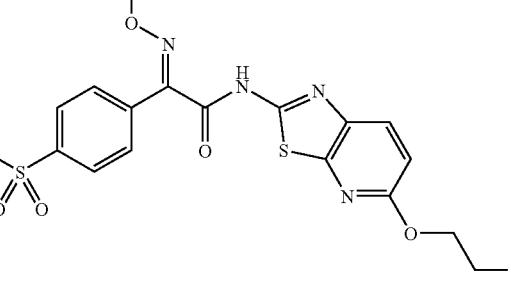 |
| 140 | 311 | 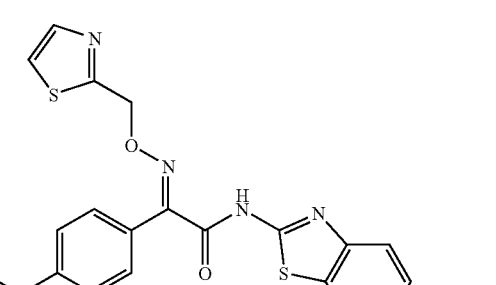 |
| 140 | 312 | 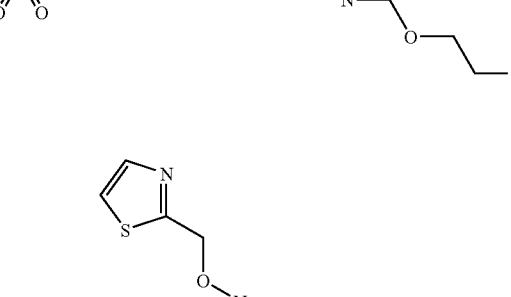 |
| 140 | 313 | 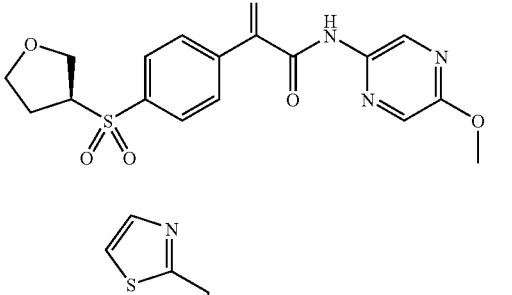 |

| EXAMPLE No. | No. | Structure |
|---|---|---|
| 140 | 314 | 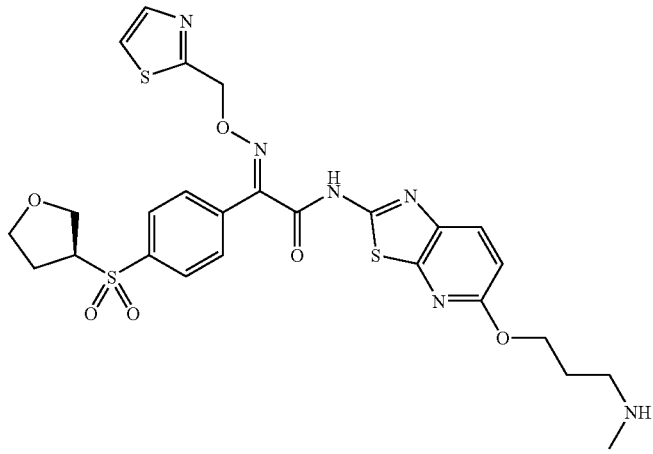 |
| 140 | 315 | 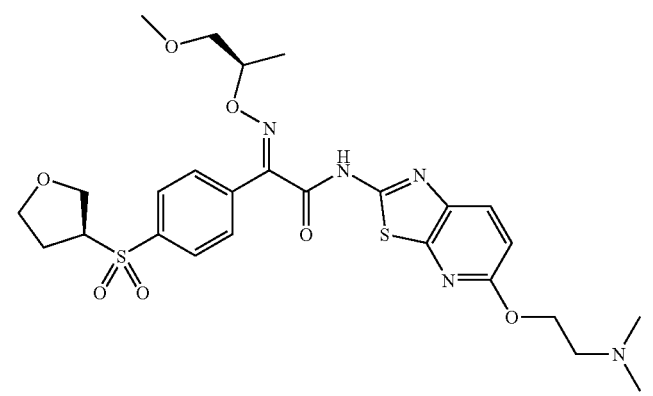 |
| 140 | 316 | 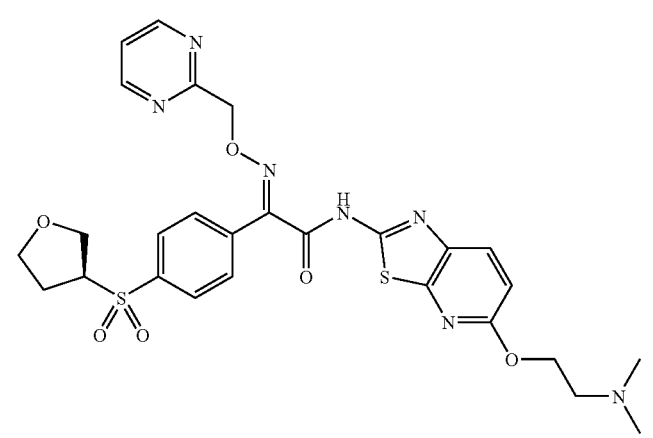 |
| 140 | 317 | 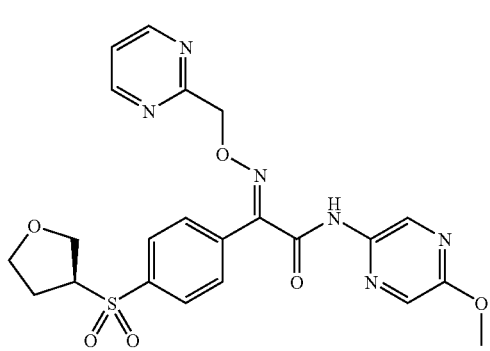 |

| EXAMPLE No. | No. | Structure |
|---|---|---|
| 140 | 318 | 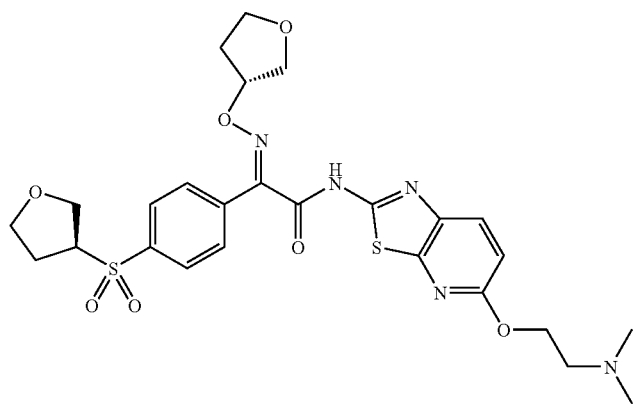 |
| 140 | 319 | 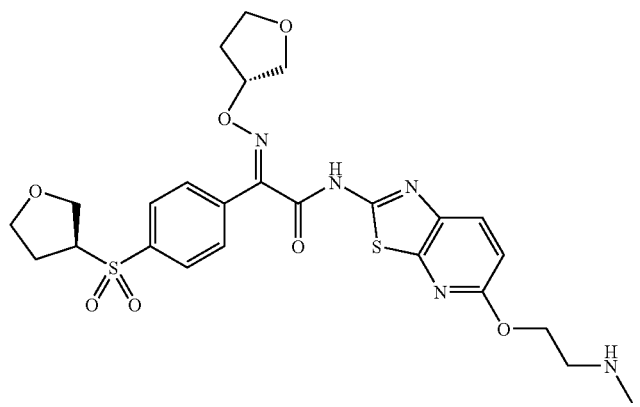 |
| 140 | 320 | 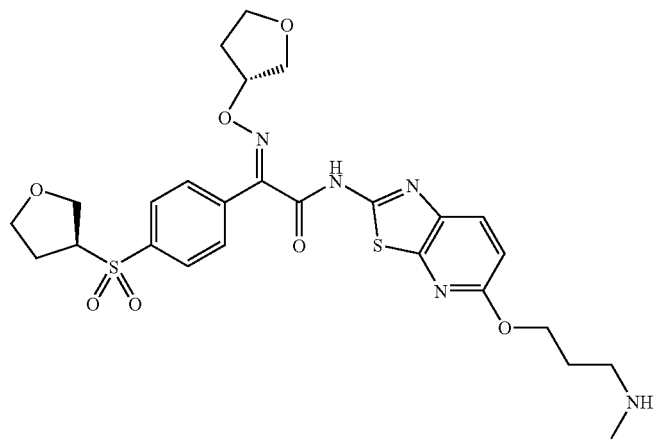 |

-continued
| EXAMPLE No. | No. | Structure |
|---|---|---|
| 140 | 321 | 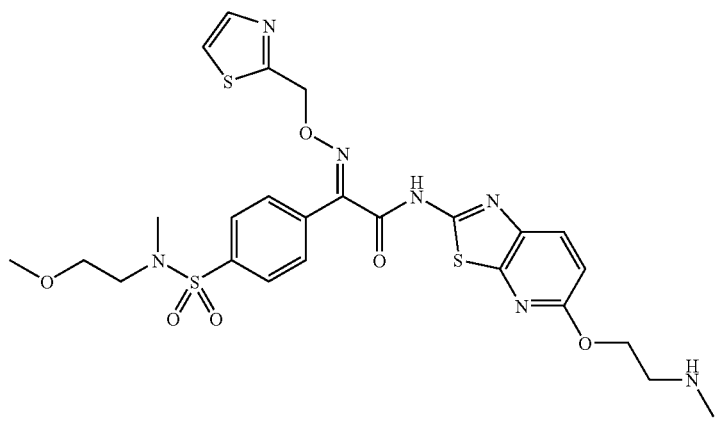 |
| 140 | 322 | 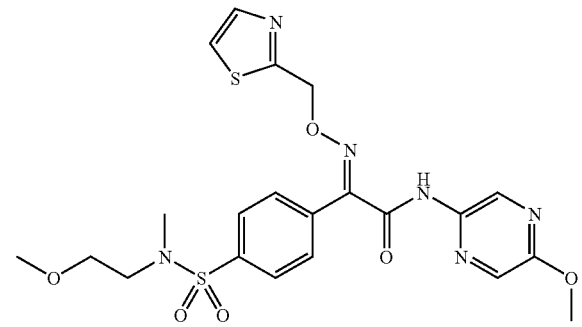 |
| 140 | 323 | 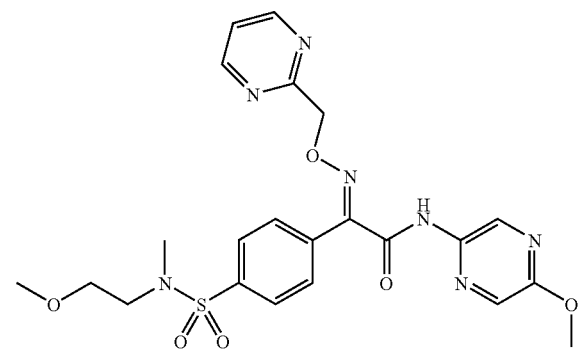 |
| 140 | 324 | 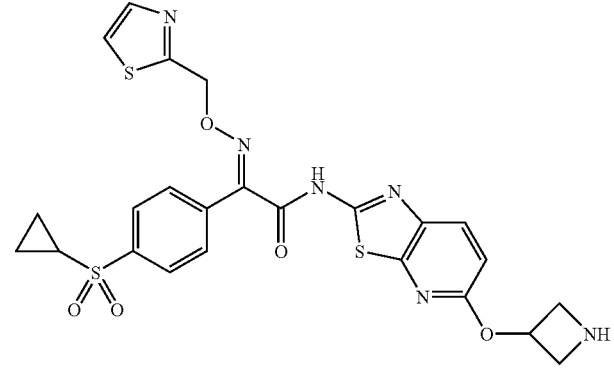 |

-continued

| EXAMPLE No. | No. | Structure |
|---|---|---|
| 140 | 325 | |
| 140 | 326 | |
| 140 | 327 | |
| 140 | 328 | |

| EXAMPLE No. | No. | Structure |
|---|---|---|
| 140 | 329 | 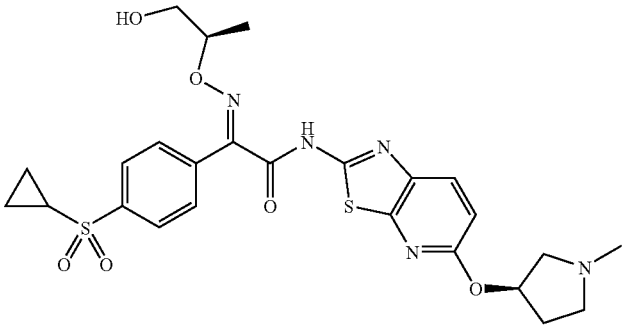 |
| 140 | 330 | 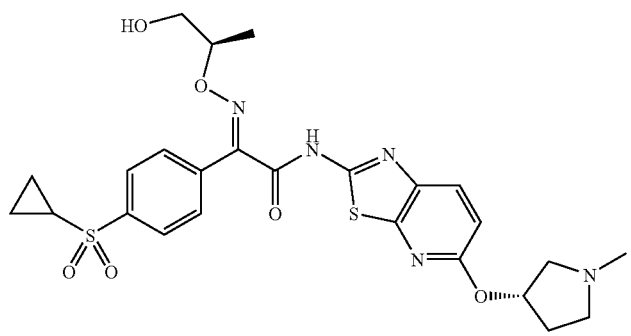 |
| 140 | 331 | 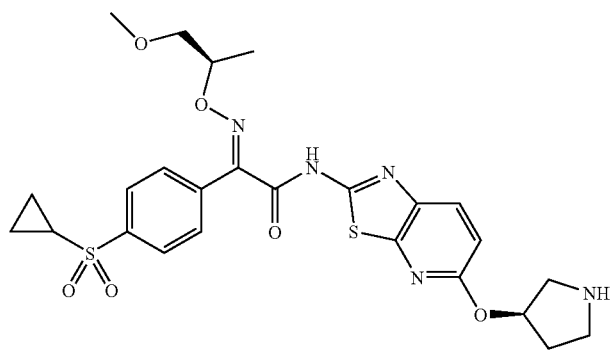 |
| 140 | 332 | 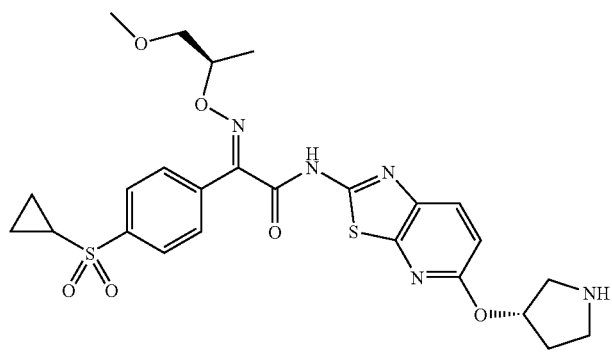 |

| EXAMPLE No. | No. | Structure |
|---|---|---|
| 140 | 333 | 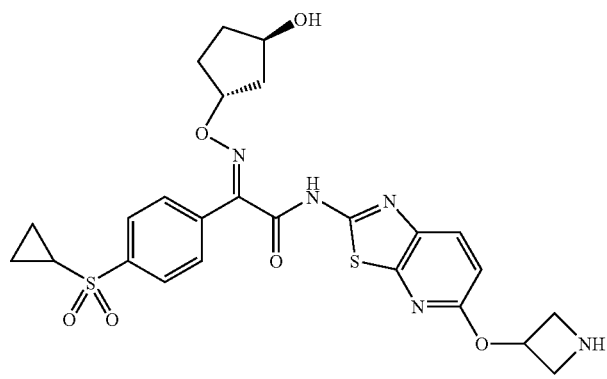 |
| 140 | 334 | 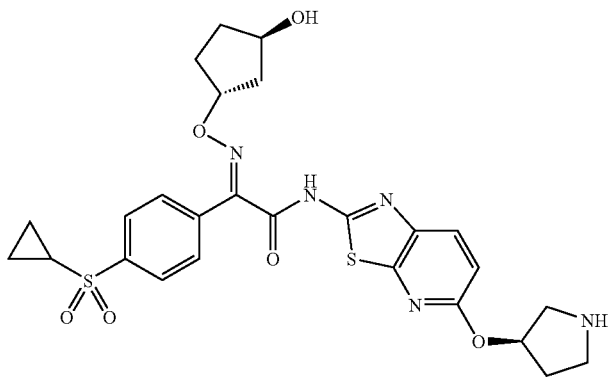 |
| 140 | 335 | 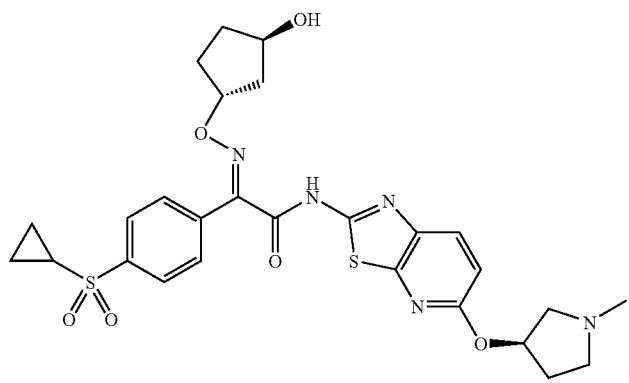 |
| 140 | 336 | 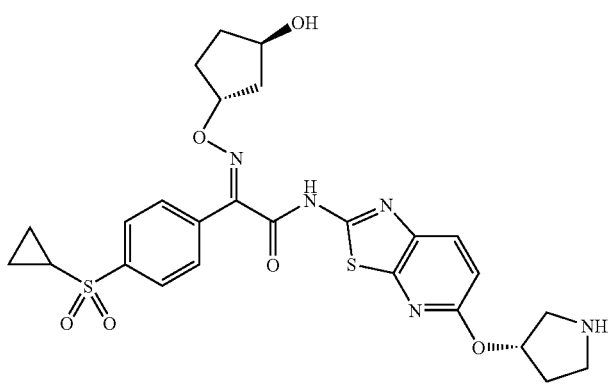 |

| EXAMPLE No. | No. | Structure |
|---|---|---|
| 140 | 337 | 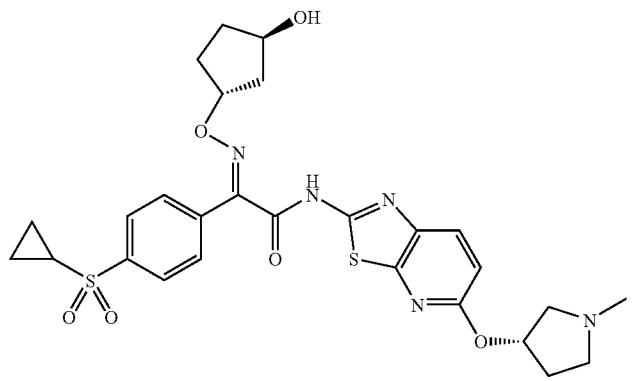 |
| 140 | 338 | 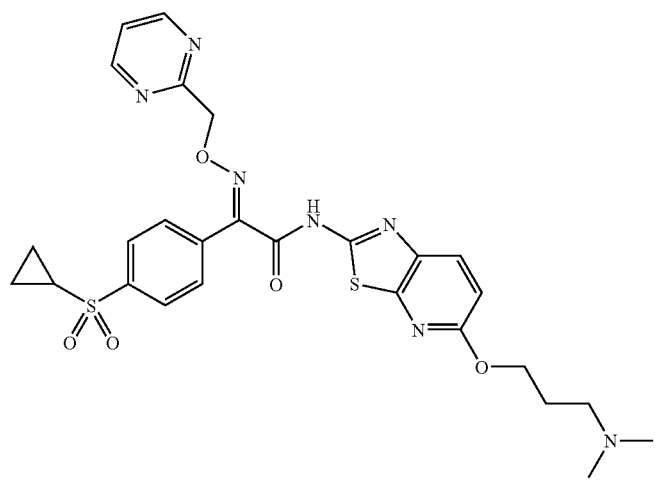 |
| 140 | 339 | 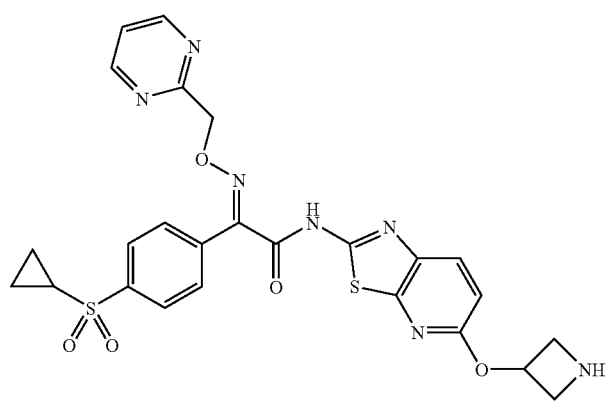 |

| EXAMPLE No. | No. | Structure |
|---|---|---|
| 140 | 340 | |
| 140 | 341 | |
| 140 | 342 | |
| 140 | 343 | |

| EXAMPLE No. | No. | Structure |
|---|---|---|
| 140 | 344 | 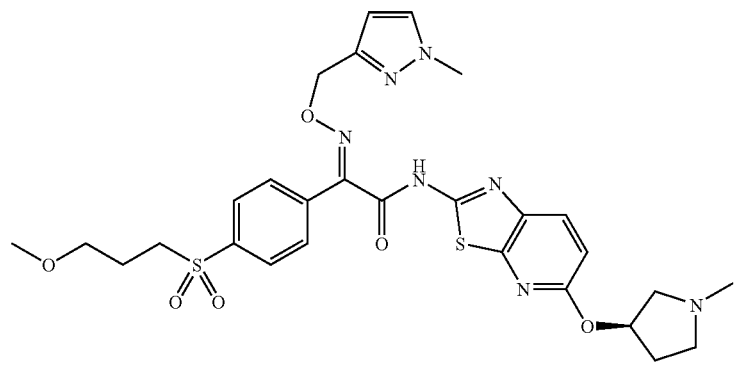 |
| 140 | 345 | 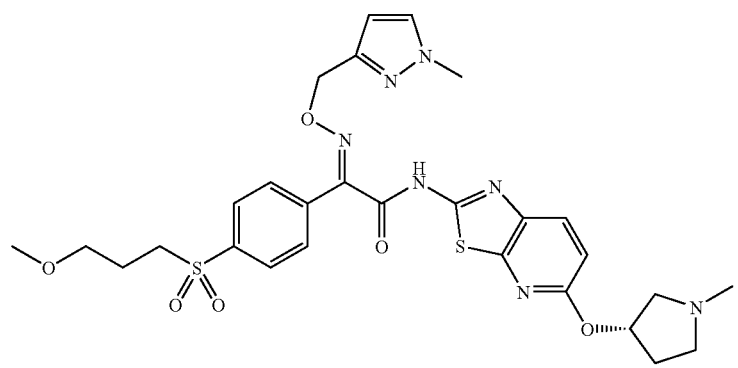 |
| 140 | 346 | 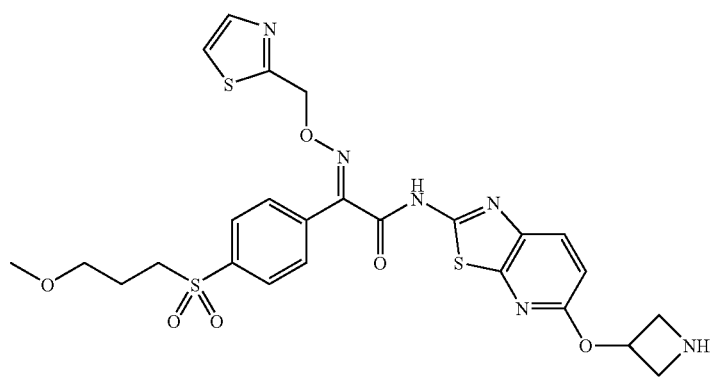 |
| 140 | 347 | 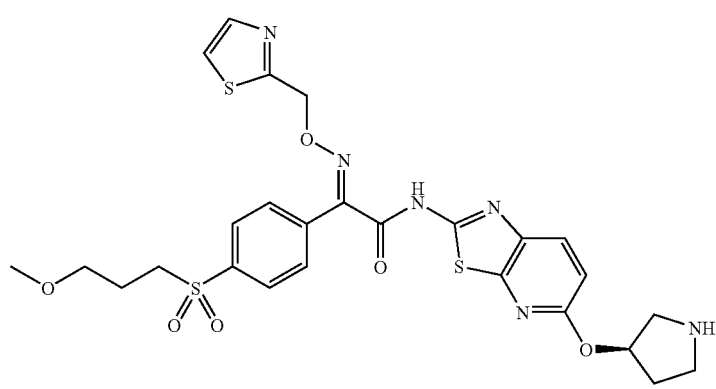 |

| EXAMPLE No. | No. | Structure |
|---|---|---|
| 140 | 348 | 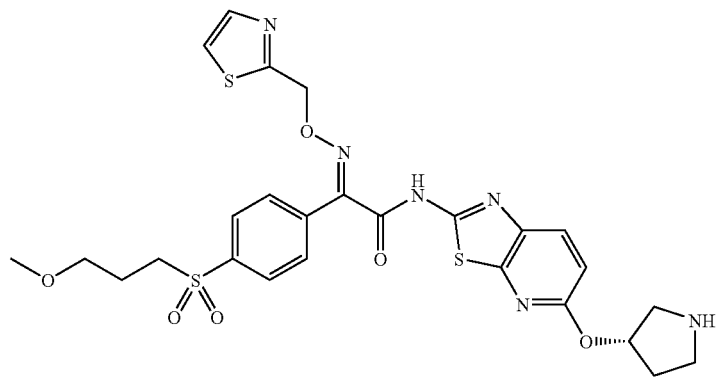 |
| 140 | 349 | 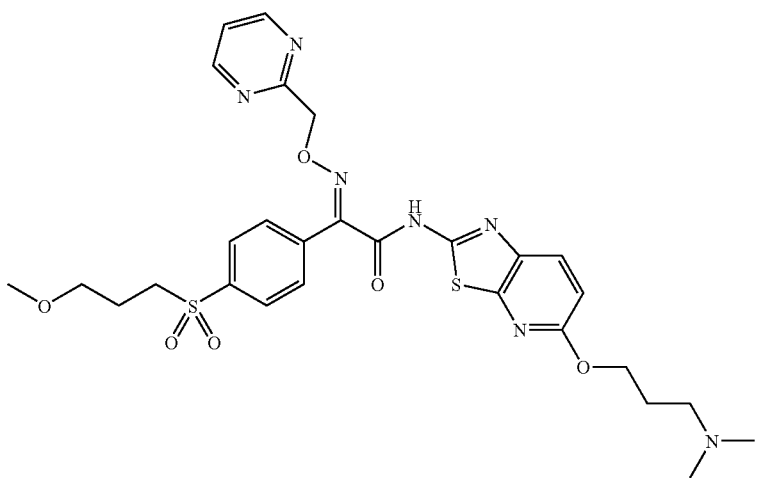 |
| 140 | 350 | 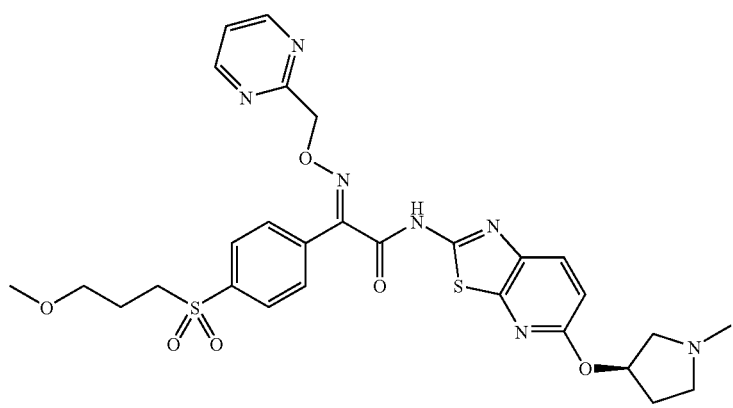 |

-continued
| EXAMPLE No. | No. | Structure |
|---|---|---|
| 140 | 351 | 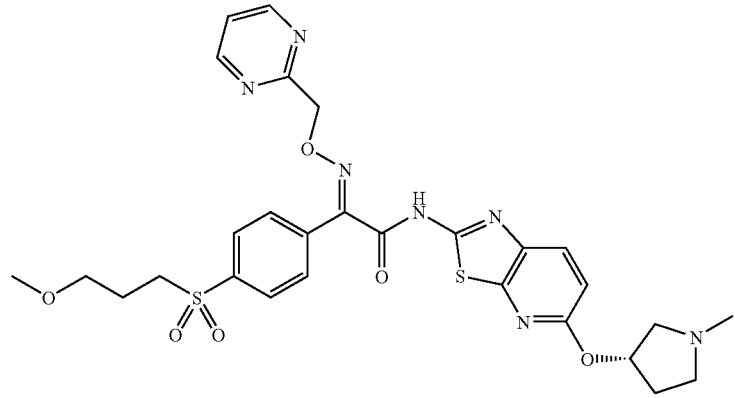 |
| 140 | 352 | 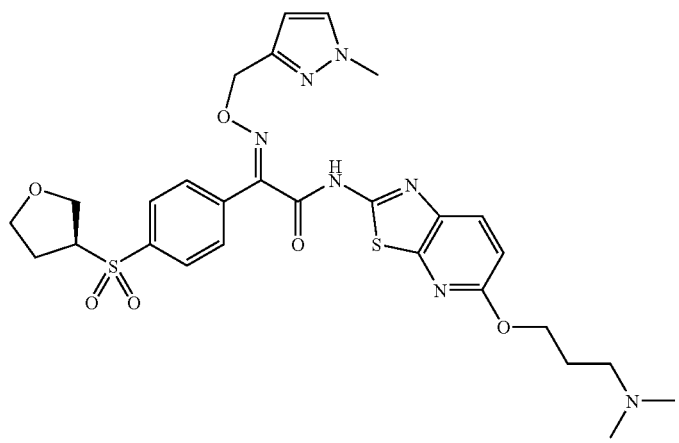 |
| 140 | 353 | 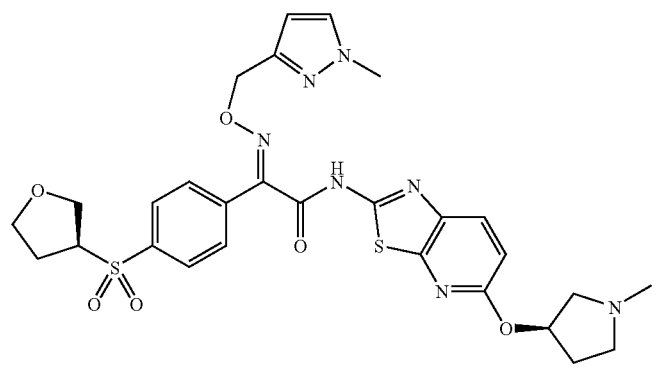 |
| 140 | 354 | 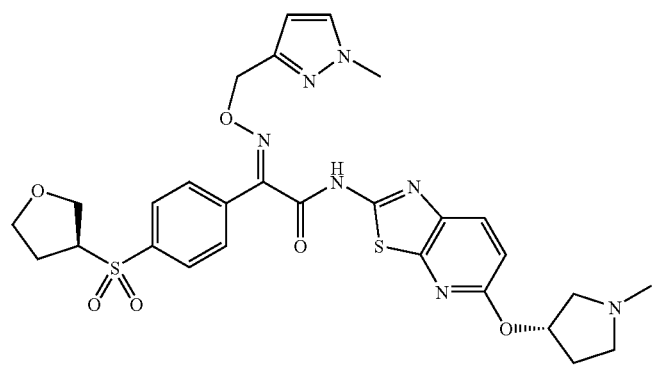 |

-continued

| EXAMPLE No. | No. | Structure |
|---|---|---|
| 140 | 355 | |
| 140 | 356 | |
| 140 | 357 | |
| 140 | 358 | |

-continued
| EXAMPLE No. | No. | Structure |
|---|---|---|
| 140 | 359 | 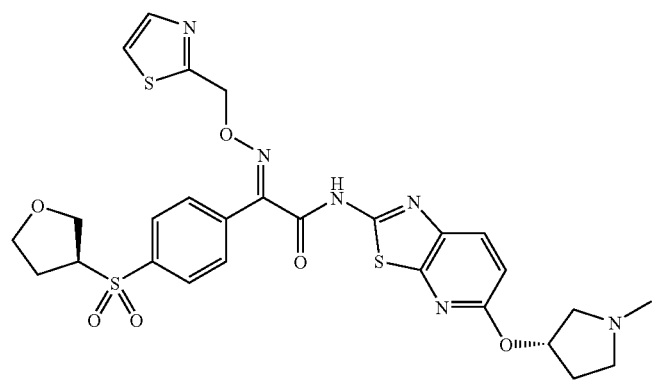 |
| 140 | 360 | 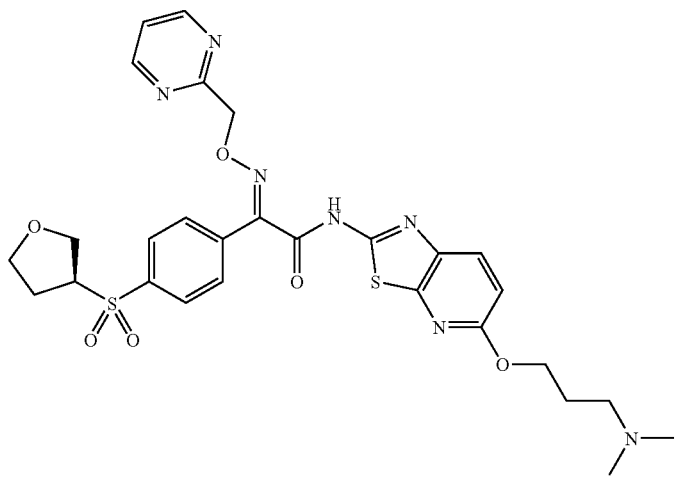 |
| 140 | 361 | 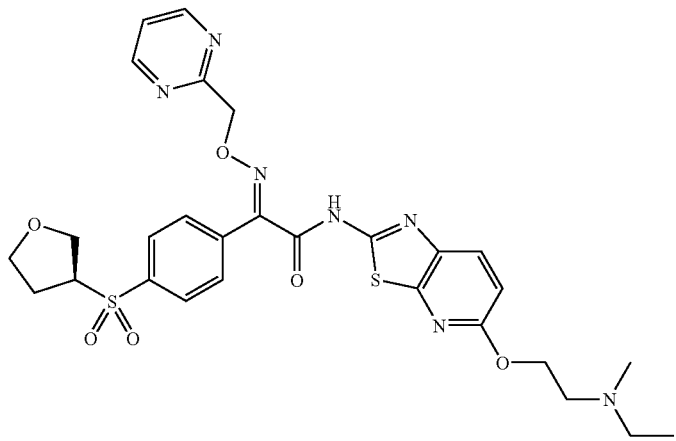 |

| EXAMPLE No. | No. | Structure |
|---|---|---|
| 140 | 362 | 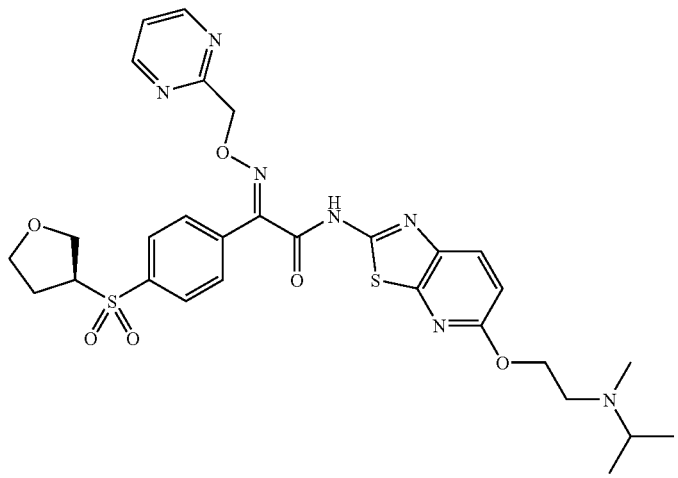 |
| 140 | 363 | 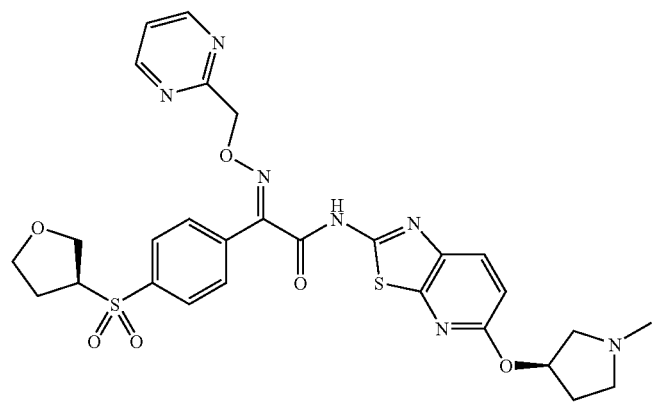 |
| 140 | 364 | 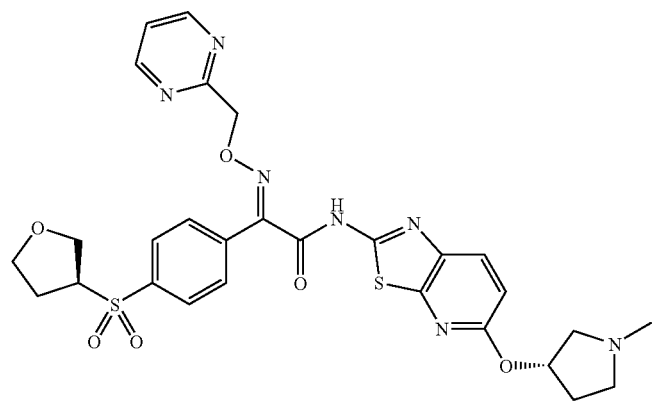 |

-continued

| EXAMPLE No. | No. | Structure |
|---|---|---|
| 140 | 365 | |
| 140 | 366 | |
| 140 | 367 | |
| 140 | 368 | |

US 8,119,626 B2
751 752
-continued
| EXAMPLE No. | No. | Structure |
|---|---|---|
| 140 | 369 | 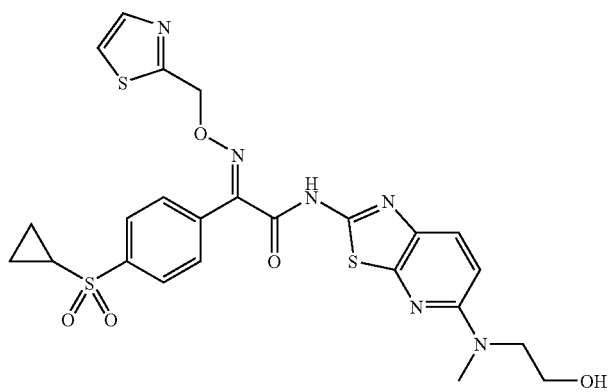 |
| 140 | 370 | 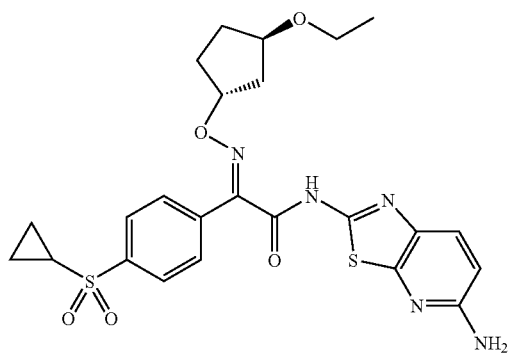 |
| 140 | 371 | 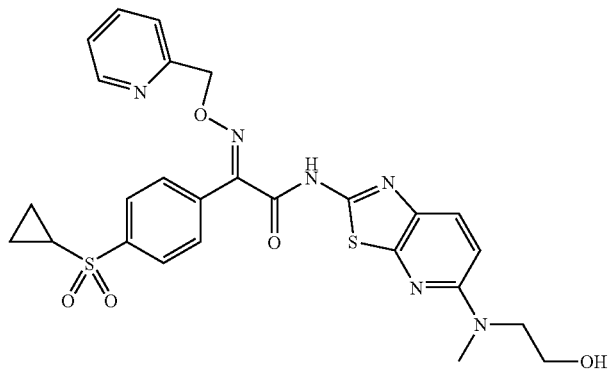 |
| 140 | 372 | 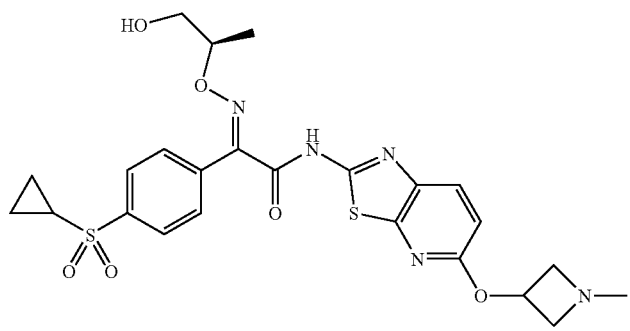 |

| EXAMPLE No. | No. | Structure |
|---|---|---|
| 140 | 373 | 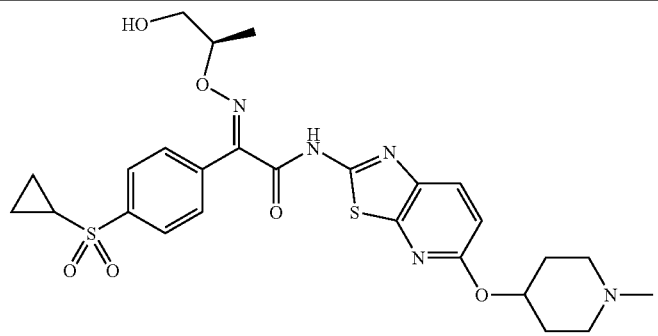 |
| 140 | 374 | 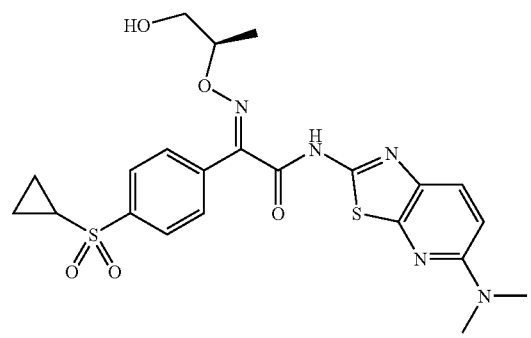 |
| 140 | 375 | 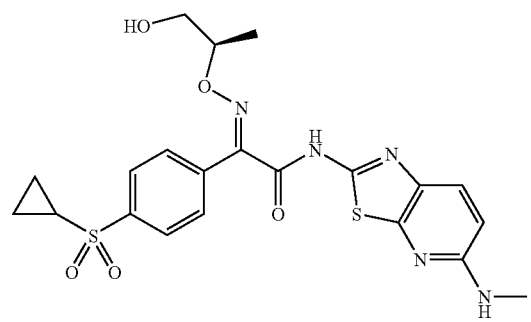 |
| 140 | 376 | 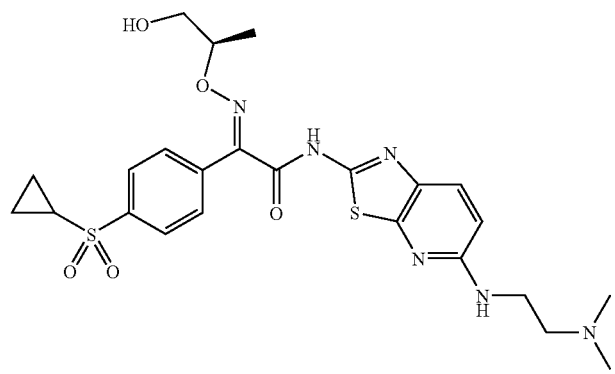 |

-continued
| EXAMPLE No. | No. | Structure |
|---|---|---|
| 140 | 377 | 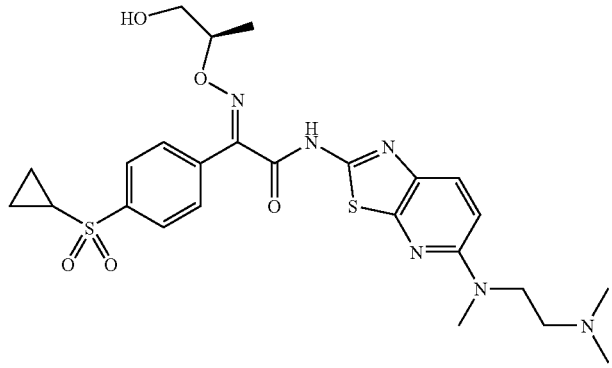 |
| 140 | 378 | 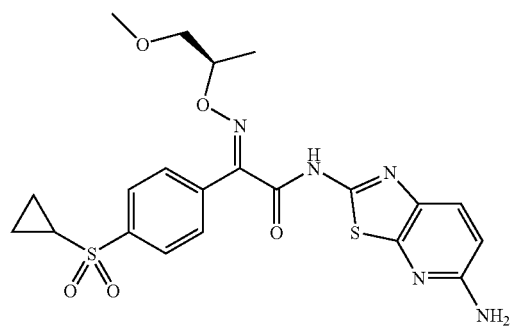 |
| 140 | 379 | 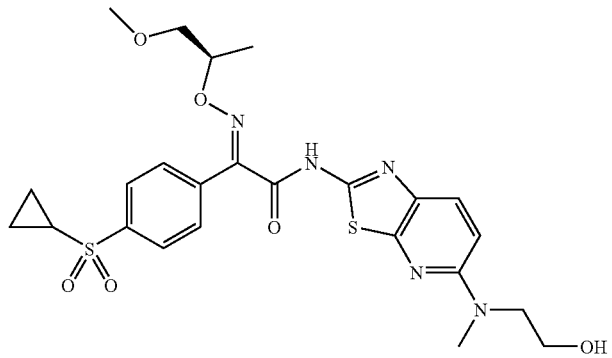 |
| 140 | 380 | 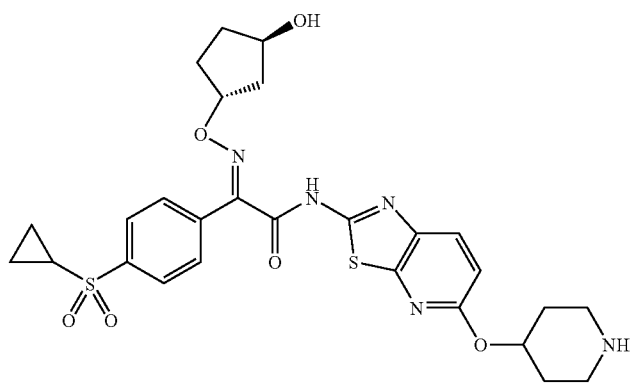 |

-continued
| EXAMPLE No. | No. | Structure |
|---|---|---|
| 140 | 381 | 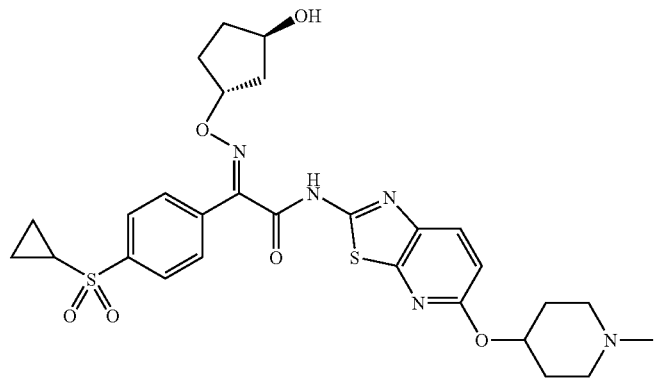 |
| 140 | 382 | 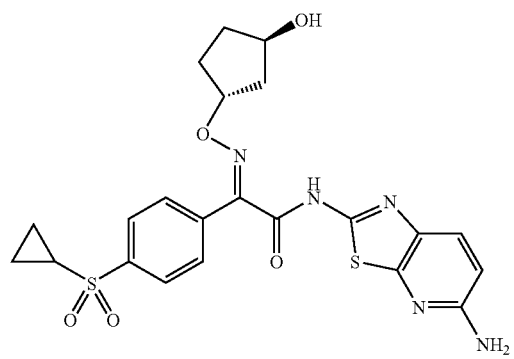 |
| 140 | 383 | 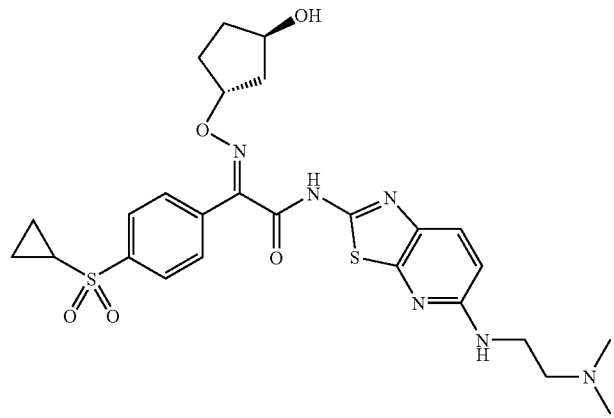 |
| 140 | 384 | 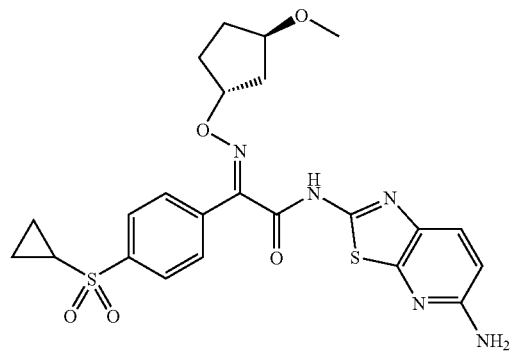 |

| EXAMPLE No. | No. | Structure |
|---|---|---|
| 140 | 385 | 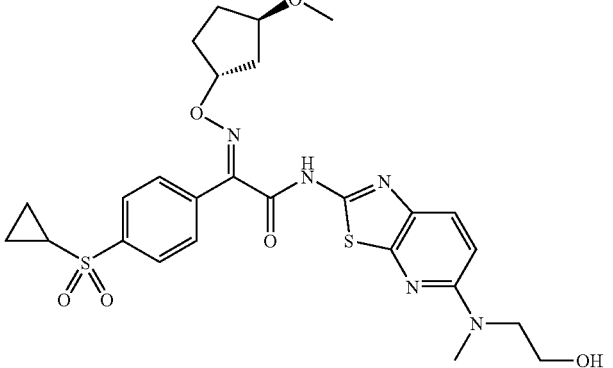 |
| 140 | 386 | 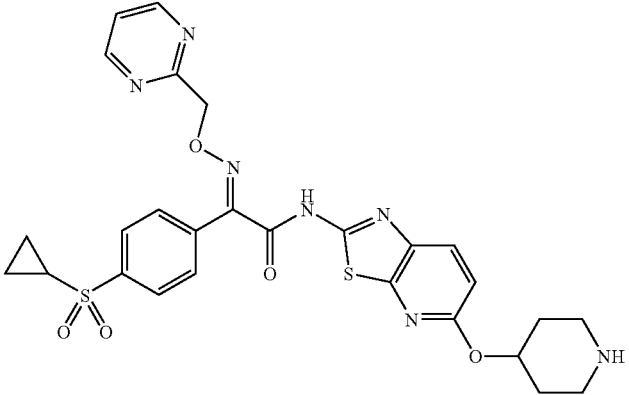 |
| 140 | 387 | 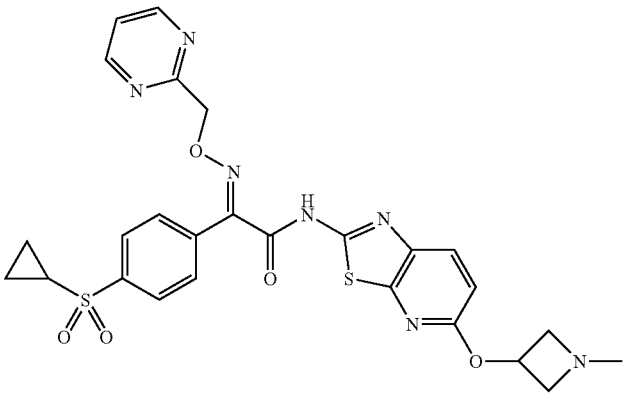 |
| 140 | 388 | 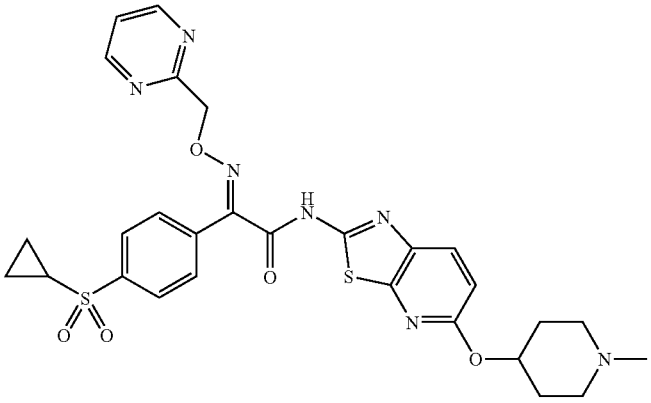 |

| EXAMPLE No. | No. | Structure |
|---|---|---|
| 140 | 389 | |
| 140 | 390 | |
| 140 | 391 | |
| 140 | 392 | |

-continued

| EXAMPLE No. | No. | Structure |
|---|---|---|
| 140 | 393 | |
| 140 | 394 | |
| 140 | 395 | |
| 140 | 396 | |

-continued

| EXAMPLE No. | No. | Structure |
|---|---|---|
| 140 | 397 | |
| 140 | 398 | |
| 140 | 399 | |
| 140 | 400 | |

| EXAMPLE No. | No. | Structure |
|---|---|---|
| 140 | 401 | 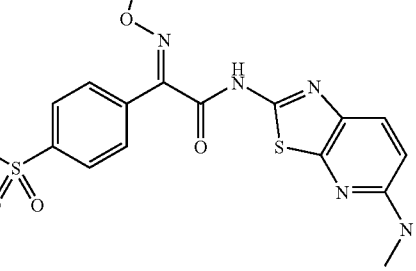 |
| 140 | 402 | 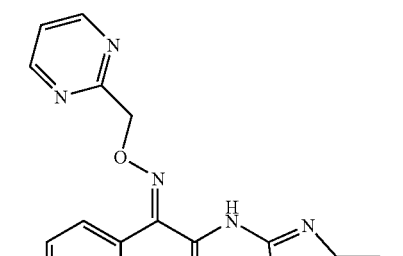 |
| 140 | 403 | 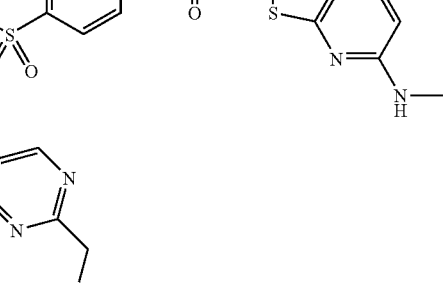 |
| 140 | 404 | 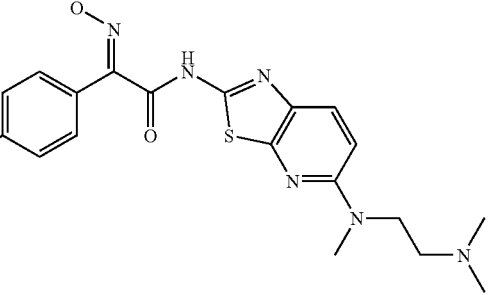 |

| EXAMPLE No. | No. | Structure |
|---|---|---|
| 140 | 405 | |
| 140 | 406 | |
| 140 | 407 | |
| 140 | 408 | |

-continued
| EXAMPLE No. | No. | Structure |
|---|---|---|
| 140 | 409 | 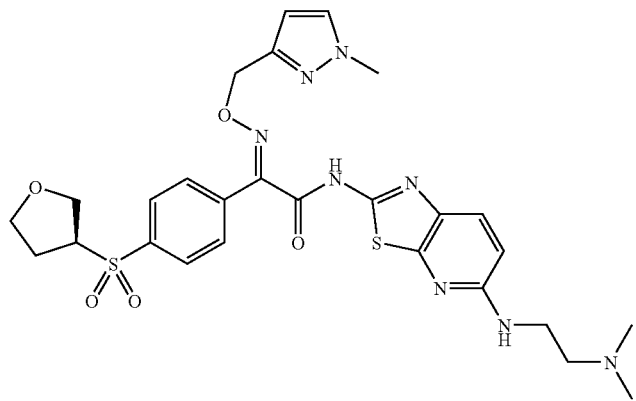 |
| 140 | 410 | 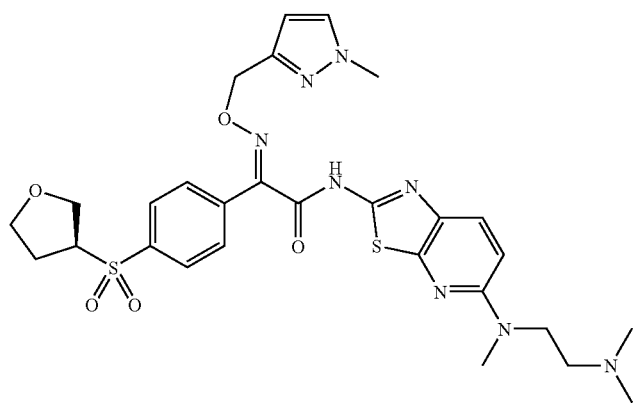 |
| 140 | 411 | 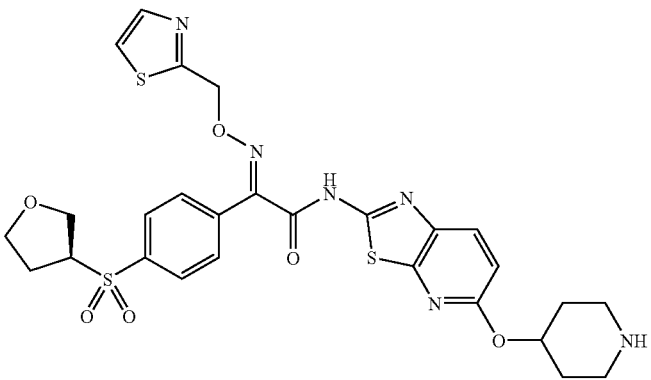 |
| 140 | 412 | 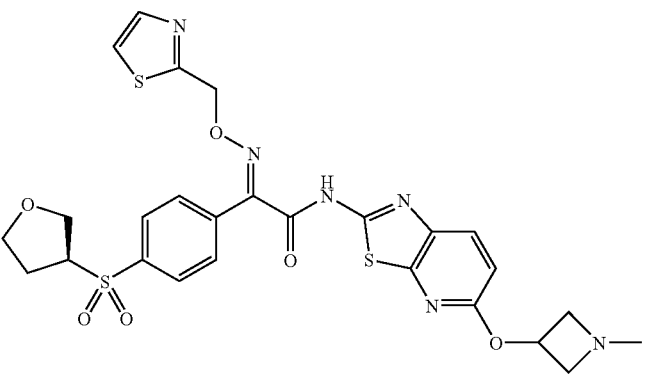 |

-continued

| EXAMPLE No. | No. | Structure |
|---|---|---|
| 140 | 413 | |
| 140 | 414 | |
| 140 | 415 | |
| 140 | 416 | |

| EXAMPLE No. | No. | Structure |
|---|---|---|
| 140 | 417 | 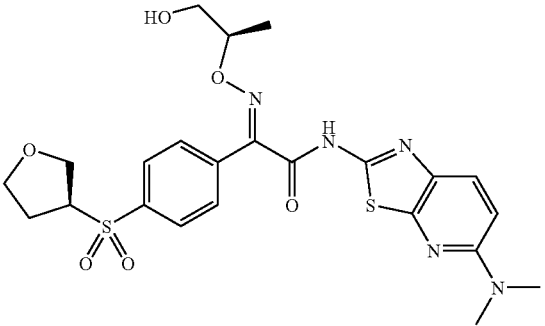 |
| 140 | 418 | 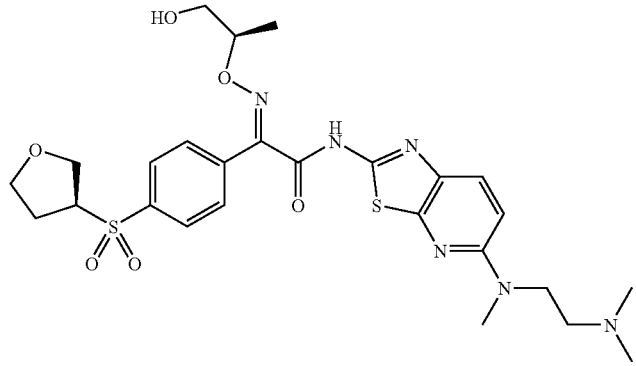 |
| 140 | 419 | 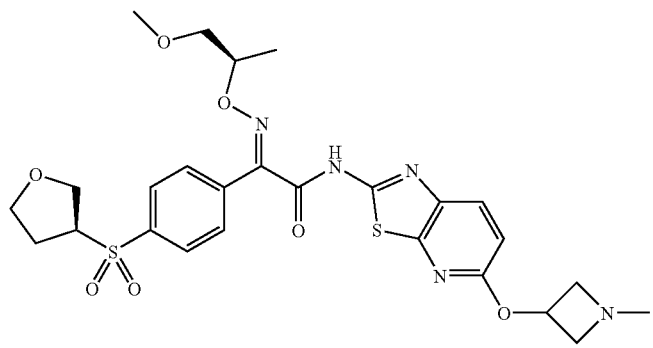 |
| 140 | 420 | 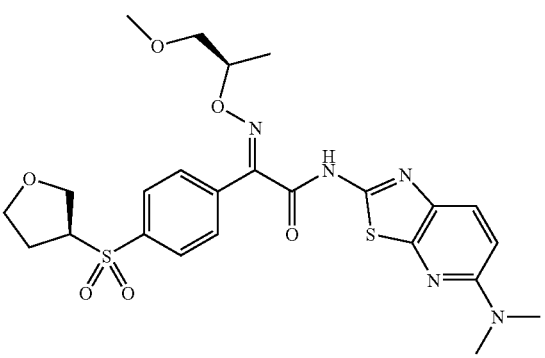 |

-continued

| EXAMPLE No. | No. | Structure |
|---|---|---|
| 140 | 421 | |
| 140 | 422 | |
| 140 | 423 | |
| 140 | 424 | |

-continued

| EXAMPLE No. | No. | Structure |
|---|---|---|
| 140 | 425 | |
| 140 | 426 | |
| 140 | 427 | |
| 140 | 428 | |

-continued
| EXAMPLE No. | No. | Structure |
|---|---|---|
| 140 | 429 | 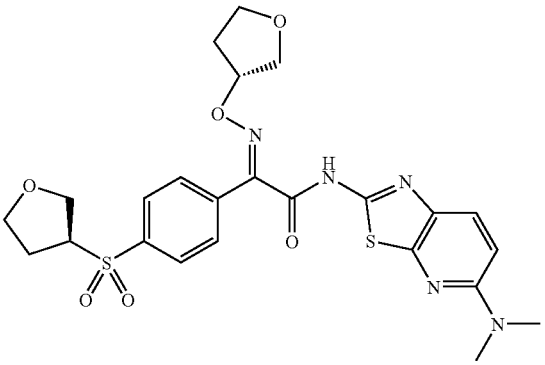 |
| 140 | 430 | 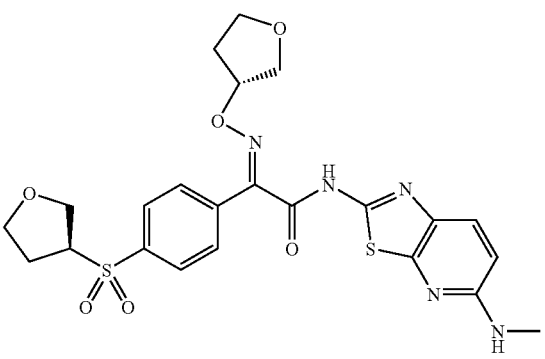 |
| 140 | 431 | 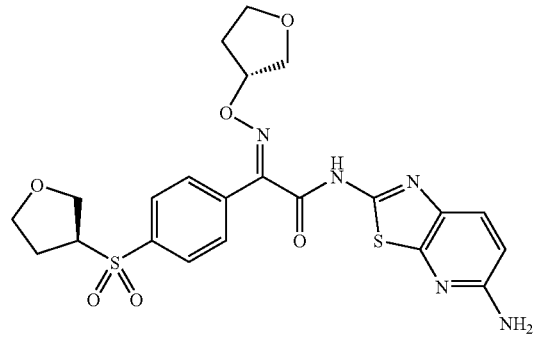 |
| 140 | 432 | 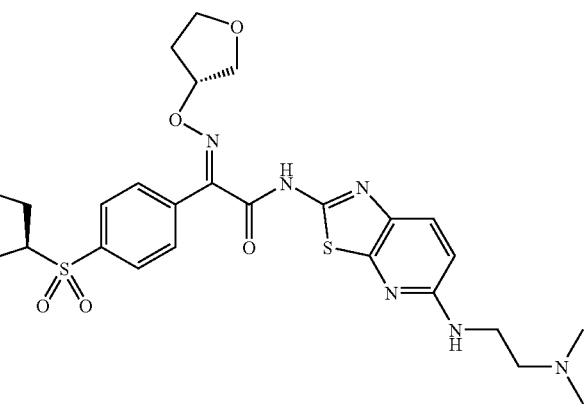 |

| EXAMPLE No. | No. | Structure |
|---|---|---|
| 140 | 433 | 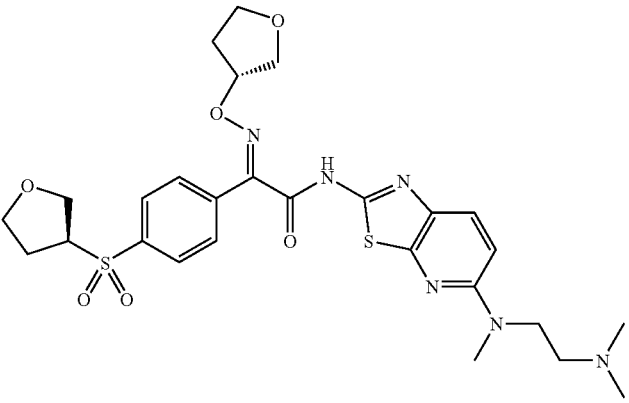 |
| 140 | 434 | 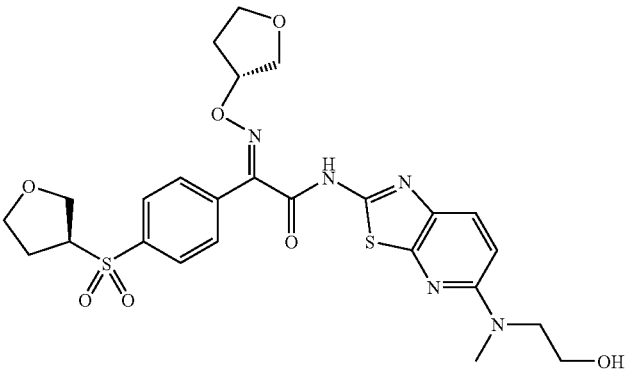 |
| 140 | 435 | 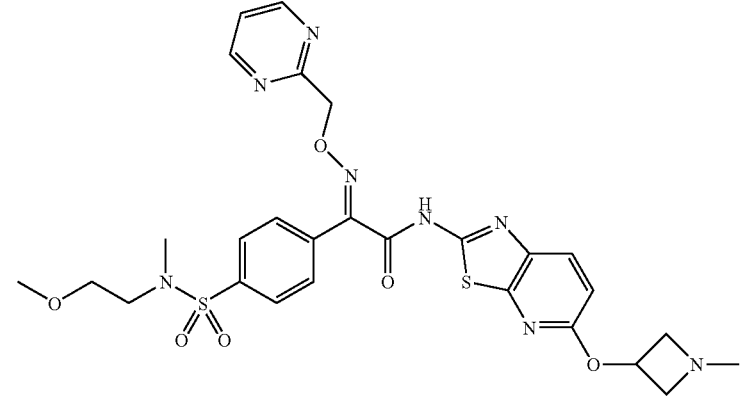 |
| 140 | 436 | 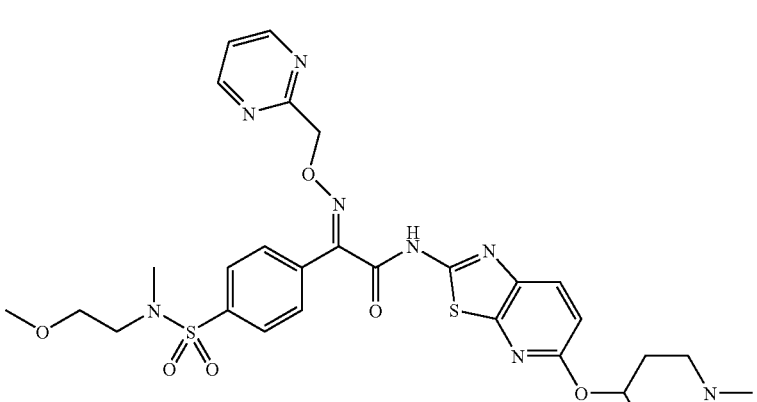 |

| EXAMPLE No. | No. | Structure |
|---|---|---|
| 140 | 437 | 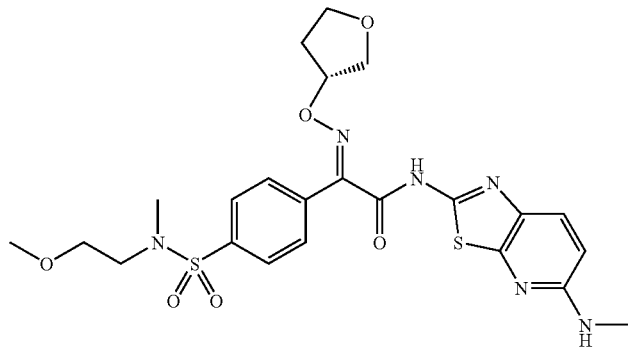 |
| 140 | 438 | 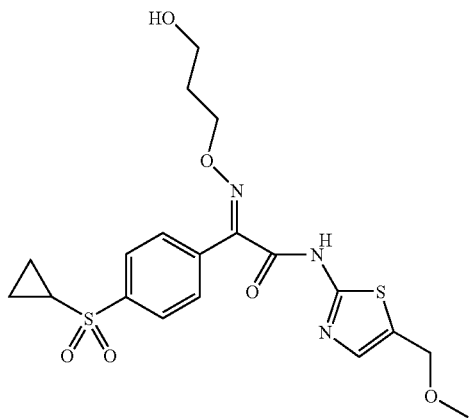 |
| 140 | 439 | 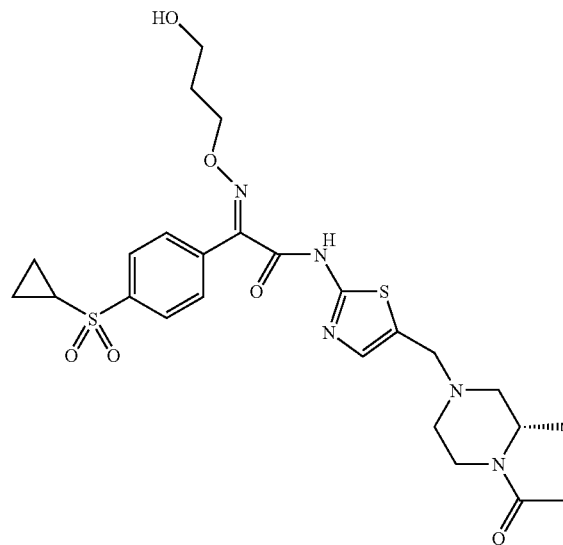 |

| EXAMPLE No. | No. | Structure |
|---|---|---|
| 140 | 440 | 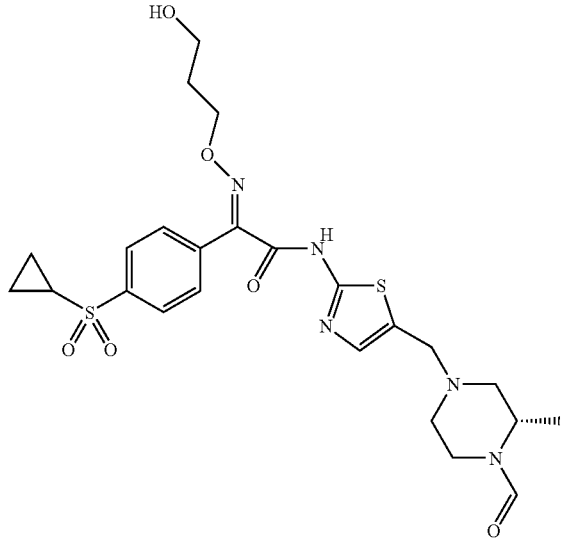 |
| 140 | 441 | 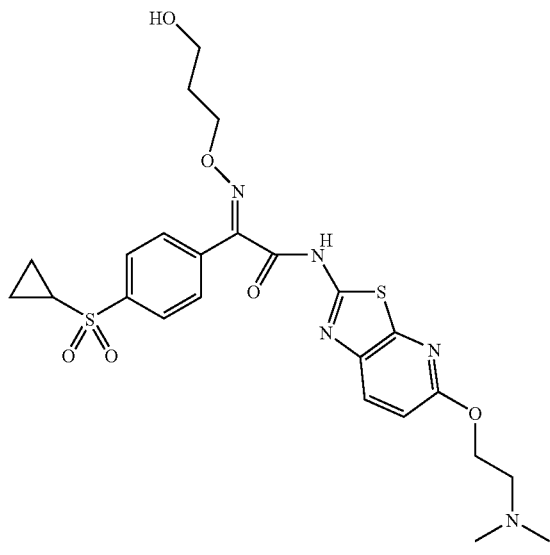 |
| 140 | 442 | 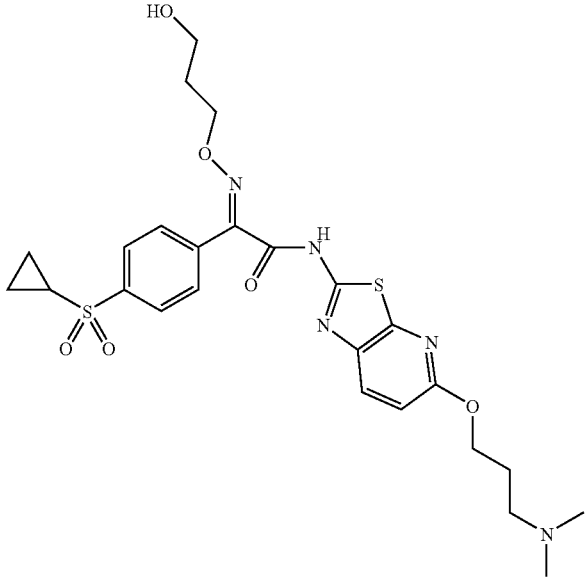 |

-continued
| EXAMPLE No. | No. | Structure |
|---|---|---|
| 140 | 443 | 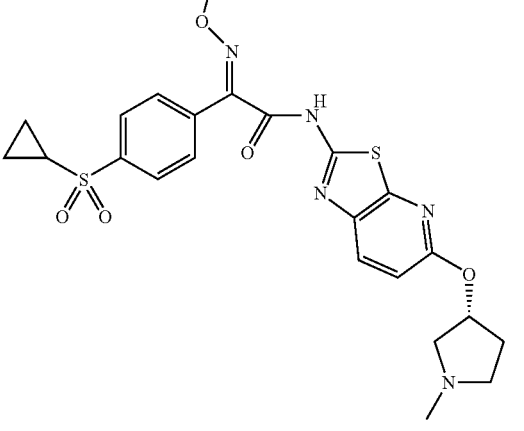 |
| 140 | 444 | 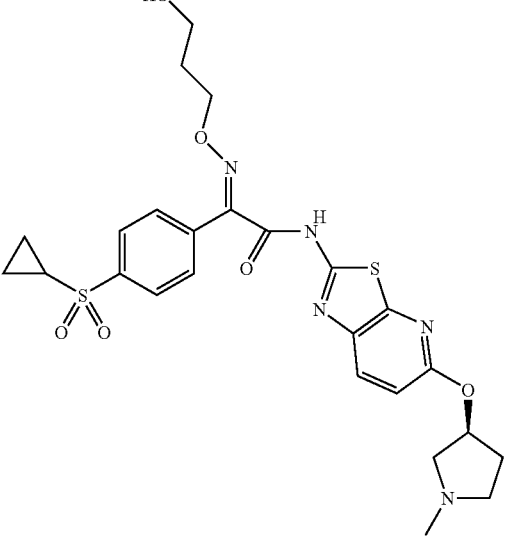 |
| 140 | 445 | 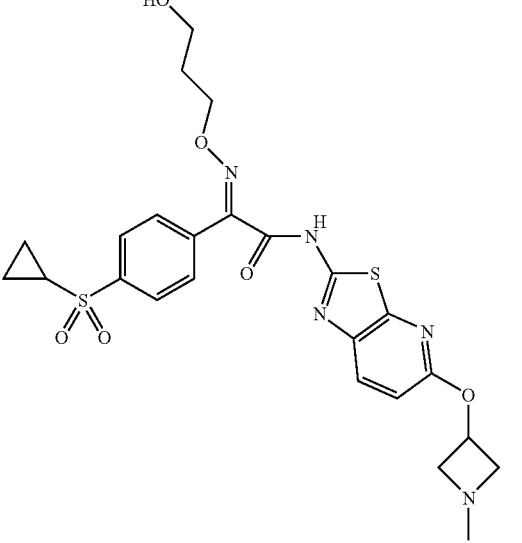 |

-continued
| EXAMPLE No. | No. | Structure |
|---|---|---|
| 140 | 446 | 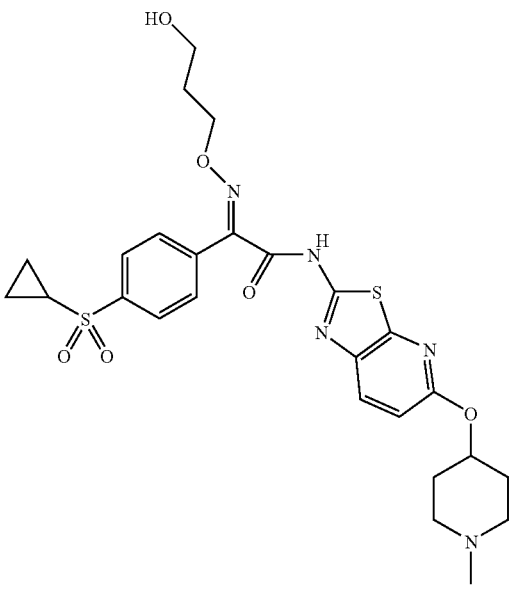 |
| 140 | 447 | 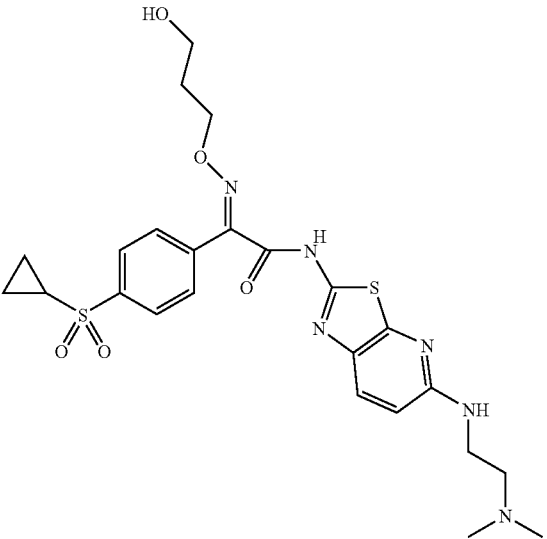 |
| 140 | 448 | 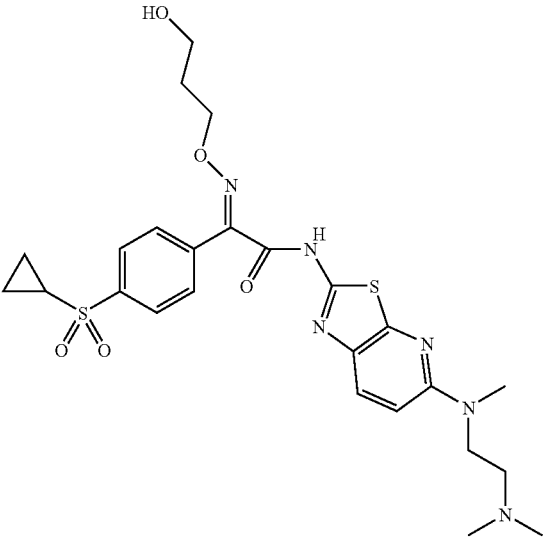 |

-continued
| EXAMPLE No. | No. | Structure |
|---|---|---|
| 140 | 449 | 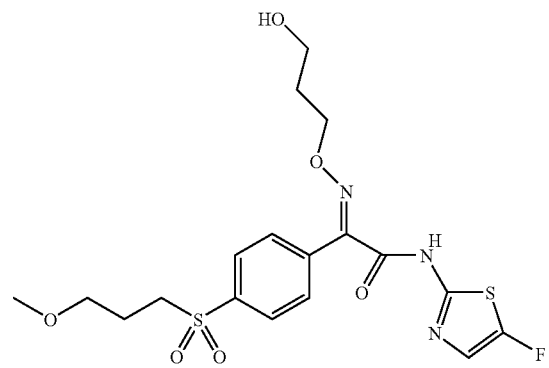 |
| 140 | 450 | 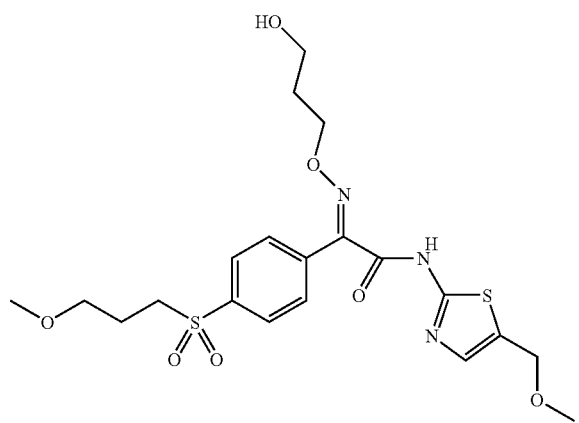 |
| 140 | 451 | 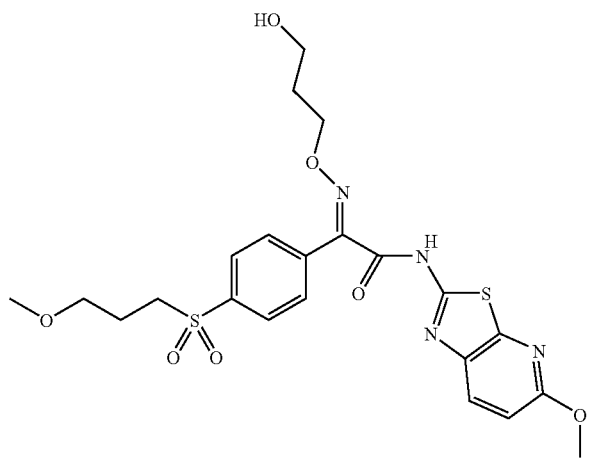 |

US 8,119,626 B2
795                                    796
-continued
| EXAMPLE No. | No. | Structure |
|---|---|---|
| 140 | 452 | 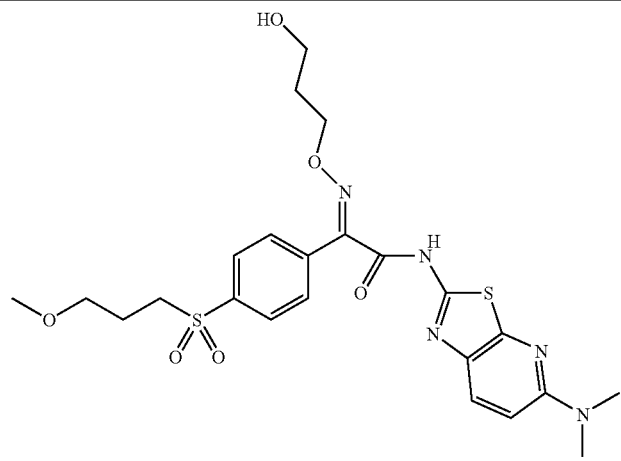 |
| 140 | 453 | 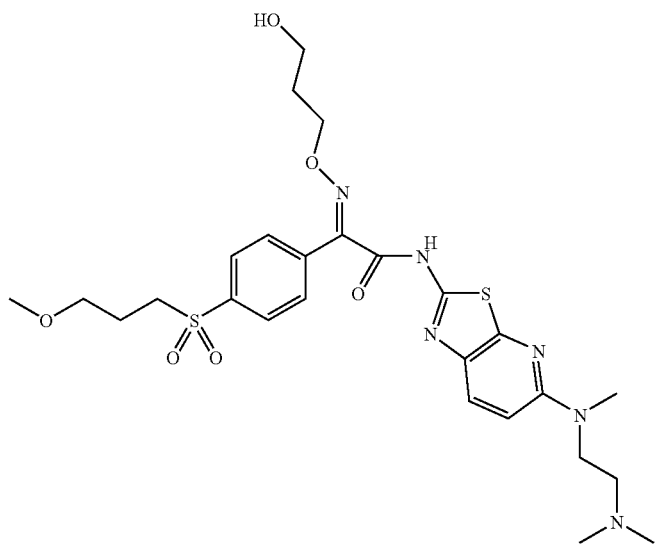 |
| 140 | 454 | 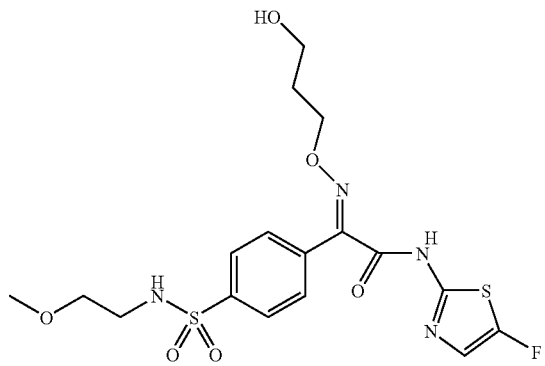 |

-continued
| EXAMPLE No. | No. | Structure |
|---|---|---|
| 140 | 455 | 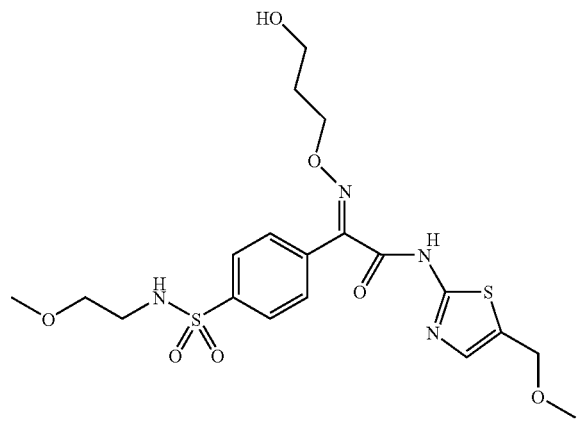 |
| 140 | 456 | 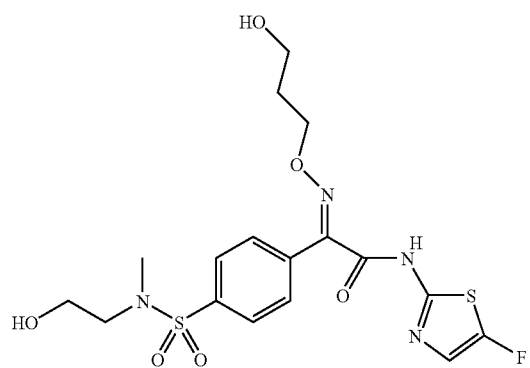 |
| 140 | 457 | 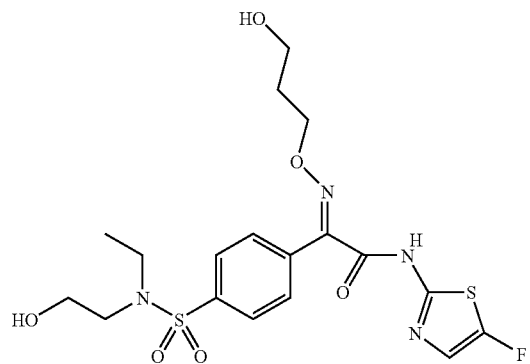 |
| 140 | 458 | 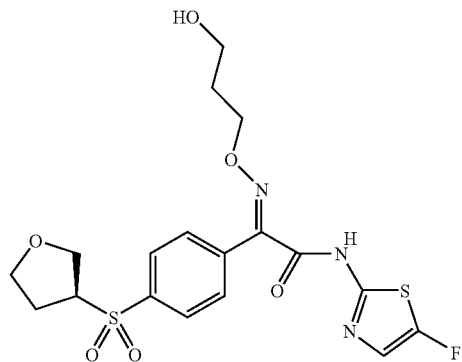 |

| EXAMPLE No. | No. | Structure |
|---|---|---|
| 140 | 459 | 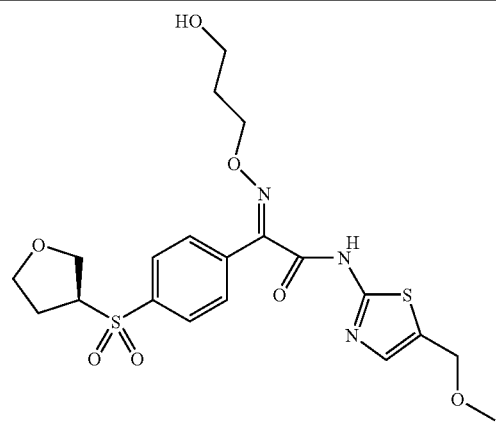 |
| 140 | 460 | 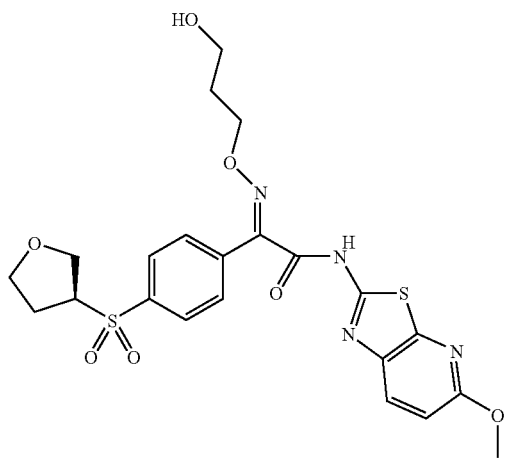 |
| 140 | 461 | 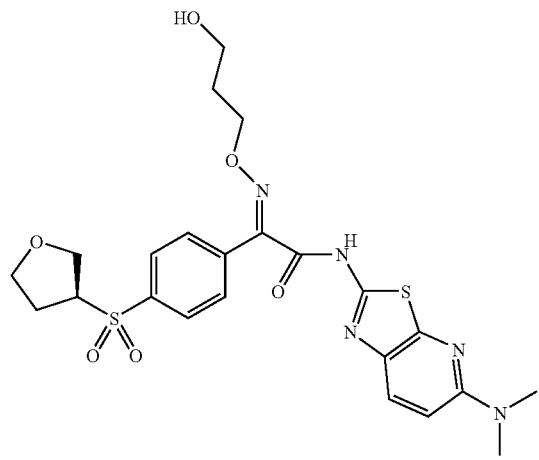 |

-continued
| EXAMPLE No. | No. | Structure |
|---|---|---|
| 140 | 462 | 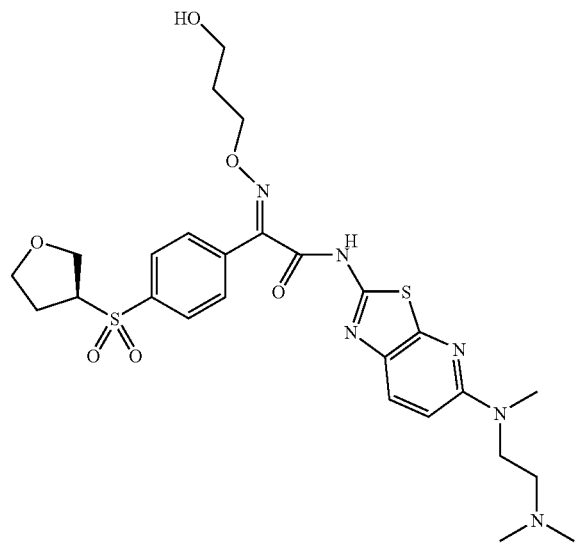 |
| 140 | 463 | 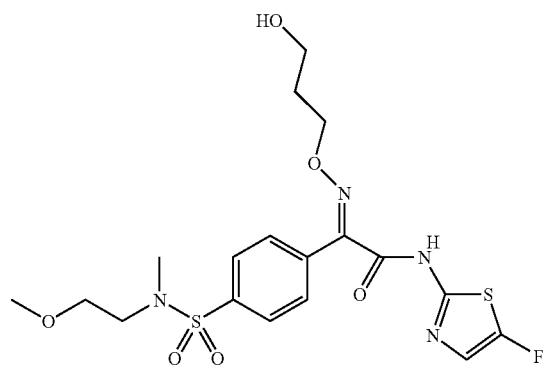 |
| 140 | 464 | 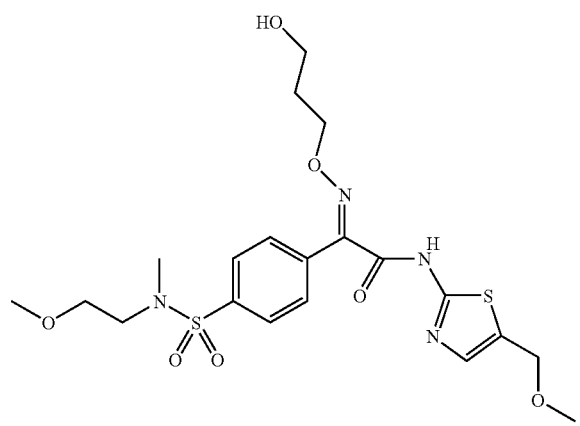 |

| EXAMPLE No. | No. | Structure |
|---|---|---|
| 140 | 465 | 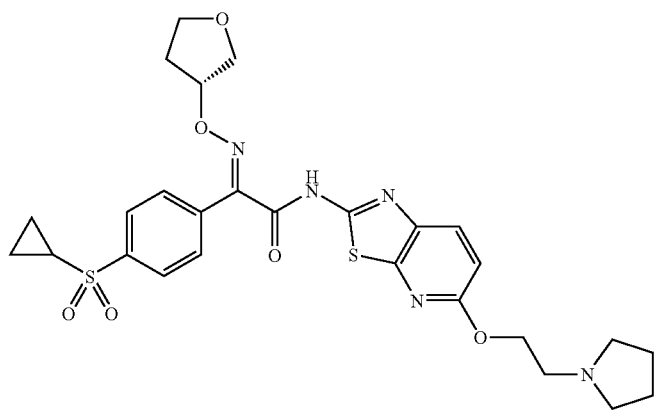 |
| 140 | 466 | 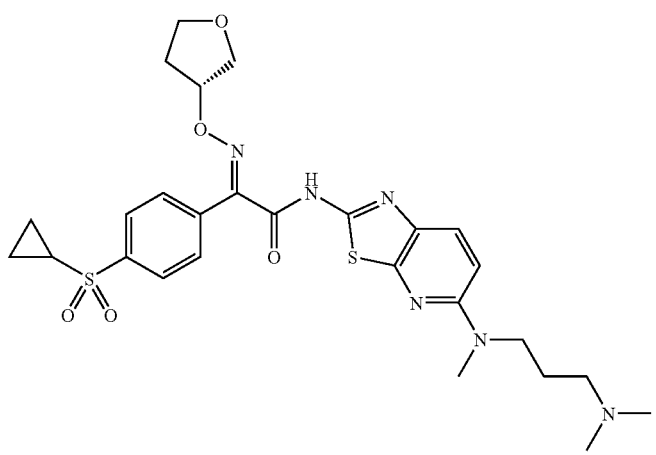 |
| 140 | 467 | 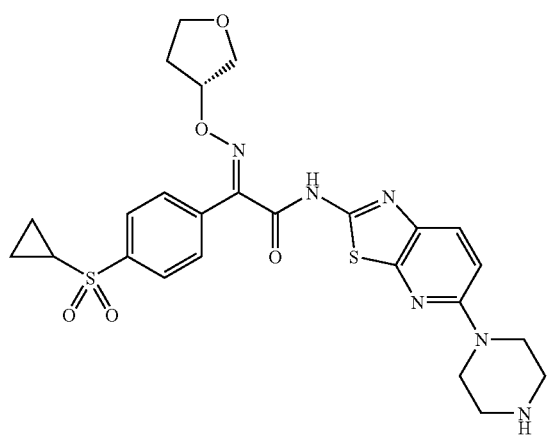 |

| EXAMPLE No. | No. | Structure |
|---|---|---|
| 140 | 468 | 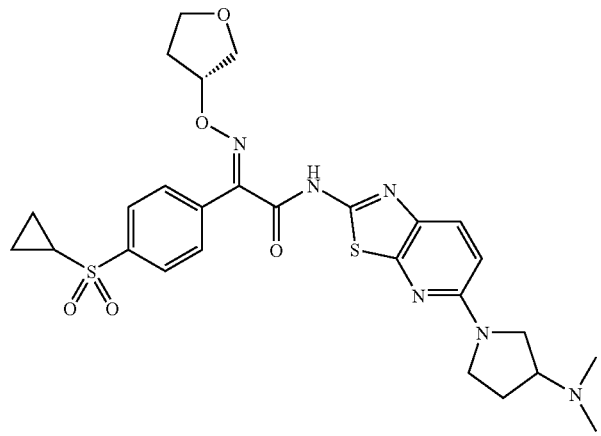 |
| 140 | 469 | 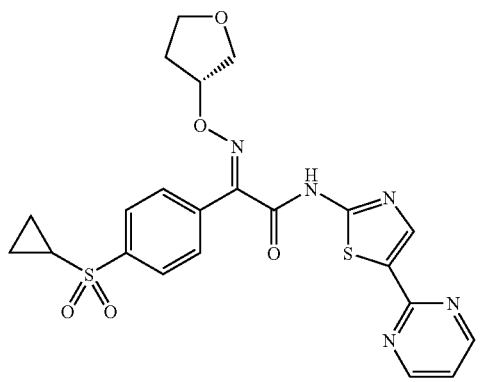 |
| 140 | 470 | 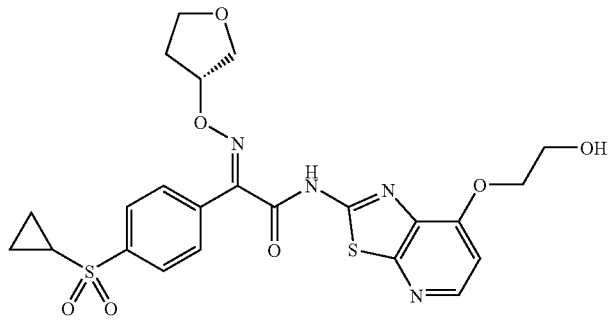 |
| 140 | 471 | 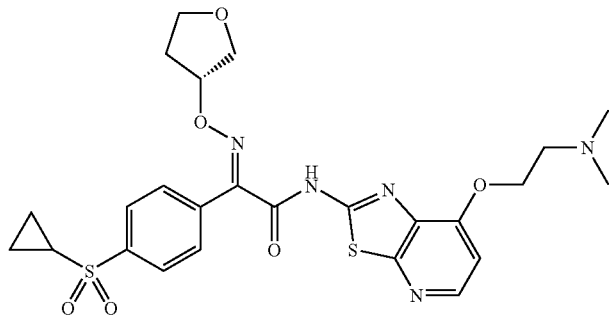 |

-continued
| EXAMPLE No. | No. | Structure |
|---|---|---|
| 140 | 472 | 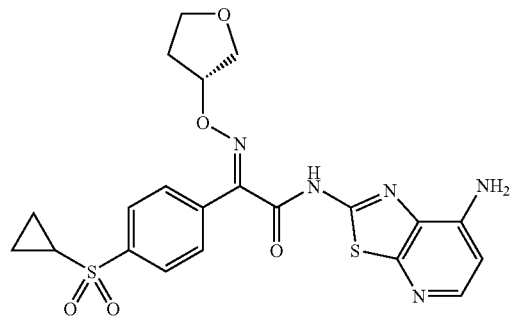 |
| 140 | 473 | 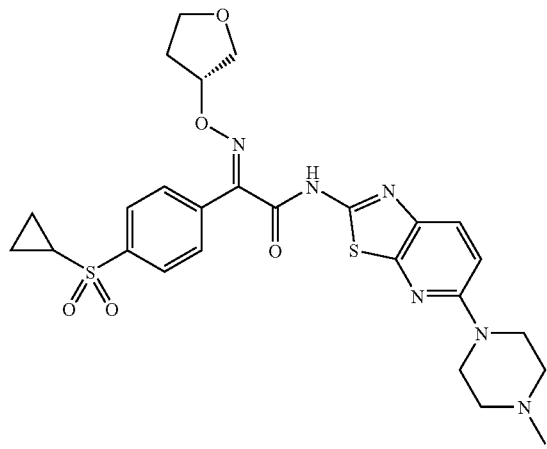 |
| 140 | 474 | 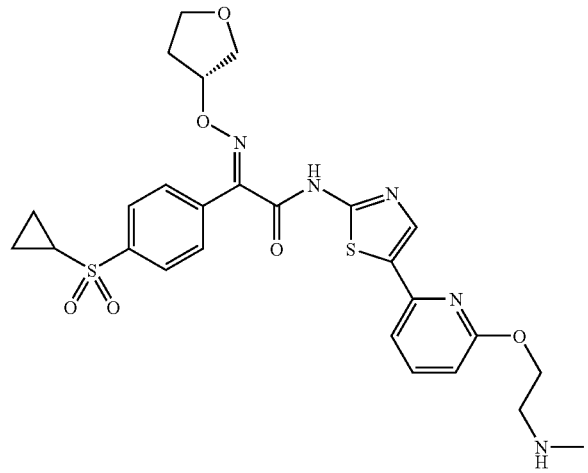 |

| EXAMPLE No. | No. | Structure |
|---|---|---|
| 140 | 475 | 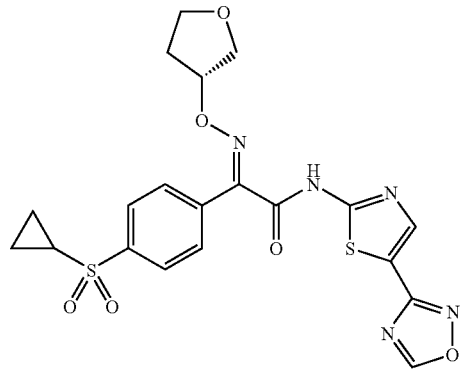 |
| 140 | 476 | 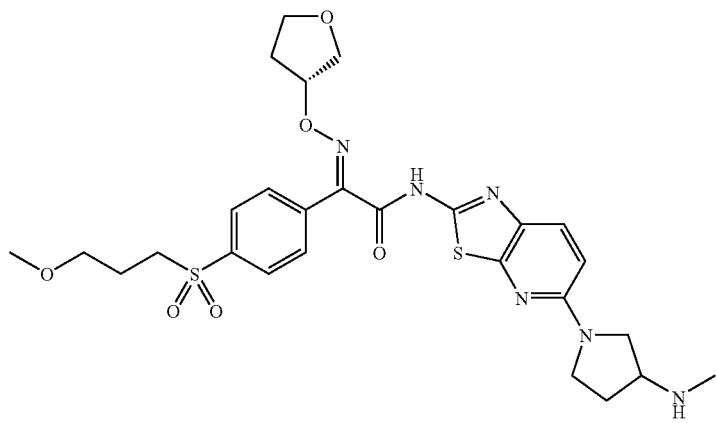 |
| 140 | 477 | 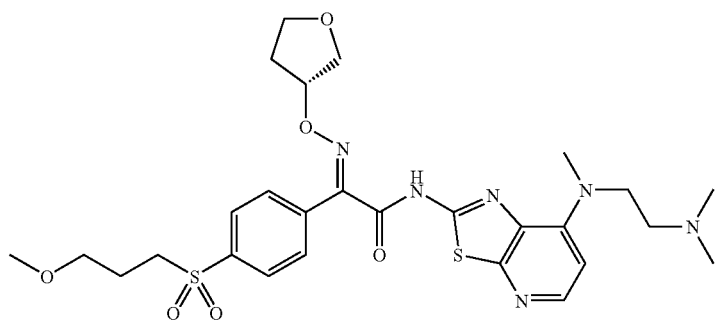 |
| 140 | 478 | 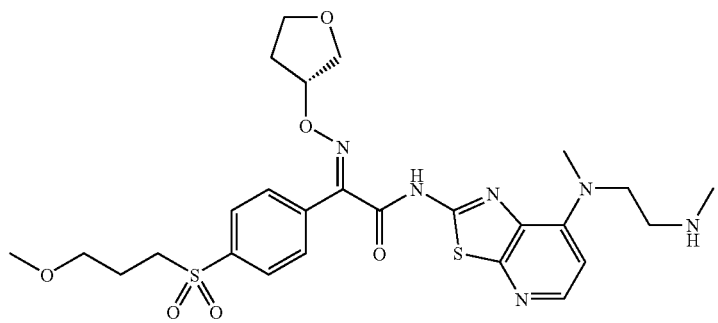 |

-continued

| EXAMPLE No. | No. | Structure |
|---|---|---|
| 140 | 479 | |
| 140 | 480 | |
| 140 | 481 | |
| 140 | 482 | |

| EXAMPLE No. | No. | Structure |
|---|---|---|
| 140 | 483 | 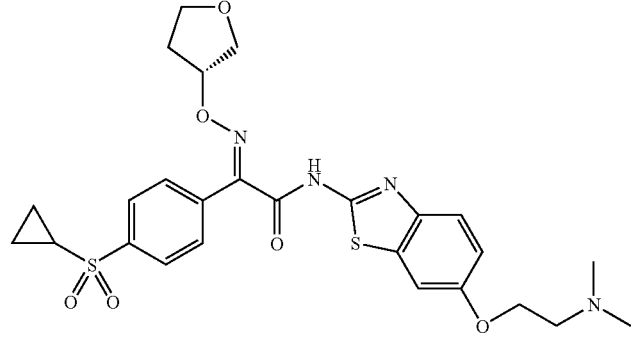 |
| 140 | 484 | 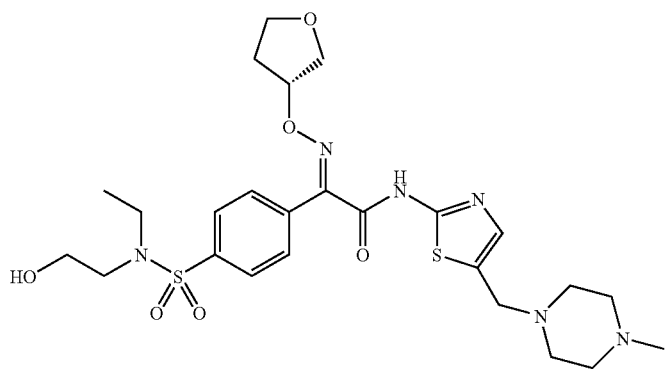 |
| 140 | 485 | 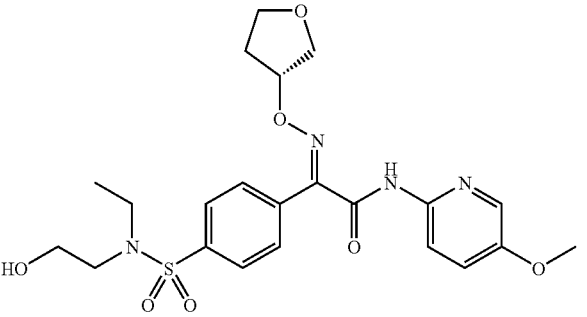 |
| 140 | 486 | 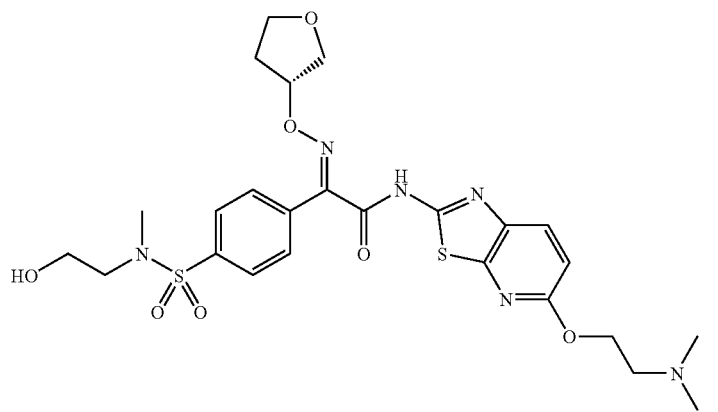 |

| EXAMPLE No. | No. | Structure |
|---|---|---|
| 140 | 487 | 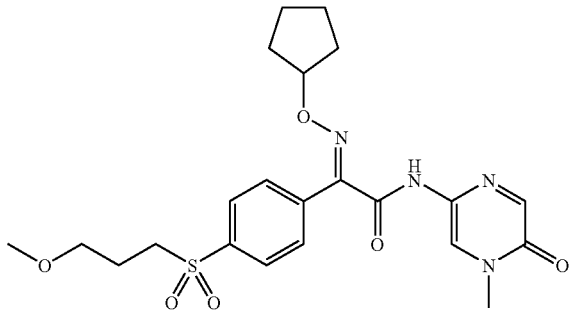 |
| 140 | 488 | 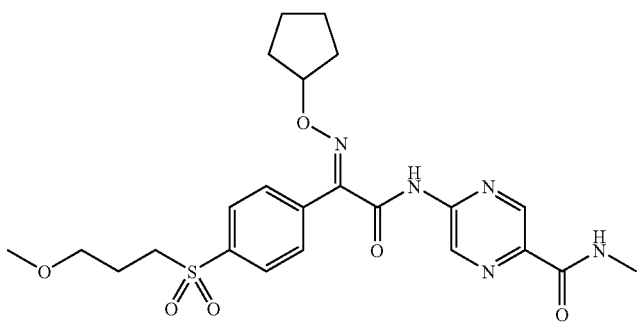 |
| 140 | 489 | 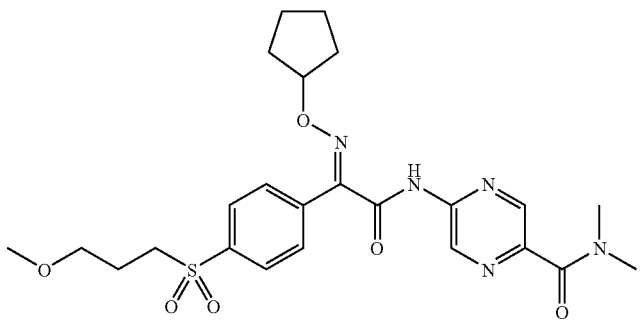 |
| 140 | 490 | 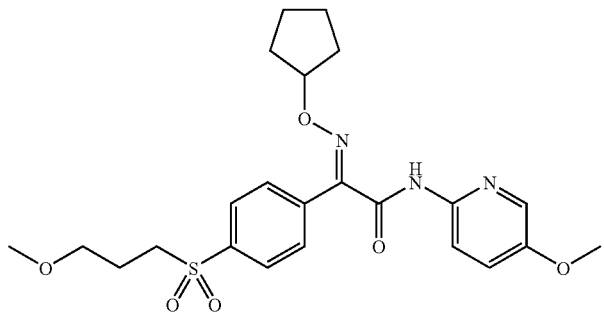 |

-continued

| EXAMPLE No. | No. | Structure |
|---|---|---|
| 140 | 491 | |
| 140 | 492 | |
| 140 | 493 | |
| 140 | 494 | |

-continued
| EXAMPLE No. | No. | Structure |
|---|---|---|
| 140 | 495 | 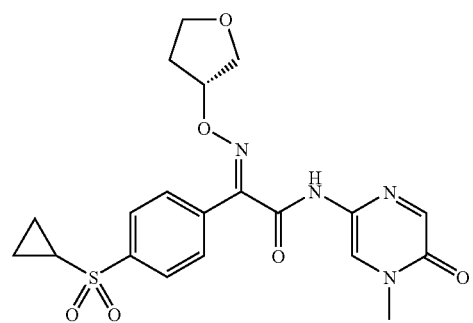 |
| 140 | 496 | 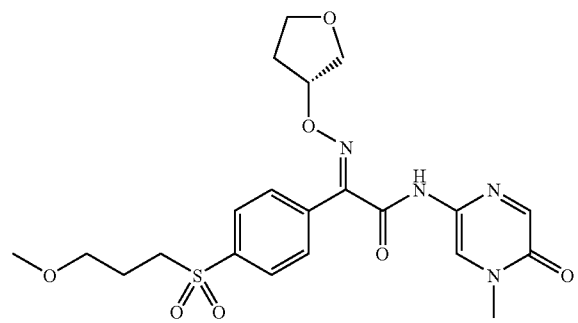 |
| 140 | 497 | 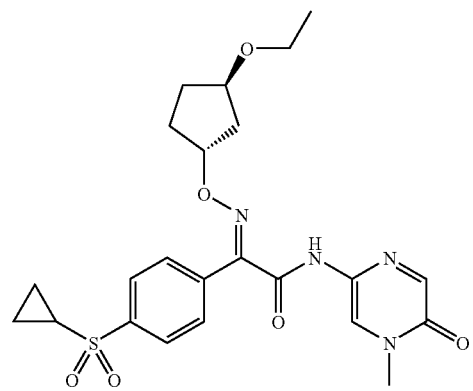 |
| 140 | 498 | 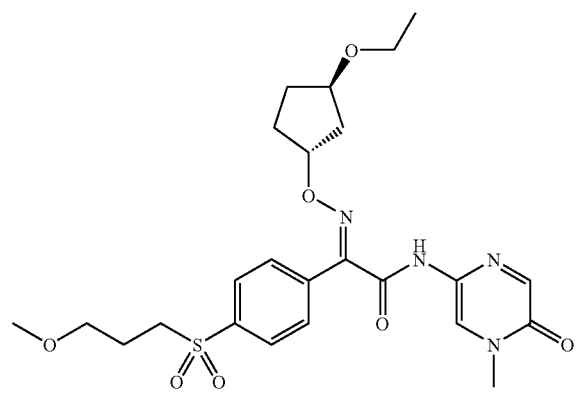 |

Reference Example 1

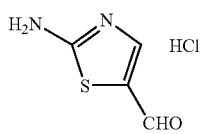

To a solution of 2-tert-butyloxycarbonylaminothiazole (88.0 g, 439 mmol) in THF (1760 ml) was added dropwise a 1.59M solution of n-butyllithium in hexane (729 ml, 1159 mmol) over 20 minutes at −78° C., and the mixture was warmed to −10° C. over 1 hour. The mixture was cooled again to −78° C. and thereto was added DMF (102 ml, 0.132 mmol) in one portion. The acetonedry ice bath was removed. The mixture was stirred for 30 minutes, and then poured into cold water (1000 ml) and thereto was added ethyl acetate (2000 ml). The organic layer was washed sequentially with water and brine, dried over anhydrous magnesium sulfate and the solvents were removed. The residue was recrystallized from ethyl acetate to give 2-tert-butyloxycarbonylaminothiazole-5-carbaldehyde (74.8 g).
mp. 173 to 175° C.
MS (m/z) APCI: 229 (M+H)$^+$ To a solution of the above 2-tert-butyloxycarbonylaminothiazole-5-carbaldehyde (64.5 g, 282 mmol) in methylene chloride (322 ml) was added dropwise trifluoroacetic acid (322 ml) under ice-cooling over 20 minutes. The mixture was stirred at room temperature for 2 hours and the solvent was removed by evaporation. Thereto was added chloroform (50 ml), and then added a 4N hydrogen chloride solution in dioxane (300 ml) dropwise under ice-cooling. After removing the solvents, the residue was washed with ethyl acetate and collected to give the titled compound (41.3 g) as monohydrochloride thereof,
mp. 190 to 194° C. (decomposed)
MS (m/z) APCI: not detected

Reference Example 2

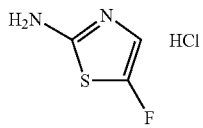

To a solution of 2-tert-butyloxycarbonylaminothiazole (60.0 g, 299 mmol) in THF (1200 ml) was added dropwise a 1.59M solution of n-butyllithium in hexane (428 ml, 659 mmol) at −78° C. over 20 minutes, and the mixture was warmed to −10° C. over 1 hour and cooled again to −78° C. Thereto was added N-fluorobenzenesulfonylimide (142 g, 449 mmol) in one portion. The acetone-dry ice bath was removed and the mixture was stirred for 30 minutes poured into cold water (1000 ml). Thereto was added ethyl acetate (1200 ml) and the organic layer was washed sequentially with 2N hydrochloric acid, water and brine, dried over anhydrous magnesium sulfate and concentrated. The residue was purified by silica gel column chromatography (15% ethyl acetate-hexane=3:1), and then recrystallized from diethyl ether to give 2-tert-butyloxycarbonylamino-5-fluorothiazole (45.1 g).
mp. 157 to 159° C.
MS (m/z) APCI: 219 (M+H)$^+$ To a solution of the above 2-tert-butyloxycarbonylamino-5-fluorothiazole (38.0 g, 174 mmol) in methylene chloride (190 ml) was added dropwise trifluoroacetic acid (190 ml) over 20 minutes under ice-cooling. The mixture was stirred at room temperature for 2.5 hours, and concentrated. Thereto was added chloroform (20 ml) and 4N hydrogen chloride solution in dioxane (180 ml) dropwise under ice-cooling. After concentration, the residue was washed with ethyl acetate and collected to give the titled compound (24.6 g) as monohydrochloride thereof.
mp. 142 to 144° C. (decomposed)
MS (m/z) APCI: 119 (M+H)$^+$

Reference Example 3

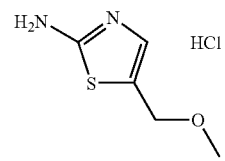

(1) To an aqueous solution (400 ml) of a compound of REFERENCE EXAMPLE 1 (80.0 g, 486 mmol) was added dropwise a 28% ammonia water (40 ml) at room temperature, and then the precipitated crystals were collected and dried to give the free aldehyde.
(2) The above product was suspended in methanol (600 ml) and thereto was added sodium borohydride (27.6 g, 729 mmol) under ice-cooling, and the mixture was stirred at room temperature for 1 hour. To the reaction solution were added acetone (30 ml) and water (50 ml), and then the mixture was concentrated in vacuo. The resulting residue was purified by silica gel column chromatography (20 to 25% methanolchloroform) to give 2-amino-5-hydroxymethylthiazole (45.2 g, yield 71%).
MS (m/z) APCI: 131 (M+H)$^+$
(3) The above product (45.2 g) was dissolved in a 2M solution of hydrogen chloride in methanol and the mixture was stirred at 60° C. for 5 hours. The reaction mixture was concentrated and then the residue was solidified with a mixture of methanol and diethyl ether to give the titled compound (49.8 g, yield 79%) as monohydrochloride thereof.
MS (m/z) APCI: 145 (M+H)$^+$

Reference Example 4

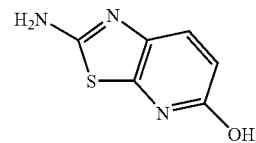

5-Methoxy[1,3]thiazolo[5,4-b]pyridin-2-amine (5.0 g, 27.6 mmol) was dissolved in 30% hydrogen bromide in acetic acid (50 ml). The mixture was stirred at 130° C. for 3 hours and cooled to room temperature, and then the solvents were removed in vacuo and the residue was solidified with diethyl ether to give 2-amino[1,3]thiazolo[5,4-b]pyridin-5-ol dihydrobromide (9.11 g, quantitatively) as colorless crystals.
MS (m/z) APCI: 168 (M+H)$^+$

Reference Example 5

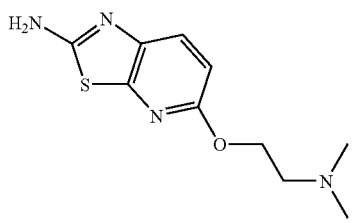

A solution of a compound of REFERENCE EXAMPLE 4 (1.18 g, 3.59 mmol), dimethylaminoethyl chloride monohydrochloride (569 mg, 3.95 mmol) and cesium carbonate (6.43 g, 19.75 mmol) in DMF (30 ml) was stirred at 60° C. for 2 hours. After cooling to room temperature, thereto was added acetic acid (2.26 ml, 39.5 mmol) and the mixture was diluted with water to a homogeneous solution and then concentrated in vacuo. The residue was purified by silica gel column chromatography (NH-silica gel; 50% ethyl acetate-hexane) to give the titled compound (273 mg, yield 32%) as pale yellow crystals.
MS (m/z) APCI: 239 (M+H)$^+$

Reference Example 6

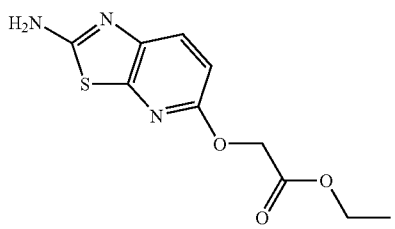

A solution of a compound of REFERENCE EXAMPLE 4 (1.54 g, 4.68 mmol), ethyl bromoacetate (0.571 ml, 5.15 mmol) and cesium carbonate (6.86 g, 21.06 mmol) in DMF (40 ml) was stirred at room temperature for 30 minutes. Thereto was added acetic acid (2.47 ml, 43.2 mmol) and the mixture was diluted with water to a homogeneous solution and the solvents were removed in vacuo. The residue was purified by silica gel column chromatography (NH-silica gel; ethyl acetate) and solidified with diisopropyl ether to give the titled compound (862 mg, yield 67%) as colorless crystals.
MS (m/z) APCI: 254 (M+H)$^+$

Reference Example 7

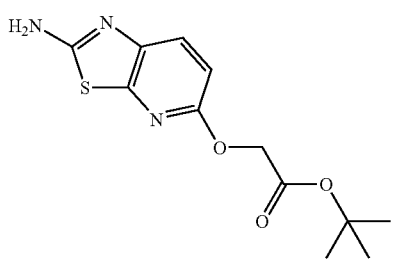

A corresponding starting compound was treated in the similar manner as REFERENCE EXAMPLE 5 to give the titled compound.
MS (m/z) APCI: 282 (M+H)$^+$

Reference Example 8

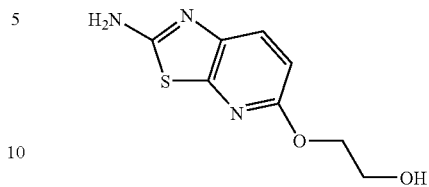

To a solution of a compound of REFERENCE EXAMPLE 6 (862 mg, 3.40 mmol) in THF (20 ml) was added lithium borohydride (222 mg, 10.21 mmol) at room temperature, and the mixture was stirred for 24 hours. To the reaction mixture was added 10% hydrochloric acid for degradation of the excess reagents. Thereto was added a saturated aqueous sodium bicarbonate solution, and the mixture was extracted with 20% methanol-chloroform. The organic layer was separated and the solvents were removed. The resulting residue was purified by silica gel column chromatography (5 to 20% methanol-chloroform) to give the titled compound (369 mg, yield 51%) as colorless crystals.
MS (m/z) APCI: 212 (M+H)$^+$ The above compound was also synthesized by the following alternative method.

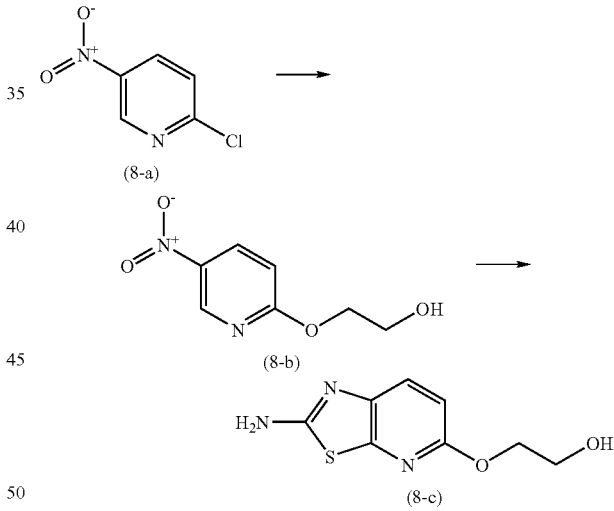

(1) To a solution of the compound (8-a) (5.18 g, 32.7 mmol) and ethylene glycol (20.28 g, 327 mmol) in DMF (20 ml) was added potassium carbonate (13.55 g, 98.0 mmol). The mixture was stirred at room temperature for 2 hours, diluted with ethyl acetate, washed with water and brine, dried over sodium sulfate and concentrated in vacuo. The residue was recrystallized from ethyl acetate-hexane to give the compound (8-b) (5.59 g, yield 93%) as yellow crystals.
MS (APCI): 185 (M+H)$^+$ (2) To a solution of the compound (8-b) (5.57 g, 30.25 mmol) in ethanol (50 ml) was added 10% Pd—C (0.50 g). The mixture was stirred vigorously for 2 hours under hydrogen and concentrated in vacuo to give the crude amine.

(3) To a solution of the above amine in acetic acid (100 ml) was added potassium thiocyanate (17.64 g, 182 mmol), and thereto was added dropwise bromine (1.62 ml, 31.8 mmol) under cooling with ice bath. The mixture was stirred at room temperature overnight, then concentrated in vacuo. The residue was chased with toluene, purified by silica gel chromatography (NH-silica gel; methanol-chloroform=20:1 to 10:1) and triturated with ethyl acetate to give the compound (8-c) (5.55 g, yield 87%) as colorless crystals.
MS (APCI): 212 (M+H)+

Reference Example 9

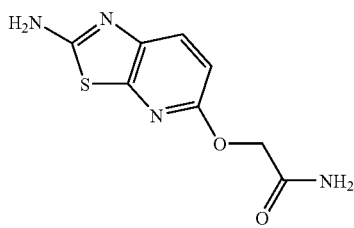

The compound of REFERENCE EXAMPLE 4 was treated with 2-bromoacetamide in the similar manner as REFERENCE EXAMPLE 5 to give the titled compound.
MS (m/z) APCI: 225 (M+H)+

Reference Example 10

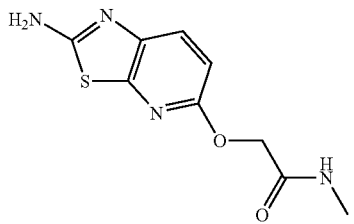

The compound of REFERENCE EXAMPLE 4 was treated with 2-bromo-N-methylacetamide in the similar manner as REFERENCE EXAMPLE 5 to give the titled compound.
MS (m/z) APCI: 239 (M+H)+

Reference Example 11

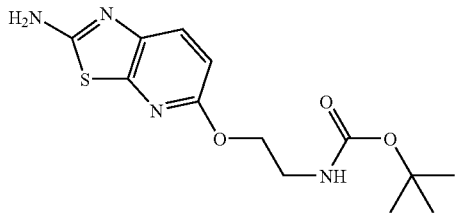

(1) To a solution of the compound of REFERENCE EXAMPLE 9 (1380 mg, 3.02 mmol) in THF (40 ml) was added lithium aluminum hydride (1.17 g, 30.8 mmol) at room temperature, and the mixture was stirred at room temperature for 20 hours. After degrading excess reagents with a 30% aqueous ammonia solution, the mixture was filtered and the filtrate was concentrated in vacuo. The resulting residue was purified by silica gel column chromatography (30% aqueous ammonia-methanol-chloroform=0.1:1:5) to give an amine (150 mg).

(2) To a suspension of the compound obtained in the above (1) (150 mg, 0.713 mmol) in THF (10 ml) was added a solution of di-tert-butyldicarbonate (187 mg, 0.856 mmol) in THF (5 ml) at room temperature, and the mixture was stirred at room temperature for 90 minutes. To the reaction mixture was added a 30% aqueous ammonia solution, and the mixture was stirred at room temperature for 30 minutes, and then diluted with ethyl acetate, washed with brine, dried over sodium sulfate and concentrated in vacuo. The resulting residue was purified by silica gel column chromatography (0 to 5% methanolchloroform) to give the titled compound (177 mg, yield 9% in 2 steps) as colorless solids.
MS (m/z) APCI: 311 (M+H)+

The above compound was also synthesized by the following alternative method.

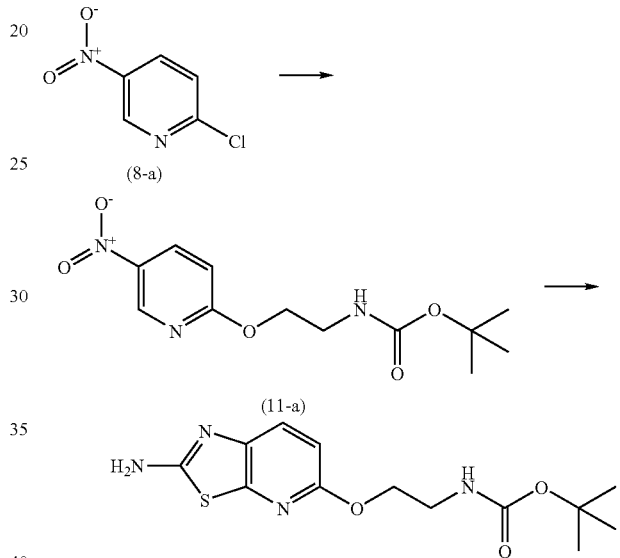

(1) To a solution of the compound (8-a) (15.0 g, 94.6 mmol) and N-(tert-butoxycarbonyl)ethanolamine (30.50 g, 189.2 mmol) in DMF (150 ml) was added portionwise potassium carbonate (26.15 g, 189.2 mmol), and the mixture was stirred at 50 to 60° C. for 4 hours, cooled to room temperature, diluted with ethyl acetate, washed with water and brine, and dried over sodium sulfate. After treating with activated charcoal, the mixture was concentrated in vacuo and the residue was crystallized from diisopropyl ether to give the compound (11-a) (11.86 g, yield 44%).
MS (m/z) APCI: 284 (M+H)+

(2) To a solution of the above compound (1.08 g, 3.81 mmol) in ethyl acetate (10 ml) was added 10% Pd—C (128 mg), and the mixture was stirred vigorously at room temperature for 1 hour under hydrogen at atmospheric pressure. The reaction mixture was filtered and the filtrate was concentrated in vacuo to give the crude amine (1.09 g).

(3) To a solution of the above amine in acetic acid (20 ml) were added potassium acetate (1.87 g, 19.3 mmol) and potassium thiocyanate (2.22 g, 22.8 mmol), and thereto was added dropwise bromine (0.234 ml, 4.57 mmol) with cooling with an ice-water bath, and then the mixture was stirred at room temperature for 1 hour. The reaction mixture was diluted with ethyl acetate, washed with water, an aqueous sodium sulfite solution and brine, and dried over sodium sulfate. After treating with activated charcoal, the mixture was concentrated in vacuo and the residue was crystallized from ethyl acetate-hexane to give the above compound (516 mg, yield 44% through the above 2 steps).
MS (m/z) APCI: 311 (M+H)+

Reference Example 12

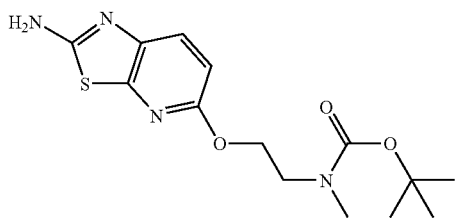

The compound of REFERENCE EXAMPLE 10 was treated in the similar manner as REFERENCE EXAMPLE 11 to give the titled compound as colorless crystals.
MS (m/z) APCI: 325 (M+H)+

The above compound was also synthesized by the following alternative method.

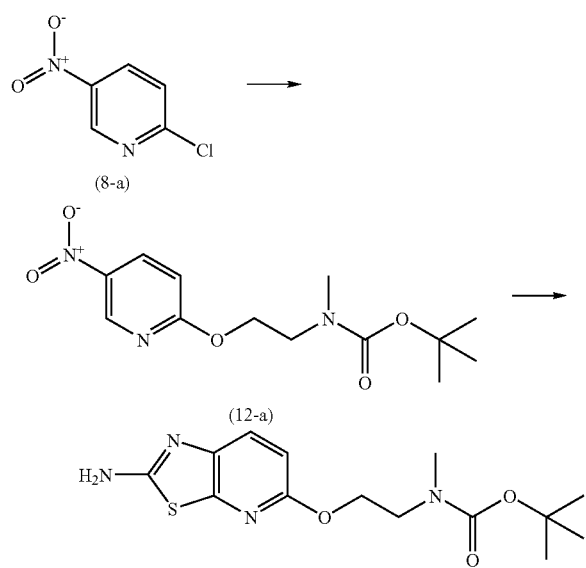

(1) To a solution of the compound (8-a) (10.0 g, 63.08 mmol) and N-(tert-butoxycarbonyl)-N-methylethanolamine (16.55 g, 94.6 mmol) in dimethylsulfoxide (100 ml) was added portionwise potassium tert-butoxide (10.62 g, 94.6 mmol) with cooling with an ice-water bath. The mixture was stirred at room temperature for 50 minutes, diluted with ethyl acetate, washed with water and brine, and dried over sodium sulfate. After treating with activated charcoal, the mixture was concentrated in vacuo to give the compound (12-a) (21.76 g).
MS (m/z) APCI: 298 (M+H)+
(2) The compound obtained in the above (1) was reacted in the similar manner as the alternative method (2) of REFERENCE EXAMPLE 11 to give the crude amine.
MS (m/z) APCI: 268 (M+H)+
(3) The compound obtained in the above (2) was treated in the similar manner as the alternative method (3) of REFERENCE EXAMPLE 11 to give the above compound.
MS (m/z) APCI: 325 (M+H)+

Reference Example 13

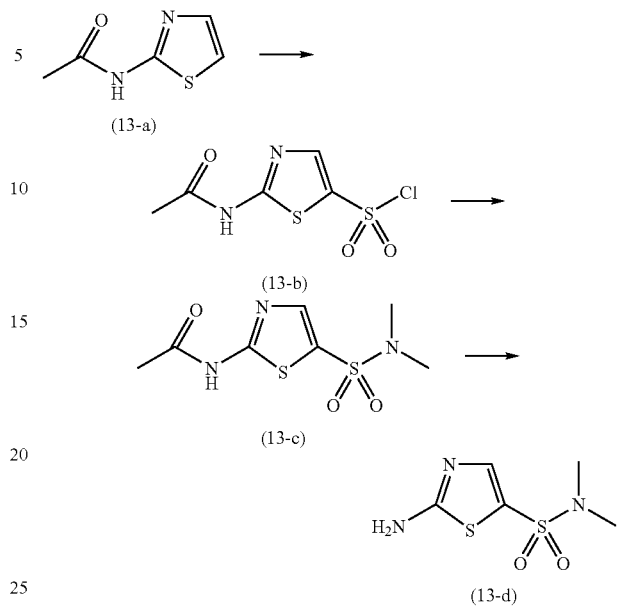

(1) Chlorosulfuric acid (80.0 g, 687 mmol) was ice-cooled, and thereto was added 2-acetamidothiazole (20.00 g, 140.6 mmol) in several portions, and the mixture was stirred at 100° C. overnight. The reaction solution was cooled to room temperature, poured into ice water and the mixture was extracted with diethyl ether. The extract was washed with water and brine, dried over sodium sulfate, and then concentrated in vacuo to give the crude product (13-b) (9.41 g) as a yellow solid.
(2) A mixture of a 2M aqueous dimethylamine solution (7.2 ml, 14.3 mmol) and pyridine (3 ml) was ice-cooled, and thereto was added the compound (13-b) (1.50 g) in several portions. The mixture was stirred at the same temperature for 15 minutes and at room temperature overnight, concentrated in vacuo and the residue was purified by silica gel chromatography (0 to 10% methanol-chloroform) to give the crude product (13-c) (677 mg) as a yellow powder.
(3) To the above compound (447 mg) was added 6N hydrochloric acid. The mixture was stirred at 110° C. for 1 hour, cooled to room temperature and concentrated in vacuo. To the residue were added water and ammonia water were to be basic, and the precipitated crystals were collected and dried to give the compound (13-d) (283 mg, yield 9% in 3 steps) as a yellow powder.
MS (APCI): 208 (M+H)+

Reference Example 14

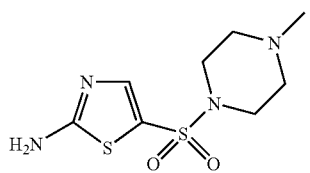

Methylpiperazine was used in the similar manner as REFERENCE EXAMPLE 13 to give the titled compound (yield 3% in 3 steps).
MS (APCI): 263 (M+H)+

Reference Example 15

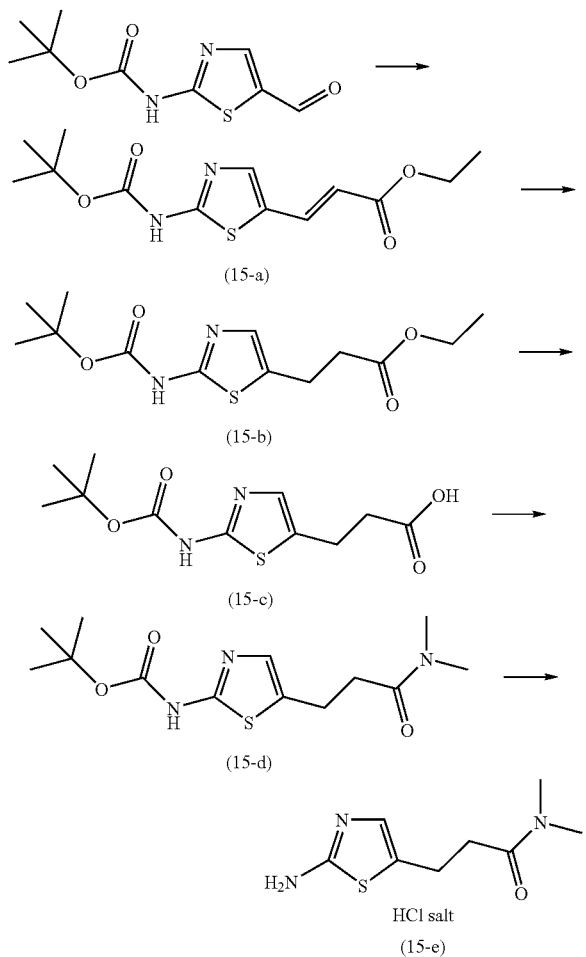

(1) To a solution of 2-tert-butyloxycarbonylaminothiazole-5-carbaldehyde of REFERENCE EXAMPLE 1 (4.37 g, 19.1 mmol) in THF (100 ml) were added diethylphosphonoacetic acid ethyl ester (9.14 ml, 45.9 mmol) and potassium tert-butoxide (5.16 g, 45.9 mmol) at room temperature, and the mixture was stirred at the same temperature overnight, and then heated to reflux for 5 hours. The reaction solution was cooled to room temperature, and thereto was added water, and the mixture was extracted with ethyl acetate. The organic layer was washed with water and brine, dried over sodium sulfate, treated with activated charcoal and then concentrated in vacuo, and the residue was crystallized from ethyl acetate-hexane (1:5) to give the compound (15-a) (4.13 g, yield 72%) as colorless crystals.
MS (APCI): 299 (M+H)$^+$ (2) A mixture of the above compound (4.10 g, 13.74 mmol), 10% Pd/C (5.0 g), ethyl acetate (50 ml) and acetic acid (50 ml) was stirred vigorously at room temperature for 24 hours under hydrogen. The reaction mixture was filtered and the filtrate was concentrated in vacuo, and then chased with toluene several times to give the compound (15-b) (4.05 g, yield 98%) as colorless crystals.
MS (APCI): 301 (M+H)$^+$ (3) A solution of the above compound (4.03 g, 13.42 mmol) in a mixed solvent of ethanol (20 ml), THF (40 ml) and water (20 ml) was ice-cooled, and thereto was added dropwise a 2N sodium hydroxide solution (16.1 ml, 32.2 mmol). The mixture was stirred at the same temperature for 2 hours and then at room temperature for 3 hours, poured into a mixture of aqueous citric acid solution and ethyl acetate. The mixture was extracted with ethyl acetate, and the extract was washed with water and brine, dried over sodium sulfate, and concentrated in vacuo. The residue was crystallized from diisopropyl ether to give the compound (15-c) (3.16 g, yield 86%) as colorless crystals.
MS (ESI): 271 (M–H)$^-$ (4) A solution of the above compound (589 mg, 2.16 mmol) and 1-hydroxybenzotriazole (584 mg, 4.33 mmol) in DMF (10 ml) was ice-cooled, and thereto was added N-ethyl-N'-(3-dimethylaminopropyl)carbodiimide monohydrochloride (1.04 g, 5.40 mmol), and the mixture was stirred at the same temperature for 15 minutes and then at room temperature for 1 hour. The reaction mixture was ice-cooled again, and thereto was added a 50% aqueous methylamine solution (5 ml). The mixture was stirred at the same temperature for 10 minutes and at room temperature for 1 hour, poured into a mixture of ethyl acetate and brine, and the mixture was extracted with ethyl acetate. The extract was washed with a saturated aqueous sodium bicarbonate solution and brine, dried over sodium sulfate, and concentrated in vacuo. The residue was crystallized from ethyl acetate-hexane (1:10) to give the compound (15-d) (597 mg, yield 92%) as colorless crystals.
MS (APCI): 300 (M+H)$^+$ (5) To a solution of the above compound (202 mg, 0.675 mmol) in formic acid (6 ml) was added a 4N solution of hydrogen chloride in dioxane (2 ml, 8 mmol), and the mixture was stirred at room temperature for 8 hours. To the mixture was added diethyl ether, and the mixture was stirred at room temperature. The resulting crystals were collected and washed with diethyl ether. To the crystals were added a 4N solution of hydrogen chloride in dioxane (2 ml, 8 mmol) and diethyl ether (10 ml), and the mixture was stirred further at room temperature overnight. The crystals were collected and washed with diethyl ether to give the compound (15-e) (175 mg) as colorless crystals in quantitative yield.
MS (APCI): 200 (M+H)$^+$

Reference Example 16

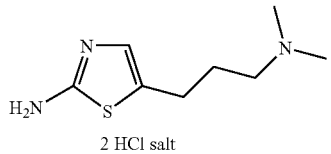

2 HCl salt

To the compound (15-e) of REFERENCE EXAMPLE 15 (173 mg, 0.734 mmol) was added ammonia water and brine, and the mixture was extracted with chloroform several times. The extract was dried over sodium sulfate and concentrated in vacuo to give colorless crystals of the free compound (112 mg, yield 76%). A solution of the above compound (112 mg, 0.560 mmol) in THF (3 ml) was ice-cooled, and thereto was added lithium aluminum hydride (65 mg, 1.71 mmol), and the mixture was stirred at the same temperature for 1 hour and at room temperature for 1 hour. To the reaction mixture was added ammonia water, and the mixture was stirred at room temperature overnight. Thereto was added sodium sulfate, and then the mixture was filtered. The filtrate was concentrated in vacuo and the resulting residue was dissolved in ethyl acetate, and thereto were added a 4N solution of hydrogen chloride in dioxane (0.5 ml, 1 mmol) and diethyl ether, and the mixture was stirred at room temperature. The precipitate was collected and dried to give the titled compound (98 mg, yield 68%) as a colorless powder.

MS (APCI): 186 (M+H)$^+$

Reference Example 17

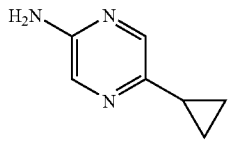

A mixture of 2-amino-5-bromopyrazine (2.00 g, 11.5 mmol), cyclopropylboronic acid (1.28 g, 14.9 mmol), palladium acetate (258 mg, 1.15 mmol), tricyclohexylphosphine (644 mg, 2.30 mmol) and tripotassium phosphate (8.50 g, 40.23 mmol) in toluene-water (20:1) (53 ml) was heated to reflux for 18 hours. The mixture was cooled to room temperature, diluted with ethyl acetate, washed with water and brine, dried over magnesium sulfate, and then concentrated in vacuo. The resulting residue was purified by silica gel column chromatography (50 to 100% ethyl acetate-hexane) to give the titled compound (329 mg, yield 21%) as a colorless powder.

MS (APCI): 136 (M+H)$^+$

Reference Example 18

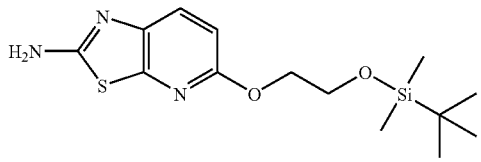

To a solution of the compound of REFERENCE EXAMPLE 8 (176 mg, 0.833 mmol) and imidazole (188 mg, 2.76 mmol) in DMF (4 ml) was added dropwise a solution of tert-butyldimethylchlorosilane (188 mg, 1.25 mmol) in DMF (2 ml) under ice-cooling. The mixture was stirred at room temperature overnight, diluted with ethyl acetate, washed with water and brine, and then dried over sodium sulfate and concentrated in vacuo. Then, the residue was purified by silica gel chromatography (40 to 70% ethyl acetate-hexane) to give the titled compound (172 mg, yield 64%) as colorless crystals.

MS (APCI): 326 (M+H)$^+$

Reference Example 19

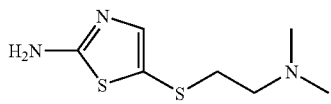

To a solution of 2-amino-5-bromothiazole hydrobromide (3.00 g, 11.5 mmol) and 2-dimethylaminoethanethiol monohydrochloride (2.45 g, 17.31 mmol) in water (15 ml)-ethanol (20 ml) was added a 1N aqueous sodium hydroxide solution (23.5 ml, 23.5 mmol) at room temperature, and the mixture was heated to reflux for 2 hours. The reaction solution was cooled to room temperature and concentrated in vacuo, and thereto was added a saturated aqueous sodium bicarbonate solution and sodium chloride to saturation, and the mixture was extracted with ethyl acetate several times. The extract was dried over magnesium sulfate, concentrated in vacuo, and then the residue was purified by silica gel chromatography (NH-silica gel; methanol-chloroform=49:1 to 19:1) to give the titled compound (2.10 g, yield 89%) as a brown solid.

MS (APCI): 204 (M+H)$^+$

Reference Example 20

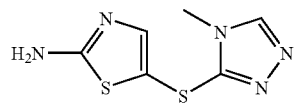

3-Mercapto-4-methyl-4H-1,2,4-triazole was used in the similar manner as REFERENCE EXAMPLE 19 to give the titled compound.

MS (APCI): 214 (M+H)$^+$

Reference Example 21

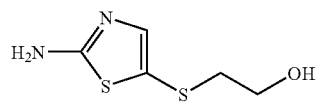

2-Mercaptoethanol was used in the similar manner as REFERENCE EXAMPLE 19 to give the titled compound.

MS (APCI): 177 (M+H)$^+$

Reference Example 22

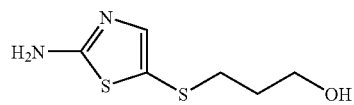

3-Mercaptopropanol was used in the similar manner as REFERENCE EXAMPLE 19 to give the titled compound.

MS (APCI): 191 (M+H)$^+$

Reference Example 23

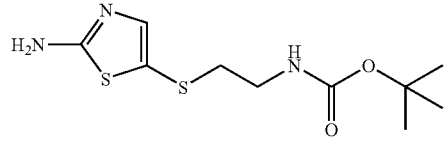

To a mixture of 2-amino-5-bromothiazole hydrobromide (5.50 g, 21.2 mmol), tert-butyl-N-(2-mercaptoethyl)carbamate (5.25 g, 29.6 mmol) and ethanol (80 ml) was added 1,8-diazabicyclo[5.4.0]-7-undecene (7.73 g, 50.8 mmol) under ice-cooling, and the mixture was stirred at room temperature for 7 hours. The reaction solution was concentrated in vacuo, and the residue was diluted with ethyl acetate, and then washed with water and brine, dried over magnesium sulfate and concentrated in vacuo. Then, the residue was purified by silica gel chromatography (ethyl acetate-hexane=3:1) to give the titled compound 5.72 g, yield 98%) as a colorless powder.

MS (APCI): 276 (M+H)$^+$

Reference Example 24

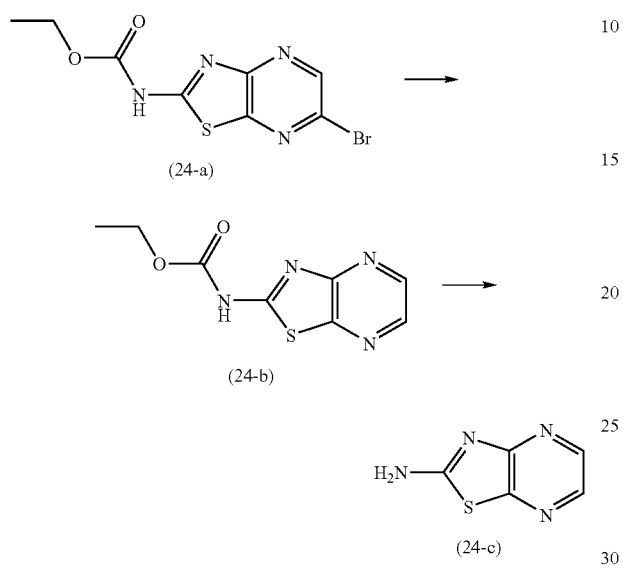

(1) To a solution of the compound (24-a) synthesized according to the known method (B. Koren et al., Heterocycles, 1987, 26(3) 689.) (1.00 g, 3.30 mmol) in DMF (40 ml) were added water (10 ml), sodium formate (4.50 g, 66.2 mmol) and 10% Pd—C (200 mg), and the mixture was stirred at 85° C. for 14 hours. After cooling to room temperature, the reaction mixture was filtered and the filtrate was concentrated in vacuo. To the residue was added water, and the mixture was acidified with an aqueous citric acid solution, and then the precipitated crystals were collected and dried to give the compound (24-b) (720 mg, yield 97%) as a yellow powder.

MS (APCI): 225 (M+H)$^+$ (2) To the above compound (700 mg, 3.12 mmol) was added a 10% aqueous sodium hydroxide solution (20 ml), and the mixture was stirred at 100° C. for 4.5 hours. The reaction solution was cooled to room temperature, and then 10% hydrochloric acid was added to neutralize and the precipitate was filtered off. The filtrate was extracted with ethyl acetate and the extract was concentrated in vacuo. The resulting residue was washed with diethyl ether to give the compound (24-c) (228 mg, yield 48%) as a yellow powder.

MS (APCI): 153 (M+H)$^+$

Reference Example 25

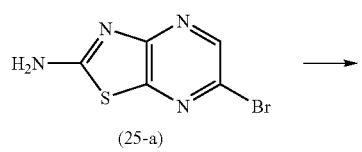

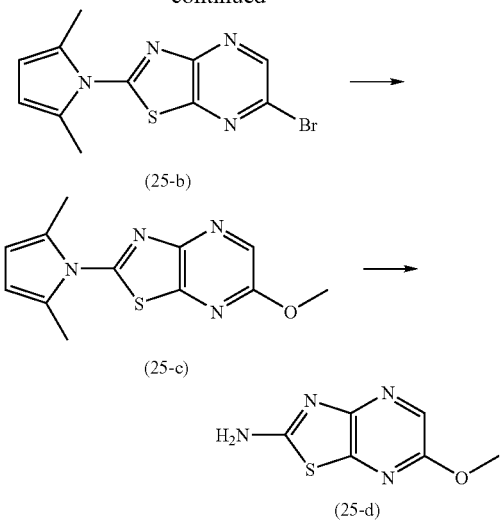

(1) A mixture of the compound (25-a) synthesized according to the known method (B. Koren et al., Heterocycles, 1987, 26(3) 689.) (482 mg, 2.09 mmol), 2,5-hexanedione (0.490 ml, 4.17 ml), p-toluenesulfonic acid monohydrate (40 mg, 0.21 mmol) and toluene (5 ml) was heated to reflux for 3 hours with removing water by a Dean-Stark apparatus. The reaction mixture was cooled to room temperature, and then diluted with ethyl acetate and a small amount of methanol, washed with a saturated aqueous sodium bicarbonate solution and brine, and then dried over sodium sulfate. After concentration in vacuo, the residue was purified by silica gel chromatography (NH-silica gel; ethyl acetate-hexane=10:1, then ethyl acetate) to give the compound (25-b) (598 mg, yield 93%) as pale brown crystals.

MS (APCI): 309/311 (M+H)$^+$ (2) A solution of the above compound (533 mg, 1.72 mmol) in methanol (15 ml)-DMF (15 ml) was ice-cooled, and thereto was added sodium methoxide (464 mg, 8.60 mmol). The mixture was stirred at room temperature for 42 hours, diluted with ethyl acetate, washed with water and brine, and then dried over sodium sulfate. After treatment with activated charcoal, the mixture was concentrated in vacuo to give the compound (25-c) (339 mg, yield 76%) as brown crystals.

MS (APCI): 261 (M+H)$^+$ (3) A suspension of the above compound (330 mg, 1.27 mmol) in water (30 ml) was ice-cooled, and thereto was added trifluoroacetic acid (30 ml). The mixture was stirred at 60° C. for 4 hours, then cooled to room temperature and concentrated in vacuo. The residue was chased with toluene, and purified by silica gel chromatography (NH-silica gel; methanol-chloroform=1:20 to 1:5). The resulting crude crystals were washed with ethyl acetate-hexane (1:3) to give the compound (25-d) (154 mg, yield 67%) as reddish brown crystals.

MS (APCI); 183 (M+H)$^+$

Reference Example 26

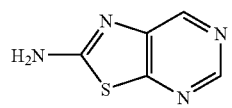

To a solution of potassium thiocyanate (6.10 g, 63 mmol) in acetic acid (25 ml) was added 5-aminopyrimidine (1.00 g, 10.5 mmol); and thereto was added dropwise a solution of bromine (1.08 ml, 21.0 mmol) in acetic acid (3 ml) with cooling by ice bath. The mixture was stirred at room temperature for 3 days and concentrated in vacuo. The residue was neutralized with a saturated aqueous sodium bicarbonate solution and then concentrated in vacuo. To the residue were added chloroform and THF, and the mixture was dried over magnesium sulfate and filtered. The filtrate was concentrated in vacuo and the resulting residue was purified by silica gel chromatography (methanol-chloroform=1:20 to 1:10) to give the titled compound (287 mg, yield 18%) as a yellow powder.

MS (APCI): 153 (M+H)$^+$

Reference Example 27

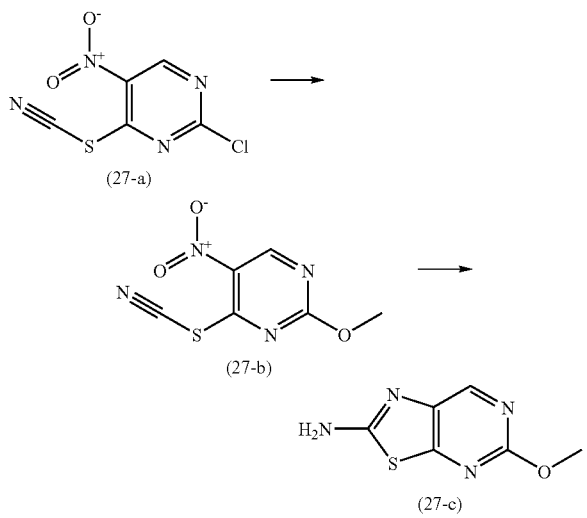

(1) A suspension of the compound (27-a) synthesized according to the known method (T. Takahashi et al., Chemical & Pharmaceutical Bulletin, 1958, 6, 334.) (1.00 g, 4.62 mmol) in methanol (20 ml) was cooled to −40° C., and thereto was added a solution of 28% sodium methoxide in methanol (0.305 ml, 4.85 mmol), and the mixture was stirred at the same temperature for 6 hours. Water was added, and the mixture was extracted with ethyl acetate. The organic layer was dried over sodium sulfate and concentrated in vacuo. The residue was purified by silica gel chromatography (15 to 35% ethyl acetate-hexane) to give the compound (27-b) (194 mg, yield 20%) as a yellow powder.

(2) To a solution of the above compound (663 mg, 3.12 mmol) in acetic acid (6 ml) was added iron powder (678 mg, 12.2 mmol) at room temperature, and the mixture was stirred at 60° C. for 4 hours. After cooling to room temperature, the mixture was diluted with ethyl acetate, and filtered through Celite. The filtrate was concentrated and then the residue was diluted with ethyl acetate, and thereto was added a saturated aqueous sodium bicarbonate solution, and then the insoluble was filtered off. The filtrate was extracted with ethyl acetate, and the organic layer was dried over sodium sulfate and concentrated in vacuo. The residue was purified by silica gel chromatography (ethyl acetate) to give the compound (27-c) (231 mg, yield 41%) as a yellow powder.

MS (APCI): 183 (M+H)$^+$

Reference Example 28

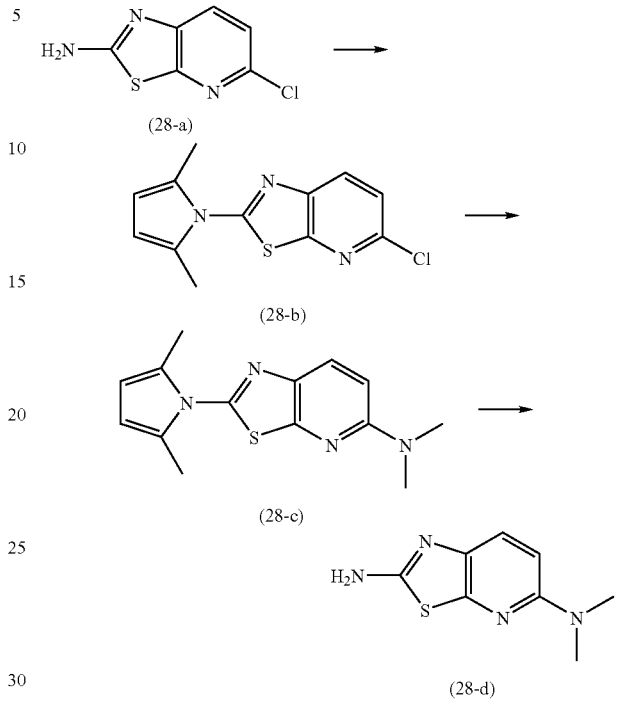

(1) A mixture of the compound (28-a) (3.05 g, 16.4 mmol), 2,5-hexanedione (3.85 ml, 32.9 mmol), p-toluenesulfonic acid monohydrate (313 mg, 1.64 mmol) in toluene (30 ml) was heated to reflux for 6 hours with removing water by a Dean-Stark apparatus. The reaction mixture was cooled to room temperature, and then diluted with ethyl acetate, washed with a saturated aqueous sodium bicarbonate solution and brine, and dried over sodium sulfate. After concentration in vacuo, the residue was purified by silica gel chromatography (ethyl acetate-hexane=1:10) to give the compound (28-b) (3.84 g, yield 89%) as pale brown crystals.

MS (APCI): 264/266 (M+H)$^+$ (2) To a suspension of the above compound (600 mg, 2.27 mmol), bis(dibenzylideneacetone)palladium (131 mg, 0.227 mmol), 2-dicyclohexylphosphono-2'-(N,N'-dimethylamino)biphenyl (89 mg, 0.226 mmol) and sodium tert-butoxide (437 mg, 4.55 mmol) in toluene (10 ml) was added a 2M solution of dimethylamine in THF (6.81 ml, 13.6 mmol) at room temperature under argon, and the mixture was stirred at the same temperature for 5 days. Water was added, and the mixture was extracted with ethyl acetate. The organic layer was washed with water and brine, dried over sodium sulfate and then concentrated in vacuo.

The residue was purified by silica gel chromatography (10 to 35% ethyl acetate-hexane) to give the compound (28-c) (419 mg, yield 68%) as brown crystals.

MS (APCI): 273 (M+H)$^+$ (3) A suspension of the above compound (410 mg, 1.51 mmol) in water (30 ml) was ice-cooled, and thereto was added trifluoroacetic acid (30 ml). The mixture was stirred at 50° C. for 1 hour, cooled to room temperature, and then concentrated in vacuo. The residue was extracted with ethyl acetate. The organic layer was washed with a saturated aqueous sodium bicarbonate solution and brine, dried over sodium sulfate, and then treated with activated charcoal. After concentration in vacuo, the residue was crystallized from ethyl acetatehexane (3:1) to give the compound (28-d) (194 mg, yield 66%) as a colorless powder.

MS (APCI): 195 (M+H)+

Reference Example 29

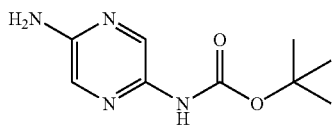

A mixture of 2-amino-5-bromopyrazine (2.61 g, 15.0 mmol), tert-butylcarbamate (2.11 g, 18.0 mmol), copper (I) iodide (290 mg, 1.50 mmol), N,N'-dimethylethylenediamine (260 mg, 3.00 mmol), potassium carbonate (4.15 g, 30.0 mmol) in dioxane (80 ml) was heated to reflux for 16 hours. The mixture was cooled to room temperature, poured into water and extracted with ethyl acetate. The extract was filtered through Celite and the filtrate was concentrated in vacuo, and the resulting residue was purified by silica gel chromatography (30 to 80% ethyl acetate-hexane) to give the titled compound (yield 18%) as a colorless powder.

MS (APCI): 211 (M+H)+

Reference Example 30

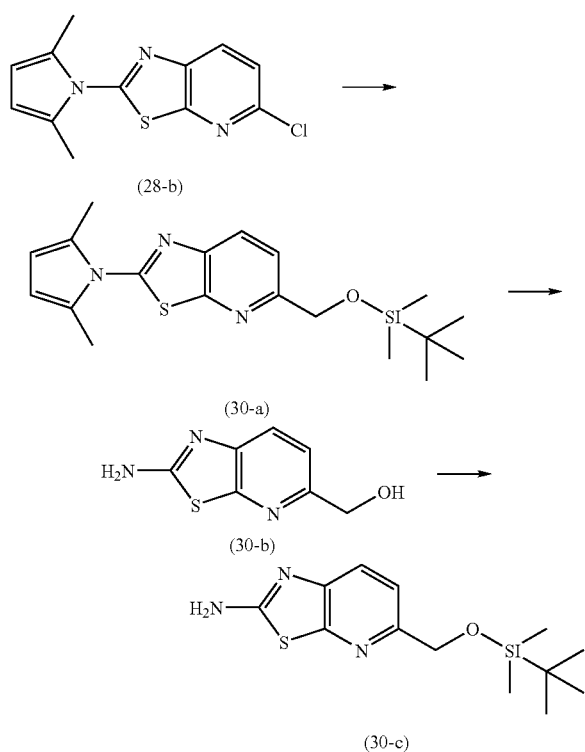

(1) A suspension of the compound (28-b) (1.86 g, 7.05 mmol), tert-butyldimethyl(tributylstannylmethoxy)silane (6.14 g, 14.1 mmol) and dichlorobis(triphenylphosphine)palladium (495 mg, 0-701 mmol) in dioxane (20 ml) was heated to reflux for 41 hours under argon. The reaction mixture was cooled to room temperature, and thereto was added activated charcoal. The mixture was filtered, and the filtrate was concentrated in vacuo. To the resulting residue was dissolved ethyl acetate, washed with a saturated aqueous sodium bicarbonate solution and brine, dried over sodium sulfate and concentrated in vacuo to give the compound (30-a) (10.44 g) as a yellow oil.

(2) A mixture of the above compound (10.4 g) in water (60 ml) was ice-cooled, and thereto was added trifluoroacetic acid (60 ml). The mixture was stirred at 50° C. for 1 hour, cooled to room temperature, and then concentrated in vacuo. To the resulting residue was added a saturated aqueous sodium bicarbonate solution, and the mixture was saturated with sodium chloride and extracted with ethyl acetate. The extract was dried over sodium sulfate and then concentrated in vacuo, and the residue was chased with toluene and then crystallized from a mixed solvent of ethyl acetate-hexane to give the compound (30-b) (1.10 g) as a brown powder.

(3) To a solution of the above compound (1.10 g) and imidazole (1.54 g, 22.6 mmol) in DMF (30 ml) was added tert-butyldimethylchlorosilane (1.70 g, 11.3 mmol) under ice-cooling. The mixture was stirred at room temperature for 1 hour, diluted with ethyl acetate, washed with a saturated aqueous sodium bicarbonate solution and brine, and dried over sodium sulfate. After concentration in vacuo, the resulting residue was purified by silica gel column chromatography (NH-silica gel; 60 to 100% ethyl acetate-hexane) to give the compound (30-c) (354 mg, yield 16% in 3 steps) as pale yellow crystals.

MS (APCI): 296 (M+H)+

Reference Example 31

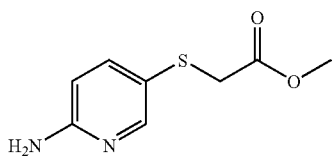

A mixture of 2-amino-5-iodopyridine (1.00 g, 4.55 mmol), methyl thioglycolate (0.482 g, 4.55 mmol), tris(dibenzylideneacetone)dipalladium (208 mg, 0.227 mmol), bis(2-diphenylphosphinophenyl)ether (245 mg, 0.455 mmol) and potassium tert-butoxide (561 mg, 5.00 mmol) in toluene (20 ml) was stirred at 100° C. for 3 hours under argon. The reaction mixture was cooled to room temperature and filtered through Celite, and the filtrate was concentrated in vacuo. The residue was purified by silica gel chromatography (NH-silica gel, 0 to 3% methanol-chloroform) to give the titled compound (268 mg, yield 30%) as a pale yellow solid.

MS (APCI): 199 (M+H)+

Reference Example 32

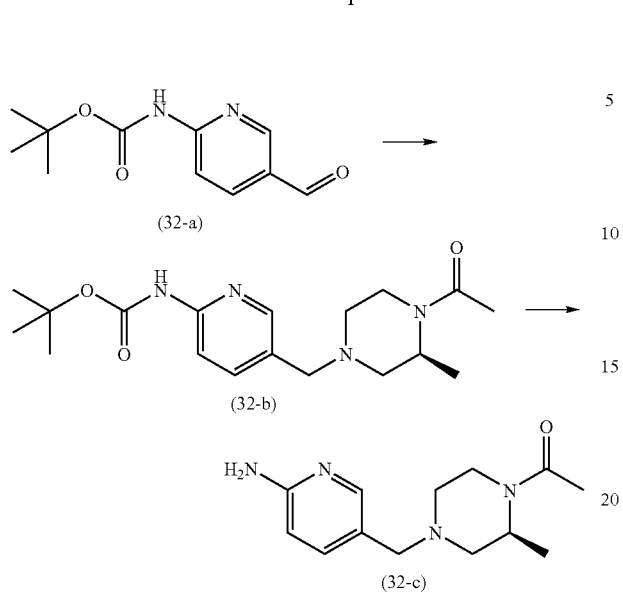

(1) The compound (32-a), (S)-1-acetyl-2-methylpiperazine hydrochloride and diisopropylethylamine were treated in the similar manner as EXAMPLE 2 to give the compound (32-b).
MS (m/z) APCI: 349 (M+H)$^+$
(2) The compound obtained in the above (1) was treated in the similar manner as EXAMPLE 138-(2) to give the compound (32-c).
MS (m/z) APCI: 249 (M+H)$^+$

Reference Example 33

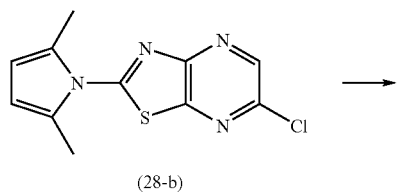

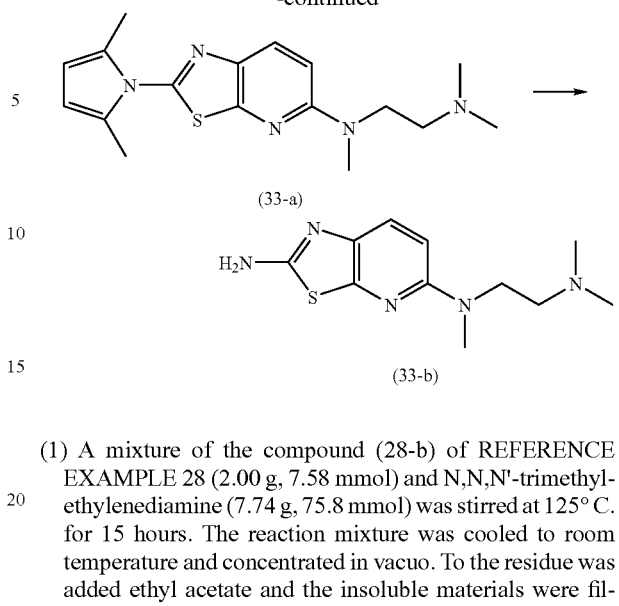

(1) A mixture of the compound (28-b) of REFERENCE EXAMPLE 28 (2.00 g, 7.58 mmol) and N,N,N'-trimethylethylenediamine (7.74 g, 75.8 mmol) was stirred at 125° C. for 15 hours. The reaction mixture was cooled to room temperature and concentrated in vacuo. To the residue was added ethyl acetate and the insoluble materials were filtered off. The filtrate was concentrated in vacuo and the residue was purified by silica gel column chromatography (NH-silica gel; 15 to 35% ethyl acetate-hexane) to give the compound (33-a) (2.33 g, yield 93%).
MS (m/z) APCI: 330 (M+H)$^+$ (2) To a solution of the above compound (530 mg, 1.61 mmol) in methanol (2 ml) was added 10% hydrochloric acid (3.3 ml), and the mixture was stirred at 60° C. for 19 hours, cooled to room temperature, neutralized with sodium bicarbonate and concentrated in vacuo. To the residue was added chloroform, and the mixture was dried over magnesium sulfate and filtered, and the filtrate was concentrated in vacuo. The resulting crude crystals were washed with ethyl acetatediethyl ether to give the compound (33-b) (201 mg, yield 50%).
MS (m/z) APCI: 252 (M+H)$^+$ Corresponding starting compounds were treated in the similar manner as the above REFERENCE EXAMPLE 33, REFERENCE EXAMPLE 11-(2) or REFERENCE EXAMPLE 18 or an appropriate combination thereof to give the following compounds.

| REFERENCE EXAMPLE No. | No | Structure | MS (m/z) |
|---|---|---|---|
| 33 | 1 | ![structure] | 338 APCI [M + H]$^+$ |
| 33 | 2 | ![structure] | 238 APCI [M + H]$^+$ |

| REFERENCE EXAMPLE No. | No | Structure | MS (m/z) |
|---|---|---|---|
| 33 | 3 | | 339 APCI [M + H]+ |
| 33 | 4 | | 325 APCI [M + H]+ |

Reference Example 34

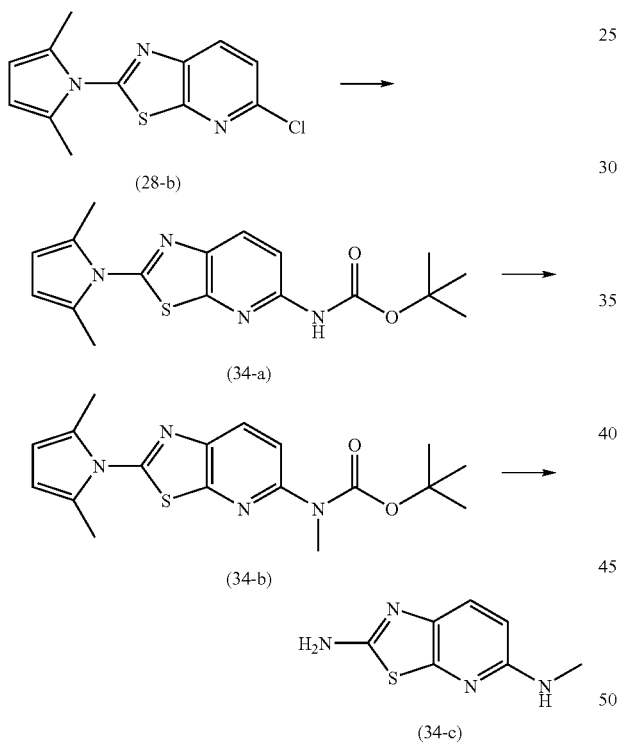

(1) A mixture of the compound (28-b) (500 mg, 1.90 mmol), tert-butylcarbamate (333 mg, 2.84 mmol), cesium carbonate (1235 mg, 3.79 mmol), palladium (II) acetate (21.3 mg, 0.095 mmol), 4,5-bis(diphenylphosphino)-9,9-dimethylxanthene (87.7 mg, 0.152 mmol) and dioxane (5 ml) was stirred at 100° C. for 15 hours under argon. The reaction mixture was cooled to room temperature, and thereto was added water, and the mixture was extracted with ethyl acetate. The extract was concentrated in vacuo. The residue was purified by silica gel chromatography (5 to 15% ethyl acetate-hexane) to give the compound (34-a) (727 mg, quantitatively).

MS (m/z) APCI: 345 (M+H)+

(2) A solution of the compound obtained in the above (1) (633 mg, 1.84 mmol) in DMF (4 ml) was ice-cooled, and thereto were added sequentially methyl iodide (0.126 ml, 2.02 mmol) and 60% sodium hydride (110 mg, 2.76 mmol), and the mixture was stirred at the same temperature for 10 minutes, poured into water and extracted with ethyl acetate. The extract was concentrated in vacuo, and the residue was purified by silica gel chromatography (NH-silica gel, 0 to 10% ethyl acetate-hexane) to give the compound (34-b) (556 mg, yield 84%).

MS (m/z) APCT: 359 (M+H)+

(3) A mixture of the compound obtained in the above (2) (556 mg, 1.55 mmol), 10% hydrochloric acid (7 ml) and methanol (6 ml) was stirred at 75° C. for 23 hours. The reaction mixture was cooled to room temperature, and thereto was added a saturated aqueous sodium bicarbonate solution and the mixture was extracted with chloroform. The extract was concentrated in vacuo to give the compound (34-c) (300 mg, quantitatively).

MS (m/z) APCI: 181 (M+H)+

Reference Example 35

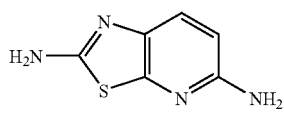

The compound (34-a) of REFERENCE EXAMPLE 34 was treated in the similar manner as the method of REFERENCE EXAMPLE 34-(3) to give the titled compound.

MS (m/z) APCI: 167 (M+H)+

Reference Example 36

Corresponding starting compounds were reacted in the similar manner as the alternative method of REFERENCE EXAMPLE 11 or REFERENCE EXAMPLE 12 to give the following compounds.

| REFERENCE EXAMPLE No. | No | Structure | MS (m/z) |
|---|---|---|---|
| 36 | 1 | | 351 APCI [M + H]+ |
| 36 | 2 | | 337 APCI [M + H]+ |
| 36 | 3 | | 337 APCI [M + H]+ |
| 36 | 4 | | 323 APCI [M + H]+ |
| 36 | 5 | | 339 APCI [M + H]+ |
| 36 | 6 | | 339 APCI [M + H]+ |

Reference Example 37

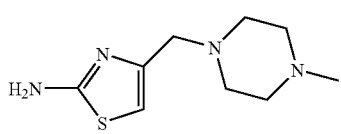

To a suspension of 2-amino-4-chloromethylthiazole hydrochloride (2.00 g, 10.8 mmol) in dioxane (15 ml) was added N-methylpiperazine (12 ml, 108 mmol), and the mixture was stirred at room temperature for 110 hours. To the reaction mixture was added a saturated aqueous sodium bicarbonate solution (5 ml) and the organic layer was separated by Chem Elut 1010® (manufactured by VARIAN) and the column was further eluted with chloroform. The eluate was concentrated in vacuo and the residue was purified by silica gel column chromatography (NH-silica gel; 2% methanol-chloroform) to give the above compound (1.18 g, yield 52%).

MS (m/z) APCI: 213 (M+H)+

Reference Example 38

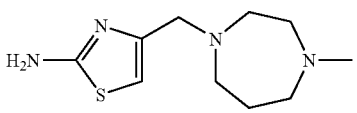

A corresponding starting compound was treated in the similar manner as REFERENCE EXAMPLE 38 to give the above compound.

MS (m/z) APCI: 227 (M+H)+

Reference Example 39

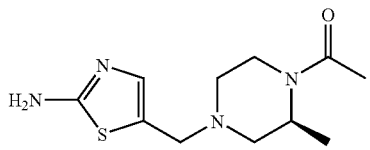

To a solution of the compound of REFERENCE EXAMPLE 1 (10.00 g, 60.7 mmol), (S)-2-methyl-1-acetylpiperazine hydrochloride (15.0 g, 85.0 mmol) and diisopropylethylamine (26.0 ml, 149 mmol) in chloroform (300 ml) was added sodium triacetoxyborohydride (18.0 g, 85.0 mmol), and the mixture was stirred at room temperature for 17 hours. To the reaction mixture was added a saturated aqueous sodium bicarbonate solution, and the mixture was extracted with chloroform. The extract was dried over magnesium sulfate. After concentration in vacuo the residue was purified by silica gel column chromatography (6% methanol-chloroform) and crystallized from ethyl acetate-diethyl ether to give the above compound (10.99 g, yield 71%).

MS (m/z) APCI: 255 (M+H)$^+$

Reference Example 40

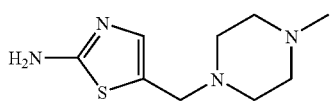

A corresponding starting compound was treated in the similar manner as EXAMPLE 39 to give the above compound.

MS (m/z) APCI: 213 (M+H)$^+$

Reference Example 41

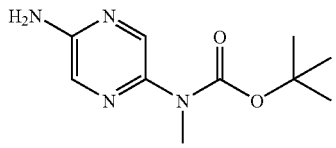

A solution of the compound of REFERENCE EXAMPLE 29 (1.61 g, 7.70 mmol) in DMF (16 ml) was ice-cooled, and thereto was added potassium tert-butoxide (945 mg, 8.42 mmol). The mixture was stirred at room temperature for 10 minutes, ice-cooled again and thereto was added methyl iodide (572 ml, 9.19 mmol). The mixture was stirred at room temperature for 6 hours. To the reaction mixture was added water, and the mixture was extracted with chloroform. The extract was washed sequentially with water and brine, dried over sodium sulfate and then concentrated in vacuo. The residue was purified by column chromatography (NH-silica gel, 10 to 35% ethyl acetate-hexane) to give the above compound (1.51 g, yield 88%).

MS (m/z) APCI: 225 (M+H)$^+$

Reference Example 42

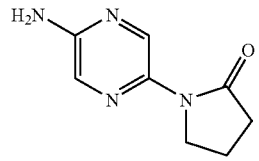

A mixture of 2-amino-5-bromopyrazine (5.00 g, 28.74 mmol), 2-pyrrolidinone (10.90 ml, 143.7 mmol), cuprous iodide (1.10 g, 5.75 mmol), (1R,2R)-(–)-1,2-diaminocyclohexane (1.38 ml, 11.50 mmol), potassium carbonate (7.94 g, 57.5 mmol) and dioxane (86 ml) was stirred at 120° C. for 17 hours under argon. The reaction mixture was cooled to room temperature and thereto was added ethyl acetate-methanol (10:1), and the mixture was filtered through Celite. The filtrate was concentrated in vacuo, and the residue was purified by silica gel column chromatography (5% methanol-chloroform) and crystallized from diethyl ether to give the above compound (2.77 g, yield 54%).

MS (m/z) APCI: 179 (M+H)$^+$

Reference Example 43

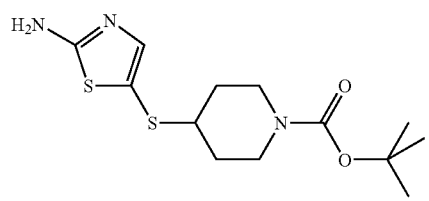

1-tert-Butoxycarbonyl-4-acetylthiopiperidine (4.60 g, 17.69 mmol) and 2-amino-5-bromothiazole hydrobromide were reacted in the similar manner as REFERENCE EXAMPLE 19 to give the above compound.

MS (m/z) APCI: 316 (M+H)$^+$

Reference Example 44

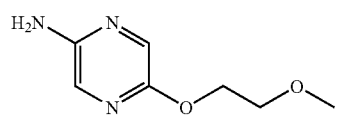

To 2-methoxyethanol (55 ml) were added sequentially 60% sodium hydride (1.83 g, 45.8 mmol), 2-amino-5-bromopyrazine (7.00 g, 40.23 mmol) and copper powder (2.91 g, 53.9 mmol) under ice-cooling, and the mixture was stirred at 160° C. for 20 hours in a sealed tube. The reaction mixture was cooled to room temperature, and thereto were added water, ammonia water and ethyl acetate, and the mixture was stirred and then filtered through Celite. The filtrate was extracted with ethyl acetate. The extract was dried over sodium sulfate, and after concentration in vacuo the residue was purified by silica gel column chromatography (40% ethyl acetate-hexane) to give the titled compound (2.74 g, yield 40%).

MS (m/z) APCI: 170 (M+H)$^+$

Corresponding starting compounds were treated in the similar manner as the above REFERENCE EXAMPLE 44, REFERENCE EXAMPLE 11-(2) or REFERENCE EXAMPLE 18 or an appropriate combination thereof to give the following compounds.

| REFERENCE EXAMPLE No. | No | Structure | MS (m/z) |
|---|---|---|---|
| 44 | 1 | | 270 APCI [M + H]+ |
| 44 | 2 | | 154 APCI [M + H]+ |

Reference Example 45

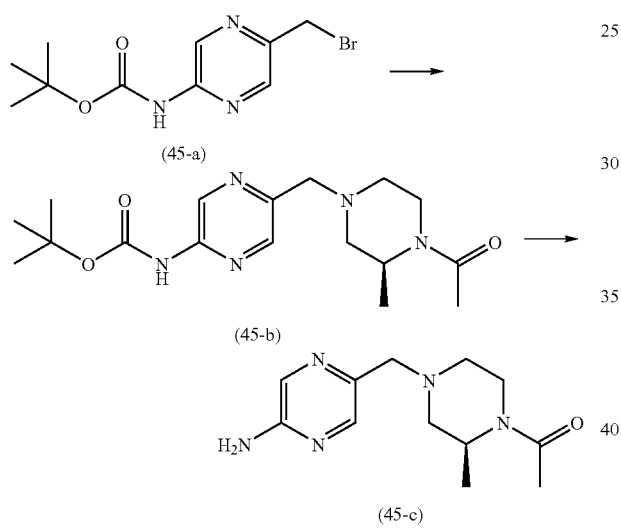

(1) A solution of (S)-1-acetyl-2-methylpiperazine hydrochloride (0.800 g, 4.50 mmol) and diisopropylethylamine (1.81 ml, 10.4 mmol) in DMF (10 ml) was ice-cooled, and thereto was added the compound (45-a). The mixture was stirred at the same temperature for 3 hours, diluted with water, extracted with ethyl acetate and the extract was concentrated in vacuo. The residue was purified by silica gel column chromatography (ethyl acetate) to give the compound (45-b) (0.930 g, yield 76%).

MS (m/z) APCI: 350 (M+H)+

(2) The compound obtained in the above (1) was reacted in the similar manner as EXAMPLE 138-(2) to give the compound (45-c).

MS (m/z) APCI: 250 (M+H)+

Reference Example 46

Corresponding starting compounds were treated with 2-amino-6-hydroxybenzothiazole in the similar manner as REFERENCE EXAMPLE 5 to give the following compounds.

| REFERENCE EXAMPLE No. | No | Structure | MS (m/z) |
|---|---|---|---|
| 46 | 1 | | 325 APCI [M + H]+ |
| 46 | 2 | | 324 APCI [M + H]+ |

849

Reference Example 47

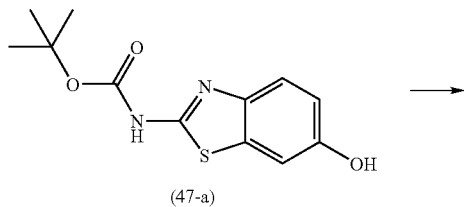

(47-a)

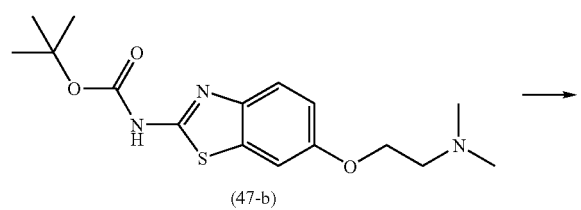

(47-b)

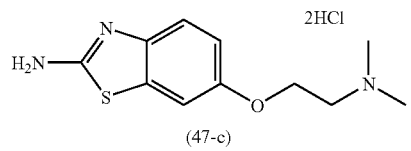

(47-c)

(1) A solution of the compound (47-a) (1.50 g, 5.63 mmol) and N,N-dimethylethanolamine (535 mg, 6.00 mmol) in THF (20 ml) was ice-cooled, and thereto were added triphenylphosphine (1.57 g, 6.00 mmol) and diethyl azodicarboxylate (1.04 g, 6.00 mmol), and the mixture was stirred at the same temperature overnight. To the reaction mixture were added ethyl acetate and diluted hydrochloric acid. The aqueous layer was separated and basified with an aqueous sodium hydroxide solution. After extraction with ethyl acetate, the extract was dried over sodium sulfate and concentrated in vacuo, and the residue was purified by silica gel chromatography (40 to 60% acetone-chloroform) and then washed with diisopropyl ether to give the compound (47-b) (606 mg, yield 32%) as a colorless powder.

(2) To a solution of the compound (47-b) obtained in the above (1) (337 mg, 1.0 mmol) in methanol (5 ml) was added a 4 M hydrogen chloride solution in dioxane (2.5 ml) at room temperature, and the mixture was stirred at the same temperature overnight. The reaction mixture was concentrated in vacuo and the residue was washed with diethyl ether to give the compound (47-c) (302 mg, yield 97%) as a colorless powder.

MS (m/z) APCI: 238 (M+H)$^+$

INDUSTRIAL APPLICABILITY

The compound of the present invention or a pharmaceutically acceptable salt thereof can provide an agent for preventing or treating diseases involving glucokinase because of having an excellent glucokinase activation effect.

Also, the method for preparing 5-substituted 2-aminothiazole compound of the present invention and a salt thereof is industrially advantageous.

The invention claimed is:

1. A method for treating diabetes, which comprises administering an effective dose of a compound of the general formula [I]:

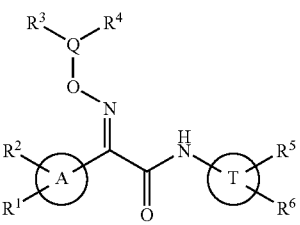

[I]

wherein Ring A is aryl;

Q is alkyl;

Ring T is heteroaryl or heterocycle of

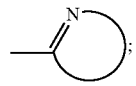

;

$R^1$ is hydrogen atom, halogen atom, cycloalkylsulfonyl, alkylsulfonyl, alkylsulfinyl, alkylthio, or substituted or unsubstituted tetrazolyl;

$R^2$ is hydrogen atom, halogen atom, cycloalkylsulfonyl, substituted or unsubstituted alkylsulfonyl, substituted or unsubstituted alkylthio, nitro, substituted or unsubstituted amino, substituted or unsubstituted aminosulfonyl, substituted or unsubstituted heterocyclyl-thio, substituted or unsubstituted heterocyclyl-sulfinyl, substituted or unsubstituted heterocyclyl-sulfonyl, substituted or unsubstituted heteroarylsulfonyl, alkenyloxy, substituted or unsubstituted alkoxy, substituted or unsubstituted alkylsulfinyl, substituted or unsubstituted heteroaryl, substituted or unsubstituted heteroarylthio;

$R^3$ is substituted or unsubstituted heterocycle, substituted or unsubstituted heteroaryl, alkoxyalkoxy, substituted or unsubstituted cycloalkyl, substituted or unsubstituted carbamoyl, alkanoyl, substituted or unsubstituted aryloxy, oxo, or substituted or unsubstituted arylcarbonyloxy;

$R^4$ is hydrogen atom, alkoxy, substituted or unsubstituted heterocycle, substituted or unsubstituted heteroaryl, alkoxyalkoxy, substituted or unsubstituted cycloalkyl, cyano, substituted or unsubstituted aryl, substituted or unsubstituted carbamoyl, hydroxy, alkanoyl, alkylthio, alkoxycarbonyl, substituted or unsubstituted aryloxy, halogen atom, oxo, or substituted or unsubstituted arylcarbonyloxy;

$R^5$ is hydrogen atom, formyl, halogen atom, oxo, substituted or unsubstituted alkoxy, substituted or unsubstituted aminosulfonyl, substituted or unsubstituted alkylthio, cyano, substituted or unsubstituted heterocyclylsulfonyl, nitro, substituted or unsubstituted cycloalkyl, alkoxycarbonyl, alkenyl, alkylsulfonyl, substituted or unsubstituted carbamoyl, substituted or unsubstituted heteroarylthio, substituted or unsubstituted amino, carboxyl, substituted or unsubstituted heteroaryl, substituted or unsubstituted alkynyl, substituted or unsubstituted heterocyclyl-carbonyl, substituted or unsubstituted heterocyclyl-oxy, substituted or unsubstituted heterocycle, substituted or unsubstituted heterocyclyl-thio, substituted or unsubstituted cycloalkyloxy, alkanoyl, or substituted or unsubstituted alkyl;

$R^6$ is hydrogen atom, substituted or unsubstituted alkyl, halogen atom, or carboxyl;

or a pharmaceutically acceptable salt thereof.

2. An oxime derivative of the general formula [I]:

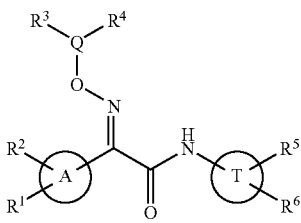

wherein Ring A is aryl;
Q is alkyl;
Ring T is heteroaryl or heterocycle of

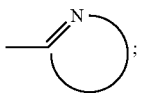

$R^1$ is hydrogen atom, halogen atom, cycloalkylsulfonyl, alkylsulfonyl, alkylsulfinyl, alkylthio, or substituted or unsubstituted tetrazolyl;

$R^2$ is hydrogen atom, halogen atom, cycloalkylsulfonyl, substituted or unsubstituted alkylsulfonyl, substituted or unsubstituted alkylthio, nitro, substituted or unsubstituted amino, substituted or unsubstituted aminosulfonyl, substituted or unsubstituted heterocyclyl-thio, substituted or unsubstituted heterocyclyl-sulfinyl, substituted or unsubstituted heterocyclyl -sulfonyl, substituted or unsubstituted heteroarylsulfonyl, alkenyloxy, substituted or unsubstituted alkoxy, substituted or unsubstituted alkylsulfinyl, substituted or unsubstituted heteroaryl, substituted or unsubstituted heteroarylthio;

$R^3$ is substituted or unsubstituted heterocycle, substituted or unsubstituted heteroaryl, alkoxyalkoxy, substituted or unsubstituted cycloalkyl, substituted or unsubstituted carbamoyl, alkanoyl, substituted or unsubstituted aryloxy, oxo, or substituted or unsubstituted arylcarbonyloxy;

$R^4$ is hydrogen atom, alkoxy, substituted or unsubstituted heterocycle, substituted or unsubstituted heteroaryl, alkoxyalkoxy, substituted or unsubstituted cycloalkyl, cyano, substituted or unsubstituted aryl, substituted or unsubstituted carbamoyl, hydroxy, alkanoyl, alkylthio, alkoxycarbonyl, substituted or unsubstituted aryloxy, halogen atom, oxo, or substituted or unsubstituted arylcarbonyloxy;

$R^5$ is hydrogen atom, formyl, halogen atom, oxo, substituted or unsubstituted alkoxy, substituted or unsubstituted aminosulfonyl, substituted or unsubstituted alkylthio, cyano, substituted or unsubstituted heterocyclyl-sulfonyl, nitro, substituted or unsubstituted cycloalkyl, alkoxycarbonyl, alkenyl, alkylsulfonyl, substituted or unsubstituted carbamoyl, substituted or unsubstituted heteroarylthio, substituted or unsubstituted amino, carboxyl, substituted or unsubstituted heteroaryl, substituted or unsubstituted alkynyl, substituted or unsubstituted heterocyclyl-carbonyl, substituted or unsubstituted heterocyclyl-oxy, substituted or unsubstituted heterocycle, substituted or unsubstituted heterocyclyl-thio, substituted or unsubstituted cycloalkyloxy, alkanoyl, or substituted or unsubstituted alkyl;

$R^6$ is hydrogen atom, substituted or unsubstituted alkyl, halogen atom, or carboxyl;

or a pharmaceutically acceptable salt thereof.

3. The oxime derivative of claim 2 wherein $R^1$ is hydrogen atom or halogen atom, or a pharmaceutically acceptable salt thereof.

4. The oxime derivative of claim 2 wherein $R^1$ is hydrogen atom, or a pharmaceutically acceptable salt thereof.

5. The oxime derivative of claim 2 wherein $R^2$ is cycloalkylsulfonyl, substituted or unsubstituted alkylsulfonyl, substituted or unsubstituted alkylthio, nitro, substituted or unsubstituted amino, substituted or unsubstituted aminosulfonyl, substituted or unsubstituted heterocyclyl-thio, substituted or unsubstituted heterocyclyl-sulfonyl, substituted or unsubstituted alkylsulfinyl, substituted or unsubstituted heteroarylsulfonyl, substituted or unsubstituted heteroarylthio, or substituted or unsubstituted heteroaryl, or a pharmaceutically acceptable salt thereof.

6. The oxime derivative of claim 2 wherein $R^2$ is cycloalkylsulfonyl, substituted or unsubstituted alkylsulfonyl, substituted or unsubstituted aminosulfonyl, or substituted or unsubstituted heterocyclyl-sulfonyl, or a pharmaceutically acceptable salt thereof.

7. The oxime derivative of claim 2 wherein $R^2$ is cycloalkylsulfonyl, substituted or unsubstituted alkylsulfonyl, or substituted or unsubstituted aminosulfonyl, or a pharmaceutically acceptable salt thereof.

8. The oxime derivative of claim 2 wherein $R^2$ is cycloalkylsulfonyl, or a pharmaceutically acceptable salt thereof.

9. The oxime derivative of claim 2 wherein the substituent of "substituted aminosulfonyl" in $R^2$ is substituted or unsubstituted alkyl, cycloalkyl, substituted or unsubstituted heterocycle, or alkoxy, or a pharmaceutically acceptable salt thereof.

10. The oxime derivative of claim 2 wherein the substituent of "substituted alkylsulfonyl" in $R^2$ is alkoxy, or a pharmaceutically acceptable salt thereof.

11. The oxime derivative of claim 2 wherein $R^3$ is substituted or unsubstituted heterocycle, substituted or unsubstituted heteroaryl, substituted or unsubstituted cycloalkyl, substituted or unsubstituted carbamoyl, alkanoyl, substituted or unsubstituted aryloxy, oxo, or substituted or unsubstituted arylcarbonyloxy, $R^4$ is hydrogen atom, alkoxy, substituted or unsubstituted heterocycle, substituted or unsubstituted heteroaryl, substituted or unsubstituted cycloalkyl, substituted or unsubstituted aryl, substituted or unsubstituted carbamoyl, hydroxy, alkanoyl, alkylthio, substituted or unsubstituted aryloxy, halogen atom, oxo, or substituted or unsubstituted arylcarbonyloxy, or a pharmaceutically acceptable salt thereof.

12. The oxime derivative of claim 2 wherein the group of -Q($R^3$)($R^4$) is alkyl substituted with 1 to 2 groups of substituted or unsubstituted heteroaryl, or a pharmaceutically acceptable salt thereof.

13. The oxime derivative of claim 2 wherein Ring T is heteroaryl of

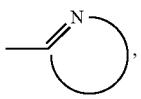

or a pharmaceutically acceptable salt thereof.

14. The oxime derivative of claim 2 wherein Ring T is thiazolyl, thiazolopyridinyl, pyridyl, pyrazinyl, benzothiazolyl, quinolyl, thiadiazolyl, pyrazolyl, thiazolopyrazinyl, thiazolopyrimidinyl, cyclohexanothiazolyl or dihydrothiazolopyridinyl, or a pharmaceutically acceptable salt thereof.

15. The oxime derivative of claim 2 wherein Ring T is thiazolyl, thiazolopyridinyl, pyridyl, pyrazinyl, benzothiazolyl, thiadiazolyl, thiazolopyrazinyl, thiazolopyrimidinyl, cyclohexanothiazolyl or dihydrothiazolopyridinyl, or a pharmaceutically acceptable salt thereof.

16. The oxime derivative of claim 2 wherein Ring T is thiazolyl, thiazolopyridinyl, pyrazinyl, thiadiazolyl, thiazolopyrazinyl, thiazolopyrimidinyl, or a pharmaceutically acceptable salt thereof.

17. The oxime derivative of claim 2 wherein Ring T is thiazolyl or thiazolopyridinyl, or a pharmaceutically acceptable salt thereof.

18. The oxime derivative of claim 2 wherein $R^5$ is hydrogen atom, formyl, halogen atom, oxo, substituted or unsubstituted alkoxy, substituted or unsubstituted aminosulfonyl, substituted or unsubstituted alkylthio, cyano, substituted or unsubstituted heterocyclyl-sulfonyl, nitro, substituted or unsubstituted cycloalkyl, alkoxycarbonyl, alkenyl, alkanoyl, substituted or unsubstituted carbamoyl, substituted or unsubstituted heteroarylthio, substituted or unsubstituted amino, substituted or unsubstituted heteroaryl, substituted or unsubstituted alkynyl, substituted or unsubstituted heterocyclyl-oxy, or substituted or unsubstituted alkyl, or a pharmaceutically acceptable salt thereof.

19. The oxime derivative of claim 4 wherein $R^5$ is hydrogen atom, halogen atom, substituted or unsubstituted alkoxy, substituted or unsubstituted alkylthio, cyano, substituted or unsubstituted cycloalkyl, alkanoyl, substituted or unsubstituted carbamoyl, substituted or unsubstituted amino, substituted or unsubstituted heterocyclyl-oxy, or substituted or unsubstituted alkyl, or a pharmaceutically acceptable salt thereof.

20. The oxime derivative of claim 2 wherein $R^5$ is halogen atom, substituted or unsubstituted alkoxy, substituted or unsubstituted alkylthio, substituted or unsubstituted amino, substituted or unsubstituted heterocyclyl-oxy, or substituted or unsubstituted alkyl, or a pharmaceutically acceptable salt thereof.

21. The oxime derivative of claim 2 wherein $R^5$ is substituted or unsubstituted alkoxy, substituted or unsubstituted amino, substituted or unsubstituted heterocyclyl-oxy, or substituted or unsubstituted alkyl, or a pharmaceutically acceptable salt thereof.

22. The oxime derivative of claim 2 wherein the substituent of "substituted alkyl" in $R^5$ is substituted or unsubstituted heterocycle, substituted or unsubstituted amino, substituted or unsubstituted alkoxy, substituted or unsubstituted carbamoyl, hydroxy, trialkylsilyloxy, alkylthio, alkylsulfonyl, substituted or unsubstituted heterocyclyl-oxy, heteroaryl, substituted or unsubstituted hydroxyimino, halogen atom, carboxyl, alkoxycarbonyl, or alkanoyloxy, or a pharmaceutically acceptable salt thereof.

23. The oxime derivative of claim 2 wherein $R^6$ is hydrogen atom, or substituted or unsubstituted alkyl, or a pharmaceutically acceptable salt thereof.

24. The oxime derivative of claim 2 wherein $R^6$ is hydrogen atom, or a pharmaceutically acceptable salt thereof.

25. A method for preparing an oxime derivative of the general formula [I]:

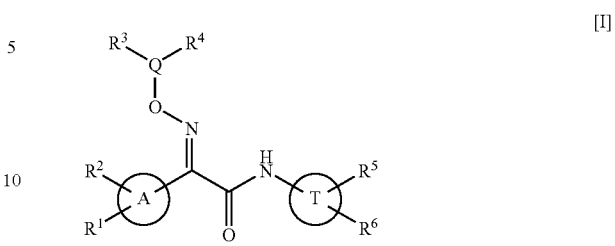

wherein the symbols have the same meanings as defined in claim 2, which comprises reacting a compound of the general formula [II]:

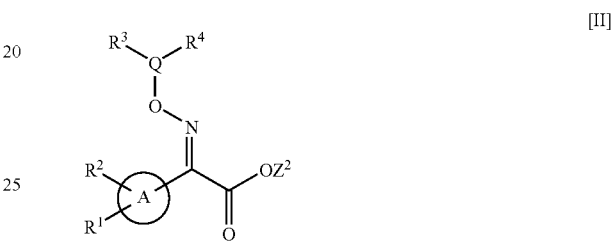

wherein $Z^2$ is hydrogen atom or alkyl and the other symbols have the same meanings as defined in claim 2 with a compound of the general formula [III]:

wherein the symbols have the same meanings as defined in claim 2.

26. A method for preparing an oxime derivative of the general formula [I]:

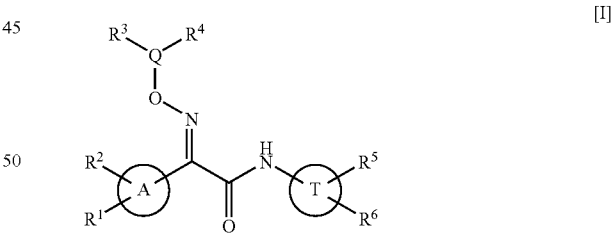

wherein the symbols have the same meanings as defined in claim 2, which comprises reacting a compound of the general formula [IX]:

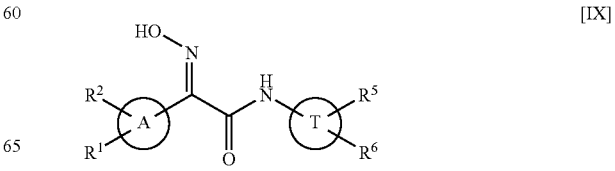

wherein the symbols have the same meanings as defined in claim 2, with a compound of the general formula [V]:

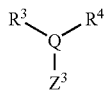

[V]

wherein $Z^3$ is hydroxy, halogen atom, arylsulfonyloxy or alkylsulfonyloxy and the other symbols have the same meanings as defined in claim 2.

27. A method for preparing an oxime derivative of the general formula [I]:

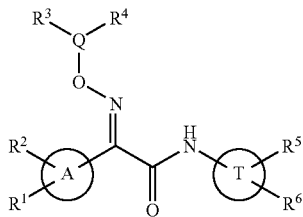

[I]

wherein the symbols have the same meanings as defined in claim 2, which comprises reacting a compound of the general formula [X]:

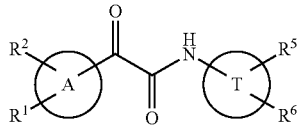

[X]

wherein the symbols have the same meanings as defined in claim 4, with a compound of the general formula [XI]:

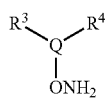

[XI]

wherein the symbols have the same meanings as defined in claim 4.

* * * * *